(12) United States Patent
Chan et al.

(10) Patent No.: US 11,254,744 B2
(45) Date of Patent: Feb. 22, 2022

(54) ANTIGEN BINDING CONSTRUCTS TO TARGET MOLECULES

(71) Applicant: IMAGINAB, INC., Inglewood, CA (US)

(72) Inventors: Chio Mui Chan, Los Angeles, CA (US); Jean Gudas, Los Angeles, CA (US); Tove Olafsen, Reseda, CA (US); Daulet Kadyl Satpayev, Los Angeles, CA (US); Michael Yuri Torgov, Hawthorne, CA (US)

(73) Assignee: IMAGINAB, INC., Inglewood, CA (US)

( * ) Notice: Subject to any disclaimer, the term of this patent is extended or adjusted under 35 U.S.C. 154(b) by 0 days.

(21) Appl. No.: 15/228,616

(22) Filed: Aug. 4, 2016

(65) Prior Publication Data

US 2017/0051044 A1    Feb. 23, 2017

Related U.S. Application Data

(60) Provisional application No. 62/202,665, filed on Aug. 7, 2015.

(51) Int. Cl.
```
C07K 16/28     (2006.01)
C07K 16/30     (2006.01)
A61K 39/00     (2006.01)
```

(52) U.S. Cl.
CPC ...... *C07K 16/2809* (2013.01); *C07K 16/2815* (2013.01); *C07K 16/30* (2013.01); *C07K 16/3069* (2013.01); *A61K 2039/505* (2013.01); *C07K 2317/53* (2013.01); *C07K 2317/622* (2013.01)

(58) Field of Classification Search
CPC ............ C07K 2317/53; C07K 2317/60; C07K 2317/622
USPC ..................................... 424/133.1; 530/387.3
See application file for complete search history.

(56) References Cited

U.S. PATENT DOCUMENTS

| | | |
|---|---|---|
| 4,281,061 A | 7/1981 | Zuk et al. |
| 4,709,015 A | 11/1987 | Kung et al. |
| 4,816,567 A | 3/1989 | Cabilly et al. |
| 4,892,824 A | 1/1990 | Skaletsky |
| 4,943,525 A | 7/1990 | Dawson |
| 4,946,778 A | 8/1990 | Ladner et al. |
| 5,256,395 A | 10/1993 | Barbet et al. |
| 5,332,567 A | 7/1994 | Goldenberg |
| 5,376,249 A | 12/1994 | Afeyan et al. |
| 5,518,889 A | 5/1996 | Lander et al. |
| 5,521,297 A | 5/1996 | Daggett et al. |
| 5,523,210 A | 6/1996 | Paulus |
| 5,534,254 A | 7/1996 | Huston et al. |
| 5,538,866 A | 7/1996 | Israeli et al. |
| 5,582,996 A | 12/1996 | Curtis |
| 5,591,828 A | 1/1997 | Bosslet et al. |
| 5,601,819 A | 2/1997 | Wong et al. |
| 5,627,078 A | 5/1997 | Karl et al. |
| 5,637,481 A | 6/1997 | Ledbetter et al. |
| 5,688,690 A | 11/1997 | Valiante et al. |
| 5,693,477 A | 12/1997 | Cornell et al. |
| 5,705,614 A | 1/1998 | Ring |
| 5,712,136 A | 1/1998 | Wickham et al. |
| 5,747,035 A | 5/1998 | Presta et al. |
| 5,762,930 A | 6/1998 | Fanger et al. |
| 5,807,689 A | 9/1998 | Daggett et al. |
| 5,821,333 A | 10/1998 | Carter et al. |
| 5,830,473 A | 11/1998 | Thierfelder |
| 5,830,478 A | 11/1998 | Raso et al. |
| 5,837,242 A | 11/1998 | Holliger et al. |
| 5,837,821 A | 11/1998 | Wu |
| 5,840,854 A | 11/1998 | Hellstrom et al. |
| 5,844,094 A | 12/1998 | Hudson et al. |
| 5,851,527 A | 12/1998 | Hudson et al. |
| 5,852,186 A | 12/1998 | Sodroski et al. |
| 5,859,205 A | 1/1999 | Adair |
| 5,861,156 A | 1/1999 | George et al. |
| 5,863,765 A | 1/1999 | Berry et al. |
| 5,869,049 A | 2/1999 | Noelle et al. |
| 5,869,053 A | 2/1999 | Stern et al. |
| 5,869,620 A | 2/1999 | Whitlow et al. |
| 5,876,691 A | 3/1999 | Chester et al. |
| 5,877,291 A | 3/1999 | Mezes et al. |
| 5,912,122 A | 6/1999 | Daggett et al. |
| 5,932,448 A | 8/1999 | Tso et al. |
| 5,935,818 A | 8/1999 | Israeli et al. |
| 5,942,229 A | 8/1999 | Noelle et al. |
| 5,951,982 A | 9/1999 | Zöller et al. |

(Continued)

FOREIGN PATENT DOCUMENTS

| | | |
|---|---|---|
| CA | 2903587 A1 | 9/2014 |
| CN | 1356341 | 7/2002 |

(Continued)

OTHER PUBLICATIONS

US 8,748,586 B2, 06/2014, Ho et al. (withdrawn)
//bioinfo3d.cs.tau.ac.il/HingeProt/hingeprot.html (pp. 1-2; Aug. 26, 2018).*
Sljoka et al. (International Conference on Applied Mathematics, Modeling & Computational Science, Waterloo, Canada, Jul. 25-29, 2011; pp. 1-4).*

(Continued)

*Primary Examiner* — Lynn A Bristol

(74) *Attorney, Agent, or Firm* — Knobbe, Martnes, Olson & Bear, LLP

(57) ABSTRACT

Antigen binding constructs that bind to desired targets are disclosed, for example antibodies, including antibody fragments (such as scFv and minibodies) that bind to a target molecule, and have one or more of the disclosed hinges are described herein. Methods of use are described herein.

32 Claims, 157 Drawing Sheets

Specification includes a Sequence Listing.

(56) References Cited

U.S. PATENT DOCUMENTS

| | | |
|---|---|---|
| 5,959,083 A | 9/1999 | Bosslet et al. |
| 5,977,322 A | 11/1999 | Marks et al. |
| 5,980,896 A | 11/1999 | Hellstrom et al. |
| 5,989,830 A | 11/1999 | Davis et al. |
| 5,990,275 A | 11/1999 | Whitlow et al. |
| 6,001,581 A | 12/1999 | Johnson et al. |
| 6,010,902 A | 1/2000 | Ledbetter et al. |
| 6,030,792 A | 2/2000 | Otterness et al. |
| 6,051,688 A | 4/2000 | Stormann et al. |
| 6,071,490 A | 6/2000 | Griffiths et al. |
| 6,077,675 A | 6/2000 | Stormann et al. |
| 6,083,763 A | 7/2000 | Balch |
| 6,084,084 A | 7/2000 | Stormann et al. |
| 6,096,871 A | 8/2000 | Presta et al. |
| 6,099,841 A | 8/2000 | Hillan et al. |
| 6,103,524 A | 8/2000 | Belagaje et al. |
| 6,107,090 A | 8/2000 | Bander |
| 6,121,022 A | 9/2000 | Presta et al. |
| 6,136,311 A | 10/2000 | Bander |
| 6,150,508 A | 11/2000 | Murphy et al. |
| 6,193,966 B1 | 2/2001 | Deo et al. |
| 6,197,298 B1 | 3/2001 | Chang |
| 6,200,765 B1 | 3/2001 | Murphy et al. |
| 6,201,167 B1 | 3/2001 | Pothier |
| 6,221,609 B1 | 4/2001 | Belagaje et al. |
| 6,228,610 B1 | 5/2001 | Flor et al. |
| 6,241,961 B1 | 6/2001 | Benes et al. |
| 6,248,516 B1 | 6/2001 | Winter et al. |
| 6,284,742 B1 | 9/2001 | Curiel et al. |
| 6,294,391 B1 | 9/2001 | Badley et al. |
| 6,312,694 B1 | 11/2001 | Thorpe et al. |
| 6,329,503 B1 | 12/2001 | Afar et al. |
| 6,342,587 B1 | 1/2002 | Barbas, III et al. |
| 6,361,774 B1 | 3/2002 | Griffiths et al. |
| 6,362,316 B1 | 3/2002 | Daggett et al. |
| 6,368,596 B1 | 4/2002 | Ghetie et al. |
| 6,383,759 B1 | 5/2002 | Murphy et al. |
| 6,384,205 B1 | 5/2002 | Belagaje et al. |
| 6,387,350 B2 | 5/2002 | Goldenberg |
| 6,399,068 B1 | 6/2002 | Goldenberg |
| 6,413,764 B1 | 7/2002 | Daggett et al. |
| 6,458,933 B1 | 10/2002 | Hansen |
| 6,485,919 B1 | 11/2002 | Daggett et al. |
| 6,491,916 B1 | 12/2002 | Bluestone et al. |
| 6,492,123 B1 | 12/2002 | Hollinger et al. |
| 6,515,107 B2 | 2/2003 | Flor et al. |
| 6,569,432 B1 | 5/2003 | Israeli et al. |
| 6,602,684 B1 | 8/2003 | Umana et al. |
| 6,608,176 B2 | 8/2003 | Chaudhari et al. |
| 6,642,356 B1 | 11/2003 | Humphreys |
| 6,649,163 B1 | 11/2003 | Bander |
| 6,709,844 B1 | 3/2004 | Levy |
| 6,767,711 B2 | 7/2004 | Bander |
| 6,770,450 B1 | 8/2004 | Bander |
| 6,824,780 B1 | 11/2004 | Devaux et al. |
| 6,833,438 B1 | 12/2004 | Afar et al. |
| 6,835,866 B1 | 12/2004 | Mangelsdorf et al. |
| 6,861,234 B1 | 3/2005 | Simard et al. |
| 6,869,620 B2 | 3/2005 | Moore |
| 6,870,034 B2 | 3/2005 | Breece et al. |
| 6,887,975 B2 | 5/2005 | Afar et al. |
| 6,953,668 B1 | 10/2005 | Israeli et al. |
| 6,977,074 B2 | 12/2005 | Kundig et al. |
| 6,994,851 B1 | 2/2006 | Kundig et al. |
| 7,037,647 B1 | 5/2006 | Israeli et al. |
| 7,045,605 B2 | 5/2006 | Bander et al. |
| 7,053,186 B2 | 5/2006 | Afar et al. |
| 7,070,782 B1 | 7/2006 | Israeli et al. |
| 7,105,159 B1 | 9/2006 | Israeli et al. |
| 7,112,412 B1 | 9/2006 | Bander |
| 7,157,250 B2 | 1/2007 | San Gabriel et al. |
| 7,163,680 B2 | 1/2007 | Bander |
| 7,166,714 B2 | 1/2007 | Afar et al. |
| 7,192,586 B2 | 3/2007 | Bander |
| 7,232,682 B2 | 6/2007 | Simard et al. |
| 7,235,641 B2 | 6/2007 | Kufer et al. |
| 7,253,257 B2 | 8/2007 | Flor et al. |
| 7,258,971 B2 | 8/2007 | Karicheti et al. |
| 7,262,280 B1 | 8/2007 | Stormann et al. |
| 7,319,006 B2 | 1/2008 | Afar et al. |
| 7,323,553 B2 | 1/2008 | Fahrner et al. |
| 7,335,760 B2 | 2/2008 | Alexandrov et al. |
| 7,364,729 B2 | 4/2008 | Kundig et al. |
| 7,375,078 B2 | 5/2008 | Feng |
| 7,390,654 B2 | 6/2008 | Levy |
| 7,399,461 B2 | 7/2008 | Heston et al. |
| 7,435,416 B2 | 10/2008 | Devaux et al. |
| 7,446,190 B2 | 11/2008 | Sadelain et al. |
| 7,452,539 B2 | 11/2008 | Emery et al. |
| 7,455,991 B2 | 11/2008 | Afar et al. |
| 7,485,299 B2 | 2/2009 | Afar et al. |
| 7,485,704 B2 | 2/2009 | Fahrner et al. |
| 7,494,646 B2 | 2/2009 | Jakobovits et al. |
| 7,498,298 B2 | 3/2009 | Doronina et al. |
| 7,514,078 B2 | 4/2009 | Bander et al. |
| 7,517,670 B2 | 4/2009 | Umana et al. |
| 7,521,541 B2 | 4/2009 | Eigenbrot et al. |
| 7,524,813 B2 | 4/2009 | Zundel et al. |
| 7,541,441 B2 | 6/2009 | Rosen et al. |
| 7,569,389 B2 | 8/2009 | Feldmann et al. |
| 7,575,749 B2 | 8/2009 | Afar et al. |
| 7,595,379 B2 | 9/2009 | Gudas et al. |
| 7,597,876 B2 | 10/2009 | McBride et al. |
| 7,611,904 B2 | 11/2009 | Afar et al. |
| 7,612,181 B2 | 11/2009 | Wu et al. |
| 7,622,569 B2 | 11/2009 | Raitano et al. |
| 7,642,054 B2 | 1/2010 | Afar et al. |
| 7,662,936 B2 | 2/2010 | Kadkhodayan et al. |
| 7,666,414 B2 | 2/2010 | Bander |
| 7,666,425 B1 | 2/2010 | Bander |
| 7,678,371 B2 | 3/2010 | Lugovskoy et al. |
| 7,727,533 B2 | 6/2010 | Afar et al. |
| 7,745,394 B2 | 6/2010 | Doronina et al. |
| 7,754,681 B2 | 7/2010 | Feng |
| 7,785,801 B2 | 8/2010 | Tureci et al. |
| 7,790,850 B2 | 9/2010 | Kobilka et al. |
| 7,807,799 B2 | 10/2010 | Fahrner et al. |
| 7,820,166 B2 | 10/2010 | Lanzavecchia |
| 7,834,146 B2 | 11/2010 | Kovalic et al. |
| 7,838,637 B2 | 11/2010 | Kontermann et al. |
| 7,855,275 B2 | 12/2010 | Eigenbrot et al. |
| 7,867,483 B2 | 1/2011 | Delcayre et al. |
| 7,884,179 B2 | 2/2011 | Faris et al. |
| 7,888,035 B2 | 2/2011 | Klass et al. |
| 7,888,479 B2 | 2/2011 | De Fougerolles et al. |
| 7,897,356 B2 | 3/2011 | Klass et al. |
| 7,906,329 B2 | 3/2011 | Umana et al. |
| 7,928,201 B2 | 4/2011 | Afar et al. |
| 7,939,503 B2 | 5/2011 | Jakobovits et al. |
| 7,947,276 B2 | 5/2011 | Jakobovits et al. |
| 7,947,459 B2 | 5/2011 | Hubert et al. |
| 7,947,839 B2 | 5/2011 | Gazzard et al. |
| 7,960,109 B2 | 6/2011 | Hessels et al. |
| 7,964,566 B2 | 6/2011 | Doronina et al. |
| 7,964,567 B2 | 6/2011 | Doronina et al. |
| 7,968,307 B2 | 6/2011 | Afar et al. |
| 7,989,434 B2 | 8/2011 | Feng |
| 7,994,135 B2 | 8/2011 | Doronina et al. |
| 7,998,701 B2 | 8/2011 | Chua et al. |
| 8,007,994 B2 | 8/2011 | Mangelsdorf et al. |
| 8,008,442 B2 | 8/2011 | Jakobovits et al. |
| 8,012,937 B2 | 9/2011 | Raitano et al. |
| 8,013,128 B2 | 9/2011 | Gudas et al. |
| 8,013,135 B2 | 9/2011 | Jakobovits et al. |
| 8,043,830 B2 | 10/2011 | Barat et al. |
| 8,071,742 B2 | 12/2011 | Kobilka et al. |
| 8,106,174 B2 | 1/2012 | Kovalic et al. |
| 8,139,715 B2 | 3/2012 | Kobilka et al. |
| 8,147,799 B2 | 4/2012 | McBride et al. |
| 8,147,800 B2 | 4/2012 | McBride et al. |
| 8,153,101 B2 | 4/2012 | McBride et al. |
| 8,178,655 B2 | 5/2012 | Kobilka et al. |
| 8,202,509 B2 | 6/2012 | McBride et al. |
| 8,206,932 B2 | 6/2012 | Gudas et al. |

(56) References Cited

U.S. PATENT DOCUMENTS

| | | |
|---|---|---|
| 8,260,596 B2 | 9/2012 | Kobilka et al. |
| 8,278,424 B2 | 10/2012 | Gudas et al. |
| 8,329,432 B2 | 12/2012 | Kobilka et al. |
| 8,343,460 B2 | 1/2013 | McBride et al. |
| 8,383,778 B2 | 2/2013 | Hsieh et al. |
| 8,444,956 B2 | 5/2013 | McBride et al. |
| 8,470,561 B2 | 6/2013 | Kobilka |
| 8,487,077 B2 | 7/2013 | Olma et al. |
| 8,586,006 B2 | 11/2013 | Hood et al. |
| 8,637,639 B2 | 1/2014 | Kobilka et al. |
| 8,658,380 B2 | 2/2014 | Rabbani |
| 8,680,237 B2 | 3/2014 | Strome et al. |
| 8,709,382 B2 | 4/2014 | D'Souza et al. |
| 8,728,738 B2 | 5/2014 | Broet et al. |
| 8,758,726 B2 | 6/2014 | D'Souza et al. |
| 8,772,459 B2 | 7/2014 | Ho et al. |
| 8,795,977 B2 | 8/2014 | Wieland |
| 8,889,100 B2 | 11/2014 | D'Souza et al. |
| 8,889,377 B2 | 11/2014 | Kobilka |
| 8,940,298 B2 | 1/2015 | Wu et al. |
| 8,940,871 B2 | 1/2015 | Wu et al. |
| 8,951,737 B2 | 2/2015 | Bander |
| 8,999,654 B2 | 4/2015 | Gaitanaris et al. |
| 9,028,800 B2 | 5/2015 | D'Souza et al. |
| 9,045,561 B2 | 6/2015 | Kobilka et al. |
| 9,115,172 B2 | 8/2015 | D'Souza et al. |
| 9,255,131 B2 | 2/2016 | Tureci et al. |
| 9,334,324 B2 | 5/2016 | Choo et al. |
| 9,512,208 B2 | 12/2016 | Strome et al. |
| 9,512,210 B2 | 12/2016 | Strome et al. |
| 9,518,119 B2 | 12/2016 | Bergstein |
| 9,540,438 B2 | 1/2017 | Barfield et al. |
| 9,701,754 B1 | 7/2017 | Wu et al. |
| 9,765,155 B2 | 9/2017 | Wu et al. |
| 10,301,389 B2 | 5/2019 | Ho et al. |
| 10,377,826 B2 | 8/2019 | Ho et al. |
| 10,414,820 B2 | 9/2019 | Ho et al. |
| 10,882,909 B2 | 1/2021 | Ho et al. |
| 2002/0004215 A1 | 1/2002 | Osbourn et al. |
| 2002/0018749 A1 | 2/2002 | Hudson et al. |
| 2002/0037289 A1 | 3/2002 | Thorpe et al. |
| 2002/0119096 A1 | 8/2002 | Griffiths |
| 2002/0119153 A1 | 8/2002 | Thorpe et al. |
| 2002/0122798 A1 | 9/2002 | Young |
| 2002/0127638 A1 | 9/2002 | Flor et al. |
| 2002/0132979 A1 | 9/2002 | Chen |
| 2002/0136689 A1 | 9/2002 | Reiter et al. |
| 2002/0151052 A1 | 10/2002 | Chaudhari et al. |
| 2003/0113868 A1 | 6/2003 | Flor et al. |
| 2003/0118583 A1 | 6/2003 | Emery et al. |
| 2003/0143668 A1 | 7/2003 | Suwa et al. |
| 2003/0170228 A1 | 9/2003 | Ashkenazi et al. |
| 2003/0175900 A1 | 9/2003 | Ashkenazi et al. |
| 2003/0211096 A1 | 11/2003 | Ashkenazi et al. |
| 2003/0235833 A1 | 12/2003 | Suwa et al. |
| 2004/0018519 A1 | 1/2004 | Wright |
| 2004/0018557 A1 | 1/2004 | Qu et al. |
| 2004/0033511 A1 | 2/2004 | Pfizenmaier et al. |
| 2004/0038339 A1 | 2/2004 | Kufer et al. |
| 2004/0071690 A1 | 4/2004 | Hudson et al. |
| 2004/0162411 A1 | 8/2004 | Lanzavecchia |
| 2004/0172684 A1 | 9/2004 | Kovalic et al. |
| 2004/0197825 A1 | 10/2004 | Karicheti et al. |
| 2004/0209314 A1 | 10/2004 | Lang et al. |
| 2004/0214272 A1 | 10/2004 | Varagona et al. |
| 2004/0241817 A1 | 12/2004 | Umana et al. |
| 2005/0003481 A1 | 1/2005 | Gabriel et al. |
| 2005/0026178 A1 | 2/2005 | Nilsen-Hamilton |
| 2005/0118676 A1 | 6/2005 | Qi et al. |
| 2005/0136050 A1 | 6/2005 | Kufer et al. |
| 2005/0175618 A1 | 8/2005 | Carroll et al. |
| 2005/0176028 A1 | 8/2005 | Hofmeister et al. |
| 2005/0215769 A1 | 9/2005 | Breece et al. |
| 2005/0232929 A1 | 10/2005 | Kadkhodayan et al. |
| 2005/0244333 A1 | 11/2005 | Yazaki et al. |
| 2005/0272128 A1 | 12/2005 | Umana et al. |
| 2005/0281740 A1 | 12/2005 | Gong et al. |
| 2006/0002933 A1 | 1/2006 | Bluestone et al. |
| 2006/0062793 A1 | 3/2006 | Webb et al. |
| 2006/0099582 A1 | 5/2006 | Papdopoulos et al. |
| 2006/0134105 A1 | 6/2006 | Lazar et al. |
| 2006/0134109 A1 | 6/2006 | Gaitanaris et al. |
| 2006/0150283 A1 | 7/2006 | Alexandrov et al. |
| 2006/0159689 A1 | 7/2006 | Chiang et al. |
| 2006/0234226 A1 | 10/2006 | Fahrner et al. |
| 2006/0234271 A1 | 10/2006 | Su |
| 2006/0235212 A1 | 10/2006 | Alexandrov et al. |
| 2006/0235213 A1 | 10/2006 | Alexandrov et al. |
| 2006/0257407 A1 | 11/2006 | Chen et al. |
| 2006/0269540 A1 | 11/2006 | Robert et al. |
| 2006/0275312 A1 | 12/2006 | Chua et al. |
| 2007/0009916 A1 | 1/2007 | Suwa et al. |
| 2007/0039067 A1 | 2/2007 | Feldmann et al. |
| 2007/0059306 A1 | 3/2007 | Grosmaire |
| 2007/0081993 A1 | 4/2007 | Kufer |
| 2007/0134243 A1 | 6/2007 | Gazzard et al. |
| 2007/0212331 A1 | 9/2007 | Baldassare et al. |
| 2007/0214517 A1 | 9/2007 | Alexandrov et al. |
| 2007/0243950 A1 | 10/2007 | Billings |
| 2007/0253950 A1 | 11/2007 | Jacobsen |
| 2007/0271633 A9 | 11/2007 | Kovalic et al. |
| 2007/0286858 A1 | 12/2007 | Clancy |
| 2008/0095770 A1 | 4/2008 | Umana et al. |
| 2008/0152586 A1 | 6/2008 | Hudson et al. |
| 2008/0171040 A1 | 7/2008 | Ebens et al. |
| 2008/0193376 A1 | 8/2008 | Tawakol et al. |
| 2008/0193454 A1 | 8/2008 | Tureci et al. |
| 2008/0206192 A1 | 8/2008 | Moller et al. |
| 2008/0213256 A1 | 9/2008 | Kufer et al. |
| 2008/0213921 A1 | 9/2008 | Robertson et al. |
| 2008/0227736 A1 | 9/2008 | Chen et al. |
| 2008/0260650 A1 | 10/2008 | Tawakol et al. |
| 2008/0260744 A1 | 10/2008 | Gaitanaris et al. |
| 2008/0267872 A1 | 10/2008 | Raitano et al. |
| 2008/0269471 A1 | 10/2008 | Alexandrov et al. |
| 2008/0279850 A1 | 11/2008 | Brady et al. |
| 2008/0305105 A1 | 12/2008 | Kufer et al. |
| 2008/0305476 A1 | 12/2008 | Robertson et al. |
| 2009/0004109 A1 | 1/2009 | Jacobovits et al. |
| 2009/0022738 A1 | 1/2009 | Hofmeister et al. |
| 2009/0041758 A1 | 2/2009 | Glaser |
| 2009/0041791 A1 | 2/2009 | Feng |
| 2009/0053223 A1 | 2/2009 | Hoffmann et al. |
| 2009/0087878 A9 | 4/2009 | La Rosa et al. |
| 2009/0099344 A1 | 4/2009 | Fahrner et al. |
| 2009/0118474 A1 | 5/2009 | Kobilka et al. |
| 2009/0136475 A1 | 5/2009 | Barth |
| 2009/0144848 A1 | 6/2009 | Kovalic et al. |
| 2009/0155290 A1 | 6/2009 | Carroll et al. |
| 2009/0178153 A1 | 7/2009 | Gaitanaris et al. |
| 2009/0202548 A1 | 8/2009 | Gudas et al. |
| 2009/0214539 A1 | 8/2009 | Grosmaire |
| 2009/0226465 A1 | 9/2009 | Jackson |
| 2009/0238755 A1 | 9/2009 | Bander |
| 2009/0252729 A1 | 10/2009 | Farrington et al. |
| 2009/0252748 A1 | 10/2009 | Mi et al. |
| 2009/0272169 A1 | 11/2009 | Pan |
| 2009/0275081 A1 | 11/2009 | Barat et al. |
| 2009/0280120 A1 | 11/2009 | Bander et al. |
| 2009/0286258 A1 | 11/2009 | Kaur et al. |
| 2009/0311181 A1 | 12/2009 | Wu et al. |
| 2010/0003766 A1 | 1/2010 | Eigenbrot et al. |
| 2010/0033105 A1 | 2/2010 | Yamauchi et al. |
| 2010/0034837 A1 | 2/2010 | Beria et al. |
| 2010/0047239 A1 | 2/2010 | Wu et al. |
| 2010/0058803 A1 | 3/2010 | Ransbarger |
| 2010/0069616 A1 | 3/2010 | Wu et al. |
| 2010/0083407 A1 | 4/2010 | Feldmann et al. |
| 2010/0111856 A1 | 5/2010 | Gill et al. |
| 2010/0111959 A1 | 5/2010 | Swanson et al. |
| 2010/0135900 A1 | 6/2010 | Cerveny |
| 2010/0184046 A1 | 7/2010 | Klass et al. |
| 2010/0189651 A1 | 7/2010 | Stagliano |
| 2010/0209343 A1 | 8/2010 | Bander et al. |

(56) References Cited

U.S. PATENT DOCUMENTS

| | | |
|---|---|---|
| 2010/0215581 A1 | 8/2010 | Hoffman |
| 2010/0239633 A1 | 9/2010 | Strome et al. |
| 2010/0247440 A1 | 9/2010 | Morton |
| 2010/0255479 A1 | 10/2010 | Mikolajczyk et al. |
| 2010/0266491 A1 | 10/2010 | Farokhzad et al. |
| 2010/0267933 A1 | 10/2010 | Wilson |
| 2010/0278919 A1 | 11/2010 | Denes et al. |
| 2010/0297004 A1 | 11/2010 | Wu et al. |
| 2010/0298542 A1 | 11/2010 | Igawa et al. |
| 2010/0303715 A1 | 12/2010 | Israeli |
| 2010/0303814 A1 | 12/2010 | Cizeau et al. |
| 2010/0303821 A1 | 12/2010 | Ashman |
| 2010/0310452 A1 | 12/2010 | Israeli |
| 2010/0310584 A1 | 12/2010 | Carroll et al. |
| 2010/0322861 A1 | 12/2010 | Gambhir et al. |
| 2011/0006466 A1 | 1/2011 | Ichikawa |
| 2011/0009001 A1 | 1/2011 | Chen |
| 2011/0009603 A1 | 1/2011 | Kobilka et al. |
| 2011/0014628 A1 | 1/2011 | Tureci et al. |
| 2011/0020327 A1 | 1/2011 | Moya et al. |
| 2011/0054151 A1 | 3/2011 | Lazar et al. |
| 2011/0069019 A1 | 3/2011 | Carpendale et al. |
| 2011/0076287 A1 | 3/2011 | Cohen et al. |
| 2011/0081345 A1 | 4/2011 | Moore |
| 2011/0086050 A1 | 4/2011 | Presta |
| 2011/0104059 A1 | 5/2011 | St. Croix et al. |
| 2011/0110852 A1 | 5/2011 | Miller et al. |
| 2011/0110854 A1 | 5/2011 | McBride et al. |
| 2011/0117023 A1 | 5/2011 | Yamauchi |
| 2011/0123532 A1 | 5/2011 | Gurney et al. |
| 2011/0137017 A1 | 6/2011 | Eigenbrot et al. |
| 2011/0164731 A1 | 7/2011 | Kobilka et al. |
| 2011/0171728 A1 | 7/2011 | Kobilka et al. |
| 2011/0183924 A1 | 7/2011 | Mintz et al. |
| 2011/0185439 A1 | 7/2011 | Gaitanaris et al. |
| 2011/0189756 A1 | 8/2011 | Kobilka et al. |
| 2011/0207155 A1 | 8/2011 | Pengo et al. |
| 2011/0214189 A1 | 9/2011 | Gaitanaris et al. |
| 2011/0227023 A1 | 9/2011 | Bethune et al. |
| 2011/0262968 A1 | 10/2011 | Gudas et al. |
| 2011/0268656 A1 | 11/2011 | Ho et al. |
| 2011/0269637 A1 | 11/2011 | Broet et al. |
| 2012/0076728 A1 | 3/2012 | Wu et al. |
| 2012/0087862 A1 | 4/2012 | Hood et al. |
| 2012/0136137 A1 | 5/2012 | Kobilka et al. |
| 2012/0144110 A1 | 6/2012 | Smith |
| 2012/0159672 A1 | 6/2012 | Alexandrov et al. |
| 2012/0183566 A1 | 7/2012 | Barfield et al. |
| 2012/0276563 A1 | 11/2012 | Wieland |
| 2012/0283418 A1 | 11/2012 | Wu et al. |
| 2012/0301899 A1* | 11/2012 | Choo .............. C07K 16/28 435/7.21 |
| 2012/0309941 A1 | 12/2012 | Choo et al. |
| 2013/0059337 A1 | 3/2013 | Bendig et al. |
| 2013/0137975 A1 | 5/2013 | Bugaj et al. |
| 2013/0197192 A1 | 8/2013 | Kobilka et al. |
| 2013/0247233 A1 | 9/2013 | Gaitanaris et al. |
| 2013/0315830 A1 | 11/2013 | Bander |
| 2013/0323236 A1 | 12/2013 | Humphreys et al. |
| 2014/0017244 A1 | 1/2014 | Duerr et al. |
| 2014/0105913 A1 | 4/2014 | Strome et al. |
| 2014/0106981 A1 | 4/2014 | Hood et al. |
| 2014/0120085 A1 | 5/2014 | Tureci et al. |
| 2014/0162341 A1 | 6/2014 | Kobilka |
| 2014/0194595 A1 | 7/2014 | Kobilka et al. |
| 2014/0234215 A1 | 8/2014 | Ho et al. |
| 2014/0271462 A1 | 9/2014 | Ho et al. |
| 2014/0286951 A1* | 9/2014 | Gurney .......... A61K 39/39558 424/136.1 |
| 2014/0302035 A1 | 10/2014 | Harms et al. |
| 2014/0335075 A1 | 11/2014 | Strome et al. |
| 2015/0017169 A1 | 1/2015 | Humphreys et al. |
| 2015/0018529 A1 | 1/2015 | Humphreys et al. |
| 2015/0056185 A1 | 2/2015 | Strome et al. |
| 2015/0057166 A1 | 2/2015 | Kobilka |
| 2015/0064177 A1 | 3/2015 | Bendig et al. |
| 2015/0086482 A1 | 3/2015 | Regino et al. |
| 2015/0118252 A1 | 4/2015 | Ho et al. |
| 2015/0191543 A1 | 7/2015 | Wu et al. |
| 2015/0210751 A1 | 7/2015 | Kobilka et al. |
| 2016/0024209 A1 | 1/2016 | Ho et al. |
| 2016/0045626 A1 | 2/2016 | McBride et al. |
| 2016/0068613 A1 | 3/2016 | Regula et al. |
| 2016/0083450 A1 | 3/2016 | Wu et al. |
| 2016/0159894 A1 | 6/2016 | Hartmann et al. |
| 2016/0193335 A1 | 7/2016 | Tureci et al. |
| 2016/0194389 A1 | 7/2016 | Regula et al. |
| 2016/0219845 A1 | 8/2016 | Gaitanaris et al. |
| 2016/0272990 A1 | 9/2016 | Kovalic et al. |
| 2016/0280768 A1 | 9/2016 | Strome et al. |
| 2016/0282365 A1 | 9/2016 | Gaitanaris et al. |
| 2016/0347840 A1 | 12/2016 | Anderson et al. |
| 2016/0355570 A1 | 12/2016 | Strome et al. |
| 2016/0362473 A1* | 12/2016 | Wang .................. C07K 14/565 |
| 2016/0362474 A1* | 12/2016 | Wang .................... C07K 14/57 |
| 2017/0007727 A1 | 1/2017 | Goldenberg |
| 2017/0029507 A1 | 2/2017 | Ho et al. |
| 2017/0283442 A1 | 10/2017 | D'Souza et al. |
| 2018/0002393 A1 | 1/2018 | Bancel et al. |
| 2018/0051254 A1 | 2/2018 | Fricke et al. |
| 2018/0142210 A1 | 5/2018 | Delaney et al. |
| 2018/0162927 A1 | 6/2018 | Hawkins et al. |
| 2018/0221507 A1 | 8/2018 | Gudas et al. |
| 2018/0244749 A1 | 8/2018 | Swanson et al. |
| 2018/0256644 A1 | 9/2018 | Swanson et al. |
| 2018/0280551 A1 | 10/2018 | Rashidian et al. |
| 2018/0346605 A1* | 12/2018 | Chiu .................. C07K 16/46 |
| 2018/0355318 A1 | 12/2018 | Delaney et al. |
| 2019/0023790 A1 | 1/2019 | Giurleo et al. |
| 2019/0192691 A1 | 6/2019 | Barrett et al. |
| 2019/0241633 A1 | 8/2019 | Fotin-Mleczek et al. |
| 2019/0382487 A1 | 12/2019 | Ho et al. |
| 2019/0382488 A1 | 12/2019 | Ho et al. |
| 2020/0140550 A1 | 5/2020 | Ho |
| 2020/0157204 A1 | 5/2020 | Humphreys et al. |
| 2021/0371527 A1 | 12/2021 | Mascioni et al. |

FOREIGN PATENT DOCUMENTS

| | | |
|---|---|---|
| CN | 1854295 | 11/2006 |
| EP | 0 668 777 | 8/1995 |
| EP | 0 956 506 | 7/1996 |
| EP | 1 005 494 | 3/1997 |
| EP | 1 487 879 | 12/2004 |
| EP | 1 550 729 | 7/2005 |
| EP | 1 629 011 | 3/2006 |
| EP | 1 997 514 | 12/2008 |
| EP | 1 483 294 | 8/2010 |
| EP | 2 226 394 | 9/2010 |
| EP | 2 260 858 | 12/2010 |
| EP | 1 587 550 | 7/2011 |
| EP | 2 476 754 A1 | 7/2012 |
| EP | 2966085 | 1/2016 |
| EP | 2 117 604 | 7/2017 |
| EP | 3 266 465 | 1/2018 |
| JP | H02-501190 | 4/1990 |
| JP | H06-506362 | 7/1994 |
| JP | H08-500979 A | 2/1996 |
| JP | 2001-502922 A | 3/2001 |
| JP | 2003-504414 | 2/2003 |
| JP | 2003-530092 | 10/2003 |
| JP | 2007-14267 | 1/2007 |
| JP | 2008-528668 | 7/2008 |
| WO | WO 89/01974 | 3/1989 |
| WO | WO 1993/015199 | 8/1993 |
| WO | WO 1994/009820 | 5/1994 |
| WO | WO 95/22609 A2 | 8/1995 |
| WO | WO 1996/008570 | 3/1996 |
| WO | WO 1996/026272 | 8/1996 |
| WO | WO 97/035616 | 10/1997 |
| WO | WO 1997/035616 | 10/1997 |
| WO | WO 98/45332 | 10/1998 |
| WO | WO 1998/052975 | 11/1998 |
| WO | WO 99/15549 | 4/1999 |

(56) References Cited

FOREIGN PATENT DOCUMENTS

| | | |
|---|---|---|
| WO | WO 1999/056779 | 11/1999 |
| WO | WO 2000/014234 | 3/2000 |
| WO | WO 2001/005427 | 1/2001 |
| WO | WO 2001/009303 | 2/2001 |
| WO | WO 2001/082963 | 11/2001 |
| WO | WO 2002/022680 | 3/2002 |
| WO | WO 04/058298 | 7/2002 |
| WO | WO 2003/038098 | 5/2003 |
| WO | WO 2004/108158 | 12/2004 |
| WO | WO 2005/026334 | 3/2005 |
| WO | WO 2005/043165 | 5/2005 |
| WO | WO 2005/061547 | 7/2005 |
| WO | WO 2005/068616 | 7/2005 |
| WO | WO 2005/094882 | 10/2005 |
| WO | WO 07/009064 | 1/2007 |
| WO | WO 2007/064345 | 6/2007 |
| WO | WO 07/087673 | 8/2007 |
| WO | WO 2007/109321 | 9/2007 |
| WO | WO 2007/137117 | 11/2007 |
| WO | WO 2009/017823 | 2/2009 |
| WO | WO 2009/032949 | 3/2009 |
| WO | WO 2009/041613 | 4/2009 |
| WO | WO 2009/076099 | 6/2009 |
| WO | WO 2009/082443 | 7/2009 |
| WO | WO 2009/097128 | 8/2009 |
| WO | WO 2009/130575 | 10/2009 |
| WO | WO 2010/003108 | 1/2010 |
| WO | WO 2010/003118 | 1/2010 |
| WO | WO 2010/037397 | 4/2010 |
| WO | WO 2010/040105 | 4/2010 |
| WO | WO 2010/042904 | 4/2010 |
| WO | WO 2010/065578 | 6/2010 |
| WO | WO 2010/102195 | 9/2010 |
| WO | WO 10/136492 | 12/2010 |
| WO | WO 2011/000054 | 1/2011 |
| WO | WO 2011/056983 | 5/2011 |
| WO | WO 2011/069019 | 6/2011 |
| WO | WO 2011/075786 | 6/2011 |
| WO | WO 2011/090762 | 7/2011 |
| WO | WO 2011/096894 A2 | 8/2011 |
| WO | WO 2011/107480 A1 | 9/2011 |
| WO | WO 2011/109440 | 9/2011 |
| WO | WO 2012/022982 | 2/2012 |
| WO | WO 2012/143524 | 10/2012 |
| WO | WO 2013/020074 A2 | 2/2013 |
| WO | WO 13/072406 | 5/2013 |
| WO | WO 13/072415 | 5/2013 |
| WO | WO 20140/25828 | 2/2014 |
| WO | WO 14/164553 | 10/2014 |
| WO | WO 2015/107015 A1 | 7/2015 |
| WO | WO 2015/107025 A1 | 7/2015 |
| WO | WO 2015/107026 A1 | 7/2015 |
| WO | WO 2015/175357 A1 | 11/2015 |
| WO | WO 2016/016299 A1 | 2/2016 |
| WO | WO 2017/027325 A1 | 2/2017 |
| WO | WO 17/140735 | 8/2017 |
| WO | WO 2017/176769 | 10/2017 |
| WO | WO 17/186928 | 11/2017 |
| WO | WO 18/007258 | 1/2018 |
| WO | WO 18/053328 | 3/2018 |
| WO | WO 18/111973 | 6/2018 |
| WO | WO 18/134691 | 7/2018 |
| WO | WO 2018/147960 | 8/2018 |
| WO | WO 18/187215 | 10/2018 |
| WO | WO 18/209055 | 11/2018 |
| WO | WO 18/232188 | 12/2018 |
| WO | WO 19/012147 | 1/2019 |
| WO | WO 19/023148 | 1/2019 |
| WO | WO 19/032661 | 2/2019 |
| WO | WO 19/033043 | 2/2019 |
| WO | WO 19/040740 | 2/2019 |
| WO | WO 19/060750 | 3/2019 |
| WO | WO 19/161271 | 8/2019 |
| WO | WO 19/178218 | 9/2019 |
| WO | WO 20/069433 | 4/2020 |

OTHER PUBLICATIONS

Bander et al., "Targeting Metastatic Prostate Cancer with Radiolabeled Monoclonal Antibody J591 to the Extracellular Domain of Prostate Specific Membrane Antigen", The Journal of Urology, Nov. 2003, vol. 170, pp. 1717-1721.

Bander et al., "Phase I trial of 177 Lutetium-labeled J591, a monoclonal antibody to prostate-specific membrane antigen, in patients with androgen-independent prostate cancer," Journal of Clinical Oncology, Jul. 20, 2005, pp. 4591-4601, vol. 23, No. 21.

Batzer et al., Enhanced Evolutionary PCR Using Oligonuleotides with Inosine at the 3'—Terminus, E Nucleic Acid Res. 19:5081 (1991).

Chatenoud, L. and Bluestone, J.A. CD3-specific antibodies: a portal to the treatment of autoimmunity Nature Reviews Immunology 2007, 7: 622-632).

Liu et al., "Monoclonal antibodies to the extracellular domain of prostate-specific membrane antigen also react with tumor vascular endothelium", Cancer Research, vol. 57, pp. 3629-3634 (Sep. 1, 1997).

Milowsky et al., "Phase I Trial of yttrium-90-labeled anti-prostate-specific membrane antigen monoclonal antibody J591 for androgen-independent prostate cancer", Journal of Clinical Oncology, vol. 22 No. 13, pp. 2522-2531 (Jul. 1, 2004).

Milowsky et al., "Vascular targeted therapy with anti-prostate-specific membrane antigen monoclonal antibody J591 in advanced solid tumors", Journal of Clinical Oncology, vol. 25 No. 5, pp. 540-547 (Feb. 10, 2007).

Ohtsuka et al., An Alternative Approach to Dexoyoligonucleotides as Hybridization Probes by Insertion of Deoxyinosine at Ambiguous Codon Positions J. Biol. Chem. 260:2605-2608 (1985).

Olson et al., "Clinical trials of cancer therapies targeting prostate-specific membrane antigen", Reviews on Recent Clinical Trials, vol. 2, pp. 182-190 (2007).

Rossolini, G.M. et al., "Use of deoxyinosine-containing primers vs degenerate primers for polymerase chain reaction based on ambiguous sequence information," Molecular Cellular Probes, vol. 8, No. 2, pp. 91-98; 1994.

Saruta, M. et al., "Characterization of FOXP3+CD4+ regulatory T cells in Crohn's disease," Clinical Immunology, vol. 125, No. 3, pp. 281-290; 2007.

International Search Report and Written Opinion, dated Jan. 5, 2017, in International Application No. PCT/US2016/045580.

NCBI Predicted: Low Quality Protein: zinc finger protein 345-like [Microtus ochrogaster]; NCBI Reference Sequence: XP_013202654.1; Reference bears a date of Aug. 7, 2015, however, as this item refers to a webpage, it may have been available in some form at an earlier date; Accessed, downloaded, and printed on Dec. 19, 2017.

NCBI Predicted: zinc finger protein 135, partial [Erinaceus europaeus]; NCBI Reference Sequence: XP_016050621.1; Reference bears a date of Apr. 11, 2016, however, as this item refers to awebpage, it may have been available in some form at an earlier date; Accessed, downloaded, and printed on Dec. 19, 2017.

NCBI Predicted: mitochondria-eating protein [Parus major]; NCBI Reference Sequence: XP_015479149.1; Reference bears a date of Nov. 14, 2016; however, as this item refers to a webpage, it may have been available in some form at an earlier date; Accessed, downloaded, and printed on Dec. 20, 2017.

NCBI Predicted: uncharacterized protein C12orf60 homolog [Sarcophilus harrisii]; NCBI Reference Sequence: XP_012406148.1; Reference bears a date of May 15, 2015; however, as this item refers to a webpage, it may have been available in some form at an earlier date; Accessed, downloaded, and printed on Dec. 20, 2017.

NCBI Predicted; serpin B9 isoform X1 [Ovis aries]; NCBI Reference Sequence: XP_011956764.1; Reference bears a date of Dec. 17, 2015; however, as this item refers to a webpage, it may have been available in some form at an earlier date; Accessed, downloaded, and printed on Dec. 20, 2017.

NCBI Predicted: small proline-rich protein 2E [Sus scrota]; NCBI Reference Sequence: XP_005663482.1; Reference bears a date of May 13, 2017; however, as this item refers to a webpage, it may

(56) References Cited

OTHER PUBLICATIONS have been available in some form at an earlier date; Accessed, downloaded, and printed on Dec. 20, 2017.
NCBI Predicted: late cornified envelope-like proline-rich protein 1 [Vicugna pacos]; NCBI Reference Sequence: XP_006214801.1; Reference bears a date of Dec. 29, 2015; however, as this item refers to a webpage, it may have been available in some form at an earlier date; Accessed, downloaded, and printed on Dec. 20, 2017.
NCBI Predicted: late cornified envelope-like proline-rich protein 1 [Mus musculus]; NCBI Reference Sequence: NP_081318.1; Reference bears a date of Oct. 31, 2017; however, as this item refers to a webpage, it may have been available in some form at an earlier date; Accessed, downloaded, and printed on Dec. 20, 2017.
NCBI Predicted: late cornified envelope-like proline-rich protein 1 [Mesocricetus auratus]; NCBI Reference Sequence: XP_005080368.1; Reference bears a date of May 22, 2017; however, as this item refers to a webpage, it may have been available in some form at an earlier date; Accessed, downloaded, and printed on Dec. 20, 2017.
NCBI Predicted: late cornified envelope-like proline-rich protein 1 [Peromyscus maniculatus bairdii]; NCBI Reference Sequence: XP_006976519.1; Reference bears a date of Mar. 21, 2016; however, as this item refers to a webpage, it may have been available in some form at an earlier date; Accessed, downloaded, and printed on Dec. 20, 2017.
Predicted: late cornified envelope-like proline-rich protein 1 [Microtus ochrogaster]; NCBI Reference Sequence: XP_005367325.1; Reference bears a date of Aug. 7, 2015; however, as this item refers to a webpage, it may have been available in some form at an earlier date; Accessed, downloaded, and printed on Dec. 20, 2017.
NCBI Predicted: late cornified envelope-like proline-rich protein 1 [Erinaceus europaeus]; NCBI Reference Sequence: XP_007525458.1; Reference bears a date of Apr. 11, 2016; however, as this item refers to a webpage, it may have been available in some form at an earlier date; Accessed, downloaded, and printed on Dec. 20, 2017.
NCBI Predicted: late cornified envelope-like proline-rich protein 1 [Cricetulus griseus] NCBI Reference Sequence: XP_007650016.1; Reference bears a date of May 27, 2016; however, as this item refers to a webpage, it may have been available in some form at an earlier date; Accessed, downloaded, and printed on Dec. 20, 2017.
NCBI Predicted: late cornified envelope-like proline-rich protein 1 [Pteropus vampyrus]; NCBI Reference Sequence: XP_011379372.1; Reference bears a date of Feb. 23, 2015; however, as this item refers to a webpage, it may have been available in some form at an earlier date; Accessed, downloaded, and printed on Dec. 20, 2017.
NCBI Predicted: LIM domain only protein 7 [Astyanax mexicanus]; NCBI Reference Sequence: XP_015461938.1; Reference bears a date of Feb. 11, 2016; however, as this item refers to a webpage, it may have been available in some form at an earlier date; Accessed, downloaded, and printed on Dec. 20, 2017.
NCBI Predicted: galectin-7-like [Python bivittatus]; NCBI Reference Sequence: XP_007443107.1; Reference bears a date of Mar. 11, 2016; however, as this item refers to a webpage, it may have been available in some form at an earlier date; Accessed, downloaded, and printed on Dec. 21, 2017.
U.S. Appl. No. 09/147,142 (also published as 2002/0018749), filed Mar. 5, 1999, Hudson et al.
U.S. Appl. No. 10/367,956 (also published as 2004/0071690), filed Feb. 19, 2003, Hudson et al.
U.S. Appl. No. 10/690,990, Wu et al.
U.S. Appl. No. 11/692,643 (also published as 2008/0152586), filed Mar. 28, 2007, Hudson et al.
U.S. Appl. No. 11/939,422 (also published as 2009/0238755), filed Sep. 24, 2009, Bander.
U.S. Appl. No. 12/293,860 (also published as 2009/0311181), filed Sep. 22, 2008, Wu.
U.S. Appl. No. 12/363,678 (also published as 2009/0275081), filed Jan. 30, 2009, Barat et al.
U.S. Appl. No. 12/413,435 (also published as 2009/0202548), filed Mar. 27, 2009, Gudas.
U.S. Appl. No. 12/537,145 (also published as 2010/0069616), filed Aug. 6, 2009, Wu et al.
U.S. Appl. No. 12/676,348 (also published as 2010/0297004), filed Aug. 5, 2010, Wu.
U.S. Appl. No. 12/788,477, filed May 27, 2010, Wu et al.
U.S. Appl. No. 12/959,230 (also published as 2012/0144110), filed Dec. 2, 2010, Smith.
U.S. Appl. No. 12/959,340 (also published as 2011/0268656), filed Dec. 2, 2010, Ho.
U.S. Appl. No. 13/094,730 (also published as 2011/0262968), filed Apr. 26, 2011, Gudas.
U.S. Appl. No. 13/554,306 (also published as 2012/0283418), filed Jul. 20, 2012, Wu et al.
Adams et al., "Highly specific in vivo tumor targeting by monovalent and divalent forms of 741F8 anti-c-erbB-2 single-chain Fv," Cancer Res., Sep. 1, 1993, pp. 4026-4034, vol. 53, No. 17.
Albrecht et al., "Development of anti-MUC1 di-scFvs for molecular targeting of epithelial cancers, such as breast and prostate cancers," Dec. 2007, pp. 304-313, vol. 51, No. 4.
Al-Lazikani et al., "Standard conformations for the canonical structures of immunoglobulins", Journal of Molecular Biology, vol. 273, Issue 4, pp. 927-948, 1997.
Almagro et al., "Humanization of antibodies", Frontiers in Bioscience 13, Jan. 1, 2008, pp. 1619-1633.
Altschul et al., "Basic local alignment search tool", Journal of Molecular Biology, vol. 215, Issue 3, Oct. 5, 1990, pp. 403-410.
Altschul et al., "Gapped BLAST and PSI-BLAST: a new generation of protein database search programs", Nucleic Acids Research, 1997, vol. 25, No. 17 3389-3402.
Atwell et al., "scFv multimers of the anti-neuranminidase antibody NC10: length of the linker between VH and VL domains dictates precisely the transition between diabodies and triabodies," Protein Engineering, Jul. 1999, vol. 12, No. 7, pp. 597-604.
Ausubel et al., "Current protocols in molecular biology, vol. 1, cap. 2—Preparation and analysis of DNA. Phenol extraction and ethanol precipitation of DNA." by John Wiley & Sons, Inc. 2.1.1-2.1.3 (1995).
Baeuerle et al., "Bispecific T-Cell Engaging Antibodies for Cancer Therapy", Cancer Res (2009), vol. 69, pp. 4941-4944.
Barat et al., "Cys-Diabody Quantum Dot Conjugates (immunoQdots) for Cancer Marker Detection," Bioconjug. Chem., Aug. 19, 2009, pp. 1474-1481, vol. 20(8).
Brochet et al., "IMGT/V-QUEST: the highly customized and integrated system for IG and TR standardized V-J and V-D-J sequence analysis," Nucl. Acids Res, 36, W503-508, 2008.
Caldas et al., "Humanization of the Anti-CD18 Antibody 6.7: an unexpected effect of a framework residue in binding to antigen," Mol. Immunol. May 2003; 39 (15): 941-952.
Carmichael et al., "The crystal structure of an anti-CEA scFv diabody assembled from T84.66 scFvs in V(L)-to-V(H) orientation: Implications for diabody flexibility," J. Mol. Biol., Feb. 14, 2003, pp. 341-351, vol. 326, No. 2.
Carter et al., "Engineering antibodies for imaging and therapy", Curr. Opin. Biotechnol., Aug. 1997, vol. 8, No. 4, pp. 449-454.
Casset et al., "A Peptide Mimetic of an Anti-CD4 Monoclonal Antibody by Rational Design," Biochem. Biophys. Res. Commun. Jul. 18, 2003; 307 (1 ): 198-205.
Chaderjian et al., "Effect of Copper Sulfate on Performance of a Serum-Free CHO Cell Culture Process and the Level of Free Thiol in the Recombinant Antibody Expressed," Biotechnol. Prag. 2005, 21, 550-553 14/40744014/407440.
Chang et al., "Prostate-Specific Membrane Antigen is Produced in Tumor-Associated Neovasculature1," Clin. Cancer Res., Oct. 1999, pp. 2674-2681, vol. 5.
Chien et al., "Significant Structural and Functional Change of an Antigen-Bidning Site by a Distant Amino Acid Substitution: Proposal of a Structural Mechanism," Proc. Natl. Acad. Sci. USA. Jul. 1989; 86 (14): 5532-5536.
Chothia et al., "Canonical structures for the hypervariable regions of immunoglobulins", Journal of Molecular Biology, vol. 196, Issue 4, Aug. 20, 1987, pp. 901-917.
Chothia et al., "Conformations of immunoglobulin hypervariable regions", Nature, 342:878-883 (1989).

(56) References Cited

OTHER PUBLICATIONS

Chothia et al., "Structural repertoire of the human VH segments", Journal of Molecular Biology, vol. 227, Issue 3, Oct. 5, 1992, pp. 799-817.

Cipponi et al., "Tumor-infiltrating lymphocytes: apparently good for melanoma patients. But why?", Cancer Immunol Immunother, vol. 60, pp. 1153-1160, 2011.

City of Hope National Medical Center, "Anti-CEA antibody T84.66 humanized," Medical Imaging Law Weekly, copyright 2004, http://www.newsrx.com/newsletters/Medical-Imaging-Law-Weekly; dated for online publication Nov. 27, 2004.

Cole et al., "Monoclonal Antibodies and Cancer Therapy", pp. 77-96. Alan R. Liss, Inc., 1985.

Communication pursuant to Rules 70(2) and 70a(2) EPC dated Dec. 28, 2010, received in EP Appl. No. 08799192.3, 11 pages.

Communication pursuant to Article 94(3) EPC dated Aug. 26, 2014 in European Application No. 10835159.4.

Communication pursuant to Article 94(3) EPC dated Nov. 10, 2014 in European Application No. 10835159.4.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol. 2002; 169 (6): 3076-3084.

Deri et al., "PET Imagining with $^{89}$Zr: From Radiochemistry to the Clinic", Nucl Med Biol., vol. 40, No. 1, 27 pages, Jan. 2013.

Desplancq et al., "Multimerization behaviour of single chain Fv variants for the tumour-binding antibody B72.3," Protein Engineering, Aug. 1994, vol. 7, No. 8, pp. 1027-1033.

Extended European Search Report dated Aug. 1, 2016 in Application No. 14779573.6.

Extended European Search Report dated Aug. 29, 2016 in Application No. 13804247.8.

Extended European Search Report dated Jan. 18, 2017 in Application No. 16191132.6.

Fitzgerald et al., "Improved tumour targeting by disulphide stabilized diabodies expressed in Pichia pastoris," Protein Engineering, 1997, pp. 1221-1225, vol. 10, No. 10.

Galati et al., "Increased Resistance of Peptides to Serum Proteases by Modification of their Amino Groups", Z. Naturforsch, 58 c, pp. 558-561, 2003.

George et al., "Radiometal labeling of recombinant proteins by a genetically engineered minimal chelation site: technetium-99m coordination by single-chain Fv antibody fusion proteins through a C-terminal cysteinyl peptide," Proc. Natl. Acad. Sci. USA, Aug. 1995, vol. 92, No. 18, pp. 8358-8362.

Gillies et al., "Antigen Binding and Biological Activities of Engineered Mutant Chimeric Antibodies with Human Tumor Specificities," Hum Antibodies Hybridomas. 1990;1(1):47-54.

Giudicelli et al., "IMGT/LIGM-DB, the IMGT® comprehensive database of immunoglobulin and T cell receptor nucleotide sequences", Nucleic Acids Research, 2006, vol. 34, pp. D781-D784.

Giusti et al., "Somatic Diversification of S107 from an Antiphosphocholine to an anti-DNA Autoantibody is due to a Single Base Changes in its Heavy Chain Variable Region," Proc. Natl. Acad. Sci. USA. May 1987; 84 (9): 2926-2930).

Glockshuber et al., "A comparison of strategies to stabilize immunoglobulin Fv-fragments," Biochemistry, 1990, pp. 1362-1367, vol. 29, No. 6.

Goldsby et al., Immunology, 5th edition, 2002, Chapter 4 pp. 79-83.

Gu et al., "Biological activity and microPET imaging properties of chimeric and humanized anit-prostate stem cell antigen (PSCA) antibodies," Proc Amer Assoc Cancer Res., 2005, vol. 46, Abstract #696 [Retrieved on May 14, 2012], URL: http://aacrmeetingabstracts.org/cgi/content/abstract/2005/1/164-b.

Gussow et al. (Methods in Enzymology. 1991; 203: 99-121).

Harlow and Lane, "Using Antibodies", A Laboratory Manual, 1998, Cold Spring Harbo Laboratory, USA.

Haurum JS, "Recombinant polyclonal antibodies: the next generation of antibody therapeutics?", Drug Discovery Today, vol. 11, Nos. 13/14, Jul. 2006.

Henikoff et al., "Amino acid substitution matrices from protein blocks", Proc. Natl. Acad. Sci. USA, vol. 89, pp. 10915-10919, Nov. 1992.

Hollinger et al., ""Diabodies": Small bivalent and bispecific antibody fragments," Proc. Natl. Acad. Sci. USA, Jul. 1993, pp. 6444-6448, vol. 90.

Holm et al., "Functional Mapping and Single Chain Construction of the Anti-Cytokeratin 8 Monoclonal Antibody TS1," Mol. Immunol. Feb. 2007; 44 (6): 1075-1084).

Hopp et al., "A Computer Program for Predicting Protein Antigenic Determinants," Molecular Immunology, 1983, pp. 483-489, vol. 20 (4).

Hu et al., "Minibody: A Novel engineered anti-carcinoembryonic antigen antibody fragment (Single-Chain Fv-CH3) which exhibits rapid, high-level targeting of xenografts1", Cancer Research, vol. 56, pp. 3055-3061 (Jul. 1, 1996).

International Search Report and Written Opinion dated Nov. 15, 2013 in International Application No. PCT/US2013/045719.

International Search Report and Written Opinion dated Aug. 1, 2014 in Application No. PCT/US14/22782.

InvivoGen, "Engineering Fc regions for altered properties", retrieved using the WayBackMachine Internet Archive captured on Dec. 13, 2011 (with banner on top removed), 2011.

InvivoGen, "Engineering Fc regions for altered properties", retrieved using the WayBackMachine Internet Archive captured on Dec. 13, 2011 (including banner on top), 2011.

Issekutz et al. "Coexpression of Chemokine Receptors CCR5, CXCR3, and CCR4 and Ligands for P- and E-Selectin on T Lymphocytes of Patients With Juvenile Idiopathic Arthritis", Arthritis & Rheumatism, Nov. 2011, vol. 63, No. 11, pp. 3467-3476.

Janeway et al., Immunobiology, $5^{th}$ Ed., Garland Science, pp. 94-105 (2001).

Johnson et al., "Effector cell recruitment with novel Fv-based dual-affinity re-targeting protein leads to potent tumor cytolysis and in vivo B-cell depletion," J. Mol. Biol., Jun. 11, 2010, pp. 436-449, vol. 399, No. 3.

Jones et al., "Replacing the complementarity-determining regions in a human antibody with those from a mouse", Nature, vol. 321, pp. 522-525, May 29, 1986.

Kabat et al., "Sequences of Proteins of Immunological Interest", 5th ed., NIH Publication No. 91-3242, 1991.

Karlin et al., "Applications and statistics for multiple high-scoring segments in molecular sequences", Proc. Natl. Acad. Sci. USA, vol. 90, pp. 5873-5877, Jun. 1993.

Keymeulen et al., "Transient Epstein-Barr virus reactivation in CD3 monoclonal antibody-treated patients," Blood, vol. 115, No. 6, pp. 1145-1155, Feb. 11, 2010.

Kim et al., "Anti-CD30 diabody-drug conjugates with potent antitumor activity," Mol. Cancer Ther., Aug. 2008, pp. 2486-2497, vol. 7, No. 8.

Kjer-Nielsen et al., Crystal Structure of the Human T Cell Receptor CD3{epsilon}[gamma] Heterodimer Complexed to the therapeutic mAb OKT3, PNAS, 2004, vol. 101, No. 20, 7675-7680.

Klein et al., "Melan-A—specific Cytotoxic T Cells Are Associated with Tumor Regression and Autoimmunity Following Treatment with Anti-CTLA-4", Clin Cancer Res, vol. 15, No. 7, pp. 2507-2513, Apr. 1, 2009.

Köhler et al., "Continuous cultures of fused cells secreting antibody of predefined specificity", Nature, vol. 256, Issue 5517, pp. 495-497 (1975).

Kozbor et al., "The production of monoclonal antibodies from human lymphocytes", Immunology Today, vol. 4, Issue 3, Mar. 1983, pp. 72-79.

Kuby, "Immunology", 4th ed., Chapter 4. W.H. Freeman & Co., New York, 2000.

Kukis et al., "Effect of the extent of chelate substitution on the immunoreactivity and biodistribution of 2IT-BAT-Lym-1 immunoconjugates", Cancer Research, vol. 55, pp. 878-884 (Feb. 1, 1995).

(56) References Cited

OTHER PUBLICATIONS

Lefranc et al., "IMGT unique numbering for immunoglobulin and T cell receptor variable domains and Ig superfamily V-like domains", Developmental & Comparative Immunology, vol. 27, Issue 1, Jan. 2003, pp. 55-77.
Leung, S., "Engineering a unique glycosylation site for site-specific conjugation of haptens to antibody fragments," The Journal of Immunology, 1995, pp. 5919-5926, vol. 154.
Lewis et al., "An improved method for conjugating monoclonal antibodies with N-Hydroxysulfosuccinimidyl DOTA", Bioconjugate Chem, vol. 12, pp. 320-324 (2001).
Leyton et al., "Humanized radioiodinated minibody for imaging of prostate stem cell antigen-expressing tumors", Clinical Cancer Research, vol. 14 No. 22, pp. 7488-7496 (Nov. 15, 2008).
Li et al., "Improved biodistribution and radioimmunoimaging with poly(ethylene glycol)-DOTA-conjugated anti-CEA diabody," Bioconjug. Chem., Jan.-Feb. 2006, pp. 68-76, vol. 17, No. 1.
Li et al., "Mammalian Cell Expression of Dimeric Small Immune Proteins (SIP)," Protein Engineering vol. 10, No. 6 pp. 731-736, 1997.
Li et al., "Reduction of kidney uptake in radiometal labeled peptide linkers conjugated to recombinant antibody fragments, site-specific conjugation of DOTA-peptides to a Cys-diabody," Bioconjugate Chem., 2002, pp. 985-995, vol. 13, No. 5.
Liu et al., "Constitutive and antibody-induced internalization of prostate-specific membrane antigen", Cancer Research, vol. 58, pp. 4055-4060 (Sep. 1, 1998).
Liu et al., "Prostate-Specific Membrane Antigen Retargeted Measles Virotherapy for the Treatment of Prostate Cancer", Prostate, Jul. 1, 2009, vol. 69, No. 10, pp. 1128-1141.
Lo, B.K.C., "Antibody Humanization by CDR Grafting", Methods in Molecular Biology, vol. 248, pp. 135-159, 2004.
Lopes et al., Use of 99mTc-anti-CD3 Scintigraphy in the Differential Diagnosis of Rheumatic Diseases, Rheumatology 2010;49:933-939.
MacCallum et al., "Antibody-antigen Interactions: Contact Analysis and Binding Site Topography", Journal of Molecular Biology, vol. 262, Issue 5, Oct. 11, 1996, pp. 732-745.
Mariuzza et al., "The Structural Basics of Antigen-Antibody Recognition," Annu. Rev. Biophys. Biophys. Chem. 1987; 16: 139-159.
Marks et al., "By-Passing Immunization: Building High Affinity Human Antibodies by Chain Shuffling", Nature Biotechnology 10, 779-783 (1992).
Martin et al., "Modeling antibody hypervariable loops: A combined algorithm", Proc. Natl. Acad. Sci. USA, vol. 86, pp. 9268-9272, Dec. 1989.
Martin, A., "Chapter 3—Protein Sequence and Structure Analysis of Antibody Variable Domains", Antibody Engineering vol. 2 (2010), pp. 33-51.
Martins et al., "Monitoring Rheumatoid Arthristis Synovitis with $^{99m}$Tc-anti-CD3," Br J Radiol. Jan. 2008;81 (961 ):25-9. Feb. 11, 2010.
Marty et al., "Production of functionalized single-chain Fv antibody fragments binding to the ED-B domain of the B-isoform of fibronectin in Pichia pastoris," Protein Expression and Purification, Feb. 2001, vol. 21, Issue 1, pp. 156-164.
McCafferty et al., "Phage antibodies: filamentous phage displaying antibody variable domains", Nature 348, pp. 552-554, Dec. 6, 1990.
McCartney et al., "Engineering disulfide-linked single-chain Fv dimers [(sFv')2] with improved solution and targeting properties: Anti-digoxin 26-10 (sFv')2 and anti-c-erbB-2 741F8 (sFv')2 made by protein folding and bonded through C-terminal cysteinyl peptides," Protein Eng., Mar. 1995, pp. 301-314, vol. 8, No. 3.
McCartney et al., Refolding of single-chain Fv with C-terminal cysteine (sFv); formation of disulfide-bonded homodimers of antic-A£'r/7B-2 and anti-digoxin sFv', Miami Short Rep., 1993, vol. 3, p. 91.
Moore et al., "Application of dual affinity retargeting molecules to achieve optimal redirected T-cell killing B-cell lymphoma," Blood, Apr. 28, 2011, pp. 4542-4551, vol. 117, No. 17.

Morris et al., "Pilot trial of unlabeled and indium-111-labeled anti-prostate-specific membrane antigen antibody J591 for castrate metastatic prostate cancer", Clinical Cancer Research, vol. 11, pp. 7454-7461 (2005).
Nagengast et al., "VEGF-PET Imaging Is a Noninvasive Biomarker Showing Differential Changes in the Tumor during Sunitinib Treatment", Cancer Res, vol. 71, No. 1, pp. 143-153, Jan. 1, 2011.
Nanus et al., "Clinical Use of Monoclonal Antibody HuJ591 Therapy: Targeting Prostate Specific Membrane Antigen", The Journal of Urology, vol. 170, pp. S84-S89, Dec. 2003.
Needleman et al., "A general method applicable to the search for similarities in the amino acid sequence of two proteins", Journal of Molecular Biology, vol. 48, Issue 3, Mar. 28, 1970, pp. 443-453.
Neumaier et al., "Cloning of the genes for T84.66, and antibody that has a high specificity and affinity for carcinoembryonic antigen, and expression of chimeric human/mouse T84.66 genes in myeloma and Chinese hamster ovary cells," Cancer Research, 1990, vol. 50, pp. 2128-2134.
Notice of Allowance dated Jan. 30, 2014 in U.S. Appl. No. 12/959,340.
Notice of Allowance dated May 10, 2018 in U.S. Appl. No. 14/773,710.
O'Brien et al., "Humanization of Monoclonal Antibodies by CDR Grafting", PubMed, vol. 207, pp. 81-100, 2003.
Office Action dated Jun. 24, 2013 in Chinese Application No. 201080062988.4 (with English Translation).
Office Action dated Feb. 4, 2013 in U.S. Appl. No. 12/959,340.
Office Action dated Apr. 24, 2013 in Russian Application No. 2012123550/20 (035853) (English Translation).
Office Action dated Oct. 18, 2013 in U.S. Appl. No. 12/959,340.
Office Action dated Jan. 30, 2014 in Chinese Application No. 201080062988.4 with English Translation.
Office Action dated Mar. 5, 2014 in European Application No. 10835159.4.
Office Action dated Jul. 7, 2014 in Chinese Application No. 201080062988.4 with English Translation.
Office Action dated Oct. 23, 2014 in Chinese Application No. 201080062988.4 with English Translation.
Office Action dated Dec. 8, 2014 in Mexican Application No. MX/a/2012/006301 with English Translation.
Office Action dated Dec. 9, 2014 in Russian Application No. 2012123550 with English Translation.
Office Action dated Jan. 8, 2015 in Australian Application No. 2010325969.
Office Action dated Feb. 23, 2015 in Japanese Application No. 2012-542204 with English translation.
Office Action dated Mar. 13, 2015 in Mexican Application No. MX/a/2012/006301 with English translation.
Office Action dated May 7, 2015 in Russian Application No. 2012123550 with English Translation.
Office Action dated Jul. 24, 2015 in U.S. Appl. No. 14/202,999.
Office Action dated Jul. 28, 2015 in U.S. Appl. No. 14/407,440.
Office Action dated Oct. 26, 2015, received in Japanese Patent Application No. 2012-542204 (with English translation).
Office Action dated Feb. 22, 2016 in U.S. Appl. No. 14/407,440.
Office Action dated Mar. 7, 2016 in U.S. Appl. No. 14/202,999.
Office Action dated Aug. 4, 2016 in Russian Application No. 2012123550 with English Translation.
Office Action dated Sep. 5, 2016 in Mexican Application No. MX/a/2016/003128 with summary translation.
Office Action dated Sep. 14, 2016 in U.S. Appl. No. 14/407,440.
Office Action dated Oct. 27, 2016 in Canadian Application No. 2,782,333.
Office Action dated Nov. 16, 2016 in Mexican Application No. MX/a/2016/003128 with summary English Translation.
Office Action dated Dec. 23, 2016 in Russian Application No. 2012123550 with English Translation.
Office Action dated Jan. 4, 2017 in Japanese Application No. 2016-34045 with English Translation.
Office Action dated Jan. 4, 2017 in U.S. Appl. No. 14/773,710.
Office Action dated Mar. 9, 2017 in U.S. Appl. No. 14/407,440.
Office Action dated Mar. 15, 2017 in Chinese Patent App. No. 201480024657.X, with English Translation.

(56) References Cited

OTHER PUBLICATIONS

Office Action dated Mar. 27, 2017 in Japanese Application No. 2012-542204 with English Translation.
Office Action dated May 19, 2017 in U.S. Appl. No. 14/773,710.
Office Action dated Jun. 9, 2017 in Mexican Application No. MX/a/2016/003128 with summary English Translation.
Office Action dated Aug. 29, 2017 in European Application No. 13804247.8.
Office Action dated Nov. 1, 2017 in Canadian Application No. 2782333.
Office Action dated Nov. 1, 2017 in U.S. Appl. No. 14/407,440.
Office Action dated Nov. 22, 2017 in U.S. Appl. No. 14/773,710.
Office Action dated Dec. 13, 2017 in European App. No. 14 779 573.6.
Office Action dated Dec. 28, 2017 in Chinese App. No. 201510333807.1.
Office Action dated Dec. 20, 2017 in European Application No. 16191132.6.
Office Action dated Jan. 4, 2018 in Australian App. No. 2014249243.
Office Action dated Feb. 23, 2018 in Chinese Patent App. No. 201480024657X, with English translation.
Office Action dated Feb. 6, 2018 in Japanese Patent App. No. 2016-501063, with English translation.
Office Action dated Mar. 6, 2018 in Indian Patent App. No. 5792/DELNP/2012.
Office Action dated Mar. 13, 2018 in U.S. Appl. No. 14/407,440.
Office Action dated Aug. 24, 2012 in U.S. Appl. No. 12/788,477, filed May 27, 2012 in 22 pages.
Olafsen et al., "Antibody Vectors for Imaging", Seminars in Nuclear Medicine, vol. 40, No. 3, pp. 167-181, May 1, 2010.
Olafsen et al., "Chapter 6—Generation of Single-Chain Fv Fragments and Multivalent Derivatives scFv-Fc and scFv-CH3 (Minibodies)", Antibody Engineering vol. 2 (2010), pp. 69-84.
Olafsen et al., "Characterization of engineered anti-p185 HER-2 (scFv-CH3)2 antibody fragments (minibodies) for tumor targeting", Protein Engineering, Design & Selection, vol. 17 No. 4, pp. 315-323, Oxford University Press (2004).
Olafsen et al., "Covalent disulfide-linked anti-CEA diabody allows site-specific conjugation and radiolabeling for tumor targeting applications," Protein Eng. Des. Sel., Jan. 2004, pp. 21-27, vol. 17, No. 1.
Olafsen, T. et al., "Development and clinical translation of 89Zr-Df-IAB22M2C for detecting CD8+ T Cells for immunotherapy applications," Abstract # 442 presented at the 31$^{st}$ Annual Meeting and Associated Programs of the Society of Immunotherapy of Cancer (SITC 2016), The abstract and corresponding poster are provided in 13 pages. Nov. 11-13, 2016.
Olafsen et al., "ImmunoPET imaging of B-cell lymphoma using 124I-anti-CD20 scFv dimers (diabodies)," Protein Eng. Des. Sel., Apr. 2010, pp. 243-249, vol. 23, No. 4.
Olafsen, T. et al., "Pet imaging of cytotoxic human T cells using an 89Zr-labeled anti-CD8 minibody," Abstract # P338 presented at the 30$^{th}$ Annual Meeting and Associated Programs of the Society for Immunotherapy of Cancer (SITC 2015), The abstract and corresponding poster are provided in 12 pages. Nov. 4-8, 2015.
Olafsen et al., "Recombinant anti-CD20 antibody fragments for small-animal PET imaging of B-Cell lymphomas", The Journal of Nuclear Medicine, vol. 50 No. 9, pp. 1500-1508 (Sep. 2009).
Olafsen et al., "Tunable pharmacokinetics: modifying the in vivo half-life of antibodies by directed mutagenesis of the Fc fragment", Nature Protocols, vol. 1 No. 4, pp. 2048-2060 (2006).
Overwijk et al., "Tumor Regression and Autoimmunity after Reversal of a Functionally Tolerant State of Self-reactive CD8+ T Cells", The Journal of Experimental Medicine, vol. 198, No. 4, pp. 569-580, Aug. 18, 2003.
Padlan, Eduardo, "Anatomy of the Antibody Molecule," Mol Immunol. Feb. 1994;31 (3):169-217.
Pandit-Taskar, Neeta First-in-Human Imaging with Zr-Df-IAB2M Anti-PSMA Minibody in Patients with Metastatic Prostate Cancer: Pharmacokinetics, Biodistribution, Dosimetry, and Lesion Uptake, The Journal of Nuclear Medicine, vol. 57, No. 12, pp. 1858-1864, Dec. 2016.
Paul, Fundamental Immunology, 3d ed. (1993), Raven Press, Ltd. New York.
Pearson et al., "Improved tools for biological sequence comparison", Proc. Nat'l. Acad. Sci. USA, vol. 85, pp. 2444-2448, Apr. 1988.
Peng et al., "PD-1 Blockade Enhances T-cell Migration to Tumors by Elevating IFN-γ Inducible Chemokines", Cancer Res, vol. 72, No. 20, pp. 5209-5218, Oct. 15, 2012.
Preliminary Amendment filed on Dec. 21, 2011 in U.S. Appl. No. 12/788,477 (Filing Date: May 27, 2012) in 9 pages.
Presta, "Antibody engineering", Current Opinion in Biotechnology, vol. 3, Issue 4, Aug. 1992, pp. 394-398.
Raag et al., "Single-chain Fvs." FASEB J., Jan. 1995, vol. 9, No. 1, pp. 73-80.
Remington, "The Science and Practice of Pharmacy 21st Edition", Pharmaceutical Press, London, Reprinted 2011, Copyrights 1889-2006.
Restriction Requirement dated Aug. 7, 2012 in U.S. Appl. No. 12/959,340.
Riechmann et al., "Reshaping human antibodies for therapy", Nature, vol. 332, pp. 323-327, Mar. 1988.
Rudikoff et al., "Singe Amino Acid Substitution Altering Antigen-Binding Specificity," Proc. Natl. Acad. Sci. USA, Marcy 1982, pp. 1979-1983, vol. 79.
Sharon et al., "Recombinant polyclonal antibodies for cancer therapy",J Cell Biochem., Oct. 1, 2005, vol. 96, No. 2, pp. 305-313.
Sirk et al., "Site-specific, thiol-mediated conjugation of fluorescent probes to cysteine-modified diabodies targeting CD20 or HER2," Dec. 2008, pp. 2527-2534, vol. 19, No. 12.
Slovin, "Targeting novel antigens for prostate cancer treatment: focus on prostate-specific membrane antigen", NIH Public Access: Author Manuscript, Expert Opinon Ther Targets, vol. 9 No. 3, pp. 561-570 (Jun. 2005).
Smith and Waterman, "Comparison of Biosequences", Adv. Appl. Math., 2, pp. 482-489, 1981.
Stimmel et al., Site-specific conjugation on serine → Cysteine variant monoclonal antibodies, The Journal of Biological Chemistry, Sep. 29, 2000, pp. 30445-30450, vol. 275, No. 39.
Summons to attend oral proceedings dated Jul. 10, 2015 in European Patent Application No. 10835159.4.
Supplementary Partial Search Report dated May 3, 2016 in European Application No. 13804247.8.
Tai et al., "Targeting c-erbB-2 expressing tumors using single-chain Fv monomers and dimers," Cancer Res., Dec. 1, 1995, pp. 5983s-5989s, vol. 55, No. 23 Suppl.
Tavare, "Engineered Anti-Murine CD8 Minibody Fragment for Cu-64 ImmunoPET Imaging of CD8 Expression in Vivo", IBC's 23$^{rd}$ Annual International Conference, Diagnostic Antibody Engineering, Abstract No. F3. 02-06, Dec. 2012, San Diego, CA.
Urva et al., "Physiologically based pharmacokinetic (PBPK) model for T.84.66, a monoclonal anti-CEA antibody," Am. Assoc. Pharm. Sci. 10 (Supp. 2), 2008, pp. 957.
Vaidyanathan et al., "Evaluation of an anti-p. 185HER2 (scFv-CH2-CH2)2 fragment following radioiodination using two different residualizing labels: SGMIB and IB-Mal-D-GEEEK*," Nuclear Medicine and Biology, 2009, pp. 671-680, vol. 36.
Vajdos et al., "Comprehensive Functional Maps of the Antigen-binding Site of an Anti-ErbB2 Antibody Obtained with Shotgun Scanning Mutagenesis", J. Mol. Biol. (2002), vol. 320, pp. 415-428.
Verhaar et al., "Technetium-99m radiolabeling using a phage-derived single-chain Fv with a C-terminal cysteine," The Journal of Nuclear Medicine, May 1996, pp. 868-872, vol. 37, No. 5.
Verhoeyen et al., Reshaping Human Antibodies: Grafting an Antilysozyme Activity, Science, 239:1534-1536, 1988.
Veri et al., "Therapeutic control of B cell activation via recruitment of Fcgamma receptor IIb (CD32B) inhibitory function with a novel bispecific antibody scaffold," Arthritis Rheum., Jul. 2010, pp. 1933-1943, vol. 62, No. 7.
Viola-Villegas et al., "Noninvasive Imaging of PSMA in Prostate Tumors with 89 Zr-Labeled huJ591 Engineered Antibody Frag-

(56) References Cited

OTHER PUBLICATIONS ments: The Faster Alternatives", Molecular Pharmaceutics, vol. 11, No. 11, pp. 3965-3973, Nov. 2014.

Vosjan et al., Nanobodies Targeting the Hepatocyte Growth Factor: Potential New Drugs for Molecular Cancer Therapy, Mol Cancer Ther, vol. 11, No. 4, pp. 1017-1025, Apr. 2012.

Wahlin et al., "CD8+ T-Cell Content in Diagnostic Lymph Nodes Measured by Flow Cytometry Is a Predictor of Survival in Follicular Lymphoma", Clin Cancer Res (2007), vol. 13, No. 2.

Wang, S., "Advances in the production of human monoclonal antibodies", Antibody Technology Journal, vol. 1, pp. 1-4, 2011.

Whitlow et al., "Multivalent Fvs: characterization of single-chain Fv oligomers and preparation of a bispecific Fv," Protein Engineering, Aug. 1994, vol. 7, No. 8, pp. 1017-1026.

Winkler et al., Changing the Antigen Binding Specificity by Single Point Mutations of an Anti-p24 (HIV-1) Antibody, J. Immunol. Oct. 15, 2000; 165 (8): 4505-4514.

Wong et al., "Pilot trial evaluating an 123I-Labeled 80-Kilodalton engineered anticarcinoembryonic antigen antibody fragment (cT84.66 minibody) in patients with colorectal cancer", Clinical Cancer Research, vol. 10, pp. 5014-5021 (Aug. 1, 2004).

International Search Report and Written Opinion dated Mar. 21, 2012 for International Application No. PCT/US2010/058803, filed Dec. 2, 2010.

Written Opinion dated Apr. 22, 2009, from Int'l Appl. No. PCT/US2008/075291 (WO 2009/032949).

Written Opinion dated Apr. 23, 2008, from Int'l Appl. No. PCT/US2007/007020 (WO 2007/109321).

Wu et al., "An analysis of the sequences of the variable regions of Bence Jones proteins and myeloma light chains and their implications for antibody complementarity", J. Exp. Med. vol. 132, pp. 211-250, 1970.

Wu et al., "Antibodies and antimatter: The Resurgence of Immuno-PET", The Journal of Nuclear Medicine, vol. 50 No. 1, pp. 2-5 (Jan. 2009).

Wu et al, "Antibodies for molecular imaging of cancer", The Cancer Journal, vol. 14 No. 3, pp. 191-197 (May/Jun. 2008).

Wu et al., "Anti-carcinoembryonic antigen (CEA) diabody for rapid tumor targeting and imaging," Tumor Targeting, 1999, pp. 47-58, vol. 4.

Wu et al., "Arming antibodies: prospects and challenges for immunoconjugates", Nature Biotechnology, vol. 23 No. 9, pp. 1137-1146 (Sep. 2005).

Wu et al., "High-resolution microPET imaging of carcinoembryonic antigen-positive xenografts by using a copper-64-labeled engineered antibody fragment," Proc. Natl. Acad. Sci. USA, 2000, pp. 8495-8500, vol. 97, No. 15.

Wu et al., "Humanization of a Murine Monoclonal Antibody by Simultaneous Optimization of Framework and CDR Residues," J. Mol. Biol. Nov. 19, 1999; 294 (1): 151-162.

Wu et al., "Tumor localization of anti-CEA single-chain Fvs: Improved targeting by non-convalent dimmers," Immunotechnology, 1996, pp. 21-36, vol. 2.

Yamaguchi et al., "Development of a Sensitive Screening Method for Selecting Monoclonal Antibodies to be Internalized by Cells," Biochem. Biophys. Res. Commun. Nov. 1, 2014; 454 (4): 600-603.

Yazaki et al., "Mammalian expression and hollow fiber bioreactor production of recombinant anti-CEA diabody and minibody for clinical applications," Journal of Immunological Methods, 2001, pp. 195-208, vol. 253.

Yazaki et al., "Tumor targeting of radiometal labeled anti-CEA recombinant T84.66 diabody and T84.66 minibody: Comparison to radioiodinated fragments," Bioconjugate Chem., 2001, pp. 220-228, vol. 12.

You et al., "Expression, purification, and characterization of a two domain carcinoembryonic antigen minigene (N-A3) in pichia pastoris the essential role of the N-domain," Anticancer Research, 1998, pp. 3193-3202, vol. 18.

Zhou et al., "T-cell receptor gene transfer exclusively to human CD8+cells enhances tumor cell killing", Blood, Nov. 22, 2012, vol. 120, No. 22, pp. 4334-4342 and Supplemental pp. 1-6.

File History, U.S. Appl. No. 08/256,156, filed Jun. 24, 1994.
File History, U.S. Appl. No. 08/838,682, filed Apr. 9, 1997.
File History, U.S. Appl. No. 08/895,914, filed Jul. 17, 1997.
File History, U.S. Appl. No. 09/357,707, filed Jul. 20, 1999.
File History, U.S. Appl. No. 09/357,708, filed Jul. 20, 1999.
File History, U.S. Appl. No. 09/357,709, filed Jul. 20, 1999.
File History, U.S. Appl. No. 09/929,546, filed Aug. 13, 2001.
File History, U.S. Appl. No. 09/357,704, filed Jul. 20, 1999.
File History, U.S. Appl. No. 10/160,505, filed May 30, 2002.
File History, U.S. Appl. No. 10/449,379, filed May 30, 2003.
File History, U.S. Appl. No. 10/690,990, filed Oct. 23, 2003.
File History, U.S. Appl. No. 11/219,563, filed Sep. 2, 2005.
File History, U.S. Appl. No. 11/218,813, filed Sep. 2, 2005.
File History, U.S. Appl. No. 12/293,860, filed Sep. 22, 2008.
File History, U.S. Appl. No. 12/363,678, filed Jan. 30, 2009.
File History, U.S. Appl. No. 12/371,399, filed Feb. 13, 2009.
File History, U.S. Appl. No. 12/537,145, filed Aug. 6, 2009.
File History, U.S. Appl. No. 12/676,348, filed Aug. 5, 2010.
File History, U.S. Appl. No. 12/788,477, filed May 27, 2010.
File History, U.S. Appl. No. 12/959,340, filed Dec. 2, 2010.
File History, U.S. Appl. No. 13/554,306, filed Jul. 20, 2012.

Office Action dated Apr. 1, 2019 in Japanese Patent Application No. 2018-526609.

Notice of Allowance dated Mar. 27, 2019 in U.S. Appl. No. 15/230,085.

Notice of Allowance dated Mar. 27, 2019 in U.S. Appl. No. 14/773,710.

Extended European Search Report dated Apr. 26, 2019 in European Patent Application No. 16835664.0.

Schaefer, J. et al., Chapter 7: Miniantibodies in Knotermann & Duebel Antibody Engineering, vol. 2, pp. 85-100, (2010).

Examination Report dated May 28, 2019 in New Zealand Patent Application No. 739721.

Office Action dated Apr. 16, 2019 in European App. No. 14 779 573.6.

Office Action dated May 7, 2019 in Japanese Patent Application No. 2016-501063 with English Translation.

Office Action dated Jul. 11, 2019 in Russian Patent Application No. 2018105374 with English Translation.

Aarntzen E.H. et al., Early identification of antigen-specific immune responses in vivo by [18F]-labeled 3'-fluoro-3'-deoxy-thymidine ([18F]FLT) PET imaging. Proc Natl Acad Sci US A. Nov. 8, 2011:108(45):18396-1839.

Adlersberg, J.,. The immunoglobulin hinge (interdomain) region., Ric Clin Lab, vol. 6, No. 3. pp. 191-205, (1976).

Ali, N., Flutter, B., Sanchez Rodriguez, R., Sharif-Paghaleh, E., Barber, L. D., Lombardi, G., & Nestle, F. O. (2012). Xenogeneic graft-versus-host-disease in NOD-scid IL2Rgammanull mice display a T-effector memory phenotype. PLoS One, 7(8), e44219. doi:10.1371/journal.pone.0044219.

Asano R et al.: Humanization of the bispecific epidermal growth factor receptor x CD3 diabody and its efficacy as a potential clinical reagent, Clinical Cancer Research, vol. 12, No. 13, pp. 4036-4042, (2006).

Basu S. et al., Positron emission tomography as a diagnostic tool in infection: present role and future possibilities. Semin Nucl Med. Jan. 2009;39(1):36-51.

Boerman and Oyen, Immuno-PET of Cancer: A Revival of Antibody Imaging, J. Nucl Med. 52(8) 1171-2.) , 2011.

Brahmer, J. et al., (2012), Safety and activity of anti-PD-L1 antibody in patients with advanced cancer. N Engl J Med, 366(26), 2455-2465. doi:10.1056/NEJMoa1200694.

Brezski et al., The in vitro resistance of IgG2 to proteolytic attack concurs with a comparative paucity of autoantibodies against peptide analogs of the IgG2 hinge. MAbs. 3: 558-567, 2011.

Chen et al Analysis of Immune Signatures in Longitudinal Tumor Samples Yields Insight into Biomarkers of Response and Mechanisms of Resistance to Immune Checkpoint Blockade Cancer Discovery Cancer Discov 2016;6:827-837. Published OnlineFirst Jun. 14, 2016.

(56) References Cited

OTHER PUBLICATIONS

Clemente CG, Mihm MC Jr, Bufalino R, Zurrida S, Collini P, Cascinelli N. Prognostic value of tumor infiltrating lymphocytes in the vertical growth phase of primary cutaneous melanoma, Cancer 1996;77:1303-1310.
Devine, L., & Kavathas, P. B. (1999). Molecular analysis of protein interactions mediating the function of the cell surface protein CD8. Immunol Res, 19(2-3), 201-210. doi:10.1007/bf02786488.
Eisenhauer, E. A., et al. (2009). New response evaluation criteria in solid tumours: revised RECIST guideline (version 1.1). Eur J Cancer, 45(2), 228-247. doi:10.1016/j.ejca.2008.10.026.
Elzinga E.H. et al., 2-Deoxy-2-[F-18]fluoro-D-glucose joint uptake on positron emission tomography images: rheumatoid arthritis versus osteoarthritis. Mal Imaging Biol. Nov.-Dec. 2007;9(6):357-360.
Feng Z., et al., Multispectral imaging of formalin fixed tissue predicts ability to generate tumor-infiltration lymphocytes from melanoma. Journal for Immunotherapy of Cancer (2015) 3: 47, doi: 10.1186/s40425-015-0091-z.
First Examination Report dated Oct. 10, 2018 in New Zealand Patent Application No. 739721.
Final Office Action dated Aug. 1, 2018 in U.S. Appl. No. 14/407,440.
Fukunaga A, Miyamoto M, Cho Y, Murakami S, Kawarada Y, Oshikiri T, et al. (2004) CD8+ tumor-infiltrating lymphocytes together with CD4+ tumor-infiltrating lymphocytes and dendritic cells improve the prognosis of patients with pancreatic adenocarcinoma. Pancreas 28:e26-e31.
Galon J, Costes A, Sanchez-Cabo F, Kirilovsky A, Mlecnik B, Lagorce-Pagès C, et al. Type, density, and location of immune cells within human colorectal tumors predict clinical outcome. Science 2006;313:1960-1964.
Garon E.B., Rizvi N.A., Hui R., Leighl N., Balmanoukian A.S., Eder J.P. Gandhi, L. et al. Pembrolizumab for the Treatment of Non-Small-Cell Lung Cancer. N Engl J Med, 372(21), 2018-28.
Glaser, S. et al., Novel Antibody Hinge Regions for Efficient Production of CH2 Domain-deleted Antibodies, Joural of Biloogical Chemistyr, vol. 280, pp. 41494-41503, (2005).
Hamanishi J, Mandai M, Iwasaki M, Okazaki T, Tanaka Y, Yamaguchi K, et al. Programmed cell death I ligand 1 and tumor-infiltrating CD8+ T lymphocytes are prognostic factors of human ovarian cancer. Proc. Natl Acad. Sci. USA 2007;104:3360-3365.
Hiraoka N, Onozato K, Kosuge T, Hirohashi S. Prevalence of FOXP3+ regulatory T cells increases during the progression of pancreatic ductal adenocarcinoma and its premalignant lesions. Clin. Cancer Res. 2006;12:5423-5434.
Hodi, F. S., O'Day, S. J., McDermott, D. F., Weber, R. W., Sosman, J. A., Haanen, J. B., . . . Urba, W. J. (2010). Improved survival with ipilimumab in patients with metastatic melanoma. N Engl J Med, 363(8), 711-723.doi:10.1056/NEJMoa1003466.
Hoffman et al., Simple and rapid measurement of human T lymphocytes and their subclasses in peripheral blood. Proc Natl Acad Sci U S A, 77: 4914-7, 1980.
International Search Report dated Oct. 14, 2013 in International Application No. PCT/US2013/053862.
International Search Report and Written Opinion, dated May 15, 2018, in International Application No. PCT/US2018/013117.
Jochems, C. & Schlom, J. (2011). Tumor-infiltrating immune cells and prognosis: the potential link between conventional cancer therapy and immunity. Exp Biol Med (Maywood), 236(5), 567-579.
Juweid M.E.et al., Positron-emission tomography and assessment of cancer therapy. N Engl J Med. Feb. 2, 2006;354(5):496-507.
Karja V, Aaltomaa S, Lipponen P, Isotalo P, Talja M, Mokka R, et al. Tumour-infiltrating lymphocytes: a prognostic factor of PSA-free survival in patients with local prostate carcinoma treated by radical prostatectomy. Anticancer Res. 2005;25:4435-4438.
Knappik, et al. "Fully synthetic human combinatorial antibody libraries (HuCAL) based on modular consensus frameworks and CDRs randomized with trinucleotides", J.Mol. Biol., vol. 296, Issue 1, pp. 57-86 (2000).
Knowles S.M. et al., Advances in immuno-positron emission tomography: antibodies for molecular imaging in oncology. J Clin Oneal. Nov. 1, 2012;30(31):3884-3892 Knowles S.M. et al., Advances in immuno-positron emission tomography: antibodies for molecular imaging in oncology. J Clin Oneal, Nov. 1, 2012;30(31):3884-3892.
Koya R.C. et al., Kinetic phases of distribution and tumor targeting by T cell receptor engineered lymphocytes inducing robust antitumor responses. Proc Natl Acad Sci USA. Aug. 10, 2010;107(32):14286-14291.
Laing R.E. et al., Visualizing cancer and immune cell function with metabolic positron emission tomography, Curr Opin Genet Dev, Feb. 2010;20(1): 100-105.
Le Gall F et al.: Immunosuppressive properties of anti-CD3 single-chain Fv and diabody, Journal of Immunological Meth, vol. 285, No. 1,pp. 111-127, (2004).
Liu S, Lachapelle J, Leung S, Gao D, Foulkes WD, Nielsen TO. CD8+ lymphocyte infiltration is an independent favorable prognostic indicator in basal-like breast cancer. Breast Cancer Res. Mar. 15, 2012;14(2).
Mackensen A. Ferradini L, Carcelain G, Triebel F, Faure F. Evidence for in situ amplification of cytotoxic T-lymphocytes with antitumor activity in a human regressive melanoma. Cancer Res. 1993;53:3569-3573.
Mahmoud, S. M., Paish, E. C., Powe, D. G., Macmillan, R. D., Grainge, M. J., Lee, A. H., Ellis, I. O. & Green, A. R. (2011). Tumor-infiltrating CD8+ lymphocytes predict clinical outcome in breast cancer. J Clin Oncol., 29(15), 1949-1955.
Mahmoud S, Lee A, Ellis IGreen A. CD8+ T lymphocytes infiltrating breast cancer: A promising new prognostic marker? Oncoimmunology. May 1, 2012; 1(3):364-365.
Malviya, et al Targeting T and B lymphocytes with radiolabelled antibodies for diagnostic and herapeutic applications, Journal of Nuclear Medicine and Molecular Imagining, (2014.
Mamede M. et al., Differential uptake of (18)F-fluorodeoxyglucose by experimental tumors xenografted into immunocompetent and immunodeficient mice and the effect of immunomodification. Neoplasia. Mar.-Apr. 2003;5(2): 179-183.
Massoud T. et al. Molecular Imaging in Living Subjects: Seeing Fundamental Biological Processes in a New Light, Genes Dev, vol. 17, No. 5, pp. 545-580, (2003).
Matsui K. et al., Quantitation and visualization of tumor-specific cells in the secondary lymphoid organs during and after tumor elimination by PET. Nucl Med Biol. Nov. 2004;31(8): 1021-1031.
McCracken et al. Advances in PET Detection of the Antitumor T Cell Response, Adv Immunol vol. 131, (2016).
McDevitt, M. et al. An Particle Emmitting Antibody for Radioimmunotherapy of Prostate Acnecer, Cancer Research, vol. 60, pp. 6095-6100, (2000).
Mellman, I., Coukos, G., & Dranoff, G. (2011). Cancer immunotherapy comes of age. Nature, 480(7378), 480-489. doi:10.1038/nature10673.
Mlecnik B, Tosolini M, Kirilovsky A, Berger A, Bindea G, Meatchi T, et al. Histopathologio-based prognostic factors of colorectal cancers are associated with the state of the local immune reaction. J Clin Oncol. Feb. 20, 2011; 29(6).
Moebius, U., Kober, G., Griscelli, A. L., Hercend, T., & Meuer, S. C. (1991). Expression of different CD8 isoforms on distinct human lymphocyte subpopulations. Eur J Immunol, 21(8), 1793-1800. doi:10.1002/eji.1830210803.
Nair-Gill E.D. et al., Non-invasive imaging of adaptive immunity using positron emission tomography. Immunol Rev. Feb. 2008;221:214-228.
Nair-Gill E. et al., PET probes for distinct metabolic pathways have different cell specificities during immune responses in mice. J Clin Invest. Jun. 2010;120(6):2005-2015.
Nakano O, Sato M, Naito Y, Suzuki K, Orikasa S, Aizawa M, et al. Proliferative activity of intratumoral CD8(+) T-lymphocytes as a prognostic factor in human renal cell carcinoma: Clinicopathologic demonstration of antitumor immunity. Cancer Res. 2001;61:5132-5136.
Nakakubo Y, Miyamoto M, Cho Y, Hida Y, Oshikiri T, Suzuoki M, et al. Clinical significance of immune cell infiltration within gallbladder cancer. Br. J. Cancer 2003;89:1736-1742.

(56) References Cited

OTHER PUBLICATIONS

Notice of Allowance dated Sep. 17, 2018 in U.S. Appl. No. 14/773,710.
Notice of Allowance dated Jun. 25, 2018 in U.S. Appl. No. 15/230,085.
Notice of Allowance dated Sep. 24, 2018 in U.S. Appl. No. 15/230,085.
Notice of Allowance dated Jan. 3, 2019 in U.S. Appl. No. 14/407,440.
Office Action dated Mar. 4, 2016 in U.S. Appl. No. 14/266,391.
Office Action dated Sep. 28, 2016 in U.S. Appl. No. 14/266,391.
Office Action dated Mar. 29, 2017 in U.S. Appl. No. 15/230,085.
Office Action dated Jun. 27, 2017 in U.S. Appl. No. 14/266,391.
Office Action dated Feb. 16, 2018 in U.S. Appl. No. 14/266,391.
Office Action dated Nov. 1, 2017 in U.S. Appl. No. 15/230,085.
Office Action dated Sep. 4, 2018 in Japanese Patent Application No. 2016-201063; 7 pages.
Office Action dated Sep. 12, 2018 in U.S. Appl. No. 14/266,391.
Office Action dated Sep. 18, 2018 in European Patent Application No. 14 779 573.6; 5 pages.
Office Action dated Oct. 9, 2018 in Chinese Patent Application No. 201480024657X; 14 pages.
Office Action Dated Nov. 7, 2018 in Canadian Patent Application No. 2,994, 951.
Pagès F, Kirilovsky A, Mlecnik B, Asslaber M, Tosolini M, Bindea G, et al. In situ cytotoxic and memory T cells predict outcome in patients with early-stage colorectal cancer. J Clin Oncol 2009;27:5944-5951.
Pardoll, D., & Drake, C. (2012). Immunotherapy earns its spot in the ranks of cancer therapy. J Exp Med, 209(2), 201-209. doi:10.1084/jem.20112275.
Park, IJ, et al. Prediction of radio-responsiveness with immune-profiling in patients with rectal cancer, Oncotarget. 8:79793-79802, (2017).
Perk, L. R., Visser, O. J., Stigter-van Walsum, M., Vosjan, M. J., Visser, G. W., Zijlstra, J. M., et al. (2006). Preparation and evaluation of (89)Zr-Zevalin for monitoring of (90)Y-Zevalin biodistribution with positron emission tomography. European Journal of Nuclear Medicine and Molecular Imaging, 33, 1337.
Pillay V. et al., Antibodies in oncology. N Bioteehnol. Sep. 2011;28(5):518-529.
Piittet M.J. et al., In vivo imaging of T cell delivery to tumors after adoptive transfer therapy. Proc Natl Acad Sci US A. Jul. 24, 2007;104(30):12457-12461.
Radiosynthesis Database of PET Probes, dated Mar. 31, 2017 accessed on the World Wide Web at < http://www.nirs.qst.go.jp/research/division/mic/db2/>, as this item refers to a webpage, it may have been available in some form at an earlier date.
Radu, C. et al., Positron emission tomography with computed tomography imaging of neuroinflammation in experimental autoimmune encephalomyelitis., Proc Natl Acad Sci USA, vol. 104, No. 6, pp. 1937-1942, (2007).
Radu, C. et al., Molecular imaging of lymphoid organs and immune activation by positron emission tomography with a new[18F]-labeled 2'-deoxycytidine analog, Nat Med, vol. 14, No. 7, pp. 783-780, (2008).
Randall, K. J., & Pearse, G. (2008). A dual-label technique for the immunohistochemical demonstration of T-lymphocyte subsets in formalin-fixed, paraffin-embedded rat lymphoid tissue. Toxicol Pathol, 36(6), 795-804. doi:10.1177/0192623308322311.
Richardsen E, Uglehus R.D, Due J, Busch C, Busund L T. The prognostic impact of M CSF, CSF 1 receptor, CD68 and CD3 in prostatic carcinoma. Histopathology 2008;53:30-38.
Romer, P., et al. (2011). Preculture of PBMCs at high cell density increases sensitivity of T-cell responses, revealing cytokine release by CD28 superagonist TGN1412. Blood, 118(26), 6772-6782. doi:10.1182/blood-2010-12-319780.
Rizvi, S. N., Visser, O. J., Vosjan, M. J., van Lingen, A., Hoekstra, O. S., Zijlstra, J. M., et al. (2012). Biodistribution, radiation dosimetry and scouting of 90Y-ibritumomab tiuxetan therapy in patients with relapsed B-cell non-Hodgkin's lymphoma using 89Zribritumomab tiuxetan and PET. European Journal of Nuclear Medicine and Molecular Imaging, 39, 512.
Robert, C. et al. Wolchok, J. D. (2011). Ipilimumab plus dacarbazine for previously untreated metastatic melanoma. N Engl J Med, 364(26), 2517-2526. doi:10.1056/NEJMoa1104621.
Rothe A. et al., Recombinant proteins in rheumatology—recent advances. N Bioteehnol. Sep. 2011;28(5):502-51.
Rudd J.H. et al., Inflammation imaging in atherosclerosis. Arterioscler Thromb.
Salgado et al. The evaluation of tumor-infiltrating lymphocytes (TILs) in breast cancer: recommendations by an International TILs Working Group 2014 Annals of Oncology, vol. 26, Issue 2, Feb. 1, 2015, pp. 259-271.
Sato E, Olson SH, Ahn J, Bundy B, Nishikawa H, Qian F, et al. (2005) Intraepithelial CD8+ tumor-infiltrating lymphocytes and a high CD8+/regulatory T cell ratio are associated with favorable prognosis in ovarian cancer. Proc Natl Acad Sci U S A 102:18538-18543.
Sathaliyawala, T., Kubota, M., Yudanin, N., Turner, D., Camp, P., Thome, J. J., . . . Farber, D. L. (2013). Distribution and compartmentalization of human circulating and tissue-resident memory T cell subsets. Immunity, 38(1), 187-197. doi:10.1016/j.immuni.2012.09.020.
Shore, D.A. et al. The crystal structure of CD8a~ in complex with YTS156.7.7 Fab and interaction with other CDS antibodies define the binding mode of CD8a to MHC class I. J Mol Biol, 2008, 384 (5), p. 1190-1202.
Shultz, L. D., Lyons B. L., Burzenski, L. M., Gott, B., Chen, X., Chaleff, S., Kotb, M., Gillies, S. D., King, M., Mangada, J., Greiner, D.L. & Handgretinger, R. (2005). Human lymphoid and myeloid cell development in NOD/LtSz-scid IL2R gamma null mice engrafted with mobilized human hemopoietic stem cells. J Immunol., 174(10), 6477-89.
Sharif-Paghaleh E. et al., In vivo SPECT reporter gene imaging of regulatory T cells. PLoS One. 2011;6(10):e25857.
Sharma, P., Shen, Y., Wen, S., Yamada, S., Jungbluth, A. A., Gnjatic, S., Bajorin, D. F., Reuter, V. E., Herr, H., Old, L. J. & Sato, E. (2007). CD8 tumor-infiltrating lymphocytes are predictive of survival in muscle-invasive urothelial carcinoma. Proc Natl Acad Sci U S A, 104(10), 3967-3972.
Sharma, P Wagner K, Wolchok JD, Allison JP, Novel cancer immunotherapy agents with survival benefit: recent successes and next steps. Nat Rev Cancer. Oct. 24, 2011;11 (11):805-12. doi: 10.1038/nrc3153.
Stebbings, R., Findlay, L., Edwards, C., Eastwood, D., Bird, C., North, D., Mistry, Y., Dilger, P., Liefooghe, E., Cludts, I., Fox, B., Tarrant, G., Robinson, J., Meager, T., Dolman, C., Thorpe, S. J., Bristow, A., Wadhwa, M., Thorpe, R. & Poole, S. (2007). "Cytokine storm" in the phase I trial of monoclonal antibody TGN1412: better understanding the causes to improve preclinical testing of immunotherapeutics. J Immunol. 179(5), 3325-31.
Stelljes M. et al., Clinical molecular imaging in intestinal graft-versus-host disease: mapping of disease activity, prediction, and monitoring of treatment efficiency by positron emission tomography. Blood. Mar. 1, 2008;111(5):2909-2918.
Summons to attend oral proceedings dated Sep. 25, 2018 in European Patent Application No. 16191132.6.
Summons to Attend Oral Proceeding Pursuant to Rules 115(1) EPC dated Jul. 27, 2018 in European Patent Application No. 13804247.8.
Sundaresan Gobalakrishan et al., J-Labeled Engineered Anti-CEA Minibodies and Diabodies Allow High-Contrast, Antigen-Specific Small-Animal PET Imaging of Xenografts in Athymic Mice. The Journal of Nuclear Medicine, 2003, vol. 44, No. 12, pp. 1962-1969.
Tan, L. et al., Influence of the hinge region on complement activation, Ciq binding, and segmental flexibility in chimeric, Proc. Natl. Acad, Sci. USA; vol. 87, pp. 162-166, (1990).
Tavaré, R., Witte, O., Ribas, A., Wu, A.M., et al., An Effective Immuno-PET Imaging Method to Monitor CD8-Dependent Responses to Immunotherapy Cancer Research 76(1), 73-82, 2016.
Tefany FJ, Barnetson RS, Halliday G. M., McCarthy SW. McCarthy WH. Immunocytochemical analysis of the cellular infiltrate in primary regressing and non-regressing malignant melanoma. J. Invest. Dermatol. 1991;97:197-202.

(56) References Cited

OTHER PUBLICATIONS

Topalian, S. L., Sznol, M., McDermott, D. F., Kluger, H. M., Carvajal, R. D., Sharfman, W. H., . . . Hodi, F. S. (2014). Survival, durable tumor remission, and long-term safety in patients with advanced melanoma receiving nivolumab. J Clin Oncol, 32(10), 1020-1030. doi: 10.1200/jco.2013.53.0105.
Tumeh, P. et al., PET Imaging of Cancer Immunotherapy, J. Uncl Med, vol. 49, No. 6, pp. 865-868, (2008).
Tumeh, P, et al., PD-1 blockade induces responses by inhibiting adaptive immune resistance. Nature, 515(7528), 568-571.
Van Oijen M, Bins A, Elias S, Sein J, Weder P, de Gast G, et al. On the role of melanoma-specific CD8+ T-cell immunity in disease progression of advanced-stage melanoma patients. Clin Cancer Res 2004;10:4754-4760.
Wang, X et al., Disulfide Scrambling in IgG2 Monoclonal Antibodies: Insights from Molecular Dynamics Simulations, Pharmacetuical Research, vol. 28, No. 12, pp. 3128-3144, (2011).
Westermann, J., & Pabst, R. (1992). Distribution of lymphocyte subsets and natural killer cells in the human body. Clin Investig, 70(7), 539-544.
Williamson, S. et al. . Horne, C. H. (1998). New monoclonal antibodies to the T cell antigens CD4 and CD8. Production and characterization in formalin-fixed paraffin-embedded tissue. Am J Pathol, 152(6), 1421-1426.
Wolchok, J et al. (2009). Guidelines for the evaluation of immune therapy activity in solid tumors: immune-related response criteria. Clin Cancer Res, 15(23), 7412-7420. doi:10.1158/1078-0432.ccr-09-1624.
Yaghoubi S.S. et al.,. Positronemission tomography reporter genes and reporter probes: gene and cell therapy applications. Theranostics. 2012;2(4):374-3.
Ziai CD8+ T cell infiltration in breast and colon cancer: A histologic and statistical analysis, Pios One, (2018).
File History of U.S. Appl. No. 12/483,300.
File History of U.S. Appl. No. 14/419,225.
Office Action dated Nov. 18, 2019 in Japanese Application No. 2018-526609 with English Translation.
Office Action dated Dec. 5, 2019 in European Application No. 16835664.0.
Notice of Acceptance dated Dec. 24, 2018 in Australian Application No. 2014249243.
Notice of Allowance dated Oct. 2, 2019 in U.S. Appl. No. 16/417,482.
Notice of Allowance dated Oct. 22, 2019 in U.S. Appl. No. 16/417,474.
Office Action dated Oct. 2, 2019 in U.S. Appl. No. 16/394,957.
Office Action dated Dec. 19, 2019 in Canadian Application No. 2,994,951.
PCT Invitation to Pay Additional Fees dated Dec. 10, 2019 in International Application No. PCT/US19/53642.
ATCC, 2014, Hybridomas by Antigenic Determinant, pp. 1 and 1-23.
Gill et al., Jan. 2020, The production, quality control, and characterization of ZED8, a CD8-specific 89Zr-labeled immuno-PET clinical imaging agent, The AAPS, Journal, 22:22.
O'Brien et al., 2003, Humanization of Monoclonal Antibodies by CDR Grafting, PubMed, 207:81-100.
Creative Biolabs, Recombinant Anti-CD8 Antibody scFV Fragment <https://www.creativebiolabs.net/anti-cd8-antibody-scfv-fragment-81105.htm>, accessed on Jan. 14, 2019, 8 pp.
Wu et al, May/Jun. 2008, Antibodies for molecular imaging of cancer, The Cancer Journal, 14(3):191-197.
Zhou et al., Nov. 22, 2012 T-cell receptor gene transfer exclusively to human CD8+cells enhances tumor cell killing, Blood, 120(22).
Notice of Allowability dated Jul. 8, 2019 in U.S. Appl. No. 15/230,085.
Notice of Abandonment dated Jan. 24, 2020 in U.S. Appl. No. 16/417,482.
Notice of Abandonment dated Feb. 11, 2020 in U.S. Appl. No. 16/417,474.
Office Action dated Jan. 20, 2020 in Canadian patent application No. 2904969.
Office Action dated Apr. 16, 2019, in European Patent Application No. 14779573.6; 5 pages.
Reconsideration Report dated Jan. 7, 2020 in Japanese Patent Application No. 2016-501063.
Notice of Reasons for Rejection dated Jan. 14, 2020 in Japanese patent application No. 2018-230270.
International Search Report and Written Opinion dated Feb. 4, 2020 in application No. PCT/US19/53642.
File History, U.S. Appl. No. 16/417,482, filed May 20, 2019.
File History, U.S. Appl. No. 16/417,474, filed May 20, 2019.
Pre-Appeal Examination Report dated Apr. 22, 2020 in Japanese Application No. 2018-526609 with English Translation.
Barbie et al., 1998, The human immunoglobulin kappa variable (IGKV) genes and joining (IGKJ) segments, Exp Clin Immunogenet, 15:171-183.
Gasset et al. Jul. 18, 2003, A peptide mimetic of an anti-CD4 monoclonal antibody by rational design, Biochem. Biophys. Res. Commun., 307(1):198-205.
Diamond et al., Sep. 1984, Somatic mutation of the T15 heavy chain gives rise to an antibody with autoantibody specificity, Proc. Natl. Acad. Sci. USA, 81:5841-5844.
Hasemann et al., 1991, Mutational analysis of arsonate binding by a CRIA+ antibody. VH and VL junctional diversity are essential for binding activity. Journal of Biological Chemistry, 266(12):7626-7632.
Hiraoka Net al., 2006, Prevalence of FOXP3+ regulatory T cells increases during the progression of pancreatic ductal adenocarcinoma and its premalignant lesions. Clin. Cancer Res., 12:5423-5434.
Hirchhaeuser et al., 2009, Test system for trifunctional antibodies in 3D MCTS culture, Journal of Biomulecular Screening, 2009:980-990.
IMGT Repertoire (IG and TR), Gene table: human (*Homo sapiens*) IGKJ, Jun. 2016, 2 pp.
Ohno et. al., May 1985, Antigen-binding specificities of antibodies are primarily determined by seven/esidues of VH, Proc. Natl. Acad. Sci. USA, 82:2945-2949.
Padlan, Feb. 2004, Anatomy of the antibody molecule, Mol Immunol., 31 (3):169-217.
Pulito et al., 1996, Humanization and molecular modeling of the anti-CD4 monoclonal antibody, OKT4A, The Journal of Immunology, 156:2840-2850.
Examination report No. 1 dated May 29, 2020 for Australian patent application No. 201920676.
Summons to attend oral proceedings dated Jul. 30, 2020 in Application No. 14779573.6.
Notice of Reasons for Rejection dated Jul. 21, 2020 in Japanese patent application No. 2016-501063.
Notice of Preliminary Rejection dated May 14, 2020 in Korean patent application No. 10-2015-7028748.
Notice of Allowance dated Jun. 17, 2020 in U.S. Appl. No. 16/394,957.
Office Action dated Aug. 24, 2020 in European Application No. 16835664.0.
Office Action dated Mar. 11, 2020 in Russian Patent Application No. 2018105374 with English Translation.
Office Action dated Aug. 10, 2020 in Russian Patent Application No. 2018105374 with English Translation.
Office action dated Oct. 15, 2020 in U.S. Appl. No. 15/866,870.
International Search Report and Written Opinion dated Oct. 4, 2019 in application No. PCT/US2019/035550.
Notification of Reexamination dated Sep. 18, 2020 in Chinese Patent App. No. 201480024657X, with English translation.
"Practical Clinical Nuclear Medicine", edited by MA, Jixiao et al., Atomic Energy Press, May 2002, p. 121.
"Clinical Immunology and Allergiology" eds. L.Jeger, 2nd ed., translation from German, Moscow, Medicine, 1990, in 3 volumes, V.2, p. 484-485 [A Russian translation of ISBN-13 : 978-3437112553 in German].

(56) References Cited

OTHER PUBLICATIONS

"Immunology", in 3 volumes, eds. W. Paul, translated from English, Moscow: Mir, 1987-1989, V.1 (1987), pp. 212-215 [A Russian translation of the 1st edition of Fundamental Immunology by William E. PauL.
Yarilin A.A., "Osnovy Immunologii" ("Basics of Immunology"), Moscow.: Medicine, 1999, pp. 176-177 [a reference in Russian].
De Genst et al., Antibody Repertoire Development in Camelids, Development & Comparative Immunology, vol. 30, pp. 187-198, 2006.
Yoshinaga et al., Ig-L-chain Shuffling for Affinity Maturation of Phage Library-Derived Human antihuman MCP-1 Antibody Blocking its Chemotactic Activity, The Japanese Biochemical Society, vol. 143, pp. 593-601, 2008.
Almargo et al., Humanization of Antibodies, Frontiers in Bioscience, vol. 13, pp. 1619-1633, 2008.
Rodrigues et al., Engineering Fab' Fragments for Efficient F(ab)2 formation in *Escherichia coli* and for Improved in Vivo Stability, SinoBiological, vol. 151, pp. 6954-6961, 1993.
Notice of Reasons for Rejection dated Sep. 23, 2020 in Japanese Application No. 2018-230270.
Office Action dated Jan. 4, 2021 in Canadian patent application No. 2904969.
Pecision of reexamination dated Dec. 22, 2020 in Chinese patent application No. 201480024657X.
Notice of Rejection Decision dated Nov. 11, 2020 in Korean patent application No. 10/2015-7028748.
Notice of Rejection Decision dated Dec. 30, 2020 in Korean patent application No. 10/2015-7028748.
Partial European Search Report dated Jan. 29, 2021 in patent application No. 19185381.1.
Office Action dated Jan. 7, 2021 in Canadian Application No. 2,994,951.
Notification of the First Office Action dated Nov. 12, 2020 in Chinese patent application No. 2016800583411.
Amendment and response dated Jan. 13, 2021 in U.S. Appl. No. 15/866,870.
Angal et al., 1993, A single amino acid substitution abolishes the heterogeneity of chimeric mouse/human (IgG4) antibody. Molecular Immunology, 30(1):105-108.
Chiu et al., Dec. 3, 2019, Antibody Structure and Function: The Basis for Engineering Therapeutics, Antibodies 8:55:1-80.
Wei et al., May 2018, Noninvasive PET imaging of T cells, Trends in Cancer, 4(5):359-373.
Notice of Reason for Refusal dated May 9, 2021, in Korean patent application No. 10-2021-7003074.
Extended European Search Report dated May 11, 2021 in patent application No. 19185381.1.
Search Report dated Jan. 19, 2021 in Brazilian patent application No. BR112018002451-1.
Notice of Reasons for Rejection dated May 10, 2021, in Japanese Application No. 2018-526609.
Notice of Reasons for Rejection dated May 17, 2021, in Japanese Application No. 2020-047973.
Office Action dated Apr. 9, 2021 in Russian Patent Application No. 2018105374.
Office action dated Apr. 12, 2012 in U.S. Appl. No. 15/866,870.
International Search Report and Written Opinion dated May 25, 2021 in application No. PCT/US20/63023.
Notification of the Second Office Action dated Jul. 5, 2021 in Chinese patent application No. 2016800583411.
ImaginAb, Patient 2—Subject: 64 years old, male metastatic hepatocellular carcinoma, PowerPoint slide, 1 p., ASCO, Jun. 2018.
ImaginAb, Unlocking the immune system for cancer therapy, PowerPoint presentation, 18 pp., Feb. 2018.
Joshi et al., PET scanner harmonization for multi-center clinical trials using 89Zr tracers in partnership with clinical trials network (CTN), Poster No. 1201, 1 p., 2019.
Pandit-Tasker, First in human phase 1 imaging study with 89Zr-Df-IAB22M2C anti-CD8 minibody in patients with solid tumors, PowerPoint presentation, 15 pp., SNMMI, 2018.
Pandit-Tasker, First in human trial of 89Zr-Dr-IAB22M2C anti-CD8 minibody in patients with solid tumors, PowerPoint presentation, 18 pp., WMIC, 2018.
Pandit-Tasker, First-in-human imaging with $^{89}$Zr-Df-IAB22M2C anti-CD8 minibody in patients with solid malignancies: preliminary pharmacokinetics, biodistribution, and lesion targeting, 2019. 32 pp.
Wu, May 2, 2016, Zr-labeled antibodies and fragments for imaging immune cells, NCI/SNMM/CTN Immune Modulation Therapy and Imaging Workshop, Shady Grove, MD, PowerPoint presentation, 349 pp.
Notice of Allowance dated Jul. 19, 2021 in U.S. Appl. No. 16/273,849.
Extended European Search Report dated Aug. 13, 2021 in patent application No. 21171344.1.
Advisory Action dated Jul. 27, 2021 in U.S. Appl. No. 15/866,870.
Notice of Allowance dated Sep. 1, 2021 in U.S. Appl. No. 15/866,870.
Gordon, Imaging of tumor infiltrating T cells with an anti-CD8 minibody 89Zr-IAB22M2C in advanced solid tumors: a phase 1 first-in-human study, PowerPoint presentation, 14 pp., Oct. 2018.
Gordon, Imaging of tumor infiltrating T cells with an anti-CD8 minibody 89Zr-IAB22M2C in Advanced solid tumors: a phase 1 first-in-human study, Abstract, 5 pp., Sep. 2018.
ImaginAb, Apr. 2019, Accelerating Immuno-Oncology through Imaging Immune System, PowerPoint presentation, 28 pp.
ImaginAb, ASCO Meeting, PowerPoint presentation, 30 pp., 2019.
ImaginAb, Better biomarkers will be able to predict efficacy, photo with PowerPoint slide, 1 p., ASCO-SITC Clinical Immuno-Oncology Symposium, 2018.
ImaginAb, Improvement on Radiolabeling Process for Zr-89 labeled CD8 Tracer, SNMMI Abstract, 2019.
ImaginAb, Jul. 2018, Accelerating Immuno-Oncology Beyond Biopsy, PowerPower presentation, 79 pp.
ImaginAb, Jun. 1, 2018, CD8 ImmunoPET accelerating immuno-oncology, PowerPower presentation, 26 pp.
ImaginAb, Jun. 18, 2018, CD8 ImmunoPET accelerating immuno-oncology, PowerPower presentation, 26 pp.
ImaginAb, Jun. 2018, Accelerating Immuno-Oncology Beyond Biopsy, PowerPoint presentation, 19 pp.
ImaginAb, Jun. 2019, Investment Presentation, PowerPoint presentation, 34 pp.
ImaginAb, May 2019, Investment Presentation, PowerPoint presentation, 32 pp.
ImaginAb, Nov. 2018, Accelerating Immuno-Oncology through Imaging Immune System, PowerPoint presentation, 20 pp.
ImaginAb, Oct. 11, 2018, In vivo clinical PET imaging of CD8 T cells using the Zr89 minibody IAB22M2C, Advances in Immuno-Oncology USA Congress, PowerPoint presentation, 17 pp.
Notice of Reasons for Rejection dated Aug. 23, 2021, in Japanese Application No. 2018-526609.
Notice of Allowance dated Oct. 13, 2021 in U.S. Appl. No. 15/866,870 in 10 pages.
Official Filing Receipt received Dec. 6, 2021 in U.S. Appl. No. 17/454,938 in 3 pages.
U.S. Appl. No. 17/454,938, filed Nov. 15, 2021, Chan et al.

* cited by examiner

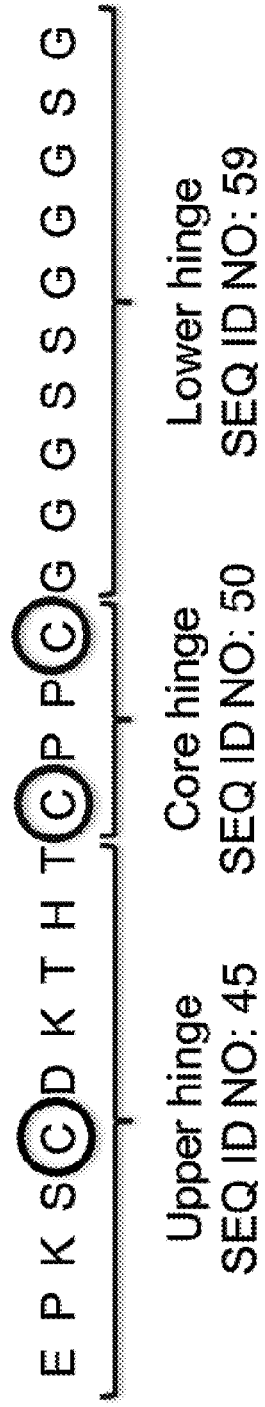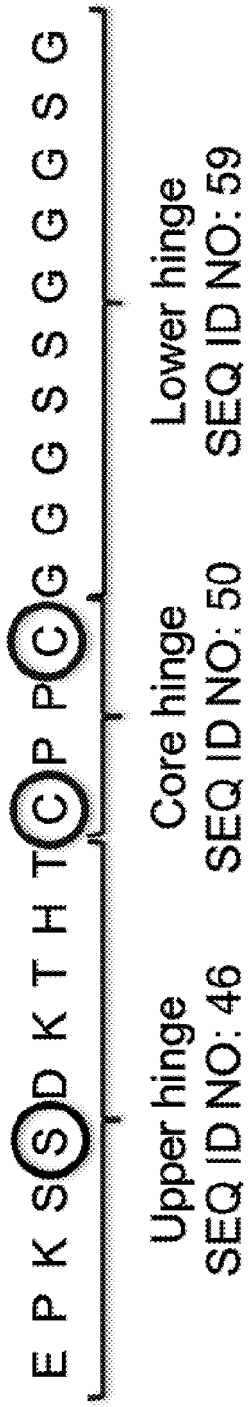
FIG. 2

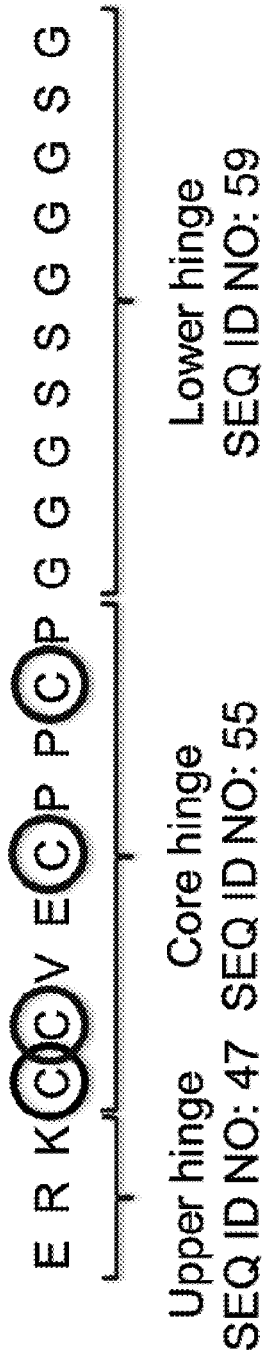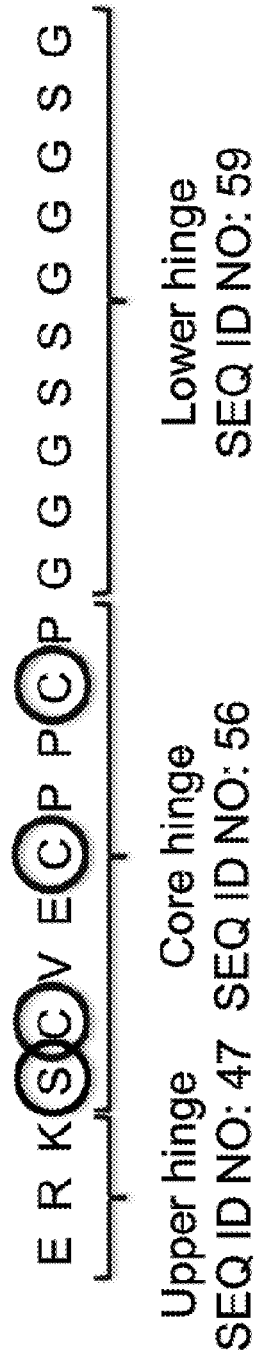
FIG. 3

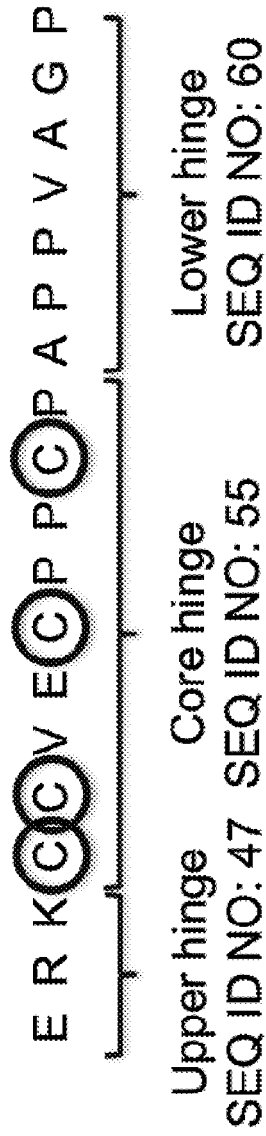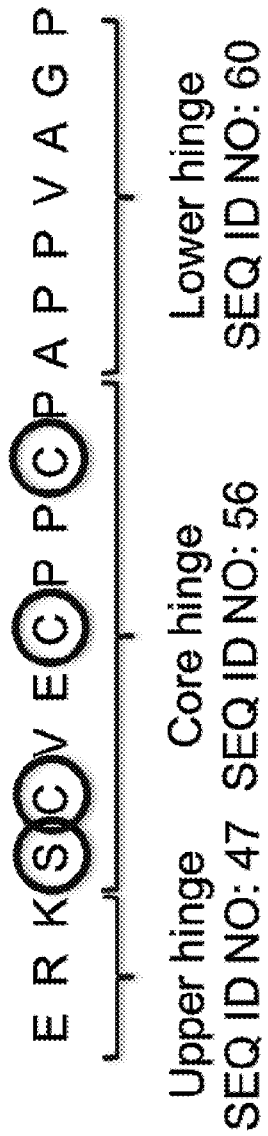
FIG. 4

IAB2M γ1 EH1 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFTLT
ISSLQPEDFADYFCQQYNSYPLTFGGGTKLEIK (SEQ ID NO: 13)

Linker
GSTSGGGGSGGGGSGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVDK
STSTAYMELSSLRSEDTAVYYCAAGWNFDYWGQGTTVTVSS (SEQ ID NO: 14)

Full hinge (EH1)
EPKSCDKTHTCPPCGGGSSGGGSG (SEQ ID NO: 22)

Upper hinge
EPKSCDKTHT (SEQ ID NO: 45)

Core hinge
CPPC (SEQ ID NO: 50)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 41)

FIG. 5B

IAB2M γ1 EH2 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFTL
TISSLQPEDFADYFCQQYNSYPLTFGGGTKLEIK (SEQ ID NO: 13)

Linker
GSTSGGGSGGGSGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVD
KSTSTAYMELSSLRSEDTAVYYCAAGWNFDYWGQGTTVTVSS (SEQ ID NO: 14)

Full hinge (EH2)
EPKSSDKTHTCPPCGGGSSGGGGSG (SEQ ID NO: 24)

Upper hinge
EPKSSDKTHT (SEQ ID NO: 46)

Core hinge
CPPC (SEQ ID NO: 50)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 41)

FIG. 5C

IAB2M γ2 EH2 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFT
LTISSLQPEDFADYFCQQYNSYPLTFGGGTKLEIK (SEQ ID NO: 13)

Linker
GSTSGGGSGGGGSGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVD
KSTSTAYMELSSLRSEDTAVYYCAAGWNFDYWGQGTTVTVSS (SEQ ID NO: 14)

Full hinge (EH2)
ERKSCVECPPCPGGGSSGGGSG (SEQ ID NO: 34)

Upper hinge
ERK (SEQ ID NO: 47)

Core hinge
SCVECPPCP (SEQ ID NO: 56)

Lower hinge
GGGSSGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLTV
DKSRWQQGNVFSCSVMHEALHNHYTQKSLSLSPGK (SEQ ID NO: 42)

FIG. 5D

IAB2M γ2 EH1 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFTL
TISSLQPEDFADYFCQQYNSYPLTFGGGTKLEIK (SEQ ID NO: 13)

Linker
GSTSGGGSGGGSGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVD
KSTSTAYMELSSLRSEDTAVYYCAAGWNFDYWGQGTTVTVSS (SEQ ID NO: 14)

Full hinge (EH1)
ERKCCVECPPCPGGGSSGGGSG (SEQ ID NO: 32)

Upper hinge
ERK (SEQ ID NO: 47)

Core hinge
CCVECPPCP (SEQ ID NO: 55)

Lower hinge
GGGSSGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLTV
DKSRWQQGNVFSCSVMHEALHNHYTQKSLSLSPGK (SEQ ID NO: 42)

FIG. 5E

IAB2M γ1 EH3 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFT
LTISSLQPEDFADYFCQQYNSYPLTFGGGTKLEIK (SEQ ID NO: 13)

Linker
GSTSGGGSGGGGSGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVD
KSTSTAYMELSSLRSEDTAVYYCAAGWNFDYWGQGTTVTVSS (SEQ ID NO: 14)

Full hinge (EH3)
EPKSSDKTHTCPPCPPCGGGGSSGGGGSG (SEQ ID NO: 26)

Upper hinge
EPKSSDKTHT (SEQ ID NO: 46)

Core hinge
CPPCPPC (SEQ ID NO: 52)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK (SEQ ID NO: 41)

FIG. 7C

IAB2M γ1 EH3 (N- to C-terminal)

IAB2M γ1 EH3 (M1) (SEQ ID NO: 7)
DIVMTQSPSSLSASVGDRVTITCKASQDVGTAVDWYQQKPGKAPKLLIYWASTRHTGVPDR
FTGSGSGTDFTLTISSLQPEDFADYFCQQYNSYPLTFGGGTKLEIKGSTSGGGSGGGSGGG
GSSEVQLVQSGAEVKKPGASVKISCKTSGYTFTEYTIHWVKQASGKGLEWIGNINPNNGGTT
YNQKFEDRATLTVDKSTSTAYMELSSLRSEDTAVYYCAAGWNFDYWGQGTTVTVSSEPKSS
DKTHTCPPCPPCGGGSSGGGSGGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQ
KSLSLSPG (SEQ ID NO: 7)

IAB2M γ1 EH3 (M2) (SEQ ID NO: 10)
EVQLVQSGAEVKKPGASVKISCKTSGYTFTEYTIHWVKQASGKGLEWIGNINPNNGGTTYNQ
KFEDRATLTVDKSTSTAYMELSSLRSEDTAVYYCAAGWNFDYWGQGTTVTVSSGSTSGGGS
GGGSGGGGSSDIVMTQSPSSLSASVGDRVTITCKASQDVGTAVDWYQQKPGKAPKLLIYWA
STRHTGVPDRFTGSGSGTDFTLTISSLQPEDFADYFCQQYNSYPLTFGGGTKLEIKEPKSSD
KTHTCPPCPPCGGGSSGGGSGGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKS
LSLSPG (SEQ ID NO: 10)

FIG. 7D

IAB2M γ1 EH3

IAB2M γ1 EH3 (M1) (SEQ ID NO: 162)

gatattgtgatgacccagagcccgagcagcctgagcgcgagcgtgggcgatcgcgtgacc
attacctgcaaagcgagccaggatgtgggcaccgcggtggattggtatcagcagaaaccg
ggcaaagcgccgaaactgctgatttattgggcgagcacccgccataccggcgtgccggat
cgctttaccggcagcggcagcggcaccgattttaccctgaccattagcagcctgcagccg
gaagattttgcggattatttttgccagcagtataacagctatccgctgacctttggcggc
ggcaccaaactggaaattaaaggcagcaccagcggcggcggcagcggcggcggcagcggc
ggcggcggcagcagcgaagtgcagctggtgcagagcggcgcggaagtgaaaaaaccgggc
gcgagcgtgaaaattagctgcaaaaccagcggctatacctttaccgaatataccattcat
tgggtgaaacaggcgagcggcaaaggcctggaatggattggcaacattaacccgaacaac
ggcggcaccacctataaccagaaatttgaagatcgcgcgaccctgaccgtggataaaagc
accagcaccgcgtatatggaactgagcagcctgcgcagcgaagataccgcggtgtattat
tgcgcggcgggctggaactttgattattggggccagggcaccaccgtgaccgtgagcagc
gaaccgaaaagcagcgataaaacccatacctgcccgccgtgcccgccgtgcggcggcggc
agcagcggcggcggcagcggcggccagccgcgcgaaccgcaggtgtataccctgccgccg
agccgcgaagaaatgaccaaaaaccaggtgagcctgacctgcctggtgaaaggcttttat
ccgagcgatattgcggtggaatgggaaagcaacggccagccggaaaacaactataaaacc
accccgccggtgctggatagcgatggcagctttttttctgtatagcaaactgaccgtggat
aaaagccgctggcagcagggcaacgtgtttagctgcagcgtgatgcatgaagcgctgcat
aaccattatacccagaaaagcctgagcctgagcccgggc (SEQ ID NO: 162)

FIG. 7E

IAB2M γ1 EH3

IAB2M γ1 EH3 (M2) (SEQ ID NO: 165)

gaagtgcagctggtgtgcagagcgcggaagtgaaaaaccgggcgcgagcgtgaaaatt
agctgcaaaccagcggctatacctttaccgaatataccattcattggtgaaacaggcg
agcggcaaaggcctggaatgattggcaacaacattaaccgaacaacggcgccaccacctat
aaccagaaatttgaagatcgcgcgacctgaccgtggataaaagcaccagcaccgcgtat
atggaactgagcagcctgcgcagcgaagatac Disulfide-containing peptides identified within IAB2M γ1 EH1 dimer

| Link/Modification | Sequence Location[a] | Sequence | Theor. Mass (Da)[b] | Obs. Mass (Da)[c] | Delta ppm | RT (mins) | Abundance[d] |
|---|---|---|---|---|---|---|---|
| Not observed | A22-A96 | N/A | N/A | N/A | N/A | N/A | N/A |
| Cysteine disulfide bond(A156-A221)* | A(152-157) + A(195-236) | VTITCK [SEQ ID NO: 183] + FTGSGSGTDFTLTISSLQPEDFADYFCQQYNSYPLTFGGGTK [SEQ ID NO: 184] | 5208.3897 | 5208.3864 | -0.63 | 89.9 | 1580663 |
| Cysteine disulfide bond(A156-A221)* | A(152-157) + A(188-236) | VTITCK + [SEQ ID NO: 183] HTGVPDRFTGSGSGTDFTLTISSLQPEDFADYFCQQYNSYPLTFGGGTK [SEQ ID NO: 185] | 5970.7669 | 5970.7586 | -1.40 | 86.1 | 166671 |
| Cysteine disulfide bond(A251-B251) Cysteine disulfide bond(A254-B254) | A(248-268) + B(248-268) | THTCPPCGGGSSGGGSGGGQPR [SEQ ID NO: 186] + THTCPPCGGGSSGGGSGGGQPR [SEQ ID NO: 186] | 3707.5067 | 3707.5060 | -0.18 | 22.1 | 583626 |
| Cysteine disulfide bond(A245-A291) | A(244-247) + A(285-294) | SCDK [SEQ ID NO: 187] + NQVSLTCLVK [SEQ ID NO: 188] | 1552.7589 | 1552.7590 | 0.07 | 43.8 | 84406 |
| Cysteine disulfide bond(A291-A349)* | A(285-294) + A(341-363) | NQVSLTCLVK [SEQ ID NO: 188] + WQQGNVFSCSVMHEALHNHYTQK [SEQ ID NO: 189] | 3844.8236 | 3844.8202 | -0.89 | 55.2 | 4949532 |
| Cysteine disulfide bond(A291-A349)* | A(285-294) + A(339-363) | NQVSLTCLVK [SEQ ID NO: 188] + SRWQQGNVFSCSVMHEALHNHYTQK [SEQ ID NO: 190] | 4087.9568 | 4087.9615 | 1.16 | 54.0 | 647751 |
| Alkylation (vinyl pyridine)(A291) | A(285-294) | NQVSLTCLVK [SEQ ID NO: 188] | 1208.6587 | 1208.6578 | -0.81 | 47.2 | 51583 |
| Alkylation (vinyl pyridine)(A349) | A(341-363) | WQQGNVFSCSVMHEALHNHYTQK [SEQ ID NO: 189] | 2848.2962 | 2848.2955 | -0.24 | 49.1 | 74838 |

[a] Sequence location A: heavy chain #1; B: heavy chain #2.
[b] Theoretical molecular masses (mono-isotopic) were calculated using MassHunter BioConfirm software (Agilent, Santa Clara, CA).
[c] Observed masses (mono-isotopic) are all within 3 ppm of their theoretical value.
[d] Abundances were determined using MassHunter software (Agilent, Santa Clara, CA).
RT: retention time.
* Peptides displaying alternative cleavages.

FIG. 8

Illustration of a mapping of the disulfide bonds of IAB2M γ2 EH1
(SEQ ID NO: 180)

```
         10         20         30         40         50         60
    EVQLVQSGAE VKKPGASVKI SCKSSGYTFT EYTIHWVKQA SGKGLEWIGN INPNNGGTTY
         70         80         90        100        110        120
    NQKFEDRATL TVDKSTSTAY MELSSLRSED TAVYYCAAGW NFDYWGQGTT VTVSSGSTSG
        130        140        150        160        170        180
    GGSGGGSGGG GSSDIVMTQS PSSLSASVGD RVTITCKASQ DVGTAVDWYQ QKPGKAPKLL
        190        200        210        220        230        240
    IYWASTRHTG VPDRFTGSGS GTDFTLTISS LQPEDFADYF CQQYNSYPLT FGGGTKLEIK
                 250        260        270        280        290        300
    ERKCCVECPP CPGGGSSGGG SGGQPREPQV YTLPPSREEM TKNQVSLTCL VKGFYPSDIA
                 310        320        330        340        350        360
    VEWESNGQPE NNYKTTPPML DSDGSFFLYS KLTVDKSRWQ QGNVFSCSVM HEALHNHYTQ

KSLSLSPGK 10         20         30         40         50         60
    EVQLVQSGAE VKKPGASVKI SCKSSGYTFT EYTIHWVKQA SGKGLEWIGN INPNNGGTTY
         70         80         90        100        110        120
    NQKFEDRATL TVDKSTSTAY MELSSLRSED TAVYYCAAGW NFDYWGQGTT VTVSSGSTSG
        130        140        150        160        170        180
    GGSGGGSGGG GSSDIVMTQS PSSLSASVGD RVTITCKASQ DVGTAVDWYQ QKPGKAPKLL
        190        200        210        220        230        240
    IYWASTRHTG VPDRFTGSGS GTDFTLTISS LQPEDFADYF CQQYNSYPLT FGGGTKLEIK
                 250        260        270        280        290        300
    ERKCCVECPP CPGGGSSGGG SGGQPREPQV YTLPPSREEM TKNQVSLTCL VKGFYPSDIA
                 310        320        330        340        350        360
    VEWESNGQPE NNYKTTPPML DSDGSFFLYS KLTVDKSRWQ QGNVFSCSVM HEALHNHYTQ

KSLSLSPGK
```

——— Conventional disulfides

----- Disulfides not detected by LC/MS but likely to exist

● Cysteine

FIG. 10

IAB22M γ2 EH1 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTIS
SLQPEDVATYYCQQHNENPLTFGGGTKVEIK (SEQ ID NO: 15)

Linker
GSTSGGGSGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSK
NTAYLQMNSLRAEDTAVYYCGRGYGYYVFDHWGQGTLVTVSS (SEQ ID NO: 16)

Full hinge (EH1)
ERKCCVECPPCPGGGSSGGGSG (SEQ ID NO: 32)

Upper hinge
ERK (SEQ ID NO: 47)

Core hinge
CCVECPPCP (SEQ ID NO: 55)

Lower hinge
GGGSSGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 42)

FIG. 14B

IAB22M γ2 EH2 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFT
LTISSLQPEDVATYYCQQHNENPLTFGGGTKVEIK (SEQ ID NO: 15)

Linker
GSTSGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISA
DTSKNTAYLQMNSLRAEDTAVYYCGRGYGYYVFDHWGQGTLVTVSS (SEQ ID NO: 16)

Full hinge (EH2)
ERKSCVECPPCPGGGSSGGGSG (SEQ ID NO: 34)

Upper hinge
ERK (SEQ ID NO: 47)

Core hinge
SCVECPPCP (SEQ ID NO: 56)

Lower hinge
GGGSSGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLT
VDKSRWQQGNVFSCSVMHEALHNHYTQKSLSLSPGK (SEQ ID NO: 42)

FIG. 15B

IAB22M γ1 EH1 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTISSLQPE
DVATYYCQQHNENPLTFGGGTKVEIK (SEQ ID NO: 15)

Linker
GSTSGGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSKNTAY
LQMNSLRAEDTAVYYCGRGYGYYVFDHWGQGTLVTVSS (SEQ ID NO: 16)

Full hinge (EH1)
EPKSCDKTHTCPPCGGGSSGGGGSG (SEQ ID NO: 22)

Upper hinge
EPKSCDKTHT (SEQ ID NO: 45)

Core hinge
CPPC (SEQ ID NO: 50)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 41)

FIG. 16B

IAB22M γ2 NH1 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTISSL
QPEDVATYYCQQHNENPLTFGGGTKVEIK (SEQ ID NO: 15)

Linker
GSTSGGGSGGGSGGGSGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSKN
TAYLQMNSLRAEDTAVYYCGRGYGYYVFDHWGQGTLVTVSS (SEQ ID NO: 16)

Full hinge (NH1)
ERKCCVECPPCPAPPVAGP (SEQ ID NO: 31)

Upper hinge
ERK (SEQ ID NO: 47)

Core hinge
CCVECPPCP (SEQ ID NO: 55)

Lower hinge
APPVAGP (SEQ ID NO: 60)

Human IgG2 CH3
GQPREPQVYTLPPSREEMTKNQVSLTCLVKGFYPSDIAVEWESNGQPENNYKTTPPMLDSDGSFFLYSKLTVDKS
RWQQGNVFSCSVMHEALHNHYTQKSLSLSPGK (SEQ ID NO: 42)

FIG. 16C

IAB22M γ2 NH2 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTIS
SLQPEDVATYYCQQHNENPLTFGGGTKVEIK (SEQ ID NO: 15)

Linker
GSTSGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSK
NTAYLQMNSLRAEDTAVYYCGRGYGYYVFDHWGQGTLVTVSS (SEQ ID NO: 16)

Full hinge (NH2)
ERKSCVECPPCPAPPVAGP (SEQ ID NO: 33)

Upper hinge
ERK (SEQ ID NO: 47)

Core hinge
SCVECPPCP (SEQ ID NO: 56)

Lower hinge
APPVAGP (SEQ ID NO: 60)

Human IgG2 CH3
GQPREPQVYTLPPSREEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 42)

FIG. 16D

Biodistribution (%ID/g) at 41 hrs (n=4)

|  | HPB-ALL | STD | Daudi | STD |
|---|---|---|---|---|
| Blood | 0.74 | 0.09 | 0.45 | 0.11 |
| Liver | 15.94 | 1.21 | 12.18 | 1.20 |
| R Kidney | 31.94 | 3.81 | 20.62 | 1.00 |
| L Kidney | 32.75 | 3.61 | 21.38 | 1.86 |
| Spleen | 47.19 | 8.88 | 51.91 | 3.15 |
| Heart | 4.56 | 0.76 | 3.89 | 0.57 |
| Lungs | 3.74 | 0.58 | 3.10 | 0.93 |
| Stomach | 2.28 | 0.19 | 1.72 | 0.19 |
| Muscle | 0.51 | 0.07 | 0.45 | 0.11 |
| Bone | 5.56 | 0.80 | 3.70 | 0.86 |
| Tumor | 10.04* | 2.38 | 1.58 | 0.38 |
| Carcass | 1.65 | 0.19 | 1.34 | 0.09 |

* n=3

FIG. 19

IAB22M γ1 EH3 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTISSLQPED
VATYYCQQHNENPLTFGGGTKVEIK (SEQ ID NO: 15)

Linker
GSTSGGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSKNTAYLQ
MNSLRAEDTAVYYCGRGYGYYVFDHWGQGTLVTVSS (SEQ ID NO: 16)

Full hinge (EH3)
EPKSSDKTHTCPPCPPCPPCGGGGSSGGGGSG (SEQ ID NO: 46)

Upper hinge
EPKSSDKTHT (SEQ ID NO: 52)

Core hinge
CPPCPPC (SEQ ID NO: 52)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 41)

FIG. 20C

IAB22M γ1 EH5 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTISSLQPEDV
ATYYCQQHNENPLTFGGGTKVEIK (SEQ ID NO: 15)

Linker
GSTSGGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSKNTAYLQ
MNSLRAEDTAVYYCGRGYYYVFDHWGQGTLVTVSS (SEQ ID NO: 16)

Full hinge (EH5)
EPKSSDKTHTCPPCPPCPPCGGGSSGGGSG (SEQ ID NO: 30)

Upper hinge
EPKSSDKTHT (SEQ ID NO: 46)

Core hinge
CPPCPPCPPC (SEQ ID NO: 54)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 41)

FIG. 20D

IAB22M γ3/γ1 EH6 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTISSLQPE
DVATYYCQQHNENPLTFGGGTKVEIK (SEQ ID NO: 15)

Linker
GSTSGGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSKNTAYL
QMNSLRAEDTAVYYCGRGYGYYVFDHWGQGTLVTVSS (SEQ ID NO: 16)

Full hinge (EH6)
ELKTPLGDTTHTCVECPPCGGGSSGGGSG (SEQ ID NO: 35)

Upper hinge
ELKTPLGDTTHT (SEQ ID NO: 48)

Core hinge
CVECPPC (SEQ ID NO: 57)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 41)

FIG. 20E

IAB22M γ3/γ1 EH7 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTISSLQPE
DVATYYCQQHNENPLTFGGGTKVEIK (SEQ ID NO: 15)

Linker
GSTSGGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSKNTAY
LQMNSLRAEDTAVYYCGRGYGYYVFDHWGQGTLVTVSS (SEQ ID NO: 16)

Full hinge (EH7)
ELKTPLGDTTHTCPPCPPCGGGSSGGGGSG (SEQ ID NO: 48)

Upper hinge
ELKTPLGDTTHT (SEQ ID NO: 52)

Core hinge
CPPCPPC (SEQ ID NO: 52)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 41)

FIG. 20F

IAB22M γ3/γ1 EH8 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTISSLQPED
VATYYCQQHNENPLTFGGGTKVEIK (SEQ ID NO: 15)

Linker
GSTSGGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADTSKNTAYLQ
MNSLRAEDTAVYYCGRGYGYYVFDHWGQGTLVTVSS (SEQ ID NO: 16)

Full hinge (EH8)
ELKTPLGDTTHTCPPCPPCPPCGGGSSGGGSG (SEQ ID NO: 37)

Upper hinge
ELKTPLGDTTHT (SEQ ID NO: 48)

Core hinge
CPPCPPCPPC (SEQ ID NO: 54)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 41)

FIG. 20G

IAB2M γ1 EH5 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFTLTISSLQPE
DFADYFCQQYNSYPLTFGGGTKLEIK (SEQ ID NO: 13)

Linker
GSTSGGGGSGGGGSGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVDKSTSTAYM
ELSSLRSEDTAVYYCAAGWNFDYWGQGTTVTVSS (SEQ ID NO: 14)

Full hinge (EH5)
EPKSSDKTHTCPPCPPCPPCGGGSSGGGSG (SEQ ID NO: 30)

Upper hinge
EPKSSDKTHT (SEQ ID NO: 46)

Core hinge
CPPCPPCPPC (SEQ ID NO: 54)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 41)

FIG. 21B

IAB2M γ3/γ1 EH6 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFTLTISSLQPE
DFADYFCQQYNSYPLTFGGGTKLEIK (SEQ ID NO: 13)

Linker
GSTSGGGGSGGGGSGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVDKSTSTAYM
ELSSLRSEDTAVYYCAAGWNFDYWGQGTTVTVSS (SEQ ID NO: 14)

Full hinge (EH6)
ELKTPLGDTTHTCVECPPCGGGSSGGGGSG (SEQ ID NO: 35)

Upper hinge
ELKTPLGDTTHT (SEQ ID NO: 48)

Core hinge
CVECPPC (SEQ ID NO: 57)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 41)

FIG. 21C

IAB2M γ3/γ1 EH7 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFTLTISSLQPEDF
ADYFCQQYNSYPLTFGGGTKLEIK (SEQ ID NO: 13)

Linker
GSTSGGGSGGGGSGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVDKSTSTAYMEL
SSLRSEDTAVYYCAAGWNFDYWGQGTTVTVSS (SEQ ID NO: 14)

Full hinge (EH7)
ELKTPLGDTTHTCPPCPGGGSSGGGSG (SEQ ID NO: 36)

Upper hinge
ELKTPLGDTTHT (SEQ ID NO: 48)

Core hinge
CPPCPPC (SEQ ID NO: 52)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO: 41)

FIG. 21D

IAB2M γ3/γ1 EH8 (N- to C-terminal)

Anti-PSMA variable light (VL) sequence
DIVMTQSPSSLSASVGDRVTITCKASQDVGTAVDWYQQKPGKAPKLLIYWASTRHTGVPDRFTGSGSGTDFTLTISSL
QPEDFADYFCQQYNSYPLTFGGGTKLEIK (SEQ ID NO: 13)

Linker
GSTSGGGGSGGGGGGSS (SEQ ID NO: 62)

Anti-PSMA variable heavy (VH) sequence
EVQLVQSGAEVKKPGASVKISCKTSGYTFTEYTIHWVKQASGKGLEWIGNINPNNGGTTYNQKFEDRATLTVDKSTST
AYMELSSLRSEDTAVYYCAAGWNFDYWGQGTTVTVSS (SEQ ID NO: 14)

Full hinge (EH8)
ELKTPLGDTTHTCPPCPPCGGGSSGGGSG (SEQ ID NO: 37)

Upper hinge
ELKTPLGDTTHT (SEQ ID NO: 48)

Core hinge
CPPCPPC (SEQ ID NO: 54)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 41)

FIG. 21E

IAB22M γ1 EH2 (N- to C-terminal)

Anti-CD8 variable light (VL) sequence
DVQITQSPSSLSASVGDRVTITCRTSRSISQYLAWYQQKPGKVPKLLIYSGSTLQSGVPSRFSGSGSGTDFTLTI
SSLQPEDVATYYCQQHNENPLTFGGGTKVEIK (SEQ ID NO: 15)

Linker
GSTSGGGSGGGGSGGGGSS (SEQ ID NO: 62)

Anti-CD8 variable heavy (VH) sequence
EVQLVESGGGLVQPGGSLRLSCAASGFNIKDTYIHFVRQAPGKGLEWIGRIDPANDNTLYASKFQGKATISADT
SKNTAYLQMNSLRAEDTAVYYCGRGYGYYVFDHWGQGTLVTVSS (SEQ ID NO: 16)

Full length (EH2)
EPKSSDKTHTCPPCGGGSSGGGSG (SEQ ID NO: 24)

Upper hinge
EPKSSDKTHT (SEQ ID NO: 46)

Core hinge
CPPC (SEQ ID NO: 50)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 41)

FIG. 22B

IAB20M γ1 EH1 (N- to C-terminal)

Anti-5T4 variable light (VL) sequence
DIVMTQSPATLSVSPGERATLSCKASQSVSNDVAWYQQKPGQAPRLLISYTSSRYAGVPDRFSGSGSGTDFTLTISSLQ
AEDVAVYYCQQDYNSPPTFGQGTKVEIK (SEQ ID NO: 17)

Linker
GSTSGGGGSGGGGSGGGGSS (SEQ ID NO: 62)

Anti-5T4 variable heavy (VH) sequence
QVQLVQSGAEVKKPGASVKVSCKASGYSFTGYYMHWVRQAPGQGLEWIGRINPNNGVTLYNQKFKDRVTMTVDTSIS
TAYMELSRLRSDDTAVYYCARSTMITNYVMDYWGQGTLVTVSS (SEQ ID NO: 18)

Full hinge (EH1)
EPKSCDKTHTCPPCGGGSSGGGGSG (SEQ ID NO: 22)

Upper hinge
EPKSCDKTHT (SEQ ID NO: 45)

Core hinge
CPPC (SEQ ID NO: 50)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 41)

FIG. 28B

IAB20M γ1 EH3 (N- to C-terminal)

Anti-5T4 variable light (VL) sequence
DIVMTQSPATLSVSPGERATLSCKASQSVSNDVAWYQQKPGQAPRLLISYTSSRYAGVPDRFSGSGSGTDFTLTISSLQA
EDVAVYYCQQDYNSPPTFGQGTKVEIK (SEQ ID NO: 17)

Linker
GSTSGGGGSGGGGSGGGGSS (SEQ ID NO: 62)

Anti-5T4 variable heavy (VH) sequence
QVQLVQSGAEVKKPGASVKVSCKASGYSFTGYYMHWVRQAPGQGLEWIGRINPNNGVTLYNQKFKDRVTMTVDTSIST
AYMELSRLRSDDTAVYYCARSTMITNYVMDYWGQGTLVTVSS (SEQ ID NO: 18)

Full hinge (EH3)
EPKSSDKTHTCPPCPPCGGGSSGGGGSG (SEQ ID NO: 26)

Upper hinge
EPKSSDKTHT (SEQ ID NO: 46)

Core hinge
CPPCPPC (SEQ ID NO: 52)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 41)

FIG. 28C

IAB20M γ1 EH2 (N- to C-terminal)

Anti-5T4 variable light (VL) sequence
DIVMTQSPATLSVSPGERATLSCKASQSVSNDVAWYQQKPGQAPRLLISYTSSRYAGVPDRFSGSGSGTDFTLTISSLQA
EDVAVYYCQQDYNSPPTFGGGTKVEIK (SEQ ID NO: 17)

Linker
GSTSGGGGSGGGGSGGGGSS (SEQ ID NO: 62)

Anti-5T4 variable heavy (VH) sequence
QVQLVQSGAEVKKPGASVKVSCKASGYSFTGYYMHWVRQAPGQGLEWIGRINPNNGVTLYNQKFKDRVTMTVDTSIST
AYMELSRLRSDDTAVYYCARSTMITNYVMDYWGQGTLVTVSS (SEQ ID NO: 18)

Full hinge (EH2)
EPKSSDKTHTCPPCGGGGSSGGGGSG (SEQ ID NO: 24)

Upper hinge
EPKSSDKTHT (SEQ ID NO: 46)

Core hinge
CPPC (SEQ ID NO: 50)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 41)

FIG. 28D

IAB20M γ1 EH5 (N- to C-terminal)

Anti-5T4 variable light (VL) sequence
DIVMTQSPATLSVSPGERATLSCKASQSVSNDVAWYQQKPGQAPRLLISYTSSRYAGVPDRFSGSGSGTDFTLTISSLQAE
DVAVYYCQQDYNSPPTFGQGTKVEIK (SEQ ID NO: 17)

Linker
GSTSGGGGSGGGGSGGGGSS (SEQ ID NO: 62)

Anti-5T4 variable heavy (VH) sequence
QVQLVQSGAEVKKPGASVKVSCKASGYSFTGYYMHWVRQAPGQGLEWIGRINPNNGVTLYNQKFKDRVTMTVDTSISTA
YMELSRLRSDDTAVYYCARSTMITNYVMDYWGQGTLVTVSS (SEQ ID NO: 18)

Full hinge (EH5)
EPKSSDKTHTCPPCPPCPPCGGGSSGGGSG (SEQ ID NO: 30)

Upper hinge
EPKSSDKTHT (SEQ ID NO: 46)

Core hinge
CPPCPPCPPC (SEQ ID NO: 54)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 41)

FIG. 28E

IAB1M γ1 EH1 (N- to C-terminal)

Anti-PSCA (A11) variable light (VL) sequence
DIQLTQSPSTLSASVGDRVTITCSASSSVRFIHWYQQKPGKAPKRLIYDTSKLASGVPSRFSGSGSGTDFTLTISS
LQPEDFATYYCQQWGSSPFTFGQGTKVEIK (SEQ ID NO: 67)

Linker
GSTSGGGGSGGGGSGGGGSS (SEQ ID NO: 62)

Anti-PSCA (A11) variable heavy (VH) sequence
EVQLVEYGGGLVQPGGSLRLSCAASGFNIKDYYIHWVRQAPGKGLEWVAWIDPENGDTEFVPKFQGRATMSAD
TSKNTAYLQMNSLRAEDTAVYYCKTGGFWGQGTLVTVSS (SEQ ID NO: 68)

Full hinge (EH1)
EPKSCDKTHTCPPCGGGSSGGGGSG (SEQ ID NO: 22)

Upper hinge
EPKSCDKTHT (SEQ ID NO: 45)

Core hinge
CPPC (SEQ ID NO: 50)

Lower hinge
GGGSSGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 41)

FIG. 29B

IAB1M γ2 EH2 (N- to C-terminal)

Anti-PSCA (A11) variable light (VL) sequence
DIQLTQSPSTLSASVGDRVTITCSASSSVRFIHWYQQKPGKAPKRLIYDTSKLASGVPSRFSGSGSGTDFTLTI
SSLQPEDFATYYCQQWGSSPFTFGQGTKVEIK (SEQ ID NO: 67)

Linker
GSTSGGGGSGGGGSGGGGSS (SEQ ID NO: 62)

Anti-PSCA (A11) variable heavy (VH) sequence
EVQLVEYGGGLVQPGGSLRLSCAASGFNIKDYYIHWVRQAPGKGLEWVAWIDPENGDTEFVPKFQGRATMS
ADTSKNTAYLQMNSLRAEDTAVYYCKTGGFWGQGTLVTVSS (SEQ ID NO: 68)

Full hinge (EH2)
ERKSCVECPPCPGGGSSGGGGSG (SEQ ID NO: 34)

Upper hinge
ERK (SEQ ID NO: 47)

Core hinge
SCVECPPCP (SEQ ID NO: 56)

Lower hinge
GGGSSGGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLTV
DKSRWQQGNVFSCSVMHEALHNHYTQKSLSLSPGK (SEQ ID NO: 42)

FIG. 29C

IAB1M γ1 EH3 (N- to C-terminal)

Anti-PSCA (A11) variable light (VL) sequence
DIQLTQSPSTLSASVGDRVTITCSASSSVRFIHWYQQKPGKAPKRLIYDTSKLASGVPSRFSGSGSGTDFTLTIS
SLQPEDFATYYCQQWGSSPPFTFGQGTKVEIK (SEQ ID NO: 67)

Linker
GSTSGGGGSGGGGSGGGGSS (SEQ ID NO: 62)

Anti-PSCA (A11) variable heavy (VH) sequence
EVQLVEYGGGLVQPGGSLRLSCAASGFNIKDYYIHWVRQAPGKGLEWVAWIDPENGDTEFVPKFQGRATMSA
DTSKNTAYLQMNSLRAEDTAVYYCKTGGFWGQGTLVTVSS (SEQ ID NO: 68)

Full hinge (EH3)
EPKSSDKTHTCPPCPPCGGGSSGGGGSG (SEQ ID NO: 26)

Upper hinge
EPKSSDKTHT (SEQ ID NO: 46)

Core hinge
CPPCPPC (SEQ ID NO: 52)

Lower hinge
GGGSSGGGGSG (SEQ ID NO: 59)

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 41)

FIG. 29D

IAB20M γ2 EH2 (N- to C-terminal)

Anti-5T4 variable light (VL) sequence
DIVMTQSPATLSVSPGERATLSCKASQSVSNDVAWYQQKPGQAPRLLISYTSSRYAGVPDRFSGSGSGTDFTLTIS
SLQAEDVAVYYCQQDYNSPPTFGQGTKVEIK (SEQ ID NO: 17)

Linker
GSTSGGGSGGGGSGGGGSS (SEQ ID NO: 62)

Anti-5T4 variable heavy (VH) sequence
QVQLVQSGAEVKKPGASVKVSCKASGYSFTGYYMHWVRQAPGQGLEWIGRINPNNGVTLYNQKFKDRVTMTVD
TSISTAYMELSRLRSDDTAVYYCARSTMITNYVMDYWGQGTLVTVSS (SEQ ID NO: 18)

Full hinge (EH2)
ERKSCVECPPCPGGGSSGGGGSG (SEQ ID NO: 34)

Upper hinge
ERK (SEQ ID NO: 47)

Core hinge
SCVECPPCP (SEQ ID NO: 56)

Lower hinge
GGGSSGGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLTVDKS
RWQQGNVFSCSVMHEALHNHYTQKSLSLSPGK (SEQ ID NO: 42)

FIG. 32

IAB25M γ2 EH2 (N- to C-terminal)

Anti-CD3 variable light (VL) sequence
EIVLTQSPATLSLSPGERATLSCSASSSVSYMNWYQQKPGQAPRLLIYDTSKLASGVPAHFRGSGSGTDFTLTI
SSLEPEDFAVYYCQQWSSNPFTFGQGTKVEIK (SEQ ID NO: 19)

Linker
GSTSGGGGSGGGGSGGGGSS (SEQ ID NO: 62)

Anti-CD3 variable heavy (VH) sequence
QVQLVQSGAEVKKPGASVKVSCKASGYTFTRYTMHWVRQAPGQGLEWMGYINPSRGYTNYNQKFKDRVTM
TTDTSISTAYMELSRLRSDDTAVYYCARYYDDHYSLDYWGQGTLVTVSS (SEQ ID NO: 20)

Full hinge (EH2)
ERKSCVECPPCPGGGSSGGGSG (SEQ ID NO: 34)

Upper hinge
ERK (SEQ ID NO: 47)

Core hinge
SCVECPPCP (SEQ ID NO: 56)

Lower hinge
GGGSSGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLTVD
KSRWQQGNVFSCSVMHEALHNHYTQKSLSLSPGK (SEQ ID NO: 42)

IAB2M γ1 EH3 (M1) (SEQ ID NO: 162)

gatattgtgatgacccagagcccgagcctgagcgcagcctgagcgtggcgatcgcgtgacc
attacctgcaaagcgagccagagcgtgggcaccgcggattggtatcagcagaaccg
ggcaaagcgccgaaactgctgatttattgggagagcaacccgccatacccggctgccgat
cgctttaccggcagcggcagcggcaccggatttaccctgaccattagcagcctgcagccg
gaagatttgcggattattttgccagtataacagctatccgctgacctttggcggc
ggcacaaactggaaattaaaagcgagcagcaccagccaggctccaagcgccagcggc
ggcggcggcagcggcgaagtgcagctggtgcagagcggcgcgaagtgaaaaaaccgggc
gcgagcgtgaaagtgagctgcaaaaccagcggctataccttaccgaatataccattcat
tgggtgaaacaggcgagcggcaaagaatttgaagatcgcgcgacccctgaccgtggataaaagc
ggcggcaccacccgctatatggaactgagcagcctgcgcagcgaagatacggcggtgtattat
tgcgcggggctggatggatggcatacccatccctgccgcgccaccgtgaccgtgagcagc
gaaccagcgggaaaatgacagcaaaaccaggtgagcctgacctgcctggtaaaggctttat
agccgcgatattgcggtggaatgcgatagcggcaacgtgttttctgtatagcaaactgaccgtggat
acccgcggtgctgcagcgagcagcaacgtgtttagcgcagcgtgatgcatgaagcgctgcat
aaaagccgcgctgcagccaggcaacgtgttttagctgcagcgtgatgcatgaagcgctgcat
aaccattataccagaaaagcctgagcctgagcccgggc (SEQ ID NO: 162)

FIG. 34A

IAB2M γ1 EH5 (M1) (SEQ ID NO: 163)

```
gatattgtgatgacccagagcctgagcgcgagcgtgggcgatcgcgtgacc
attacctgcaaagcgagccaggatgtgggcaccggtgtgtatcagcagaaccg
gcaaagcgccgaaactgctgatttattgggcgagcaccctgccatattagcggcgtgccgat
cgctttaccggcgagcggcagcggcaccctgaccctgaccatcagcagcctgcagccg
gaagatttttgcggattatttttgccagcagtataacagctatccgctgaccttttggcggc
ggcaccaaactggaaattaaaggcagcaccagcggcggcggcagcggcggcggcagcggc
ggcggcggcagcggcgaagtgcagctggtggaaagcggcggaagtgaaaaaaccgggc
gcgagcgtgaaagttagctgcaaagcgggctataccttttaccgaatacattcat
tgggtgaaacaggcgccgggccaaggcctggaatggattggcaatattaaccctgaacaac
ggcggcaccacccgctatatggaacagcggctttattggggcaaggtgccaccgtgagcagc
tgcgcggcgggcgtggaactttgattatgggcaccctgccctgtgaccaccgtgagcagc
gaaccggcgaaaagcagcgataaaaccagcacggcggtggaaagcaaggccagcgtgtacc
ggcggcgccgagcgaccgcgaagaatgaccagcaagaccaaagccaggccaacaac
ctgccgcccgagcgatattgcggttggattagcgatggcagctttttctgtatagcaaactg
ggcttttatccaccaccgctgctggcagccgatggccagctttttttagctgcagcttttagcgat
tataaaaccgataaaccgcgtgctggcagggcaacgtgtttagctgcagcgtgatgcatgaa
accgtggataaaagccgcattataccccagaaaagcctgagcctgagcccgggc
                                                    (SEQ ID NO: 163)
```

IAB2M γ1 EH8 (M1) (SEQ ID NO: 164)

```
gatattgtgatgaccagagcccgagcagcctgagcgcgagcgtggcgatcgcgtgacc
attacctgcaaagcgagcgagccaggatgtgggcaccggtggattggtatcagcagaaccg
ggcaagcgcgagaactgctgctgatttattgccgagcgccaccgccatacggcgtgccgat
cgctttaccgcgcagcgcggcaccgattttacccgtgccagtacagcagcctgagcagccg
gaagatttgcggattatttttgccagcagtataacagctatccgctgacctttggcggc
ggcaccaaactggaaattaaaggcagcagccagcgcggcggcgcggcagcggcagcggc
gcgagcgtgaaacaggcgagcggcaaagaaattgaagatcgcgacccctgaaaaagc
tgggtgaaacaggcgagcggcaaagaaatttgaagatcgcgacccctgaaaaagc
ggcggcaccacccgctatatggaacttgattgcgcgcagcggcaccaccgccgtgagcagc
tgcgcggggctggaacccgctgggcagcggcaccatgaccgccgcgaaccgcaggtg
ccgtgccgggccgccgccgccggggcgcggccaggacagcagcagccaggtgagcctgcctg
tataagcttatccgagcgatattgcggtggaatgccgagcagcagccagccgaa
gtgaaagctttatccgagcgatattgcggtggatgccgagcagcagccagccgaa
aacaactataaaaccaccccggataaaaaccgcggcagcaggcaacgtgtttagctgcagcgtgatg
catgaagcgctgcataaccattataccagaaaagcctgagcctgagcccgggc (SEQ ID NO: 164)
```

FIG. 34C

IAB2M γ1 EH3 (M2) (SEQ ID NO: 165)

```
gaagtgcagctggtgcagagcggcggcggaagtgaaaaaccgggcgcgagcgtgaaatt
agctgcaaaaccagcggctataccttaccgaatataccattggtgaaacaggcg
agcggcaaaggcctggaatgattggcaacattaacccgaacaacggcaccacctat
aaccagaaatttgaagatcgcgcagcgcgaagatacgcggtgtattattgcgcggcggctgg
atggaactgagcagcctgcgcagcgaagatacgcggtgtattattgcgcggcggctgg
aactttgattattggggccagggcaccctggtgaccgtgagcagcggcagcaccagcggc
ggcggcggcagcggcggcggcgagcagcggcggcgatattgtgatgacccagagc
ccgagcagcctgagcgcgcggtgggcgatcgcgtgaccattacctgcaaagcgagccag
gatgtgggcacccgcgatggcgtggattgtatcagcagaaacgggcaaagcgcgaaactgctg
atttattggcaccgcatattctcgaccctgcagtctgccgaaagatttgccgaaagattttgcggattattttt
ggcaccgattttaccctgaccattagcagcctgcagccggaagatttgcggattttgccgattattttt
tgccagcagtataaacagcatcgctgaccctacctgcggcggcaccgaaactgaaattaaa
gaaccgaaaagcagcgatataaaaacccatcagcggaaccagcagggtataccctgcgccgg
agcagcggcgaaatgacccaaaaaccaggtgggaaagcaacggccagctgcctggtaaggctttat
agccgcgatattgcggtggatgcgatagcgatggcagctgtttttagctgcagcagtgatggat
ccgagcgatatgcggtgggatagcgatggcaacgtgttttagcagcagtgatggat
accccgcgcttgctggcagcagggcaacgtgttttagcgtgatggcgtctgcat
aaaagcctgcagccctgagcctgagccctgatagcaacctgatatagcaacggtggat
aaccattaccccagaaaagcctgagcctgagccccgggc (SEQ ID NO: 165)
```

FIG. 34D

IAB2M γ1 EH5 (M2) (SEQ ID NO: 5)

```
gaagtgcagctggtgcagagcggcgcggaagtgaaaaaaccggggagcgtgaaatt
agctgcaaaaccagcggctataccttaccgaatataccattgggtgaaacaggcg
agcggcaaagccctggaattggcaacggccgatggcagggcaccacctat
aaccagaaatttgaaagatcgcgcgacccctgaccgtggataaaagcaccaccgcgtat
atggaactgagcagcctgcgcagcgaagataccggcgtgtattattgcgcgcggctgg
aactttgattattgggcaggcgcgggccaccaccggcgcagcaccagcggc
ggcggcagcggcggcggcagcggcggcggcagcggccagcagcagcagcagagc
ccgagcagcctgagcgcggcgagcgtgggcgatcgcgttaccggcagcggcagc
gatgtggcaccggctggattggtatcagcagaaaccggatcgcttaccggcagcggcagc
atttattgggcgagcaccctgaccctgaccggcgatccgaccccagcagcagcagcagc
ggcaccgattttaccct

IAB2M γ1 EH8 (M2) (SEQ ID NO: 6)

```
gaagtgcagctggtgcagagcggcgcggaagtgaaaaaacggcgcgagcgtgaaatt
agctgcaaaaccagcggctataccttaccgaatataccattcattgggtgaaacaggcg
agcggcaaaggcctggaatggattggcaacattaacccgaacaacggcaccacctat
aaccagaaatttgaagatcgcgcgacccctgaccgtggataaaagcaccacccgtat
atggaactgagcagcctgcgcagcgaagataccgcggtgtattattgcgcgggctgg
aactttgattattggggccagggcaccaccgtgaccgtgagccgtagcagccagcgcc
ggcggcagcggcctgagcgcgagcggtgggcggcgatcgcgtgaccattacctgcaaaagccgaaactgctg
ccgagcagcctgagccgcgagcggtgggcgaaccggatcgcgaaccggatcgcgcagcggcagc
gatgtgggcaccgcgcggtggattggtatcagcagaaaccggattgtgcggattattt
atttattgggcaccggcgagcaccctgaccctgaccctgaccagcagctagcggtatcgcggatcgcgaaactgaaattaaa
ggcaccgatttacctcgctgaccatcatcccgctgaccatccaccatccgctgaccctgggcggcaccctggcgggcgatacctgccgcgtccgtgcccg
tgccagcagtataaccaccccgctgggcgatacctgccgcgtccgtgcccg
gaactgaaaaaccgtcggcgccagcgcggccagagcaccaggaccaaaaccaggtgagcctgaccttgtccctg
ccgtgcgggcgccgatacctggaaatgtcgagcgcagcaacggccagcctgcctg
tatacccgccgcgagcgcgatatgcggtggatagcgatggcagcttttttcgtatagc
gtgaaaggcttttatccgagcgatattgcggtggaatgggaagcagccagccgaa
aacaactacaagacccaccccgctgatggcagcaggcgcaacgtgtttagctgcagcgtgatg
catgaagcgctgcataaccattataccagaaaagcctgagcctgagcccgggc
```
(SEQ ID NO: 6)

FIG. 34F

M1 = VL – VH
M2 = VH – VL
Linkers
Hinges

IAB2M γ1 EH3 (M1) (SEQ ID NO: 7)
DIVMTQSPSSLSASVGDRVTITCKASQDVGTAVDWYQQKPGKTAVDWYQQKPGKAPKLLIYWASTRHTGVPDRFTGSGSGTDFTLTI
SSLQPEDFADYFCQQYNSYPLTFGGGTKLEIKGSTSGGGSGGGSGGGSSEVQLVQSGAEVKKPGASVKISCKTS
GYTFTEYTIHWVKQASGKGLEWIGNINPNNGGTTYNQKFEDRATLTVDKSTSTAYMELSSLRSEDTAVYYCAAG
WNFDYWGQGTTVTVSSEPKSSDKTHTCPPCPGGGSGGGGSGQPREPQVYTLPPSREEMTKNQVSLTCLVK
GFYPSDIAVEWESNGQPENNYKTTPPVLDSDGSFFLYSKLTVDKSRWQQGNVFSCSVMHEALHNHYTQKSLSLS
PG (SEQ ID NO: 7)

IAB2M γ1 EH5 (M1) (SEQ ID NO: 8)
DIVMTQSPSSLSASVGDRVTITCKASQDVGTAVDWYQQKPGKAPKLLIYWASTRHTGVPDRFTGSGSGTDFTLTI
SSLQPEDFADYFCQQYNSYPLTFGGGTKLEIKGSTSGGGSGGGSGGGSSEVQLVQSGAEVKKPGASVKISCKTS
GYTFTEYTIHWVKQASGKGLEWIGNINPNNGGTTYNQKFEDRATLTVDKSTSTAYMELSSLRSEDTAVYYCAAG
WNFDYWGQGTTVTVSSEPKSSDKTHTCPPCPCPGGGSGGGGSGQPREPQVYTLPPSREEMTKNQVSLTC
LVKGFYPSDIAVEWESNGQPENNYKTTPPVLDSDGSFFLYSKLTVDKSRWQQGNVFSCSVMHEALHNHYTQKSL
SLSPG (SEQ ID NO: 8)

FIG. 35A

IAB2M γ1 EH8 (M1) (SEQ ID NO: 9)

DIVMTQSPSSLSASVGDRVTITCKASQDVGTAVDWYQQKPGKAPKLLIYWASTRHTGVPDRFTGSGSGTDFTLTISSLQPEDFADYFCQQYNSYPLTFGGGTKLEIKGSTSGGGSGGGGSGGGGSEVQLVQSGAEVKKPGASVKISCKTSGYTFTEYTIHWVKQASGKGLEWIGNINPNNGGTTYNQKFEDRATLTVDKSTSTAYMELSSLRSEDTAVYYCAAGWNFDYWGQGTTVTVSSELKTPLGDTTHTCPPCPPCGGGSGGGSGGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 9)

IAB2M γ1 EH3 (M2) (SEQ ID NO: 10)

EVQLVQSGAEVKKPGASVKISCKTSGYTFTEYTIHWVKQASGKGLEWIGNINPNNGGTTYNQKFEDRATLTVDKSTSTAYMELSSLRSEDTAVYYCAAGWNFDYWGQGTTVTVSSGSTSGGGSGGGGSGGGGSDIVMTQSPSSLSASVGDRVTITCKASQDVGTAVDWYQQKPGKAPKLLIYWASTRHTGVPDRFTGSGSGTDFTLTISSLQPEDFADYFCQQYNSYPLTFGGGTKLEIKEPKSSDKTHTCPPCPPCGGGSGGGSGGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 10)

FIG. 35B

IAB2M γ1 EH5 (M2) (SEQ ID NO: 11)
EVQLVQSGAEVKKPGASVKISCKTSGYTFTEYTIHWVKQASGKGLEWIGNINPNNGGTTYNQKFEDRATLTVDKS
TSTAYMELSSLRSEDTAVYYCAAGWNFDYWGQGTTVTVSSGSTSGGGSGGGSSDIVMTQSPSSLSASV
GDRVTITCKASQDVGTAVDWYQQKPGKAPKLLIYWASTRHTGVPDRFTGSGSGTDFTLTISSLQPEDFADYFCQ
QYNSYPLTFGGGTKLEIKEPKSSDKTHTCPPCPPCGGGSGGGSGGQPREPQVYTLPPSREEMTKNQVSLTC
LVKGFYPSDIAVEWESNGQPENNYKTTPPVLDSDGSFFLYSKLTVDKSRWQQGNVFSCSVMHEALHNHYTQKSL
SLSPG (SEQ ID NO: 11)

IAB2M γ1 EH8 (M2) (SEQ ID NO: 12)
EVQLVQSGAEVKKPGASVKISCKTSGYTFTEYTIHWVKQASGKGLEWIGNINPNNGGTTYNQKFEDRATLTVDKS
TSTAYMELSSLRSEDTAVYYCAAGWNFDYWGQGTTVTVSSGSTSGGGSGGGSSDIVMTQSPSSLSASV
GDRVTITCKASQDVGTAVDWYQQKPGKAPKLLIYWASTRHTGVPDRFTGSGSGTDFTLTISSLQPEDFADYFCQ
QYNSYPLTFGGGTKLEIKELKTPLGDTTHTCPPCPPCGGGSGGGSGGQPREPQVVYTLPPSREEMTKNQVSL
TCLVKGFYPSDIAVEWESNGQPENNYKTTPPVLDSDGSFFLYSKLTVDKSRWQQGNVFSCSVMHEALHNHYTQK
SLSLSPG (SEQ ID NO: 12)

FIG. 35C

VH and VL domains

IAB2M variable light (VL) and heavy (VH) sequences

VL
DIVMTQSPSSLSASVGDRVTITCKASQDVGTAVDWYQQKPGKAPKLLIYWASTRH
TGVPDRFTGSGSGTDFTLTISSLQPEDFADYFCQQYNSYPLTFGGGTKLEIK
(SEQ ID NO: 13)

VH
EVQLVQSGAEVKKPGASVKISCKTSGYTFTEYTIHWVKQASGKGLEWIGNINPNN
GGTTYNQKFEDRATLTVDKSTSTAYMELSSLRSEDTAVYYCAAGWNFDYWGQGTT
VTVSS (SEQ ID NO: 14)

FIG. 36A

IAB22M variable light (VL) and heavy (VH) sequences

VL
DVQITQSPSSLSASVGDRVTITCRTSRSISQYLAWYQQKPGKVPKLLIYSGSTL
QSGVPSRFSGSGSGTDFTLTISSLQPEDVATYYCQQHNENPLTFGGGTKVEIK
(SEQ ID NO: 15)

VH
EVQLVESGGGLVQPGGSLRLSCAASGFNIKDTYIHFVRQAPGKGLEWIGRIDPA
NDNTLYASKFQGKATISADTSKNTAYLQMNSLRAEDTAVYYCGRGYGYVFDHW
GQGTLVTVSS (SEQ ID NO: 16)

FIG. 36B

IAB20M variable light (VL) and heavy (VH) sequences

VL
DIVMTQSPATLSVSPGERATLSCKASQSVSNDVAWYQQKPGQAPRLLISYTSSR
YAGVPDRFSGSGSGTDFTLTISSLQAEDVAVYYCQQDYNSPPTFGQGTKVEIK
(SEQ ID NO: 17)

VH
QVQLVQSGAEVKKPGASVKVSCKASGYSFTGYYMHWVRQAPGQGLEWIGRINPN
NGVTLYNQKFKDRVTMTVDTSISTAYMELSRLRSDDTAVYYCARSTMITNYVMD
YWGQGTLVTVSS (SEQ ID NO: 18)

FIG. 36C

Anti-CD3 variable light (VL) and heavy (VH) sequences

VL
EIVLTQSPATLSLSPGERATLSCSASSSVSYMNWYQQKPGQAPRLLIYDTSKLA
SGVPAHFRGSGSGTDFTLTISSLEPEDFAVYYCQQWSSNPFTFGQGTKVEIK
(SEQ ID NO: 19)

VH
QVQLVQSGAEVKKPGASVKVSCKASGYTFTRYTMHWVRQAPGQGLEWMGYINPS
RGYTNYNQKFKDRVTMTTDTSISTAYMELSRLRSDDTAVYYCARYYDDHYSLDY
WGQGTLVTVSS (SEQ ID NO: 20)

FIG. 36D

IAB1M (A11) variable light (VL) and heavy (VH) sequences

VL
DIQLTQSPSTLSASVGDRVTITCSASSSVRFIHWYQQKPGKAPKRLIYDTSKLA
SGVPSRFSGSGSGTDFTLTISSLQPEDFATYYCQQWGSSPFTFGQGTKVEIK
(SEQ ID NO: 67)

VH
EVQLVEYGGGLVQPGGSLRLSCAASGFNIKDYYIHWVRQAPGKGLEWVAWIDPE
NGDTEFVPKFQGRATMSADTSKNTAYLQMNSLRAEDTAVYYCKTGGFWGQGTLV
TVSS (SEQ ID NO: 68)

FIG. 36E

Linker sequences:

| | | |
|---|---|---|
| GGGGS | 5 aa | (SEQ ID NO: 66) |
| GGGGSGGGGS | 10 aa | (SEQ ID NO: 65) |
| GGGGSGGGGSGGGGS | 15 aa | (SEQ ID NO: 64) |
| GSTSGGGSGGGS | 12 aa | (SEQ ID NO: 63) |
| GSTSGGGSGGGSGGGGSS | 18 aa | (SEQ ID NO: 62) |

FIG. 37

| Full hinge: | Upper | Core | Lower |
|---|---|---|---|
| Human IgG1 NH1 (SEQ ID NO: 21) | EPKSCDKTHT (SEQ ID NO: 45) | CPPCP (SEQ ID NO: 51) | APELLGGP (SEQ ID NO: 58) |
| Human IgG1 EH1 (SEQ ID NO: 22) | EPKSCDKTHT (SEQ ID NO: 45) | CPPC (SEQ ID NO: 50) | GGGSSGGGSG (SEQ ID NO: 59) |
| Human IgG1 NH2 (SEQ ID NO: 23) | EPKSSDKTHT (SEQ ID NO: 46) | CPPCP (SEQ ID NO: 51) | APELLGGP (SEQ ID NO: 58) |
| Human IgG1 EH2 (SEQ ID NO: 24) | EPKSSDKTHT (SEQ ID NO: 46) | CPPC (SEQ ID NO: 50) | GGGSSGGGSG (SEQ ID NO: 59) |
| Human IgG1 NH3 (SEQ ID NO: 25) | EPKSSDKTHT (SEQ ID NO: 46) | CPPCPPC (SEQ ID NO: 52) | APELLGGP (SEQ ID NO: 58) |
| Human IgG1 EH3 (SEQ ID NO: 26) | EPKSSDKTHT (SEQ ID NO: 46) | CPPCPPC (SEQ ID NO: 52) | GGGSSGGGSG (SEQ ID NO: 59) |
| Human IgG1 NH4 (SEQ ID NO: 27) | EPKSSDKTHT (SEQ ID NO: 46) | CPPCVECPPC (SEQ ID NO: 53) | APELLGGP (SEQ ID NO: 58) |
| Human IgG1 EH4 (SEQ ID NO: 28) | EPKSSDKTHT (SEQ ID NO: 46) | CPPCVECPPC (SEQ ID NO: 53) | GGGSSGGGSG (SEQ ID NO: 59) |
| Human IgG1 NH5 (SEQ ID NO: 29) | EPKSSDKTHT (SEQ ID NO: 46) | CPPCPPCPPC (SEQ ID NO: 54) | APELLGGP (SEQ ID NO: 58) |
| Human IgG1 EH5 (SEQ ID NO: 30) | EPKSSDKTHT (SEQ ID NO: 46) | CPPCPPCPPC (SEQ ID NO: 54) | GGGSSGGGSG (SEQ ID NO: 59) |

FIG. 38

| Full hinge: | Upper | Core | Lower |
|---|---|---|---|
| Human IgG2 NH1 (SEQ ID NO: 31) | ERK (SEQ ID NO: 47) | CCVECPPCP (SEQ ID NO: 55) | APPVAGP (SEQ ID NO: 60) |
| Human IgG2 EH1 (SEQ ID NO: 32) | ERK (SEQ ID NO: 47) | CCVECPPCP (SEQ ID NO: 55) | GGGSSGGGSG (SEQ ID NO: 59) |
| Human IgG2 NH2 (SEQ ID NO: 33) | ERK (SEQ ID NO: 47) | SCVECPPCP (SEQ ID NO: 56) | APPVAGP (SEQ ID NO: 60) |
| Human IgG2 EH2 (SEQ ID NO: 34) | ERK (SEQ ID NO: 47) | SCVECPPCP (SEQ ID NO: 56) | GGGSSGGGSG (SEQ ID NO: 59) |
| IgG3/IgG1 EH6 (SEQ ID NO: 35) | ELKTPLGDTTHT (SEQ ID NO: 48) | CVECPPC (SEQ ID NO: 57) | GGGSSGGGSG (SEQ ID NO: 59) |
| IgG3/IgG1 EH7 (SEQ ID NO: 36) | ELKTPLGDTTHT (SEQ ID NO: 48) | CPPCPPC (SEQ ID NO: 52) | GGGSSGGGSG (SEQ ID NO: 59) |
| IgG3/IgG1 EH8 (SEQ ID NO: 37) | ELKTPLGDTTHT (SEQ ID NO: 48) | CPPCPPCPPC (SEQ ID NO: 54) | GGGSSGGGSG (SEQ ID NO: 59) |
| IgG4 NH (SEQ ID NO: 38) | ESKYGPP (SEQ ID NO: 49) | CPPCP (SEQ ID NO: 51) | APEFLGGP (SEQ ID NO: 61) |
| IgG4 EH (SEQ ID NO: 39) | ESKYGPP (SEQ ID NO: 49) | CPPCP (SEQ ID NO: 51) | GGGSSGGGSG (SEQ ID NO: 59) |

FIG. 38 continued

CH3 domains:

Human IgG1 CH3 (G1m1 allotype)
GQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 40)

Human IgG1 CH3 (nG1m1 allotype)
GQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 41)

Human IgG2 CH3
GQPREPQVYTLPPSREEMTKNQVSLTCLVKGFYPSDIAVEWESNGQPENNYKTTPPMLDSDGSFFLYSKLTVD
KSRWQQGNVFSCSVMHEALHNHYTQKSLSLSPGK (SEQ ID NO: 42)

Human IgG3 CH3
GQPREPQVYTLPPSREEMTKNQVSLTCLVKGFYPSDIAVEWESSGQPENNYNTTPPMLDSDGSFFLYSKLTVD
KSRWQQGNIFSCSVMHEALHNRFTQKSLSLSPGK (SEQ ID NO: 43)

Human IgG4 CH3
GQPREPQVYTLPPSQEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK (SEQ ID NO: 44)

FIG. 39

Alignment compared IAB22M γ1 EH1(M1) (SEQ ID NO: 105) vs IAB22M γ1 EH3 (M1) (SEQ ID NO: 106), differences shown in box.

```
IAB22M γ1 EH1(M1)  METDTLLLWVLLLWVPGSTGDVQITQSPSSLSASVGDRVTITCRTSRSISQYLAWYQQKP  60
IAB22M γ1 EH3(M1)  METDTLLLWVLLLWVPGSTGDVQITQSPSSLSASVGDRVTITCRTSRSISQYLAWYQQKP  60

IAB22M γ1 EH1(M1)  GKVPKLLIYSGSTLQSGVPSRFSGSGSGTDFTLTISSLQPEDVATYYCQQHNENPLTFGG  120
IAB22M γ1 EH3(M1)  GKVPKLLIYSGSTLQSGVPSRFSGSGSGTDFTLTISSLQPEDVATYYCQQHNENPLTFGG  120

IAB22M γ1 EH1(M1)  GTKVEIKGSTSGGGSGGGGSGGGGSSEVQLVESGGGLVQPGGSLRLSCAASGFNIKDTYIH  180
IAB22M γ1 EH3(M1)  GTKVEIKGSTSGGGSGGGGSGGGGSSEVQLVESGGGLVQPGGSLRLSCAASGFNIKDTYIH  180

IAB22M γ1 EH1(M1)  FVRQAPGKGLEWIGRIDPANDNTLYASKFQGKATISADTSKNTAYLQMNSLRAEDTAVYY  240
IAB22M γ1 EH3(M1)  FVRQAPGKGLEWIGRIDPANDNTLYASKFQGKATISADTSKNTAYLQMNSLRAEDTAVYY  240

IAB22M γ1 EH1(M1)  CGRGYGYYVFDHWGQGTLVTVSSEPKS C DKTHTCP ---- PCGGGSSGGGSGGQREPQVYT  297
IAB22M γ1 EH3(M1)  CGRGYGYYVFDHWGQGTLVTVSSEPKS S DKTHTCP PCP PCGGGSSGGGSGGQREPQVYT  300

IAB22M γ1 EH1(M1)  LPPSR DEL  TKNQVSLTCLVKGFYPSDIAVEWESNGQPENNYKTTPPVLDSDGSFFLYSKL  357
IAB22M γ1 EH3(M1)  LPPSR EEM  TKNQVSLTCLVKGFYPSDIAVEWESNGQPENNYKTTPPVLDSDGSFFLYSKL  360

IAB22M γ1 EH1(M1)  TVDKSRWQQGNVFSCSVMHEALHNHYTQKSLSLSPG K  394  (SEQ ID NO: 105)
IAB22M γ1 EH3(M1)  TVDKSRWQQGNVFSCSVMHEALHNHYTQKSLSLSPG -  396  (SEQ ID NO: 106)
```

FIG. 40

IAB22M γ1 EH3(M1), CDR regions are defined by Chothia definition (SEQ ID NO: 106)

```
atggagaccgatacctgctgctgtgggtgctgctgctgtgggtgcccggctccacaggc
 M   E   T   D   L   L   L   W   V   L   L   L   W   V   P   G   S   T   G
```
Signal peptide sequence

```
gatgtgcagatcacacagagccctagcagcctgagcgccagcgtgggagatagagtcacc
 D   V   Q   I   T   Q   S   P   S   S   L   S   A   S   V   G   D   R   V   T
```
VL

```
Atcacatgc aggaccagcagaagcattagccagtacctggcc tggtaccagcaaaagccc
 I   T   C   R   T   S   R   S   I   S   Q   Y   L   A   W   Y   Q   Q   K   P
```
                            LCDR1

```
Ggcaaggtgcccaagctgctgatctac agcggctccaccctgcagagc ggcgtgcccagc
 G   K   V   P   K   L   L   I   Y   S   G   S   T   L   Q   S   G   V   P   S
```
                              LCDR2

```
agattctccggctccggaagcggcacagactttaccctgaccatctcctccctgcagccc
 R   F   S   G   S   G   S   G   T   D   F   T   L   T   I   S   S   L   Q   P
```

```
gaggatgtcgccacctactactgc cagcagcacaacgaaaaccccctgaca tttggcggc
 E   D   V   A   T   Y   Y   C   Q   Q   H   N   E   N   P   L   T   F   G   G
```
                              LCDR3

```
ggcaccaaggtggagatcaag ggcagcaccagcggtggaggaagtggaggtggaagtgga
 G   T   K   V   E   I   K   G   S   T   S   G   G   G   S   G   G   G   S   G
```
                              Linker

```
Ggaggcggaagcagc gaggtgcagctggtggagagtggtggaggactggtgcagcccgga
 G   G   G   S   S   E   V   Q   L   V   E   S   G   G   G   L   V   Q   P   G
```
Linker         VH

```
Ggcagcctgagactgagctgtgctgcctcc ggattcaatatcaaggacacc tacatccac
 G   S   L   R   L   S   C   A   A   S   G   F   N   I   K   D   T   Y   I   H
```
                              HCDR1

```
ttcgtgagacaggcccccggcaagggactggagtggattggaaggatc gaccccgccaac
 F   V   R   Q   A   P   G   K   G   L   E   W   I   G   R   I   D   P   A   N
```
                                HCDR2

```
gacaac accctgtacgccagcaaattccagggcaaggccacaatcagcgccgacaccagc
 D   N   T   L   Y   A   S   K   F   Q   G   K   A   T   I   S   A   D   T   S
```
HCDR2

```
aagaacaccgcctatctgcagatgaactccctgagagccgaggacacagccgtgtactac
 K   N   T   A   Y   L   Q   M   N   S   L   R   A   E   D   T   A   V   Y   Y
```

FIG. 41

```
tgcggcagg ggctacggctattacgtgttcgaccac tggggccagggcaccctggtgaca
 C   G  R  G  Y  G  Y  Y  V  F  D  H  W  G  Q  G  T  L  V  T
                    HCDR3 gtgagcagc gaacccaagagctccgacaagacccacacc tgtccccttgccctccttgt
 V  S  S  E  P  K  S  S  D  K  T  H  T   C  P  P  C  P  P  C
            Upper hinge                       Core hinge ggcggaggaagctccggaggcggaagcggag gacagcctagggagccccaggtgtatacc
 G  G  G  S  S  G  G  G  S  G    G  Q  P  R  E  P  Q  V  Y  T
       Lower hinge                      CH3 ctccccccctccagggaagagatgaccaagaaccaggtgagcctgacctgcctcgtgaag
 L  P  P  S  R  E  E  M  T  K  N  Q  V  S  L  T  C  L  V  K ggcttttatccctccgatatcgccgtggagtgggagagcaacggccagcctgagaacaat
 G  F  Y  P  S  D  I  A  V  E  W  E  S  N  G  Q  P  E  N  N tacaagaccaccccccctgtgctggactccgatggcagcttcttcctgtattccaagctg
 Y  K  T  T  P  P  V  L  D  S  D  G  S  F  F  L  Y  S  K  L accgtcgacaagtccaggtggcaacagggcaacgtcttcagctgcagcgtgatgcacgag
 T  V  D  K  S  R  W  Q  Q  G  N  V  F  S  C  S  V  M  H  E gccctgcacaatcactacacccagaagtccctctccctgagccccggctga (SEQ ID NO: 140)
 A  L  H  N  H  Y  T  Q  K  S  L  S  L  S  P  G  Stop (SEQ ID NO: 106)
```

FIG. 41
continued

IAB22M γ1 EH5(M1) (SEQ ID NO: 107)

```
atggagacagacaccctcctcctgtgggtgctgctgctgtgggtgcccggatccaccgga
 M  E  T  D  T  L  L  W  V  L  L  W  V  P  G  S  T  G
gacgtgcagatcacacagagccccagctccctgtccgctagcgtgggcgacagagtgacc
 D  V  Q  I  T  Q  S  P  S  S  L  S  A  S  V  G  D  R  V  T
atcacctgcaggaccagcaggagcatctcccagtacctcgcttggtaccagcagaagcct
 I  T  C  R  T  S  R  S  I  S  Q  Y  L  A  W  Y  Q  Q  K  P
ggcaaggtgcccaagctgctgatttacagcggatccaccctgcagagcggcgtgcctagc
 G  K  V  P  K  L  L  I  Y  S  G  S  T  L  Q  S  G  V  P  S
aggtttagcggcagcggatccggaacagacttcaccctgaccatcagcagcctgcagcct
 R  F  S  G  S  G  S  G  T  D  F  T  L  T  I  S  S  L  Q  P
gaagatgtggccacctactactgtcagcagcacaacgaaaaccccctcaccttcggcggc
 E  D  V  A  T  Y  Y  C  Q  Q  H  N  E  N  P  L  T  F  G  G
ggcacaaaggtggaaatcaagggcagcacctccggaggaggcagcggcggaggcagcgga
 G  T  K  V  E  I  K  G  S  T  S  G  G  S  G  G  G  S  G
ggcggcggctccagcgaagtgcagctggtcgagagcggaggcggactggtgcaacccgga
 G  G  G  S  S  E  V  Q  L  V  E  S  G  G  G  L  V  Q  P  G
ggaagcctgaggctgagctgtgccgccagcggcttcaacatcaaggacacatacattcac
 G  S  L  R  L  S  C  A  A  S  G  F  N  I  K  D  T  Y  I  H
tttgtgaggcaggctcctggaaagggcctggagtggatcggcagaatcgaccccgctaac
 F  V  R  Q  A  P  G  K  G  L  E  W  I  G  R  I  D  P  A  N
gacaacaccctgtacgccagcaagttccagggcaaggccaccatctccgccgacacaagc
 D  N  T  L  Y  A  S  K  F  Q  G  K  A  T  I  S  A  D  T  S
aagaataccgcctacctgcagatgaactccctgagggccgaggataccgccgtgtactac
 K  N  T  A  Y  L  Q  M  N  S  L  R  A  E  D  T  A  V  Y  Y
tgcggcaggggctatggctactacgtgtttgaccactggggccagggcacactggtgaca
 C  G  R  G  Y  G  Y  Y  V  F  D  H  W  G  Q  G  T  L  V  T
gtgagctccgagcccaagagctccgacaagacacacacctgccctccttgcccccttgt
 V  S  S  E  P  K  S  S  D  K  T  H  T  C  P  P  C  P  P  C
cctccctgtggaggaggaagcagcggaggaggaagcggcggacagcccagagagcctcaa
 P  P  C  G  G  G  S  S  G  G  G  S  G  G  Q  P  R  E  P  Q
gtgtatacactgccccctccagggaagagatgaccaagaaccaggtgagcctgacatgc
 V  Y  T  L  P  P  S  R  E  E  M  T  K  N  Q  V  S  L  T  C
ctggtcaaaggcttctaccccagcgatattgctgtggagtgggagagcaacggccagccc
 L  V  K  G  F  Y  P  S  D  I  A  V  E  W  E  S  N  G  Q  P
gagaacaactacaagaccacaccccccgtcctggatagcgatggcagcttcttcctgtac
```

FIG. 42

```
E   N   N   Y   K   T   T   P   P   V   L   D   S   D   G   S   F   F   L   Y
agcaagctgaccgtggacaagtccaggtggcagcagggcaacgtcttctcctgcagcgtg
S   K   L   T   V   D   K   S   R   W   Q   Q   G   N   V   F   S   C   S   V
atgcacgaggctctgcataaccactacacacagaagtccctcagcctgagccctggatga  (SEQ ID NO: 141)
M   H   E   A   L   H   N   H   Y   T   Q   K   S   L   S   L   S   P   G   Stop  (SEQ ID NO: 107)
```

FIG. 42
continued

IAB22M γ1 EH7(M1) (SEQ ID NO: 108)

```
atggagacagacaccctcctcctgtgggtgctgctgctgtgggtgccgggatccaccgga
 M  E  T  D  T  L  L  W  V  L  L  L  W  V  P  G  S  T  G
gacgtgcagatcacacagagccccagctccctgtccgctagcgtgggcgacagagtgacc
 D  V  Q  I  T  Q  S  P  S  S  L  S  A  S  V  G  D  R  V  T
atcacctgcaggaccagcaggagcatctcccagtacctcgcttggtaccagcagaagcct
 I  T  C  R  T  S  R  S  I  S  Q  Y  L  A  W  Y  Q  Q  K  P
ggcaaggtgcccaagctgctgatttacagcggatccaccctgcagagcggcgtgcctagc
 G  K  V  P  K  L  L  I  Y  S  G  S  T  L  Q  S  G  V  P  S
aggtttagcggcagcggatccggaacagacttcaccctgaccatcagcagcctgcagcct
 R  F  S  G  S  G  S  G  T  D  F  T  L  T  I  S  S  L  Q  P
gaagatgtggccacctactactgtcagcagcacaacgaaaaccccctcaccttcggcggc
 E  D  V  A  T  Y  Y  C  Q  Q  H  N  E  N  P  L  T  F  G  G
ggcacaaaggtggaaatcaagggcagcacctccggaggaggcagcggcggaggcagcgga
 G  T  K  V  E  I  K  G  S  T  S  G  G  S  G  G  G  S  G
ggcggcggctccagcgaagtgcagctggtcgagagcggaggcggactggtgcaacccgga
 G  G  G  S  S  E  V  Q  L  V  E  S  G  G  G  L  V  Q  P  G
ggaagcctgaggctgagctgtgccgccagcggcttcaacatcaaggacacatacattcac
 G  S  L  R  L  S  C  A  A  S  G  F  N  I  K  D  T  Y  I  H
tttgtgaggcaggctcctggaaagggcctggagtggatcggcagaatcgacccgctaac
 F  V  R  Q  A  P  G  K  G  L  E  W  I  G  R  I  D  P  A  N
gacaacaccctgtacgccagcaagttccagggcaaggccaccatctccgccgacacaagc
 D  N  T  L  Y  A  S  K  F  Q  G  K  A  T  I  S  A  D  T  S
aagaataccgcctacctgcagatgaactccctgagggccgaggataccgccgtgtactac
 K  N  T  A  Y  L  Q  M  N  S  L  R  A  E  D  T  A  V  Y  Y
tgcggcaggggctatggctactacgtgtttgaccactggggccagggcacactggtgaca
 C  G  R  G  Y  G  Y  Y  V  F  D  H  W  G  Q  G  T  L  V  T
gtgagctccagctgaagacacctctgggcgacacaacacacacctgcccccttgtcct
 V  S  S  E  L  K  T  P  L  G  D  T  T  H  T  C  P  P  C  P
ccctgtggaggaggaagcagcggaggaggaagcggcggacagcccagagagcctcaagtg
 P  C  G  G  G  S  S  G  G  G  S  G  G  Q  P  R  E  P  Q  V
tataccctgccccctccagggaagagatgaccaagaaccaggtgagcctgacatgcctg
 Y  T  L  P  P  S  R  E  E  M  T  K  N  Q  V  S  L  T  C  L
gtcaaaggcttctaccccagcgatattgctgtggagtgggagagcaacggccagcccgag
 V  K  G  F  Y  P  S  D  I  A  V  E  W  E  S  N  G  Q  P  E
aacaactacaagaccacaccccccgtcctggatagcgatggcagcttcttcctgtacagc
 N  N  Y  K  T  T  P  P  V  L  D  S  D  G  S  F  F  L  Y  S
```

FIG. 43

```
aagctgaccgtggacaagtccaggtggcagcagggcaacgtcttctcctgcagcgtgatg
 K   L  T  V  D  K  S  R  W  Q  Q  G  N  V  F  S  C  S  V  M
cacgaggctctgcataaccactacacacagaagtccctcagcctgagccctggatga    (SEQ ID NO: 142)
 H   E  A  L  H  N  H  Y  T  Q  K  S  L  S  L  S  P  G  Stop (SEQ ID NO: 108)
```

FIG. 43
continued

IAB22M γ1 EH8(M1) (SEQ ID NO: 109)

```
atggagacagacaccctcctcctgtgggtgctgctgctgtgggtgcccggatccaccgga
 M  E  T  D  T  L  L  W  V  L  L  L  W  V  P  G  S  T  G
gacgtgcagatcacacagagccccagctccctgtccgctagcgtgggcgacagagtgacc
 D  V  Q  I  T  Q  S  P  S  S  L  S  A  S  V  G  D  R  V  T
atcacctgcaggaccagcaggagcatctcccagtacctcgcttggtaccagcagaagcct
 I  T  C  R  T  S  R  S  I  S  Q  Y  L  A  W  Y  Q  Q  K  P
ggcaaggtgcccaagctgctgatttacagcggatccaccctgcagagcggcgtgcctagc
 G  K  V  P  K  L  L  I  Y  S  G  S  T  L  Q  S  G  V  P  S
aggtttagcggcagcggatccggaacagacttcaccctgaccatcagcagcctgcagcct
 R  F  S  G  S  G  S  G  T  D  F  T  L  T  I  S  S  L  Q  P
gaagatgtggccacctactactgtcagcagcacaacgaaaaccccctcaccttcggcggc
 E  D  V  A  T  Y  Y  C  Q  Q  H  N  E  N  P  L  T  F  G  G
ggcacaaaggtggaaatcaagggcagcacctccggaggaggcagcggcggaggcagcgga
 G  T  K  V  E  I  K  G  S  T  S  G  G  G  S  G  G  G  S  G
ggcggcggctccagcgaagtgcagctggtcgagagcggaggcggactggtgcaacccgga
 G  G  G  S  S  E  V  Q  L  V  E  S  G  G  G  L  V  Q  P  G
ggaagcctgaggctgagctgtgccgccagcggcttcaacatcaaggacacatacattcac
 G  S  L  R  L  S  C  A  A  S  G  F  N  I  K  D  T  Y  I  H
tttgtgaggcaggctcctggaaagggcctggagtggatcggcagaatcgaccccgctaac
 F  V  R  Q  A  P  G  K  G  L  E  W  I  G  R  I  D  P  A  N
gacaacaccctgtacgccagcaagttccagggcaaggccaccatctccgccgacacaagc
 D  N  T  L  Y  A  S  K  F  Q  G  K  A  T  I  S  A  D  T  S
aagaataccgcctacctgcagatgaactccctgagggccgaggataccgccgtgtactac
 K  N  T  A  Y  L  Q  M  N  S  L  R  A  E  D  T  A  V  Y  Y
tgcggcaggggctatggctactacgtgtttgaccactggggccagggcacactggtgaca
 C  G  R  G  Y  G  Y  Y  V  F  D  H  W  G  Q  G  T  L  V  T
gtgagctccgagctgaagacacctctgggcgacacaacacacacctgccctccttgcccc
 V  S  S  E  L  K  T  P  L  G  D  T  T  H  T  C  P  P  C  P
ccttgtcctccctgtggaggaggaagcagcggaggaggaagcggcggacagcccagagag
 P  C  P  P  C  G  G  G  S  S  G  G  G  S  G  G  Q  P  R  E
cctcaagtgtataccctgcccccctccagggaagagatgaccaagaaccaggtgagcctg
 P  Q  V  Y  T  L  P  P  S  R  E  E  M  T  K  N  Q  V  S  L
acatgcctggtcaaaggcttctaccccagcgatattgctgtggagtgggagagcaacggc
 T  C  L  V  K  G  F  Y  P  S  D  I  A  V  E  W  E  S  N  G
cagccggagaacaactacaagaccacacccccgtcctggatagcgatggcagcttcttc
 Q  P  E  N  N  Y  K  T  T  P  P  V  L  D  S  D  G  S  F  F
```

FIG. 44

```
ctgtacagcaagctgaccgtggacaagtccaggtggcagcagggcaacgtcttctcctgc
 L  Y  S  K  L  T  V  D  K  S  R  W  Q  Q  G  N  V  F  S  C agcgtgatgcacgaggctctgcataaccactacacacagaagtccctcagcctgagccct
 S  V  M  H  E  A  L  H  N  H  Y  T  Q  K  S  L  S  L  S  P ggatga (SEQ ID NO: 143)
 G Stop (SEQ ID NO: 109)
```

FIG. 44
continued

IAB22M γ2 EH2(M1) (SEQ ID NO: 110)

```
atggaaaccgacacactgctgctgtgggtgctgctgctgtgggtccctggctccaccgga
 M  E  T  D  T  L  L  L  W  V  L  L  L  W  V  P  G  S  T  G
gacgtccagatcacacagagccccagcagcctgtccgccagcgtgggagacagggtgacc
 D  V  Q  I  T  Q  S  P  S  S  L  S  A  S  V  G  D  R  V  T
atcacctgcaggaccagcagatccatctcccagtatctggcctggtaccaacagaagccc
 I  T  C  R  T  S  R  S  I  S  Q  Y  L  A  W  Y  Q  Q  K  P
ggcaaggtccccaaactgctgatctacagcggctccaccctgcagtccggcgtgcctagc
 G  K  V  P  K  L  L  I  Y  S  G  S  T  L  Q  S  G  V  P  S
aggttctccggcagcggatccggcaccgacttcaccctgaccatcagctccctgcagcct
 R  F  S  G  S  G  S  G  T  D  F  T  L  T  I  S  S  L  Q  P
gaggacgtggctacctactactgccaacagcacaacgagaaccccctgacctttggaggc
 E  D  V  A  T  Y  Y  C  Q  Q  H  N  E  N  P  L  T  F  G  G
ggcaccaaggtggaaatcaagggcagcaccagcggcggaggaagcggaggaggatccgga
 G  T  K  V  E  I  K  G  S  T  S  G  G  G  S  G  G  G  S  G
ggaggcggaagctccgaggtgcagctggtggaaagcggcggcggactggtgcagcctgga
 G  G  G  S  S  E  V  Q  L  V  E  S  G  G  G  L  V  Q  P  G
ggaagcctcagactgagctgtgccgccagcggattcaacatcaaagacacctacattcat
 G  S  L  R  L  S  C  A  A  S  G  F  N  I  K  D  T  Y  I  H
ttcgtgagacaggcccccggcaagggcctcgaatggatcggaaggatcgaccccgctaac
 F  V  R  Q  A  P  G  K  G  L  E  W  I  G  R  I  D  P  A  N
gacaataccctgtacgcctccaagttccagggaaaggccaccatctccgccgataccacc
 D  N  T  L  Y  A  S  K  F  Q  G  K  A  T  I  S  A  D  T  S
aagaacaccgcctacctccagatgaactccctgagggccgaagataccgccgtctactac
 K  N  T  A  Y  L  Q  M  N  S  L  R  A  E  D  T  A  V  Y  Y
tgtggcaggggctacggctactatgtgttcgatcactggggccaaggaaccctggtgacc
 C  G  R  G  Y  G  Y  Y  V  F  D  H  W  G  Q  G  T  L  V  T
gtgagcagcgaaaggaagagctgcgtggagtgtcctccttgtcccggcggcggctccagc
 V  S  S  E  R  K  S  C  V  E  C  P  P  C  P  G  G  G  S  S
ggcggaggctccggcggccagcctagagaacctcaggtgtacaccctccccccctccaga
 G  G  G  S  G  G  Q  P  R  E  P  Q  V  Y  T  L  P  P  S  R
gaggagatgaccaagaaccaggtgtccctgacctgcctggtgaaaggcttctatcccagc
 E  E  M  T  K  N  Q  V  S  L  T  C  L  V  K  G  F  Y  P  S
gacatcgccgtggaatgggagtccaacggccagcccgagaacaactacaagaccacccct
 D  I  A  V  E  W  E  S  N  G  Q  P  E  N  N  Y  K  T  T  P
cccatgctggattccgacggcagcttttttcctgtacagcaagctcaccgtggacaagagc
 P  M  L  D  S  D  G  S  F  F  L  Y  S  K  L  T  V  D  K  S
```

FIG. 45

```
agatggcagcagggcaacgtgttcagctgcagcgtgatgcacgaggctctgcataaccac
 R   W  Q  Q  G  N  V  F  S  C  S  V  M  H  E  A  L  H  N  H
tacacccagaagagcctgtccctgtcccccggatga (SEQ ID NO: 144)
 Y  T  Q  K  S  L  S  L  S  P  G  Stop (SEQ ID NO: 110)
```

FIG. 45
continued

IAB22M γ2 EH2(M1)(VH-K67R) (SEQ ID NO: 111)

```
atggagaccgacaccctcctcctgtgggtgctgctgctgtgggtgcctggaagcaccggc
 M  E  T  D  T  L  L  L  W  V  L  L  L  W  V  P  G  S  T  G
gatgtgcagatcacccagagccctagcagcctgtccgcttccgtgggcgacagggtgacc
 D  V  Q  I  T  Q  S  P  S  S  L  S  A  S  V  G  D  R  V  T
atcacctgtaggacctccaggagcatctccagtacctggcctggtaccagcagaagccc
 I  T  C  R  T  S  R  S  I  S  Q  Y  L  A  W  Y  Q  Q  K  P
ggcaaggtgcccaaactgctcatctactccggcagcacactccagagcggcgtccctagc
 G  K  V  P  K  L  L  I  Y  S  G  S  T  L  Q  S  G  V  P  S
agattcagcggaagcggcagcggcaccgacttcaccctgaccatcagctccctgcagccc
 R  F  S  G  S  G  S  G  T  D  F  T  L  T  I  S  S  L  Q  P
gaggacgtggccacctattactgtcagcagcacaacgaaaaccccctgaccttcggcggc
 E  D  V  A  T  Y  Y  C  Q  Q  H  N  E  N  P  L  T  F  G  G
ggcacaaaagtggagatcaagggcagcaccagcggaggcggatccggcggcggcagcggc
 G  T  K  V  E  I  K  G  S  T  S  G  G  G  S  G  G  G  S  G
ggcggaggatccagcgaagtgcagctggtcgaaagcggaggcggactggtgcagcctgga
 G  G  G  S  S  E  V  Q  L  V  E  S  G  G  G  L  V  Q  P  G
ggaagcctgagactcagctgcgccgcctccggattcaacatcaaggacacctacatccac
 G  S  L  R  L  S  C  A  A  S  G  F  N  I  K  D  T  Y  I  H
ttcgtgaggcaggctcccggcaaaggcctcgagtggattggaaggattgaccccgccaac
 F  V  R  Q  A  P  G  K  G  L  E  W  I  G  R  I  D  P  A  N
gacaacaccctgtacgccagcaagttccaaggaagggccaccatctccgccgacaccagc
 D  N  T  L  Y  A  S  K  F  Q  G  R  A  T  I  S  A  D  T  S
aagaataccgcctacctgcagatgaactccctgagggctgaggacaccgccgtgtactac
 K  N  T  A  Y  L  Q  M  N  S  L  R  A  E  D  T  A  V  Y  Y
tgcggcagaggctacggctactacgtgttcgaccactggggacagggcacactggtgaca
 C  G  R  G  Y  G  Y  Y  V  F  D  H  W  G  Q  G  T  L  V  T
gtgagcagcgagaggaaaagctgcgtggagtgcccccctgccctggcggcggcagctcc
 V  S  S  E  R  K  S  C  V  E  C  P  P  C  P  G  G  G  S  S
ggcggaggaagcggaggacaacccagggagccccaggtgtacacactccccccctagcagg
 G  G  G  S  G  G  Q  P  R  E  P  Q  V  Y  T  L  P  P  S  R
gaagagatgaccaagaaccaggtgtccctgacctgcctcgtgaagggattctaccccagc
 E  E  M  T  K  N  Q  V  S  L  T  C  L  V  K  G  F  Y  P  S
gacattgccgtcgagtgggagagcaacggccagcctgagaacaactacaagacaacccc
 D  I  A  V  E  W  E  S  N  G  Q  P  E  N  N  Y  K  T  T  P
cctatgctcgatagcgatggctccttcttcctgtactccaagctcaccgtcgacaagagc
 P  M  L  D  S  D  G  S  F  F  L  Y  S  K  L  T  V  D  K  S
```

FIG. 46

```
aggtggcagcagggcaacgtcttctcctgtagcgtgatgcacgaggctctgcacaaccac
 R   W  Q  Q  G  N  V  F  S  C  S  V  M  H  E  A  L  H  N  H
tacacccagaagagcctgagcctgagccccggctga (SEQ ID NO: 145)
 Y  T  Q  K  S  L  S  L  S  P  G  Stop (SEQ ID NO: 111)
```

FIG. 46
continued

Alignment compared IAB2M γ1 EH1 (M2) (SEQ ID NO: 112) vs IAB2M γ1 EH3 (M2) (SEQ ID NO: 113), differences shown in box.

```
IAB2M γ1 EH1 (M2)    METDTLLLWVLLLWVPGSTGEVQLVQSGAEVKKPGASVKISCKTSGYTFTEYTIHWVKQA   60
IAB2M γ1 EH3 (M2)    METDTLLLWVLLLWVPGSTGEVQLVQSGAEVKKPGASVKISCKTSGYTFTEYTIHWVKQA   60
IAB2M γ1 EH1 (M2)    SGKGLEWIGNINPNNGGTTYNQKFEDRATLTVDKSTSTAYMELSSLRSEDTAVYYCAAGW  120
IAB2M γ1 EH3 (M2)    SGKGLEWIGNINPNNGGTTYNQKFEDRATLTVDKSTSTAYMELSSLRSEDTAVYYCAAGW  120
IAB2M γ1 EH1 (M2)    NFDYWGQGTTVTVSSGSTSGGGSGGGGSGGGGSDIVMTQSPSSLSASVGDRVTITCKASQ  180
IAB2M γ1 EH3 (M2)    NFDYWGQGTTVTVSSGSTSGGGSGGGGSGGGGSDIVMTQSPSSLSASVGDRVTITCKASQ  180
IAB2M γ1 EH1 (M2)    DVGTAVDWYQQKPGKAPKLLIYWASTRHTGVPDRFTGSGSGTDFTLTISSLQPEDFADYF  240
IAB2M γ1 EH3 (M2)    DVGTAVDWYQQKPGKAPKLLIYWASTRHTGVPDRFTGSGSGTDFTLTISSLQPEDFADYF  240
IAB2M γ1 EH1 (M2)    CQQYNSYPLTFGGGTKLEIKEPKS DKTHTCP ----PCGGGSGGGSGGGQPREPQVYTLPP  297
IAB2M γ1 EH3 (M2)    CQQYNSYPLTFGGGTKLEIKEPKS DKTHTCP PCP PCGGGSGGGSGGGQPREPQVYTLPP  300
IAB2M γ1 EH1 (M2)    SR DEL TKNQVSLTCLVKGFYPSDIAVEWESNGQPENNYKTTPPVLDSDGSFFLYSKLTVD  357
IAB2M γ1 EH3 (M2)    SR EEM TKNQVSLTCLVKGFYPSDIAVEWESNGQPENNYKTTPPVLDSDGSFFLYSKLTVD  360
IAB2M γ1 EH1 (M2)    KSRWQQGNVFSCSVMHEALHNHYTQKSLSLSPG K  391 (SEQ ID NO: 112)
IAB2M γ1 EH3 (M2)    KSRWQQGNVFSCSVMHEALHNHYTQKSLSLSPG -  393 (SEQ ID NO: 113)
```

FIG. 47

IAB2M γ1 EH3(M2), CDR regions are defined by Chothia definition (SEQ ID NO: 113)

```
atggaaaccgacaccctgctgctgtgggtgctgctgctgtgggtgccaggatctacaggc
 M  E  T  D  T  L  L  L  W  V  L  L  L  W  V  P  G  S  T  G
```
Signal peptide sequence

```
gaggtgcagctggtgcagtctggcgccgaagtgaagaaacctggcgcctccgtgaagatc
 E  V  Q  L  V  Q  S  G  A  E  V  K  K  P  G  A  S  V  K  I
```
VH

```
tcctgcaagacctcc ggctacaccttcaccgagtac accatccactgggtcaagcaggcc
 S  C  K  T  S   G  Y  T  F  T  E  Y   T  I  H  W  V  K  Q  A
                         HCDR1
```

```
tccggcaagggcctggaatggatcggc aacatcaaccccaacaacggcggc accacctac
 S  G  K  G  L  E  W  I  G   N  I  N  P  N  N  G  G   T  T  Y
                                    HCDR2
```

```
aaccagaagttcgaggaccgggccaccctgaccgtggacaagtctacctccaccgcctac
 N  Q  K  F  E  D  R  A  T  L  T  V  D  K  S  T  S  T  A  Y
```

```
atggaactgtcctccctgcggagcgaggacaccgccgtgtactattgtgccgct ggctgg
 M  E  L  S  S  L  R  S  E  D  T  A  V  Y  Y  C  A  A   G  W
                                                        HCDR3
```

```
aacttcgactac tggggccagggcaccaccgtgacagtgtcctct ggctctacctccggc
 N  F  D  Y   W  G  Q  G  T  T  V  T  V  S  S   G  S  T  S  G
  HCDR3                                             Linker
```

```
ggaggaagtggcggaggatcaggcggaggcggctcctctg atatcgtgatgacccagtcc
 G  G  S  G  G  G  S  G  G  G  G  S  S   D  I  V  M  T  Q  S
        Linker                            VL
```

```
ccctccagcctgtctgcttccgtgggcgacagagtgaccatcacatgc aaggcctcccag
 P  S  S  L  S  A  S  V  G  D  R  V  T  I  T  C   K  A  S  Q
                                                      LCDR1
```

```
gacgtgggcaccgctgtggac tggtatcagcagaagcctggcaaggcccccaagctgctg
 D  V  G  T  A  V  D   W  Y  Q  Q  K  P  G  K  A  P  K  L  L
  LCDR1
```

```
atctac tgggcctctaccagacacacc ggcgtgcccgatagattcaccggctctggatcc
 I  Y   W  A  S  T  R  H  T   G  V  P  D  R  F  T  G  S  G  S
         LCDR2
```

```
ggcaccgactttaccctgaccatcagctccctgcagcccgaggacttcgccgactacttc
 G  T  D  F  T  L  T  I  S  S  L  Q  P  E  D  F  A  D  Y  F
```

```
tgc cagcagtacaactcctacccccctgacc tttggcggaggcaccaagctggaaatcaaa
 C   Q  Q  Y  N  S  Y  P  L  T   F  G  G  G  T  K  L  E  I  K
```

FIG. 48

LCDR3

| gagcccaagtcctccgacaagacccacacc | tgtccccttgccctccatgt | ggtggcgga |
|---|---|---|
| E  P  K  S  S  D  K  T  H  T | C  P  P  C  P  P  C | G  G  G |

Upper hinge             Core hinge         Lower hinge

| agttctgggggaggttctggt | ggccagcctcgggaacctcaggtgtacacactgcccct |
|---|---|
| S  S  G  G  G  S  G | G  Q  P  R  E  P  Q  V  Y  T  L  P  P |

Lower hinge            CH3 agccgggaagagatgaccaagaaccaggtgtccctgacctgcctcgtgaagggcttctac

S  R  E  E  M  T  K  N  Q  V  S  L  T  C  L  V  K  G  F  Y ccctccgatatcgccgtggaatggagtccaacggccagcccgagaacaactacaagacc

P  S  D  I  A  V  E  W  E  S  N  G  Q  P  E  N  N  Y  K  T accccccctgtgctggactccgacggctcattcttcctgtactccaagctgacagtggat

T  P  P  V  L  D  S  D  G  S  F  F  L  Y  S  K  L  T  V  D aagtcccggtggcagcagggcaacgtgttctcctgctccgtgatgcacgaggccctgcac

K  S  R  W  Q  Q  G  N  V  F  S  C  S  V  M  H  E  A  L  H aaccactatacccagaagtccctgtccctgagccccggctga (SEQ ID NO: 146)

N  H  Y  T  Q  K  S  L  S  L  S  P  G  Stop (SEQ ID NO: 113)

FIG. 48
continued

IAB2M γ1 EH3(M2) (G1m1 allotype) (SEQ ID NO: 114)

```
atggaaaccgatacactgctgctgtgggtgctgctgctgtgggtgccgggcagcaccggc
 M   E   T   D   T   L   L   L   W   V   L   L   L   W   V   P   G   S   T   G
gaagtgcagctggtgcagagcggcgcggaagtgaaaaaaccgggcgcgagcgtgaaaatt
 E   V   Q   L   V   Q   S   G   A   E   V   K   K   P   G   A   S   V   K   I
agctgcaaaaccagcggctatacctttaccgaatataccattcattgggtgaaacaggcg
 S   C   K   T   S   G   Y   T   F   T   E   Y   T   I   H   W   V   K   Q   A
agcggcaaaggcctggaatggattggcaacattaacccgaacaacggcggcaccacctat
 S   G   K   G   L   E   W   I   G   N   I   N   P   N   N   G   G   T   T   Y
aaccagaaatttgaagatcgcgcgaccctgaccgtggataaaagcaccagcaccgcgtat
 N   Q   K   F   E   D   R   A   T   L   T   V   D   K   S   T   S   T   A   Y
atggaactgagcagcctgcgcagcgaagataccgcggtgtattattgcgcggcgggctgg
 M   E   L   S   S   L   R   S   E   D   T   A   V   Y   Y   C   A   A   G   W
aactttgattattggggccagggcaccaccgtgaccgtgagcagcggcagcaccagcggc
 N   F   D   Y   W   G   Q   G   T   T   V   T   V   S   S   G   S   T   S   G
ggcggcagcggcggcggcagcggcggcggcggcagcagcgatattgtgatgacccagagc
 G   G   S   G   G   G   S   G   G   G   G   S   S   D   I   V   M   T   Q   S
ccgagcagcctgagcgcgagcgtgggcgatcgcgtgaccattacctgcaaagcgagccag
 P   S   S   L   S   A   S   V   G   D   R   V   T   I   T   C   K   A   S   Q
gatgtgggcaccgcggtggattggtatcagcagaaaccgggcaaagcgccgaaactgctg
 D   V   G   T   A   V   D   W   Y   Q   Q   K   P   G   K   A   P   K   L   L
atttattgggcgagcacccgccataccggcgtgccggatcgctttaccggcagcggcagc
 I   Y   W   A   S   T   R   H   T   G   V   P   D   R   F   T   G   S   G   S
ggcaccgattttaccctgaccattagcagcctgcagccggaagattttgcggattatttt
 G   T   D   F   T   L   T   I   S   S   L   Q   P   E   D   F   A   D   Y   F
tgccagcagtataacagctatccgctgacctttggcggcggcaccaaactggaaattaaa
 C   Q   Q   Y   N   S   Y   P   L   T   F   G   G   G   T   K   L   E   I   K
gaaccgaaaagcagcgataaaacccatacctgcccgccgtgcccgccgtgcggcggcggc
 E   P   K   S   S   D   K   T   H   T   C   P   P   C   P   P   C   G   G   G
agcagcggcggcagcggcggccagccgcgcgaaccgcaggtgtataccctgccgccg
 S   S   G   G   S   G   G   Q   P   R   E   P   Q   V   Y   T   L   P   P
agccgcgatgaactgaccaaaaaccaggtgagcctgacctgcctggtgaaaggcttttat
 S   R   D   E   L   T   K   N   Q   V   S   L   T   C   L   V   K   G   F   Y
ccgagcgatattgcggtggaatgggaaagcaacggccagccggaaaacaactataaaacc
 P   S   D   I   A   V   E   W   E   S   N   G   Q   P   E   N   N   Y   K   T
acccggccggtgctggatagcgatggcagctttttcctgtatagcaaactgaccgtggat
 T   P   P   V   L   D   S   D   G   S   F   F   L   Y   S   K   L   T   V   D
```

FIG. 49

```
aaaagccgctggcagcagggcaacgtgtttagctgcagcgtgatgcatgaagcgctgcat
 K  S  R  W  Q  Q  G  N  V  F  S  C  S  V  M  H  E  A  L  H
aaccattatacccagaaaagcctgagcctgagcccgggctga (SEQ ID NO: 147)
 N  H  Y  T  Q  K  S  L  S  L  S  P  G Stop (SEQ ID NO: 114)
```

FIG. 49
continued

IAB2M γ1 EH5(M2) (SEQ ID NO: 115)

```
atggaaaccgatacoctgctgctgtgggtgctgctgctgtgggtgccgggcagcaccggc
 M   E   T   D   T   L   L   W   V   L   L   W   V   P   G   S   T   G
gaagtgcagctggtgcagagcggcgcggaagtgaaaaaaccgggcgcgagcgtgaaaatt
 E   V   Q   L   V   Q   S   G   A   E   V   K   K   P   G   A   S   V   K   I
agctgcaaaaccagcggctataccttttaccgaatataccattcattggtgaaacaggcg
 S   C   K   T   S   G   Y   T   F   T   E   Y   T   I   H   W   V   K   Q   A
agcggcaaaggcctggaatggattggcaacattaacccgaacaacggcggcaccacctat
 S   G   K   G   L   E   W   I   G   N   I   N   P   N   N   G   G   T   T   Y
aaccagaaatttgaagatcgcgcgaccctgaccgtggataaaagcaccagcaccgcgtat
 N   Q   K   F   E   D   R   A   T   L   T   V   D   K   S   T   S   T   A   Y
atggaactgagcagcctgcgcagcgaagataccgcggtgtattattgcgcggcgggctgg
 M   E   L   S   S   L   R   S   E   D   T   A   V   Y   Y   C   A   A   G   W
aactttgattattggggccagggcaccaccgtgaccgtgagcagcggcagcaccagcggc
 N   F   D   Y   W   G   Q   G   T   T   V   T   V   S   S   G   S   T   S   G
ggcggcagcggcggcggcagcggcggcggcggcagcagcgatattgtgatgacccagagc
 G   G   S   G   G   G   S   G   G   G   G   S   S   D   I   V   M   T   Q   S
ccgagcagcctgagcgcgagcgtgggcgatcgcgtgaccattacctgcaaagcgagccag
 P   S   S   L   S   A   S   V   G   D   R   V   T   I   T   C   K   A   S   Q
gatgtgggcaccgcggtggattggtatcagcagaaaccgggcaaagcgccgaaactgctg
 D   V   G   T   A   V   D   W   Y   Q   Q   K   P   G   K   A   P   K   L   L
atttattgggcgagcacccgccataccggcgtgccggatcgctttaccggcagcggcagc
 I   Y   W   A   S   T   R   H   T   G   V   P   D   R   F   T   G   S   G   S
ggcaccgattttaccctgaccattagcagcctgcagccggaagattttgcggattatttt
 G   T   D   F   T   L   T   I   S   S   L   Q   P   E   D   F   A   D   Y   F
tgccagcagtataacagctatccgctgacctttggcggcggcaccaaactggaaattaaa
 C   Q   Q   Y   N   S   Y   P   L   T   F   G   G   G   T   K   L   E   I   K
gaaccgaaaagcagcgataaaacccatacctgcccgccgtgcccgccgtgcccgccgtgc
 E   P   K   S   S   D   K   T   H   T   C   P   P   C   P   P   C   P   P   C
ggcggcggcagcagcggcggcggcagcggcggccagccgcgcgaaccgcaggtgtatacc
 G   G   G   S   S   G   G   G   S   G   G   Q   P   R   E   P   Q   V   Y   T
ctgccgccgagccgcgaagaaatgaccaaaaaccaggtgagcctgacctgcctggtgaaa
 L   P   P   S   R   E   E   M   T   K   N   Q   V   S   L   T   C   L   V   K
ggcttttatccgagcgatattgcggtggaatgggaaagcaacggccagccggaaaacaac
 G   F   Y   P   S   D   I   A   V   E   W   E   S   N   G   Q   P   E   N   N
tataaaaccaccccgccggtgctggatagcgatggcagcttttttctgtatagcaaactg
 Y   K   T   T   P   P   V   L   D   S   D   G   S   F   F   L   Y   S   K   L
```

FIG. 50

```
accgtggataaaagccgctggcagcagggcaacgtgtttagctgcagcgtgatgcatgaa
 T   V  D  K  S  R  W  Q  Q  G  N  V  F  S  C  S  V  M  H  E
gcgctgcataaccattatacccagaaaagcctgagcctgagcccgggctga
 A  L  H  N  H  Y  T  Q  K  S  L  S  L  S  P  G Stop
```
(SEQ ID NO: 148)

(SEQ ID NO: 115)

FIG. 50
continued

IAB2M γ1 EH7(M2) (SEQ ID NO: 116)

atggagacagacaccctcctcctgtgggtgctgctgctgtgggtcccggaagcaccgga
M　E　T　D　L　L　L　W　V　L　L　L　W　V　P　G　S　T　G gaagtgcagctggtgcaatccggagccgaggtgaagaaacccggcgccagcgtgaagatt
E　V　Q　L　V　Q　S　G　A　E　V　K　K　P　G　A　S　V　K　I agctgcaaaaccagcggctacaccttcaccgagtacaccatccactgggtcaagcaggcc
S　C　K　T　S　G　Y　T　F　T　E　Y　T　I　H　W　V　K　Q　A agcggcaagggcctggagtggatcggcaacattaaccccaataacggcggcaccacctac
S　G　K　G　L　E　W　I　G　N　I　N　P　N　N　G　G　T　Y aatcagaaattcgaggacagggccaccctgaccgtggataagtccacctccaccgcctac
N　Q　K　F　E　D　R　A　T　L　T　V　D　K　S　T　S　T　A　Y atggagctgtcctccctgagaagcgaggatacagccgtctactactgcgctgccggatgg
M　E　L　S　S　L　R　S　E　D　T　A　V　Y　Y　C　A　A　G　W aatttcgactactggggccagggcacaaccgtgaccgtgagcagcggatccacctccggc
N　F　D　Y　W　G　Q　G　T　T　V　T　V　S　S　G　S　T　S　G ggcggcagcggaggcggcagcggcggaggaggcagcagcgacatcgtgatgacacagtcc
G　G　S　G　G　S　G　G　G　S　S　D　I　V　M　T　Q　S cccagcagcctgtccgctagcgtgggcgacagagtgaccatcacctgcaaggcctccag
P　S　S　L　S　A　S　V　G　D　R　V　T　I　T　C　K　A　S　Q gacgtgggaaccgctgtggactggtaccagcagaagcccggcaaggcccccaagctgctg
D　V　G　T　A　V　D　W　Y　Q　Q　K　P　G　K　A　P　K　L　L atctactgggccagcaccagacacacggcgtgcctgacagattcaccggctccggaagc
I　Y　W　A　S　T　R　H　T　G　V　P　D　R　F　T　G　S　G　S ggcaccgacttcaccctgaccatcagctccctccagcccgaggacttcgccgactacttc
G　T　D　F　T　L　T　I　S　S　L　Q　P　E　D　F　A　D　Y　F tgccagcagtataatagctaccccctgaccttcggcggcggcacaaagctcgaaatcaag
C　Q　Q　Y　N　S　Y　P　L　T　F　G　G　G　T　K　L　E　I　K gagctgaagacccctctgggagacaccacccacacctgccccccttgccctccctgtgga
E　L　K　T　P　L　G　D　T　T　H　T　C　P　P　C　P　P　C　G ggcggaagcagcggaggaggaagcggaggacagcccagggaaccccaggtgtacacactg
G　G　S　S　G　G　S　G　G　Q　P　R　E　P　Q　V　Y　T　L cccccctccagagaggagatgacaaagaaccaggtgtccctcacctgcctggtgaaaggc
P　P　S　R　E　E　M　T　K　N　Q　V　S　L　T　C　L　V　K　G ttctatcccagcgacatcgccgtggagtgggagtccaacggccaacccgaaaacaactac
F　Y　P　S　D　I　A　V　E　W　E　S　N　G　Q　P　E　N　N　Y aagaccaccccctcccgtgctggattccgacggctccttttttcctgtacagcaagctgacc
K　T　T　P　P　V　L　D　S　D　G　S　F　F　L　Y　S　K　L　T

FIG. 51

```
gtggacaagtccaggtggcagcagggcaatgtctttagctgcagcgtcatgcacgaggcc
 V  D  K  S  R  W  Q  Q  G  N  V  F  S  C  S  V  M  H  E  A
ctgcataaccactatacccagaagtccctgtccctcagccctggatga (SEQ ID NO: 149)
 L  H  N  H  Y  T  Q  K  S  L  S  L  S  P  G Stop (SEQ ID NO: 116)
```

FIG. 51
continued

IAB2M γ1 EH8(M2) (SEQ ID NO: 117)

atggaaaccgatacoctgctgctgtgggtgctgctgctgtgggtgccgggcagcaccggc
M  E  T  D  T  L  L  W  V  L  L  L  W  V  P  G  S  T  G gaagtgcagctggtgcagagcggcgcggaagtgaaaaaaccgggcgcgagcgtgaaaatt
E  V  Q  L  V  Q  S  G  A  E  V  K  K  P  G  A  S  V  K  I agctgcaaaaccagcggctataccttaccgaatataccattcattgggtgaaacaggcg
S  C  K  T  S  G  Y  T  F  T  E  Y  T  I  H  W  V  K  Q  A agcggcaaaggcctggaatggattggcaacattaacccgaacaacggcggcaccacctat
S  G  K  G  L  E  W  I  G  N  I  N  P  N  N  G  G  T  T  Y aaccagaaatttgaagatcgcgcgaccctgaccgtggataaaagcaccagcaccgcgtat
N  Q  K  F  E  D  R  A  T  L  T  V  D  K  S  T  S  T  A  Y atggaactgagcagcctgcgcagcgaagataccgcggtgtattattgcgcggcgggctgg
M  E  L  S  S  L  R  S  E  D  T  A  V  Y  Y  C  A  A  G  W aactttgattattggggccagggcaccaccgtgaccgtgagcagcggcagcaccagcggc
N  F  D  Y  W  G  Q  G  T  T  V  T  V  S  S  G  S  T  S  G ggcggcagcggcggcggcagcggcggcggcggcagcagcgatattgtgatgacccagagc
G  G  S  G  G  G  S  G  G  G  G  S  S  D  I  V  M  T  Q  S ccgagcagcctgagcgcgagcgtgggcgatcgcgtgaccattacctgcaaagcgagccag
P  S  S  L  S  A  S  V  G  D  R  V  T  I  T  C  K  A  S  Q gatgtgggcaccgcggtggattggtatcagcagaaaccgggcaaagcgccgaaactgctg
D  V  G  T  A  V  D  W  Y  Q  Q  K  P  G  K  A  P  K  L  L atttattgggcgagcacccgccataccggcgtgccggatcgctttaccggcagcggcagc
I  Y  W  A  S  T  R  H  T  G  V  P  D  R  F  T  G  S  G  S ggcaccgatttaccctgaccattagcagcctgcagccggaagattttgcggattatttt
G  T  D  F  T  L  T  I  S  S  L  Q  P  E  D  F  A  D  Y  F tgccagcagtataacagctatccgctgacctttggcggcggcaccaaactggaaattaaa
C  Q  Q  Y  N  S  Y  P  L  T  F  G  G  G  T  K  L  E  I  K gaactgaaaaccccgctgggcgataccacccatacctgcccgccgtgcccgccgtgcccg
E  L  K  T  P  L  G  D  T  T  H  T  C  P  P  C  P  P  C  P ccgtgcggcggcggcagcagcggcggcggcagcggcggccagccgcgcgaaccgcaggtg
P  C  G  G  G  S  S  G  G  G  S  G  G  Q  P  R  E  P  Q  V tataccctgccgccgagccgcgaagaaatgaccaaaaaccaggtgagcctgacctgcctg
Y  T  L  P  P  S  R  E  E  M  T  K  N  Q  V  S  L  T  C  L gtgaaaggcttttatccgagcgatattgcggtggaatgggaaagcaacggccagccggaa
V  K  G  F  Y  P  S  D  I  A  V  E  W  E  S  N  G  Q  P  E aacaactataaaaccaccccgccggtgctggatagcgatggcagcttttttctgtatagc
N  N  Y  K  T  T  P  P  V  L  D  S  D  G  S  F  F  L  Y  S

FIG. 52 aaactgaccgtggataaaagccgctggcagcagggcaacgtgtttagctgcagcgtgatg

K   L   T   V   D   K   S   R   W   Q   Q   G   N   V   F   S   C   S   V   M catgaagcgctgcataaccattatacccagaaaagcctgagcctgagcccgggctga (SEQ ID NO: 150)

H   E   A   L   H   N   H   Y   T   Q   K   S   L   S   L   S   P   G   Stop (SEQ ID NO: 117)

FIG. 52
continued

IAB2M γ1 EH3(M1) (SEQ ID NO: 118)

```
atggaaaccgataccctgctgctgtgggtgctgctgctgtgggtgccgggcagcaccggc
 M   E   T   D   T   L   L   W   V   L   L   L   W   V   P   G   S   T   G
gatattgtgatgacccagagcccgagcagcctgagcgcgagcgtgggcgatcgcgtgacc
 D   I   V   M   T   Q   S   P   S   S   L   S   A   S   V   G   D   R   V   T
attacctgcaaagcgagccaggatgtgggcaccgcggtggattggtatcagcagaaaccg
 I   T   C   K   A   S   Q   D   V   G   T   A   V   D   W   Y   Q   Q   K   P
ggcaaagcgccgaaactgctgatttattgggcgagcacccgccataccggcgtgccggat
 G   K   A   P   K   L   L   I   Y   W   A   S   T   R   H   T   G   V   P   D
cgctttaccggcagcggcagcggcaccgatttttaccctgaccattagcagcctgcagccg
 R   F   T   G   S   G   S   G   T   D   F   T   L   T   I   S   S   L   Q   P
gaagattttgcggattatttttgccagcagtataacagctatccgctgacctttggcggc
 E   D   F   A   D   Y   F   C   Q   Q   Y   N   S   Y   P   L   T   F   G   G
ggcaccaaactggaaattaaaggcagcaccagcggcggcggcagcggcggcggcagcggc
 G   T   K   L   E   I   K   G   S   T   S   G   G   G   S   G   G   G   S   G
ggcggcggcagcagcgaagtgcagctggtgcagagcggcgcggaagtgaaaaaaccgggc
 G   G   G   S   S   E   V   Q   L   V   Q   S   G   A   E   V   K   K   P   G
gcgagcgtgaaaattagctgcaaaaccagcggctataccttaccgaatataccattcat
 A   S   V   K   I   S   C   K   T   S   G   Y   T   F   T   E   Y   T   I   H
tgggtgaaacaggcgagcggcaaaggcctggaatggattggcaacattaacccgaacaac
 W   V   K   Q   A   S   G   K   G   L   E   W   I   G   N   I   N   P   N   N
ggcggcaccacctataaccagaaatttgaagatcgcgcgaccctgaccgtggataaaagc
 G   G   T   T   Y   N   Q   K   F   E   D   R   A   T   L   T   V   D   K   S
accagcaccgcgtatatggaactgagcagcctgcgcagcgaagataccgcggtgtattat
 T   S   T   A   Y   M   E   L   S   S   L   R   S   E   D   T   A   V   Y   Y
tgcgcggcgggctggaactttgattattggggccagggcaccaccgtgaccgtgagcagc
 C   A   A   G   W   N   F   D   Y   W   G   Q   G   T   T   V   T   V   S   S
gaaccgaaaagcagcgataaaacccatacctgcccgccgtgcccgccgtgcggcggcggc
 E   P   K   S   S   D   K   T   H   T   C   P   P   C   P   P   C   G   G   G
agcagcggcggcggcagcggcggccagccgcgcgaaccgcaggtgtataccctgccgccg
 S   S   G   G   G   S   G   G   Q   P   R   E   P   Q   V   Y   T   L   P   P
agccgcgaagaaatgaccaaaaaccaggtgagcctgacctgcctggtgaaaggctttat
 S   R   E   E   M   T   K   N   Q   V   S   L   T   C   L   V   K   G   F   Y
ccgagcgatattgcggtggaatgggaaagcaacggccagccggaaaacaactataaaacc
 P   S   D   I   A   V   E   W   E   S   N   G   Q   P   E   N   N   Y   K   T
acccogccggtgctggatagcgatggcagcttttttctgtatagcaaactgaccgtggat
 T   P   P   V   L   D   S   D   G   S   F   F   L   Y   S   K   L   T   V   D
```

FIG. 53

```
aaaagccgctggcagcagggcaacgtgtttagctgcagcgtgatgcatgaagcgctgcat
 K   S   R   W   Q   Q   G   N   V   F   S   C   S   V   M   H   E   A   L   H aaccattatacccagaaaagcctgagcctgagcccgggctga (SEQ ID NO: 151)
 N   H   Y   T   Q   K   S   L   S   L   S   P   G  Stop (SEQ ID NO: 118)
```

FIG. 53
continued

Alignment compared IAB20M γ1 EH1(M2) (SEQ ID NO: 119) vs IAB20M γ1 EH3 (M2) (VL-Q79E, V83E; VH-Q1E, Q6E) (SEQ ID NO: 120), differences shown in box.

```
IAB20M γ1 EH1(M2)  METDTLLLWVLLLWVPGSTG Q VQLV Q SGAEVKKPGASVKVSCKASGYSFTGYYMHWVRQA 60
IAB20M γ1 EH3(M2)  METDTLLLWVLLLWVPGSTG E VQLV E SGAEVKKPGASVKVSCKASGYSFTGYYMHWVRQA 60

IAB20M γ1 EH1(M2)  PGQGLEWIGRINPNNGVTLYNQKFKDRVTMTVDTSISTAYMELSRLRSDDTAVYYCARST 120
IAB20M γ1 EH3(M2)  PGQGLEWIGRINPNNGVTLYNQKFKDRVTMTVDTSISTAYMELSRLRSDDTAVYYCARST 120

IAB20M γ1 EH1(M2)  MITNYVMDYWGQGTLVTVSSGSTSGGGSGGGGSGGGGSSDIVMTQSPATLSVSPGERATLS 180
IAB20M γ1 EH3(M2)  MITNYVMDYWGQGTLVTVSSGSTSGGGSGGGGSGGGGSSDIVMTQSPATLSVSPGERATLS 180

IAB20M γ1 EH1(M2)  CKASQSVSNDVAWYQQKPGQAPRLLISYTSSRYAGVPDRFSGSGSGTDFTLTISSL Q AED 240
IAB20M γ1 EH3(M2)  CKASQSVSNDVAWYQQKPGQAPRLLISYTSSRYAGVPDRFSGSGSGTDFTLTISSL E AED 240

IAB20M γ1 EH1(M2)  AVYYCQQDYNSPPTFGQGTKVEIKEPKS C DKTHTCP --- PCGGGSGGGSGGGGQPREPQV 297
IAB20M γ1 EH3(M2)  AVYYCQQDYNSPPTFGQGTKVEIKEPKS S DKTHTCP PCP PCGGGSGGGSGGGGQPREPQV 300

IAB20M γ1 EH1(M2)  YTLPPSRDELTKNQVSLTCLVKGFYPSDIAVEWESNGQPENNYKTTPPVLDSDGSFFLYS 357
IAB20M γ1 EH3(M2)  YTLPPSREEMTKNQVSLTCLVKGFYPSDIAVEWESNGQPENNYKTTPPVLDSDGSFFLYS 360

IAB20M γ1 EH1(M2)  KLTVDKSRWQQGNVFSCSVMHEALHNHYTQKSLSLSPG K 396    (SEQ ID NO: 119)
IAB20M γ1 EH3(M2)  KLTVDKSRWQQGNVFSCSVMHEALHNHYTQKSLSLSPG - 398    (SEQ ID NO: 120)
```

FIG. 54

IAB20M γ1 EH3(M2)(VL-Q79E, V83E; VH-Q1E, Q6E), CDR regions are defined by Chothia definition (SEQ ID NO: 120)

| atggaaaccgataccctgctgctgtgggtgctgctgctgtgggtgcctggcagcacagga |
| M E T D T L L L W V L L L W V P G S T G |

Signal peptide sequence gaggtgcagctggtggagagcggcgctgaagtgaagaagcccggcgccagcgtgaaggtg

E V Q L V E S G A E V K K P G A S V K V

VH agctgcaaggccagc | ggctacagcttcacaggctac | tacatgcactgggtgagacaagcc

S C K A S | G Y S F T G Y | Y M H W V R Q A

HCDR1 cctggccagggcctcgagtggattggaaggatc | aaccccaacaacggagtg | acactgtac

P G Q G L E W I G R I | N P N N G V | T L Y

HCDR2 aaccagaaattcaaggacagggtcaccatgaccgtggacaccagcatcagcaccgcctat

N Q K F K D R V T M T V D T S I S T A Y atggagctgtccaggctgaggagcgacgacaccgctgtgtactactgcgccagg | agcacc

M E L S R L R S D D T A V Y Y C A R | S T

HCDR3

| atgatcaccaactacgtgatggattat | tggggccagggcacactggtgacagtgagcagc

| M I T N Y V M D Y | W G Q G T L V T V S S

HCDR3

| ggcagcaccagcggaggaggcagcggaggaggaagcggcggaggcggctcctcc | gatatc

| G S T S G G G S G G G S G G G S S | D I

Linker             VL gtcatgacccagagccccgctaccctcagcgtgtcccctggcgagagagccaccctgagc

V M T Q S P A T L S V S P G E R A T L S tgc | aaggccagccagtccgtgtccaacgacgtggcc | tggtatcaacagaagcccggccag

C | K A S Q S V S N D V A | W Y Q Q K P G Q

LCDR1 gctcctaggctgctgatctcc | tacaccagcagcaggtacgcc | ggcgtgcctgataggttc

A P R L L I S | Y T S S R Y A | G V P D R F

LCDR2 agcggctccggcagcggcacagacttcaccctgacaatcagcagcctggaggccgaggat

```
gaggccgtgtactactgt cagcaggactacaactccccccccacc ttcggccagggcaca
E   A   V   Y   Y   C   Q   Q   D   Y   N   S   P   P   T   F   G   Q   G   T
                        LCDR3 aaggtc gagatcaaggagcccaagtcctccgacaagacccacacc tgtccccctgccct
K   V   E   I   K   E   P   K   S   S   D   K   T   H   T   C   P   P   C   P
        Upper hinge                                          Core hinge cctTgt ggaggcggaagcagcggaggcgggagcgga ggacagcccagagaaccccaggtg
P   C   G   G   G   S   S   G   G   G   S   G   G   Q   P   R   E   P   Q   V
Core            Lower hinge                     CH3 tatacectgccccctccagggaggagatgaccaaaaaccaggtgagcctgacatgcctg
Y   T   L   P   P   S   R   E   E   M   T   K   N   Q   V   S   L   T   C   L gtgaagggcttctacccctccgacatcgccgtggagtgggaaagcaacggccagcccgag
V   K   G   F   Y   P   S   D   I   A   V   E   W   E   S   N   G   Q   P   E aacaactacaagaccacaccccccgtgctggatagcgacggctccttcttcctgtacagc
N   N   Y   K   T   T   P   P   V   L   D   S   D   G   S   F   F   L   Y   S aagctgaccgtggataaaagcaggtggcagcaaggcaacgtgttctcctgctccgtcatg
K   L   T   V   D   K   S   R   W   Q   Q   G   N   V   F   S   C   S   V   M cacgaggctctgcataaccactacacccaaaaatccctgagcctgagccccggctga (SEQ ID NO: 152)
H   E   A   L   H   N   H   Y   T   Q   K   S   L   S   L   S   P   G   Stop (SEQ ID NO: 120)
```

FIG. 55 continued

IAB20M γ1 EH3(M2) (SEQ ID NO: 121)

```
atggaaaccgatacccctgctgctgtgggtgctgctgctgtgggtgccggcagcaccggc
 M  E  T  D  T  L  L  W  V  L  L  L  W  V  P  G  S  T  G
caggtgcagctggtgcagagcggcgcggaagtgaaaaaaccgggcgcgagcgtgaaagtg
 Q  V  Q  L  V  Q  S  G  A  E  V  K  K  P  G  A  S  V  K  V
agctgcaaagcgagcggctatagctttaccggctattatatgcattgggtgcgccaggcg
 S  C  K  A  S  G  Y  S  F  T  G  Y  Y  M  H  W  V  R  Q  A
ccgggccagggcctggaatggattggccgcattaacccgaacaacggcgtgaccctgtat
 P  G  Q  G  L  E  W  I  G  R  I  N  P  N  N  G  V  T  L  Y
aaccagaaatttaaagatcgcgtgaccatgaccgtggataccagcattagcaccgcgtat
 N  Q  K  F  K  D  R  V  T  M  T  V  D  T  S  I  S  T  A  Y
atggaactgagccgcctgcgcagcgatgataccgcggtgtattattgcgcgcgcagcacc
 M  E  L  S  R  L  R  S  D  D  T  A  V  Y  Y  C  A  R  S  T
atgattaccaactatgtgatggattattggggccagggcaccctggtgaccgtgagcagc
 M  I  T  N  Y  V  M  D  Y  W  G  Q  G  T  L  V  T  V  S  S
ggcagcaccagcggcggcggcagcggcggcggcagcggcggcggcggcagcagcgatatt
 G  S  T  S  G  G  G  S  G  G  G  S  G  G  G  G  S  S  D  I
gtgatgacccagagcccggcgaccctgagcgtgagcccgggcgaacgcgcgaccctgagc
 V  M  T  Q  S  P  A  T  L  S  V  S  P  G  E  R  A  T  L  S
tgcaaagcgagccagagcgtgagcaacgatgtggcgtggtatcagcagaaaccgggccag
 C  K  A  S  Q  S  V  S  N  D  V  A  W  Y  Q  Q  K  P  G  Q
gcgccgcgcctgctgattagctataccagcagccgctatgcgggcgtgccggatcgcttt
 A  P  R  L  L  I  S  Y  T  S  S  R  Y  A  G  V  P  D  R  F
agcggcagcggcagcggcaccgattttaccctgaccattagcagcctgcaggcggaagat
 S  G  S  G  S  G  T  D  F  T  L  T  I  S  S  L  Q  A  E  D
gtggcggtgtattattgccagcaggattataacagcccgccgacctttggccagggcacc
 V  A  V  Y  Y  C  Q  Q  D  Y  N  S  P  P  T  F  G  Q  G  T
aaagtggaaattaaagaaccgaaaagcagcgataaaacccatacctgcccgccgtgcccg
 K  V  E  I  K  E  P  K  S  S  D  K  T  H  T  C  P  P  C  P
ccgtgcggcggcggcagcagcggcggcggcagcggcggccagccgcgcgaaccgcaggtg
 P  C  G  G  G  S  S  G  G  G  S  G  G  Q  P  R  E  P  Q  V
tataccctgccgccgagccgcgaagaaatgaccaaaaaccaggtgagcctgacctgcctg
 Y  T  L  P  P  S  R  E  E  M  T  K  N  Q  V  S  L  T  C  L
gtgaaaggcttttatccgagcgatattgcggtggaatgggaaagcaacggccagccggaa
 V  K  G  F  Y  P  S  D  I  A  V  E  W  E  S  N  G  Q  P  E
aacaactataaaaccaccccgccggtgctggatagcgatggcagcttttttctgtatagc
 N  N  Y  K  T  T  P  P  V  L  D  S  D  G  S  F  F  L  Y  S
```

FIG. 56

```
aaactgaccgtggataaaagccgctggcagcagggcaacgtgtttagctgcagcgtgatg
 K   L   T   V   D   K   S   R   W   Q   Q   G   N   V   F   S   C   S   V   M
catgaagcgctgcataaccattatacccagaaaagcctgagcctgagcccgggctga (SEQ ID NO: 153)
 H   E   A   L   H   N   H   Y   T   Q   K   S   L   S   L   S   P   G Stop (SEQ ID NO: 121)
```

FIG. 56
continued

IAB20M γ1 EH3(M2)(VL-A9D, T10S, S12A, P15L, L21I, S22N; VH-Q1E, Q6E) (SEQ ID NO: 122)

```
atggaaaccgatacctgctgctgtgggtgctgctgctgtgggtgctggcagcacagga
 M  E  T  D  T  L  L  W  V  L  L  L  W  V  P  G  S  T  G gaggtgcagctggtggagagcggcgctgaagtgaagaagcccggcgccagcgtgaaggtg
 E  V  Q  L  V  E  S  G  A  E  V  K  K  P  G  A  S  V  K  V agctgcaaggccagcggctacagcttcacaggctactacatgcactgggtgagacaagcc
 S  C  K  A  S  G  Y  S  F  T  G  Y  Y  M  H  W  V  R  Q  A cctggccagggcctcgagtggattggaaggatcaaccccaacaacggagtgacactgtac
 P  G  Q  G  L  E  W  I  G  R  I  N  P  N  N  G  V  T  L  Y aaccagaaattcaaggacagggtcaccatgaccgtggacaccagcatcagcaccgcctat
 N  Q  K  F  K  D  R  V  T  M  T  V  D  T  S  I  S  T  A  Y atggagctgtccaggctgaggagcgacgacaccgctgtgtactactgcgccaggagcacc
 M  E  L  S  R  L  R  S  D  D  T  A  V  Y  Y  C  A  R  S  T atgatcaccaactacgtgatggattattggggccagggcacactggtgacagtgagcagc
 M  I  T  N  Y  V  M  D  Y  W  G  Q  G  T  L  V  T  V  S  S ggcagcaccagcggaggaggcagcggaggaggaagcggcggaggcggctcctccgatatc
 G  S  T  S  G  G  G  S  G  G  G  S  G  G  G  G  S  S  D  I gtcatgacccagagccccgatagcctggccgtgagcctgggcgagagagccaccatcaat
 V  M  T  Q  S  P  D  S  L  A  V  S  L  G  E  R  A  T  I  N tgcaaggccagccagtccgtgtccaacgacgtggcctggtatcaacagaagcccggccag
 C  K  A  S  Q  S  V  S  N  D  V  A  W  Y  Q  Q  K  P  G  Q gctcctaggctgctgatctcctacaccagcagcaggtacgccggcgtgcctgataggttc
 A  P  R  L  L  I  S  Y  T  S  S  R  Y  A  G  V  P  D  R  F agcggctccggcagcggcacagacttcaccctgacaatcagcagcctgcaagccgaagat
 S  G  S  G  S  G  T  D  F  T  L  T  I  S  S  L  Q  A  E  D gtggccgtgtactactgtcagcaggactacaactccccccccaccttcggccagggcaca
 V  A  V  Y  Y  C  Q  Q  D  Y  N  S  P  P  T  F  G  Q  G  T aaggtcgagatcaaggagcccaagtcctccgacaagacccacacctgtccccctgccct
 K  V  E  I  K  E  P  K  S  S  D  K  T  H  T  C  P  P  C  P ccttgtggaggcggaagcagcggaggcgggagcggaggacagcccagagaacccaggtg
 P  C  G  G  G  S  S  G  G  G  S  G  G  Q  P  R  E  P  Q  V tatacccctgccccctccagggaggagatgaccaaaaaccaggtgagcctgacatgcctg
 Y  T  L  P  P  S  R  E  E  M  T  K  N  Q  V  S  L  T  C  L gtgaagggcttctaccctccgacatcgccgtggagtgggaaagcaacggccagcccgag
 V  K  G  F  Y  P  S  D  I  A  V  E  W  E  S  N  G  Q  P  E aacaactacaagaccacccccccgtgctggatagcgacggctccttctttctgtacagc
 N  N  Y  K  T  T  P  P  V  L  D  S  D  G  S  F  F  L  Y  S
```

FIG. 57

```
aagctgaccgtggataaaagcaggtggcagcaaggcaacgtgttctcctgctccgtcatg

K   L   T   V   D   K   S   R   W   Q   Q   G   N   V   F   S   C   S   V   M cacgaggctctgcataaccactacacccaaaaatccctgagcctgagccccggctga  (SEQ ID NO: 154)

H   E   A   L   H   N   H   Y   T   Q   K   S   L   S   L   S   P   G  Stop (SEQ ID NO: 122)
```

FIG. 57
continued

IAB20M γ1 EH5(M2)(VL-Q79E, V83E; VH-Q1E, Q6E) (SEQ ID NO: 123)

```
atggagacagacaccctcctcctgtgggtcctgctcctgtgggtgcccggatccacaggc
 M  E  T  D  T  L  L  L  W  V  L  L  L  W  V  P  G  S  T  G
gaggtccagctggtggaatccggagccgaggtgaagaaacccggcgcctccgtgaaagtc
 E  V  Q  L  V  E  S  G  A  E  V  K  K  P  G  A  S  V  K  V
tcctgcaaggcctccggctactccttcaccggctactacatgcactgggtgaggcaggcc
 S  C  K  A  S  G  Y  S  F  T  G  Y  Y  M  H  W  V  R  Q  A
cctggacagggactggaatggatcggcaggattaaccccaacaacggagtgaccctgtac
 P  G  Q  G  L  E  W  I  G  R  I  N  P  N  N  G  V  T  L  Y
aaccagaagttcaaggacagggtcaccatgaccgtggacaccagcatttccaccgcctac
 N  Q  K  F  K  D  R  V  T  M  T  V  D  T  S  I  S  T  A  Y
atggagctgtccaggctgagaagcgacgacaccgctgtgtactactgcgccaggagcacc
 M  E  L  S  R  L  R  S  D  D  T  A  V  Y  Y  C  A  R  S  T
atgatcaccaactacgtgatggattattggggccagggcaccctcgtgacagtgagcagc
 M  I  T  N  Y  V  M  D  Y  W  G  Q  G  T  L  V  T  V  S  S
ggatccacaagcggaggcggaagcggaggcggcagcggcggcggcggcagcagcgatatc
 G  S  T  S  G  G  G  S  G  G  G  S  G  G  G  G  S  S  D  I
gtgatgacccagagccccgccaccctgagcgtgagccccggcgaaagggccacactgagc
 V  M  T  Q  S  P  A  T  L  S  V  S  P  G  E  R  A  T  L  S
tgcaaggccagccagtccgtctccaacgatgtggcctggtaccagcagaagcccggacag
 C  K  A  S  Q  S  V  S  N  D  V  A  W  Y  Q  Q  K  P  G  Q
gcccctaggctcctgatctcctacaccagctccaggtacgccggcgtccctgacagattc
 A  P  R  L  L  I  S  Y  T  S  S  R  Y  A  G  V  P  D  R  F
tccggcagcggcagcggcaccgatttcaccctcaccatcagcagcctggaagccgaagat
 S  G  S  G  S  G  T  D  F  T  L  T  I  S  S  L  E  A  E  D
gaagctgtgtattactgcagcaggactacaacagccccccacatttggccagggaacc
 E  A  V  Y  Y  C  Q  Q  D  Y  N  S  P  P  T  F  G  Q  G  T
aaggtggagatcaaggagcccaagagcagcgacaagacccatacctgccctccttgccct
 K  V  E  I  K  E  P  K  S  S  D  K  T  H  T  C  P  P  C  P
ccttgtcctccctgtggaggcggaagctccggaggaggatccggaggccagcctagagag
 P  C  P  P  C  G  G  S  S  G  G  G  S  G  G  Q  P  R  E
ccccaggtgtacaccctgcccctagcagggaggagatgaccaagaaccaggtgagcctg
 P  Q  V  Y  T  L  P  P  S  R  E  E  M  T  K  N  Q  V  S  L
acatgtctggtcaaggcttttaccccagcgacatcgccgtggagtgggagagcaacggc
 T  C  L  V  K  G  F  Y  P  S  D  I  A  V  E  W  E  S  N  G
cagcctgagaacaactacaagaccacccctcctgtgctggactccgacggcagcttttc
 Q  P  E  N  N  Y  K  T  T  P  P  V  L  D  S  D  G  S  F  F
```

FIG. 58

```
ctgtacagcaagctgaccgtggataagagcaggtggcagcagggcaacgtcttcagctgc
 L  Y  S  K  L  T  V  D  K  S  R  W  Q  Q  G  N  V  F  S  C
agcgtgatgcacgaggctctgcataaccactacacccagaagagcctgagcctgagccct
 S  V  M  H  E  A  L  H  N  H  Y  T  Q  K  S  L  S  L  S  P
ggatga (SEQ ID NO: 155)
 G Stop (SEQ ID NO: 123)
```

FIG. 58
continued

IAB20M γ1 EH5(M2)(VL-A9D, T10S, S12A, P15L, L21I, S22N; VH-Q1E, Q6E) (SEQ ID NO: 124)

```
atggagacagacaccctcctcctgtgggtcctgctcctgtgggtgccggatccacaggc
 M  E  T  D  T  L  L  W  V  L  L  L  W  V  P  G  S  T  G
gaggtccagctggtggaatccggagccgaggtgaagaaacccggcgcctccgtgaaagtc
 E  V  Q  L  V  E  S  G  A  E  V  K  K  P  G  A  S  V  K  V
tcctgcaaggcctccggctactccttcaccggctactacatgcactgggtgaggcaggcc
 S  C  K  A  S  G  Y  S  F  T  G  Y  Y  M  H  W  V  R  Q  A
cctggacagggactggaatggatcggcaggattaaccccaacaacggagtgaccctgtac
 P  G  Q  G  L  E  W  I  G  R  I  N  P  N  N  G  V  T  L  Y
aaccagaagttcaaggacagggtcaccatgaccgtggacaccagcatttccaccgcctac
 N  Q  K  F  K  D  R  V  T  M  T  V  D  T  S  I  S  T  A  Y
atggagctgtccaggctgagaagcgacgacaccgctgtgtactactgcgccaggagcacc
 M  E  L  S  R  L  R  S  D  D  T  A  V  Y  Y  C  A  R  S  T
atgatcaccaactacgtgatggattattggggccagggcaccctcgtgacagtgagcagc
 M  I  T  N  Y  V  M  D  Y  W  G  Q  G  T  L  V  T  V  S  S
ggatccacaagcggaggcggaagcggaggcggcagcggcggcggcggcagcagcgatatc
 G  S  T  S  G  G  G  S  G  G  G  S  G  G  G  G  S  S  D  I
gtgatgacccagagccccgattccctcgccgtgagcctgggcgaaagggccacaatcaac
 V  M  T  Q  S  P  D  S  L  A  V  S  L  G  E  R  A  T  I  N
tgcaaggccagccagtccgtctccaacgatgtggcctggtaccagcagaagcccggacag
 C  K  A  S  Q  S  V  S  N  D  V  A  W  Y  Q  Q  K  P  G  Q
gcccctaggctcctgatctcctacaccagctccaggtacgccggcgtccctgacagattc
 A  P  R  L  L  I  S  Y  T  S  S  R  Y  A  G  V  P  D  R  F
tccggcagcggcagcggcaccgatttcaccctcaccatcagcagcctgcaggccgaggac
 S  G  S  G  S  G  T  D  F  T  L  T  I  S  S  L  Q  A  E  D
gtggctgtgtattactgccagcaggactacaacagccccccacatttggccagggaacc
 V  A  V  Y  Y  C  Q  Q  D  Y  N  S  P  P  T  F  G  Q  G  T
aaggtggagatcaaggagcccaagagcagcgacaagacccatacctgccctccttgccct
 K  V  E  I  K  E  P  K  S  S  D  K  T  H  T  C  P  P  C  P
ccttgtcctccctgtggaggcggaagctccggaggaggatccggaggccagcctagagag
 P  C  P  P  C  G  G  G  S  S  G  G  G  S  G  G  Q  P  R  E
cccaggtgtacaccctgcccctagcagggaggagatgaccaagaaccaggtgagcctg
 P  Q  V  Y  T  L  P  P  S  R  E  E  M  T  K  N  Q  V  S  L
acatgtctggtcaaggcttttacccagcgacatcgccgtggagtgggagagcaacggc
 T  C  L  V  K  G  F  Y  P  S  D  I  A  V  E  W  E  S  N  G
cagcctgagaacaactacaagaccacccctcctgtgctggactccgacggcagcttttc
 Q  P  E  N  N  Y  K  T  T  P  P  V  L  D  S  D  G  S  F  F
```

FIG. 59 ctgtacagcaagctgaccgtggataagagcaggtggcagcagggcaacgtcttcagctgc
L   Y   S   K   L   T   V   D   K   S   R   W   Q   Q   G   N   V   F   S   C agcgtgatgcacgaggctctgcataaccactacacccagaagagcctgagcctgagccct
S   V   M   H   E   A   L   H   N   H   Y   T   Q   K   S   L   S   L   S   P ggatga (SEQ ID NO: 156)

G Stop (SEQ ID NO: 124)

FIG. 59
continued

Alignment compared IAB1M γ1 EH1(M1) (SEQ ID NO: 125) vs IAB1M γ1 EH3(M1) (SEQ ID NO: 126), differences shown in box.

```
IAB1M γ1 EH1(M1) METDTLLLWVLLLWVPGSTGDIQLTQSPSTLSASVGDRVTITCSASSSVRFIHWYQQKPG 60
IAB1M γ1 EH3(M1) METDTLLLWVLLLWVPGSTGDIQLTQSPSTLSASVGDRVTITCSASSSVRFIHWYQQKPG 60
IAB1M γ1 EH1(M1) KAPKRLIYDTSKLASGVPSRFSGSGSGTDFTLTISSLQPEDFATYYCQQWGSSPFTFGQG 120
IAB1M γ1 EH3(M1) KAPKRLIYDTSKLASGVPSRFSGSGSGTDFTLTISSLQPEDFATYYCQQWGSSPFTFGQG 120
IAB1M γ1 EH1(M1) TKVEIKGSTSGGGSGGGSGGGGSSEVQLVEYGGGLVQPGGSLRLSCAASGFNIKDYYIHW 180
IAB1M γ1 EH3(M1) TKVEIKGSTSGGGSGGGSGGGGSSEVQLVEYGGGLVQPGGSLRLSCAASGFNIKDYYIHW 180
IAB1M γ1 EH1(M1) VRQAPGKGLEWVAWIDPENGDTEFVPKFQGRATMSADTSKNTAYLQMNSLRAEDTAVYYC 240
IAB1M γ1 EH3(M1) VRQAPGKGLEWVAWIDPENGDTEFVPKFQGRATMSADTSKNTAYLQMNSLRAEDTAVYYC 240
IAB1M γ1 EH1(M1) KTGGFWGQGTLVTVSSEPKS [C] DKTHTCP [---] PCGGGSSGGGSGGQPREPQVYTLPPSR [DE] 297
IAB1M γ1 EH3(M1) KTGGFWGQGTLVTVSSEPKS [S] DKTHTCP [PCP] PCGGGSSGGGSGGQPREPQVYTLPPSR [EE] 300
IAB1M γ1 EH1(M1) [L] TKNQVSLTCLVKGFYPSDIAVEWESNGQPENNYKTTPPVLDSDGSFFLYSKLTVDKSRW 357
IAB1M γ1 EH3(M1) [M] TKNQVSLTCLVKGFYPSDIAVEWESNGQPENNYKTTPPVLDSDGSFFLYSKLTVDKSRW 360
IAB1M γ1 EH1(M1) QQGNVFSCSVMHEALHNHYTQKSLSLSPG [K] 387 (SEQ ID NO: 125)
IAB1M γ1 EH3(M1) QQGNVFSCSVMHEALHNHYTQKSLSLSPG [-] 389 (SEQ ID NO: 126)
```

FIG. 60

IAB1M γ1 EH3(M1) (SEQ ID NO: 126), CDR regions are defined by Chothia definition

```
atggagaccgataccctgctgctgtgggtgctgctgctgtgggtgcctggcagcaccggc
 M  E  T  D  T  L  L  L  W  V  L  L  L  W  V  P  G  S  T  G
```
Signal peptide sequence

```
gacattcagctgacccagtccccttccacactgagcgcctccgtgggcgacagggtcaca
 D  I  Q  L  T  Q  S  P  S  T  L  S  A  S  V  G  D  R  V  T
```
VL

```
attacatgt tccgcctccagcagcgtcaggtttatccac tggtatcagcagaagcccggc
 I  T  C   S  A  S  S  S  V  R  F  I  H   W  Y  Q  Q  K  P  G
           LCDR1
```

```
aaggcccccaagagactgatctac gacacaagcaagctggcctcc ggagtgcccagcaga
 K  A  P  K  R  L  I  Y   D  T  S  K  L  A  S   G  V  P  S  R
                          LCDR2
```

```
ttcagcggcagcggatccggcaccgatttcacactgaccatcagcagcctgcagcccgaa
 F  S  G  S  G  S  G  T  D  F  T  L  T  I  S  S  L  Q  P  E
```

```
gacttcgccacctactactgc cagcagtggggctcctccccttcacc ttcggacagggc
 D  F  A  T  Y  Y  C   Q  Q  W  G  S  S  P  F  T   F  G  Q  G
                       LCDR3
```

```
accaaggtggagatcaag ggctccacaagcggcggcggaagcggcggcggcagcggcggc
 T  K  V  E  I  K   G  S  T  S  G  G  G  S  G  G  G  S  G  G
                    Linker
```

```
ggcggctccagc gaagtgcagctggtggagtacggcggcggactggtccagcctggagga
 G  G  S  S   E  V  Q  L  V  E  Y  G  G  G  L  V  Q  P  G  G
 Linker       VH
```

```
agcctgaggctgagctgcgccgcctcc ggctttaacatcaaagattac tacattcactgg
 S  L  R  L  S  C  A  A  S   G  F  N  I  K  D  Y   Y  I  H  W
                             HCDR1
```

```
gtcagacaggcccctggcaaaggcctggagtgggtggcctggatc gatcccgagaacgga
 V  R  Q  A  P  G  K  G  L  E  W  V  A  W  I   D  P  E  N  G
                                                HCDR2
```

```
gac accgagttcgtgcccaagttccagggaagagccaccatgagcgccgacaccagcaag
 D   T  E  F  V  P  K  F  Q  G  R  A  T  M  S  A  D  T  S  K
HCDR2
```

```
aacaccgcctacctgcagatgaattccctcagggccgaggataccgctgtgtactactgc
 N  T  A  Y  L  Q  M  N  S  L  R  A  E  D  T  A  V  Y  Y  C
```

```
aagacc ggcggattt tggggccagggaaccctggtgaccgtcagctcc gagcctaagagc
 K  T   G  G  F   W  G  Q  G  T  L  V  T  V  S  S   E  P  K  S
```

FIG. 61

HCDR3                                                              Upper hinge

| agcgataagacccacacc | tgccctccttgccccccttgt | ggcggaggatcctccggagga |
|---|---|---|
| S  D  K  T  H  T | C  P  P  C  P  P  C | G  G  G  S  S  G  G |

Upper hinge            Core hinge           Lower hinge

| ggatccgga | ggacagcccagggagcctcaggtgtacaccctccctcccagcagggaggag |
|---|---|
| G  S  G | G  Q  P  R  E  P  Q  V  Y  L  P  P  S  R  E  E |

Lower hinge CH3 atgaccaagaaccaggtgtccctgacctgcctcgtcaagggcttctaccccagcgacatc

M  T  K  N  Q  V  S  L  T  C  L  V  K  G  F  Y  P  S  D  I gctgtggagtgggagagcaacggccagcccgaaaacaactacaagaccacccctcccgtg

A  V  E  W  E  S  N  G  Q  P  E  N  N  Y  K  T  T  P  P  V ctggacagcgacggcagcttcttcctctactccaagctgacagtggacaagagcaggtgg

L  D  S  D  G  S  F  F  L  Y  S  K  L  T  V  D  K  S  R  W cagcagggcaacgtgttcagctgctccgtgatgcacgaggccctgcacaatcactatacc

Q  Q  G  N  V  F  S  C  S  V  M  H  E  A  L  H  N  H  Y  T cagaagtccctgtccctctcccccggctag (SEQ ID NO: 157)

Q  K  S  L  S  L  S  P  G  Stop (SEQ ID NO: 126)

FIG. 61
continued

IAB1M γ2 EH2(M1) (SEQ ID NO: 127)

```
atggagaccgatacccctgctgctgtgggtgctgctgctgtgggtgcctggcagcaccggc
 M  E  T  D  L  L  L  W  V  L  L  W  V  P  G  S  T  G
gacattcagctgacccagtccccttccacactgagcgcctccgtgggcgacagggtcaca
 D  I  Q  L  T  Q  S  P  S  T  L  S  A  S  V  G  D  R  V  T
attacatgttccgcctccagcagcgtcaggtttatccactggtatcagcagaagcccggc
 I  T  C  S  A  S  S  S  V  R  F  I  H  W  Y  Q  Q  K  P  G
aaggcccccaagagactgatctacgacacaagcaagctggcctccggagtgcccagcaga
 K  A  P  K  R  L  I  Y  D  T  S  K  L  A  S  G  V  P  S  R
ttcagcggcagcggatccggcaccgatttcacactgaccatcagcagcctgcagcccgaa
 F  S  G  S  G  S  G  T  D  F  T  L  T  I  S  S  L  Q  P  E
gacttcgccacctactactgccagcagtggggctcctccccttcaccttcggacagggc
 D  F  A  T  Y  Y  C  Q  Q  W  G  S  S  P  F  T  F  G  Q  G
accaaggtggagatcaagggctccacaagcggcggcggaagcggcggcggcagcggcggc
 T  K  V  E  I  K  G  S  T  S  G  G  G  S  G  G  G  S  G  G
ggcggctccagcgaagtgcagctggtggagtacggcggcggactggtccagcctggagga
 G  G  S  S  E  V  Q  L  V  E  Y  G  G  G  L  V  Q  P  G  G
agcctgaggctgagctgcgccgcctccggctttaacatcaaagattactacattcactgg
 S  L  R  L  S  C  A  A  S  G  F  N  I  K  D  Y  Y  I  H  W
gtcagacaggcccctggcaaaggcctggagtgggtggcctggatcgatcccgagaacgga
 V  R  Q  A  P  G  K  G  L  E  W  V  A  W  I  D  P  E  N  G
gacaccgagttcgtgcccaagttccagggaagagccaccatgagcgccgacaccagcaag
 D  T  E  F  V  P  K  F  Q  G  R  A  T  M  S  A  D  T  S  K
aacaccgcctacctgcagatgaattccctcagggccgaggatacggctgtgtactactgc
 N  T  A  Y  L  Q  M  N  S  L  R  A  E  D  T  A  V  Y  Y  C
aagaccggcggatttggggccagggaacctggtgaccgtcagctccgagagaaagagc
 K  T  G  G  F  W  G  Q  G  T  L  V  T  V  S  S  E  R  K  S
tgcgtggagtgtcctccttgtccggcggaggatcctccggaggaggatccggaggacag
 C  V  E  C  P  P  C  P  G  G  G  S  S  G  G  G  S  G  G  Q
cccagggagcctcaggtgtacacccctcctcccagcagggaggagatgaccaagaaccag
 P  R  E  P  Q  V  Y  T  L  P  P  S  R  E  E  M  T  K  N  Q
gtgtccctgacctgcctcgtcaagggcttctacccagcgacatcgctgtggagtgggag
 V  S  L  T  C  L  V  K  G  F  Y  P  S  D  I  A  V  E  W  E
agcaacggccagccggaaaacaactacaagaccacccctcccatgctggacagcgacggc
 S  N  G  Q  P  E  N  N  Y  K  T  T  P  P  M  L  D  S  D  G
agcttcttcctctactccaagctgacagtggacaagagcaggtggcagcagggcaacgtg
```

FIG. 62

```
        S   F   F   L   Y   S   K   L   T   V   D   K   S   R   W   Q   Q   G   N   V
ttcagctgctccgtgatgcacgaggccctgcacaatcactatacccagaagtccctgtcc
        F   S   C   S   V   M   H   E   A   L   H   N   H   Y   T   Q   K   S   L   S
ctctcccccggctag (SEQ ID NO: 158)
  L   S   P   G   Stop (SEQ ID NO: 127)
```

FIG. 62
continued

IAB1M γ1 EH5(M1) (SEQ ID NO: 128)

```
atggaaaccgatacoctgctgctgtgggtgctgctgctgtgggtgccgggcagcaccggc
 M  E  T  D  T  L  L  W  V  L  L  L  W  V  P  G  S  T  G
gatattcagctgacccagagcccgagcaccctgagcgcgagcgtgggcgatcgcgtgacc
 D  I  Q  L  T  Q  S  P  S  T  L  S  A  S  V  G  D  R  V  T
attacctgcagcgcgagcagcagcgtgcgctttattcattggtatcagcagaaaccggc
 I  T  C  S  A  S  S  S  V  R  F  I  H  W  Y  Q  Q  K  P  G
aaagcgccgaaacgcctgatttatgataccagcaaactggcgagcggcgtgccgagccgc
 K  A  P  K  R  L  I  Y  D  T  S  K  L  A  S  G  V  P  S  R
tttagcggcagcggcagcggcaccgattttaccctgaccattagcagcctgcagccggaa
 F  S  G  S  G  S  G  T  D  F  T  L  T  I  S  S  L  Q  P  E
gattttgcgacctattattgccagcagtggggcagcagcccgtttacctttggccagggc
 D  F  A  T  Y  Y  C  Q  Q  W  G  S  S  P  F  T  F  G  Q  G
accaaagtggaaattaaaggcagcaccagcggcggcggcagcggcggcggcagcggcggc
 T  K  V  E  I  K  G  S  T  S  G  G  G  S  G  G  G  S  G  G
ggcggcagcagcgaagtgcagctggtggaatatggcggcggcctggtgcagccgggcggc
 G  G  S  S  E  V  Q  L  V  E  Y  G  G  G  L  V  Q  P  G  G
agcctgcgcctgagctgcgcggcgagcggctttaacattaaagattattatattcattgg
 S  L  R  L  S  C  A  A  S  G  F  N  I  K  D  Y  Y  I  H  W
gtgcgccaggcgccgggcaaaggcctggaatgggtggcgtggattgatccggaaaacggc
 V  R  Q  A  P  G  K  G  L  E  W  V  A  W  I  D  P  E  N  G
gataccgaatttgtgccgaaatttcagggccgcgcgaccatgagcgcggataccagcaaa
 D  T  E  F  V  P  K  F  Q  G  R  A  T  M  S  A  D  T  S  K
aacaccgcgtatctgcagatgaacagcctgcgcgcggaagataccgcggtgtattattgc
 N  T  A  Y  L  Q  M  N  S  L  R  A  E  D  T  A  V  Y  Y  C
aaaaccggcggcttttggggccagggcaccctggtgaccgtgagcagcgaaccgaaaagc
 K  T  G  G  F  W  G  Q  G  T  L  V  T  V  S  S  E  P  K  S
agcgataaaacccataccctgcccgccgtgccgccgtgcccgccgtgcggcggcggcagc
 S  D  K  T  H  T  C  P  P  C  P  P  C  P  P  C  G  G  G  S
agcggcggcggcagcggcggccagccgcgcgaaccgcaggtgtataccctgccgccgagc
 S  G  G  G  S  G  G  Q  P  R  E  P  Q  V  Y  T  L  P  P  S
cgcgaagaaatgaccaaaaaccaggtgagcctgacctgcctggtgaaaggcttttatccg
 R  E  E  M  T  K  N  Q  V  S  L  T  C  L  V  K  G  F  Y  P
agcgatattgcggtggaatgggaaagcaacggccagccggaaaacaactataaaaccacc
 S  D  I  A  V  E  W  E  S  N  G  Q  P  E  N  N  Y  K  T  T
ccgccggtgctggatagcgatggcagcttttttctgtatagcaaactgaccgtggataaa
 P  P  V  L  D  S  D  G  S  F  F  L  Y  S  K  L  T  V  D  K
```

FIG. 63

```
agccgctggcagcagggcaacgtgtttagctgcagcgtgatgcatgaagcgctgcataac
 S   R   W   Q   Q   G   N   V   F   S   C   S   V   M   H   E   A   L   H   N
cattatacccagaaaagcctgagcctgagcccgggctga (SEQ ID NO: 159)
 H   Y   T   Q   K   S   L   S   L   S   P   G  Stop (SEQ ID NO: 128)
```

FIG. 63
continued

IAB1M γ1 EH7(M1) (SEQ ID NO: 129)

```
atggaaaccgatacctgctgctgtgggtgctgctgctgtgggtgccggcagcaccggc
 M  E  T  D  T  L  L  W  V  L  L  L  W  V  P  G  S  T  G
gatattcagctgacccagagcccgagcaccctgagcgcgagcgtgggcgatcgcgtgacc
 D  I  Q  L  T  Q  S  P  S  T  L  S  A  S  V  G  D  R  V  T
attacctgcagcgcgagcagcagcgtgcgctttattcattggtatcagcagaaaccgggc
 I  T  C  S  A  S  S  S  V  R  F  I  H  W  Y  Q  Q  K  P  G
aaagcgccgaaacgcctgatttatgataccagcaaactggcgagcggcgtgccgagccgc
 K  A  P  K  R  L  I  Y  D  T  S  K  L  A  S  G  V  P  S  R
tttagcggcagcggcagcggcaccgattttaccctgaccattagcagcctgcagccggaa
 F  S  G  S  G  S  G  T  D  F  T  L  T  I  S  S  L  Q  P  E
gattttgcgacctattattgccagcagtggggcagcagccgtttacctttggccagggc
 D  F  A  T  Y  Y  C  Q  Q  W  G  S  S  P  F  T  F  G  Q  G
accaaagtggaaattaaaggcagcaccagcggcggcggcagcggcggcggcagcggcggc
 T  K  V  E  I  K  G  S  T  S  G  G  G  S  G  G  G  S  G  G
ggcggcagcagcgaagtgcagctggtggaatatggcggcggcctggtgcagccgggcggc
 G  G  S  S  E  V  Q  L  V  E  Y  G  G  G  L  V  Q  P  G  G
agcctgcgcctgagctgcgcggcgagcggctttaacattaaagattattatattcattgg
 S  L  R  L  S  C  A  A  S  G  F  N  I  K  D  Y  Y  I  H  W
gtgcgccaggcgccgggcaaaggcctggaatgggtggcgtggattgatccggaaaacggc
 V  R  Q  A  P  G  K  G  L  E  W  V  A  W  I  D  P  E  N  G
gataccgaatttgtgccgaaatttcagggccgcgcgaccatgagcgcggataccagcaaa
 D  T  E  F  V  P  K  F  Q  G  R  A  T  M  S  A  D  T  S  K
aacaccgcgtatctgcagatgaacagcctgcgcgcggaagataccgcggtgtattattgc
 N  T  A  Y  L  Q  M  N  S  L  R  A  E  D  T  A  V  Y  Y  C
aaaaccggcggcttttggggccagggcaccctggtgaccgtgagcagcgaactgaaaacc
 K  T  G  G  F  W  G  Q  G  T  L  V  T  V  S  S  E  L  K  T
ccgctgggcgataccacccataccctgccgccgtgcccgccgtgcggcggcggcagcagc
 P  L  G  D  T  T  H  T  C  P  P  C  P  P  C  G  G  G  S  S
ggcggcggcagcggcggccagccgcgcgaaccgcaggtgtataccctgccgccgagccgc
 G  G  G  S  G  G  Q  P  R  E  P  Q  V  Y  T  L  P  P  S  R
gaagaaatgaccaaaaaccaggtgagcctgacctgcctggtgaaaggctttatccgagc
 E  E  M  T  K  N  Q  V  S  L  T  C  L  V  K  G  F  Y  P  S
gatattgcggtggaatgggaaagcaacggccagccggaaaacaactataaaaccacccg
 D  I  A  V  E  W  E  S  N  G  Q  P  E  N  N  Y  K  T  T  P
ccggtgctggatagcgatggcagcttttttctgtatagcaaactgaccgtggataaaagc
 P  V  L  D  S  D  G  S  F  F  L  Y  S  K  L  T  V  D  K  S
```

FIG. 64 cgctggcagcagggcaacgtgtttagctgcagcgtgatgcatgaagcgctgcataaccat

R  W  Q  Q  G  N  V  F  S  C  S  V  M  H  E  A  L  H  N  H tatacccagaaaagcctgagcctgagcccgggctga (SEQ ID NO: 160)

Y  T  Q  K  S  L  S  L  S  P  G  Stop (SEQ ID NO: 129)

FIG. 64
continued

IAB1M γ1 EH8(M1) (SEQ ID NO: 130)

```
atggaaaccgataccctgctgctgtgggtgctgctgctgtgggtgccgggcagcaccggc
 M  E  T  D  T  L  L  L  W  V  L  L  L  W  V  P  G  S  T  G
gatattcagctgacccagagcccgagcaccctgagcgcgagcgtgggcgatcgcgtgacc
 D  I  Q  L  T  Q  S  P  S  T  L  S  A  S  V  G  D  R  V  T
attacctgcagcgcgagcagcagcgtgcgctttattcattggtatcagcagaaaccgggc
 I  T  C  S  A  S  S  S  V  R  F  I  H  W  Y  Q  Q  K  P  G
aaagcgccgaaacgcctgatttatgataccagcaaactggcgagcggcgtgccgagccgc
 K  A  P  K  R  L  I  Y  D  T  S  K  L  A  S  G  V  P  S  R
tttagcggcagcggcagcggcaccgattttaccctgaccattagcagcctgcagccggaa
 F  S  G  S  G  S  G  T  D  F  T  L  T  I  S  S  L  Q  P  E
gattttgcgacctattattgccagcagtggggcagcagcccgtttacctttggccagggc
 D  F  A  T  Y  Y  C  Q  Q  W  G  S  S  P  F  T  F  G  Q  G
accaaagtggaaattaaaggcagcaccagcggcggcggcagcggcggcggcagcggcggc
 T  K  V  E  I  K  G  S  T  S  G  G  G  S  G  G  G  S  G  G
ggcggcagcagcgaagtgcagctggtggaatatggcggcggcctggtgcagccgggcggc
 G  G  S  S  E  V  Q  L  V  E  Y  G  G  G  L  V  Q  P  G  G
agcctgcgcctgagctgcgcggcgagcggctttaacattaaagattattatattcattgg
 S  L  R  L  S  C  A  A  S  G  F  N  I  K  D  Y  Y  I  H  W
gtgcgccaggcgccgggcaaaggcctggaatgggtggcgtggattgatccggaaaacggc
 V  R  Q  A  P  G  K  G  L  E  W  V  A  W  I  D  P  E  N  G
gataccgaatttgtgccgaaatttcagggccgcgcgaccatgagcgcggataccagcaaa
 D  T  E  F  V  P  K  F  Q  G  R  A  T  M  S  A  D  T  S  K
aacaccgcgtatctgcagatgaacagcctgcgcgcggaagataccgcggtgtattattgc
 N  T  A  Y  L  Q  M  N  S  L  R  A  E  D  T  A  V  Y  Y  C
aaaaccggcggcttttggggccagggcaccctggtgaccgtgagcagcgaactgaaaacc
 K  T  G  G  F  W  G  Q  G  T  L  V  T  V  S  S  E  L  K  T
ccgctgggcgataccacccatacctgcccgccgtgcccgccgtgcccgccgtgcggcggc
 P  L  G  D  T  T  H  T  C  P  P  C  P  P  C  P  P  C  G  G
ggcagcagcggcggcggcagcggcggccagccgcgcgaaccgcaggtgtataccctgccg
 G  S  S  G  G  G  S  G  G  Q  P  R  E  P  Q  V  Y  T  L  P
ccgagccgcgaagaaatgaccaaaaaccaggtgagcctgacctgcctggtgaaaggcttt
 P  S  R  E  E  M  T  K  N  Q  V  S  L  T  C  L  V  K  G  F
tatccgagcgatattgcggtggaatgggaaagcaacggccagccggaaaacaactataaa
 Y  P  S  D  I  A  V  E  W  E  S  N  G  Q  P  E  N  N  Y  K
accaccccgccggtgctggatagcgatggcagcttttttctgtatagcaaactgaccgtg
 T  T  P  P  V  L  D  S  D  G  S  F  F  L  Y  S  K  L  T  V
```

FIG. 65A

```
gataaaagccgctggcagcagggcaacgtgtttagctgcagcgtgatgcatgaagcgctg
 D   K   S   R   W   Q   Q   G   N   V   F   S   C   S   V   M   H   E   A   L
cataaccattatacccagaaaagcctgagcctgagcccgggctga  (SEQ ID NO: 161)
 H   N   H   Y   T   Q   K   S   L   S   L   S   P   G Stop  (SEQ ID NO: 130)
```

FIG. 65A
continued

IAB25M γ2 NH (M1)

```
ATGGAAACCGACACCCTGCTGCTGTGGGTGCTGCTGCTCTGGGTCCCAGGCTCCACCGGT
 M   E   T   D   T   L   L   L   W   V   L   L   L   W   V   P   G   S   T   G
Signal Peptide
GAAATTGTGTTGACACAGTCTCCAGCCACCCTGTCTTTGTCTCCAGGGGAAAGAGCCACC
 E   I   V   L   T   Q   S   P   A   T   L   S   L   S   P   G   E   R   A   T
VL
CTCTCCTGC|AGTGCCAGCTCAAGTGTAAGTTACATGAAC|TGGTACCAACAGAAACCTGGC
 L   S   C |S   A   S   S   S   V   S   Y   M   N |W   Y   Q   Q   K   P   G
                       LCDR1
CAGGCTCCCAGGCTCCTCATCTAT|GACACATCCAAACTGGCTTCT|GGAGTCCCTGCTCAC
 Q   A   P   R   L   L   I   Y |D   T   S   K   L   A   S |G   V   P   A   H
                                      LCDR2
TTCAGGGGCAGTGGGTCTGGGACAGACTTCACTCTCACCATCAGCAGCCTAGAGCCTGAA
 F   R   G   S   G   S   G   T   D   F   T   L   T   I   S   S   L   E   P   E
GATTTTGCAGTTTATTACTGT|CAGCAGTGGAGTAGTAACCCATTCACG|TTCGGCCAAGGG
 D   F   A   V   Y   Y   C |Q   Q   W   S   S   N   P   F   T |F   G   Q   G
                               LCDR3
ACCAAGGTGGAAATCAAA|GGCTCCACATCCGGCGGAGGCTCTGGCGGTGGATCTGGCGGA
 T   K   V   E   I   K |G   S   T   S   G   G   G   S   G   G   G   S   G   G
                           Linker
|GGCGGCTCATCC|CAGGTGCAGCTGGTGCAGTCTGGGGCTGAGGTGAAGAAGCCTGGGGCC
 G   G   S   S |Q   V   Q   L   V   Q   S   G   A   E   V   K   K   P   G   A
Linker
TCAGTGAAGGTCTCCTGCAAGGCTTCT|GGATACACCTTCACCAGGTAC|ACGATGCACTGG
 S   V   K   V   S   C   K   A   S |G   Y   T   F   T   R   Y |T   M   H   W
                                         HCDR1
GTGCGACAGGCCCCTGGACAAGGGCTTGAGTGGATGGGATACATT|AATCCTAGCCGTGGT
 V   R   Q   A   P   G   Q   G   L   E   W   M   G   Y   I |N   P   S   R   G
                                                              HCDR2
|TAT|ACTAATTACAATCAGAAGTTCAAGGACAGGGTCACCATGACCACAGACACGTCCATC
 Y |T   N   Y   N   Q   K   F   K   D   R   V   T   M   T   T   D   T   S   I
HCDR2
AGCACAGCCTACATGGAGCTGAGCAGGCTGAGATCTGACGACACGGCCGTGTATTACTGT
 S   T   A   Y   M   E   L   S   R   L   R   S   D   D   T   A   V   Y   Y   C
GCGAGA|TATTATGATGATCATTACTCACTTGACTAC|TGGGGCCAGGGCACCCTGGTCACC
 A   R |Y   Y   D   D   H   Y   S   L   D   Y |W   G   Q   G   T   L   V   T
              HCDR3
GTCTCCTCA|GAGCGCAAA|TGTTGTGTCGAGTGCCCACCGTGCCCA|GCACCACCTGTGGCA
 V   S   S |E   R   K |C   C   V   E   C   P   P   C   P |A   P   P   V   A
            Upper hinge  Core hinge                        Lower hinge (LH)
|GGACCG|GGGCAGCCCCGAGAACCACAGGTGTACACCCTGCCCCCATCCCGGGAGGAGATG
 G   P |G   Q   P   R   E   P   Q   V   Y   T   L   P   P   S   R   E   E   M
(LH)             CH3
ACCAAGAACCAGGTCAGCCTGACCTGCCTGGTCAAAGGCTTCTACCCCAGCGACATCGCC
 T   K   N   Q   V   S   L   T   C   L   V   K   G   F   Y   P   S   D   I   A
GTGGAGTGGGAGAGCAATGGGCAGCCGGAGAACAACTACAAGACCACGCCTCCCATGCTG
```

FIG. 65B

```
         V   E   W   E   S   N   G   Q   P   E   N   N   Y   K   T   T   P   P   M   L
GACTCCGACGGCTCCTTCTTCCTCTACAGCAAGCTCACCGTGGACAAGAGCAGGTGGCAG
         D   S   D   G   S   F   F   L   Y   S   K   L   T   V   D   K   S   R   W   Q

CAGGGGAACGTCTTCTCATGCTCCGTGATGCATGAGGCTCTGCACAACCACTACACGCAG
         Q   G   N   V   F   S   C   S   V   M   H   E   A   L   H   N   H   Y   T   Q

AAGAGCCTCTCCCTGTCTCCGGGTAAA    (SEQ ID NO: 231)
     K   S   L   S   L   S   P   G   K     (SEQ ID NO: 232)
```

FIG. 65B
continued

IAB25M γ2 EH (M1)

```
ATGGAGACCGACACCCTCCTCCTGTGGGTCCTGCTGCTGTGGGTGCCTGGAAGCACCGGC
 M   E   T   D   T   L   L   L   W   V   L   L   L   W   V   P   G   S   T   G
```
Signal Peptide Sequence
```
GAGATTGTGCTGACCCAGTCCCCTGCCACCCTGAGCCTGTCCCCTGGAGAAAGAGCCACA
 E   I   V   L   T   Q   S   P   A   T   L   S   L   S   P   G   E   R   A   T
```
VL
```
CTGAGCTGTTCCGCCTCCTCCAGCGTGAGCTACATGAACTGGTACCAGCAGAAGCCCGGA
 L   S   C   S   A   S   S   S   V   S   Y   M   N   W   Y   Q   Q   K   P   G
                        LCDR1
CAGGCTCCCAGGCTGCTCATCTACGACACAAGCAAGCTGGCTAGCGGCGTGCCCGCTCAT
 Q   A   P   R   L   L   I   Y   D   T   S   K   L   A   S   G   V   P   A   H
                                   LCDR2
TTCAGAGGCAGCGGAAGCGGCACAGATTTTACCCTGACCATTTCCTCCCTGGAGCCTGAG
 F   R   G   S   G   S   G   T   D   F   T   L   T   I   S   S   L   E   P   E GACTTCGCCGTGTATTACTGCCAGCAGTGGAGCTCCAACCCCTTCACATTCGGCCAGGGC
 D   F   A   V   Y   Y   C   Q   Q   W   S   S   N   P   F   T   F   G   Q   G
                            LCDR3
ACCAAGGTGGAAATCAAGGGATCCACAAGCGGAGGCGGCAGCGGCGGCGGCAGCGGAGGC
 T   K   V   E   I   K   G   S   T   S   G   G   G   S   G   G   G   S   G   G
                              Linker
GGAGGCAGCAGCCAGGTGCAACTGGTGCAGAGCGGAGCCGAGGTGAAGAAGCCCGGAGCC
 G   G   S   S   Q   V   Q   L   V   Q   S   G   A   E   V   K   K   P   G   A
```
Linker    VH
```
AGCGTGAAGGTGTCCTGCAAAGCCTCCGGATACACCTTCACCAGGTACACAATGCACTGG
 S   V   K   V   S   C   K   A   S   G   Y   T   F   T   R   Y   T   M   H   W
                                   HCDR1
GTGAGGCAGGCTCCCGGCCAGGGCCTGGAGTGGATGGGATACATCAACCCCAGCAGGGGC
 V   R   Q   A   P   G   Q   G   L   E   W   M   G   Y   I   N   P   S   R   G
                                                         HCDR2
TACACCAACTATAACCAGAAGTTCAAGGACAGGGTGACCATGACCACCGACACCAGCATT
 Y   T   N   Y   N   Q   K   F   K   D   R   V   T   M   T   T   D   T   S   I
```
HCDR2
```
TCCACCGCTTATATGGAGCTCAGCAGACTGAGGTCCGACGACACCGCCGTGTACTACTGC
 S   T   A   Y   M   E   L   S   R   L   R   S   D   D   T   A   V   Y   Y   C GCCAGGTATTACGACGACCACTACAGCCTGGACTACTGGGGCCAGGGAACACTCGTGACC
 A   R   Y   Y   D   D   H   Y   S   L   D   Y   W   G   Q   G   T   L   V   T
          HCDR3
GTGTCCAGCGAGAGGAAGTGCTGCGTGGAATGTCCCCCTTGTCCTGAGGCGGAAGCTCC
 V   S   S   E   R   K   C   C   V   E   C   P   P   C   P   G   G   G   S   S
         Upper hinge    Core hinge                  Lower hinge
GGAGGAGGATCCGGCGGACAGCCCAGGGAACCTCAGGTGTACACCCTGCCCCCCAGCAGG
 G   G   G   S   G   Q   P   R   E   P   Q   V   Y   T   L   P   P   S   R
```
Lower hinge    CH3
```
GAGGAGATGACAAAGAACCAGGTGAGCCTGACCTGTCTGGTGAAGGGCTTCTACCCCAGC
 E   E   M   T   K   N   Q   V   S   L   T   C   L   V   K   G   F   Y   P   S
```

FIG. 65C

```
GACATCGCCGTGGAGTGGGAGAGCAACGGCCAGCCTGAGAACAACTACAAGACAACCCCC
 D   I   A   V   E   W   E   S   N   G   Q   P   E   N   N   Y   K   T   T   P

CCTATGCTGGATAGCGACGGCAGCTTCTTCCTGTACTCCAAGCTCACCGTGGATAAGAGC
 P   M   L   D   S   D   G   S   F   F   L   Y   S   K   L   T   V   D   K   S

AGGTGGCAGCAGGGAAACGTCTTTAGCTGTTCCGTGATGCACGAGGCCCTGCACAACCAC
 R   W   Q   Q   G   N   V   F   S   C   S   V   M   H   E   A   L   H   N   H

TACACCCAGAAGAGCCTCTCCCTGTCCCCCGGCAAG  (SEQ ID NO: 233)
 Y   T   Q   K   S   L   S   L   S   P   G   K   (SEQ ID NO: 234)
```

FIG. 65C
continued

IAB22M variable heavy (VH-K67R) sequence

VH
EVQLVESGGGLVQPGGSLRLSCAASGFNIKDTYIHFVRQAPGKGLEWIGRIDP
ANDNTLYASKFQGRATISADTSKNTAYLQMNSLRAEDTAVYYCGRGYGYYVFD
HWGQGTLVTVSS (SEQ ID NO: 99)

FIG. 66

IAB20M variable light (VL-Q79E, V83E)
VL
DIVMTQSPATLSVSPGERATLSCKASQSVSNDVAWYQQKPGQAPRLLISYTSSRY
AGVPDRFSGSGSGTDFTLTISSLEAEDEAVYYCQQDYNSPPTFGQGTKVEIK
(SEQ ID NO: 100)

IAB20M variable light (VL-A9D, T10S, S12A, P15L, L21I, S22N)
VL
DIVMTQSPDSLAVSLGERATINCKASQSVSNDVAWYQQKPGQAPRLLISYTSSRY
AGVPDRFSGSGSGTDFTLTISSLQAEDVAVYYCQQDYNSPPTFGQGTKVEIK
(SEQ ID NO: 101)

FIG. 67

IAB20M variable heavy (VH-Q1E, Q6E)
VH
EVQLVESGAEVKKPGASVKVSCKASGYSFTGYYMHWVRQAPGQGLEWIGRINP
NNGVTLYNQKFKDRVTMTVDTSISTAYMELSRLRSDDTAVYYCARSTMITNYV
MDYWGQGTLVTVSS (SEQ ID NO: 102)

FIG. 68

Anti-CD3 variable light (VL, R62S) sequence
EIVLTQSPATLSLSPGERATLSCSASSSVSYMNWYQQKPGQAPRLLIYDTSKLASGVP
AHFSGSGSGTDFTLTISSLEPEDFAVYYCQQWSSNPFTFGQGTKVEIK **(SEQ ID
NO: 103)**

Anti-CD3 variable heavy (VH, Q1E, Q6E) sequence
EVQLVESGAEVKKPGASVKVSCKASGYTFTRYTMHWVRQAPGQGLEWMGYINPSRGYT
NYNQKFKDRVTMTTDTSISTAYMELSRLRSDDTAVYYCARYYDDHYSLDYWGQGTLVT
VSS (SEQ ID NO: 104)

FIG. 69

PSMA (Prostate-Specific Membrane Antigen), Glutamate carboxypeptidase 2, Homo sapiens
UniProtKB/SwissProt: Q04609 (SEQ ID NO: 131)

MWNLLHETDSAVATARRPRWLCAGALVLAGGFFLLGFLFGWFIKSSNEATNITPKHNMKAFLDELKAENI

KKFLYNFTQIPHLAGTEQNFQLAKQIQSQWKEFGLDSVELAHYDVLLSYPNKTHPNYISIINEDGNEIFN

TSLFEPPPPGYENVSDIVPPFSAFSPQGMPEGDLVYVNYARTEDFFKLERDMKINCSGKIVIARYGKVFR

GNKVKNAQLAGAKGVILYSDPADYFAPGVKSYPDGWNLPGGGVQRGNILNLNGAGDPLTPGYPANEYAYR

RGIAEAVGLPSIPVHPIGYYDAQKLLEKMGGSAPPDSSWRGSLKVPYNVGPGFTGNFSTQKVKMHIHSTN

EVTRIYNVIGTLRGAVEPDRYVILGGHRDSWVFGGIDPQSGAAVVHEIVRSFGTLKKEGWRPRRTILFAS

WDAEEFGLLGSTEWAEENSRLLQERGVAYINADSSIEGNYTLRVDCTPLMYSLVHNLTKELKSPDEGFEG

KSLYESWTKKSPSPEFSGMPRISKLGSGNDFEVFFQRLGIASGRARYTKNWETNKFSGYPLYHSVYETYE

LVEKFYDPMFKYHLTVAQVRGGMVFELANSIVLPFDCRDYAVVLRKYADKIYSISMKHPQEMKTYSVSFD

SLFSAVKNFTEIASKFSERLQDFDKSNPIVLRMMNDQLMFLERAFIDPLGLPDRPFYRHVIYAPSSHNKY

AGESFPGIYDALFDIESKVDPSKAWGEVKRQIYVAAFTVQAAAETLSEVA (SEQ ID NO: 131)

FIG. 70

PSCA (Prostate Stem Cell Antigen), Homo sapiens
UniProtKB/SwissProt: O43653 (SEQ ID NO: 132)

MKAVLLALLMAGLALQPGTALLCYSCKAQVSNEDCLQVENCTQLGEQCWTARIRAVGLLTVISKGCSLNC VDDSQDYYVGKKNITCCDTDLCNASGAHALQPAAAILALLPALGLLLWGPGQL (SEQ ID NO: 132)

FIG. 71

5T4 (gi|435655|e5T4 oncofetal trophoblast glycoprotein, Homo sapiens UniProtKB/SwissProt: Q13641 (SEQ ID NO: 133)

MPGGCSRGPAAGDGRLRLARLALVLLGWVSSSSPTSSASSFSSSAPFLASAVSAQPPLPDQCPALCECSE
AARTVKCVNRNLTEVPTDLPAYVRNLFLTGNQLAVLPAGAFARRPPLAELAALNLSGSRLDEVRAGAFEH
LPSLRQLDLSHNPLADLSPFAFSGSNASVSAPSPLVELILNHIVPPEDERQNRSFEGMVVAALLAGRALQ
GLRRLELASNHFLYLPRDVLAQLPSLRHLDLSNNSLVSLTYVSFRNLTHLESLHLEDNALKVLHNGTLAE
LQGLPHIRVFLDNNPWCCDCHMADMVTWLKETEVVQGKDRLTCAYPEKMRNRVLLELNSADLDCDPILPP
SLQTSYVFLGIVLALIGAIFLLVLYLNRKGIKKWMHNIRDACRDHMEGYHYRYEINADPRLTNLSSNSDV (SEQ ID NO: 133)

FIG. 72

T-cell surface glycoprotein CD8 alpha chain, Homo sapiens
UniProtKB/SwissProt: P01732 (SEQ ID NO: 134)

MALPVTALLLPLALLLHAARPSQFRVSPLDRTWNLGETVELKCQVLLSNPTSGCSWLFQPRGAAASPTFL
LYLSQNKPKAAEGLDTQRFSGKRLGDTFVLTLSDFRRENEGYYFCSALSNSIMYFSHFVPVFLPAKPTTT
PAPRPPTPAPTIASQPLSLRPEACRPAAGGAVHTRGLDFACDIYIWAPLAGTCGVLLLSLVITLYCNHRN
RRRVCKCPRPVVKSGDKPSLSARYV (SEQ ID NO: 134)

FIG. 73

T-cell surface glycoprotein CD8 beta chain, Homo sapiens
UniProtKB/SwissProt: P10966 (SEQ ID NO: 135)

MRPRLWLLLAAQLTVLHGNSVLQQTPAYIKVQTNKMVMLSCEAKISLSNMRIYWLRQRQAPSSDSHHEFLALWDSAK

GTIHGEEVEQEKIAVFRDASRFILNLTSVKPEDSGIYFCMIVGSPELTFGKGTQLSVVDFLPTTAQPTKKSTLKKRV

CRLPRPETQKGPLCSPVTLGLLVAGVLVLLVSLGVAMHLCCRRRRARLRFMKQFYK  (SEQ ID NO: 135)

FIG. 74

T-cell surface glycoprotein CD3 delta chain, Homo sapiens
UniProtKB/SwissProt: P04234 (SEQ ID NO: 136)

MEHSTFLSGLVLATLLSQVSPFKIPIEELEDRVFVNCNTSITWVEGTVGTLLSDITRLDLGKRILDPRGI

YRCNGTDIYKDKESTVQVHYRMCQSCVELDPATVAGIIVTDVIATLLLALGVFCFAGHETGRLSGAADTQ

ALLRNDQVYQPLRDRDDAQYSHLGGNWARNK (SEQ ID NO: 136)

FIG. 75

T-cell surface glycoprotein CD3 gamma chain, Homo sapiens
UniProtKB/SwissProt: P09693 (SEQ ID NO: 137)

MEQGKGLAVLILAIILLQGTLAQSIKGNHLVKVYDYQEDGSVLLTCDAEAKNITWFKDGKMIGFLTEDKK
KWNLGSNAKDPRGMYQCKGSQNKSKPLQVYYRMCQNCIELNAATISGFLFAEIVSIFVLAVGVYFIAGQD
GVRQSRASDKQTLLPNDQLYQPLKDREDDQYSHLQGNQLRRN (SEQ ID NO: 137)

FIG. 76

T-cell surface glycoprotein CD3 epsilon chain
UniProtKB/SwissProt: P07766 (SEQ ID NO: 138)

MQSGTHWRVL GLCLLSVGVW GQDGNEEMGG ITQTPYKVSI SGTTVILTCP
QYPGSEILWQ HNDKNIGGDE DDKNIGSDED HLSLKEFSEL EQSGYYVCYP
RGSKPEDANF YLYLRARVCE NCMEMDVMSV ATIVIVDICI TGGLLLVYY
WSKNRKAKAK PVTRGAGAGG RQRGQNKERP PPVPNPDYEP IRKGQRDLYS
GLNQRRI   (SEQ ID NO: 138)

FIG. 77

T-cell surface glycoprotein CD3 zeta chain, Homo sapiens
UniProtKB/SwissProt: P20963 (SEQ ID NO: 139)

MKWKALFTAA ILQAQLPITE AQSFGLLDPK LCYLLDGILF IYGVILTALF
LRVKFSRSAD APAYQQGQNQ LYNELNLGRR EEYDVLDKRR GRDPEMGGKP
QRRKNPQEGL YNELQKDKMA EAYSEIGMKG ERRRGKGHDG LYQGLSTATK
DTYDALHMQA LPPR (SEQ ID NO: 139)

FIG. 78

IAB25M γ2 EH2 (N- to C-terminal)

IAB25 variable light (VL) sequence
EIVLTQSPATLSLSPGERATLSCSASSSVSYMNWYQQKPGQAPRLLIYDTSKLASGVPAHFRGSGSGTDFTLTISSLEPE
DFAVYYCQQWSSNPFTFGQGTKVEIK (SEQ ID NO: 19)

Linker
GSTSGGGSGGGGSGGGGSS (SEQ ID NO: 62)

IAB25 variable heavy (VH) sequence
QVQLVQSGAEVKKPGASVKVSCKASGYTFTRYTMHWVRQAPGQGLEWMGYINPSRGYTNYNQKFKDRVTMTTDTSIS
TAYMELSRLRSDDTAVYYCARYYDDHYSLDYWGQGTLVTVSS (SEQ ID NO: 20)

Full hinge (EH2)
ERKSCVECPPCPGGGSSGGGSG (SEQ ID NO: 34)

Upper hinge
ERK (SEQ ID NO: 47)

Core hinge
SCVECPPCP (SEQ ID NO: 56)

Lower hinge
GGGSSGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLTVDKSRWQ
QGNVFSCSVMHEALHNHYTQKSLSLSPGK (SEQ ID NO: 42)

Human IgG2 CH3 T26S, L28A, M57V
GQPREPQVYTLPPSREEMTKNQVSLSCAVKGFYPSDIAVEWESNGQPENNYKTTPPVLDSDGSFFLVSKLTVDKSRW
QQGNVFSCSVMHEALHNHYTQKSLSLSPG (SEQ ID NO: 181)

Human IgG2 CH3 T26W
GQPREPQVYTLPPSREEMTKNQVSLWCLVKGFYPSDIAVEWESNGQPENNYKTTPPVLDSDGSFFLYSKLTVDKSRW
QQGNVFSCSVMHEALHNHYTQKSLSLSPG (SEQ ID NO: 182)

FIG. 79

IAB20M γ2 EH2 (N- to C-terminal)

Anti-5T4 variable light (VL) sequence
DIVMTQSPATLSVSPGERATLSCKASQSVSNDVAWYQQKPGQAPRLLISYTSSRYAGVPDRFSGSGSGTDFTLTISSLQA
EDVAVYYCQQDYNSPPTFGQGTKVEIK (SEQ ID NO: 17)

Linker
GSTSGGGGSGGGGSGGGGSS (SEQ ID NO: 62)

Anti-5T4 variable heavy (VH) sequence
QVQLVQSGAEVKKPGASVKVSCKASGYSFTGYYMHWVRQAPGQGLEWIGRINPNNGVTLYNQKFKDRVTMTVDTSIST
AYMELSRLRSDDTAVYYCARSTMITNYVMDYWGQGTLVTVSS (SEQ ID NO: 18)

Full hinge (EH2)
ERKSCVECPPCPGGGSSGGGGSG (SEQ ID NO: 34)

Upper hinge
ERK (SEQ ID NO: 47)

Core hinge
SCVECPPCP (SEQ ID NO: 56)

Lower hinge
GGGSSGGGGSG (SEQ ID NO: 59)

Human IgG2 CH3
GQPREPQVYTLPPSREEMTKNQVSLTCLVKGFYPSDIAVEWESNGQPENNYKTTPPMLDSDGSFFLYSKLTVDKSRWQ
QGNVFSCSVMHEALHNHYTQKSLSLSPGK (SEQ ID NO: 42)

Human IgG2 CH3 T26S, L28A, M57V
GQPREPQVYTLPPSREEMTKNQVSLSCAVKGFYPSDIAVEWESNGQPENNYKTTPPVLDSDGSFFLVSKLTVDKSRWQ
QGNVFSCSVMHEALHNHYTQKSLSLSPG (SEQ ID NO: 181)

Human IgG2 CH3 T26W
GQPREPQVYTLPPSREEMTKNQVSLWCLVKGFYPSDIAVEWESNGQPENNYKTTPPVLDSDGSFFLYSKLTVDKSRWQ
QGNVFSCSVMHEALHNHYTQKSLSLSPG (SEQ ID NO: 182)

ANTIGEN BINDING CONSTRUCTS TO TARGET MOLECULES

CROSS REFERENCE TO RELATED APPLICATIONS

This application claims the benefit of U.S. Provisional Application No. 62/202,665, filed on Aug. 7, 2015, which is hereby incorporated by reference in its entirety.

REFERENCE TO SEQUENCE LISTING

The present application is being filed along with a Sequence Listing in electronic format. The Sequence Listing is provided as a file entitled IGNAB030ASEQUENCE.TXT, which was created and last modified on Aug. 3, 2016, which is 270,445 bytes in size. The information in the electronic Sequence Listing is hereby incorporated by reference in its entirety.

FIELD

Embodiments described herein relate generally to hinge structures in antigen binding constructs (such as any scFv fusion proteins, such as minibodies), as well as the antigen binding constructs themselves, as well as methods for their use.

BACKGROUND

There are a wide variety of antigen binding constructs known in the art. Such constructs frequently vary by the sequences in their CDR sections, less frequently with variations in their framework regions and other sections of the antibodies (such as $C_H3$ and hinge regions).

SUMMARY

In some aspects, an amino acid hinge region comprising a sequence of SEQ ID NO: 1 ($X_{n1}CX_{n2}X_{n3}CX_{n4}X_{n5}C$) is provided. $X_{n1}$ can be any amino acid that does not naturally form a covalent crosslinking bond. $X_{n2}$ is one of: A, R, N, D, E, Q, G, H, I, L, K, M, F, P, S, T, W, Y, or V. $X_{n3}$ can be any amino acid. $X_{n4}$ can be any amino acid. $X_{n5}$ can be any amino acid.

In some aspects, $X_{n1}$ does not form a covalent crosslinking bond with another amino acid (SEQ ID NO: 191). In some aspects, $X_{n1}$ is not a cysteine (SEQ ID NO: 192). In some aspects, $X_{n1}$ is one of: A, R, N, D, E, Q, G, H, I, L, K, M, F, P, S, T, W, Y, or V (SEQ ID NO: 193). In some aspects, $X_{n2}$ is P, V, or E (SEQ ID NO: 194). In some aspects, $X_{n2}$ is P or V (SEQ ID NO: 195). In some aspects, $X_{n4}$ is P, V, or E (SEQ ID NO: 196). In some aspects, $X_{n4}$ P or V (SEQ ID NO: 197). In some aspects, $X_{n3}$ is P or E (SEQ ID NO: 198). In some aspects, $X_{n5}$ is P or E (SEQ ID NO: 199). In some aspects, $X_{n3}$ P or E (SEQ ID NO: 200). In some aspects, $X_{n2}X_{n3}$ is VE (SEQ ID NO: 201). In some aspects, $X_{n2}X_{n3}$ is PP (SEQ ID NO: 202). In some aspects, $X_{n4}X_{n5}$ is VE (SEQ ID NO: 203). In some aspects, $X_{n4}X_{n5}$ is PP (SEQ ID NO: 204). In some aspects, $X_{n2}X_{n3}$ is VE and $X_{n4}X_{n5}$ is PP (SEQ ID NO: 205). In some aspects, $X_{n2}X_{n3}$ is PP and $X_{n4}X_{n5}$ is PP or VE (SEQ ID NO: 206). In some aspects, $X_{n2}X_{n3}$ is VE and $X_{n4}X_{n5}$ is VE or PP (SEQ ID NO: 207). In some aspects, the hinge further comprises an extension or lower hinge sequence C-terminal to the last cysteine in $X_{n1}CX_{n2}X_{n3}CX_{n4}X_{n5}C$ (SEQ ID NO: 1). In some aspects, the extension or lower hinge sequence comprises at least one of S, G, A, P, or V. In some aspects, the extension sequence comprises at least GGGSSGGGSG (SEQ ID NO: 59). In some aspects, the linker sequence comprises at least APPVAGP (SEQ ID NO: 60). In some aspects, the hinge region of claim 1 is part of a core hinge region. In some aspects, the hinge further comprises an upper hinge region adjacent to the core hinge region. In some aspects, the hinge further comprises a lower hinge or extension region adjacent to the core hinge region. In some aspects, it further comprises an upper hinge region adjacent to the core hinge region. In some aspects, $X_{n1}$ comprises a serine, a threonine, or an alanine (SEQ ID NO: 209). In some aspects, $X_{n1}$ comprises a serine (SEQ ID NO: 210). In some aspects, $X_{n1}$ comprises an alanine (SEQ ID NO: 211). In some aspects, the amino acid hinge region comprises at least one of the following sequences: SCVECPPCP (SEQ ID NO: 56) or TCPPCPPC (SEQ ID NO: 166). In some aspects, the amino acid hinge region comprises at least one of the following sequences: ERKSCVECPPCP (SEQ ID NO: 167), EPKSSDKTHT (SEQ ID NO: 46), and CPPCPPC (SEQ ID NO: 52). In some aspects, the amino acid hinge region comprises at least one of the following sequences: ERKSCVECPPCPGGGSSGGGSG (SEQ ID NO: 34) or ERKSCVECPPCPAPPVAGP (SEQ ID NO: 33) or EPKSSDKTHTCPPCPPCGGGSSGGGSG (SEQ ID NO: 26) or EPKSSDKTHTCPPCPPCAPELLGGP (SEQ ID NO: 25).

In some aspects, an amino acid hinge region is provided. The amino acid hinge region comprises a sequence of SEQ ID NO: 2 ($X_{n1}X_{n2}X_{n3}X_{n4}X_{n5}$ $X_{n6}CX_{n7}X_{n8}CX_{n9}X_{n10}C$). $X_{n1}$ can be any m amino acids (where m is any number of amino acids of any type). $X_{n2}$ can be any amino acid. $X_{n3}$ can be any amino acid. $X_{n4}$ can be any amino acid. $X_{n5}$ can be any amino acid. $X_{n6}$ can be any amino acid other than a cysteine. $X_{n7}$ can be any amino acid. $X_{n8}$ can be any amino acid. $X_{n9}$ can be any amino acid. $X_{n10}$ can be any amino acid (see, e.g., SEQ ID NO: 212). In some aspects, $X_{n1}$ is not a cysteine (see, e.g., SEQ ID NO: 213). In some aspects, $X_{n2}$ is not a cysteine (see, e.g., SEQ ID NO: 214). In some aspects, $X_{n2}$ is a D (see, e.g., SEQ ID NO: 215). In some aspects, $X_{n3}$ is a K (see, e.g., SEQ ID NO: 216). In some aspects, $X_{n4}$ is a T (see, e.g., SEQ ID NO: 217). In some aspects, $X_{n5}$ is a H (see, e.g., SEQ ID NO: 218). In some aspects, $X_{n6}$ is a T (see, e.g., SEQ ID NO: 219). In some aspects, $X_{n7}$ is a P or a V (see, e.g., SEQ ID NO: 220). In some aspects, $X_{n8}$ is a P or a E (see, e.g., SEQ ID NO: 221). In some aspects, $X_{n9}$ is a P or a V (see, e.g., SEQ ID NO: 222). In some aspects, $X_{n10}$ is a P or a E (see, e.g., SEQ ID NO: 223). In some aspects, the amino acid hinge region further comprises a CXXC (see, e.g., SEQ ID NO: 224) or CXXC (see, e.g., SEQ ID NO: 225) motif that is positioned in front of $X_{n1}$. In some aspects, the amino acid hinge region further comprises a $X_{n11}X_{n12}C$ sequence immediately attached to the c-terminal cysteine in SEQ ID NO: 2, wherein $X_{n11}$ can be any amino acid, and wherein $X_{n12}$ can be any amino acid (see, e.g., SEQ ID NO: 226). In some aspects, $X_{n11}$ is a P or a V, and $X_{n12}$ is a P or an E (see, e.g., SEQ ID NO: 227). In some aspects, $X_{n1}$ is a serine, $X_{n2}$ is a D, $X_{n3}$ is a K, $X_{n4}$ is a T, $X_{n5}$ is a H, $X_{n6}$ is a T, $X_{n7}$ is a P, $X_{n8}$ is a P, $X_{n9}$ is a P, and $X_{n10}$ is a P (see, e.g., SEQ ID NO: 228). In some aspects, the hinge region comprises at least one of the following sequences: CPPCPPC (SEQ ID NO: 52), CPPCVECPPC (SEQ ID NO: 53), or CPPCPPCPPC (SEQ ID NO: 54). In some aspects, the hinge region comprises at least one of the following sequences: EPKSSDKTHTCPPCPPC (SEQ ID NO: 168), EPKSSDKTHTCPPCVECPPC (SEQ ID NO: 169), or EPKSSDKTHTCPPCPPCPPC (SEQ ID NO: 170). In some aspects, the hinge region comprises at least one of the following sequences: EPKSSDKTH-TCPPCPPCGGGSSGGGSG (SEQ ID NO: 26), EPKSSDKTHTCPPCVECPPCGGGSSGGGSG (SEQ ID NO: 28), or EPKSSDKTHTCPPCPPCPPCGGGSSGGGSG (SEQ ID NO: 30).

In some aspects, an amino acid hinge region is provided. The hinge region comprises a core hinge sequence of at least one of: CVECPPCP (SEQ ID NO: 57), CPPCPPC (SEQ ID NO: 52), or CPPCPPCPPC (SEQ ID NO: 54), or CPPCVECPPC (SEQ ID NO: 53) linked to an upper hinge sequence of ELKTPLGDTTHT (SEQ ID NO: 48) or EPKSSDKTHT (SEQ ID NO: 46).

In some aspects, an amino acid hinge region for an antibody is provided, it can comprise an upper hinge region that comprises no amino acids capable of crosslinking with a corresponding amino acid; and a core hinge region connected to a C-terminus of the upper hinge region, wherein the core hinge region comprises at least three cysteines per strand. In some aspects, the amino acid hinge region further comprises a lower hinge or extension region connected C-terminal to the core hinge region, wherein the lower hinge or extension sequence is at least one of: APPVAGP (SEQ ID NO: 60), APELLGGP (SEQ ID NO: 58), and/or GGGSSGGGSG (SEQ ID NO: 59). In some aspects, the upper hinge region comprises no cysteines that crosslink within the upper hinge region. In some aspects, the upper hinge region comprises no cysteines. In some aspects, it further comprises a lower hinge or extension region. In some aspects, the lower hinge or extension region comprises at least one of: GGGSSGGGSG (SEQ ID NO: 59) or APPVAGP (SEQ ID NO: 60) or APELLGGP (SEQ ID NO: 58). In some aspects, when located within a minibody, and wherein when the minibody is administered to a human subject, clearance of the minibody from the subject occurs primarily through a liver. In some aspects, when located within a minibody, and wherein when the minibody is administered to a human subject, clearance of the minibody from the subject does not occur primarily through a kidney. In some aspects, the hinge region is within an antibody. In some aspects, the hinge region is within an antibody binding fragment. In some aspects, the hinge region is within a minibody. In some aspects, the hinge region is within a monospecific antibody. In some aspects, the hinge region comprises at least three cysteines per strand. In some aspects, the hinge region comprises at least four cysteines per strand. In some aspects, the hinge region comprises at least five cysteines per strand. In some aspects, cysteines are distributed throughout the amino acid hinge region in a repeating CXX or CXY motif. In some aspects, the hinge region is within a bispecific antibody. In some aspects, the bispecific antibody is assembled in a 1:1 ratio. In some aspects, the bispecific antibody comprises an antibody fragment. In some aspects, the bispecific antibody is a minibody.

In some aspects, a pharmaceutical composition is provided. The pharmaceutical composition can comprise the amino acid hinge region of any of those disclosed herein. In some embodiments, this results in less than 5% aggregation of an antibody is present in the composition.

In some aspects, a pharmaceutical composition comprising the amino acid hinge region of any of those provided herein is provided. In some aspects, at least 1 microgram to 100 mg of the antibody is present.

In some aspects, a minibody comprising a core hinge region is provided. The core hinge region comprises at least three cysteines per strand forming at least three disulfide bonds within the core hinge region. In some aspects, the first residue of the core region is a serine. In some aspects, the core hinge region comprises SCVECPPCP (SEQ ID NO: 56).

In some aspects, a minibody is provided. The minibody can comprise a sequence $X_{n1}CX_{n2}X_{n3}CX_{n4}X_{n5}C$ (SEQ ID NO: 3). This sequence can be located as the core hinge region of the minibody. $X_{n1}$ can be any amino acid or no amino acid. $X_{n2}$ can be any amino acid. $X_{n3}$ can be any amino acid. $X_{n4}$ can be any amino acid. $X_{n5}$ can be any amino acid. In some aspects, $X_{n1}$ is any amino acid other than a cysteine (SEQ ID NO: 229). In some aspects, $X_{n1}$ is a serine (SEQ ID NO: 230).

In some aspects, a variant minibody hinge is provided. The variant hinge can comprise a first altered amino acid position. The first altered position is an amino acid that in a native antibody hinge would be a cysteine, and has been altered in the first altered position so that it does not form a disulfide bond. The variant hinge can also comprise at least three cysteines per strand C-terminal to the first altered amino acid position. In some aspects, the hinge region consists of SEQ ID NO: 1. In some aspects, SEQ ID NO: 1 is a core hinge region, and wherein the core hinge region essentially consists of SEQ ID NO: 1. In some aspects, the core hinge region consists of SEQ ID NO: 1.

In some aspects, a minibody is provided. The minibody that binds to a target antigen, wherein the target antigen is at least one of CD3, CD8, 5T4, PSMA, or PSCA. The minibody comprising a polypeptide that comprises: a single-chain variable fragment (scFv) that binds to the target antigen, the scFv comprising a variable heavy ($V_H$) domain linked a variable light ($V_L$) domain; and a variant hinge region comprising at least three cysteines on each strand of the hinge.

In some aspects, the minibody further comprises a human IgG $C_H3$ sequence. In some aspects, the minibody further comprises a detectable marker selected from the group consisting of a radioactive substance, a dye, a contrast agent, a fluorescent compound, a bioluminescent compound, an enzyme, an enhancing agent, and a nanoparticle.

In some aspects, the minibody comprises: a HCDR1 of the HCDR1 as disclosed herein; a HCDR2 of the HCDR2 as disclosed herein; a HCDR3 of the HCDR3 as disclosed herein; a LCDR1 of the LCDR1 as disclosed herein; a LCDR2 of the LCDR2 as disclosed herein; and a LCDR3 of the LCDR3 as disclosed herein.

In some aspects, the variable heavy ($V_H$) domain and the variable light ($V_L$) domain are human sequences.

In some aspects, a nucleic acid encoding a minibody as disclosed herein is provided.

In some aspects, a cell line producing the minibody as disclosed herein is provided.

In some aspects, a kit comprising any of the minibodies provided herein and a detectable marker is provided.

In some aspects, a method of detecting the presence or absence of a target antigen is provided. The target antigen is at least one of CD3, CD8, 5T4, PSMA, or PSCA. The method comprises applying a minibody as disclosed herein to a sample; and detecting a binding or an absence of binding of the antigen binding construct thereof to the target antigen.

In some aspects, the minibody comprises a detectable marker selected from the group consisting of a radioactive substance, a dye, a contrast agent, a fluorescent compound, a bioluminescent compound, an enzyme, an enhancing agent, and a nanoparticle. In some aspects, applying the minibody comprises administering the minibody to a subject. In some aspects, detecting binding or absence of binding of the minibody thereof to target antigen comprises positron emission tomography. In some aspects, the method further comprising applying a secondary antibody or fragment thereof to the sample, wherein the secondary antibody or fragment thereof binds specifically to the minibody. In some aspects, the minibody thereof is incubated with the sample for no more than 1 hour.

In some aspects, a method of targeting a therapeutic agent to a target antigen is provided. The target antigen is at least one of CD3, CD8, 5T4, PSMA, or PSCA. The method comprises administering to a subject a minibody as disclosed herein, wherein the minibody is conjugated to a therapeutic agent.

In some aspects, a method of neutralizing a B or T lymphocyte cell in a subject in need thereof is provided. The method comprising administering to the subject a minibody as disclosed herein that binds to CD8 and/or CD3. In some aspects, the subject has at least one of the disorders as noted herein.

In some aspects, an antibody and/or minibody that binds to a target antigen (such as CD8, CD3, 5T4, PSMA, PSCA) is provided. The antibody and/or minibody comprises a hinge region, wherein the hinge region comprises at least one of the following:
  a) an amino acid hinge region comprising a sequence of SEQ ID NO: 1 ($X_{n1}CX_{n2}X_{n3}CX_{n4}X_{n5}C$), wherein $X_{n1}$ can be any amino acid that does not naturally form a covalent crosslinking bond, wherein $X_{n2}$ is one of: A, R, N, D, E, Q, G, H, I, L, K, M, F, P, S, T, W, Y, or V, wherein $X_{n3}$ can be any amino acid, wherein $X_{n4}$ can be any amino acid, and wherein $X_{n5}$ can be any amino acid;
  b) an amino acid hinge region comprising a sequence of SEQ ID NO: 2 ($X_{n1}$ $X_{n2}$ $X_{n3}$ $X_{n4}X_{n5}$ $X_{n6}CX_{n7}X_{n8}CX_{n9}X_{n10}C$), wherein $X_{n1}$ can be any m amino acids (where m is any number of amino acids of any type), wherein $X_{n2}$ can be any amino acid, wherein $X_{n3}$ can be any amino acid, wherein $X_{n4}$ can be any amino acid, wherein $X_{n5}$ can be any amino acid, wherein $X_{n6}$ can be any amino acid other than a cysteine, wherein $X_{n7}$ can be any amino acid, wherein $X_{n8}$ can be any amino acid, wherein $X_{n9}$ can be any amino acid, and wherein $X_{n10}$ can be any amino acid;
  c) a core hinge sequence of at least one of: CVECPPCP (SEQ ID NO: 57), CPPCPPC (SEQ ID NO: 52), or CPPCPPCPPC (SEQ ID NO: 54), or CPPCVECPPC (SEQ ID NO: 53) linked to; an upper hinge sequence of ELKTPLGDTTHT (SEQ ID NO: 48) or EPKSSDKTHT (SEQ ID NO: 46);
  d) an upper hinge region that comprises no amino acids capable of crosslinking with a corresponding amino acid; and a core hinge region connected to a C-terminus of the upper hinge region, wherein the core hinge region comprises at least three cysteines per strand;
  e) an antibody and/or minibody comprising a core hinge region, wherein the core hinge region comprises at least three cysteines per strand forming at least three disulfide bonds within the core hinge region; or
  f) a first altered amino acid position, wherein the first altered position is an amino acid that in a native antibody hinge would be a cysteine, and has been altered in the first altered position so that it does not form a disulfide bond; and at least three cysteines per strand C-terminal to the first altered amino acid position.

In some aspects, any minibody provided herein can instead be formatted as a full length antibody. In some embodiments, the minibody body comprises a humanized amino acid sequence.

In some aspects, a method of manufacturing the minibody provided herein comprises expressing the minibody in a cell line.

In some aspects, a method of treating a condition in a subject in need thereof is provided. The method comprises administering to the subject any one or more of the minibodies provided herein to treat any one or more of a CD3, CD8, PSCA, PSMA, and/or 5T4 disorder provided herein.

BRIEF DESCRIPTION OF THE DRAWINGS

FIG. 2 shows an illustration of various embodiments of Mb hinges based on human IgG1 (γ1 EH1 top and γ1 EH2 bottom).

FIG. 3 shows an illustration of various embodiments of Mb hinges based on human IgG2 (γ2 EH1 top and γ2 EH2 bottom).

FIG. 4 shows an illustration of various embodiments of additional Mb hinges based on human IgG2 (γ2 NH1 top and γ2 NH2 bottom).

FIG. 5B shows protein sequence information for some embodiments of IAB2M γ1 EH1.

FIG. 5C shows protein sequence information for some embodiments of IAB2M γ1 EH2.

FIG. 5D shows protein sequence information for some embodiments of IAB2M γ2 EH2.

FIG. 5E shows protein sequence information for some embodiments of IAB2M-γ2 EH1.

FIG. 7C shows protein sequence information for some embodiments of IAB2M γ1 EH3 without a canonical signal sequence.

FIG. 7D shows protein sequence information for some embodiments of IAB2M γ1 EH3 without a canonical signal sequence.

FIG. 7E shows DNA sequence information for IAB2M γ1 EH3 without a canonical signal sequence.

FIG. 8 shows a list of disulfide-containing peptides identified within IAB2M γ1 EH1 dimer.

FIG. 10 shows an illustration of a mapping of the disulfide bonds of IAB2M γ2 EH1 suggesting the absence of mispaired cysteines.

FIG. 14B shows protein sequence information for some embodiments of IAB22M γ2 EH1.

FIG. 15B shows protein sequence information for some embodiments of IAB22M γ2 EH2 variant.

FIG. 16B shows protein sequence information for some embodiments of IAB22M γ1 EH1.

FIG. 16C shows protein sequence information for some embodiments of IAB22M γ2 NH1.

FIG. 16D shows protein sequence information for some embodiments of IAB22M γ2 NH2.

FIG. 19 is an illustration of some embodiments of hinge variants listed in Table 3 (γ1 EH1 top, γ1 EH3 middle, γ1 EH4 bottom).

FIG. 20C shows protein sequence information for some embodiments of IAB22M γ1 EH3.

FIG. 20D shows protein sequence information for some embodiments of IAB22M γ1 EH5.

FIG. 20E shows protein sequence information for some embodiments of IAB22M γ3/γ1 EH6.

FIG. 20F shows protein sequence information for some embodiments of IAB22M γ3/γ1 EH7.

FIG. 20G shows protein sequence information for some embodiments of IAB22M γ3/γ1 EH8.

FIG. 21B shows protein sequence information for some embodiments of IAB2M γ1 EH5.

FIG. 21C shows protein sequence information for some embodiments of IAB2M γ3/γ1 EH6.

FIG. 21D shows protein sequence information for some embodiments of IAB2M γ3/γ1 EH7.

FIG. 21E shows protein sequence information for some embodiments of IAB2M γ3/γ1 EH8.

FIG. 22B shows protein sequence information for some embodiments IAB22M γ1 EH2.

FIG. 25A shows the total ion chromatogram of the IAB22M γ2 EH1 variant (FIG. 14B) under reverse phase conditions (upper panel). Middle panel shows the deconvoluted intact masses confirming the presence of half molecules and the lower panel shows the full-size masses that were identified. Note that the heterogeneity results from the terminal lysine clipping. FIG. 25B shows a deconvoluted full range scan (upper panel) of the IAB22M γ2 EH2 variant (FIG. 15B) identifies the sole species with m/z of 79053.1 Da. Zoomed-in full-size molecular weight is shown on the middle panel and the half molecule is of low abundance and just above the level of noise (bottom panel).

FIG. 28B shows protein sequence information for some embodiments of IAB20M γ1 EH1.

FIG. 28C shows protein sequence information for some embodiments of IAB20M γ1 EH3.

FIG. 28D shows protein sequence information for some embodiments of IAB20M γ1 EH2.

FIG. 28E shows protein sequence information for some embodiments of IAB20M γ1 EH5.

FIG. 29B shows protein sequence information for some embodiments of IAB1M γ1 EH1.

FIG. 29C shows protein sequence information for some embodiments of IAB1M γ2 EH2.

FIG. 29D shows protein sequence information for some embodiments of IAB1M γ1 EH3.

FIG. 32 shows protein sequence information for some embodiments of IAB20M γ2 EH2.

FIG. 33 shows protein sequence information for some embodiments of IAB25M-γ2 EH2.

FIG. 34A shows the DNA sequence encoding some embodiments of the IAB2M Mb.

FIG. 34B shows the DNA sequence encoding some embodiments of the IAB2M Mb.

FIG. 34C shows the DNA sequence encoding some embodiments of the IAB2M Mb.

FIG. 34D shows the DNA sequence encoding some embodiments of the IAB2M Mb.

FIG. 34E shows the DNA sequence encoding some embodiments of the IAB2M Mb.

FIG. 34F shows the DNA sequence encoding some embodiments of the IAB2M Mb.

FIG. 35A shows protein sequence information of IAB2M Mb hinge variants.

FIG. 35B shows protein sequence information of IAB2M Mb hinge variants.

FIG. 35C shows protein sequence information of IAB2M Mb hinge variants.

FIG. 36A shows protein sequence information of VL and VH domains of Mbs with different antigen-specificities.

FIG. 36B shows protein sequence information of VL and VH domains of Mbs with different antigen-specificities.

FIG. 36C shows protein sequence information of VL and VH domains of Mbs with different antigen-specificities.

FIG. 36D shows protein sequence information of VL and VH domains of Mbs with different antigen-specificities.

FIG. 36E shows protein sequence information of VL and VH domains of Mbs with different antigen-specificities.

FIG. 37 shows protein sequence information of various embodiments of linker sequences.

FIG. 38 shows protein sequence information of various embodiments of hinge regions.

FIG. 39 shows protein sequence information of various embodiments of $C_H3$ domains.

FIG. 40 shows an alignment of protein sequences of an embodiment each of IAB22M γ1 EH1(M1) and IAB22M γ1 EH3(M1). Sequence differences are shown in boxes.

FIG. 41 shows the DNA and translated protein sequence of an embodiment of IAB22M γ1 EH3(M1). In boxes are shown the signal, CDR, linker and hinge sequences.

FIG. 42 shows the DNA and translated protein sequence of an embodiment of IAB22M γ1 EH5(M1).

FIG. 43 shows the DNA and translated protein sequence of an embodiment of IAB22M γ1 EH7(M1).

FIG. 44 shows the DNA and translated protein sequence of an embodiment of IAB22M γ1 EH8(M1).

FIG. 45 shows the DNA and translated protein sequence of an embodiment of IAB22M γ2 EH2(M1).

FIG. 46 shows the DNA and translated protein sequence of an embodiment of IAB22M γ2 EH2(M1) with VH-K67R polymorphism.

FIG. 47 shows an alignment of protein sequences of an embodiment each of IAB2M γ1 EH1(M2) and IAB2M γ1 EH3(M2). Sequence differences are shown in boxes.

FIG. 48 shows the DNA and translated protein sequence of an embodiment of IAB2M γ1 EH3(M2). In boxes are shown the signal, CDR, linker and hinge sequences.

FIG. 49 shows the DNA and translated protein sequence of an embodiment of IAB2M γ1 EH3 (M2) (G1m1).

FIG. 50 shows the DNA and translated protein sequence of an embodiment of IAB2M γ1 EH5(M2).

FIG. 51 shows the DNA and translated protein sequence of an embodiment of IAB2M γ1 EH7(M2).

FIG. 52 shows the DNA and translated protein sequence of an embodiment of IAB2M γ1 EH8(M2).

FIG. 53 shows the DNA and translated protein sequence of an embodiment of IAB2M γ1 EH3(M1).

FIG. 54 shows an alignment of protein sequences of an embodiment each of IAB20M γ1 EH1 (M2) and IAB20M γ1 EH3 (M2) with VL-Q79E, V83E; VH-Q1E, Q6E polymorphisms. Sequence differences are shown in boxes.

FIG. 55 shows the DNA and translated protein sequence of an embodiment of IAB20M γ1 EH3(M2) with VL-Q79E, V83E; VH-Q1E, Q6E polymorphisms. In boxes are shown the signal, CDR, linker and hinge sequences.

FIG. 56 shows the DNA and translated protein sequence of an embodiment of IAB20M γ1 EH3(M2).

FIG. 57 shows the DNA and translated protein sequence of an embodiment of IAB20M γ1 EH3 (M2) with VL-A9D, T10S, S12A, P15L, L21I, S22N; VH-Q1E, Q6E polymorphisms.

FIG. 58 shows the DNA and translated protein sequence of an embodiment of IAB20M γ1 EH5 (M2) with VL-Q79E, V83E; VH-Q1E, Q6E polymorphisms.

FIG. 59 shows the DNA and translated protein sequence of an embodiment of IAB20M γ1 EH5 (M2) with VL-A9D, T10S, S12A, P15L, L21I, S22N; VH-Q1E, Q6E polymorphisms.

FIG. 60 shows an alignment of protein sequences of an embodiment each of IAB1M γ1 EH1(M1) and IAB1M γ1 EH3 (M1). Sequence differences are shown in boxes.

FIG. 61 shows the DNA and translated protein sequence of an embodiment of IAB1M γ1 EH3(M1). In boxes are shown the signal, CDR, linker and hinge sequences.

FIG. 62 shows the DNA and translated protein sequence of an embodiment of IAB1M γ2 EH2 (M1).

FIG. 63 shows the DNA and translated protein sequence of an embodiment of IAB1M γ1 EH5 (M1).

FIG. 64 shows the DNA and translated protein sequence of an embodiment of IAB1M γ1 EH7 (M1).

FIG. 65A shows the DNA and translated protein sequence of an embodiment of IAB1M γ1 EH8(M1).

FIG. 65B shows the DNA and translated protein sequence of an embodiment of IAB25M γ2 NH(M1).

FIG. 65C shows the DNA and translated protein sequence of an embodiment of IAB25M γ2 EH(M1).

FIG. 66 shows the protein sequence of an embodiment of IAB22M VH domain.

FIG. 67 shows the protein sequence of some embodiments of IAB20 VL domain.

FIG. 68 shows the protein sequence of an embodiment of IAB20 VH domain.

FIG. 69 shows the protein sequence of some embodiments of anti-CD3 VL and VH domains.

FIG. 70 shows the protein sequence of an embodiment of PSMA (Prostate-Specific Membrane Antigen) also known as glutamate carboxypeptidase 2 from *Homo sapiens*.

FIG. 71 shows the protein sequence of an embodiment of PSCA (Prostate Stem Cell Antigen) from *Homo sapiens*.

FIG. 72 shows the protein sequence of an embodiment of 5T4 oncofetal trophoblast glycoprotein from *Homo sapiens*.

FIG. 73 shows the protein sequence of an embodiment of T-cell surface glycoprotein CD8 alpha chain from *Homo sapiens*.

FIG. 74 shows the protein sequence of an embodiment of T-cell surface glycoprotein CD8 beta chain from *Homo sapiens*.

FIG. 75 shows the protein sequence of an embodiment of T-cell surface glycoprotein CD3 delta chain from *Homo sapiens*.

FIG. 76 shows the protein sequence of an embodiment of T-cell surface glycoprotein CD3 gamma chain from *Homo sapiens*.

FIG. 77 shows the protein sequence of an embodiment of T-cell surface glycoprotein CD3 epsilon chain from *Homo sapiens*.

FIG. 78 shows the protein sequence of an embodiment of T-cell surface glycoprotein CD3 zeta chain from *Homo sapiens*.

FIG. 79 shows protein sequence information for some embodiments of IAB25M-γ2 EH2.

FIG. 80 shows protein sequence information for some embodiments of IAB20M-γ2 EH2.

DETAILED DESCRIPTION

Figure 1:
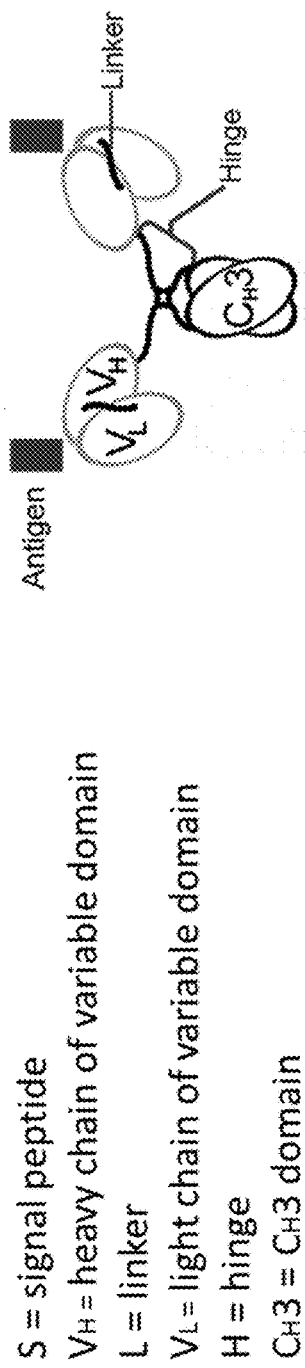
FIG. 1 shows an illustration of an engineered minibody (Mb).

Described herein are components for antigen binding constructs, including antibodies and fragments thereof, such as minibodies, that bind to a target molecule. In some embodiments, these components are novel hinge sequences and/or sequences associated with and/or part of the hinge sequence. These hinge sequences can provide various benefits. Also provided herein are the antigen binding constructs (such as antibodies, minibodies, etc.) that include one or more of the hinge sequences or subsequences provided herein.

In some embodiments, the antigen binding constructs can be useful for targeting therapeutic agents to cells that express the target molecule. In some embodiments, methods are provided for detecting the presence or absence of a target molecule (or "target") using antigen binding constructs (including antibodies, and constructs such as minibodies). In some embodiments, methods are provided for using the antigen binding constructs for therapeutic purposes.

In some embodiments, scFv and minibody antibodies can have superior pharmacokinetic properties for faster diagnostic imaging while maintaining the binding specificity and affinity of the parental antibody. Current technology utilizes imaging with the full length antibodies which often requires significantly longer times (~7-8 days postinjection) to produce high contrast images due to the slow serum clearance of the intact antibody. Some embodiments of the minibodies provided herein provide the opportunity for same-day or next-day imaging. Same-day or next-day imaging also provides a logistical solution to the problem facing many patients who travel great distances to receive treatment/diagnosis since the duration of travel stays or the need to return one week later would be eliminated when imaging with minibodies versus intact antibodies.

As detailed below, in some embodiments, the antigen binding constructs are for diagnostics. When labeled with an appropriate radionuclides (e.g., the positron emitter Iodine-124, Copper-64, Fluorine-18, Gallium-68 and/or Zirconium-89 for PET imaging) or fluorophore (for fluorescent imaging), the antibody fragments can be used for preclinical imaging as shown herein and for clinical imaging in patients. These antigen binding constructs can also be used as potential SPECT imaging agents by simply changing the radio-label to single photon emitting radionuclides such as Indium-111, Iodine-123 and Lutitium-177.

In some embodiments, the antigen binding constructs can be clinical imaging agents (PET/SPECT) in humans. Accordingly, in some embodiments, antigen binding constructs can be used for targeted diagnostic detection for these disorders. In some embodiments, the antigen binding construct can be used as a therapeutic.

Definitions and Various Embodiments

The term "hinge" denotes at least a part of a hinge region for an antigen binding construct, such as an antibody or a minibody. A hinge region can include a combination of the upper hinge, core (or middle) hinge and lower hinge regions. In some embodiments, the hinge is defined according to any of the antibody hinge definitions. Native IgG1, IgG2, and IgG4 antibodies have hinge regions having of 12-15 amino acids. IgG3 has an extended hinge region, having 62 amino acids, including 21 prolines and 11 cysteines. The functional hinge region of naturally occurring antibodies, deduced from crystallographic studies, extends from amino acid residues 216-237 of the IgG1 H chain (EU numbering; ref. 12) and includes a small segment of the N terminus of the CH2 domain in the lower hinge, with the lower hinge being the N terminus of CH2 domain. The hinge can be divided into three regions; the "upper hinge," the "core," and the "lower hinge".

The term "artificial" or "non-natural" when modifying a hinge (or a subpart thereof) denotes that the sequence in question is not present, in the noted state, in nature. In the present context the hinges have been altered from their native state, so that their sequences are no longer those found in wild-type antibodies. As will be appreciated by those of skill in the art, minibodies do not naturally occur in nature, and thus, any construct which is a minibody construct is also not found in nature. This also applies to at least some of the constructs found in and/or incorporating the sequences of any of the hinge sequence tables provided herein (for example, Table 0.2). In some embodiments, any of the hinge subparts or full hinge sequences in Table 0.1 can be artificial hinge sequences, as long as the sequence (or resulting combination for the hinge) does not occur in nature.

The term "full hinge region" or "entire hinge region" denotes the presence of the entire upper, core, and lower hinge regions as a single construct. The upper, core, and lower regions can be positioned immediately adjacent to one another, or additional residues can be added between, or N- or C-terminal to the regions. In some embodiments, the native lower hinge can be replaced with an extension sequence. In some embodiments, one can combine a native lower hinge with the extension sequence. In some embodiments, an extension or other set of sequences can be added after the upper and/or core sequences.

The phrase "effective hinge region" denotes that an adequate amount of part of at least one of the upper, core and lower hinge regions is present to allow the hinge region to be effective for its intended purpose. Thus, the phrase encompasses variants of hinge regions and fragments of the various hinge regions. In some embodiments, the function of the hinge region is one or more of the following: to link the scFv with the $C_H3$ domain, provide flexibility and spacing for the two scFvs to bind to the target properly, to link two half molecules together, to provide overall stability to the molecule, and/or to provide a site for site-specific conjugation due to its solvent exposure. In some embodiments, the hinge should be close to natural as to reduce potential immunogenicity. In some embodiments, the upper hinge provides flexibility to scFv (starts at residue 216 in native IgGs), the middle hinge provides stability, and the lower hinge mediates flexibility to $C_H3$ (starts at residue 231 in native IgGs).

The term "upper hinge" denotes the first part of the hinge that starts at the end of the scFv. Examples of upper hinge regions can be found in Table 0.1. The upper hinge includes the amino acids from the end of the scFv up to, but not including, the first cysteine residue in the core hinge as shown in Table 0.1. As above, the term "effective upper hinge" denotes that enough of the sequence is present to allow the section to function as an upper hinge; the term encompasses functional variants and fragments of the designated hinge section.

The term "core hinge" denotes the second part of the hinge region that is C-terminal to the upper hinge. Examples of core hinge regions can be found in Table 0.1. The core hinge contains the inter-chain disulfide bridges and a high content of prolines. As above, the term "effective core hinge" denotes that enough of the sequence is present to allow the section to function as a core hinge; the term encompasses functional variants and fragments of the designated hinge section.

The term "lower hinge" denotes the third part of the hinge region that is C-terminal to the core hinge. Examples of lower hinge regions can be found in Table 0.1. In the context of a minibody or antibody fragment, the lower hinge connects to the $C_H3$ domain Mb. As above, the term "effective lower hinge" denotes that enough of the sequence is present to allow the section to function as a lower hinge; the term encompasses functional variants and fragments of the designated hinge section. The term "lower hinge" as used herein can encompass various amino acid sequences including naturally occurring IgG lower hinge sequences and artificial extension sequences in place of one another or a combination thereof provided herein. In some embodiments, the various extensions can be considered to be a lower hinge region in its entirety or a replacement.

The term "treating" or "treatment" of a condition can refer to preventing the condition, slowing the onset and/or rate of development of the condition, reducing the risk of developing the condition, preventing and/or delaying the development of symptoms associated with the condition, reducing or ending symptoms associated with the condition, generating a complete or partial regression of the condition, or some combination thereof. The term "prevent" does not require the absolute prohibition of the disorder or disease.

A "therapeutically effective amount" or a "therapeutically effective dose" is an amount that produces a desired therapeutic effect in a subject, such as preventing, treating a target condition, delaying the onset of the disorder and/or symptoms, and/or alleviating symptoms associated with the condition. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and/or the route of administration. One skilled in the clinical and pharmacological arts will be able to determine a therapeutically effective amount through routine experimentation, for example by monitoring a subject's response to administration of a compound and adjusting the dosage accordingly, given the present disclosure. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The term "antigen binding construct" includes all varieties of antibodies, including binding fragments thereof. Further included are constructs that include 1, 2, 3, 4, 5, and/or 6 CDRs. In some embodiments, tandem scFv s can be provided, which can provide two arms with bivalent binding. In some embodiments, these CDRs can be distributed between their appropriate framework regions in a traditional antibody. In some embodiments, the CDRs can be contained within a heavy and/or light chain variable region. In some embodiments, the CDRs can be within a heavy chain and/or a light chain. In some embodiments, the CDRs can be within a single peptide chain. Unless otherwise denoted herein, the antigen binding constructs described herein bind to the noted target molecule. The term "target" or "target molecule" denotes the protein to which the antigen binding construct binds. Examples of target proteins are known in the art, and include, for example PSMA (such as FOLH1) (FIG. 70; SEQ ID NO: 131), PSCA (FIG. 71; SEQ ID NO: 132), 5T4 (such as TPBG) (FIG. 72; SEQ ID NO: 133), CD8 (such as the α-chain) (FIG. 73; SEQ ID NO: 134), CD8 (such as the β-chain) (FIG. 74; SEQ ID NO: 135), CD3 (such as the δ-chain) (FIG. 75; SEQ ID NO: 136), CD3 (such as the γ-chain) (FIG. 76; SEQ ID NO: 137), CD3 (such as the ε-chain) (FIG. 77; SEQ ID NO: 138), CD3 (such as the ζ-chain) (FIG. 78; SEQ ID NO: 139).

The term "antibody" includes, but is not limited to, genetically engineered or otherwise modified forms of immunoglobulins, such as intrabodies, chimeric antibodies, fully human antibodies, humanized antibodies, antibody fragments, scFv, and heteroconjugate antibodies (for example, bispecific antibodies, diabodies, triabodies, tetrabodies, etc.). The term "antibody" includes scFv and minibodies. Thus, each and every embodiment provided herein in regard to "antibodies" is also envisioned as scFv and/or minibody embodiments, unless explicitly denoted otherwise. The term "antibody" includes a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. In some embodiments, a full length antibody can be composed of two identical pairs of polypeptide chains, each pair having one "light" and one "heavy" chain (connected through a disulfide bond). The recognized immunoglobulin genes include the kappa, lambda, alpha, gamma, delta, epsilon, hinge, and mu constant region genes, as well as the myriad immunoglobulin variable region genes. For full length chains, the light chains are classified as either kappa or lambda. For full length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. As used in this application, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (for example, F(ab')$_2$) with the same binding specificity. In some embodiments, the antibody binds specifically to a desired target.

The term "complementarity-determining domains" or "complementarity-determining regions ("CDRs") interchangeably refer to the hypervariable regions of $V_L$ and $V_H$. The CDRs are the target molecule-binding site of the antibody chains that harbors specificity for such target molecule. In some embodiments, there are three CDRs (CDR1-3, numbered sequentially from the N-terminus) in each $V_L$ and/or $V_H$, constituting about 15-20% of the variable domains. The CDRs are structurally complementary to the epitope of the target molecule and are thus directly responsible for the binding specificity. The remaining stretches of the $V_L$ or $V_H$, the so-called framework regions (FRs), exhibit less variation in amino acid sequence (Kuby, Immunology, 4th ed., Chapter 4. W.H. Freeman & Co., New York, 2000).

The positions of the CDRs and framework regions can be determined using various well known definitions in the art, for example, Kabat (Wu, T. T. et al., "An analysis of the sequences of the variable regions of Bence Jones proteins and myeloma light chains and their implications for antibody complementarity," J. Exp. Med., Vol. 132, No. 2, pp. 211-250, 1970; Kabat, E. A. et al., "Sequences of Proteins of Immunological Interest," 5th Ed., NIH Publication No. 91-3242, Bethesda, Md., 1991, Chothia C. et al., "Canonical structures for the hypervariable regions of immunoglobulins," J. Mol. Biol., Vol. 196, No. 4, pp. 901-917, 1987; Chothia C. et al., "Conformations of immunoglobulin hypervariable regions," Nature, Vol. 342, No. 6252, pp. 877-883, 1989; Chothia C. et al., "Structural repertoire of the human VH segments," J. Mol. Biol., Vol. 227, No. 3, pp. 799-817, 1992; Al-Lazikani B. et al., "Standard conformations for the canonical structures of immunoglobulins," J. Mol. Biol., Vol. 273, No. 4, pp. 927-748, 1997), ImMunoGeneTics database (IMGT) (on the worldwide web at imgt.org/) (Giudicelli, V. et al., "IMGT/LIGM-DB, the IMGT® comprehensive database of immunoglobulin and T cell receptor nucleotide sequences," Nucleic Acids Res., Vol. 34 (Database Issue), pp. D781-D784, 2006; Lefranc, M. P. et al., "IMGT unique numbering for immunoglobulin and T cell receptor variable domains and Ig superfamily V-like domains," Dev. Comp. Immunol., Vol. 27, No. 1, pp. 55-77, 2003; Brochet, X. et al., "IMGT/V-QUEST: the highly customized and integrated system for IG and TR standardized V-J and V-D-J sequence analysis," Nucleic Acids Res., Vol. 36 (Web Server Issue), pp. W503-508, 2008; AbM (Martin, A. C. et al., "Modeling antibody hypervariable loops: a combined algorithm," Proc. Natl. Acad. Sci. U.S.A., Vol. 86, No. 23, pp. 9268-9272, 1989); the contact definition (MacCallum, R. M. et al., "Antibody-antigen interactions: contact analysis and binding site topography," J. Mol. Biol., Vol. 262, No. 5, pp. 732-745, 1996), and/or the automatic modeling and analysis tool (Honegger, A. et al., Accessible on the world wide web at bioc.uzh.ch/plueckthun/antibody/Numbering/).

The term "binding specificity determinant" or "BSD" interchangeably refer to the minimum contiguous or noncontiguous amino acid sequence within a complementarity determining region necessary for determining the binding specificity of an antibody. A minimum binding specificity determinant can be within one or more CDR sequences. In some embodiments, the minimum binding specificity determinants reside within (i.e., are determined solely by) a portion or the full-length of the CDR3 sequences of the heavy and light chains of the antibody. In some embodiments, CDR3 of the heavy chain variable region is sufficient for the antigen binding construct specificity.

An "antibody variable light chain" or an "antibody variable heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions. In this application, antibody variable light chains and/or antibody variable heavy chains may, from time to time, be collectively referred to as "antibody chains." These terms encompass antibody chains containing mutations that do not disrupt the basic structure of $V_L$ or $V_H$, as one skilled in the art will readily recognize. In some embodiments, full length heavy and/or light chains are contemplated. In some embodiments, only the variable region of the heavy and/or light chains are contemplated as being present.

Antibodies can exist as intact immunoglobulins or as a number of fragments produced by digestion with various peptidases. Thus, for example, pepsin digests an antibody below the disulfide linkages in the hinge region to produce F(ab')$_2$, a dimer of Fab' which itself is a light chain ($V_L$-$C_L$) joined to $V_H$-$C_H$1 by a disulfide bond. The F(ab')$_2$ may be reduced under mild conditions to break the disulfide linkage in the hinge region, thereby converting the F(ab')$_2$ dimer into an Fab' monomer. The Fab' monomer is a Fab with part of the hinge region. (Paul, W. E., "Fundamental Immunology," 3d Ed., New York: Raven Press, 1993). While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies (for example, single chain Fv) or those identified using phage display libraries (see, for example, McCafferty, J. et al., "Phage antibodies: filamentous phage displaying antibody variable domains," Nature, Vol. 348, No. 66301, pp. 552-554, 1990).

For preparation of monoclonal or polyclonal antibodies, any technique known in the art can be used (see, for example, Kohler, G. et al., "Continuous cultures of fused cells secreting antibody of predefined specificity," Nature, Vol. 256, No. 5517, pp. 495-497, 1975; Kozbor, D. et al., "The production of monoclonal antibodies from human lymphocytes," Immunology Today, Vol. 4, No. 3, pp. 72-79, 1983; Cole, et al., "Monoclonal Antibodies and Cancer Therapy," Alan R. Liss, Inc., pp. 77-96, 1985; Wang, S., "Advances in the production of human monoclonal antibodies," Antibody Technology Journal, Vol. 1, pp. 1-4, 2011; Sharon, J. et al., "Recombinant polyclonal antibodies for cancer therapy," J. Cell Biochem., Vol. 96, No. 2, pp. 305-313, 2005; Haurum, J. S., "Recombinant polyclonal antibodies: the next generation of antibody therapeutics?," Drug Discov. Today, Vol. 11, No. 13-14, pp. 655-660, 2006). Techniques for the production of single chain antibodies (U.S. Pat. No. 4,946,778) can be adapted to produce antibodies to polypeptides of this invention. Also, transgenic mice, or other organisms such as other mammals, may be used to express fully human monoclonal antibodies. Alternatively, phage display technology can be used to identify high affinity binders to selected antigens (see, for example, McCafferty et al., supra; Marks, J. D. et al., "By-passing immunization: building high affinity human antibodies by chain shuffling," Biotechnology (N. Y.), Vol. 10, No. 7, pp. 779-783, 1992).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. In some embodiments, the terms "donor" and "acceptor" sequences can be employed. Humanization can be essentially performed following the method of Winter and co-workers (see, for example, Jones, P. T. et al., "Replacing the complementarity-determining regions in a human antibody with those from a mouse," Nature, Vol. 321, No. 6069, pp. 522-525, 1986; Riechmann, L. et al., "Reshaping human antibodies for therapy," Nature, Vol. 332, No. 6162, pp. 323-327, 1988; Verhoeyen, M. et al., "Reshaping human antibodies: grafting an antilysozyme activity," Science, Vol. 239, No. 4847, pp. 1534-1536, 1988; Presta, L. G., "Antibody engineering,", Curr. Op. Struct. Biol., Vol. 2, No. 4, pp. 593-596, 1992), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some complementarity determining region ("CDR") residues and possibly some framework ("FR") residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, for example, an enzyme, toxin, hormone, growth factor, and drug; or (b) the variable region, or a portion thereof, is altered, replaced or exchanged with a variable region having a different or altered antigen specificity.

Antibodies further include one or more immunoglobulin chains that are chemically conjugated to, or expressed as, fusion proteins with other proteins. It also includes bispecific antibodies. A bispecific or bifunctional antibody is an artificial hybrid antibody having two different heavy/light chain pairs and two different binding sites.

Other antigen-binding fragments or antibody portions of the invention include, bispecific scFv antibodies where the antibody molecule recognizes two different epitopes, single binding domains (sdAb or nanobodies), and minibodies.

The term "antibody fragment" includes, but is not limited to one or more antigen binding fragments of antibodies alone or in combination with other molecules, including, but not limited to Fab', F(ab')$_2$, Fab, Fv, rIgG (reduced IgG), scFv fragments, single domain fragments (nanobodies), peptibodies, minibodies. The term "scFv" refers to a single chain Fv ("fragment variable") antibody in which the variable domains of the heavy chain and of the light chain of a traditional two chain antibody have been joined to form one chain.

A pharmaceutically acceptable carrier may be a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier is "pharmaceutically acceptable" in that it is be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits. The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (for example, topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the antigen binding construct can be delivered intraoperatively as a local administration during an intervention or resection.

The term "target molecule dependent disorder" "or "target molecule associated disorder" includes any disorder in which the target molecule plays a role in the disorder itself. In some embodiments, this denotes over-expression of the target molecule. In some embodiments, the disorders can include any of the disorders discussed herein. In some embodiments, the disorder can be any for which there is a target molecule that can be targeted by binding, whose binding will result in the detection and/or treatment of the disorder. Without limitation, the target molecule can be CD8, CD3, 5T4, PSMA, and/or PSCA, for example.

A minibody is an antibody format that has a smaller molecular weight than the full-length antibody while maintaining the bivalent binding property against an antigen. Because of its smaller size, absence of CH2 domain that binds Fc-gamma and FcRN receptors, absence of glycosylation, the minibody has a faster clearance from the system and potentially enhanced penetration when targeting tumor tissue. With the ability for strong targeting combined with rapid clearance, the minibody is advantageous for diagnostic imaging and delivery of radioactive payloads for which prolonged circulation times may result in adverse patient dosing or dosimetry. In some embodiments, it can also be advantageous for delivery of a cytotoxic payload due to the above-mentioned features such as tumor penetration and faster clearance. A "minibody" as described herein, encompasses a homodimer, wherein each monomer is a single-chain variable fragment (scFv) linked to a human IgG $C_H3$ domain by a hinge sequence. In some embodiments, a minibody is a bivalent or bispecific, covalently bound homodimer of ~80 kDa. In some embodiments, each monomer (half-molecule) is comprised of a variable heavy ($V_H$) domain linked to the corresponding variable light ($V_L$) domain by an approximate 15-18 amino acid Gly-Ser-rich linker sequence.

In some embodiments, each single-chain variable fragment (scFv) is linked to a human IgG1, IgG2, IgG3 or IgG4 $C_H3$ domain by a hinge sequence.

In some embodiments a lower hinge/extension sequence can be a native IgG1, 2, 3 or 4 lower hinge, an/or $(G_3)S_n$ or $(G_4)S_n$ (n can be any number of S's; in some embodiments it is 1 or 2) and/or no lower hinge and/or any combination of amino acids (doesn't have to be G's and S's). In some embodiments, the lower hinge/extension sequence can comprise GGGSSGGGSG (SEQ ID NO: 59).

In some embodiments, a linker can be any that will work. In some embodiments, a linker sequence can include a motif that is $(G_3)S_n$ or $(G_4)S_n$ (n can be any number of S's; in some embodiments it is 1 or 2). In some embodiments, the linker can comprise GSTSGGGSGGGSGGGSS (SEQ ID NO: 62).

The phrase "specifically (or selectively) bind," when used in the context of describing the interaction between an antigen, for example, a protein, to an antibody or antibody-derived binding agent, refers to a binding reaction that is determinative of the presence of the antigen in a heterogeneous population of proteins and other biologics, for example, in a biological sample, for example, a blood, serum, plasma or tissue sample. Thus, under designated immunoassay conditions, in some embodiments, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, for example, Harlow, E. & Lane D., "Using Antibodies, A Laboratory Manual," Cold Spring Harbor Laboratory Press, 1998, for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant ($K_D$, M)" refers to the dissociation rate constant ($k_d$, time$^{-1}$) divided by the association rate constant ($k_a$, time$^{-1}$ M$^{-1}$). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M, or $10^{-13}$ M.

The term "isolated," when applied to a nucleic acid or protein, denotes that the nucleic acid or protein is essentially free of other cellular components with which it is associated in the natural state. In some embodiments, it can be in either a dry or aqueous solution. Purity and homogeneity can be determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. In some embodiments, this can denote that the nucleic acid or protein is at least 85% pure, more preferably at least 95% pure, and most preferably at least 99% pure of molecules that are present under in vivo conditions.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (for example, degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer, M. A. et al., "Enhanced evolutionary PCR using oligonucleotides with inosine at the 3'-terminus," Nucleic Acid Res., Vol. 19, No. 18, pp. 5081, 1991; Ohtsuka, E. et al., "An alternative approach to deoxyoligonucleotides as hybridization probes by insertion of deoxyinosine at ambiguous codon positions," J. Biol. Chem., Vol. 260, No. 5, pp. 2605-2608, 1985; Rossolini, G. M. et al., "Use of deoxyinosine-containing primers vs degenerate primers for polymerase chain reaction based on ambiguous sequence information," Mol. Cell. Probes, Vol. 8, No. 2, pp. 91-98, 1994).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine. Amino acid analogs refer to compounds that have the same basic chemical structure as a naturally occurring amino acid, for example, an alpha-carbon that is bound to a hydrogen, a carboxyl group, an amino group, and an R group, for example, homoserine, norleucine, methionine sulfoxide, methionine methyl sulfonium. Such analogs have modified R groups (for example, norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, for example, Creighton, T. E., "Proteins—Structures and Molecular Properties," W. H. Freeman & Co. Ltd., 1984).

The term "percentage of sequence identity" can be determined by comparing two optimally aligned sequences over a comparison window, wherein the portion of the polynucleotide sequence in the comparison window may comprise additions or deletions (i.e., gaps) as compared to the reference sequence (for example, a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (for example, 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. Some embodiments provided herein provide polypeptides or polynucleotides that are substantially identical to the polypeptides or polynucleotides, respectively, exemplified herein (for example, any one or more of the variable regions exemplified in any one of Tables 0.1, 0.2, 1, 2, or 3 and FIGS. 5B-5E, 7C, 7D, 14B, 15B, 16B-16D, 20C-20G, 21B-21E, 22B, 28B-28E, 29B-29D, 32, 33, 35A-35C, 36A-36E, 40-69, 79, 80 and any one or more of the nucleic acid sequences exemplified in any one of FIGS. 7E, 34A-34F, 41-46, 48-53, 55-59, 61-64, 65A, 65B, and 65C). Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, for example, amino acid sequences of 20 or fewer amino acids, in some embodiments, substantial identity exists when one or two amino acid residues are conservatively substituted, according to the conservative substitutions defined herein.

In some embodiments, the percent identity is over the hinge regions noted herein (the hinge region and/or its subparts of upper, core, and lower hinge regions). In such situations, the percent identity of the hinge region or its subpart can be identified separately from the rest of the protein or nucleic acid sequence. Thus, two hinge regions (or upper, core, and/or lower regions) can have a specified percentage of amino acid residues or nucleotides that are the same (for example, 70%, 75%, 80%, 85%, 90%, 95%, 96%, 97%, 98% or 99% sequence identity over a specified region, or, when not specified, over the entire sequence of a reference sequence), while allowing for the remainder of the protein to either stay 100% identical to the comparison protein, our while also allowing the remainder of the protein to also have variation by a specified percent identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (1970) Adv. Appl. Math. 2:482c, by the homology alignment algorithm of Needleman, S. B. et al., "A general method applicable to the search for similarities in the amino acid sequence of two proteins," J. Mol. Biol., Vol. 48, No. 3, pp. 443-453, 1970, by the search for similarity method of Pearson, W. R. et al., "Improved tools for biological sequence comparison," Proc. Natl. Acad. Sci. U.S.A., Vol. 85, No. 8, pp. 2444-2448, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, for example, Ausubel, F. M. et al., Current Protocols in Molecular Biology, Supplement, 1995).

Two examples of algorithms that are suitable for determining percent sequence identity and sequence similarity are the BLAST and BLAST 2.0 algorithms, which are described in Altschul, S. F. et al., "Gapped BLAST and PSI-BLAST: a new generation of protein database search programs," Nucleic Acids Res., Vol. 25, No. 17, pp. 3389-3402, 1977, and Altschul, S. F. et al., "Basic local alignment search tool," J. Mol. Biol., Vol. 215, No. 3, pp. 403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, S. F. et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see, Henikoff, S. et al., "Amino acid substitution matrices from protein blocks," Proc. Natl. Acad. Sci. U.S.A., Vol. 89, No. 22, pp. 10915-10919, 1992) alignments (B) of 50, expectation (E) of 10, M=5, N=−4, and a comparison of both strands.

The BLAST algorithm also performs a statistical analysis of the similarity between two sequences (see, for example, Karlin, S. et al., "Applications and statistics for multiple high-scoring segments in molecular sequences," Proc. Natl. Acad. Sci. U.S.A., Vol. 90, No. 12, pp. 5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, in some embodiments, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "subject," "patient," and "individual" interchangeably refer to an entity that is being examined and/or treated. This can include, for example, a mammal, for example, a human or a non-human primate mammal. The mammal can also be a laboratory mammal, for example, mouse, rat, rabbit, hamster. In some embodiments, the mammal can be an agricultural mammal (for example, equine, ovine, bovine, porcine, camelid) or domestic mammal (for example, canine, feline).

The term "co-administer" refers to the administration of two active agents in the blood of an individual or in a sample to be tested. Active agents that are co-administered can be concurrently or sequentially delivered.

Antigen Binding Constructs

It is herein appreciated that the sequences within the hinge region can be of special relevance for various antigen binding constructs. In some embodiments, the value of the hinge region can be especially high, such as in a minibody arrangement. The sequences within the hinge can include disulfide bonds which are useful for hinge function but can have varying results when altered. As disclosed herein, and shown in the examples below, in some embodiments, the hinge region sequences can be configured to prevent and/or reduce undesirable disulfide scrambling with cysteine residues present in other regions of the protein and/or contain sufficient numbers of cysteine pairs to maintain dimer integrity in vivo, prevent concatamers from forming and/or allow for site specific conjugation to one of the paired cysteines.

In some embodiments, the stability of a minibody dimer in vivo can be attributed to natural Van-der-Waals association between the $C_H3$ domains, formation of disulfide bonds within the hinge regions, and/or interactions between $V_H$ and $V_L$. To date most minibodies have been engineered using the human IgG1 upper and core hinge regions with an extension sequence linked to the human IgG1 $C_H3$ domain. In addition to the above noted variables, both orientations of a minibody (e.g., $V_L$-$V_H$ (M1) and $V_H$-$V_L$ (M2) scFv variants) are herein provided and characterized, as the orientation of the constructs can also alter their characteristics (as shown in the examples below).

Some previous hinges (e.g., huIgG1 hinge-extension or γ1 EH1) have included a native huIgG1 in the upper hinge (FIG. 2). This cysteine at position 245 in the context of human IgG1 as defined by Kabat and indicated by the first circle, creates problems with both protein heterogeneity and stability in the minibody format based on the disulfide mapping by LC/MS, SDS-PAGE analysis and in vivo biodistribution data. As shown in the examples below, in some embodiments, Cys245 can be mutated to serine, resulting in an artificial hinge or "EH2 hinge" as described herein. Thus, removal of this cysteine from a strand (as shown in the examples below), has resulted in an improved hinge region. In some embodiments, the resulting construct (which lacks the first cysteine in the hinge region) is not strong enough to maintain minibody dimer stability in vivo with the two remaining disulfide bridges (in regard to γ1 EH/EH2). Thus, as shown in the examples below, the introduction of a third or greater number of cysteines per strand can be made (for example, within the core region) to create an improved construct. In some embodiments, providing a $3^{rd}$ (or more) cysteine in the hinge (an additional cysteine over IgG1 native hinge, per strand) increases disulfide bonding and increases protein stability. In some embodiments, the added stability afforded by increasing disulfide bonds in the hinge region allows for site specific conjugation to one or more than one of the cysteines with maintenance of intact dimer. In some embodiments, the huIgG2 minibodies of IAB2M, 20M, 1M, and IAB22M involve human IgG2 (huIgG2) hinge/extension sequence linked to the huIgG2 $C_H3$ domain. Thus, in some embodiments, the $C_H3$ domain can be a huIgG2 $C_H3$ domain. In some embodiments, any option for creating a covalent bond between the two strands of the peptide can be employed instead of cysteines for forming a disulfide bond.

In the present application, when a reference to an introduction of a cysteine is made (unless otherwise noted), it denotes the introduction of a cysteine per strand of the hinge (which comprises two strands). Thus, 3, 4, 5, or 6 cysteines within a strand will mean 6, 8, 10, or 12 cysteines within a hinge, and 3, 4, 5, or 6 possible disulfide bonds being present (of course, unless noted, the number of disulfide bonds can be different, as some could be used for labels and other uses).

In some embodiments, the IgG2 hinge/extension—γ2 EH1—resulted in an increase in aggregation, where the reactive first hinge cysteine was responsible for concatamer formation in IAB2M-γ2 EH1 format. In such embodiments, the native huIgG2 upper hinge can be employed.

The above aspects were then considered in developing a second configuration of some of the embodiments of a hinge construct. In this second arrangement, the first hinge cysteine (one that pairs with the kappa light chain in a native antibody) was mutated to serine resulting in IgG2 EH2 (γ2 EH2). This construct expressed well and had good stability in vivo, had all 3 disulfide bonds formed properly as shown by intact mass analysis, and had stability demonstrated with both IAB2M and IAB22M constructs (as shown in the examples below). Thus, in some embodiments an IgG2 artificial or modified hinge, in which the first cysteine has been altered is provided herein and provides for an improved minibody construct.

As demonstrated in the examples below, the results showed that it was advantageous to mutate the first hinge cysteine of the IgG1 and IgG2 hinges to prevent cysteine mis-pairing. As demonstrated in the examples below, the results showed that it was advantageous to have more than 2 cysteine residues in core hinge region per strand to maintain structural integrity of protein. As demonstrated in the examples below, the results showed that the IgG2 hinge provides one solution to increase stability in vivo. Thus, higher in vivo stability antigen binding constructs, such as minibodies, are provided herein.

In some embodiments, an IgG2 hinge can be employed. In some embodiments, an IgG2 hinge can be employed where the first hinge cysteine is mutated. In some embodiments, mutation of the terminal lysine (K) in the Mb constructs did not impact protein expression but did generate protein with more uniform charge.

As discussed in the examples, additional Mb variants were evaluated based on upper IgG3 hinge and modified IgG1 core hinge sequences where at least 3 cysteine residues were present in the core hinge region per strand. As outlined in the examples below, IAB2M, IAB22M and IAB20M constructs were evaluated to demonstrate universality of findings across various constructs having different orientations and different targets. The results indicate that the advantages described herein regarding the presently disclosed hinges would be available and applicable to any and all antigen binding constructs and minibodies in particular.

In some embodiments, the hinges can be peptide hinges and/or nucleic acid sequences that encode for the peptide hinges. All discussions regarding the peptide form of the hinges provided herein also designate corresponding structures and functions for nucleic acid sequences encoding the peptides. In some embodiments, the hinges can be incorporated into an antigen binding construct, such as an antibody, such as a minibody. Any hinge or subpart of a hinge (such as an upper hinge, core hinge, and/or lower hinge region) can be incorporated into any of the antigen binding constructs provided herein, including, but not limited to those in: Tables 0.1, 0.2, 1, 2, or 3 and FIGS. 5B-5E, 7C, 7D, 14B, 15B, 16B-16D, 20C-20G, 21B-21E, 22B, 28B-28E, 29B-29D, 32, 33, 35A-35C, 36A-36E, 40-69, 79, 80 and any one or more of the nucleic acid sequences exemplified in any one of FIGS. 7E, 34A-34F, 41-46, 48-53, 55-59, 61-64, 65A, 65B, and 65C. In some embodiments, the hinge can include any one or more of the sequences or subparts shown in Table 0.1. In some embodiments, any of the lower hinges can then be connected directly or indirectly to a $C_H3$ domain.

TABLE 0.1

| Hinge variants (FIG. 38) | | | |
|---|---|---|---|
| Full hinge | Upper hinge | Core hinge | Lower hinge |
| Human IgG1 NH1 (SEQ ID NO: 21) | EPKSCDKTHT (SEQ ID NO: 45) | CPPCP (SEQ ID NO: 51) | APELLGGP (SEQ ID NO: 58) |
| Human IgG1 EH1 (SEQ ID NO: 22) | EPKSCDKTHT (SEQ ID NO: 45) | CPPC (SEQ ID NO: 50) | GGGSSGGGSG (SEQ ID NO: 59) |

TABLE 0.1-continued

Hinge variants (FIG. 38)

| Full hinge | Upper hinge | Core hinge | Lower hinge |
|---|---|---|---|
| Human IgG1 NH2 (SEQ ID NO: 23) | EPKSSDKTHT (SEQ ID NO: 46) | CPPCP (SEQ ID NO: 51) | APELLGGP (SEQ ID NO: 58) |
| Human IgG1 EH2 (SEQ ID NO: 24) | EPKSSDKTHT (SEQ ID NO: 46) | CPPC (SEQ ID NO: 50) | GGGSSGGGSG (SEQ ID NO: 59) |
| Human IgG1 NH3 (SEQ ID NO: 25) | EPKSSDKTHT (SEQ ID NO: 46) | CPPCPPC (SEQ ID NO: 52) | APELLGGP (SEQ ID NO: 58) |
| Human IgG1 EH3 (SEQ ID NO: 26) | EPKSSDKTHT (SEQ ID NO: 46) | CPPCPPC (SEQ ID NO: 52) | GGGSSGGGSG (SEQ ID NO: 59) |
| Human IgG1 NH4 (SEQ ID NO: 27) | EPKSSDKTHT (SEQ ID NO: 46) | CPPCVECPPC (SEQ ID NO: 53) | APELLGGP (SEQ ID NO: 58) |
| Human IgG1 EH4 (SEQ ID NO: 28) | EPKSSDKTHT (SEQ ID NO: 46) | CPPCVECPPC (SEQ ID NO: 53) | GGGSSGGGSG (SEQ ID NO: 59) |
| Human IgG1 NH5 (SEQ ID NO: 29) | EPKSSDKTHT (SEQ ID NO: 46) | CPPCPPCPPC (SEQ ID NO: 54) | APELLGGP (SEQ ID NO: 58) |
| Human IgG1 EH5 (SEQ ID NO: 30) | EPKSSDKTHT (SEQ ID NO: 46) | CPPCPPCPPC (SEQ ID NO: 54) | GGGSSGGGSG (SEQ ID NO: 59) |
| Human IgG2 NH1 (SEQ ID NO: 31) | ERK (SEQ ID NO: 47) | CCVECPPCP (SEQ ID NO: 55) | APPVAGP (SEQ ID NO: 60) |
| Human IgG2 EH1 (SEQ ID NO: 32) | ERK (SEQ ID NO: 47) | CCVECPPCP (SEQ ID NO: 55) | GGGSSGGGSG (SEQ ID NO: 59) |
| Human IgG2 NH2 (SEQ ID NO: 33) | ERK (SEQ ID NO: 47) | SCVECPPCP (SEQ ID NO: 56) | APPVAGP (SEQ ID NO: 60) |
| Human IgG2 EH2 (SEQ ID NO: 34) | ERK (SEQ ID NO: 47) | SCVECPPCP (SEQ ID NO: 56) | GGGSSGGGSG (SEQ ID NO: 59) |
| IgG3/IgG1 EH6 (SEQ ID NO: 35) | ELKTPLGDTTHT (SEQ ID NO: 48) | CVECPPC (SEQ ID NO: 57) | GGGSSGGGSG (SEQ ID NO: 59) |
| IgG3/IgG1 EH7 (SEQ ID NO: 36) | ELKTPLGDTTHT (SEQ ID NO: 48) | CPPCPPC (SEQ ID NO: 52) | GGGSSGGGSG (SEQ ID NO: 59) |
| IgG3/IgG1 EH8 (SEQ ID NO: 37) | ELKTPLGDTTHT (SEQ ID NO: 48) | CPPCPPCPPC (SEQ ID NO: 54) | GGGSSGGGSG (SEQ ID NO: 59) |
| IgG4 NH (SEQ ID NO: 38) | ESKYGPP (SEQ ID NO: 49) | CPPCP (SEQ ID NO: 51) | APEFLGGP (SEQ ID NO: 61) |
| IgG4 EH (SEQ ID NO: 39) | ESKYGPP (SEQ ID NO: 49) | CPPCP (SEQ ID NO: 51) | GGGSSGGGSG (SEQ ID NO: 59) |

In some embodiments, the hinge comprises, consists of, or consists essentially of any of the sequences in Table 0.1 above. In some embodiments, the hinge consists of each of a designated upper, core, and lower hinge region in Table 0.1. In some embodiments, any one of the above subparts (such as the upper, core and/or lower hinge) can also be provided as a variant thereof. In some embodiments, the variants have substantial identity to the sequences above. In some embodiments, the variants have one, two, or three amino acids difference from the sequences noted above. In some embodiments, the variants have one, two, or three amino acids difference from the sequences noted above and the differences are conservative differences.

In some embodiments the CPPC (SEQ ID NO: 50) motif in the core region can be altered to any other effective core motif, as long as the number and/or effectiveness of the covalent bonds presented in the table above are adequately replaced.

In some embodiments, a peptide hinge region for an antibody is provided. The hinge region can include an upper hinge region that comprises no amino acids capable of crosslinking with a corresponding amino acid. The amino acid hinge region can further include a core hinge region connected C-terminal to the upper hinge region. In some embodiments, the core hinge region comprises at least three cysteines on each side of the hinge (so at least six cysteines for the assembled structure). In some embodiments, the amino acid hinge region further comprises a lower hinge or extension region connected C-terminal to the core hinge region. In some embodiments, the lower hinge or extension region can include at least one of: APPVAGP (SEQ ID NO: 60), APELLGGP (SEQ ID NO: 58), or GGGSSGGGSG (SEQ ID NO: 59).

In some embodiments, the upper hinge region comprises no cysteines that crosslink within the upper hinge region. In some embodiments, the upper hinge region comprises no cysteines. In some embodiments, the amino acid hinge region further comprises a lower hinge region. In some embodiments, these constructs are non-naturally occurring constructs.

In some embodiments, a variant minibody hinge region is provided. The variant minibody hinge region comprises a first altered amino acid position. The first altered amino acid position is an amino acid that in a native antibody hinge would be a cysteine, and has been altered in the first altered position so that it does not form a disulfide bond. The variant minibody hinge region further includes at least three cysteines C-terminal to the first altered amino acid position per strand. In some embodiments, 4, 5, 6, or more cysteines can be present C-terminal to the first altered amino acid position per strand. In some embodiments, these additional cysteines are fully contained within the core region of the hinge (of course, the core hinge can be modified and expanded beyond wild-type sequences such that the additional cysteines can be added). In some embodiments, the hinge region consists of SEQ ID NO: 1 ($X_{n1}CX_{n2}X_{n3}CX_{n4}X_{n5}C$). In some embodiments, SEQ ID NO: 1 is a core hinge region, and the core hinge region essentially consists of SEQ ID NO: 1. In some embodiments, the core hinge region consists of SEQ ID NO: 1. In the description noted above, the number of cysteines relates to the number of cysteines in a single hinge region of the peptide chain. It will be understood that the number of cysteines in the dimeric form of the hinge (where the peptide chains are crosslinked to one another) will be twice as many, as the noted cysteines are each part of a disulfide bind involving two cysteines.

In some embodiments, Mb constructs contain antigen binding scFvs with variable linker lengths that can be in either $V_L$-$V_H$ or $V_H$-$V_L$ orientation. Any disclosure provided herein regarding one orientation also contemplates the reverse orientation and both orientations. In some embodiments, any hinge sequence described in Table 0.1 can be added C-terminal to scFvs. In some embodiments, any $C_H3$ domain from IgG1, IgG2, IgG3, or IgG4 antibodies can be added C-terminal to scFvs and appropriate hinges. In some embodiments, to ensure appropriate disulfide bonding, the first hinge cysteine (cysteine that usually pairs with light chain in native IgG1, IgG2, IgG3, and IgG4 antibodies) is mutated to a serine or alanine or other appropriate amino acid to prevent disulfide scrambling and/or concatemerization. In some embodiments, to reduce the presence or prevent formation of half-molecules and ensure optimal stability in vivo, the hinge region can contain at least 3 disulfide bonds, in some embodiments it can have more. In some embodiments, at least 3 disulfide bonds are present in the hinge located at appropriate distances from one another are included to prevent improper disulfide bonds forming and ensure proper disulfide bond formation. In some embodiments, 3 disulfide bonds in the hinge are located at appropriate distances from one another are included for protein stability in vivo and clearance through liver rather than renal clearance. In some embodiments, at least 3 disulfides bonds (for example, 4 or more) in the hinge are provided to afford using a cysteine as a handle, following gentle reduction of the disulfides, of drugs, metal chelators, radionuclides, radioisotopes, site specific conjugation of a chelator then attachment of a radioisotope to the chelator, or fluorescent dyes using cysteine as a site of attachment. As appreciated by one of skill in the art, the presence of each single disulfide bond indicates the presence of two cysteines, one on each peptide sequence of the hinge.

In some embodiments, Mbs are constructed so as to include any of the hinge components provided herein and retain similar (or the same) affinity to parent antibodies. In some embodiments, Mbs constructed as described above can be engineered to contain two different antigen binding domains.

In some embodiments, superior hinges for antigen binding constructs can be obtained by removing a first cysteine in the hinge region, as noted in Table 0.1 above and in the examples below. Thus, in some embodiments, a hinge region in which this cysteine (which would otherwise be present in the natural hinge) is removed or altered to another residue (for example a residue that cannot form a covalent bond) can be provided. In some embodiments, this adjustment is made in a human IgG1 context, or any other hinge region that includes the cysteine in the noted position in Table 0.1 (for example, γ2 EH1 altered in γ2 EH2 (Cys to Ser), and γ2 NH1 altered in γ2 NH2 (Cys to Ser)).

In some embodiments, an amino acid hinge region is provided that comprises a sequence of SEQ ID NO: 1 ($X_{n1}CX_{n2}X_{n3}CX_{n4}X_{n5}C$). $X_{n1}$ can be any amino acid that does not form a covalent crosslinking bond. In some embodiments, $X_{n2}$ is any one of: A, R, N, D, E, Q, G, H, I, L, K, M, F, P, S, T, W, Y, or V. $X_{n3}$ can be any amino acid. $X_{n4}$ is any amino acid. $X_{n5}$ is any amino acid. In some embodiments, $X_{n1}$ comprises a serine or an alanine (SEQ ID NO: 235). In some embodiments, $X_{n1}$ comprises a serine (SEQ ID NO: 210). In some embodiments, $X_{n1}$ comprises an alanine (SEQ ID NO: 211). In some embodiments, $X_{n1}$ comprises a T (SEQ ID NO: 236). In some embodiments, the first cysteine in SEQ ID NO: 1 that is altered is a cysteine in a γ2 domain. In some embodiments, the amino acid hinge region further comprises additional amino acids in front of SEQ ID NO: 1 ($X_{n1}CX_{n2}X_{n3}CX_{n4}X_{n5}C$).

In some embodiments of $X_{n1}CX_{n2}X_{n3}CX_{n4}X_{n5}C$ (SEQ ID NO: 1), $X_{n1}$ does not form a covalent crosslinking bond with another amino acid (SEQ ID NO: 191). In some embodiments, $X_{n1}$ is not a cysteine (SEQ ID NO: 192). In some embodiments of SEQ ID NO: 1, $X_{n1}$ is one of: A, R, N, D, E, Q, G, H, I, L, K, M, F, P, S, T, W, Y, or V (SEQ ID NO: 193). In some embodiments of SEQ ID NO: 1, $X_{n2}$ is P, V, or E (SEQ ID NO: 194). In some embodiments of SEQ ID NO: 1, $X_{n4}$ is P, V, or E (SEQ ID NO: 196). In some embodiments of SEQ ID NO: 1, $X_{n4}$ P or V (SEQ ID NO: 197). In some embodiments of SEQ ID NO: 1, $X_{n2}$ is P or V (SEQ ID NO: 195). In some embodiments of SEQ ID NO: 1, $X_{n3}$ is P or E (SEQ ID NO: 198). In some embodiments of SEQ ID NO: 1, $X_{n5}$ is P or E (SEQ ID NO: 199). In some embodiments of SEQ ID NO: 1, $X_{n3}$ is P or E and $X_{n5}$ is P or E (SEQ ID NO: 237). In some embodiments of SEQ ID NO: 1, $X_{n2}X_{n3}$ is VE (SEQ ID NO: 201). In some embodiments of SEQ ID NO: 1, $X_{n2}X_{n3}$ is PP (SEQ ID NO: 202). In some embodiments of SEQ ID NO: 1, $X_{n4}X_{n5}$ is VE (SEQ ID NO: 203). In some embodiments of SEQ ID NO: 1, $X_{n4}X_{n5}$ is PP (SEQ ID NO: 204). In some embodiments of SEQ ID NO: 1, $X_{n2}X_{n3}$ is VE and $X_{n4}X_{n5}$ is PP (SEQ ID NO: 205). In some embodiments of SEQ ID NO: 1, $X_{n2}X_{n3}$ is VE or PP (SEQ ID NO: 238). In some embodiments of SEQ ID NO: 1, $X_{n2}X_{n3}$ is VE (SEQ ID NO: 239).

In some embodiments, any of the above noted hinge regions further comprises a lower hinge or extension sequence C-terminal to the last cysteine in $X_{n1}CX_{n2}X_{n3}CX_{n4}X_{n5}C$ (SEQ ID NO: 1). In some embodiments, any lower hinge region can be employed. In some embodiments, any of the above noted hinge regions further comprises an extension or lower hinge sequence C-terminal to the last cysteine in $X_{n1}CX_{n2}X_{n3}CX_{n4}X_{n5}C$ (SEQ ID NO: 1).

In some embodiments, the hinge region of SEQ ID NO: 1 and/or 2 is a core hinge region. In some embodiments, the hinge further comprises an upper hinge region adjacent to the core hinge region. In some embodiments, the hinge further comprises a lower hinge or extension region adjacent to the core hinge region. In some embodiments, the amino acid hinge region further comprises an upper hinge region adjacent to the core hinge region.

In some embodiments, the amino acid hinge region comprises the following sequence: SCVECPPCP (SEQ ID NO: 56). In some embodiments, the amino acid hinge region comprises the following sequence: ERKSCVECPPCP (SEQ ID NO: 167). In some embodiments, the amino acid hinge region comprises the following sequence: EPKSSDKTHTCPPCPPC (SEQ ID NO: 168). In some embodiments, the amino acid hinge region comprises at least one of the following sequences: ERKSCVECPPCPGGGSSGGGSG (SEQ ID NO: 34) or ERKSCVECPPCPAPPVAGP (SEQ ID NO: 33). In some embodiments, the amino acid hinge region comprises at least TCPPCPPC (SEQ ID NO: 166). In some embodiments, the amino acid hinge region comprises at least EPKSSDKTHTCPPCPPCGGGSSGGGSG (SEQ ID NO: 26) or EPKSSDKTHTCPPCPPCAPELLGGP (SEQ ID NO: 25).

In some embodiments, superior hinges can be provided by removing the hinge cysteine that is responsible for linking the heavy and light chains of IgG1, IgG2, IgG3 and IgG4 respectively, as shown in Table 0.1 and 3 (for example, γ1 EH1 to γ1 EH2). Furthermore, in some embodiments, using a core region with at least three cysteines (e.g., γ1 EH3, γ1 EH4, and γ1 EH5) per strand can result in a superior construct. In some embodiments, a hinge can be provided by removing a cysteine from an upper hinge region, as shown in table 0.1 and 3 (for example, γ1 EH1 to γ1 EH2).

In some embodiments, such constructs can be described as an amino acid hinge region comprising a sequence of SEQ ID NO: 2 ($X_{n1}X_{n2}X_{n3}X_{n4}X_{n5}X_{n6}CX_{n7}X_{n8}CX_{n9}X_{n10}C$), wherein $X_{n1}$ is any amino acid that does not form a covalent crosslinking bond with another amino acid, wherein $X_{n2}$ is any amino acid, wherein $X_{n3}$ is any amino acid, wherein $X_{n4}$ is any amino acid, wherein $X_{n5}$ is any amino acid, wherein $X_{n6}$ is any amino acid, wherein $X_{n7}$ is any amino acid, wherein $X_{n8}$ is any amino acid, wherein $X_{n9}$ is any amino acid, and wherein $X_{n10}$ is any amino acid (SEQ ID NO: 240).

In some embodiments, such constructs can be described as an amino acid hinge region comprising a sequence of SEQ ID NO: 2 ($X_{n1}X_{n2}X_{n3}X_{n4}X_{n5}X_{n6}CX_{n7}X_{n8}CX_{n9}X_{n10}C$), wherein $X_{n1}$ can be any amino acid, wherein $X_{n2}$ can be any amino acid, wherein $X_{n3}$ can be any amino acid, wherein $X_{n4}$ can be any amino acid, wherein $X_{n5}$ can be any amino acid, wherein $X_{n6}$ can be any amino acid other than a cysteine, wherein $X_{n7}$ can be any amino acid, wherein $X_{n8}$ can be any amino acid, wherein $X_{n9}$ can be any amino acid, and wherein $X_{n10}$ can be any amino acid (SEQ ID NO: 241).

In some embodiments of SEQ ID NO: 2, $X_{n1}$ is not a cysteine (SEQ ID NO: 213). In some embodiments of SEQ ID NO: 2, $X_{n1}$ is a serine or alanine (SEQ ID NO: 242). In some embodiments of SEQ ID NO: 2, $X_{n2}$ is not a cysteine (SEQ ID NO: 214). In some embodiments of SEQ ID NO: 2, $X_{n2}$ is a D (SEQ ID NO: 215). In some embodiments, $X_{n3}$ is a K (SEQ ID NO: 216). In some embodiments of SEQ ID NO: 2, $X_{n4}$ is a T (SEQ ID NO: 217). In some embodiments of SEQ ID NO: 2, $X_{n5}$ is a H (SEQ ID NO: 218). In some embodiments of SEQ ID NO: 2, $X_{n6}$ is a T (SEQ ID NO: 219). In some embodiments of SEQ ID NO: 2, $X_{n7}$ is a P or a V (SEQ ID NO: 220). In some embodiments of SEQ ID NO: 2, $X_{n8}$ is a P or a E (SEQ ID NO: 221). In some embodiments of SEQ ID NO: 2, $X_{n9}$ is a P or a V (SEQ ID NO: 222). In some embodiments of SEQ ID NO: 2, $X_{n10}$ is a P or a E (SEQ ID NO: 223). In some embodiments of SEQ ID NO: 2, $X_{n2}$ is a D, $X_{n3}$ is a K, $X_{n4}$ is a T, $X_{n5}$ is a H, $X_{n6}$ is a T, $X_{n7}$ is a P or a V, $X_{n8}$ is a P or a E, and $X_{n9}$ is a P or a V (SEQ ID NO: 243).

In some embodiments, the amino acid hinge region further comprises a $X_{n11}X_{n12}C$ sequence. In some embodiments, this can be immediately attached to the C-terminal cysteine in SEQ ID NO: 1 (SEQ ID NO: 244) or SEQ ID NO: 2 (SEQ ID NO: 245). In some embodiments of SEQ ID NO: 2, $X_{n11}$ can be any amino acid, and $X_{n12}$ can be any amino acid (SEQ ID NO: 245). In some embodiments of SEQ ID NO: 2, $X_{n11}$ is a P or a V, and wherein $X_{n12}$ is a P or an E (SEQ ID NO: 246). In some embodiments of SEQ ID NO: 2, $X_{n1}$ is a serine, $X_{n2}$ is a D, $X_{n3}$ is a K, $X_{n4}$ is a T, $X_{n5}$ is a H, $X_{n6}$ is a T, $X_{n7}$ is a P, $X_{n8}$ is a P, $X_{n9}$ is a P, and $X_{n10}$ is a P (SEQ ID NO: 247).

In some embodiments, any of the hinge sequences can be preceded by any number of initial amino acids. Thus, additional linkers or spacers of amino acids can be added to the molecule before the noted sequence (such as SEQ ID NO: 1 and/or NO: 2). In some embodiments, any of the hinge sequences can be followed by any number of additional amino acids. Thus, additional linkers or spacers of amino acids can be added to the molecule after the noted sequence (such as SEQ ID NO: 1 and/or NO: 2).

In some embodiments, the hinge region comprises at least one of the following sequences: CPPCPPC (SEQ ID NO: 52), CPPCVECPPC (SEQ ID NO: 53), or CPPCPPCPPC (SEQ ID NO: 54). In some embodiments, the hinge region comprises at least one of the following sequences: ERKSCVECPPCPGGGSSGGGSG (SEQ ID NO: 34), EPKSSDKTHTCPPCPPC (SEQ ID NO: 168), EPKSSDKTHTCPPCVECPPC (SEQ ID NO: 169), or EPKSSDKTHTCPPCPPCPPC (SEQ ID NO: 170). In some embodiments, the hinge region comprises at least one of the following sequences: EPKSSDKTHTCPPCPPCGGGSSGGGSG (SEQ ID NO: 26), EPKSSDKTHTCPPCVECPPCGGGSSGGGSG (SEQ ID NO: 28), or EPKSSDKTHTCPPCPPCPPCGGGSSGGGSG (SEQ ID NO: 30).

In some embodiments, the lower hinge region/sequence can be an extension sequence (e.g., 8-25 amino acids, such as 8-20, 10-25, 10-22, 12-20, 14-16, 8, 9, 10, 11, 12, 13, 14, 15, 16, 17, 18, 19, 20, 21, 22, 23, 24, or 25 amino acids). Examples of the lower hinge are shown in Table 0.1 and Table 3. In some embodiments, the lower hinge can be a native lower hinge from γ1, γ2, γ3 or γ4. In some embodiments, one can have a native hinge sequence and add one or more spacer amino acids (for example, 1, 2, 3, 4 or more amino acids, such as G or S).

In some embodiments, an amino acid hinge region comprises a core hinge sequence of at least one of: CVECPPCP (SEQ ID NO: 57), CPPCPPC (SEQ ID NO: 52), CPPCPPCPPC (SEQ ID NO: 54), or CPPCVECPPC (SEQ ID NO: 53) linked to an upper hinge sequence of ELKTPLGDTTHT (SEQ ID NO: 48) or EPKSSDKTHT (SEQ ID NO: 46).

In some embodiments, any of the embodiments described herein can be modified or supplemented by any one or more of the following options.

In some embodiments, the hinge region comprises at least three cysteines (on each chain, for a total of at least 6 cysteines between the two strands in the dimeric hinge construct). In some embodiments, the hinge region comprises at least four cysteines (on each strand). In some embodiments, the hinge region comprises at least five cysteines (on each strand). In some embodiments, 6, 7, 8, 9, 10 or more cysteines are present (on each strand). In some embodiments, the hinge region as a whole has the above noted number of cysteines (on each strand and/or in the dimeric construct). In some embodiments, all of the noted cysteines are present in the core hinge region. In some embodiments, all of the noted cysteines are present in the core hinge region and there are no additional cysteines present in the upper hinge region and/or the lower hinge region. In some embodiments, the cysteines are distributed throughout the amino acid hinge region in a repeating "CXX" motif (such as CXXCXXCXX (SEQ ID NO: 171) or CXXCXX (SEQ ID NO: 172), or CXXCXXCXXCXX (SEQ ID NO: 173). In some embodiments, the cysteines are distributed throughout the core hinge region in a repeating CXX motif. In some embodiments, the motif repeats 1, 2, 3, 4, 5, 6, 7, 8, 9, 10 or more times. In some embodiments, each X can be either a P, V, or E (SEQ ID NO: 171, SEQ ID NO: 172, SEQ ID NO: 173). In some embodiments, X is not a cysteine (SEQ ID NO: 248, SEQ ID NO: 249, SEQ ID NO: 250).

In some embodiments, the core hinge region comprises at least three cysteines per strand forming at least three disulfide bonds within the core hinge region. In some embodiments, the constructs express much better in mammalian cells and give higher titers as well as lower aggregation and more uniform product. In some embodiments, each of the cysteines present in the core hinge region can form a disulfide bond with a corresponding cysteine on its paired chain in the hinge. In some embodiments, the disulfide bond is between corresponding cysteines on two separate protein chains, each being a hinge region. In some embodiments, at least 3 disulfide bonds are formed, for example, 3, 4, 5, 6, 7, 8, 9, 10 or more. In some embodiments, at least 3 disulfide bonds are capable of being formed, for example, 3, 4, 5, 6, 7, 8, 9, 10 or more disulfide bonds can be formed at the same time within the structure.

In some embodiments, the first residue of the core hinge region is a serine. In some embodiments, the core hinge region comprises SCVECPPCP (SEQ ID NO: 56).

In some embodiments, the $C_H3$ domain for any construct can be from γ1, γ2, or γ3 and any naturally occurring allele thereof. As used herein "γ" is an abbreviation for gamma.

In some embodiments, the extension or lower hinge region comprises at least one of S, G, A, P, or V. In some embodiments, the extension sequence comprises at least GGGSSGGGSG (SEQ ID NO: 59). In some embodiments, the extension or lower hinge region comprises at least APPVAGP (SEQ ID NO: 60). In some embodiments, the lower hinge region comprises at least one of: GGGSSGGGSG (SEQ ID NO: 59) or APPVAGP (SEQ ID NO: 60). In some embodiments, the lower hinge sequence can be a GS linker, extension sequence, and/or any native lower hinge region from γ1, γ2, γ3 and γ4.

Properties

In some embodiments, the hinges provided herein can allow for a lower percentage of the half-molecule to form and/or be present in any minibody or other antigen binding construct composition. For example, less can 7% of the composition can be the half molecule, including ranges such as less than 6, 5, 4, 3, 2, 1, and/or 0.5% of composition being the half-molecule.

In some embodiments when the hinge is located within a minibody, and when the minibody is administered to a human subject, clearance of the minibody from the subject may occur through liver and/or kidney. In some embodiments, clearance through the liver is at least 10% or more, for example 10, 20, 30, 40, 50, 60, 70 80, 90, 95, 99, or 100%. In some embodiments, when located within a minibody, and when the minibody is administered to a human subject, clearance of the minibody from the subject may occur primarily through the kidneys. In some embodiments, at least 1, 2, 3, 4, 5, 6, 7, 8, 9, 10 fold or more of the antibody is cleared through the kidney.

In some embodiments, less than 30% aggregation of an minibody is present in an minibody composition. In some embodiments, less than 20% aggregation of an minibody is present in an minibody composition. In some embodiments, less than 10% aggregation of an minibody is present in an minibody composition. In some embodiments, less than 5% aggregation of an minibody is present in an minibody composition. In some embodiments, less than 1% aggregation of a minibody is present in an minibody composition.

When the minibody remains as a dimer in circulation in vivo, then protein clearance is predicted to occur through the liver primarily. In contrast, when the half-molecule is present, then its clearance will be through the kidney. Thus, in some embodiments, the above clearance aspects are a way of characterizing the amount of resulting half-molecule present in a subject, in vivo, allowing one to determine if the administered whole molecule remains as a whole molecule in vivo, or if it breaks down to the half molecule. In some embodiments, the minibody composition is one in which clearance through the liver is relatively high compared to clearance through the kidney, and tumor uptake of the minibody is relatively high. In some embodiments, the ratio of kidney to liver is less than 1. In some embodiments, at least 1% more uptake occurs through the liver than then kidney, for example, at least 1, 10, 20, 30, 40, 50, 60, 70 80, 90, 100, or more uptake occurs through the liver than through the kidney. In some embodiments, uptake of kidney to liver is 0.9:1, 1:10, 1:100, 1:000, 1:10,000, etc. In some embodiments, the various hinge constructs provided herein have lower clearance through the kidneys than the EH1 hinge from IgG1.

In some embodiments, mutation of the first hinge cysteine to serine in IgG1 hinge region (γ1 EH2) to prevent undesired interaction with other unpaired cysteine generated a protein with a better profile in vitro. However, the high clearance through the kidneys, compared to the liver, may be indicative of protein instability and dissociation into half molecules in vivo. In some embodiments, minibodies having an IgG2 hinge are provided wherein the first hinge cysteine is mutated to a serine (γ2 EH2 and others), have the property of being cleared through the liver as predicted for proteins of approx. 80 kDa. This indicates that the molecule remains intact in vivo. In some embodiments, the molecule remains intact for 48 hours or longer.

In some embodiments, the hinge construct provided herein have less than 9% half molecules present due to an unpaired first hinge cysteine. In some embodiments, an IgG2 hinge with a first cysteine to serine has greater than 99% intact dimer protein present, such as that with γ2 EH2. In some embodiments, a γ2 hinge variant results in lower kidney uptake. In some embodiments, a Mb made with an huIgG1 hinge (γ1 EH1) is rapidly cleared through the kidney resulting in low tumor targeting. In some embodiments, a Mb made with huIgG2 hinge variants, either Extended Hinge (γ2 EH2) or Natural Hinge (γ2 NH1) shows greater stability in vivo with high tumor targeting and lower kidney clearance.

In some embodiments, γ1 minibodies with EH2 hinge assemble properly into intact dimeric molecules but inclusion of only 2 cysteine yields protein with a high amount of half molecule. In some embodiments, γ1 minibodies with EH3 hinge assemble properly into intact dimeric molecules and addition of 3rd cysteine per strand yield protein with very low levels of half molecule. In some embodiments, the level of half molecule is less than 15%, for example less than 14, 13, 12, 11, 10, 9, 8, 7, 6, 5, 4, 3, 2, or less than 1% of half molecule is present.

In some embodiments, even though the hinge region has been varied and is different from that described in the past, the CDRs, $V_H/V_L$s or full amino acid sequences of the minibodies still bind to the target molecule with the same affinity as an antibody (such as a minibody) with the previous style hinge. Thus, in some embodiments, the presence of a hinge as provided herein does not alter or negatively impact the binding affinity of the antigen binding construct, while still providing one or more of the benefits and/or structures provided herein.

In some embodiments, a minibody comprising a sequence $X_{n1}CX_{n2}X_{n3}CX_{n4}X_{n5}C$ (SEQ ID NO: 3) is provided. In some embodiments, SEQ ID NO: 3 is located as the core hinge region of the minibody. In some embodiments, $X_{n1}$ can be any amino acid or no amino acid, $X_{n2}$ can be any amino acid, $X_{n3}$ can be any amino acid, $X_{n4}$ can be any amino acid, and $X_{n5}$ can be any amino acid. In some embodiments, $X_{n1}$ cannot be a cysteine, $X_{n2}$ cannot be a cysteine, $X_{n3}$ cannot be a cysteine, $X_{n4}$ cannot be a cysteine, and/or $X_{n5}$ cannot be a cysteine (SEQ ID NO: 251). In some embodiments, $X_{n1}$ is any amino acid other than a cysteine (SEQ ID NO: 229). In some embodiments, $X_{n1}$ is a serine (SEQ ID NO: 230).

In some embodiments, a minibody comprising a sequence $X_{n1}CX_{n2}X_{n3}CX_{n4}X_{n5}CX_{n6}$ (SEQ ID NO: 4) is provided. In some embodiments, SEQ ID NO: 4 is located as the core hinge region of the minibody. In some embodiments, $X_{n1}$ can be any amino acid or no amino acid, $X_{n2}$ can be any amino acid, $X_{n3}$ can be any amino acid, $X_{n4}$ can be any amino acid, and $X_{n5}$ can be any amino acid (SEQ ID NO: 252). In some embodiments, $X_{n1}$ cannot be a cysteine, $X_{n2}$ cannot be a cysteine, $X_{n3}$ cannot be a cysteine, $X_{n4}$ cannot be a cysteine, and/or $X_{n5}$ cannot be a cysteine (SEQ ID NO: 253). In some embodiments, $X_{n1}$ is any amino acid other than a cysteine (SEQ ID NO: 254). In some embodiments, $X_{n1}$ is a serine (SEQ ID NO: 255). In some embodiments, $X_{n6}$ can be any amino acid, no amino acid, or P (SEQ ID NO: 256).

In some embodiments, any of the amino acid hinge regions or full hinges provided herein is within an antibody. In some embodiments, any of the amino acid hinge regions or full hinges provided herein is within an antibody binding fragment. In some embodiments, any of the amino acid hinge regions or full hinges provided herein is within a minibody.

In some embodiments, any of the amino acid hinge regions or full hinges provided herein is within a monospecific antibody.

In some embodiments, any of the amino acid hinge regions or full hinges provided herein is within a bispecific antibody. In some embodiments, any of the amino acid hinge regions or full hinges provided herein is assembled in a 1:1 ratio. In some embodiments, any of the amino acid hinge regions or full hinges provided herein is part of an antibody fragment that is a bispecific construct. In some embodiments, the bispecific antibody is a minibody.

Specific Antigen Binding Constructs

Antigen binding constructs that bind to the target are described herein. An antigen binding construct is a molecule that includes one or more portions of an immunoglobulin or immunoglobulin-related molecule that specifically binds to, or is immunologically reactive with the target molecule. In some embodiments, any of the hinge embodiments provided herein can be applied to any desired antigen binding construct. In some embodiments, any of the hinge embodiments provided herein can be applied to a minibody. In some embodiments, any of the hinge embodiments provided herein can be applied to a minibody that binds to CD8, CD3, 5T4, PSCA, or PSMA. A non-limiting embodiment of the PSMA antigen is shown in FIG. 70. A non-limiting embodiment of the PSCA antigen is shown in FIG. 71. A non-limiting embodiment of the 5T4 antigen is shown in FIG. 72. Some non-limiting embodiments of the CD8 antigen are shown in FIGS. 73 and 74. Some non-limiting embodiments of the CD3 antigen are shown in FIGS. 75-78. In some embodiments, any of the hinge embodiments provided herein can be applied to a minibody that specifically and/or selectively binds to CD8, CD3, 5T4, PSCA, or PSMA. In some embodiments, any of the hinge embodiments provided in Tables 0.1 or 3 can be applied to a minibody that binds to CD8, CD3, 5T4, PSCA, or PSMA. In some embodiments, any of the full hinge embodiments can be applied to a minibody that binds to CD8, CD3, 5T4, PSCA, or PSMA. In some embodiments, any of the upper hinge embodiments can be applied to a minibody that binds to CD8, CD3, 5T4, PSCA, or PSMA. In some embodiments, any of the core hinge embodiments can be applied to a minibody that binds to CD8, CD3, 5T4, PSCA, or PSMA. In some embodiments, any of the lower hinge embodiments can be applied to a minibody that binds to CD8, CD3, 5T4, PSCA, or PSMA. In some embodiments, any of the upper and core hinge embodiments can be applied to a minibody that binds to CD8, CD3, 5T4, PSCA, or PSMA. In some embodiments, any of the core and lower hinge embodiments can be applied to a minibody that binds to CD8, CD3, 5T4, PSCA, or PSMA. In some embodiments, any of the upper and lower hinge embodiments can be applied to a minibody that binds to CD8, CD3, 5T4, PSCA, or PSMA.

Additional antibody fragments, such as minibodies are provided below. The antibody fragments can be used, for example, for imaging or therapeutic purposes. Schematic representations of exemplary minibodies are illustrated in the Figures and/or outlined in Table 0.2 below (in either the M1 orientation or the M2 orientation).

TABLE 0.2

| 1 Name | 2 Signal peptide | 3 Region 1 | 4 Linker | 5 Region 2 | 6 Upper hinge | 7 Core hinge | 8 Lower hinge | 9 Remainder |
|---|---|---|---|---|---|---|---|---|
|  |  |  |  |  | Full hinge | | | |
| Minibodies (N-terminus to C-terminus) - M1 structural orientation | | | | | | | | |
| IAB2M γ1 EH1 | (SEQ ID NO: 69) | $V_L$ (SEQ ID NO: 13) | 18aa (SEQ ID NO: 62) | $V_H$ (SEQ ID NO: 14) | (SEQ ID NO: 45) | (SEQ ID NO: 50) | (SEQ ID NO: 59) | IgG1 CH3 domain (SEQ ID NO: 40 or SEQ ID NO: 41) |

TABLE 0.2-continued

| 1 Name | 2 Signal peptide | 3 Region 1 | 4 Linker | 5 Region 2 | 6 Upper hinge | 7 Core hinge | 8 Lower hinge | 9 Remainder |
|---|---|---|---|---|---|---|---|---|
| | | | | | Full hinge | | | |
| | | | | | (SEQ ID NO: 24) | | | |
| IAB2M γ1 EH2 | (SEQ ID NO: 69) | V_L (SEQ ID NO: 13) | 18aa (SEQ ID NO: 62) | V_H (SEQ ID NO: 14) | (SEQ ID NO: 46) | (SEQ ID NO: 50) | (SEQ ID NO: 59) | IgG1 CH3 domain (SEQ ID NO: 40 or SEQ ID NO: 41) |
| IAB2M γ2 EH1 | (SEQ ID NO: 69) | V_L (SEQ ID NO: 13) | 18aa (SEQ ID NO: 62) | V_H (SEQ ID NO: 14) | (SEQ ID NO: 47) | (SEQ ID NO: 55) | (SEQ ID NO: 59) | IgG2 CH3 domain (SEQ ID NO: 42) |
| IAB2M γ2 EH2 | (SEQ ID NO: 69) | V_L (SEQ ID NO: 13) | 18aa (SEQ ID NO: 62) | V_H (SEQ ID NO: 14) | (SEQ ID NO: 47) | (SEQ ID NO: 56) | (SEQ ID NO: 59) | IgG2 CH3 domain (SEQ ID NO: 42) |
| IAB2M γ1 EH3 | (SEQ ID NO: 69) | V_L (SEQ ID NO: 13) | 18aa (SEQ ID NO: 62) | V_H (SEQ ID NO: 14) | (SEQ ID NO: 46) | (SEQ ID NO: 52) | (SEQ ID NO: 59) | IgG1 CH3 domain (SEQ ID NO: 40 or SEQ ID NO: 41) |
| IAB22M γ2 EH1 | (SEQ ID NO: 69) | V_L (SEQ ID NO: 15) | 18aa (SEQ ID NO: 62) | V_H (SEQ ID NO: 16) | (SEQ ID NO: 47) | (SEQ ID NO: 55) | (SEQ ID NO: 59) | IgG2 CH3 domain (SEQ ID NO: 42) |
| IAB22M 1 γ2 EH2 | (SEQ ID NO: 69) | V_L (SEQ ID NO: 15) | 18aa (SEQ ID NO: 62) | V_H (SEQ ID NO: 16) | (SEQ ID NO: 47) | (SEQ ID NO: 56) | (SEQ ID NO: 59) | IgG2 CH3 domain (SEQ ID NO: 42) |
| IAB22M γ1 EH1 | (SEQ ID NO: 69) | V_L (SEQ ID NO: 15) | 18aa (SEQ ID NO: 62) | V_H (SEQ ID NO: 16) | (SEQ ID NO: 45) | (SEQ ID NO: 50) | (SEQ ID NO: 59) | IgG1 CH3 domain (SEQ ID NO: 40 or SEQ ID NO: 41) |
| IAB22M γ2 NH1 | (SEQ ID NO: 69) | V_L (SEQ ID NO: 15) | 18aa (SEQ ID NO: 62) | V_H (SEQ ID NO: 16) | (SEQ ID NO: 47) | (SEQ ID NO: 55) | (SEQ ID NO: 60) | IgG2 CH3 domain (SEQ ID NO: 42) |
| IAB22M γ2 NH2 | (SEQ ID NO: 69) | V_L (SEQ ID NO: 15) | 18aa (SEQ ID NO: 62) | V_H (SEQ ID NO: 16) | (SEQ ID NO: 47) | (SEQ ID NO: 56) | (SEQ ID NO: 60) | IgG2 CH3 domain (SEQ ID NO: 42) |
| IAB22M γ1 EH3 | (SEQ ID NO: 69) | V_L (SEQ ID NO: 15) | 18aa (SEQ ID NO: 62) | V_H (SEQ ID NO: 16) | (SEQ ID NO: 46) | (SEQ ID NO: 52) | (SEQ ID NO: 59) | IgG1 CH3 domain (SEQ ID NO: 40 or SEQ ID NO: 41) |
| IAB22M γ1 EH5 | (SEQ ID NO: 69) | V_L (SEQ ID NO: 15) | 18aa (SEQ ID NO: 62) | V_H (SEQ ID NO: 16) | (SEQ ID NO: 46) | (SEQ ID NO: 54) | (SEQ ID NO: 59) | IgG1 CH3 domain (SEQ ID NO: 40 or SEQ ID NO: 41) |
| IAB22M γ3/γ1 EH6 | (SEQ ID NO: 69) | V_L (SEQ ID NO: 15) | 18aa (SEQ ID NO: 62) | V_H (SEQ ID NO: 16) | (SEQ ID NO: 48) | (SEQ ID NO: 57) | (SEQ ID NO: 59) | IgG1 CH3 domain (SEQ ID NO: 40 or SEQ ID NO: 41) |
| IAB22M γ3/γ1 EH7 | (SEQ ID NO: 69) | V_L (SEQ ID NO: 15) | 18aa (SEQ ID NO: 62) | V_H (SEQ ID NO: 16) | (SEQ ID NO: 48) | (SEQ ID NO: 52) | (SEQ ID NO: 59) | IgG1 CH3 domain (SEQ ID NO: 40 or SEQ ID NO: 41) |
| IAB22M γ3/γ1 EH8 | (SEQ ID NO: 69) | V_L (SEQ ID NO: 15) | 18aa (SEQ ID NO: 62) | V_H (SEQ ID NO: 16) | (SEQ ID NO: 48) | (SEQ ID NO: 54) | (SEQ ID NO: 59) | IgG1 CH3 domain (SEQ ID NO: 40 or SEQ ID NO: 41) |
| IAB2M γ1 EH5 | (SEQ ID NO: 69) | V_L (SEQ ID NO: 13) | 18aa (SEQ ID NO: 62) | V_H (SEQ ID NO: 14) | (SEQ ID NO: 46) | (SEQ ID NO: 54) | (SEQ ID NO: 59) | IgG1 CH3 domain (SEQ ID NO: 40 or SEQ ID NO: 41) |
| IAB2M γ3/γ1 EH6 | (SEQ ID NO: 69) | V_L (SEQ ID NO: 13) | 18aa (SEQ ID NO: 62) | V_H (SEQ ID NO: 14) | (SEQ ID NO: 48) | (SEQ ID NO: 57) | (SEQ ID NO: 59) | IgG1 CH3 domain (SEQ ID NO: 40 or SEQ ID NO: 41) |

TABLE 0.2-continued

| 1 Name | 2 Signal peptide | 3 Region 1 | 4 Linker | 5 Region 2 | 6 Upper hinge (Full hinge) | 7 Core hinge (Full hinge) | 8 Lower hinge (Full hinge) | 9 Remainder |
|---|---|---|---|---|---|---|---|---|
| IAB2M γ3/γ1 EH7 | (SEQ ID NO: 69) | $V_L$ (SEQ ID NO: 13) | 18aa (SEQ ID NO: 62) | $V_H$ (SEQ ID NO: 14) | (SEQ ID NO: 48) | (SEQ ID NO: 52) | (SEQ ID NO: 59) | IgG1 CH3 domain (SEQ ID NO: 40 or SEQ ID NO: 41) |
| IAB2M-γ3/γ1 EH8 | (SEQ ID NO: 69) | $V_L$ (SEQ ID NO: 13) | 18aa (SEQ ID NO: 62) | $V_H$ (SEQ ID NO: 14) | (SEQ ID NO: 48) | (SEQ ID NO: 54) | (SEQ ID NO: 59) | IgG1 CH3 domain (SEQ ID NO: 40 or SEQ ID NO: 41) |
| IAB22M γ1 EH2 | (SEQ ID NO: 69) | $V_L$ (SEQ ID NO: 15) | 18aa (SEQ ID NO: 62) | $V_H$ (SEQ ID NO: 16) | (SEQ ID NO: 46) | (SEQ ID NO: 50) | (SEQ ID NO: 59) | IgG1 CH3 domain (SEQ ID NO: 40 or SEQ ID NO: 41) |
| IAB20M γ1 EH1 | (SEQ ID NO: 69) | $V_L$ (SEQ ID NO: 13) | 18aa (SEQ ID NO: 62) | $V_H$ (SEQ ID NO: 14) | (SEQ ID NO: 45) | (SEQ ID NO: 50) | (SEQ ID NO: 59) | IgG1 CH3 domain (SEQ ID NO: 40 or SEQ ID NO: 41) |
| IAB20M γ1 EH3 | (SEQ ID NO: 69) | $V_L$ (SEQ ID NO: 17) | 18aa (SEQ ID NO: 62) | $V_H$ (SEQ ID NO: 18) | (SEQ ID NO: 46) | (SEQ ID NO: 52) | (SEQ ID NO: 59) | IgG1 CH3 domain (SEQ ID NO: 40 or SEQ ID NO: 41) |
| IAB20M γ1 EH2 | (SEQ ID NO: 69) | $V_L$ (SEQ ID NO: 17) | 18aa (SEQ ID NO: 62) | $V_H$ (SEQ ID NO: 18) | (SEQ ID NO: 46) | (SEQ ID NO: 50) | (SEQ ID NO: 59) | IgG1 CH3 domain (SEQ ID NO: 40 or SEQ ID NO: 41) |
| IAB20M γ1 EH5 | (SEQ ID NO: 69) | $V_L$ (SEQ ID NO: 17) | 18aa (SEQ ID NO: 62) | $V_H$ (SEQ ID NO: 18) | (SEQ ID NO: 46) | (SEQ ID NO: 54) | (SEQ ID NO: 59) | IgG1 CH3 domain (SEQ ID NO: 40 or SEQ ID NO: 41) |
| IAB1M γ1 EH1 | (SEQ ID NO: 69) | $V_L$ (SEQ ID NO: 67) | 18aa (SEQ ID NO: 62) | $V_H$ (SEQ ID NO: 68) | (SEQ ID NO: 45) | (SEQ ID NO: 50) | (SEQ ID NO: 59) | IgG1 CH3 domain (SEQ ID NO: 40 or SEQ ID NO: 41) |
| IAB1M γ1 EH2 | (SEQ ID NO: 69) | $V_L$ (SEQ ID NO: 67) | 18aa (SEQ ID NO: 62) | $V_H$ (SEQ ID NO: 68) | (SEQ ID NO: 46) | (SEQ ID NO: 50) | (SEQ ID NO: 59) | IgG1 CH3 domain (SEQ ID NO: 40 or SEQ ID NO: 41) |
| IAB1M γ1 EH3 | (SEQ ID NO: 69) | $V_L$ (SEQ ID NO: 67) | 18aa (SEQ ID NO: 62) | $V_H$ (SEQ ID NO: 68) | (SEQ ID NO: 46) | (SEQ ID NO: 52) | (SEQ ID NO: 59) | IgG1 CH3 domain (SEQ ID NO: 40 or SEQ ID NO: 41) |
| IAB20M γ2 EH2 | (SEQ ID NO: 69) | $V_L$ (SEQ ID NO: 17) | 18aa (SEQ ID NO: 62) | $V_H$ (SEQ ID NO: 18) | (SEQ ID NO: 47) | (SEQ ID NO: 56) | (SEQ ID NO: 59) | IgG2 CH3 domain (SEQ ID NO: 42) |
| IAB20M γ2 EH2 | (SEQ ID NO: 69) | $V_L$ (SEQ ID NO: 17) | 18aa (SEQ ID NO: 62) | $V_H$ (SEQ ID NO: 18) | (SEQ ID NO: 47) | (SEQ ID NO: 56) | (SEQ ID NO: 59) | IgG2 CH3 T26S, L28A, M57V domain (SEQ ID NO: 181) |
| IAB20M γ2 EH2 | (SEQ ID NO: 69) | $V_L$ (SEQ ID NO: 17) | 18aa (SEQ ID NO: 62) | $V_H$ (SEQ ID NO: 18) | (SEQ ID NO: 47) | (SEQ ID NO: 56) | (SEQ ID NO: 59) | IgG2 CH3 T26W domain (SEQ ID NO: 182) |
| IAB25M γ2 EH2 | (SEQ ID NO: 69) | $V_L$ (SEQ ID NO: 19) | 18aa (SEQ ID NO: 62) | $V_H$ (SEQ ID NO: 20) | (SEQ ID NO: 47) | (SEQ ID NO: 56) | (SEQ ID NO: 59) | IgG2 CH3 domain (SEQ ID NO: 42) |
| IAB25M γ2 EH2 | (SEQ ID NO: 69) | $V_L$ (SEQ ID NO: 19) | 18aa (SEQ ID NO: 62) | $V_H$ (SEQ ID NO: 20) | (SEQ ID NO: 47) | (SEQ ID NO: 56) | (SEQ ID NO: 59) | IgG2 CH3 T26S, L28A, M57V |

TABLE 0.2-continued

| 1 Name | 2 Signal peptide | 3 Region 1 | 4 Linker | 5 Region 2 | 6 Upper hinge | 7 Core hinge | 8 Lower hinge | 9 Remainder |
|---|---|---|---|---|---|---|---|---|
| IAB25M γ2 EH2 | (SEQ ID NO: 69) | V_L (SEQ ID NO: 19) | 18aa (SEQ ID NO: 62) | V_H (SEQ ID NO: 20) | (SEQ ID NO: 34) (SEQ ID NO: 47) | (SEQ ID NO: 56) | (SEQ ID NO: 59) | domain (SEQ ID NO: 181) IgG2 CH3 T26W domain (SEQ ID NO: 182) |
| Minibodies (N- to C-terminal) - M2 structural orientation | | | | | | | | |
| IAB2M γ1 EH1 | (SEQ ID NO: 69) | V_H (SEQ ID NO: 14) | 18aa (SEQ ID NO: 62) | V_L (SEQ ID NO: 13) | (SEQ ID NO: 22) (SEQ ID NO: 45) | (SEQ ID NO: 50) | (SEQ ID NO: 59) | IgG1 CH3 domain (SEQ ID NO: 40 or SEQ ID NO: 41) |
| IAB2M γ1 EH2 | (SEQ ID NO: 69) | V_H (SEQ ID NO: 14) | 18aa (SEQ ID NO: 62) | V_L (SEQ ID NO: 13) | (SEQ ID NO: 24) (SEQ ID NO: 46) | (SEQ ID NO: 50) | (SEQ ID NO: 59) | IgG1 CH3 domain (SEQ ID NO: 40 or SEQ ID NO: 41) |
| IAB2M γ2 EH1 | (SEQ ID NO: 69) | V_H (SEQ ID NO: 14) | 18aa (SEQ ID NO: 62) | V_L (SEQ ID NO: 13) | (SEQ ID NO: 32) (SEQ ID NO: 47) | (SEQ ID NO: 55) | (SEQ ID NO: 59) | IgG2 CH3 domain (SEQ ID NO: 42) |
| IAB2M γ2 EH2 | (SEQ ID NO: 69) | V_H (SEQ ID NO: 14) | 18aa (SEQ ID NO: 62) | V_L (SEQ ID NO: 13) | (SEQ ID NO: 34) (SEQ ID NO: 47) | (SEQ ID NO: 56) | (SEQ ID NO: 59) | IgG2 CH3 domain (SEQ ID NO: 42) |
| IAB2M γ1 EH3 | (SEQ ID NO: 69) | V_H (SEQ ID NO: 14) | 18aa (SEQ ID NO: 62) | V_L (SEQ ID NO: 13) | (SEQ ID NO: 26) (SEQ ID NO: 46) | (SEQ ID NO: 52) | (SEQ ID NO: 59) | IgG1 CH3 domain (SEQ ID NO: 40 or SEQ ID NO: 41) |
| IAB22M γ2 EH1 | (SEQ ID NO: 69) | V_H (SEQ ID NO: 16) | 18aa (SEQ ID NO: 62) | V_L (SEQ ID NO: 15) | (SEQ ID NO: 32) (SEQ ID NO: 47) | (SEQ ID NO: 55) | (SEQ ID NO: 59) | IgG2 CH3 domain (SEQ ID NO: 42) |
| IAB22M γ2 EH2 | (SEQ ID NO: 69) | V_H (SEQ ID NO: 16) | 18aa (SEQ ID NO: 62) | V_L (SEQ ID NO: 15) | (SEQ ID NO: 34) (SEQ ID NO: 47) | (SEQ ID NO: 56) | (SEQ ID NO: 59) | IgG2 CH3 domain (SEQ ID NO: 42) |
| IAB22M γ1 EH1 | (SEQ ID NO: 69) | V_H (SEQ ID NO: 16) | 18aa (SEQ ID NO: 62) | V_L (SEQ ID NO: 15) | (SEQ ID NO: 22) (SEQ ID NO: 45) | (SEQ ID NO: 50) | (SEQ ID NO: 59) | IgG1 CH3 domain (SEQ ID NO: 40 or SEQ ID NO: 41) |
| IAB22M γ2 NH1 | (SEQ ID NO: 69) | V_H (SEQ ID NO: 16) | 18aa (SEQ ID NO: 62) | V_L (SEQ ID NO: 15) | (SEQ ID NO: 31) (SEQ ID NO: 47) | (SEQ ID NO: 55) | (SEQ ID NO: 60) | IgG2 CH3 domain (SEQ ID NO: 42) |
| IAB22M γ2 NH2 | (SEQ ID NO: 69) | V_H (SEQ ID NO: 16) | 18aa (SEQ ID NO: 62) | V_L (SEQ ID NO: 15) | (SEQ ID NO: 33) (SEQ ID NO: 47) | (SEQ ID NO: 56) | (SEQ ID NO: 60) | IgG2 CH3 domain (SEQ ID NO: 42) |
| IAB22M γ1 EH3 | (SEQ ID NO: 69) | V_H (SEQ ID NO: 16) | 18aa (SEQ ID NO: 62) | V_L (SEQ ID NO: 15) | (SEQ ID NO: 26) (SEQ ID NO: 46) | (SEQ ID NO: 52) | (SEQ ID NO: 59) | IgG1 CH3 domain (SEQ ID NO: 40 or SEQ ID NO: 41) |
| IAB22M γ1 EH5 | (SEQ ID NO: 69) | V_H (SEQ ID NO: 16) | 18aa (SEQ ID NO: 62) | V_L (SEQ ID NO: 15) | (SEQ ID NO: 30) (SEQ ID NO: 46) | (SEQ ID NO: 54) | (SEQ ID NO: 59) | IgG1 CH3 domain (SEQ ID NO: 40 or SEQ ID NO: 41) |
| IAB22M γ3/ γ1 EH6 | (SEQ ID NO: 69) | V_H (SEQ ID NO: 16) | 18aa (SEQ ID NO: 62) | V_L (SEQ ID NO: 15) | (SEQ ID NO: 35) (SEQ ID NO: 48) | (SEQ ID NO: 57) | (SEQ ID NO: 59) | IgG1 CH3 domain (SEQ ID NO: 40 or SEQ ID NO: 41) |
| IAB22M γ3/ γ1 EH7 | (SEQ ID NO: 69) | V_H (SEQ ID NO: 16) | 18aa (SEQ ID NO: 62) | V_L (SEQ ID NO: 15) | (SEQ ID NO: 36) (SEQ ID NO: 48) | (SEQ ID NO: 52) | (SEQ ID NO: 59) | IgG1 CH3 domain (SEQ ID NO: 40 or SEQ ID NO: 41) |

TABLE 0.2-continued

| 1 Name | 2 Signal peptide | 3 Region 1 | 4 Linker | 5 Region 2 | Full hinge | | | 9 Remainder |
|---|---|---|---|---|---|---|---|---|
| | | | | | 6 Upper hinge | 7 Core hinge | 8 Lower hinge | |
| IAB22M γ3/γ1 EH8 | (SEQ ID NO: 69) | V_H (SEQ ID NO: 16) | 18aa (SEQ ID NO: 62) | V_L (SEQ ID NO: 15) | (SEQ ID NO: 48) | (SEQ ID NO: 54) | (SEQ ID NO: 59) | (SEQ ID NO: 37) IgG1 CH3 domain (SEQ ID NO: 40 or SEQ ID NO: 41) |
| IAB2M γ1 EH5 | (SEQ ID NO: 69) | V_H (SEQ ID NO: 14) | 18aa (SEQ ID NO: 62) | V_L (SEQ ID NO: 13) | (SEQ ID NO: 46) | (SEQ ID NO: 54) | (SEQ ID NO: 59) | (SEQ ID NO: 30) IgG1 CH3 domain (SEQ ID NO: 40 or SEQ ID NO: 41) |
| IAB2M γ3/γ1 EH6 | (SEQ ID NO: 69) | V_H (SEQ ID NO: 14) | 18aa (SEQ ID NO: 62) | V_L (SEQ ID NO: 13) | (SEQ ID NO: 48) | (SEQ ID NO: 57) | (SEQ ID NO: 59) | (SEQ ID NO: 35) IgG1 CH3 domain (SEQ ID NO: 40 or SEQ ID NO: 41) |
| IAB2M γ3/γ1 EH7 | (SEQ ID NO: 69) | V_H (SEQ ID NO: 14) | 18aa (SEQ ID NO: 62) | V_L (SEQ ID NO: 13) | (SEQ ID NO: 48) | (SEQ ID NO: 52) | (SEQ ID NO: 59) | (SEQ ID NO: 36) IgG1 CH3 domain (SEQ ID NO: 40 or SEQ ID NO: 41) |
| IAB2M γ3/γ1 EH8 | (SEQ ID NO: 69) | V_H (SEQ ID NO: 14) | 18aa (SEQ ID NO: 62) | V_L (SEQ ID NO: 13) | (SEQ ID NO: 48) | (SEQ ID NO: 54) | (SEQ ID NO: 59) | (SEQ ID NO: 37) IgG1 CH3 domain (SEQ ID NO: 40 or SEQ ID NO: 41) |
| IAB22M γ1 EH2 | (SEQ ID NO: 69) | V_H (SEQ ID NO: 16) | 18aa (SEQ ID NO: 62) | V_L (SEQ ID NO: 15) | (SEQ ID NO: 46) | (SEQ ID NO: 50) | (SEQ ID NO: 59) | (SEQ ID NO: 24) IgG1 CH3 domain (SEQ ID NO: 40 or SEQ ID NO: 41) |
| IAB20M γ1 EH1 | (SEQ ID NO: 69) | V_H (SEQ ID NO: 14) | 18aa (SEQ ID NO: 62) | V_L (SEQ ID NO: 13) | (SEQ ID NO: 45) | (SEQ ID NO: 50) | (SEQ ID NO: 59) | (SEQ ID NO: 22) IgG1 CH3 domain (SEQ ID NO: 40 or SEQ ID NO: 41) |
| IAB20M γ1 EH3 | (SEQ ID NO: 69) | V_H (SEQ ID NO: 18) | 18aa (SEQ ID NO: 62) | V_L (SEQ ID NO: 17) | (SEQ ID NO: 46) | (SEQ ID NO: 52) | (SEQ ID NO: 59) | (SEQ ID NO: 26) IgG1 CH3 domain (SEQ ID NO: 40 or SEQ ID NO: 41) |
| IAB20M γ1 EH2 | (SEQ ID NO: 69) | V_H (SEQ ID NO: 18) | 18aa (SEQ ID NO: 62) | V_L (SEQ ID NO: 17) | (SEQ ID NO: 46) | (SEQ ID NO: 50) | (SEQ ID NO: 59) | (SEQ ID NO: 24) IgG1 CH3 domain (SEQ ID NO: 40 or SEQ ID NO: 41) |
| IAB20M γ1 EH5 | (SEQ ID NO: 69) | V_H (SEQ ID NO: 18) | 18aa (SEQ ID NO: 62) | V_L (SEQ ID NO: 17) | (SEQ ID NO: 46) | (SEQ ID NO: 54) | (SEQ ID NO: 59) | (SEQ ID NO: 30) IgG1 CH3 domain (SEQ ID NO: 40 or SEQ ID NO: 41) |
| IAB1M γ1 EH1 | (SEQ ID NO: 69) | V_H (SEQ ID NO: 68) | 18aa (SEQ ID NO: 62) | V_L (SEQ ID NO: 67) | (SEQ ID NO: 45) | (SEQ ID NO: 50) | (SEQ ID NO: 59) | (SEQ ID NO: 22) IgG1 CH3 domain (SEQ ID NO: 40 or SEQ ID NO: 41) |
| IAB1M γ1 EH2 | (SEQ ID NO: 69) | V_H (SEQ ID NO: 68) | 18aa (SEQ ID NO: 62) | V_L (SEQ ID NO: 67) | (SEQ ID NO: 46) | (SEQ ID NO: 50) | (SEQ ID NO: 59) | (SEQ ID NO: 24) IgG1 CH3 domain (SEQ ID NO: 40 or SEQ ID NO: 41) |
| IAB1M γ1 EH3 | (SEQ ID NO: 69) | V_H (SEQ ID NO: 68) | 18aa (SEQ ID NO: 62) | V_L (SEQ ID NO: 67) | (SEQ ID NO: 46) | (SEQ ID NO: 52) | (SEQ ID NO: 59) | (SEQ ID NO: 26) IgG1 CH3 domain (SEQ ID NO: 40 or SEQ ID NO: 41) |
| IAB20M γ2 EH2 | (SEQ ID NO: 69) | V_H (SEQ ID NO: 18) | 18aa (SEQ ID NO: 62) | V_L (SEQ ID NO: 17) | (SEQ ID NO: 47) | (SEQ ID NO: 56) | (SEQ ID NO: 59) | (SEQ ID NO: 34) IgG2 CH3 domain (SEQ ID NO: 42) |

TABLE 0.2-continued

| 1 Name | 2 Signal peptide | 3 Region 1 | 4 Linker | 5 Region 2 | 6 Upper hinge | 7 Core hinge | 8 Lower hinge | 9 Remainder |
|---|---|---|---|---|---|---|---|---|
| IAB20M γ2 EH2 | (SEQ ID NO: 69) | V_H (SEQ ID NO: 18) | 18aa (SEQ ID NO: 62) | V_L (SEQ ID NO: 17) | (SEQ ID NO: 47) | (SEQ ID NO: 34) (SEQ ID NO: 56) | (SEQ ID NO: 59) | IgG2 CH3 T26S, L28A, M57V domain (SEQ ID NO: 181) |
| IAB20M γ2 EH2 | (SEQ ID NO: 69) | V_H (SEQ ID NO: 18) | 18aa (SEQ ID NO: 62) | V_L (SEQ ID NO: 17) | (SEQ ID NO: 47) | (SEQ ID NO: 34) (SEQ ID NO: 56) | (SEQ ID NO: 59) | IgG2 CH3 T26W domain (SEQ ID NO: 182) |
| IAB25M γ2 EH2 | (SEQ ID NO: 69) | V_H (SEQ ID NO: 20) | 18aa (SEQ ID NO: 62) | V_L (SEQ ID NO: 19) | (SEQ ID NO: 47) | (SEQ ID NO: 34) (SEQ ID NO: 56) | (SEQ ID NO: 59) | IgG2 CH3 domain (SEQ ID NO: 42) |
| IAB25M γ2 EH2 | (SEQ ID NO: 69) | V_H (SEQ ID NO: 20) | 18aa (SEQ ID NO: 62) | V_L (SEQ ID NO: 19) | (SEQ ID NO: 47) | (SEQ ID NO: 34) (SEQ ID NO: 56) | (SEQ ID NO: 59) | IgG2 CH3 T26S, L28A, M57V domain (SEQ ID NO: 181) |
| IAB25M γ2 EH2 | (SEQ ID NO: 69) | V_H (SEQ ID NO: 20) | 18aa (SEQ ID NO: 62) | V_L (SEQ ID NO: 19) | (SEQ ID NO: 47) | (SEQ ID NO: 34) (SEQ ID NO: 56) | (SEQ ID NO: 59) | IgG2 CH3 T26W domain (SEQ ID NO: 182) |

Depicted in Table 0.2 are arrangements of sequences for monomers that can be used in minibodies (Table 0.2). Each row of the table represents the sequence of a monomer construct, with left-to-right representing N-terminus to C-terminus. In some embodiments, the shown sequences of each monomer construct are directly linked to each other. Thus, in some embodiments, the construct can include any of the constructs on a single row in Table 0.2. In some embodiments, the constructs can include any combination in Table 0.2. In some embodiments, for example, the first item in the first row, column 3 can be combined with the first row, column 4 to the first row column 5, to the first row column 6-8, to the first row, column 9. In some embodiments, column 3 and column 5 can be swapped with one another. In some embodiments, the first item in the first row, column 3 can be combined with the first row, column 4 to the second row column 5, to the second row column 6-8, to the second row, column 9. Thus, the tables represent all possible combinations, both within a single row and across various rows (and with columns swapped).

In some embodiments, an antigen binding construct against CD8 includes a heavy chain CDR1 (HCDR1) of the HCDR 1 in SEQ ID NO: 75; a heavy chain CDR2 (HCDR2) of the HCDR2 in SEQ ID NO: 76; a heavy chain CDR3 (HCDR3) of the HCDR3 in SEQ ID NO: 77; a light chain CDR1 (LCDR1) of the LCDR1 in SEQ ID NO: 78; a light chain CDR2 (LCDR2) of the LCDR2 in SEQ ID NO: 79; and/or a light chain CDR3 (LCDR3) of the LCDR3 in SEQ ID NO: 80. In some embodiments, an antigen binding construct against PSMA includes a heavy chain CDR1 (HCDR1) of the HCDR 1 in SEQ ID NO: 81; a heavy chain CDR2 (HCDR2) of the HCDR2 in SEQ ID NO: 82; a heavy chain CDR3 (HCDR3) of the HCDR3 in SEQ ID NO: 83; a light chain CDR1 (LCDR1) of the LCDR1 in SEQ ID NO: 84; a light chain CDR2 (LCDR2) of the LCDR2 in SEQ ID NO: 85; and/or a light chain CDR3 (LCDR3) of the LCDR3 in SEQ ID NO: 86. In some embodiments, an antigen binding construct against 5T4 includes a heavy chain CDR1 (HCDR1) of the HCDR 1 in SEQ ID NO: 87; a heavy chain CDR2 (HCDR2) of the HCDR2 in SEQ ID NO: 88; a heavy chain CDR3 (HCDR3) of the HCDR3 in SEQ ID NO: 89; a light chain CDR1 (LCDR1) of the LCDR1 in SEQ ID NO: 90; a light chain CDR2 (LCDR2) of the LCDR2 in SEQ ID NO: 91; and/or a light chain CDR3 (LCDR3) of the LCDR3 in SEQ ID NO: 92. In some embodiments, an antigen binding construct against PSCA includes a heavy chain CDR1 (HCDR1) of the HCDR1 in SEQ ID NO: 93; a heavy chain CDR2 (HCDR2) of the HCDR2 in SEQ ID NO: 94; a heavy chain CDR3 (HCDR3) of the HCDR3 in SEQ ID NO: 95; a light chain CDR1 (LCDR1) of the LCDR1 in SEQ ID NO: 96; a light chain CDR2 (LCDR2) of the LCDR2 in SEQ ID NO: 97; and/or a light chain CDR3 (LCDR3) of the LCDR3 in SEQ ID NO: 98. In some embodiments, an antigen binding construct against CD3 includes a heavy chain CDR1 (HCDR1) of the HCDR1 in FIG. 65B or 65C; a heavy chain CDR2 (HCDR2) of the HCDR2 in FIG. 65B or 65C; a heavy chain CDR3 (HCDR3) of the HCDR3 in FIG. 65B or 65C; a light chain CDR1 (LCDR1) of the LCDR1 in FIG. 65B or 65C; a light chain CDR2 (LCDR2) of the LCDR2 in FIG. 65B or 65C; and/or a light chain CDR3 (LCDR3) of the LCDR3 in FIG. 65B or 65C. Some embodiments of CDR sequences that can be used with any one or more of the hinge sequences provided herein are shown in Table 8.

TABLE 8

CDR sequences

| | IAB22M (CD8) | IAB2M (PSMA) | IAB20M (5T4) | IAB1M (PSCA) | IAB25M (CD3) |
|---|---|---|---|---|---|
| HCDR 1 | GFNIKDT (SEQ ID NO: 75) | GYTFTEY (SEQ ID NO: 81) | GYSFTGY (SEQ ID NO: 87) | GFNIKDY (SEQ ID NO: 93) | GYTFTRY (SEQ ID NO: 174) |
| HCDR 2 | DPANDN (SEQ ID NO: 76) | NINPNNGG (SEQ ID NO: 82) | NPNNGV (SEQ ID NO: 88) | DPENGD (SEQ ID NO: 94) | NPSRGY (SEQ ID NO: 175) |
| HCDR 3 | GYGYYVFDH (SEQ ID NO: 77) | GWNFDY (SEQ ID NO: 83) | STMITNYVMDY (SEQ ID NO: 89) | GGF (SEQ ID NO: 95) | YYDDHYSLDY (SEQ ID NO: 176) |
| LCDR 1 | RTSRSISQYLA (SEQ ID NO: 78) | KASQDVGTAVD (SEQ ID NO: 84) | KASQSVSNDVA (SEQ ID NO: 90) | SASSSVRFIH (SEQ ID NO: 96) | SASSSVSYMN (SEQ ID NO: 177) |
| LCDR 2 | SGSTLQS (SEQ ID NO: 79) | WASTRHT (SEQ ID NO: 85) | YTSSRYA (SEQ ID NO: 91) | DTSKLAS (SEQ ID NO: 97) | DTSKLAS (SEQ ID NO: 97) |
| LCDR 3 | QQHNENPLT (SEQ ID NO: 80) | QQYNSYPLT (SEQ ID NO: 86) | QQDYNSPPT (SEQ ID NO: 92) | QQWGSSPFT (SEQ ID NO: 98) | QQWSSNPFT (SEQ ID NO: 178) |

These constructs can be in any of the forms provided herein, including minibodies, scFv, etc. In some embodiments, the antigen binding construct includes 6, 5, 4, 3, 2, or 1, the above CDRs (some embodiments of the CDRs are indicated in FIG. 41, 48, 55, 61, 65B, or 65C). In some embodiments, any of the hinge sections provided herein can be combined with any of the CDRs provided herein. In some embodiments, any of the upper hinge sections provided herein can be combined with any of the CDRs provided herein. In some embodiments, any of the core hinge sections provided herein can be combined with any of the CDRs provided herein. In some embodiments, any of the lower hinge sections provided herein can be combined with any of the CDRs provided herein. In some embodiments, any of the full hinge sections provided herein can be combined with any of the CDRs provided herein. In some embodiments, any of the upper and core hinge sections provided herein can be combined with any of the CDRs provided herein. In some embodiments, any of the core and lower hinge sections provided herein can be combined with any of the CDRs provided herein. In some embodiments, any of these CDR based embodiments can be part of a minibody. In some embodiments, the antigen binding construct includes heavy chain CDR3 (HCDR3). In some embodiments, the antigen binding construct binds specifically to the target molecule. In some embodiments, the antigen binding construct competes for binding with one or more of the antibodies having the herein provided CDRs. In some embodiments, the antigen binding construct includes at least the 3 heavy chain CDRs noted herein. In some embodiments, the antigen binding construct includes heavy chain CDR3. In some embodiments, the antigen binding construct further includes any one of the heavy chain CDR2 sequences provided herein. In some embodiments, any of these embodiments can be applied to a minibody that binds to CD8, CD3, 5T4, PSCA, or PSMA.

In some embodiments, the antigen binding construct is human or humanized. When used in the context of a minibody, the term human does not denote that the construct is identical to that found in nature in humans, but rather that the construct has sequences that are human. In some embodiments, the antigen binding construct includes at least one human framework region (for example, those sections shown before, between, and after the CDRs shown in FIG. 41, 48, 55, 61, 65B, or 65C, or a framework region with at least about 80% sequence identity, for example at least about 80%, 85%, 90%, 93%, 95%, 97%, or 99% identity to a human framework region. In some embodiments, the antigen binding construct includes 8, 7, 6, 5, 4, 3, 2, or 1 of the listed FRs. In some embodiments, any of the hinge sections provided herein can be combined with any of the FRs provided herein. In some embodiments, any of the upper hinge sections provided herein can be combined with any of the FRs provided herein. In some embodiments, any of the core hinge sections provided herein can be combined with any of the FRs provided herein. In some embodiments, any of the lower hinge sections provided herein can be combined with any of the FRs provided herein. In some embodiments, any of the full hinge sections provided herein can be combined with any of the FRs provided herein. In some embodiments, any of the upper and core hinge sections provided herein can be combined with any of the FRs provided herein. In some embodiments, any of the core and lower hinge sections provided herein can be combined with any of the FRs provided herein. In some embodiments, any of these FR based embodiments can be part of a minibody. In some embodiments, any of these embodiments can be applied to a minibody that binds to CD8, CD3, 5T4, PSCA, or PSMA.

In some embodiments, the antigen binding construct has a heavy chain variable region of the heavy chain variable region in SEQ ID NOs: 14 (PSMA), 16 or 99 (CD8), 18 or 102 (5T4), 68 (PSCA), or, 20 or 104 (or FIGS. 65B and 65C) (CD3). In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NOs: 14 (PSMA), 16 or 99 (CD8), 18 or 102 (5T4), 68 (PSCA), or, 20 or 104 (or FIGS. 65B and 65C) (CD3). In some embodiments, the antigen binding construct has a light chain variable region that includes SEQ ID NO: 13 (PSMA), 15 (CD8), 17 or 100 or 101 (5T4), 67 (PSCA), or, 19 or 103 (or FIGS. 65B and 65C) (CD3). In some embodiments, the antigen binding construct has a light chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 13 (PSMA), 15 (CD8), 17 or 100 or 101 (5T4), 67 (PSCA), or, 19 or 103 (or FIGS. 65B and 65C) (CD3). In some embodiments, the antigen binding construct is a human antigen binding construct and has a heavy chain variable region, a light chain variable region, or a heavy and light chain that is at least as identical as at least the heavy and/or light chain variable sequences noted above. In some embodiments, any one of the above embodiments is combined with any one of the hinge embodiments provided herein, including, for example, in a minibody context. In some embodiments, any of the hinge sections provided herein can be combined with any of the $V_H$ and $V_L$ pairings provided herein. In some embodiments, any of the upper hinge sections provided herein can be combined with any of the $V_H$ and $V_L$ pairings provided herein. In some embodiments, any of the core hinge sections provided herein can be combined with any of the $V_H$ and $V_L$ pairings provided herein. In some embodiments, any of the lower hinge sections provided herein can be combined with any of the $V_H$ and $V_L$ pairings provided herein. In some embodiments, any of the full hinge sections provided herein can be combined with any of the $V_H$ and $V_L$ pairings provided herein. In some embodiments, any of the upper and core hinge sections provided herein can be combined with any of the $V_H$ and $V_L$ pairings provided herein. In some embodiments, any of the core and lower hinge sections provided herein can be combined with any of the $V_H$ and $V_L$ pairings provided herein. In some embodiments, any of these $V_H$ and $V_L$ pairings based embodiments can be part of a minibody. In some embodiments, any of these embodiments can be applied to a minibody that binds to CD8, CD3, 5T4, PSCA, or PSMA.

In some embodiments, the antigen binding construct includes a detectable marker. In some embodiments, the antigen binding construct includes a therapeutic agent.

In some embodiments, the antigen binding construct is bivalent. Bivalent antigen binding construct can include at least a first antigen binding domain, for example a first scFv, and at least a second antigen binding domain, for example a second scFv. In some embodiments, a bivalent antigen binding construct is a multimer that includes at least two monomers, for example at least 2, 3, 4, 5, 6, 7, or 8 monomers, each of which has an antigen binding domain. In some embodiments, the antigen binding construct is a minibody. In some embodiments, one or more subparts of the hinges provided herein are included in the bivalent construct. The minibody can include any of the CDR and heavy chain variable region and/or light chain variable region embodiments provided herein (for example, the CDR sequences provided in FIG. 41, 48, 55, 61, 65B, or 65C). In some embodiments, the antigen binding construct is a monovalent scFv. In some embodiments, a monovalent scFv is provided that includes the heavy chain CDR1 (HCDR1) in the HCDR1 of FIG. 41, 48, 55, 61, 65B, or 65C the heavy chain CDR2 (HCDR2) in the HCDR2 of FIG. 41, 48, 55, 61, 65B, or 65C, the HCDR3 in the HCDR3 of FIG. 41, 48, 55, 61, 65B, or 65C, the light chain CDR1 (LCDR1) in the LCDR1 of FIG. 41, 48, 55, 61, 65B, or 65C, the light chain CDR2 (LCDR2) in the LCDR2 of FIG. 41, 48, 55, 61, 65B, or 65C, and the light chain CDR3 (LCDR3) in the LCDR3 of FIG. 41, 48, 55, 61, 65B, or 65C. In some embodiments, the monovalent scFv includes the heavy chain variable region of the heavy chain variable region in FIG. 36A, 36B, 36C, 36D, 36E, 65B, or 65C. In some embodiments, the monovalent scFv includes the light chain variable region of the light chain variable region in FIG. 36A, 36B, 36C, 36D, 36E, 65B, or 65C. In some embodiments, the monovalent scFv includes the heavy chain variable region of the heavy chain variable region in FIG. 66, 68 or 69, and the light chain variable region of the light chain variable region in FIG. 67 or 69.

In some embodiments, the antigen binding construct is bispecific. Bispecific constructs can include at least a first binding domain, for example an scFv that binds specifically to a first epitope, and at least a second binding domain, for example an scFv that binds specifically to a second epitope. Thus, bispecific antigen binding constructs can bind to two or more epitopes. In some embodiments, the first epitope and the second epitope are part of the same antigen, and the bispecific antigen binding construct can thus bind to two epitopes of the same antigen. In some embodiments, the first epitope is part of a first antigen, and the second epitope is part of a second antigen, and the bispecific antigen binding construct can thus bind to two different antigens. In some embodiments, the antigen binding construct binds to two epitopes simultaneously.

In some embodiments, the antigen binding construct has a heavy chain variable region of the heavy chain variable region in SEQ ID NO: 14, 16, 18, 20, 68, 99, 102 or 104, and/or the sequences in FIGS. 65B and 65C. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 14, 16, 18, 20, 68, 99, 102 or 104 and/or the sequences in FIGS. 65B and 65C. In some embodiments, the antigen binding construct has a light chain variable region that includes SEQ ID NO: 13, 15, 17, 19, 67, 100, 101 or 103 and/or the sequences in FIGS. 65B and 65C. In some embodiments, the antigen binding construct has a light chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 13, 15, 17, 19, 67, 100, 101 or 103 and/or the sequences in FIGS. 65B and 65C. In some embodiments, the antigen binding construct is a human antigen binding construct and has a heavy chain variable region, a light chain variable region, or a heavy and light chain that is at least as identical as at least the heavy and/or light chain variable sequences noted above.

Some embodiments provided herein include an antigen binding construct that competes for binding to the target molecule with one or more antigen binding constructs provided herein, and includes one or more of the hinge subparts provided herein (such as in Table 0.1). In some embodiments, the competing antigen binding construct binds to the same epitope on the target molecule as the reference antigen binding construct. In some embodiments, the reference antigen binding construct binds to a first epitope of the target molecule, and the competing antigen binding construct binds to a second epitope of the target molecule, but interferes with binding of the reference antigen binding construct to the target molecule, for example by sterically blocking binding of the reference antigen binding construct, or by inducing a conformational change in the target molecule. In some embodiments, the first epitope overlaps with the second epitope.

In some embodiments, the scFv and/or minibody formats have advantageous pharmacokinetic characteristics for diagnostic imaging and certain therapeutic applications while maintaining the high binding affinity and specificity of a parental antibody. Compared to imaging with the full-length parental antibody, the pharmacokinetics are more desirable for these fragments in that they are able to target the antigen and then rapidly clear the system for rapid high-contrast imaging. In some embodiments, the shorter circulation half-lives for the minibody allow for optimal imaging over a range of times from approximately 6-48 72 hours (depends on clearance and level of antigen "sink" and half-life of isotope that is chelated to Mb) hours post injection for the minibody. The rapid blood clearance together with better tissue penetration can allow for same day imaging, which can provide a significant advantage in the clinic with respect to patient care management.

In some embodiments, the antibody fragments can comprise one, two, or three of the variable light region CDRs and/or one, two, or three of the variable heavy region CDRs from a PSCA, 5T4, PSMA, CD3 or CD8 antibody. For example, an antibody fragment may contain one, two or three of the variable region CDRs and/or one, two, or three of the variable heavy region CDRs of murine versions of the PSCA, 5T4, PSMA, CD3 or CD8 antibody. In some embodiments, an antibody fragment comprises one or more CDR regions from the variable heavy or light regions of a humanized PSCA, 5T4, PSMA, CD3 or CD8 antibody.

In some embodiments, antigen binding constructs that bind the PSCA antigen can be antibodies, minibodies and/or fragments thereof such as scFv. Some non-limiting embodiments of antigen binding constructs against PSCA are shown in FIGS. 29B-29D, 36E, 60 (SEQ ID NOs: 125 and 126), 61 (SEQ ID NO: 126), 62 (SEQ ID NO: 127), 63 (SEQ ID NO: 128), 64 (SEQ ID NO: 129), 65A (SEQ ID NO: 130). In some embodiments, antigen binding constructs that bind the 5T4 antigen can be antibodies, minibodies and/or fragments thereof such as scFv. Some non-limiting embodiments of antigen binding constructs against 5T4 are shown in FIGS. 28B-28E, 32, 36C, 54 (SEQ ID NOs: 119 and 120), 55 (SEQ ID NO: 120), 56 (SEQ ID NO: 121), 57 (SEQ ID NO: 122), 58 (SEQ ID NO: 123), 59 (SEQ ID NO: 124), 67, 68. In some embodiments, antigen binding constructs that bind the PSMA antigen can be antibodies, minibodies and/or fragments thereof such as scFv. Some non-limiting embodiments of antigen binding constructs against PSMA are shown in FIGS. 5B-5E, 7C-7E, 21B-21E, 34A-34F, 35A-35C, 36A, 47 (SEQ ID NOs: 112 and 113), 48 (SEQ ID NO: 113), 49 (SEQ ID NO: 114), 50 (SEQ ID NO: 115), 51 (SEQ ID NO: 116), 52 (SEQ ID NO: 117), 53 (SEQ ID NO: 118). In some embodiments, antigen binding constructs that bind the CD3 antigen can be antibodies, minibodies and/or fragments thereof such as scFv. Some non-limiting embodiments of antigen binding constructs against CD3 are shown in FIGS. 33, 36D, 69, 65B, and 65C. In some embodiments, antigen binding constructs that bind the CD8 antigen can be antibodies, minibodies and/or fragments thereof such as scFv. Some non-limiting embodiments of antigen binding constructs against CD8 are shown in FIGS. 14B, 15B, 16B-16D, 20C-20G, 22B, 36B, 40 (SEQ ID NOs: 105 and 106), 41 (SEQ ID NO: 106), 42 (SEQ ID NO: 107), 43 (SEQ ID NO: 108), 44 (SEQ ID NO: 109), 45 (SEQ ID NO: 110), 46 (SEQ ID NO: 111), and 66.

Linker Options

In some embodiments, for individual antigen binding constructs, the heavy and light chain variable domains can associate in different ways. For this reason, the use of different linker lengths between the $V_H$ and $V_L$ domains allows for conformational flexibility and range-of-motion to ensure formation of the disulfide bonds.

In some embodiments, the two linker lengths can be somewhere between (and including) about 1 to 50 amino acids, for example, 2 to 15, 2 to 14, 3 to 13, 4 to 10, or 5 amino acids to 8 amino acids. In some embodiments, each linker within a pair for a minibody can be the same length. In some embodiments, each linker within the pair can be a different length. In some embodiments, any combination of linker length pairs can be used, as long as they allow and/or promote the desired combinations. In some embodiments, a modified amino acid can be used.

Table 0.2 provides minibody variants. Producing and testing the expression and binding of the variants allows for identification of a desired format for protein production for each new minibody.

In some embodiments, the linker is a GlySer linker. The GlySer linker can be a polypeptide that is rich in Gly and/or Ser residues. In some embodiments, at least about 40% of the amino acid residues of the GlySer linker are Gly, Ser, or a combination of Gly and Ser, for example at least about 40%, 50%, 60%, 70%, 80%, or 90%. In some embodiments, the GlySer linker is at least about 2 amino acids long, for example at least about 3, 4, 5, 6, 7, 8, 9, 10, 11, 12, 13, 14, 15, 16, 17, 18, 19, 20, 25, 30, 35, or 40 amino acids long. In some embodiments, the linker motif can be $(G_3)S_n$ or $(G_4)S_n$ (n can be any number of S's; and in some embodiments is 1 or 2). For example, a) GGGGS 5 aa, (SEQ ID NO: 66); b) GGGGSGGGGS 10 aa, (SEQ ID NO: 65); c) GGGGSGGGGSGGGGS 15 aa, (SEQ ID NO: 64); d) GSTSGGGSGGGS 12 aa, (SEQ ID NO: 63); or e) GSTSGGGSGGGSGGGGSS 18 aa (SEQ ID NO: 62). In some embodiments, the linker comprises at least one threonine.

Tables 0.1 and 0.2 depict various optional sequences that can be used in some embodiments of the scFv and/or minibodies. In some embodiments, the scFv can be any of those provided herein, but with any of the sequences provided in Table 0.1. In some embodiments, the minibody can be any of those provided herein, but with any of the sequences provided in a full row in Table 0.1. In some embodiments, any of the antigen binding constructs provided herein can include any of the hinge sequence subparts provided in Table 0.1.

A "minibody" as described herein, encompasses a homodimer, wherein each monomer is a single-chain variable fragment (scFv) linked to a human $C_H3$ domain by a hinge sequence. In some embodiments, the hinge sequence is a human IgG1 hinge sequence. In some embodiments, the hinge sequence is any one or more of the hinge sequences provided herein, such as any of those described herein and/or in Table 0.1 (including any subpart or combination of subparts thereof).

In some embodiments, the hinge sequence is an artificial hinge sequence. In some embodiments, the hinge sequence can be a natural or artificial IgG hinge, or subpart or combination of subparts thereof, from any one or more of the four classes of IgG hinges.

In some embodiments, the minibody sequence can include CDR and/or FR, and or variable region sequences that are similar a sequence described herein (for example, as found in the Figures or Table 0.2. In some embodiments, the minibody has a sequence (CDR, CDRs, full set of 6 CDRS, heavy chain variable region, light chain variable region, heavy and light chain variable regions, etc) that is at identical to a scFv of a minibody described herein.

In some embodiments, the polypeptide of the monomer includes sequences as shown in Table 0.2. In some embodiments, the polypeptide of the monomer includes a sequence with least about 80% identity, for example at least about 80%, 85%, 86%, 87%, 88%, 89%, 90%, 91%, 92%, 93%, 94%, 95%, 96%, 97%, 98%, or 99% identity to the sequence of the $V_L V_H$ minibody monomer shown in Table 0.2.

In some embodiments, the minibody has a variable chain region (heavy, light or heavy and light chain variable region) that is at least about 80% identical to a heavy chain sequence in SEQ ID NO: 14, 16, 18, 20, 68, 99, 102 or 104 (and/or the relevant sequences in FIG. 65B or 65C) and/or a light chain sequence in SEQ ID NO: 13, 15, 17, 19, 67, 100, 101 or 103 (and/or the sequences in FIG. 65B or 65C), for example at least about 80%, 85%, 86%, 87%, 88%, 89%, 90%, 91%, 92%, 93, 94, 95%, 96%, 97%, 98%, or 99% identity.

The scFv can have a $V_H V_L$ or a $V_L V_H$ orientation. In some embodiments, the $V_H$ and $V_L$ are linked to each other by an amino acid linker sequence. The amino acid linker can be a linker as described herein. In some embodiments, the linker is Gly-Ser-rich and approximately 15-20 amino acids in length. In another embodiment, the linker is GlySer rich and is 18 amino acids in length. In some embodiments, the linker length varies between (and including) about 1 to 50 amino acids, for example, 2 to 30, 3 to 20, 4 to 15, or 5 amino acids to 8 amino acids. In some embodiments, the linker is GSTSGGGSGGGSGGGSS (SEQ ID NO. 62). In some embodiments, the minibody scFv has a sequence that is at least about 80% identical to a scFv described herein, for example at least about 80%, 85%, 86%, 87%, 88%, 89%, 90%, 91%, 92%, 93, 94, 95%, 96%, 97%, 98%, or 99% identity. The scFv can have a $V_H V_L$ or a $V_L V_H$ orientation.

In some embodiments, each monomer of the minibody includes the following elements, from N-terminus to C-terminus: (a) an scFv sequence that includes a $V_H$ domain linked to a $V_L$ domain and that binds to the target molecule, (b) a hinge domain (e.g., an upper and core hinge region combined with a lower hinge and/or extension region), and (c) a human IgG $C_H 3$ sequence. In some embodiments, each monomer of the minibody includes a IgG1, IgG2, an IgG3, or an IgG4 $C_H 3$ domain. In some embodiments, the minibody is encoded by a nucleic acid can be expressed by a cell, a cell line or other suitable expression system as described herein. Thus, a signal sequence can be fused to the N-terminus of the scFv to enable secretion of the minibody when expressed in the cell or cell line. In some embodiments, other signal sequences such as human serum albumin (SEQ ID NO: 70) can be used. In some embodiments, different signal sequences can improve secretion depending on context and cell line used for expression. In some embodiments, a human immunoglobulin kappa light chain signal sequence (SEQ ID NO: 69) can be employed and/or included in a nucleic acid encoding for an amino acid sequence provided herein. In some embodiments, a single sequence can be selected from the list shown in Table 7 depending on the context and cell line used for expression.

TABLE 7

Signal peptide sequences

| Signal peptide source | Signal peptide sequence |
| --- | --- |
| Mouse Ig kappa light chain | METDTLLLWVLLLWVPGSTG (SEQ ID NO: 69) |
| Human Serum Albumin (HSA) | MKWVTFISLLFLFSSAYS (SEQ ID NO: 70) |
| Human Azurocidin (HAZ) | MTRLTVLALLAGLLASSRA (SEQ ID NO: 71) |
| Prolactin | MDSKGSSQKGSRLLLLLWSNLLLCQGWS (SEQ ID NO: 72) |
| LCMV-GPC | MGQIVTMFEALPHIIDEVININVIIVLIIITSIKAVYNFATCGILALVSFLFLAGRSCG (SEQ ID NO: 73) |
| MMTV-Rem | MPNHQSGSPTGSSDLLLSGKKQRPHLALRRKRRREMRKINRKVRRMNLAPIKEKT AWQHLQALISEAEEVLKTSQTPQNSLTLFLALLSVLGPPPVTG (SEQ ID NO: 74) |
| Mammalia | Accessible on the world wide web at signalpeptide.de/index.php?m=listspdb_mammalia** |
| Drosophila | Accessible on the world wide web at signalpeptide.de/index.php?m=listspdb_drosophila** |
| Bacteria | Accessible on the world wide web at signalpeptide.de/index.php?=m=listspdb_bacteria** |
| Viruses | Accessible on the world wide web at signalpeptide.de/index.php?m=listspdb_viruses** |

**Signal Peptides referred to at the world wide web locations referenced above are described in the Signal Peptide Database, which can be accessed on the world wide web at signalpeptide.de and via the hyperlinks above, is hereby incorporated by reference in its entirety.

In some embodiments, a chimeric minibody that binds to the target molecule is provided. In some embodiments, the chimeric minibody includes a monomer in the $V_L V_H$ format, and includes the sequence of a light chain variable region that includes SEQ ID NO: 13, 15, 17, 19, 67, 100, 101 or 103 (and/or the relevant sequences in FIG. 65B or 65C) and the sequence of a heavy chain variable region that includes SEQ ID NO: 14, 16, 18, 20, 68, 99, 102 or 104 (and/or the sequences in FIG. 65B or 65C) or a monomer as shown in Table 0.2, or a sequence having at least about 80% identity thereto, for example at least about 80%, 85%, 90%, 95%, 96%, 97%, 98%, or 99%% identity thereto. In some embodiments, the chimeric minibody includes a monomer in the $V_H V_L$ format, and includes the sequence of a light chain variable region that includes SEQ ID NO: 13, 15, 17, 19, 67, 100, 101 or 103 (and/or the relevant sequences in FIG. 65B or 65C) and the sequence of a heavy chain variable region that includes SEQ ID NO: 14, 16, 18, 20, 68, 99, 102 or 104 (and/or the relevant sequences in FIG. 65B or 65C) or a monomer as shown in Table 0.2, or a sequence having at least about 80% identity thereto, for example at least about 80%, 85%, 90%, 95%, 96%, 97%, 98%, or 99%% identity thereto. In some embodiments, the minibody comprises one or more of the CDRs outlined in FIG. 41, 48, 55, 61, 65B, or 65C. In some embodiments, the minibody comprises one or more of the variable regions in the FIG. 36A, 36B, 36C, 36D, 36E, 66, 67, 68, 69, 65B, or 65C or Table 0.2.

In some embodiments, the minibody includes the heavy chain variable region as outlined in the FIG. 36A, 36B, 36C, 36D, 36E, 66, 68, 69, 65B, or 65C. In some embodiments, the minibody includes the light chain variable region as outlined in the FIG. 36A, 36B, 36C, 36D, 36E, 67, 69, 65B, or 65C.

In some embodiments, the minibody includes one or more of the CDRs provided in the CDRs in FIG. 41, 48, 55, 61, 65B, or 65C.

Nucleic Acids

In some embodiments, the polypeptides of the antigen binding constructs can be encoded by nucleic acids and expressed in vivo or in vitro, or these peptide can be synthesized chemically. Thus, in some embodiments, a nucleic acid encoding an antigen binding construct is provided. In some embodiments, the nucleic acid encodes one part or monomer of a minibody or other antigen binding construct. In some embodiments, the nucleic acid encodes two or more monomers, for example, at least 2 monomers. Nucleic acids encoding multiple monomers can include nucleic acid cleavage sites between at least two monomers, can encode transcription or translation start site between two or more monomers, and/or can encode proteolytic target sites between two or more monomers.

In some embodiments, an expression vector contains a nucleic acid encoding an antigen binding construct as disclosed herein. In some embodiments, the expression vector includes pcDNA3.1™/myc-His (−) Version A vector for mammalian expression (Invitrogen, Inc.) or a variant thereof. The pcDNA3.1 expression vector features a CMV promoter for mammalian expression and both mammalian (Neomycin) and bacterial (Ampicillin) selection markers. In some embodiments, the expression vector includes a plasmid. In some embodiments, the vector includes a viral vector, for example a retroviral or adenoviral vector. In embodiments, the vector includes a cosmid, YAC, or BAC.

In some embodiments, the nucleotide sequence encoding at least one of the minibody monomers comprises at least one of SEQ ID NOs: provided herein, including those disclosed herein for binding to CD3, CD8, 5T4, PSMA, and PSCA, or a sequence having at least about 80% identity, for example about 80%, 85%, 86%, 87%, 88%, 89%, 90%, 91%, 92%, 93, 94, 95%, 96%, 97%, 98%, 99%, or greater identity thereto.

Cell Lines

In some embodiments, a cell line is provided that expresses at least one of the antigen binding constructs described herein (which can include at least a subpart of a hinge provided herein). In some embodiments, a mammalian cell line (for example, CHO-K1 cell line) is an expression system to produce the minibodies, scFv, or other antibodies as described herein. In some embodiments, the minibodies, scFv, and other antibodies or antibody fragments described herein are non-glycosylated, and a mammalian expression system is not required, as such post-translational modifications are not needed. Thus, in some embodiments, one or more of a wide variety of mammalian or non-mammalian expression systems are used to produce the antigen binding constructs disclosed herein (for example, minibodies) including, but not limited to mammalian expression systems (for example, CHO-K1 cells), bacterial expression systems (for example, *E. coli, B. subtilis*) yeast expression systems (for example, *Pichia, S. cerevisiae*) or any other known expression system. Other systems can include insect cells and/or plant cells.

Antigen Binding Construct Modifications

In some embodiments, the antigen binding construct includes at least one modification. Exemplary modifications include, but are not limited to, antigen binding constructs that have been modified by glycosylation, acetylation, pegylation, phosphorylation, amidation, derivatization by known protecting/blocking groups, proteolytic cleavage, and linkage to a cellular ligand or other protein. Any of numerous chemical modifications may be carried out by known techniques, including, but not limited to, specific chemical cleavage, acetylation, and metabolic synthesis of tunicamycin. In some embodiments, the derivative can contain one or more non-natural amino acids.

In some embodiments, the antigen binding construct is conjugated to another substance to form an anti-target conjugate. The conjugates described herein can be prepared by known methods of linking antigen binding constructs with lipids, carbohydrates, protein or other atoms and molecules. In some embodiments, the conjugate is formed by site-specific conjugation using a suitable linkage or bond. Site-specific conjugation is more likely to preserve the binding activity of an antigen binding construct. The substance may be conjugate or attached at the hinge region of a reduced antigen binding construct via thioether bond formation. In some embodiments, tyrosine conjugation can be employed. Other linkages or bonds used to form the conjugate can include, but are not limited to, a covalent bond, a non-covalent bond, a disulfide linkage, a hydrazone linkage, an ester linkage, an amido linkage, and amino linkage, an imino linkage, a thiosemicarbazone linkage, a semicarbazone linkage, an oxime linkage and a carbon-carbon linkage. In some embodiments, no cysteine or other linking aspect, need be included in the antigen binding construct.

Detectable Markers

In some embodiments, a modified antigen binding construct is conjugated to a detectable marker. As used herein, a "detectable marker" includes an atom, molecule, or compound that is useful in diagnosing, detecting or visualizing a location and/or quantity of a target molecule, cell, tissue, organ and the like. Detectable markers that can be used in accordance with the embodiments herein include, but are not limited to, radioactive substances (for example, radioisotopes, radionuclides, radiolabels or radiotracers), dyes, contrast agents, fluorescent compounds or molecules, bioluminescent compounds or molecules, enzymes and enhancing agents (for example, paramagnetic ions). In addition, some nanoparticles, for example quantum dots and metal nanoparticles (described below) can be suitable for use as a detection agent. In some embodiments, the detectable marker is Indo-Cyanine Green (ICG), Zirconium-89, IR800, and/or another near infrared dye.

Exemplary radioactive substances that can be used as detectable markers in accordance with the embodiments herein include, but are not limited to, $^{18}$F, $^{18}$F-FAC, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Sc, $^{77}$As, $^{86}$Y, $^{90}$Y, $^{89}$Sr, $^{89}$Zr, $^{94}$Tc, $^{94}$Tc, $^{99}$mTc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Exemplary paramagnetic ions substances that can be used as detectable markers include, but are not limited to ions of transition and lanthanide metals (for example metals having atomic numbers of 6 to 9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the detectable marker is a radioactive metal or paramagnetic ion, in some embodiments, the marker can be reacted with a reagent having a long tail with one or more chelating groups attached to the long tail for binding these ions. In some embodiments the reagent may carry a reactive group designed to covalently tether the antibody fragment chains. The long tail can be a polymer such as a polylysine, polysaccharide, polyethylene glycol (PEG) or other derivatized or derivatizable chain having pendant groups to which may be bound to a chelating group for binding the ions. Examples of chelating groups that may be used according to the embodiments herein include, but are not limited to, ethylenediaminetetraacetic acid (EDTA), diethylenetriaminepentaacetic acid (DTPA), DOTA, NOTA, NODAGA, NETA, deferoxamine (Df, which may also be referred to as DFO), porphyrins, polyamines, crown ethers, bis-thiosemicarbazones, polyoximes, and like groups. The same chelates, when complexed with non-radioactive metals, such as manganese, iron and gadolinium are useful for MRI, when used along with the antigen binding constructs and carriers described herein. Macrocyclic chelates such as NOTA, NODAGA, DOTA, and TETA are of use with a variety of metals and radiometals including, but not limited to, radionuclides of gallium, yttrium and copper, respectively. Other ring-type chelates such as macrocyclic polyethers, which are of interest for stably binding radionuclides, such as Radium-223 for RAIT may be used. In certain embodiments, chelating moieties may be used to attach a PET imaging agent, such as an Aluminum-$^{18}$F or Zirconium-89 complex, to a targeting molecule for use in PET analysis.

Exemplary contrast agents that can be used as detectable markers in accordance with the embodiments of the disclosure include, but are not limited to, barium, diatrizoate, ethiodized oil, gallium citrate, iocarmic acid, iocetamic acid, iodamide, iodipamide, iodoxamic acid, iogulamide, iohexyl, iopamidol, iopanoic acid, iprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as detectable markers in accordance with the embodiments of the disclosure include, but are not limited to, fluorescein, fluorescein isothiocyanate (FITC), OREGON GREEN™, rhodamine, Texas red, tetrarhodimine isothiocynate (TRITC), Cy3, Cy5, and the like, fluorescent markers (for example, green fluorescent protein (GFP), phycoerythrin, and the like), autoquenched fluorescent compounds that are activated by tumor-associated proteases, enzymes (for example, luciferase, horseradish peroxidase, alkaline phosphatase, and the like), nanoparticles, biotin, digoxigenin or combination thereof.

Enzymes that can be used as detectable markers in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

In some embodiments, the antigen binding construct is conjugated to a nanoparticle. The term "nanoparticle" refers to a microscopic particle whose size is measured in nanometers, for example, a particle with at least one dimension less than about 100 nm. Nanoparticles can be used as detectable substances because they are small enough to scatter visible light rather than absorb it. For example, gold nanoparticles possess significant visible light extinction properties and appear deep red to black in solution. As a result, compositions comprising antigen binding constructs conjugated to nanoparticles can be used for the in vivo imaging of T-cells in a subject. At the small end of the size range, nanoparticles are often referred to as clusters. Metal, dielectric, and semiconductor nanoparticles have been formed, as well as hybrid structures (for example core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to an antigen binding construct, can be used as imaging agents for the in vivo detection of T-cells as described herein.

In some embodiments, having a stable hinge will impart stability to the targeting agent. In some embodiments, this results in better biodistribution, higher sensitivity, and/or reduced renal clearance. Therefore, these constructs can be more applicable for higher degree of specific activity. In some embodiments, this imparts substantially improved sensitivity without high dose to the kidney, which is a radiosensitive organ. In some embodiments, these constructs are more suitable for RIT for the same reason—low renal uptake. In some embodiments, a site-specific conjugation to cysteines can now be employed because chemical reduction under mild condition will break 1 or 2 disulfide bonds to use these as a handle but keep the remaining disulfides intact. In some embodiments, this will preserve the integrity of the minibody conjugate.

Therapeutic Agents and Compositions

In some embodiments, the pharmaceutical composition can also include a pharmaceutically acceptable carrier. A pharmaceutically acceptable carrier can be a pharmaceutically acceptable material, composition, or vehicle that is involved in carrying or transporting a compound of interest from one tissue, organ, or portion of the body to another tissue, organ, or portion of the body. For example, the carrier can be a liquid or solid filler, diluent, excipient, solvent, or encapsulating material, or some combination thereof. Each component of the carrier is "pharmaceutically acceptable" in that it is compatible with the other ingredients of the formulation. It is also suitable for contact with any tissue, organ, or portion of the body that it can encounter, meaning that, ideally it will not carry a significant risk of toxicity, irritation, allergic response, immunogenicity, or any other complication that excessively outweighs its therapeutic benefits.

The pharmaceutical compositions described herein can be administered by any suitable route of administration. A route of administration can refer to any administration pathway known in the art, including but not limited to aerosol, enteral, nasal, ophthalmic, oral, parenteral, rectal, transdermal (e.g., topical cream or ointment, patch), or vaginal. "Transdermal" administration can be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the antigen binding construct can be delivered intraoperatively as a local administration during an intervention or resection.

In some embodiments, an antigen binding construct is conjugated to a therapeutic agent. A "therapeutic agent" as used herein is an atom, molecule, or compound that is useful in the treatment of a disorder related to a target molecule. Examples of therapeutic agents include, but are not limited to, drugs, chemotherapeutic agents, therapeutic antibodies and antibody fragments, toxins, radioisotopes, enzymes (for example, enzymes to cleave prodrugs to a cytotoxic agent at the site of the antigen binding construct binding), nucleases, hormones, immunomodulators, antisense oligonucleotides, chelators, boron compounds, photoactive agents and dyes, and nanoparticles. Examples of disorders include those related to one or more target molecules. In some embodiments, the target molecules can be one or more of: CD8, CD3, PSMA, PSCA, and 5T4.

Chemotherapeutic agents are often cytotoxic or cytostatic in nature and may include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as detectable markers in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Toxins that may be used in accordance with the embodiments of the disclosure include, but are not limited to, Auristatin E, Auristatin F, Dolastatin 10, Dolastatin 15, combretastatin and their analogs, maytansinoid, calicheamicin, alpha-amanitin, pyrrolobenzodiazepine dimers, epothilones, duocarmycin and their analogs, tubulysin D, basillistatins, ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

In some embodiments nanoparticles are used in therapeutic applications as drug carriers that, when conjugated to an antigen binding construct, deliver chemotherapeutic agents, hormonal therapeutic agents, radiotherapeutic agents, toxins, or any other cytotoxic or anti-cancer agent known in the art to cancerous cells that overexpress the target on the cell surface.

Any of the antigen binding constructs described herein may be further conjugated with one or more additional therapeutic agents, detectable markers, nanoparticles, carriers or a combination thereof. For example, an antigen binding construct may be radiolabeled with Iodine-131 and conjugated to a lipid carrier, such that the anti-target molecule-lipid conjugate forms a micelle. The micelle can incorporate one or more therapeutic or detectable markers. Alternatively, in addition to the carrier, the antigen binding construct may be radiolabeled with Iodine-131 I (for example, at a tyrosine residue) and conjugated to a drug (for example, at the epsilon amino group of a lysine residue), and the carrier may incorporate an additional therapeutic or detectable marker.

In some embodiments, antigen binding constructs are conjugated to a therapeutic agent. While these antigen binding constructs can have a shorter circulation half-life compared to a full-length antibody, in some embodiments, these formats can exhibit improved tumor penetration based on their smaller size and be therapeutically effective when appropriately armed with a cytotoxic drug or radioisotope. In some embodiments, an antibody drug-conjugate approach can be employed. In some embodiments, a therapeutic approach includes radioimmunotherapy by attaching an appropriate radiolabel such as, Iodine-131, a beta-emitter, such as, Yttrium-90, Lutetium-177, Copper-67, Astatine-211, Lead-212/Bismuth-212, Actinium-225/Bismuth-213, and Thorium, which can deliver cell damage and death to a target tissue. In some embodiments, treatment with these fragments armed with a cytotoxic drug or radionuclide result in less nonspecific toxicity as they will be cleared from the body more rapidly.

In some embodiments, the antigen binding construct can be connected to a therapeutic agent to a disorder associated with the expression of the target molecule.

In some embodiments, target molecule antigen binding constructs are used as a stand-alone medicament (e.g. antigen binding construct in the absence of therapeutic agent) in the treatment of a disorder associated with the expression of the target molecule.

In some embodiments, a pharmaceutical composition is provided comprising the amino acid hinge region of any of the embodiments provided herein. In some embodiments, less than 30% aggregation (or high molecular weight construct) of a minibody is present in the composition, for example, less than 20, 10, 5, or 1% aggregation.

In some embodiments, a pharmaceutical composition comprising the amino acid hinge region of any of the constructs provided herein is provided. In some embodiments, an amount of 1 micrograms to 100 mg can be used. In some embodiments, such a composition can have a reduced level of aggregation compared to constructs without the noted hinge arrangements.

In some embodiments, the disorder is one associated with 5T4, CD8, CD3, PSCA, or PSMA. However, the various hinges disclosed herein can be applied to any target molecule or antigen binding construct that includes a hinge.

Kits

In some embodiments, kits are provided. In some embodiments, the kit includes an antigen binding construct as described herein. In some embodiments, the kit includes a nucleic acid that encodes an antigen binding construct as described herein. In some embodiments, the kit includes a cell line that produces an antigen binding construct as described herein. In some embodiments, the kit includes a detectable marker as described herein. In some embodiments, the kit includes a therapeutic agent as described herein. In some embodiments, the kit includes buffers. In some embodiments, the kit includes positive controls, for example target specific cells, or fragments thereof. In some embodiments, the kit includes negative controls, for example a surface or solution that is substantially free of the target. In some embodiments, the kit includes packaging. In some embodiments, the kit includes instructions.

Methods of Detecting the Presence or Absence of the Target Molecule

Antigen binding constructs can be used to detect the presence or absence of the target molecule in vivo and/or in vitro. Accordingly, some embodiments include methods of detecting the presence or absence of the target. The method can include applying an antigen binding construct to a sample. The method can include detecting a binding or an absence of binding of the antigen binding construct to the target molecule. In some embodiments, any target molecule could be detected through the options provided herein. In some embodiments, the target molecule to be detected is one or more of 5T4, CD8, CD3, PSCA, or PSMA. In some embodiments, the target molecule is detected using one or more of the minibody arrangements provided in the figures and/or in the Tables, such as Table 0.2 (or at least employing a hinge arrangement as outlined in Table 0.1).

Methods of detecting the presence or absence of the target molecule are provided herein. It will be appreciated that the processes below can be performed in any sequence, and/or can be optionally repeated and/or eliminated, and that additional steps can optionally be added to the method. In some embodiments, an antigen binding construct as described herein can be applied to a sample. In some embodiments, an optional wash can be performed. Optionally, a secondary antigen binding construct can be applied to the sample. An optional wash can be performed. In some embodiments, a binding or absence of binding of the antigen binding construct to the target molecule can be detected.

In some embodiments, an antigen binding construct as described herein is applied to a sample in vivo. The antigen binding construct can be administered to a subject. In some embodiments, the subject is a human. In some embodiments, the subject is a non-human mammal, for example a rat, mouse, guinea pig, hamster, rabbit, dog, cat, cow, horse, goat, sheep, donkey, pig, monkey, or ape. In some embodiments, the antigen binding construct is infused into the subject. In some embodiments, the infusion is intravenous. In some embodiments, the infusion is intraperitoneal. In some embodiments, the antigen binding construct is applied topically or locally (as in the case of an interventional or intraoperative application) to the subject. In some embodiments, a capsule containing the antigen binding construct is applied to the subject, for example orally or intraperitoneally. In some embodiments, the antigen binding construct is selected to reduce the risk of an immunogenic response by subject. For example, for a human subject, the antigen binding construct can be humanized as described herein. In some embodiments, following in vivo application of the antigen binding construct, the sample, or a portion of the sample is removed from the host. In some embodiments, the antigen binding construct is applied in vivo, is incubated in vivo for a period of time as described herein, and a sample is removed for analysis in vitro, for example in vitro detection of antigen binding construct bound to the target molecule or the absence thereof as described herein.

In some embodiments, the antigen binding construct is applied to a sample in vitro. In some embodiments, the sample is freshly harvested from a subject, for example a biopsy. In some embodiments, the sample is incubated following harvesting from a subject. In some embodiments, the sample is fixed. In some embodiments the sample includes a whole organ and/or tissue. In some embodiments, the sample includes one or more whole cells. In some embodiments the sample is from cell extracts, for example lysates. In some embodiments, antigen binding construct in solution is added to a solution in the sample. In some embodiments, antigen binding construct in solution is added to a sample that does not contain a solution, for example a lyophilized sample, thus reconstituting the sample. In some embodiments, lyophilized antigen binding construct is added to a sample that contains solution, thus reconstituting the antigen binding construct.

In some embodiments, the antigen binding construct is optionally incubated with the sample. The antigen binding construct can be incubated for a period of no more than about 14 days, for example no more than about 14 days, 13, 12, 11, 10, 9, 8, 7, 6, 5, 4, 3, 2, or 1 day, or no more than about 23 hours, for example no more than about 23 hours, 22, 21, 20, 19, 18, 17, 16, 15, 14, 13, 12, 11, 10, 9, 8, 7, 6, 5, 4, 3, 2, 1, 0.75, 0.5, 0.25, or 0.1 hour, including ranges between any two of the listed values. In some embodiments, the incubation is within a subject to which the antigen binding construct was administered. In some embodiments, the incubation is within an incubator. In some embodiments, the incubator is maintained at a fixed temperature, for example about 21° C., room temperature, 25° C., 29° C., 34° C., 37° C., or 40° C.

In some embodiments, the antigen binding construct that is not bound to the target is optionally removed from the sample. In some embodiments, the sample is washed. Washing a sample can include removing the solution that contains unbound antigen binding construct, and adding solution that does not contain antigen binding construct, for example buffer solution. In some embodiments, an in vitro sample is washed, for example by aspirating, pipetting, pumping, or draining solution that contains unbound antigen binding construct, and adding solution that does not contain antigen binding construct. In some embodiments, an in vivo sample is washed, for example by administering to the subject solution that does not contain antigen binding construct, or by washing a site of topical antigen binding construct administration. In some embodiments, the wash is performed at least two times, for example at least 2, 3, 4, 5, 6, 7, 8, 9, 10, 15, or 20 times. In some embodiments, following the wash or washes, at least about 50% of unbound antibody is removed from the sample, for example at least about 50%, 60%, 70%, 75%, 80%, 85%, 90%, 95%, 97%, 98%, 99% or greater.

In some embodiments, unbound antigen binding construct is eliminated from the sample. Following application of the antigen binding construct to the sample, antigen binding construct bound to the target reaches an equilibrium with antigen binding construct unbound to the target, so that at some time after application of the antigen binding construct, the amount of antigen binding construct bound to the target does not substantially increase. After this time, at least part of the quantity of the antigen binding construct that is unbound to the target can be eliminated. In some embodiments, unbound antigen binding construct is eliminated by metabolic or other bodily processes of the subject to whom the antibody or fragment was delivered. In some embodiments, unbound antigen binding construct is eliminated by the addition of an agent that destroys or destabilized the unbound antigen binding construct, for example a protease or a neutralizing antibody. In some embodiments, 1 day after application of the antigen binding construct, at least about 30% of the antigen binding construct that was applied has been eliminated, for example at least about 30%, 40%, 60%, 70%, 75%, 80%, 85%, 90%, 95%, 97%, 98%, 99%, or 99.9%. In some embodiments, 2 days after application of the antigen binding construct, at least about 40% of the antigen binding construct that was applied has been eliminated, for example at least about 40%, 50%, 60%, 70%, 75%, 80%, 85%, 90%, 95%, 97%, 98%, 99%, or 99.9%.

In some embodiments, the presence or absence of the target molecule is detected. The presence or absence of the target can be detected based on the presence or absence of the antigen binding construct in the sample. After removal and/or elimination of the antigen binding construct from the sample, for example by washing and/or metabolic elimination, remaining antigen binding construct in the sample can indicate the presence of the target, while an absence of the antigen binding construct in the sample can indicate the absence of the target.

In some embodiments, the antigen binding construct includes a detectable marker as described herein. Thus, the presence of the antigen binding construct can be inferred by detecting the detectable marker.

In some embodiments, a secondary antigen binding construct is used to detect the antigen binding construct. The secondary antigen binding construct can bind specifically to the antigen binding construct. For example, the secondary antigen binding construct can include a polyclonal or monoclonal antibody, diabody, minibody, etc. against the host type of the antibody, or against the antigen binding construct itself. The secondary antigen binding construct can be conjugated to a detectable marker as described herein. The secondary antigen binding construct can be applied to the sample. In some embodiments, the secondary antigen binding construct is applied to the sample in substantially the same manner as the antigen binding construct. For example, if the antigen binding construct was infused into a subject, the secondary antigen binding construct can also be infused into the subject.

In some embodiments, binding or the absence of binding of the antigen binding construct is detected via at least one of: positron emission tomography (PET), single-photon emission computed tomography (SPECT), magnetic resonance imaging (NMR), or detection of fluorescence emissions. PET can include, but is not limited to small animal PET imaging. In some embodiments, binding of the absence of binding of the antigen binding construct is detected via two or more forms of imaging. In some embodiments, detection can be via near-infrared (NIR) and/or Cerenkov.

In some embodiments, any combination of imaging modalities is possible, including, by way of example, PET+NIR, PET+SPECT etc.

Methods of Targeting a Therapeutic Agent to a Cell

Antigen binding constructs can be used to target a therapeutic molecule, for example a cytotoxin, to a target positive cell, such as a cell expressing the target molecule. Thus, some embodiments include methods of targeting a therapeutic agent to a target positive cell. The method can include administering an antigen binding construct as described herein to a subject. The subject can be a subject in need, for example a subject in need of elimination or neutralization of at least some target positive cells. In some embodiments, the antigen binding construct includes at least on therapeutic agent as described herein. In some embodiments, the therapeutic can be directly conjugated to the antigen binding construct via a covalent bond, such as a disulfide bond. In some embodiments, the subject can benefit from the localization of a target molecule positive cell to another cell or agent.

Optionally, before and/or after administration of the antigen binding construct that includes at least one therapeutic agent, the number and/or localization of the target positive cells of the patient is determined. For example, determining the number and/or localization of target positive cells prior to administration can indicate whether the patient is likely to benefit from neutralization and/or elimination of the target positive cells. Determining the number and/or localization of the target positive cells after administration can indicate whether the target positive cells were eliminated in the patient.

In some embodiments, the antigen binding construct can be used as a therapeutic agent as stand-alone construct (for example, without a toxin conjugated thereto). While the fragments have a shorter half-life compared to the intact antibody which would be less optimal for therapy, these formats can exhibit improved tumor penetration based on their smaller size and be therapeutically effective when appropriately armed with a cytotoxic drug or radioisotope.

In some embodiments, another therapeutic approach is radioimmunotherapy via attaching an appropriate radiolabel such as the Iodine-131, a beta-emitter, such as, Yttrium-90, Lutetium-177, Copper-67, Astatine-211, Lead-212/Bismuth-212, Actinium-225/Bismuth-213, and Thorium, which can deliver cell damage and death.

In some embodiments, the antigen binding construct is used to target cells expressing the target molecule. In some embodiments, the therapeutic agent is appropriate for one or more of a disorder associated with at least one of the following: CD8, CD3, PSMA, PSCA, or 5T4, for example. In some embodiments, the therapeutic agent is appropriate for treating one or more of the following disorders:

Specific Targets/Constructs

In some embodiments, any of the compositions, methods (for example, methods of treatment, methods of making, methods of detection, etc.), kits, agents, antigen binding construct modifications, cell lines, nucleic acids, etc. provided herein can be used for any target molecule. In some embodiments, the target molecule can be one associated with cancer immunotherapy. In some embodiments, the target molecule can be one or more of CD8, CD3, 5T4, PSCA, or PSMA, including variants thereof.

In some embodiments, one or more of the antigen binding constructs, such as the minibody, can be used for the treatment of a subject having a target molecule associated disorder. In some embodiments, the target molecule can be any target molecule for which one has an antigen binding construct that will bind. In some embodiments, the target molecule can be at least one of the following: CD8, CD3, PSMA, PSCA, or 5T4, and thus, the disorder to be treated can be one relating to at least one of the following: CD8, CD3, PSMA, PSCA, or 5T4. In some embodiments, one or more of the antigen binding constructs, such as the minibody, can be used for the diagnostic of a subject as to whether or not they have a target molecule associated disorder.

As used herein, the term "subject" refers to any animal (e.g., a mammal), including but not limited to humans, non-human primates, rodents, dogs, pigs, and the like.

Each of the sections below outlines various embodiments for some of the various antigen binding constructs provided herein. All of these embodiments are provided as various forms of antigen binding constructs, including minibodies and scFvs. The below sections are explicitly provided for target specific embodiments; however, they are contemplated as aspects that are combinable with any of the appropriate options provided elsewhere in the present specification. Thus, the present embodiments are not exclusive of the other embodiments, but instead are options that can be combined with any of the other embodiments provided herein. For example, any of the hinge arrangements provided herein can be used in any one or more of the noted constructs and/or methods. Similarly, the various embodiments outlined below in regard to any one of the five targets of CD8, CD3, PSMA, PSCA, or 5T4 can also be swapped with the other noted targets. Thus, while the PSCA discussion is directed to PSCA, it will be understood that the embodiments can also be applied to CD8, CD3, PSMA, or 5T4 constructs. Similarly, disclosures to CD8 can also be applied to CD3, PSMA, PSCA, or 5T4, for example.

In some embodiments, chemotherapeutic agents can be used with any one or more of the CD8, CD3, PSMA, PSCA, or 5T4 constructs provided herein. Chemotherapeutic agents are often cytotoxic or cytostatic in nature and can include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that can be used as diagnostic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, *bacillus* calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

In some embodiments, any one or more of the constructs, for example, CD8, CD3, PSMA, PSCA, or 5T4 antigen binding constructs, can be linked via one or more of the cysteine in the hinge to chelators, drug, or any of the other components described herein.

PSCA-IAB1M

Prostate stem cell antigen (PSCA) is a cell surface glycoprotein expressed in normal human prostate and bladder and is over-expressed in prostate cancers (40% of primary tumors and 60-100% of lymph node and bone marrow metastases). It is also highly expressed in transitional carcinomas of the bladder and pancreatic carcinoma. An example of PSCA protein is shown with SEQ ID NO: 132. IG8, an anti-PSCA mouse monoclonal antibody specific for PSCA demonstrated anti-tumor targeting activity in vivo (Gu, Z. et al., "Anti-prostate stem cell antigen monoclonal antibody 1G8 induces cell death in vitro and inhibits tumor growth in vivo via a Fc-independent mechanism," Cancer Res., Vol. 65, No. 20, pp. 9495-9500, 2005). This antibody was humanized by grafting on a human framework (Trastuzumab) and named 2B3 (Olafsen, T. et al., "Targeting, imaging, and therapy using a humanized antiprostate stem cell antigen (PSCA) antibody," Immunotherapy, Vol. 30, No. 4, pp. 396-405, 2007).

In some embodiments, embodiments involving antigen binding constructs to PSCA can provide agents that have appropriate pharmacodynamics properties to target and image tumors that express PSCA. There is a value in the field for effective agents to image cancers with sensitivity and specificity, particularly early stage tumors or ones with early metastasis not imagable by traditional means. As PSCA is highly expressed by most prostate, bladder and pancreatic tumors, it is a valuable target in the detection, diagnosis, prognosis, and treatment of these cancers. Some embodiments provided herein provide constructs with characteristics for tumor imaging and targeting. They can also be used for tumor targeting of gene therapy, radioactivity therapy, and can have therapeutic utility by themselves.

Provided herein are engineered antigen binding constructs that recognize a novel cell surface marker in prostate and other cancers with high affinity. These genetically engineered antigen binding constructs can be tailored specifically for in vivo use for targeting and detection. PSCA is highly expressed by most prostate, bladder and pancreatic tumors and is a promising target. Embodiments provided herein describe an innovative molecule with optimal characteristics for tumor imaging. It can also be useful for tumor targeting of gene therapy, radioactivity or can have therapeutic utility by itself.

In some embodiments, the PSCA targeted by the anti-PSCA antibody is human PSCA. In some embodiments, the immunoconjugate can be used for targeting the effector moiety to a PSCA-positive cell, particularly cells, which overexpress the PCSA protein. In some embodiments, the PSCA targeted by the anti-PSCA minibody is human PSCA.

In some embodiments, the constructs provided herein can provide agents that have appropriate pharmacodynamics properties to target and image tumors that express PSCA. In some embodiments, the minibody provides an effective agent to image cancers with sensitivity and specificity, particularly early stage tumors or ones with early metastasis not imagable by traditional means.

In some embodiments, antigen binding constructs that bind the PSCA antigen can be antibodies, minibodies and/or other fragments of antibodies such as scFv. Some non-limiting embodiments of antigen binding constructs against PSCA are shown in FIGS. 29B-29D, 36E, 60 (SEQ ID NOs: 125 and 126), 61 (SEQ ID NO: 126), 62 (SEQ ID NO: 127), 63 (SEQ ID NO: 128), 64 (SEQ ID NO: 129), and 65A (SEQ ID NO: 130).

In some embodiments, the construct allows for imaging of cancer, in early diagnosis or diagnosis of metastatic disease. In particular, there is value in better agents for imaging prostate cancer for detection and staging. PSCA antigen binding construct imaging will be very useful for imaging bone metastases and assessing response to treatment. In some embodiments, a method of the detection of pancreatic cancer is provided. In some embodiments, a high-affinity, highly specific engineered minibody is tailored for in vivo targeting and detection of PSCA in prostate cancer, bladder cancer, and pancreatic cancer patients. In some embodiments, a "PSCA dependent disorder" can include a prostate tumor, a prostate cancer, a bladder tumor, a transitional carcinoma of the urinary bladder, a pancreatic tumor, a pancreatic carcinoma, any tumor associated with PSCA expression, any cancer associated with PSCA expression, or any disorder associated with PSCA expression.

In some embodiments, a high affinity PSCA antigen binding construct which can be used in the treatment and detection of cancers which overexpress PSCA is provided.

In some embodiments, the antigen binding construct can also be linked to therapeutic agents or detectable markers. In some embodiments, the therapeutic agent is a cytotoxic agent. For instance, the agent can be ricin, ricin A-chain, doxorubicin, daunorubicin, taxol, ethidium bromide, mitomycin, etoposide, tenoposide, vincristine, vinblastine, colchicine, dihydroxy anthracin dione, actinomycin D, diphtheria toxin, Pseudomonas exotoxin (PE) A, PE40, abrin, arbrin A chain, modeccin A chain, alpha-sarcin, gelonin mitogellin, retstrictocin, phenomycin, enomycin, curicin, crotin, calicheamicin, Sapaonaria officinalis inhibitor, maytansinoids, or glucocorticoidricin. In other embodiments, the therapeutic agent is a radioactive isotope. The radioactive isotope can be selected, for instance, from the group consisting of $^{212}$Bi, $^{131}$I, $^{111}$In, $^{90}$Y and $^{186}$Re. In other embodiments the construct is linked to an anti-cancer pro-drug activating enzyme capable of converting a pro-drug to its active form.

In some embodiments, the anti-PSCA construct is labeled with a detectable marker. The marker can be for instance, a radioisotope, a fluorescent compound, a bioluminescent compound, chemiluminescent compound, a metal chelator or an enzyme. Many radionuclides can be used as imaging labels, including without limitation, $^{124}$I, $^{86}$Y, $^{18}$F, $^{94m}$Tc, and the like. One of skill in the art will know of other radionuclides particularly well suited for use in the present embodiment. In some embodiments, the method can kill the cancer cell. In some embodiments, the construct recognizes and binds the PSCA protein as shown below beginning with leucine at amino acid position 22 and ending with alanine at amino acid position 99. In additional embodiments, the method further comprises administering to a chemotherapeutic drug, radiation therapy. In some embodiments, the subject is also treated with hormone ablation therapy or hormone antagonist therapy.

In some embodiments, the treatments can be given to the patient or subject by intravenously, intraperitoneally, intramuscularly, intratumorally, or intradermally. In some embodiments, contacting comprises administering the construct directly into a prostate cancer, a bladder cancer, a pancreatic cancer or a metastasis thereof.

In some embodiments, methods of detecting a cancerous cell in a subject by contacting the cancer cell with a construct which bears a detectable marker is provided. The methods can be used in screening patients at increased risk of cancer or to monitory response to therapy or to develop a prognosis for the cancer (e.g., prostate, bladder, or pancreatic cancers. The methods are particularly advantageous in detecting metastases of the cancer. Provided herein are minibody fragments with tumor targeting/imaging aptitude. In some embodiments, with regard to the constructs provided herein, there is a proviso that the construct comprises a VH or VL domain that is not identical to a corresponding domain or the 2B3 antibody.

In some embodiments, the antigen binding construct is conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme. Further, herein provided are embodiments wherein the antigen binding construct is linked to an enzyme that converts a prodrug into a cytotoxic agent. Examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, diphtheria toxin, Pseudomonas exotoxin (PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

In some embodiments, the antigen binding protein constructs can be used to systemically to treat cancer alone or when conjugated with an effector moiety. PSCA-targeting constructs conjugated with toxic agents, such as ricin, as well as unconjugated antibodies can be useful therapeutic agents naturally targeted to PSCA bearing cancer cells. Such constructs can be useful in blocking invasiveness.

In some embodiments, the antigen-binding protein constructs can be used to treat cancer. In such a situation, the construct is joined to at least a functionally active portion of a second protein or toxic molecule having therapeutic activity. The second protein can include, but is not limited to, an enzyme, lymphokine, oncostatin or toxin. Suitable toxins include doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin (PE) A, PE40, ricin, abrin, glucocorticoid and radioisotopes.

In some embodiments, treatment will generally involve the repeated administration of the constructs and their immunoconjugates via an acceptable route of administration such as intravenous injection (N), at an effective dose. Dosages will depend upon various factors generally appreciated by those of skill in the art, including without limitation the type of cancer and the severity, grade, or stage of the cancer, the binding affinity and half-life of the agents used, the desired steady-state antibody concentration level, frequency of treatment, and the influence of chemotherapeutic agents used in combination with the treatment method of the embodiments provided herein. Typical daily doses can range from about 0.1 to 100 mg/kg. Doses in the range of 10-500 mg of the constructs or their immunoconjugates per week can be effective and well tolerated, although even higher weekly doses can be appropriate and/or well tolerated. The principal determining factor in defining the appropriate dose is the amount of a particular agent necessary to be therapeutically effective in a particular context. Repeated administrations can be required in order to achieve tumor inhibition or regression. Initial loading doses can be higher. The initial loading dose can be administered as an infusion. Periodic maintenance doses can be administered similarly, provided the initial dose is well tolerated.

In some embodiments, direct administration of the constructs is also possible and can have advantages in certain contexts. For example, for the treatment of bladder carcinoma, the agents can be injected directly into the bladder.

In some embodiments, the compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions can be administered depending on the dosage and frequency as required and tolerated by the patient. Other known cancer therapies can be used in combination with the methods provided herein. For example, the compositions provided herein can also be used to target or sensitize a cell to other cancer therapeutic agents such as 5FU, vinblastine, actinomycin D, cisplatin, methotrexate, and the like.

In other embodiments, the methods can be practiced together with other cancer therapies (e.g, radical prostatectomy), radiation therapy (external beam or brachytherapy), hormone therapy (e.g., orchiectomy, LHRH-analog therapy to suppress testosterone production, anti-androgen therapy), or chemotherapy.

In some embodiments, methods of imaging cancer cells or tumors in vivo through administration of antibodies, such as the minibodies provided herein, are provided. In one embodiment, a method of imaging a cancer cell in vivo is provided, the method comprising administering a labeled anti-PSCA antibody to a mammal and imaging the antibody in vivo. The methods can be used to image a cancer cell in mammal, including without limitation, a mouse, rat, hamster, rabbit, pig, human, and the like.

In some embodiments, provided herein are methods for treating a subject having cancer, or inhibiting the growth of a prostate cancer cell expressing a Prostate Stem Cell Antigen (PSCA) protein comprising contacting the cancer cell (e.g., prostate, bladder, pancreatic cancer cell, with a construct as provided herein, in an amount effective to inhibit the growth of the cancer cell. In some embodiments, the methods find particular application in the diagnosis, prognosis and treatment of cancers which overexpress PSCA, for example, prostate, pancreatic and bladder cancers. In certain embodiments the methods are applied to hormone refractory or therapy resistant cancers. In certain embodiments the methods are applied to metastatic cancers.

In some embodiments, a minibody that binds to PSCA is provided. The minibody comprises a polypeptide that comprises a single-chain variable fragment (scFv) that binds to PSCA, the scFv comprising a variable heavy ($V_H$) domain linked a variable light ($V_L$) domain; and a variant hinge region comprising at least three cysteines on each strand of the hinge. In some embodiments, the minibody further comprises a human IgG $C_H3$ sequence. In some embodiments, the minibody further comprises a detectable marker selected from the group consisting of a radioactive substance, a dye, a contrast agent, a fluorescent compound, a bioluminescent compound, an enzyme, an enhancing agent, and a nanoparticle.

In some embodiments, the minibody provided herein comprises: a HCDR1 of the HCDR1 in SEQ ID NO: 93; a HCDR2 of the HCDR2 in SEQ ID NO: 94; a HCDR3 of the HCDR3 in SEW NO: 95; a LCDR1 of the LCDR1 in SEQ ID NO: 96; a LCDR2 of the LCDR2 in SEQ ID NO: 97; and a LCDR3 of the LCDR3 in SEQ ID NO: 98. In some embodiments of the minibody provided herein the variable heavy ($V_H$) domain and the variable light ($V_L$) domain are human sequences.

In some embodiments, a nucleic acid encoding an antibody of any of the embodiments described herein is provided. In some embodiments, a cell line producing any of the minibody embodiments described herein is provided. In some embodiments, a kit comprising any of the embodiments of the minibody described herein and a detectable marker are provided.

In some embodiments, a method of detecting the presence or absence of PSCA is provided. The method comprises applying any of the minibody embodiments provided herein to a sample; and detecting a binding or an absence of binding of the antigen binding construct thereof to PSCA. In some embodiments of the method, the minibody comprises a detectable marker selected from the group consisting of a radioactive substance, a dye, a contrast agent, a fluorescent compound, a bioluminescent compound, an enzyme, an enhancing agent, and a nanoparticle. In some embodiments of the method, applying the minibody comprises administering the minibody to a subject. In some embodiments of the method, detecting binding or absence of binding of the minibody thereof to a target antigen comprises positron emission tomography. In some embodiments, the method further comprises applying a secondary antibody or fragment thereof to the sample, wherein the secondary antibody or fragment thereof binds specifically to the minibody. In some embodiments of the method, the minibody thereof is incubated with the sample for no more than 1 hour.

In some embodiments, a method of targeting a therapeutic agent to PSCA is provided. The method comprises administering to a subject any of the embodiments of the minibody provided herein, wherein the minibody is conjugated to a therapeutic agent.

In some embodiments, a method of targeting PSCA in a subject in need thereof is provided. The method comprises administering to the subject a minibody of any one of the embodiments provided herein. In some embodiments of the method, the subject has at least one or more of a prostate tumor, a prostate cancer, a bladder tumor, a transitional carcinoma of the urinary bladder, a pancreatic tumor, a pancreatic carcinoma, any tumor associated with PSCA expression, any cancer associated with PSCA expression, or any disorder associated with PSCA expression.

In some embodiments, an antigen binding construct (such as a minibody or scFv) that binds to PSCA is provided, the antigen binding construct (such as a minibody or scFv) comprising a hinge region, wherein the hinge region comprises at least one of the following: a) a peptide sequence of SEQ ID NO: 1 ($X_{n1}CX_{n2}X_{n3}CX_{n4}X_{n5}C$), wherein $X_{n1}$ can be any amino acid that does not form a covalent crosslinking bond, wherein $X_{n2}$ is one of: A, R, N, D, E, Q, G, H, I, L, K, M, F, P, S, T, W, Y, or V, wherein $X_{n3}$ can be any amino acid, wherein $X_{n4}$ can be any amino acid, and wherein $X_{n5}$ can be any amino acid; b) a peptide sequence of SEQ ID NO: 2 ($X_{n1}X_{n2}X_{n3}X_{n4}X_{n5}$ $X_{n6}CX_{n7}X_{n8}CX_{n9}X_{n10}C$), wherein $X_{n1}$ can be any amino acid that does not form a covalent crosslinking bond with another identical amino acid, wherein $X_{n2}$ can be any amino acid, wherein $X_{n3}$ can be any amino acid, wherein $X_{n4}$ can be any amino acid, wherein $X_{n5}$ can be any amino acid, wherein $X_{n6}$ can be any amino acid, wherein $X_{n7}$ can be any amino acid, wherein $X_{n8}$ can be any amino acid, wherein $X_{n9}$ can be any amino acid, and wherein $X_{n10}$ can be any amino acid (SEQ ID NO: 208); c) a core hinge sequence of at least one of: CVECPPCP (SEQ ID NO: 57), CPPCPPC (SEQ ID NO: 52), or CPPCPPCPPC (SEQ ID NO: 54), linked to an upper hinge sequence of ELKTPLGDTTHT (SEQ ID NO: 48); or d) an upper hinge region that comprises no amino acids capable of crosslinking with a corresponding amino acid, and a core hinge region connected to a C-terminus of the upper hinge region, wherein the core hinge region comprises at least three cysteines. In some embodiments, the antigen binding construct is a full length antibody. In some embodiments, the antibody is a minibody. In some embodiments of the antigen binding construct (such as a minibody or scFv), apart from the hinge region, the antigen binding construct (such as a minibody or scFv) comprises a humanized amino acid sequence. In some embodiments, the antigen binding construct (such as a minibody or scFv) comprises: a HCDR1 of the HCDR1 in SEQ ID NO: 93; a HCDR2 of the HCDR2 in SEQ ID NO: 94; a HCDR3 of the HCDR3 in SEQ ID NO: 95; a LCDR1 of the LCDR1 in SEQ ID NO: 96; a LCDR2 of the LCDR2 in SEQ ID NO: 97; and a LCDR3 of the LCDR3 in SEQ ID NO: 98.

In some embodiments, a nucleic acid encoding the hinge region of any of the antigen binding construct (such as a minibody or scFv) embodiments described herein is provided. In some embodiments of the nucleic acid, apart from the sequence encoding the hinge region, the nucleic acid comprises a human sequence. In some embodiments, a cell line expressing the antigen binding construct (such as a minibody or scFv) encoded by the nucleic acid is provided.

In some embodiments, a method of manufacturing the antigen binding construct (such as a minibody or scFv) of any of the embodiments described herein is provided, the method comprising expressing the antibody in a cell line.

In some embodiments, a method of treating a condition in a subject in need thereof is provided, the method comprising administering to the subject the antibody of any of the embodiments provided herein.

PSMA-IAB2M

Full-length antibodies that target PSMA have been developed, some of which are in various stages of preclinical and clinical development. PSMA was originally defined by a murine antibody (mAb), 7E11, which recognized an intracellular epitope of PSMA (Olson, W. C. et al., "Clinical trials of cancer therapies targeting prostate-specific membrane antigen," Rev. Recent Clin. Trials, Vol. 2, No. 3, pp. 182-190, 2007). The 7E11 mAb was later developed into a FDA-approved SPECT imaging agent called Prostascint for the detection and imaging of prostate cancer in soft tissue. However, since 7E11 recognizes an intracellular epitope, Prostascint is a relatively poor imaging agent which is limited to detecting necrotic tumor tissue (Olson, W. C. et al., 2007). Having the pharmacokinetic properties of a full-length antibody, Prostascint also requires a long period of time between injection and imaging. Furthermore, Prostascint is a murine antibody which elicits strong immune responses that prevent multiple dosing (Olson, W. C. et al., 2007).

Another full-length antibody that targets PSMA, J591, was discovered and subsequently deimmunized, the deimmunized version known as huJ591 (Liu, H. et al., "Monoclonal antibodies to the extracellular domain of prostate-specific membrane antigen also react with tumor vascular endothelium", Cancer Research, Vol. 57, No. 17, pp. 3629-3634, 1997; Bander, N. H. et al., "Targeting Metastatic Prostate Cancer with Radiolabeled Monoclonal Antibody J591 to the Extracellular Domain of Prostate Specific Membrane Antigen," J. Urol., Vol. 170, No. 5, pp. 1717-1721, 2003). The deimmunized huJ591 is an anti-human PSMA antibody that recognizes and binds an extracellular epitope on PSMA (Bander, N. H. et al., 2003). The huJ591 antibody is being developed as a potential radioimmunotherapy agent against prostate cancer. In Phase I trials, DOTA-conjugated huJ591 antibody labeled with gamma emitting isotopes Indium-111 and Lutetium-177 demonstrated excellent targeting to metastatic sites, no immunogenicity, and multiple doses were well tolerated (Bander, N. H. et al., 2003, Milowsky, M. I. et al., "Phase I Trial of yttrium-90-labeled anti-prostate-specific membrane antigen monoclonal antibody J591 for androgen-independent prostate cancer," J. Clin. Oncol., Vol. 22, No. 13, pp. 2522-2531, 2004; Bander, N. H. et al., "Phase I trial of 177 Lutetium-labeled J591, a monoclonal antibody to prostate-specific membrane antigen, in patients with androgen-independent prostate cancer," J. Clin. Oncol., Vol. 23, No. 21, pp. 4591-4601, 2005; Olson, W. C. et al., 2007). Beyond prostate cancer, Phase I studies with $^{111}$In-DOTA huJ591 demonstrated specific targeting of tumor neovasculature of advanced solid tumors (Milowsky, M. I. et al., "Vascular targeted therapy with anti-prostate-specific membrane antigen monoclonal antibody J591 in advanced solid tumors," J. Clin. Oncol., Vol. 25, No. 5, pp. 540-547, 2007).

In some embodiments, antigen binding constructs that bind the PSMA antigen can be antibodies, minibodies and/or other fragments of antibodies such as scFv. Some non-limiting embodiments of antigen binding constructs against PSMA are shown in FIGS. 5B-5E, 7C-7E, 21B-21E, 34A-34F, 35A-35C, 36A, 47 (SEQ ID NOs: 112 and 113), 48 (SEQ ID NO: 113), 49 (SEQ ID NO: 114), 50 (SEQ ID NO: 115), 51 (SEQ ID NO: 116), 52 (SEQ ID NO: 117), 53 (SEQ ID NO: 118).

Prostate Specific Membrane Antigen (PSMA), a cell-surface biomarker that is associated with prostate cancer (Slovin, S. F., "Targeting novel antigens for prostate cancer treatment: focus on prostate-specific membrane antigen," Expert Opin. Ther. Targets, Vol. 9, No. 3, pp. 561-570, 2005), is a single-pass Type II transmembrane protein possessing glutamate carboxypeptidase activity, although the functional role of PSMA is not well understood (Olson, W. C. et al., 2007). Expression of PSMA is relatively limited in normal tissues outside of the prostate including the brain, small intestines, liver, proximal kidney tubules, and salivary gland (Olson, W. C. et al., 2007). An example of PSMA protein is shown with SEQ ID NO: 131.

In some embodiments, provided herein are antigen binding constructs, such as minibodies, that targets prostate specific membrane antigen (PSMA). The PSMA antigen binding construct or thereof can be conjugated to a substance such as a diagnostic agent, a therapeutic agent or a nanoparticle to form an anti-PSMA conjugate. Also disclosed are methods that include the use of the PSMA antigen binding construct or the anti-PSMA conjugate for diagnosing, visualizing, monitoring, or treating cancer or other conditions associated with overexpression of PSMA.

PSMA antigen binding constructs are provided herein according to the embodiments described herein. A PSMA antigen binding construct is a molecule that includes one or more portions of an immunoglobulin or immunoglobulin-related molecule that specifically binds to, or is immunologically reactive with a PSMA.

The PSMA antigen binding construct or anti-PSMA conjugate can be used to target a PSMA positive cell, such as cancer cells that overexpress PSMA.

In some embodiments, a method for diagnosing a cancer associated with PSMA expression in a subject is provided. Such a method includes administering an anti-PSMA minibody conjugated to a diagnostic agent to a subject having or suspected of having a cancer associated with PSMA expression; exposing the subject to an imaging method to visualize the labeled minibody in vivo; and determining that the subject has a cancer associated with PSMA expression when the labeled minibody localizes to a tumor site.

In some embodiments, a method for treating a cancer associated with PSMA expression in a subject is provided. Some embodiments include administering a therapeutically effective amount of a pharmaceutical composition to the subject, the composition comprising an anti-PSMA minibody. In some embodiments, the anti-PSMA minibody is conjugated to a therapeutic agent.

In some embodiments, the anti-PSMA conjugate can include a PSMA antigen binding construct (such as a minibody or scFv) conjugated to a therapeutic agent. A "therapeutic agent" as used herein is an atom, molecule, or compound that is useful in the treatment of cancer or other conditions associated with PSMA. Examples of therapeutic agents include, but are not limited to, drugs, chemotherapeutic agents, therapeutic antigen binding constructs, toxins, radioisotopes, enzymes (e.g., enzymes to cleave prodrugs to a cytotoxic agent at the site of the tumor), nucleases, hormones, immunomodulators, antisense oligonucleotides, chelators, boron compounds, photoactive agents and dyes.

Chemotherapeutic agents are often cytotoxic or cytostatic in nature and can include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that can be used as diagnostic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, *bacillus* calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, enilinacil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, to situmomab, trastuzumab, tretinoin, trimitrexate, alrubicin, vincristine, vinblastine, vindestine, vinorelbine, vorinostat, or zoledronic acid.

Therapeutic antibodies and functional fragments thereof, that can be used as diagnostic agents in accordance with the embodiments of the disclosure include, but are not limited to, alemtuzumab, bevacizumab, cetuximab, edrecolomab, gemtuzumab, ibritumomab tiuxetan, panitumumab, rituximab, tositumomab, and trastuzumab.

The PSMA antigen binding construct or anti-PSMA conjugate can be used to target a PSMA positive cell, such as cancer cells that overexpress PSMA. Therefore, methods for diagnosing, detecting, visualizing, monitoring or treating a cancer or other condition associated with PSMA expression can include administering the PSMA antigen binding construct or anti-PSMA conjugate to a subject having or suspected of having a cancer or other condition associated with PSMA expression.

In some embodiments, methods for treating cancer or other condition associated with overexpression of PSMA are provided. Such methods include administering to a subject a therapeutically effective amount of a pharmaceutical composition that includes a PSMA antigen binding construct as described herein. In one embodiment, the PSMA antigen binding construct is a minibody, derived from a J591 antibody such as those J591 minibodies described herein.

In some embodiments, the pharmaceutical composition can include a therapeutic anti-PSMA conjugate, wherein the conjugate includes a PSMA antigen binding construct conjugated to one or more therapeutic agent as described herein. In some embodiments, the PSMA antigen binding construct, derived from a J591 antibody such as those J591 minibodies described herein. For example, the J591 minibodies described herein can be used in a radioimmunotherapy approach, wherein one or more of the J591 minibodies is radiolabeled with an appropriate beta-emitting radiolabel such as Yttrium-90. The radiolabeled J591 minibody or minibodies can be used to deliver cell damage and death to local cancerous tissue that expresses PSMA. Further, the use of radiolabeled J591 minibodies would likely exhibit improved tumor penetration as compared to radiolabeled full-length parental huJ591 antibody.

The therapeutic anti-PSMA conjugate can be conjugated to or associated with one or more additional substances described herein, such as diagnostic anti-PSMA conjugates (described herein), unconjugated diagnostic agents, contrast solutions, carrier lipids or nanoparticles.

PSMA expression in prostate cancer increases with tumor aggressiveness and is the highest in high-grade tumors, metastatic lesions, and androgen-independent disease (Olson, W. C. et al., 2007). Therefore, PSMA is a cancer biomarker that is a good candidate for targeting by an imaging agent. PSMA expression is also upregulated in the neovasculature of many non-prostatic solid tumors including lung, colon, breast, renal, liver and pancreatic carcinomas as well as sarcomas and melanoma (Olson, W. C. et al., 2007).

The cancer associated with PSMA expression in a subject can be lung cancer, colorectal cancer, breast cancer, renal cancer, liver cancer, bladder cancer, pancreatic cancer or melanoma. Thus, in some embodiments "PSMA dependent disorder" can include: lung cancer, colorectal cancer, breast cancer, renal cancer, liver cancer, bladder cancer, pancreatic cancer or melanoma.

Furthermore, "PSMA dependent disorder" can also include those cancers that are associated with PSMA expression including those having a cancer tumor tissue that overexpresses PSMA (e.g., prostate cancer) or those having solid tumor neovasculature that overexpresses PSMA (e.g., prostate cancer, lung cancer, colon (or colorectal) cancer, breast cancer, renal cancer, liver cancer, bladder cancer and pancreatic cancer as well as sarcomas and melanoma). Most solid tumor neovasculature expresses PSMA, making PSMA a neovasculature biomarker. Thus, in addition to cancer cells that express PSMA, a cancer that is associated with PSMA expression can include any cancer tissue with neovasculature including, but not limited to, carcinomas such as prostate cancer, lung cancer, colon (or colorectal) cancer, breast cancer, renal cancer, liver cancer, bladder cancer and pancreatic cancer as well as sarcomas and melanoma.

In some embodiments, a minibody that binds to PSMA is provided. The minibody comprises a polypeptide that comprises a single-chain variable fragment (scFv) that binds to PSMA, the scFv comprising a variable heavy ($V_H$) domain linked a variable light ($V_L$) domain; and a variant hinge region comprising at least three cysteines on each strand of the hinge. In some embodiments, the minibody further comprises a human IgG $C_H3$ sequence. In some embodiments, the minibody further comprises a detectable marker selected from the group consisting of a radioactive substance, a dye, a contrast agent, a fluorescent compound, a bioluminescent compound, an enzyme, an enhancing agent, and a nanoparticle.

In some embodiments, the minibody provided herein comprises: a HCDR1 of the HCDR1 in SEQ ID NO: 81; a HCDR2 of the HCDR2 in SEQ ID NO: 82; a HCDR3 of the HCDR3 in SEW NO: 83; a LCDR1 of the LCDR1 in SEQ ID NO: 84; a LCDR2 of the LCDR2 in SEQ ID NO: 85; and a LCDR3 of the LCDR3 in SEQ ID NO: 86. In some embodiments of the minibody provided herein the variable heavy ($V_H$) domain and the variable light ($V_L$) domain are human sequences.

In some embodiments, a nucleic acid encoding an antibody of any of the embodiments described herein is provided. In some embodiments, a cell line producing any of the minibody embodiments described herein is provided. In some embodiments, a kit comprising any of the embodiments of the minibody described herein and a detectable marker are provided.

In some embodiments, a method of detecting the presence or absence of PSMA is provided. The method comprising: applying any of the minibody embodiments provided herein to a sample; and detecting a binding or an absence of binding of the antigen binding construct thereof to PSMA. In some embodiments of the method, the minibody comprises a detectable marker selected from the group consisting of a radioactive substance, a dye, a contrast agent, a fluorescent compound, a bioluminescent compound, an enzyme, an enhancing agent, and a nanoparticle. In some embodiments of the method, applying the minibody comprises administering the minibody to a subject. In some embodiments of the method, detecting binding or absence of binding of the minibody thereof to target antigen comprises positron emission tomography. In some embodiments, the method further comprises applying a secondary antibody or fragment thereof to the sample, wherein the secondary antibody or fragment thereof binds specifically to the minibody. In some embodiments of the method, the minibody thereof is incubated with the sample for no more than 1 hour.

In some embodiments, a method of targeting a therapeutic agent to PSMA is provided. The method comprises administering to a subject any of the embodiments of the minibody provided herein, wherein the minibody is conjugated to a therapeutic agent.

In some embodiments, a method of targeting PSMA in a subject in need thereof is provided. The method comprises administering to the subject a minibody of any one of the embodiments provided herein. In some embodiments of the method, the subject has at least one of a tumor or a cancer or a disorder of prostate, brain, small intestines, liver, proximal kidney tubules, salivary gland. In some embodiments, a method of targeting PSMA in a tumor neovasculature of an advanced solid tumor is provided.

In some embodiments, an antibody that binds to PSMA is provided. The antibody comprises a hinge region, wherein the hinge region comprises at least one of the following: a) a peptide sequence of SEQ ID NO: 1 ($X_{n1}CX_{n2}X_{n3}CX_{n4}X_{n5}C$), wherein $X_{n1}$ can be any amino acid that does not form a covalent crosslinking bond, wherein $X_{n2}$ is one of: A, R, N, D, E, Q, G, H, I, L, K, M, F, P, S, T, W, Y, or V, wherein $X_{n3}$ can be any amino acid, wherein $X_{n4}$ can be any amino acid, and wherein $X_{n5}$ can be any amino acid; b) a peptide sequence of SEQ ID NO: 2 ($X_{n1}X_{n2}X_{n3}X_{n4}X_{n5}$ $X_{n6}CX_{n7}X_{n8}CX_{n9}X_{n10}C$), wherein $X_{n1}$ can be any amino acid that does not form a covalent crosslinking bond with another identical amino acid, wherein $X_{n2}$ can be any amino acid, wherein $X_{n3}$ can be any amino acid, wherein $X_{n4}$ can be any amino acid, wherein $X_{n5}$ can be any amino acid, wherein $X_{n6}$ can be any amino acid, wherein $X_{n7}$ can be any amino acid, wherein $X_{n8}$ can be any amino acid, wherein $X_{n9}$ can be any amino acid, and wherein $X_{n10}$ can be any amino acid (SEQ ID NO: 208); c) a core hinge sequence of at least one of: CVECPPCP (SEQ ID NO: 57), CPPCPPC (SEQ ID NO: 52), or CPPCPPCPPC (SEQ ID NO: 54), linked to an upper hinge sequence of ELKTPLGDTTHT (SEQ ID NO: 48); or d) an upper hinge region that comprises no amino acids capable of crosslinking with a corresponding amino acid, and a core hinge region connected to a C-terminus of the upper hinge region, wherein the core hinge region comprises at least three cysteines. In some embodiments, the antibody is a full length antibody. In some embodiments, the antibody is a minibody. In some embodiments of the antibody, apart from the hinge region, the antibody comprises a humanized amino acid sequence. In some embodiments, the antibody comprises: a HCDR1 of the HCDR1 in SEQ ID NO: 81; a HCDR2 of the HCDR2 in SEQ ID NO: 82; a HCDR3 of the HCDR3 in SEQ ID NO: 83; a LCDR1 of the LCDR1 in SEQ ID NO: 84; a LCDR2 of the LCDR2 in SEQ ID NO: 85; and a LCDR3 of the LCDR3 in SEQ ID NO: 86.

In some embodiments, a nucleic acid encoding the hinge region of any of the antibody embodiments described herein is provided. In some embodiments of the nucleic acid, apart from the sequence encoding the hinge region, the nucleic acid comprises a human sequence. In some embodiments, a cell line expressing the antibody encoded by the nucleic acid is provided.

In some embodiments, a method of manufacturing the antibody of any of the embodiments described herein is provided, the method comprising expressing the antibody in a cell line.

In some embodiments, a method of treating a condition in a subject in need thereof is provided, the method comprising administering to the subject the antibody of any of the embodiments provided herein.

CD8-IAB22M

CD8 (cluster of differentiation 8) is a transmembrane glycoprotein that is a specific marker for a subclass of T-cells including cytotoxic T-cells. Expression of CD8 is also present on some natural killer and dendritic cells as well as on a subset of T cell lymphomas. CD8 assembles as either a heterodimer of the CD8 alpha and CD8 beta subunits or a CD8 alpha homodimer. The assembled dimeric CD8 complex acts as a co-receptor together with the T-cell receptor (TCR) to recognize antigen presentation by MHC class I cells. CD8 plays a role in the development of T-cells and activation of mature T-cells. Changes in T-cell localization can reflect the progression of an immune response and can occur over time. Examples of CD8 subunits are shown with SEQ ID NOs: 134 and 135.

Described herein are antigen binding constructs, including antibodies and fragments thereof, such as minibodies that bind to a target molecule, CD8. In some embodiments, antigen binding constructs that bind the CD8 antigen can be antibodies, minibodies and/or other fragments of antibodies such as scFv. Some embodiments of antigen binding constructs against CD8 are shown in FIGS. 14E, 15D, 16B-16D, 20C-20G, 22B, 36B, 40 (SEQ ID NOs: 105 and 106), 41 (SEQ ID NO: 106), 42 (SEQ ID NO: 107), 43 (SEQ ID NO: 108), 44 (SEQ ID NO: 109), 45 (SEQ ID NO: 110), 46 (SEQ ID NO: 111), 66.

Some embodiments provided herein relate to a method of targeting a therapeutic agent to a CD8. The method can include administering to a subject an antigen binding construct as described herein, for example a CD8 antigen binding construct. In some embodiments, the antigen binding construct is conjugated to a therapeutic agent.

Antigen binding constructs can be useful for detecting the presence, localization, and/or quantities of the target molecule (CD8 and/or CD8+ cells, for example, certain classes of T-cells). Such antigen binding constructs can also be useful for targeting therapeutic agents to cells that express the target molecule. In some embodiments, methods are provided for detecting the presence or absence of the target molecule (or "target") using antigen binding constructs (including antibodies, and constructs such as minibodies). In some embodiments, methods are provided for using the antigen binding constructs for therapeutic purposes.

In some embodiments, the antigen binding constructs allow for the detection of human CD8 which is a specific biomarker found on the surface of a subset of T-cells for diagnostic imaging of the immune system. Imaging of CD8 allows for the in vivo detection of T-cell localization. Changes in T-cell localization can reflect the progression of an immune response and can occur over time as a result various therapeutic treatments or even disease states.

In addition, CD8 plays a role in activating downstream signaling pathways that are important for the activation of cytolytic T cells that function to clear viral pathogens and provide immunity to tumors. CD8 positive T cells can recognize short peptides presented within the MHCI protein of antigen presenting cells. In some embodiments, engineered fragments directed to CD8 can potentiate signaling through the T cell receptor and enhance the ability of a subject to clear viral pathogens and respond to tumor antigens. Thus, in some embodiments, the antigen binding constructs provided herein can be agonists and can activate the CD8 target.

In some embodiments, the presence or absence of the target, CD8, is detected. The presence or absence of the target can be detected based on the presence or absence of the antigen binding construct in the sample. After removal and/or elimination of the antigen binding construct from the sample, for example by washing and/or metabolic elimination, remaining antigen binding construct in the sample can indicate the presence of the target, while an absence of the antigen binding construct in the sample can indicate the absence of the target.

Some embodiments include detection of human CD8 which is a specific biomarker found on the surface of a subset of T-cells for diagnostic imaging of the immune system. Imaging of the target molecule can allow for the in vivo detection of T-cell localization. Changes in T-cell localization can reflect the progression of an immune response and can occur over time as a result various therapeutic treatments or even disease states. For example, imaging T-cell localization can be useful in immunotherapy. Adoptive immunotherapy is a form of therapy where a patient's own T-cells are manipulated in vitro and re-introduced into the patient. For this form of treatment, imaging of T-cells can be useful for monitoring and/or determining the status of the treatment. Thus, in some embodiments, monitoring the localization of the target molecule can be a useful for analyzing a mechanism of action, efficacy, and/or safety in the development of drugs and/or can aid in the clinical management of disease.

Some embodiments provided herein relate to a method of targeting a therapeutic agent to a CD8. The method can include administering to a subject an antigen binding construct as described herein, for example a CD8 antigen binding construct. In some embodiments, the antigen binding construct is conjugated to a therapeutic agent.

Toxins that can be used as detectable markers in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

In some embodiments nanoparticles are used in therapeutic applications as drug carriers that, when conjugated to an antigen binding construct, deliver chemotherapeutic agents, hormonal therapeutic agents, radiotherapeutic agents, toxins, or any other cytotoxic or anti-cancer agent known in the art to cancerous cells that overexpress the target on the cell surface.

Antigen binding constructs can be used to target a therapeutic molecule, for example a cytotoxin to a target positive cell, such as a cell expressing CD8. Thus, some embodiments include methods of targeting a therapeutic agent to a target positive cell. The method can include administering an antigen binding construct as described herein to a subject. The subject can be a subject in need, for example a subject in need of elimination or neutralization of at least some target positive cells. In some embodiments, the antigen binding construct includes at least one therapeutic agent as described herein. In some embodiments, the therapeutic can be directly conjugated to the antigen binding construct via a covalent bond, such as a disulfide bond. In some embodiments, the subject can benefit from the localization of a CD8 positive cell to another cell or agent.

Optionally, before and/or after administration of the antigen binding construct that includes at least one therapeutic agent, the number and/or localization of the target positive cells of the patient is determined. For example, determining the number and/or localization of target positive cells prior to administration can indicate whether the patient is likely to benefit from neutralization and/or elimination of the target positive cells. Determining the number and/or localization of the target positive cells after administration can indicate whether the target positive cells were eliminated in the patient.

The term "CD8 dependent disorder" includes cancers for which there is an immunological component (including response to cancer immunotherapies), autoimmune disorders inflammation disorders, etc.

In some embodiments, a minibody that binds to CD8 is provided. The minibody comprises a polypeptide that comprises a single-chain variable fragment (scFv) that binds to CD8, the scFv comprising a variable heavy ($V_H$) domain linked a variable light ($V_L$) domain; and a variant hinge region comprising at least three cysteines on each strand of the hinge. In some embodiments, the minibody further comprises a human IgG $C_H3$ sequence. In some embodiments, the minibody further comprises a detectable marker selected from the group consisting of a radioactive substance, a dye, a contrast agent, a fluorescent compound, a bioluminescent compound, an enzyme, an enhancing agent, and a nanoparticle.

In some embodiments, the minibody provided herein comprises: a HCDR1 of the HCDR1 in SEQ ID NO: 75; a HCDR2 of the HCDR2 in SEQ ID NO: 76; a HCDR3 of the HCDR3 in SEW NO: 77; a LCDR1 of the LCDR1 in SEQ ID NO: 78; a LCDR2 of the LCDR2 in SEQ ID NO: 79; and a LCDR3 of the LCDR3 in SEQ ID NO: 80. In some embodiments of the minibody provided herein the variable heavy ($V_H$) domain and the variable light ($V_L$) domain are human sequences.

In some embodiments, a nucleic acid encoding an antibody of any of the embodiments described herein is provided. In some embodiments, a cell line producing any of the minibody embodiments described herein is provided. In some embodiments, a kit comprising any of the embodiments of the minibody described herein and a detectable marker are provided.

In some embodiments, a method of detecting the presence or absence of CD8 is provided. The method comprising: applying any of the minibody embodiments provided herein to a sample; and detecting a binding or an absence of binding of the antigen binding construct thereof to CD8. In some embodiments of the method, the minibody comprises a detectable marker selected from the group consisting of a radioactive substance, a dye, a contrast agent, a fluorescent compound, a bioluminescent compound, an enzyme, an enhancing agent, and a nanoparticle. In some embodiments of the method, applying the minibody comprises administering the minibody to a subject. In some embodiments of the method, detecting binding or absence of binding of the minibody thereof to CD8 comprises positron emission tomography. In some embodiments, the method further comprises applying a secondary antibody or fragment thereof to the sample, wherein the secondary antibody or fragment thereof binds specifically to the minibody. In some embodiments of the method, the minibody thereof is incubated with the sample for no more than 1 hour.

In some embodiments, a method of targeting a therapeutic agent to CD8 is provided. The method comprises administering to a subject any of the embodiments of the minibody provided herein, wherein the minibody is conjugated to a therapeutic agent.

In some embodiments, a method of targeting a T lymphocyte cell expressing CD8 in a subject in need thereof is provided. The method comprises administering to the subject a minibody of any one of the embodiments provided herein. In some embodiments, a method of neutralizing a T lymphocyte cell expressing CD8 is provided. In some embodiments, the subject has at least one of anergic CD8 T cells, dysfunctional CD8 T cells, auto-reactive CD8 T cells, over-reactive CD8 T cells, inhibitory CD8 T cells, mislocalized CD8 T cells, or CD8 T cell lymphoma. In some embodiments, the subject has CD8 T cells associated with at least one of rheumatoid arthritis, multiple sclerosis, diabetes, systemic lupus erythematosus, autoimmune, inflammatory condition, signaling defect, or co-stimulatory defect.

In some embodiments, an antibody that binds to CD8 is provided. The antibody comprises a hinge region, wherein the hinge region comprises at least one of the following: a) a peptide sequence of SEQ ID NO: 1 ($X_{n1}CX_{n2}X_{n3}CX_{n4}X_{n5}C$), wherein $X_{n1}$ can be any amino acid that does not form a covalent crosslinking bond, wherein $X_{n2}$ is one of: A, R, N, D, E, Q, G, H, I, L, K, M, F, P, S, T, W, Y, or V, wherein $X_{n3}$ can be any amino acid, wherein $X_{n4}$ can be any amino acid, and wherein $X_{n5}$ can be any amino acid; b) a peptide sequence of SEQ ID NO: 2 ($X_{n1}X_{n2}X_{n3}X_{n4}X_{n5}$ $X_{n6}CX_{n7}X_{n8}CX_{n9}X_{n10}C$), wherein $X_{n1}$ can be any amino acid that does not form a covalent crosslinking bond with another identical amino acid, wherein $X_{n2}$ can be any amino acid, wherein $X_{n3}$ can be any amino acid, wherein $X_{n4}$ can be any amino acid, wherein $X_{n5}$ can be any amino acid, wherein $X_{n6}$ can be any amino acid, wherein $X_{n7}$ can be any amino acid, wherein $X_{n8}$ can be any amino acid, wherein $X_{n9}$ can be any amino acid, and wherein $X_{n10}$ can be any amino acid (SEQ ID NO: 208); c) a core hinge sequence of at least one of: CVECPPCP (SEQ ID NO: 57), CPPCPPC (SEQ ID NO: 52), or CPPCPPCPPC (SEQ ID NO: 54), linked to an upper hinge sequence of ELKTPLGDTTHT (SEQ ID NO: 48); or d) an upper hinge region that comprises no amino acids capable of crosslinking with a corresponding amino acid, and a core hinge region connected to a C-terminus of the upper hinge region, wherein the core hinge region comprises at least three cysteines. In some embodiments, the antibody is a full length antibody. In some embodiments, the antibody is a minibody. In some embodiments of the antibody, apart from the hinge region, the antibody comprises a humanized amino acid sequence. In some embodiments, the antibody comprises: a HCDR1 of the HCDR1 in SEQ ID NO: 75; a HCDR2 of the HCDR2 in SEQ ID NO: 76; a HCDR3 of the HCDR3 in SEQ ID NO: 77; a LCDR1 of the LCDR1 in SEQ ID NO: 78; a LCDR2 of the LCDR2 in SEQ ID NO: 79; and a LCDR3 of the LCDR3 in SEQ ID NO: 80.

In some embodiments, a nucleic acid encoding the hinge region of any of the antibody embodiments described herein is provided. In some embodiments of the nucleic acid, apart from the sequence encoding the hinge region, the nucleic acid comprises a human sequence. In some embodiments, a cell line expressing the antibody encoded by the nucleic acid is provided.

In some embodiments, a method of manufacturing the antibody of any of the embodiments described herein is provided, the method comprising expressing the antibody in a cell line.

In some embodiments, a method of treating a condition in a subject in need thereof is provided, the method comprising administering to the subject the antibody of any of the embodiments provided herein.

5T4-IAB20M

5T4 is an oncofetal glycoprotein which has weak expression in select adult tissues, but strong expression in various types of carcinomas including colorectal, renal, breast, ovarian, gastric, lung, and prostate cancer. 5T4 expression is found in both primary and metastatic cancers and expression level correlates with progression of the disease making 5T4 a very promising biomarker. An example of 5T4 protein is shown with SEQ ID NO: 133.

A 5T4-specific imaging agent can provide a significant advantage in specificity over other imaging agents such as FDG which are based on detecting changes in metabolism. Furthermore, imaging agents which specifically target 5T4 can be a valuable tool during the development of therapies targeting 5T4. For example, the imaging agent can be used to monitor patients following treatment of therapy targeting 5T4. In the case of prostate cancer, a FDA approved SPECT imaging agent is on the market called Prostascint but has considerable limitations since the intact antibody is murine (immunogenicity issue with repeat administration) and the epitope is an internal epitope of the biomarker PSMA (limits accuracy). The present 5T4 antigen binding constructs can have significant advantages over Prostascint in that they can bind an extracellular epitope of 5T4, have optimized pharmacokinetics for imaging, and are humanized.

The 5T4 protein is also known as trophoblast glycoprotein or TPBG. Examples of 5T4 proteins are known in the art, and include, for example the 5T4 protein of SEQ ID NO: 133.

Therapeutic antibodies and antibody fusion proteins have been in development against the human 5T4 target including the murine antibody "H8". Also, a cancer vaccine named Trovax is currently in clinical development against the 5T4 antigen by Oxford Biomedica.

A 5T4-specific imaging agent can provide a significant advantage in specificity over other imaging agents such as FDG which are based on detecting changes in metabolism. Furthermore, imaging agents which specifically target 5T4 can be a valuable tool during the development of therapies targeting 5T4. For example, the imaging agent can be used to monitor patients following treatment of therapy targeting 5T4. In the case of prostate cancer, a FDA approved SPECT imaging agent is on the market called Prostascint but has considerable limitations since the intact antibody is murine (immunogenicity issue with repeat administration) and the epitope is an internal epitope of the biomarker PSMA (limits accuracy). The present antigen binding constructs can have significant advantages over Prostascint in that they can bind an extracellular epitope of 5T4, have optimized pharmacokinetics for imaging, and are humanized.

In some embodiments, antigen binding constructs that bind the 5T4 antigen can be antibodies, minibodies and/or other fragments of antibodies such as scFv. Some non-limiting embodiments of antigen binding constructs against 5T4 are shown in FIGS. 28B-28E, 32, 36C, 54 (SEQ ID NOs: 119 and 120), 55 (SEQ ID NO: 120), 56 (SEQ ID NO: 121), 57 (SEQ ID NO: 122), 58 (SEQ ID NO: 123), 59 (SEQ ID NO: 124), 67, 68.

In some embodiments, the antigen binding construct can be connected to a therapeutic to treat a form of cancer, including, but not limited to: colorectal, renal, breast, ovarian, gastric, lung, and/or prostate cancer.

In some embodiments, the 5T4 antigen binding construct can be used as a therapeutic agent as a stand-alone construct (for example, without a toxin conjugated thereto). While the fragments have a shorter half-life compared to the intact antibody which would be less optimal for therapy, these formats can exhibit improved tumor penetration based on their smaller size and be therapeutically effective when appropriately armed with a cytotoxic drug or radioisotope.

5T4 is a rapidly internalizing antigen which can make it suitable for antibody drug-conjugate approaches. In some embodiments, another therapeutic approach is radio immunotherapy via attaching an appropriate radiolabel such as the beta-emitter Yttrium-90 which can deliver cell damage and death to local cancerous tissue.

In some embodiments, the antigen binding construct is used to target cells expressing 5T4 antigen, including, for example, colorectal, renal, breast, ovarian, gastric, lung, and/or prostate cancer cells.

The ability to image a patient's entire body for the presence of an antibody's target prior to and during treatment provides valuable information for personalized patient management. During the testing of an antibody therapy's safety and efficacy, it is useful to be able to select and test the treatment on patients who express the antibody's target as part of their disease progression.

5T4 is overexpressed in many different carcinomas including colorectal, renal, breast, ovarian, gastric, lung, and prostate. Imaging agents such as FDG-PET have proven quite effective for detection of many of these cancer types but current imaging practices are not sufficiently accurate for ovarian and prostate cancer. In some embodiments, any of these disorders can be diagnosed and/or treated with various 5T4 constructs provided herein.

In some embodiments, the antigen binding constructs can be clinical imaging agents (PET/SPECT) in humans. Since 5T4 is overexpressed in multiple cancer types (including colorectal, renal, breast, ovarian, gastric, lung, and prostate, these 5T4 antigen binding constructs can be used for targeted diagnostic detection for these cancers. In some embodiments, this can be used for detection of ovarian and/or prostate cancer.

The term "5T4 dependent disorder" includes any disorder in which 5T4 plays a role in the disorder itself. In some embodiments, this denotes over-expression of 5T4. Examples of the disorders include, multiple cancer types, such as colorectal, renal, breast, ovarian, gastric, lung, and prostate cancer, for example.

In some embodiments, a minibody that binds to 5T4 is provided. The minibody comprises a polypeptide that comprises a single-chain variable fragment (scFv) that binds to 5T4, the scFv comprising a variable heavy ($V_H$) domain linked a variable light ($V_L$) domain; and a variant hinge region comprising at least three cysteines on each strand of the hinge. In some embodiments, the minibody further comprises a human IgG $C_H3$ sequence. In some embodiments, the minibody further comprises a detectable marker selected from the group consisting of a radioactive substance, a dye, a contrast agent, a fluorescent compound, a bioluminescent compound, an enzyme, an enhancing agent, and a nanoparticle.

In some embodiments, the minibody provided herein comprises: a HCDR1 of the HCDR1 in SEQ ID NO: 87; a HCDR2 of the HCDR2 in SEQ ID NO: 88; a HCDR3 of the HCDR3 in SEW NO: 89; a LCDR1 of the LCDR1 in SEQ ID NO: 90; a LCDR2 of the LCDR2 in SEQ ID NO: 91; and a LCDR3 of the LCDR3 in SEQ ID NO: 92. In some embodiments of the minibody provided herein the variable heavy ($V_H$) domain and the variable light ($V_L$) domain are human sequences.

In some embodiments, a nucleic acid encoding an antibody of any of the embodiments described herein is provided. In some embodiments, a cell line producing any of the minibody embodiments described herein is provided. In some embodiments, a kit comprising any of the embodiments of the minibody described herein and a detectable marker are provided.

In some embodiments, a method of detecting the presence or absence of 5T4 is provided. The method comprising: applying any of the minibody embodiments provided herein to a sample; and detecting a binding or an absence of binding of the antigen binding construct thereof to 5T4. In some embodiments of the method, the minibody comprises a detectable marker selected from the group consisting of a radioactive substance, a dye, a contrast agent, a fluorescent compound, a bioluminescent compound, an enzyme, an enhancing agent, and a nanoparticle. In some embodiments of the method, applying the minibody comprises administering the minibody to a subject. In some embodiments of the method, detecting binding or absence of binding of the minibody to a target antigen comprises positron emission tomography. In some embodiments, the method further comprises applying a secondary antibody or fragment thereof to the sample, wherein the secondary antibody or fragment thereof binds specifically to the minibody. In some embodiments of the method, the minibody thereof is incubated with the sample for no more than 1 hour.

In some embodiments, a method of targeting a therapeutic agent to 5T4 is provided. The method comprises administering to a subject any of the embodiments of the minibody provided herein, wherein the minibody is conjugated to a therapeutic agent.

In some embodiments, a method of targeting 5T4 in a subject in need thereof is provided. The method comprises administering to the subject a minibody of any one of the embodiments provided herein. In some embodiments of the method, the subject has at least one of colorectal, renal, breast, ovarian, gastric, lung, or prostate cancer tumor or cancer. In some embodiment, the subject has at least one of a primary cancer, or metastatic cancer. In some embodiments, the subject has an early stage disorder. In some embodiments, the subject has an intermediate stage disorder. In some embodiments, the subject has a late stage disorder.

In some embodiments, an antibody that binds to 5T4 is provided. The antibody comprises a hinge region, wherein the hinge region comprises at least one of the following: a) a peptide sequence of SEQ ID NO: 1 ($X_{n1}CX_{n2}X_{n3}CX_{n4}X_{n5}C$), wherein $X_{n1}$ can be any amino acid that does not form a covalent crosslinking bond, wherein $X_{n2}$ is one of: A, R, N, D, E, Q, G, H, I, L, K, M, F, P, S, T, W, Y, or V, wherein $X_{n3}$ can be any amino acid, wherein $X_{n4}$ can be any amino acid, and wherein $X_{n5}$ can be any amino acid; b) a peptide sequence of SEQ ID NO: 2 ($X_{n1}X_{n2}X_{n3}X_{n4}X_{n5}$ $X_{n6}CX_{n7}X_{n8}CX_{n9}X_{n10}C$), wherein $X_{n1}$ can be any amino acid that does not form a covalent crosslinking bond with another identical amino acid, wherein $X_{n2}$ can be any amino acid, wherein $X_{n3}$ can be any amino acid, wherein $X_{n4}$ can be any amino acid, wherein $X_{n5}$ can be any amino acid, wherein $X_{n6}$ can be any amino acid, wherein $X_{n7}$ can be any amino acid, wherein $X_{n8}$ can be any amino acid, wherein $X_{n9}$ can be any amino acid, and wherein $X_{n10}$ can be any amino acid (SEQ ID NO: 208); c) a core hinge sequence of at least one of: CVECPPCP (SEQ ID NO: 57), CPPCPPC (SEQ ID NO: 52), or CPPCPPCPPC (SEQ ID NO: 54), linked to an upper hinge sequence of ELKTPLGDTTHT (SEQ ID NO: 48); or d) an upper hinge region that comprises no amino acids capable of crosslinking with a corresponding amino acid, and a core hinge region connected to a C-terminus of the upper hinge region, wherein the core hinge region comprises at least three cysteines. In some embodiments, the antibody is a full length antibody. In some embodiments, the antibody is a minibody. In some embodiments of the antibody, apart from the hinge region, the antibody comprises a humanized amino acid sequence.

In some embodiments, the antibody comprises: a HCDR1 of the HCDR1 in SEQ ID NO: 87; a HCDR2 of the HCDR2 in SEQ ID NO: 88; a HCDR3 of the HCDR3 in SEW NO: 89; a LCDR1 of the LCDR1 in SEQ ID NO: 90; a LCDR2 of the LCDR2 in SEQ ID NO: 91; and a LCDR3 of the LCDR3 in SEQ ID NO: 92.

In some embodiments, a nucleic acid encoding the hinge region of any of the antibody embodiments described herein is provided. In some embodiments of the nucleic acid, apart from the sequence encoding the hinge region, the nucleic acid comprises a human sequence. In some embodiments, a cell line expressing the antibody encoded by the nucleic acid is provided.

In some embodiments, a method of manufacturing the antibody of any of the embodiments described herein is provided. The method comprises expressing the antibody in a cell line.

In some embodiments, a method of treating a condition in a subject in need thereof is provided, the method comprising administering to the subject the antibody of any of the embodiments provided herein.

CD3-IAB25M

CD3 (cluster of differentiation 3) was discovered concurrently with the monoclonal antibody OKT3. Initially, OKT3 was found to bind to all mature, peripheral T cells, and later the CD3 epsilon subunit as part of the TCR-CD3 complex was determined to be the cell surface antigen bound by OKT3. (Kung, P. et al., "Monoclonal antibodies defining distinctive human T cell surface antigens," Science, Vol. 206, No. 4416, pp. 347-349, 1979). Examples of CD3 subunits are shown with SEQ ID NOs: 136-139. OKT3 was subsequently tested as an immunosuppressant for transplant rejection with the initial trial studying acute kidney allograft rejection (Cosimi, A. B. et al., "Treatment of acute renal allograft rejection with OKT3 monoclonal antibody," Transplantation, Vol. 32, No. 6, pp. 535-539, 1981).

In some embodiments, antigen binding constructs, including antibodies and fragments thereof, such as minibodies, that bind to a target molecule, CD3, are provided. Such antigen binding constructs can be useful for detecting the presence, localization, and/or quantities of the target molecule (CD3 and/or CD3+ cells). Such antigen binding constructs can also be useful for modulating the biologic activity associated with CD3 expression on immune cells and for targeting therapeutic agents to cells that express the CD3 protein. In some embodiments, methods are provided for detecting the presence or absence of the target molecule (or "target") using antigen binding constructs (including antibodies, and constructs such as minibodies). In some embodiments, methods are provided for using the antigen binding constructs for therapeutic purposes.

Some embodiments of the CD3 minibodies disclosed herein can also be used as a therapeutic minibody, for example to modulate immune system reaction by neutralizing T cells via the CD3 epsilon domain of the TCR complex and by upregulating T regulatory cells via upregulation of FOXP3 (Saruta, M. et al., "Characterization of FOXP3+ CD4+ regulatory T cells in Crohn's disease," Clin. Immunol., Vol. 125, No. 3, pp. 281-290, 2007). Such therapeutics have utility in treating not only tissue/organ allograft transplants but also autoimmune diseases such as Rheumatoid Arthritis, Multiple Sclerosis, Type 1 Diabetes, and Lupus Erythematosus to name a few.

Initial proof-of-concept preclinical imaging has been performed with a humanized anti-CD3 antibody, Visilizumab which was not derived from OKT3 (Malviya, G. et al., "Radiolabeled humanized anti-CD3 monoclonal antibody Visilizumab for imaging human T-lymphocytes," Vol. 50, No. 10, pp. 1683-1691, 2009). Imaging of CD3+ T-cells is useful for anti-CD3 therapy since the treatment is effective if the organ of interested has been entirely infiltrated with CD3+ T-cells. A potential CD3 imaging agent would allow for the selection of the patient and also a way to monitor treatment. Imaging with a full-length antibody typically requires a longer time postinjection for optimal imaging than with the fragments provided herein.

Anti-CD3 antigen binding constructs, such as minibodies are provided in some embodiments. The antigen binding constructs can be used, for example, for imaging and for treating a variety of disorders involving the immune system.

In some embodiments, antigen binding constructs that bind the CD3 antigen can be antibodies, minibodies and/or other fragments of antibodies such as scFv. Some non-limiting embodiments of antigen binding constructs against CD3 are shown in FIGS. 33, 36D, 69.

In some embodiments, the antigen binding construct can be used as a therapeutic without linkage to another molecule such as a toxin (see, for example, Chatenoud, L. et al., "CD3-specific antibodies: a portal to the treatment of autoimmunity," Nat. Rev. Immunol., Vol. 7, No. 8, pp. 622-632, 2007). Such antigen binding constructs can also be useful for modulating the biologic activity associated with CD3 expression on immune cells to treat a variety of diseases including cancer, diabetes, autoimmune and inflammatory conditions. In some embodiments, the antigen binding construct alone can be used as an immunosuppressant and shows activity to inhibit CD3 signaling.

The CD3 antigen binding constructs disclosed herein can also be used as a therapeutic antigen binding construct, for example to modulate immune system reaction by neutralizing T cells via the CD3 epsilon domain of the TCR complex and by upregulating T regulatory cells via upregulation of FOXP3 (Saruta, M. et al., 2007). Such therapeutics have utility in treating not only tissue/organ allograft transplants but also autoimmune diseases such as Rheumatoid Arthritis, Multiple Sclerosis, Type 1 Diabetes, and Lupus Erythematosus to name a few.

In some embodiments an antigen binding construct, such as a minibody, can contain one or more CDRs from the variable heavy or light regions of Teplizumab.

In some embodiments, one or more of the antigen binding constructs provided herein can be combined with other immune cell targeting agents such as antibodies directed to OX40, CD134, CD40, CD154, CD80, CD86, ICOS, CD137 and/or IL-1 receptor antagonists. In some embodiments, the minibody directed to CD3 decreases an immune response and no additional therapeutic agent need be conjugated to the antigen binding construct. Thus, in some embodiments, minibodies are provided for the treatment of autoimmune diabetes or other autoimmune conditions that involve T cells that are not conjugated to or involve a therapeutic agent.

In some embodiments, the CD3 antigen binding constructs can be used as a therapeutic antigen binding construct to modulate immune system reaction by stimulating and tolerizing T cells via the CD3 epsilon domain of the TCR complex and/or by upregulating T regulatory cells via upregulation of FOXP3 (Saruta, M. et al., 2007) Such therapeutics can be useful in treating not only tissue/organ allograft transplants but also autoimmune diseases such as Rheumatoid Arthritis, Multiple Sclerosis, Type 1 Diabetes, Lupus Erythematosus, etc.

In some embodiments, the antigen binding construct can be used as a therapeutic without linkage to another molecule such as a toxin (see, for example, Chatenoud, L. et al., 2007). Such antigen binding constructs can also be useful for modulating the biologic activity associated with CD3 expression on immune cells to treat a variety of diseases including cancer, diabetes, autoimmune and inflammatory conditions. In some embodiments, the antigen binding construct alone can be used as an immunosuppressant and shows activity to inhibit CD3 signaling.

Without being limited to any one theory, in some embodiments, a bispecific antigen binding construct binds to the target on the target positive cell, and binds to the first antigen (which can be different from CD3) on the first cell, and thus brings the target positive cell in proximity to the first cell. For example, a CD3+ cell can be brought into proximity of a cancer cell, and can facilitate an immune response against that cancer cell.

In some embodiments, the minibody can be conjugated to a therapeutic agent for the treatment of the CD3 dependent disorder.

The subject can have any of a number of CD3 dependent disorders, which, for example, can be Rheumatoid Arthritis, Multiple Sclerosis, Type 1 Diabetes or Lupus Erythematosus.

In some embodiments, an antigen binding construct as provided herein allows for significant decrease in undesirable side effects, including, but not limited to, pro-inflammatory cytokine release, T cell activation, and/or cell proliferation.

In some embodiments, a method of treatment is provided whereby the subject can benefit from the application of CD3 directed antigen binding constructs, but rather than a full length construct, a minibody is instead administered, so as to result in a lower stimulation of immune cell activation after binding of the antigen binding construct to CD3 in vivo.

In some embodiments, the amount of the minibody in a pharmaceutical composition is greater than the amount that could otherwise be administered for a full length construct (for example, full length OKT3). In some embodiments, the amount administered would induce a cytokine storm in the subject, if the amount had been administered as a full length construct. In some embodiments, the amount that can be administered without resulting in a cytokine storm or in cytokine release syndrome (CRS), is at least 10 micrograms/m2, for example, at least 10, 17, 20, 30, 40, 50, 60, 70, 80, 90, 100, 200, 300, 400, 500, 600, 700, 800, 900, or at least 1000 micrograms/$m^2$ of the minibody format can be administered. In some embodiments, this amount will not result in cytokine release syndrome. In some embodiments, this amount will not result in Grade 1 and/or Grade 2 cytokine release syndrome. In some embodiments, this amount will not result in one or more of the following symptoms: rash, headache, nausea, vomiting, and/or chills/rigors/pyrexia. In some embodiments, these symptoms, which would normally occur on Day 1 or Day 5 or 6 of dosing if a full length antibody is used, will not be present if a minibody is employed.

In some embodiments, a method is provided for the treatment of an individual in need of a CD3 blocking therapy, and wherein the individual is also at risk of developing and/or experiencing a cytokine storm. In some embodiments, the method comprises administering to the subject at risk of experiencing a cytokine storm a minibody construct of a full length antibody; however, the minibody format will allow for a reduction in the intensity of any immune cell activation that would otherwise occur, had a full length antibody been administered to the subject. In some embodiments, the minibody can share the same CDRs (or similar CDRs) and/or the same heavy and light chain variable regions (or similar heavy and light chain variable regions). In some embodiments, the administration of the minibody allows for lower stimulation of immune cell activation after binding to CD3 occurs. In some embodiments, the administration of the minibody allows for a reduction in the level of cytokines released after the binding to CD3 occurs. In some embodiments, the administration of the minibody allows for lower amounts of activation to occur following the binding to CD3, than if a full length construct had been employed.

In some embodiments, one can administer a CD3 therapy without having to administer a counter therapy, wherein the counter therapy would be designed to reduce or block a cytokine storm. In some embodiments, this comprises administering a minibody antigen binding construct to the subject, instead of a full length construct.

In some embodiments, a method of reducing an intensity and/or likelihood of a cytokine storm is provided, the method can include identifying a subject who is to receive an antigen binding construct that is to bind CD3, and administering to the subject an effective amount of a minibody that binds to CD3. In some embodiments, the construct is one or more of those provided herein.

As described herein, the ability to reduce and/or avoid a cytokine storm (or other aspect, such as reducing activation and/or proliferation) can be especially relevant for antigen binding constructs that bind to CD3. In some embodiments, the process (e.g., using a minibody format) to avoid such issues can be employed for other target proteins, for example, any target protein for which the binding of an antibody to the target results in a cytokine storm or activation/proliferation. In some embodiments, the method can be employed to allow one to avoid inappropriate and/or damaging activation in a subject, in which the activation occurs in response to a bivalent antigen binding protein. In some embodiments, rather than a CD3 antigen binding protein, one can employ a CD28 antigen binding protein (e.g., minibody) that binds to CD28).

In some embodiments, the use of a CD3 minibody allows for a subject to receive adequate levels of the antigen binding construct to allow for treatment of a CD3 dependent disorder. In some embodiments, the subject can receive the CD3 binding molecules without also and/or subsequently having to receive insulin injections. In some embodiments, the use of a CD3 minibody construct allows for one to dampen a CD3 driven response without destroying too many B cells in the process. In some embodiments, the activation/proliferation that is reduced includes activation and/or proliferation of a T cell and/or a Natural Killer (NK) cell.

In some embodiments, providing an antigen binding construct to a subject in need comprises providing an effective amount of an antigen binding construct to CD3, wherein said antigen binding construct binds to CD3, but does not result in a significant increase in an amount of at least one of cytokine release, activation, or proliferation.

In some embodiments, a method of administering a therapeutic agent that binds CD3 on an immune cell is provided. The method comprises providing an antigen binding construct as provided herein (e.g., any of the minibodies to CD3) to a subject in need of lowering an amount of CD3. The antigen binding construct binds to CD3; however, as shown by the data provided herein, the antigen binding construct does not result in a significant amount of an increase in at least one of cytokine release, activation, or proliferation. In some embodiments, the lowering of CD3 denotes a lowering of the amount of free CD3 protein available. In some embodiments, the lowering of CD3 denotes the lowering of cells expressing CD3 protein.

In some embodiments, the construct does not result in a cytokine storm at a level that would be unacceptably detrimental to the subject.

In some embodiments, a method of treating a subject having a CD3 dependent disorder is provided. The method comprises providing to the subject an effective amount of an antigen binding construct. The antigen binding construct is a minibody that binds to CD3. In some embodiments, the antigen binding construct is conjugated to a therapeutic agent. In some embodiments, the antigen binding construct comprises a bivalent arrangement comprising a first binding site and a second binding site, wherein the first binding site binds to CD3, and wherein the second binding site binds to CD3. The effective amount is a Molar amount that, had the antigen binding construct been administered in a different format—in particular in the full antibody format (for example OKT3), the Molar amount would induce an cytokine storm at an intensity that would make it unacceptable for therapeutic purposes. However, this same Molar amount, when the antigen binding construct is a minibody, is still effective for the CD3 based therapy, but does not induce a cytokine storm at unacceptable levels.

In some embodiments, as the present constructs can be used for therapies, even though they are bivalent and bind to CD3, therapeutic constructs of CD3 antigen binding constructs can be employed. In some embodiments, an antigen binding construct that binds to CD3 in vivo, but does not result in a significant amount of at least one of cytokine release, activation, or proliferation is provided.

The term "CD3 dependent disorder" includes rheumatoid arthritis, multiple sclerosis, type 1 diabetes, lupus erythematosus, inflammatory bowel disease, diabetes, organ transplant rejection, autoimmune diseases, allergies and other disorders where T and/or Natural Killer (NK) cells play a role in the pathology.

A "cytokine storm," also known as a "cytokine cascade" or "hypercytokinemia" is a potentially fatal immune reaction that involves of a positive feedback loop between cytokines and immune cells, with highly elevated levels of various cytokines. Symptoms of a cytokine storm are high fever, swelling and redness, extreme fatigue and nausea. In some cases the immune reaction may be fatal. Typically, some level of cytokine release is acceptable and necessary for instance when fighting an infection. When one has fever chills associated with flu, such symptoms are the result of the immune system fighting the virus so such levels are acceptable and are not a "cytokine storm". However, when the activation arm is overstimulated and not balanced by an inhibitory signal, these cytokines can lead to organ and tissue damage and ultimately death. In some embodiments, the constructs provided herein can be useful for avoiding and/or minimizing cytokine release syndrome, and thus, can be applied to situations where anti-T cell full length antibodies might otherwise be used. In some embodiments, any of the methods provided herein directed to cytokine storms can also be applied to cytokine release syndrome.

In some embodiments, the subject has an inflammatory and/or autoimmune condition. In some embodiments, the condition is selected from at least one of rheumatoid arthritis, multiple sclerosis, type 1 diabetes, or lupus erythematosus.

In some embodiments, the cytokines are those that are involved in cytokine storms induced from full length OKT3 antibody administration. In some embodiments, the cytokines include at least one of IFNγ, IL-2, TNF-α, or IL-17.

In some embodiments, a minibody that binds to CD3 is provided. The minibody comprises a polypeptide that comprises a single-chain variable fragment (scFv) that binds to CD3, the scFv comprises a variable heavy ($V_H$) domain linked a variable light ($V_L$) domain; and a variant hinge region comprising at least three cysteines on each strand of the hinge. In some embodiments, the minibody further comprises a human IgG $C_H3$ sequence. In some embodiments, the minibody further comprises a detectable marker selected from the group consisting of a radioactive substance, a dye, a contrast agent, a fluorescent compound, a bioluminescent compound, an enzyme, an enhancing agent, and a nanoparticle.

In some embodiments, a nucleic acid encoding an antibody of any of the embodiments described herein is provided. In some embodiments, a cell line producing any of the minibody embodiments described herein is provided. In some embodiments, a kit comprising any of the embodiments of the minibody described herein and a detectable marker are provided.

In some embodiments, a method of detecting the presence or absence of CD3 is provided. The method comprises: applying any of the minibody embodiments provided herein to a sample; and detecting a binding or an absence of binding of the antigen binding construct thereof to CD3. In some embodiments of the method, the minibody comprises a detectable marker selected from the group consisting of a radioactive substance, a dye, a contrast agent, a fluorescent compound, a bioluminescent compound, an enzyme, an enhancing agent, and a nanoparticle. In some embodiments of the method, applying the minibody comprises administering the minibody to a subject. In some embodiments of the method, detecting binding or absence of binding of the minibody thereof to target antigen comprises positron emission tomography. In some embodiments, the method further comprises applying a secondary antibody or fragment thereof to the sample, wherein the secondary antibody or fragment thereof binds specifically to the minibody. In some embodiments of the method, the minibody thereof is incubated with the sample for no more than 1 hour.

In some embodiments, a method of targeting a therapeutic agent to CD3 is provided. The method comprises administering to a subject any of the embodiments of the minibody provided herein, wherein the minibody is conjugated to a therapeutic agent.

In some embodiments, a method of targeting a T lymphocyte cell expressing CD3 in a subject in need thereof is provided. The method comprises administering to the subject a minibody of any one of the embodiments provided herein. In some embodiments, a method of neutralizing a T lymphocyte cell expressing CD3 is provided. In some embodiments, the subject has at least one of anergic CD3 T cells, dysfunctional CD3 T cells, auto-reactive CD3 T cells, over-reactive CD3 T cells, inhibitory CD3 T cells, mislocalized CD3 T cells, or CD3 T cell lymphoma. In some embodiments, the subject has CD3 T cells associated with at least one of rheumatoid arthritis, multiple sclerosis, diabetes, systemic lupus erythematosus, autoimmune, inflammatory condition, signaling defect, or co-stimulatory defect.

In some embodiments, an antibody that binds to CD3 is provided. The antibody comprises a hinge region, wherein the hinge region comprises at least one of the following: a) a peptide sequence of SEQ ID NO: 1 ($X_{n1}CX_{n2}X_{n3}CX_{n4}X_{n5}C$), wherein $X_{n1}$ can be any amino acid that does not form a covalent crosslinking bond, wherein $X_{n2}$ is one of: A, R, N, D, E, Q, G, H, I, L, K, M, F, P, S, T, W, Y, or V, wherein $X_{n3}$ can be any amino acid, wherein $X_{n4}$ can be any amino acid, and wherein $X_{n5}$ can be any amino acid; b) a peptide sequence of SEQ ID NO: 2 ($X_{n1}X_{n2}X_{n3}X_{n4}X_{n5}$ $X_{n6}CX_{n7}X_{n8}CX_{n9}X_{n10}C$), wherein $X_{n1}$ can be any amino acid that does not form a covalent crosslinking bond with another identical amino acid, wherein $X_{n2}$ can be any amino acid, wherein $X_{n3}$ can be any amino acid, wherein $X_{n4}$ can be any amino acid, wherein $X_{n5}$ can be any amino acid, wherein $X_{n6}$ can be any amino acid, wherein $X_{n7}$ can be any amino acid, wherein $X_{n8}$ can be any amino acid, wherein $X_{n9}$ can be any amino acid, and wherein $X_{n10}$ can be any amino acid (SEQ ID NO: 208); c) a core hinge sequence of at least one of: CVECPPCP (SEQ ID NO: 57), CPPCPPC (SEQ ID NO: 52), or CPPCPPCPPC (SEQ ID NO: 54), linked to an upper hinge sequence of ELKTPLGDTTHT (SEQ ID NO: 48); or d) an upper hinge region that comprises no amino acids capable of crosslinking with a corresponding amino acid, and a core hinge region connected to a C-terminus of the upper hinge region, wherein the core hinge region comprises at least three cysteines. In some embodiments, the antibody is a full length antibody. In some embodiments, the antibody is a minibody. In some embodiments of the antibody, apart from the hinge region, the antibody comprises a humanized amino acid sequence.

In some embodiments, the antibody comprises: a HCDR1 of the HCDR1 in Table 8 SEQ ID NO: 174; a HCDR2 of the HCDR2 in Table 8 SEQ ID NO: 175; a HCDR3 of the HCDR3 in Table 8 SEQ ID NO: 176; a LCDR1 of the LCDR1 in Table 8 SEQ ID NO: 177; a LCDR2 of the LCDR2 in Table 8 SEQ ID NO: 97; and a LCDR3 of the LCDR3 in Table 8 SEQ ID NO: 178 for CD3.

In some embodiments, the antibody comprises: a HCDR1 of the HCDR1 in FIG. 65B or 65C; a HCDR2 of the HCDR2 in FIG. 65B or 65C; a HCDR3 of the HCDR3 in FIG. 65B or 65C; a LCDR1 of the LCDR1 in FIG. 65B or 65C; a LCDR2 of the LCDR2 in FIG. 65B or 65C; and a LCDR3 of the LCDR3 in FIG. 65B or 65C.

In some embodiments, antigen binding constructs that bind the CD3 antigen can be antibodies, minibodies and/or other fragments of antibodies such as scFv. Some non-limiting embodiments of antigen binding constructs against CD3 are shown in FIGS. 65B and 65C.

In some embodiments, the minibody comprises: a HCDR1 of the HCDR1 in FIG. 65B or 65C; a HCDR2 of the HCDR2 in FIG. 65B or 65C; a HCDR3 of the HCDR3 in FIG. 65B or 65C; a LCDR1 of the LCDR1 in FIG. 65B or 65C; a LCDR2 of the LCDR2 in FIG. 65B or 65C; and a LCDR3 of the LCDR3 in FIG. 65B or 65C. In some embodiments of the minibody provided herein the variable heavy ($V_H$) domain and the variable light ($V_L$) domain are human sequences.

In some embodiments, a nucleic acid encoding the hinge region of any of the antibody embodiments described herein is provided. In some embodiments of the nucleic acid, apart from the sequence encoding the hinge region, the nucleic acid comprises a human sequence. In some embodiments, a cell line expressing the antibody encoded by the nucleic acid is provided.

In some embodiments, a method of manufacturing the antibody of any of the embodiments described herein is provided. The method comprises expressing the antibody in a cell line.

In some embodiments, a method of treating a condition in a subject in need thereof is provided, the method comprising administering to the subject the antibody of any of the embodiments provided herein.

Additional Embodiments

In some embodiments, the scFv or minibody have superior pharmacokinetic properties for diagnostic imaging. Current technology utilizes imaging with the intact antibody which requires significantly longer time (~7 days post-injection) to produce high contrast images due to the slow serum clearance of full length antibodies. The minibody provide the opportunity for same-day or next-day imaging. Each day is vital for patients with an aggressively progressing disease, and the ability to identify the proper therapeutic approach at an earlier time-point has the potential to improve patient survival. Same-day or next-day imaging also provides a logistical solution to the problem facing many patients who travel great distances to receive treatment/diagnosis since the duration of travel stays or the need to return one week later would be eliminated when imaging with minibody versus full length antibodies. In some embodiments, exposure to lower doses of radiation allows one to image multiple times and follow disease progression over time.

Additionally, in some embodiments, the minibody component monomers contain hinge cysteine residues that form disulfide bonds. These covalently bound cysteine residues can be opened via mild chemical reduction to provide an active thiol groups for cysteine specific conjugation while maintaining the integrity of the dimeric minibody molecule. Current chemical conjugation methods include the following site specific platforms: Introducing a cysteine in F(ab)'2 region of antibody, e.g. Thio-Mabs (Roche); a cysteine in the position of 239 in the Fc (DISH-Mab, Seattle Genetics), non-natural amino-acids, such as keto-phenylalanine (Ambrx) for alkoxyamine linker formation, phenylalanineazidomethane (Sutro) for click-cycloaddition, glutamine in the Fc region for transglutaminase-dependent conjugation (Rinat-Pfizer). Hinge-cysteines in mAbs provide a chemical handle for non-site-specific thiol-conjugation chemistry. Conjugation to lysines is also non-site-specific or random and results in the highest heterogeneity. In some embodiments, one can introduce a site specific cysteine in the scFv, framework or another portion of the antigen binding construct provided herein.

The ability to image a patient's entire body for the presence of an antibody's target prior to and during treatment provides valuable information for personalized patient management. During the testing of an antibody therapy's safety and efficacy, it is useful to be able to select and test the treatment on patients who express the antibody's target as part of their disease progression.

In some embodiments, scFv or minibody diagnostic fragments matching available antibody therapies allow matching of the patient's disease state with the appropriate antibody therapy.

In some embodiments, a method of targeting a first antigen on a target molecule positive cell to is provided. The method can include applying a bispecific antigen binding construct to a sample. The bispecific antigen binding construct can include an antigen binding construct as described herein. The bispecific antibody or fragment thereof can include an antigen binding construct that binds to the first antigen, for example 1, 2, 3, 4, 5, or 6 CDR's, a scFv, or a monomer of a minibody. In some embodiments, the bispecific antibody includes 1, 2, or 3 HCDR's of an antigen binding construct as described herein, and/or 1, 2, or 3 LCDR's of an antigen binding construct as described herein. In some embodiments, the bispecific antigen binding construct includes a scFv of an antigen binding construct as described herein. In some embodiment, the bispecific antigen binding construct includes a $V_H$ or $V_L$ sequence as described herein. In some embodiments, the bispecific antigen binding construct includes a minibody monomer as described herein. In some embodiments, the bispecific antigen binding construct is applied to a sample in vivo, for example an organ or tissue of a subject. In some embodiments, the bispecific antigen binding construct is applied to an in vitro sample. Without being limited to any one theory, in some embodiments, the bispecific antigen binding construct binds to the target on the target positive cell, and binds to the first antigen (which can be different from the first target molecule) on the first cell, and thus brings the target positive cell in proximity to the first cell. For example, a first target molecule+ cell can be brought into proximity of a cancer cell, and can facilitate an immune response against that cancer cell. In some embodiments, a bispecific antigen binding construct comprised of a first target molecule and a second target molecule fragment can bring a cytotoxic T cell in proximity of an activated first target molecule expressing immune cell or first target molecule expressing tumor cell to result in killing of the target cell. In some embodiments, one can target any immune cells (NK or B cell or dendritic cell) and bridge it to an antigen expressing cell as determined by the specificity of the second scFv.

Minibody constructs contain antigen binding scFvs with variable linker lengths that can be in either $V_L$-$V_H$ or $V_H$-$V_L$ orientation. scFvs can be linked to any of 12 hinge sequences as described on Table 0.1. scFvs and appropriate hinges can be linked with $C_H3$ domains from IgG1, IgG2, IgG3, or IgG4 antibodies. In some embodiments, the first hinge cysteine that usually pairs with light chain in native IgG1, IgG2 and IgG3 antibodies should be mutated to a serine or alanine or other appropriate amino acid to prevent disulfide scrambling and/or concatamerization. To reduce the presence or reduce the formation of half-molecules and enhance stability in vivo, the hinge region should contain at least three cysteines to form at least three disulfide bonds with the other monomer. Three cysteines per strand in the hinge located at appropriate distances from one another are useful to allow for proper disulfide bond formation (Table 3). Three disulfide bonds in the hinge within the minibody located at appropriate distances from one another are useful for protein stability in vivo and clearance through liver rather than renal clearance. At least three disulfides (or more) in the hinge are beneficial for site specific conjugation of drugs, chelators or fluorescent dyes. Mbs constructed as described above retain similar affinity to parent antibodies. In some embodiments, involving the IgG1 construct, the first cys can be left intact and it does not seem too deleterious.

In some embodiments, the hinge of a minibody or a bispecific minibody comprising an upper hinge, a core hinge and a lower hinge can be generated by combining any one of the upper hinge, any one of the core hinge and any one of the lower hinge sequences as shown in Table 3.

In some embodiments, the first cysteine residue in the hinge can be changed to any amino acid. In some embodiments, one cysteine residue in the upper hinge can be changed to any amino acid. In some embodiments, one cysteine residue in the core hinge can be changed to any amino acid. In some embodiments, two cysteine residues in the core hinge can be changed to any amino acid. In some embodiments, one cysteine residue in the upper hinge and one cysteine residue in the core hinge can be changed to any amino acid. In some embodiments, one cysteine in the upper hinge and two cysteine residues in the core hinge can be changed to any amino acid.

The sequences of the constructs for the examples are discussed in the example sections below as appropriate and are provided in Table 0.2 as well.

In addition to the items above, the following particular options are set forth:

1. An amino acid hinge region comprising a sequence of SEQ ID NO: 1 ($X_{n1}CX_{n2}X_{n3}CX_{n4}X_{n5}C$), wherein $X_{n1}$ can be any amino acid that does not naturally form a covalent crosslinking bond, wherein $X_{n2}$ is one of: A, R, N, D, E, Q, G, H, I, L, K, M, F, P, S, T, W, Y, or V, wherein $X_{n3}$ can be any amino acid, wherein $X_{n4}$ can be any amino acid, and wherein $X_{n5}$ can be any amino acid.

2. The amino acid hinge region of option 1, wherein $X_{n1}$ does not form a covalent crosslinking bond with another amino acid (SEQ ID NO: 191).

3. The amino acid hinge region of any one of options 1-2, wherein $X_{n1}$ is not a cysteine (SEQ ID NO: 192).

4. The amino acid hinge region of any one of options 1-3, wherein $X_{n1}$ is one of: A, R, N, D, E, Q, G, H, I, L, K, M, F, P, S, T, W, Y, or V (SEQ ID NO: 193).

5. The amino acid hinge region of any one of options 1-4, wherein $X_{n2}$ is P, V, or E (SEQ ID NO: 194).

6. The amino acid hinge region of any one of options 1-5, wherein $X_{n2}$ is P or V (SEQ ID NO: 195).

7. The amino acid hinge region of any one of options 1-6, wherein $X_{n4}$ is P, V, or E (SEQ ID NO: 196).

8. The amino acid hinge region of any one of options 1-7, wherein $X_{n4}$ is P or V (SEQ ID NO: 197).

9. The amino acid hinge region of any one of options 1-8, wherein $X_{n3}$ is P or E (SEQ ID NO: 198).

10. The amino acid hinge region of any one of options 1-9, wherein $X_{n5}$ is P or E (SEQ ID NO: 199).

11. The amino acid hinge region of option 9, wherein $X_{n3}$ is P or E (SEQ ID NO: 200).

12. The amino acid hinge region of any one of options 1-11, wherein $X_{n2}X_{n3}$ is VE (SEQ ID NO: 201).

13. The amino acid hinge region of any one of options 1-2, wherein $X_{n2}X_{n3}$ is PP (SEQ ID NO: 202).

14. The amino acid hinge region of any one of options 1-13, wherein $X_{n4}X_{n5}$ is VE (SEQ ID NO: 203).

15. The amino acid hinge region of any one of options 1-14, wherein $X_{n4}X_{n5}$ is PP (SEQ ID NO: 204).

16. The amino acid hinge region of any one of options 1-12 or 15, wherein $X_{n2}X_{n3}$ is VE and $X_{n4}X_{n5}$ is PP (SEQ ID NO: 205).

17. The amino acid hinge region of any one of options 1-11, 13, or 14, wherein $X_{n2}X_{n3}$ is PP and $X_{n4}X_{n5}$ is PP or VE (SEQ ID NO: 206).

18. The amino acid hinge region of any one of options 1-12, 14, or 17, wherein $X_{n2}X_{n3}$ is VE and $X_{n4}X_{n5}$ is VE or PP (SEQ ID NO: 207).

19. The amino acid hinge region of any one of options 1-18, further comprising an extension or lower hinge sequence C-terminal to the last cysteine in SEQ ID NO: 1.

20. The amino acid hinge region of option 19, wherein the extension or lower hinge sequence comprises at least one of S, G, A, P, or V.

21. The amino acid hinge region of any one of options 19-20, wherein the extension sequence comprises at least GGGSSGGGSG (SEQ ID NO: 59).

22. The amino acid hinge region of any one of options 1-21, comprising a linker sequence comprising at least APPVAGP (SEQ ID NO: 60).

23. The amino acid hinge region of any one of options 1-22, wherein the hinge region of option 1 is part of a core hinge region.

24. The amino acid hinge region of option 23, further comprising an upper hinge region adjacent to the core hinge region.

25. The amino acid hinge region of option 23, further comprising a lower hinge or extension region adjacent to the core hinge region.

26. The amino acid hinge region of option 25, further comprising an upper hinge region adjacent to the core hinge region.

27. The amino acid hinge region of any one of options 1-26, wherein $X_{n1}$ comprises a serine, a threonine, or an alanine (SEQ ID NO: 209).

28. The amino acid hinge region of any one of options 1-26, wherein $X_{n1}$ comprises a serine (SEQ ID NO: 210).

29. The amino acid hinge region of any one of options 1-26, wherein $X_{n1}$ comprises an alanine (SEQ ID NO: 211).

30. The amino acid hinge region of any one of options 1-28, wherein the amino acid hinge region comprises at least one of the following sequences: SCVECPPCP (SEQ ID NO: 56) or TCPPCPPC (SEQ ID NO: 166).

31. The amino acid hinge region of any one of options 1-30, wherein the amino acid hinge region comprises at least one of the following sequences: ERKSCVECPPCP (SEQ ID NO: 167), EPKSSDKTHT (SEQ ID NO: 46), and CPPCPPC (SEQ ID NO: 52).

32. The amino acid hinge region of any one of options 1-31, wherein the amino acid hinge region comprises at least one of the following sequences: ERKSCVECPPCPGGGSSGGGSG (SEQ ID NO: 34) or ERKSCVECPPCPAPPVAGP (SEQ ID NO: 33) or EPKSSDKTHTCPPCPPCGGGSSGGGSG (SEQ ID NO: 26) or EPKSSDKTHTCPPCPPCAPELLGGP (SEQ ID NO: 25).

33. An amino acid hinge region comprising a sequence of SEQ ID NO: 2 ($X_{n1}$ $X_{n2}$ $X_{n3}$ $X_{n4}X_{n5}$ $X_{n6}CX_{n7}X_{n8}CX_{n9}X_{n10}C$), wherein $X_{n1}$ can be any m amino acids, wherein m is any number of amino acids of any type, wherein $X_{n2}$ can be any amino acid, wherein $X_{n3}$ can be any amino acid, wherein $X_{n4}$ can be any amino acid, wherein $X_{n5}$ can be any amino acid, wherein $X_{n6}$ can be any amino acid other than a cysteine, wherein $X_{n7}$ can be any amino acid, wherein $X_{n8}$ can be any amino acid, wherein $X_{n9}$ can be any amino acid, and wherein $X_{n10}$ can be any amino acid.

34. The amino acid hinge region of option 33, wherein $X_{n1}$ is not a cysteine (SEQ ID NO: 213).

35. The amino acid hinge region of any one of options 33-34, wherein $X_{n2}$ is not a cysteine (SEQ ID NO: 214).

36. The amino acid hinge region of any one of options 33-35, wherein $X_{n2}$ is a D (SEQ ID NO: 215).

37. The amino acid hinge region of any one of options 33-36, wherein $X_{n3}$ is a K (SEQ ID NO: 216).

38. The amino acid hinge region of any one of options 33-37, wherein $X_{n4}$ is a T (SEQ ID NO: 217).

39. The amino acid hinge region of any one of options 33-38, wherein $X_{n5}$ is a H (SEQ ID NO: 218).

40. The amino acid hinge region of any one of options 33-39, wherein $X_{n6}$ is a T (SEQ ID NO: 219).

41. The amino acid hinge region of any one of options 33-40, wherein $X_{n7}$ is a P or a V (SEQ ID NO: 220).

42. The amino acid hinge region of any one of options 33-41, wherein $X_{n8}$ is a P or a E (SEQ ID NO: 221).

43. The amino acid hinge region of any one of options 33-42, wherein $X_{n9}$ is a P or a V (SEQ ID NO: 222).

44. The amino acid hinge region of any one of options 33-43, wherein $X_{n10}$ is a P or a E (SEQ ID NO: 223).

45. The amino acid hinge region of option 45, further comprising a CXXC (SEQ ID NO: 224) or CXXC (SEQ ID NO: 225) motif that is positioned in front of $X_{n1}$.

46. The amino acid hinge region of option 46, further comprising a $X_{n11}X_{n12}C$ sequence immediately attached to the C-terminal cysteine in SEQ ID NO: 1, wherein $X_{n11}$ can be any amino acid, and wherein $X_{n12}$ can be any amino acid (SEQ ID NO: 244).

47. The amino acid hinge region of option 46, wherein $X_{n11}$ is a P or a V, and wherein $X_{n12}$ is a P or an E (SEQ ID NO: 227).

48. The amino acid hinge region of any one of options 33-47, wherein $X_{n1}$ is a serine, $X_{n2}$ is a D, $X_{n3}$ is a K, $X_{n4}$ is a T, $X_{n5}$ is a H, $X_{n6}$ is a T, $X_{n7}$ is a P, $X_{n8}$ is a P, $X_{n9}$ is a P, and $X_{n10}$ is a P (SEQ ID NO: 228).

49. The amino acid hinge region of any one of options 33-48, wherein the hinge region comprises at least one of the following sequences: CPPCPPC (SEQ ID NO: 52), CPPCVECPPC (SEQ ID NO: 53), or CPPCPPCPPC (SEQ ID NO: 54).

50. The amino acid hinge region of any one of options 33-49, wherein the hinge region comprises at least one of the following sequences: EPKSSDKTHTCPPCPPC (SEQ ID NO: 168), EPKSSDKTHTCPPCVECPPC (SEQ ID NO: 169), or EPKSSDKTHTCPPCPPCPPC (SEQ ID NO: 170).

51. The amino acid hinge region of any one of options 33-50, wherein the hinge region comprises at least one of the following sequences: EPKSSDKTH-TCPPCPPCGGGSSGGGSG (SEQ ID NO: 26), EPKSSDKTHTCPPCVECPPCGGGSSGGGSG (SEQ ID NO: 28), or EPKSSDKTHTCPPCPPCPPCGGGSSGGGSG (SEQ ID NO: 30).

52. An amino acid hinge region comprising:
a core hinge sequence of at least one of: CVECPPCP (SEQ ID NO: 57), CPPCPPC (SEQ ID NO: 52), or CPPCPPCPPC (SEQ ID NO: 54), or CPPCVECPPC (SEQ ID NO: 53) linked to;
an upper hinge sequence of ELKTPLGDTTHT (SEQ ID NO: 48) or EPKSSDKTHT (SEQ ID NO: 46).

53. An amino acid hinge region for an antibody comprising:
an upper hinge region that comprises no amino acids capable of crosslinking with a corresponding amino acid; and
a core hinge region connected to a C-terminus of the upper hinge region, wherein the core hinge region comprises at least three cysteines per strand.

54. The amino acid hinge region of any one of options 52-53, wherein the amino acid hinge region further comprises a lower hinge or extension region connected C-terminal to the core hinge region, wherein the lower hinge or extension sequence is at least one of: APPVAGP (SEQ ID NO: 60), APELLGGP (SEQ ID NO: 58), and/or GGGSSGGGSG (SEQ ID NO: 59).

55. The amino acid hinge region of any one of options 52-54, wherein the upper hinge region comprises no cysteines that crosslink within the upper hinge region.

56. The amino acid hinge region of any one of options 52-54, wherein the upper hinge region comprises no cysteines.

57. The amino acid hinge region of any one of options 52-54, further comprising a lower hinge or extension region.

58. The amino acid hinge region of any one of options 52-53, wherein the lower hinge or extension region comprises at least one of: GGGSSGGGSG (SEQ ID NO: 59) or APPVAGP (SEQ ID NO: 60) or APELLGGP (SEQ ID NO: 58).

59. The amino acid hinge region of any one of options 1-58, wherein when located within a minibody, and wherein when the minibody is administered to a human subject, clearance of the minibody from the subject occurs primarily through a liver.

60. The amino acid hinge region of any one of options 1-58, wherein, when located within a minibody, and wherein when the minibody is administered to a human subject, clearance of the minibody from the subject does not occur primarily through a kidney.

61. The amino acid hinge region of any one of options 1-58, wherein the hinge region is within an antibody.

62. The amino acid hinge region of any one of options 1-58, wherein the hinge region is within an antibody binding fragment.

63. The amino acid hinge region of any one of options 1-60, wherein the hinge region is within a minibody.

64. The amino acid hinge region of any one of options 1-58, wherein the hinge region is within a monospecific antibody.

65. The amino acid hinge region of any one of options 1-64, wherein the hinge region comprises at least three cysteines per strand.

66. The amino acid hinge region of any one of options 1-64, wherein the hinge region comprises at least four cysteines per strand.

67. The amino acid hinge region of any one of options 1-64, wherein the hinge region comprises at least five cysteines per strand.

68. The amino acid hinge region of any one of options 61-63, wherein cysteines are distributed throughout the amino acid hinge region in a repeating CXX or CXY motif.

69. The amino acid hinge region of any one of options 1-58, wherein the hinge region is within a bispecific antibody.

70. The amino acid hinge region of option 69, wherein the bispecific antibody is assembled in a 1:1 ratio.

71. The amino acid hinge region of option 69, wherein the bispecific antibody comprises an antibody fragment.

72. The amino acid hinge region of option 71, wherein the bispecific antibody is a minibody.

73. A pharmaceutical composition comprising the amino acid hinge region of any one of options 1-72, wherein less than 5% aggregation of an antibody is present in the composition.

74. A pharmaceutical composition comprising the amino acid hinge region of any one of options 1-72.

75. The pharmaceutical composition of any one of options 73-74, wherein at least 1 microgram to 100 mg of the antibody is present.

76. A minibody comprising a core hinge region, wherein the core hinge region comprises at least three cysteines per strand forming at least three disulfide bonds within the core hinge region.

77. The minibody of option 76, wherein the first residue of the core region is a serine.

78. The minibody of any one of options 76-77, wherein the core hinge region comprises SCVECPPCP (SEQ ID NO: 56).

79. A minibody comprising a sequence $X_{n1}CX_{n2}X_{n3}CX_{n4}X_{n5}C$ (SEQ ID NO: 3), wherein SEQ ID NO: 3 is located as the core hinge region of the minibody, and wherein $X_{n1}$ can be any amino acid or no amino acid, $X_{n2}$ can be any amino acid, $X_{n3}$ can be any amino acid, $X_{n4}$ can be any amino acid, and $X_{n5}$ can be any amino acid.

80. The minibody of option 79, wherein $X_{n1}$ is any amino acid other than a cysteine (SEQ ID NO: 229).

81. The minibody of option 79, wherein $X_{n2}$ is a serine (SEQ ID NO: 229).

82. A variant minibody hinge comprising:
a first altered amino acid position, wherein the first altered position is an amino acid that in a native antibody hinge would be a cysteine, and has been altered in the first altered position so that it does not form a disulfide bond; and
at least three cysteines per strand C-terminal to the first altered amino acid position.

83. The amino acid hinge region of any one of options 1-72, wherein the hinge region consists of SEQ ID NO: 1.

84. The amino acid hinge region of any one of options 1-72, wherein SEQ ID NO: 1 is a core hinge region, and wherein the core hinge region essentially consists of SEQ ID NO: 1.

85. The amino acid hinge region of option 84, wherein the core hinge region consists of SEQ ID NO: 1.

Example 1—Minibody Structure

The minibody is a bivalent, covalently bound homodimer of ~80 kDa. Each monomer (half-molecule) is comprised of a variable heavy ($V_H$) domain linked to the corresponding variable light ($V_L$) domain by an approximate 15-18 amino acid Gly-Ser-rich linker sequence. Each single-chain variable fragment (scFv) is linked to a human IgG $C_H3$ domain by a hinge sequence.

The sequences encompassing the disulfide bonds of the hinge are important and were designed to prevent undesirable disulfide scrambling with cysteine residues present in other regions of the protein as well as contain sufficient numbers of cysteine pairs to maintain dimer integrity in vivo and also as a possible site for site-specific conjugation.

To date most minibodies have been engineered using the native human IgG1 upper and core hinge regions with an extension sequence linked to the human IgG1 $C_H3$ domain as shown in FIG. 1. As outlined in the following examples, scFv variants with both orientations—$V_L$-$V_H$ (M1) and $V_H$—$V_L$ (M2)—were often evaluated for the various target molecules.

Engineering Based on Human IgG1

In previous hinges (e.g., γ1 EH1), the first cysteine in the hinge (FIG. 2 top) created problems resulted in protein heterogeneity as demonstrated by the intact mass analysis results using LC/MS. Despite the clear importance of cysteines in the hinge region, it was decided to mutate this cysteine to a serine, resulting in γ1 EH2 hinge (FIG. 2 bottom). However, it was determined that this hinge construct did not achieve certain desired aspects, as it appeared that the two disulfide bonds that were formed between the two remaining cysteine residues in the core hinge (FIG. 2 bottom) were not adequate to maintain dimer stability in vivo.

IgG2 Mbs to Overcome Problems with IgG1 Hinge Sequence

To address the newly introduced aspects noted above, the minibodies were further engineered. Engineered minibodies based on huIgG2 with an extension sequence provided a third cysteine in the core hinge (an additional cysteine over IgG1 native core hinge) to increase disulfide bonding and increase protein stability. HuIgG2 minibodies of IAB2M and IAB22M were engineered using human IgG2 (huIgG2) hinge sequence linked to the huIgG2 $C_H3$ domain.

In the native IgG2 upper and core hinge sequences combined with the extension sequence as the lower hinge (γ2 EH1) an increase in aggregation was observed. The reactive cysteine (FIG. 3 top; first cysteine of the hinge) was responsible for concatamer formation in IAB2M-γ2 EH1 format with huIgG2 native hinge (FIG. 3 top) as observed by SDS-PAGE analysis shown in FIG. 5A.

Thus, similar to what was done for the IgG1 hinge (γ1 EH1) the first cysteine in the hinge (that pairs with light chain) was mutated to serine resulting in IgG2 EH2 (γ2 EH2) (FIG. 3 bottom). Antigen binding constructs with this hinge (γ2 EH2) expressed well and had good stability in vivo. All three disulfide bonds in the core hinge formed properly as detected by mass spectrometry. Stability was demonstrated with both IAB2M and IAB22M constructs with γ2 EH2.

Further engineered huIgG2 minibodies with the first cysteine altered to a serine and native upper and lower hinge sequence (γ2 NH2) was evaluated and the proteins were found to be stable in vivo (FIG. 4 bottom).

Example 2—In Vitro Data for IAB2M

Table 1 shows an overview of the IAB2M variants (SEQ ID NOS are shown in FIGS. 5B-5E). Additional embodiments of IAB2M variants are shown in FIGS. 47-53.

TABLE 1

| Name | Cys-Ser Hinge Mut | Remove Term Lys | N- to C-terminal (SEQ ID NOs) |
|---|---|---|---|
| IAB2M-γ1 EH1 | No | No | VL (SEQ ID NO: 13); linker (SEQ ID NO: 62); VH (SEQ ID NO: 14); full hinge (SEQ ID NO: 22) [upper hinge (SEQ ID NO: 45), core hinge (SEQ ID NO: 50), lower hinge (SEQ ID NO: 59)]; IgG1 CH3 (SEQ ID NO: 40 or SEQ ID NO: 41) |
| IAB2M-γ1 EH2 | Yes | Yes | VL (SEQ ID NO: 13); linker (SEQ ID NO: 62); VH (SEQ ID NO: 14); full hinge (SEQ ID NO: 24) [upper hinge (SEQ ID NO: 46), core hinge (SEQ ID NO: 50), lower hinge (SEQ ID NO: 59)]; IgG1 CH3 (SEQ ID NO: 40 or SEQ ID NO: 41) |
| IAB2M-γ2 EH1 | Yes | Yes | VL (SEQ ID NO: 13); linker (SEQ ID NO: 62); VH (SEQ ID NO: 14); full hinge (SEQ ID NO: 32) [upper hinge (SEQ ID NO: 47), core hinge (SEQ ID NO: 55), lower hinge (SEQ ID NO: 59)]; IgG2 CH3 (SEQ ID NO: 42) |
| IAB2M-γ2 EH2 | Yes | Yes | VL (SEQ ID NO: 13); linker (SEQ ID NO: 62); VH (SEQ ID NO: 14); full hinge (SEQ ID NO: 34) [upper hinge (SEQ ID NO: 47), core hinge (SEQ ID NO: 56), lower hinge (SEQ ID NO: 59)]; IgG2 CH3 (SEQ ID NO: 42) |

SDS-PAGE analysis (FIG. 5A) of IAB2M with hinge variants γ1 EH1, γ1 EH2 and γ2 EH1 and γ2 EH2 showed that the half molecule to dimer ratios were greatly improved (half molecule can be decreased from 20-30% to less than 1%) with mutation of the first hinge cysteine in the EH2 variants. The γ2 EH2 version had proper disulfide bonding and no concatemers compared to γ2 EH1 (SEQ IDS NOS. in FIGS. 5B-5E). Due to the presence of the additional cysteine in the core hinge (3 instead of 2), the γ2 EH2 hinge variant exhibited improved stability and had less half-molecules present compared to the γ1 EH2 hinge variant.

Figure 6A:
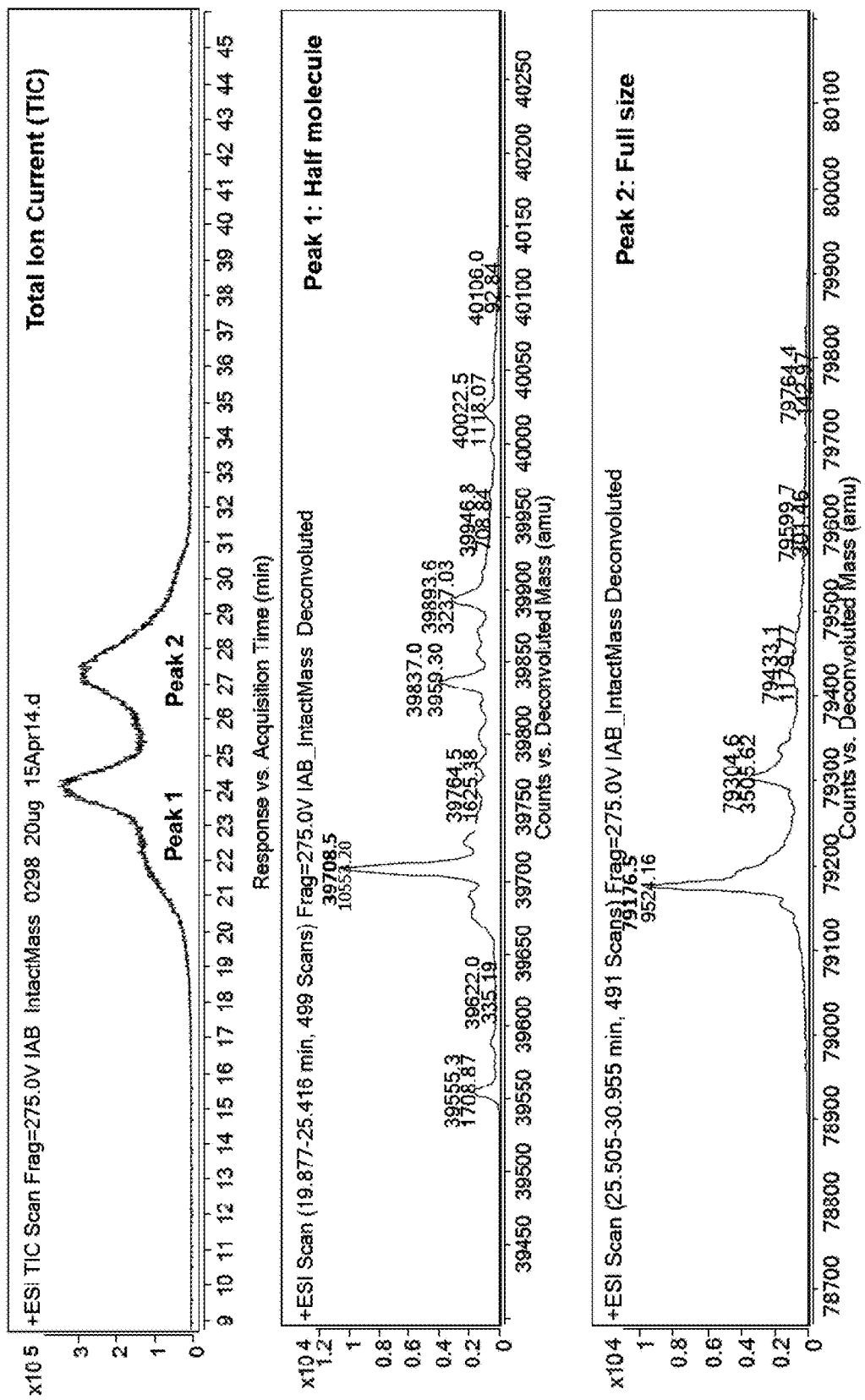
FIG. 6A shows intact mass analysis of IAB2M γ1 EH1 variant. Upper panel shows the total ion chromatogram under reverse phase conditions. Middle panel shows the deconvoluted intact masses confirming the presence of half molecules and the lower panel shows the full size masses that were identified.
Figure 6B:
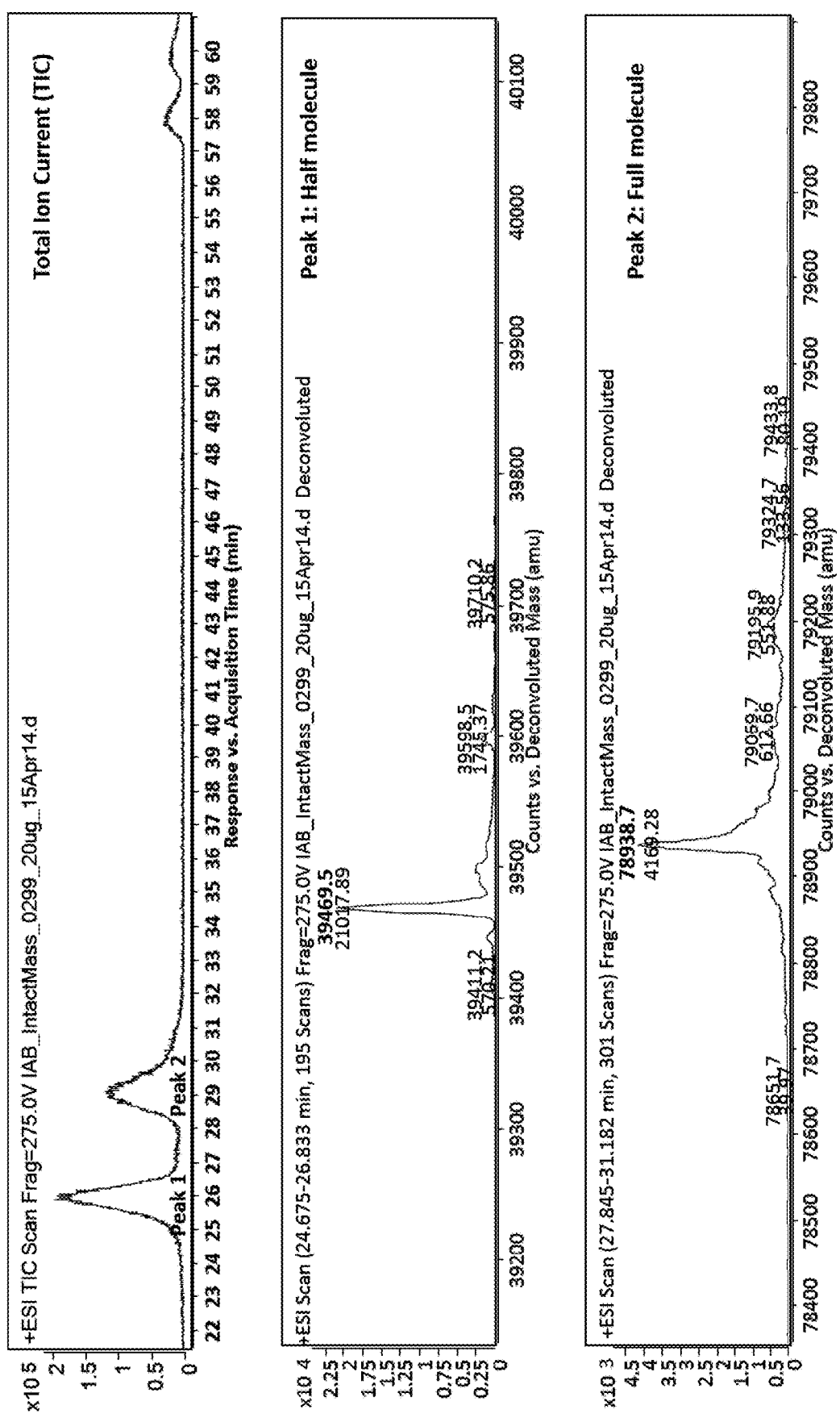
FIG. 6B shows intact mass analysis of IAB2M γ2 EH1 variant. Upper panel shows the total ion chromatogram under reverse phase conditions. Middle panel shows the deconvoluted intact masses confirming the presence of half molecules and the lower panel shows the full size molecular masses that were identified.
Figure 6C:
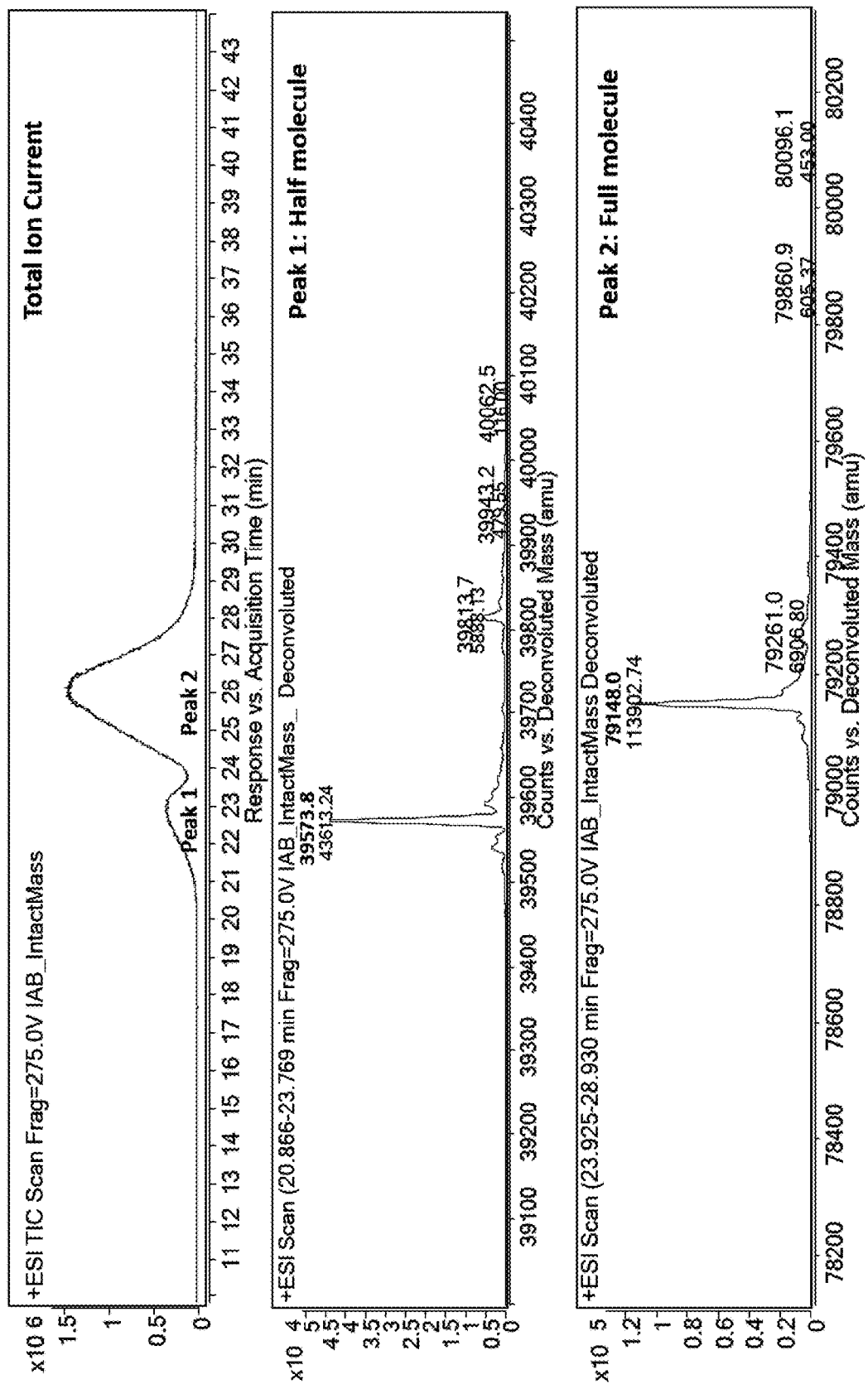
FIG. 6C shows intact mass analysis of IAB2M γ1 EH2 variant. Upper panel shows the total ion chromatogram under reverse phase conditions. Middle panel shows the deconvoluted intact masses confirming the presence of half molecules and the lower panel shows the full size molecular masses that were identified.
Figure 6D:
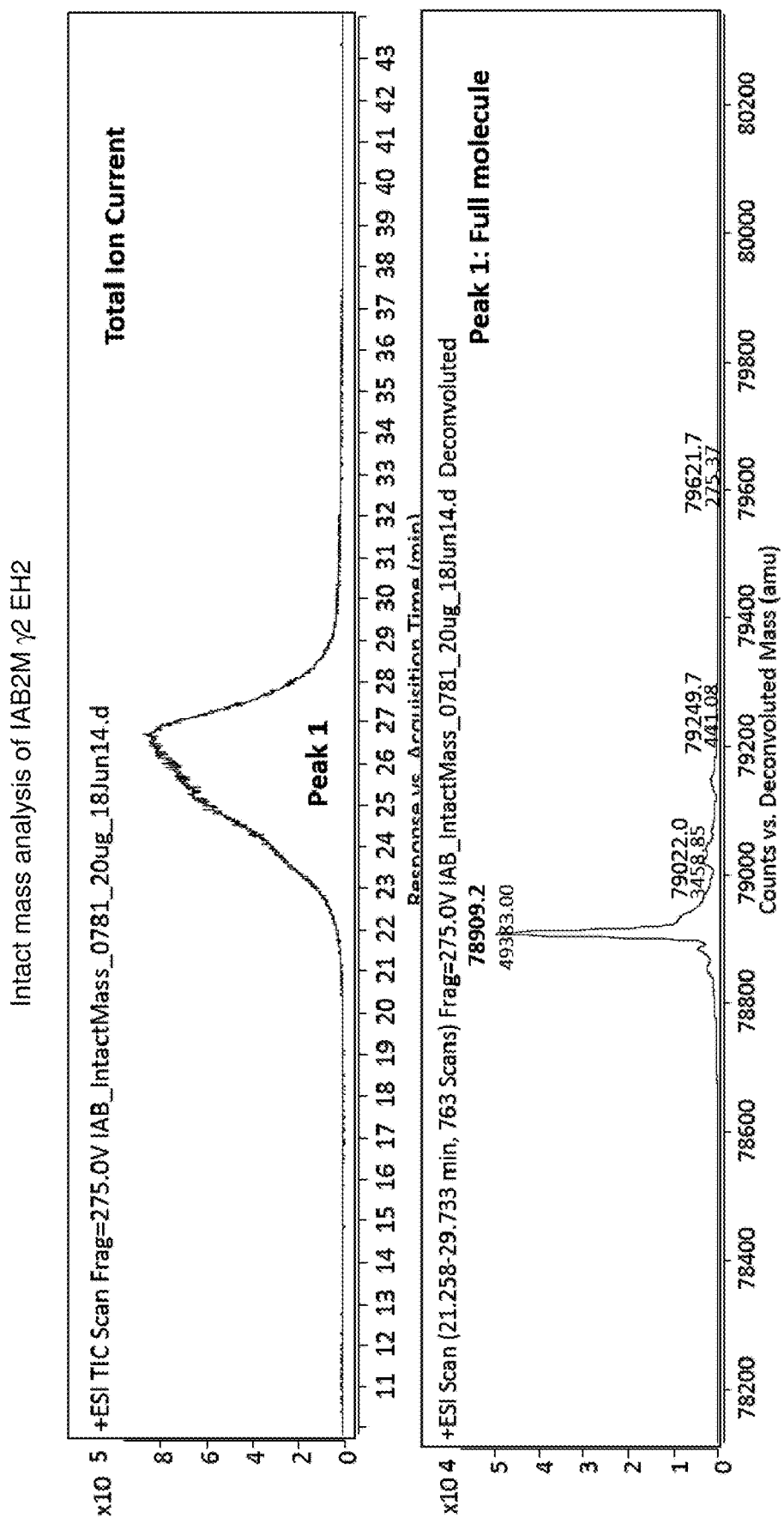
FIG. 6D shows intact mass analysis of IAB2M γ2 EH2 variant. Upper panel shows the total ion chromatogram. Lower panel shows the deconvoluted intact masses confirming the presence of the full-size mass molecules. No half molecules were detected.

Confirmation of the presence of half-molecules was performed by intact mass analysis. The protein samples were separated under reverse phase conditions using TSKgel Phenyl-5PW column (2×75 mm, Tosoh Biosciences) at 60° C. and analyzed by Agilent ESI-QTOF model 6538. FIG. 6A shows intact mass analysis of IAB2M γ1 EH1 variant. The total ion chromatograms of the separated half-molecule and full-size molecule are shown in the upper panel. The UV280 trace (not shown) was used for quantitation of the percent of half-molecules present in the minibody variant by peak integration. The deconvoluted masses were used for assignment and confirmed the identity of half molecules (Middle panel) and of the full size masses (Lower panel). FIG. 6B shows intact mass analysis of IAB2M γ2 EH1 variant. Upper panel shows the total ion chromatogram under reverse phase conditions. Middle panel shows the deconvoluted intact masses confirming the presence of half molecules and the lower panel shows the full size molecular masses that were identified. FIG. 6C shows intact mass analysis of IAB2M γ1 EH2 variant. Upper panel shows the total ion chromatogram under reverse phase conditions. Middle panel shows the deconvoluted intact masses confirming the presence of half molecules and the lower panel shows the full size molecular masses that were identified. FIG. 6D shows intact mass analysis of IAB2M γ2 EH2 variant. Upper panel shows the total ion chromatogram. Lower panel shows the deconvoluted intact masses confirming the presence of the full-size mass molecules. No half molecules were detected.

Figure 7A:
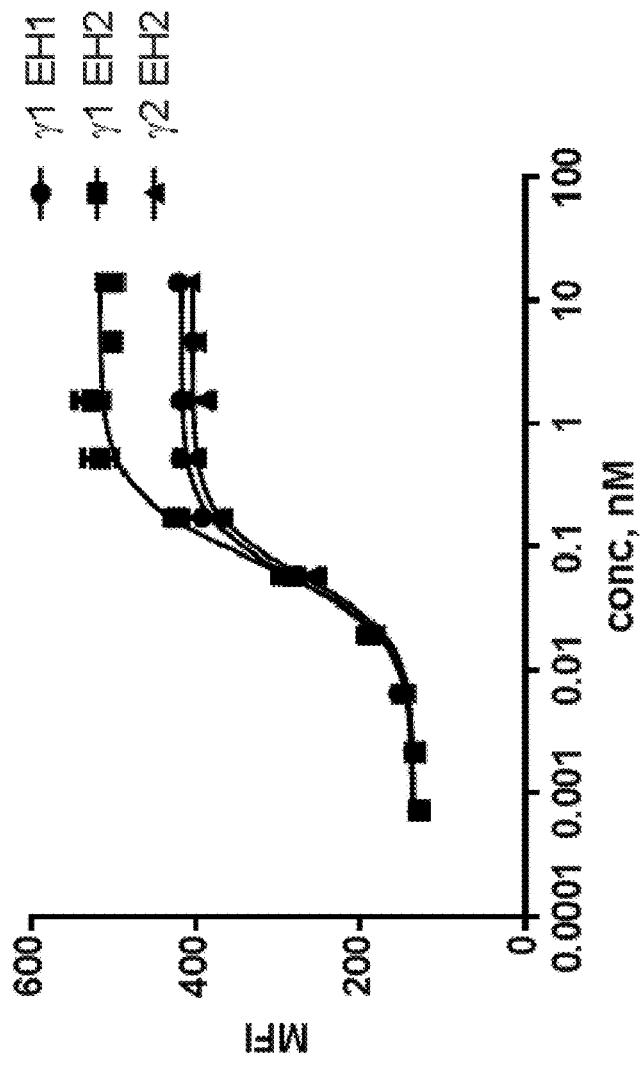
FIG. 7A shows binding curves and EC50 binding values of IAB2M engineered hinge variants determined by FACS using LNCaP-AR cells.
Figure 7B:
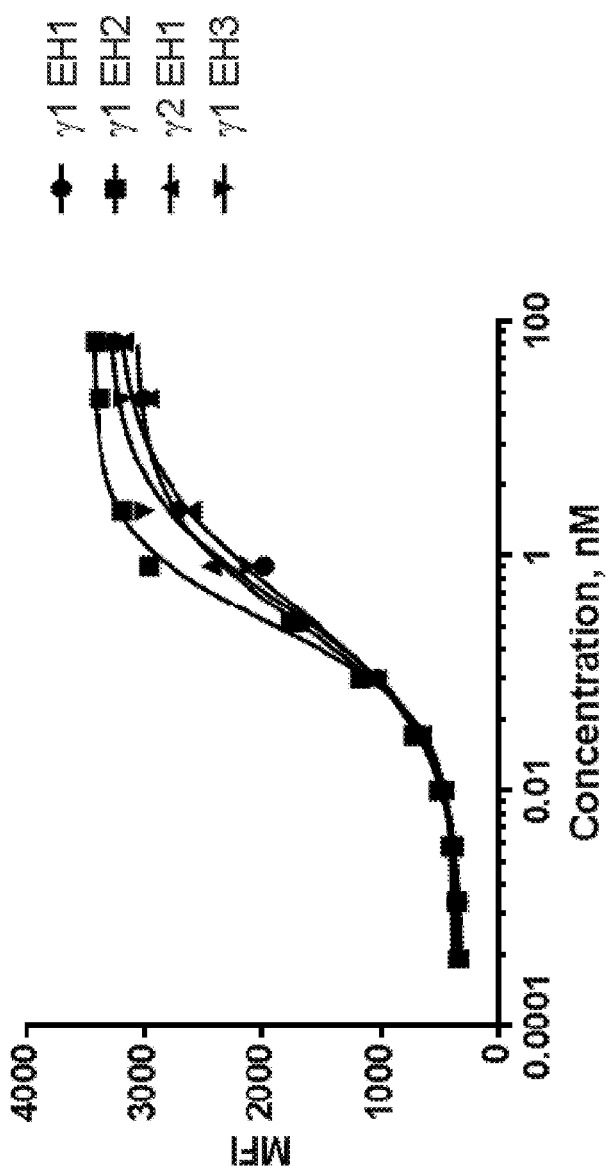
FIG. 7B shows binding curves and EC50 binding values of IAB2M engineered hinge variants determined by FACS using C4-2 XCL cells.

FAC analysis (FIGS. 7A and 7B) of IAB2M variants showed that changing the hinge from the previously used standard hinge, γ1 EH1, did not impact the binding affinity for target antigen expressed either on LNCap-AR cells (FIGS. 5B, 5C, 5D) or C4-2 XCL cells (FIGS. 5B, 5C, 5E, 7C).

For disulfide mapping to help understand the half-molecule formation, samples were prepared by denaturing the protein with 6 M guanidine HCl in TRIS (tris(hydroxymethyl)aminomethane) pH 7.5. To this, 4-vinylpyridine was added to a concentration of 30 mM followed by a 1 hr incubation in the dark to cap free cysteine. The solution was diluted to bring the concentration of guanidine to 1 M followed by digestion using trypsin/Lys-C. The digestion was allowed to proceed overnight at 37° C. The samples were frozen and dried down prior to separation. This was followed by LC/MS in which peptide mix was separated in 0.05% aqueous TFA in the gradient of 0.05% TFA in 90% acetonitrile using gradient on the Waters Xbridge BEH130 C18 4.6×150 mm column, and masses were identified using ESI-QTOF mass spectrometer 6538 (Agilent) in the positive mode and deconvoluted using the Agilent MassHunter™ software. Disulfide-containing peptides identified within IAB2M γ1 EH1 dimer is shown in FIG. 8.

Figure 9:
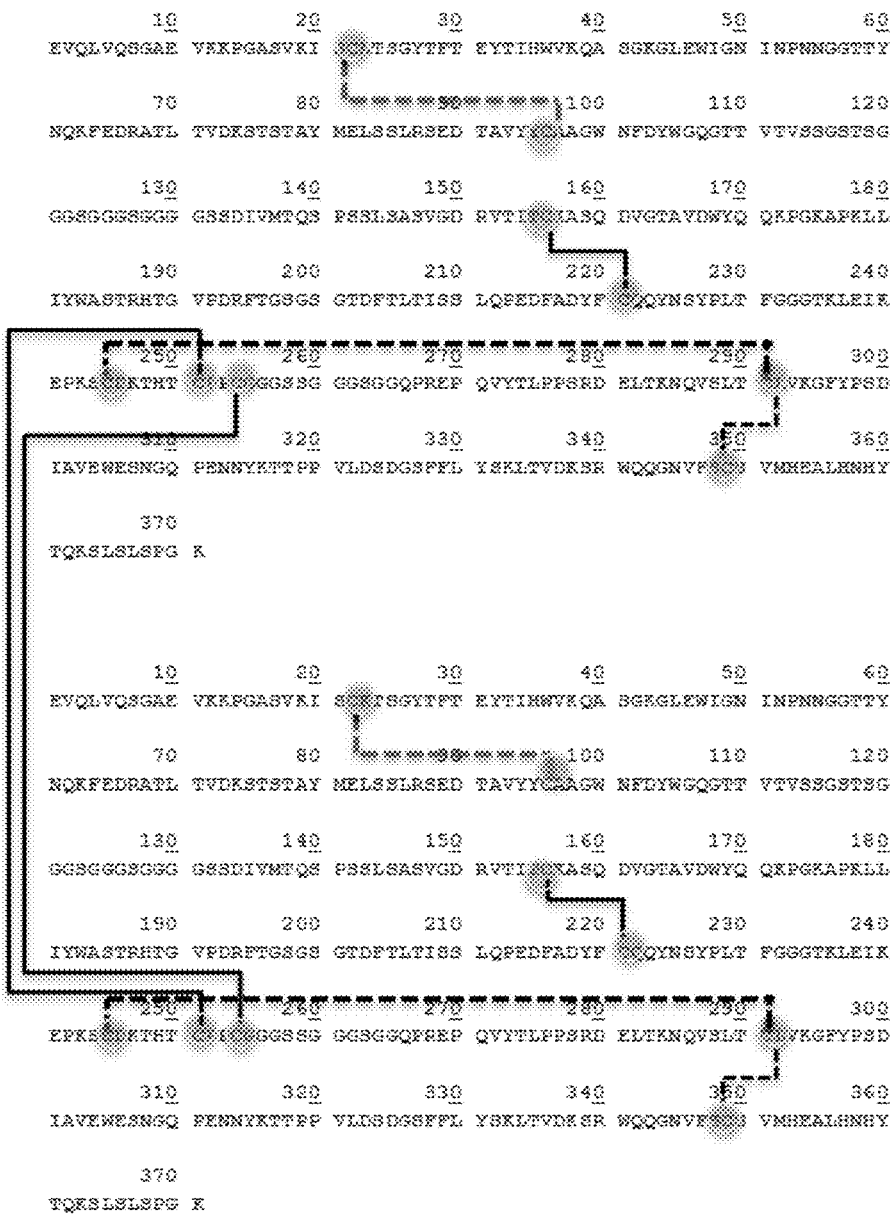
FIG. 9 shows an illustration of a mapping of the disulfide bonds of IAB2M γ1 EH1 indicating where mispaired cysteines are formed.

Disulfide Mapping of IAB2M γ1 EH1 demonstrated the presence of properly formed e.g. expected disulfides in the hinge region and also detected disulfide scrambling. FIG. 8 shows a table of the identified disulfides while FIG. 9 shows an illustration of the results. The disulfides (FIG. 8) occurred between the expected cysteine residues (cysteines of SEQ ID NO: 183 and SEQ ID NO: 184; cysteines of SEQ ID NO: 183 and SEQ ID NO: 185; SEQ ID NO: 186) and between unexpected cysteine residues present in other domains of the protein. It was hypothesized that the unpaired cysteine in the hinge could give rise to disulfide scrambling whereby conventional disulfide formation (solid lines) was discouraged (FIG. 9). Furthermore, the $V_H$ disulfides were not observed (broken lines) presumably due to the tryptic disulfide-bonded peptide not ionizing (and hence, not detected) in the mass spectrometer (FIG. 9).

Figure 5A:
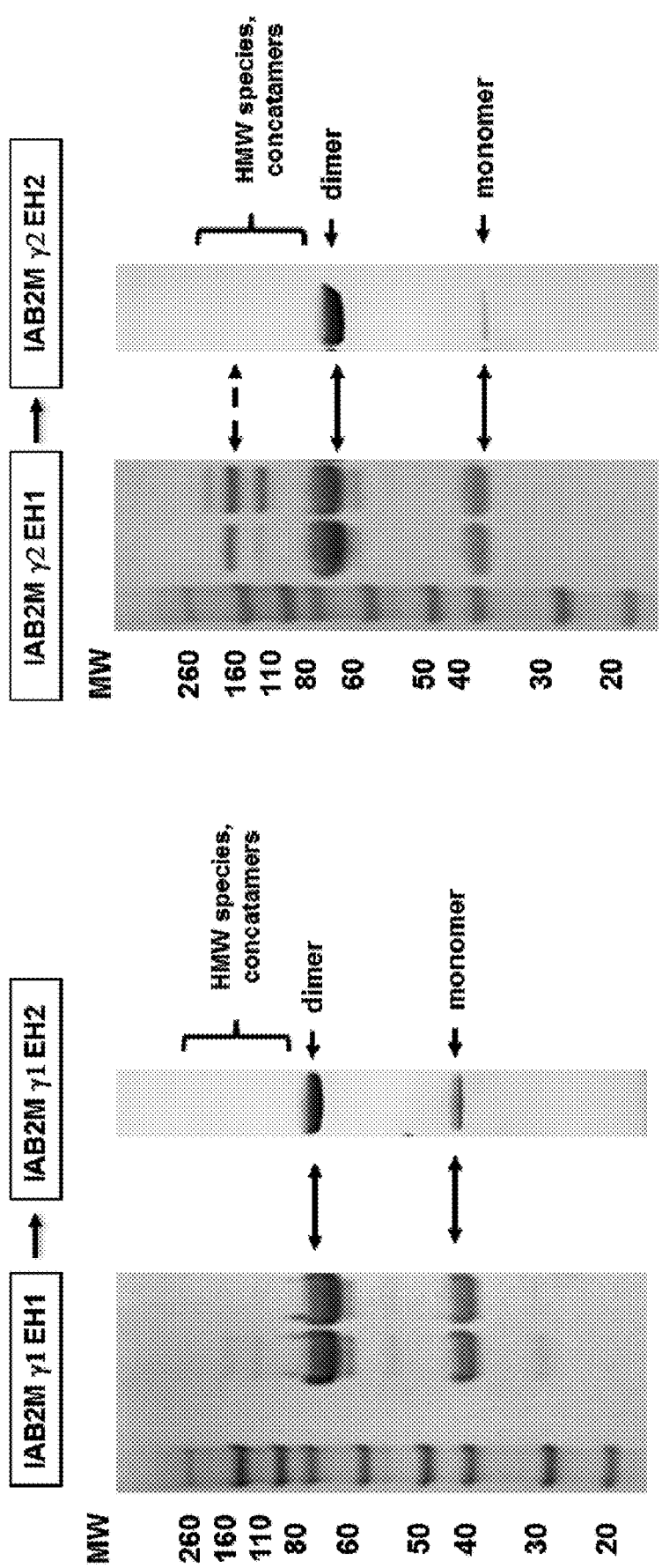
FIG. 5A shows images of non-reduced SDS-PAGE analysis of IAB2M hinge variants.

Reformatting to huIgG2 EH1 (γ2 EH1) did not improve stability of IAB2M. FIG. 10 shows a graphical representation of the identified disulfides. Significant concatamer formation was observed for γ2 EH1 by SDS-PAGE (FIG. 5A). As in IAB2M γ1 EH1, the $V_H$ disulfides were not observed (broken lines) presumably due to the tryptic disulfide-bonded peptide not ionizing efficiently and hence, not being detected in the mass spectrometer. IAB2M γ2 EH1 (FIG. 5D) exhibited >10% of half-molecule (39,469.5 Da by LC/MS) (FIG. 10 and FIG. 6B). A dominant half molecule (peak 1) was seen in chromatograms as shown on the panel (A) and (B) in FIG. 10. FIG. 6A (upper panel) shows total ion current (TIC) chromatogram of IAB2Mγ1 EH1 where peaks 1 and 2 are half molecule and full-size molecule, respectively. FIG. 6A middle panel shows UV280 channel with peak integration allowing determination of the percent half-molecule, 11.1%. FIG. 6A (Lower panel) shows molecular masses comprising the peak 2.

Example 3—In Vivo Data for IAB2M

Figure 11A:
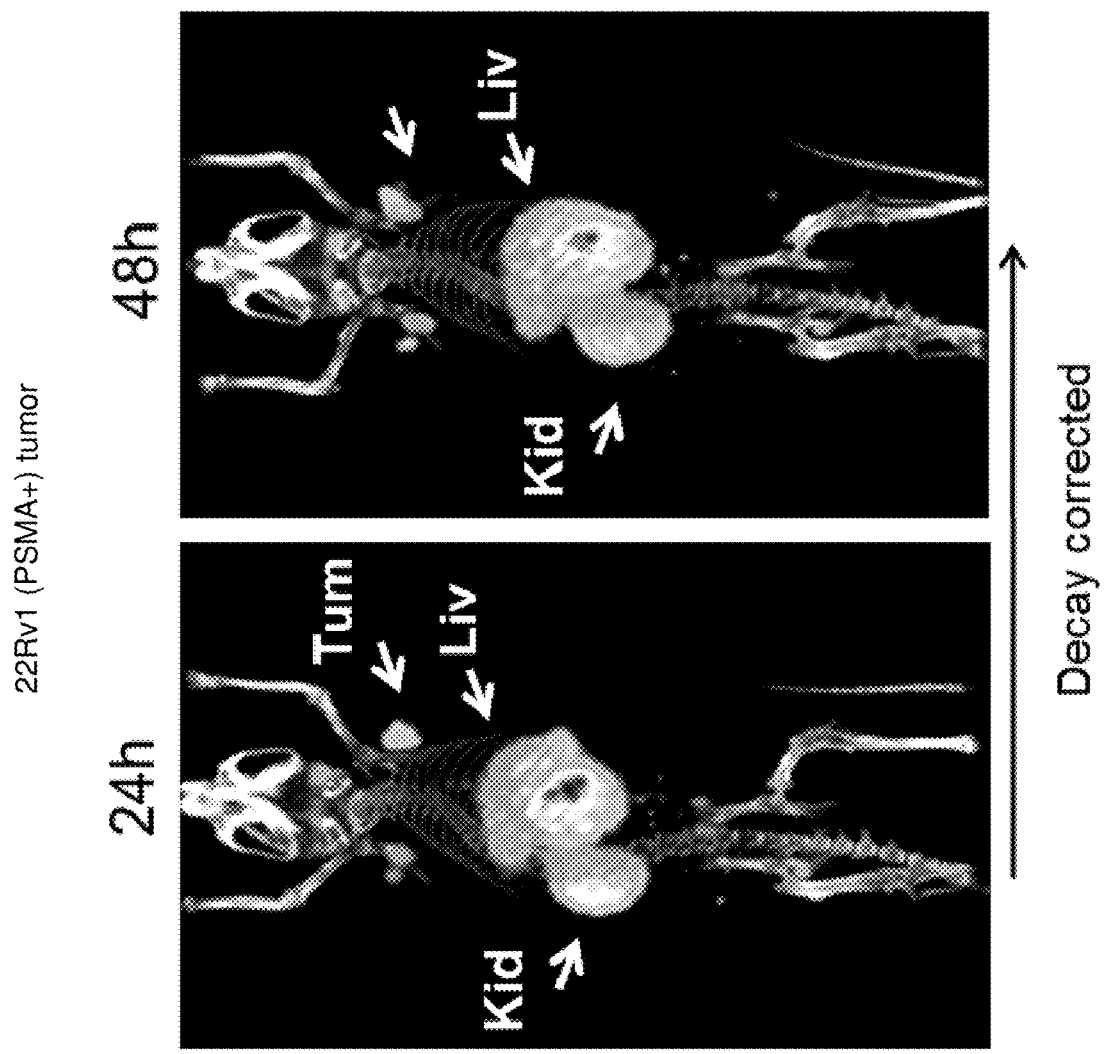
FIG. 11A shows images of PET/CT scans of $^{89}$Zr-Df-IAB2M γ1 EH1 in a nude mouse harboring 22Rv1 (PSMA+) tumor xenograft.
Figure 11B:
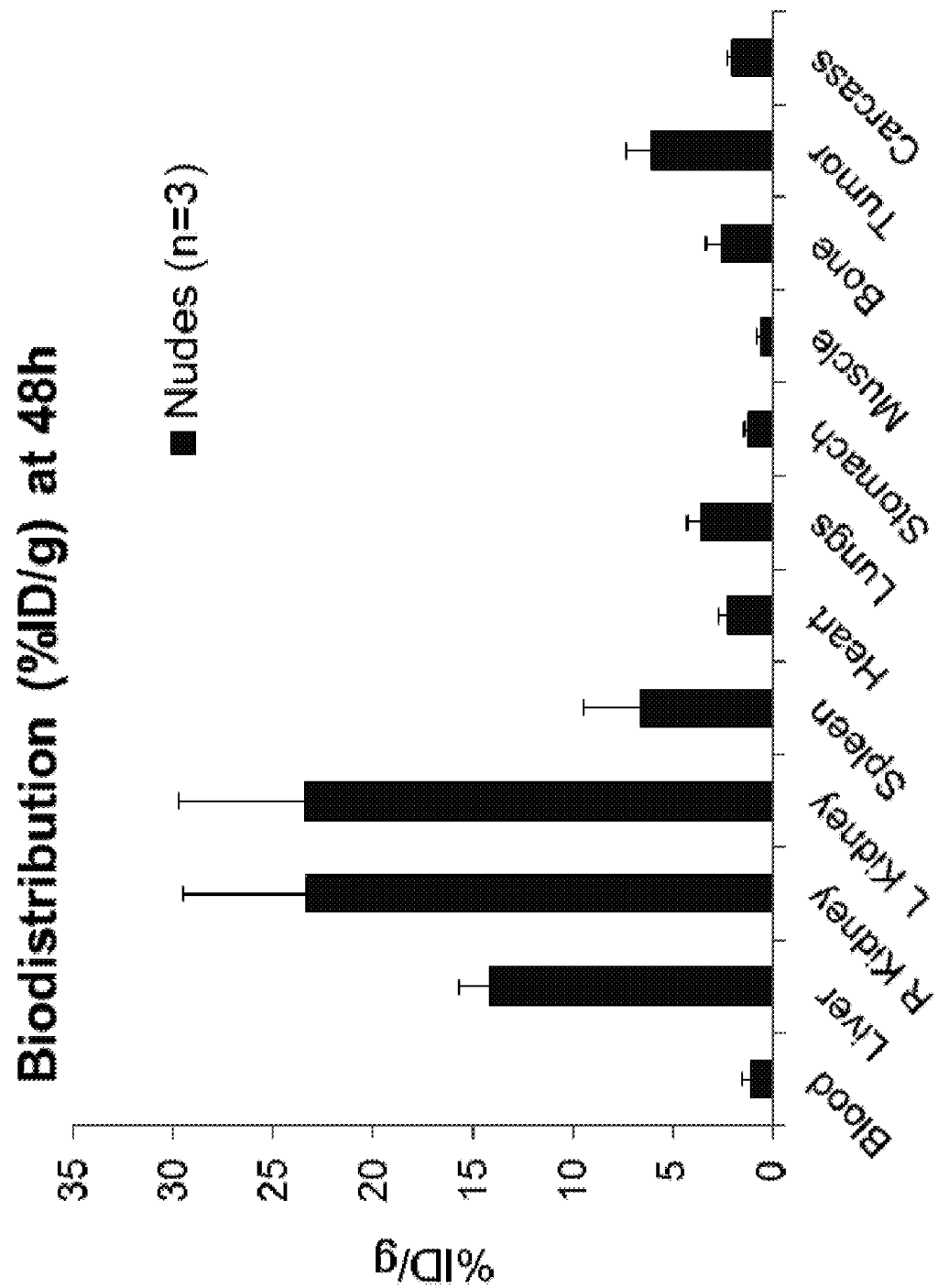
FIG. 11B shows a graph of biodistribution of $^{89}$Zr-Df-IAB2M γ1 EH1 in nude mice.

PET/CT and biodistribution of $^{89}$Zr-Df-IAB2M-γ1 EH1 (FIG. 5B) was performed in nude mice. MIP PET/CT images of a nude mouse bearing a PSMA positive 22Rv1 xenograft on the right shoulder after administration of $^{89}$Zr-Df-IAB2M-γ1-EH1 at 24 h and 48 h are shown in FIG. 11A. The average radioactive uptakes in the tissues from 3 mice at 48 h are shown as percentage of injected dose per gram (ID/g) (FIG. 11B). The tumor uptake was relatively low (6.1±1.2% ID/g) and the kidney uptake was high (23.3±6.2% ID/g); almost 2-fold higher than the liver uptake (14.1±1.6% ID/g). If the minibody remains as a dimer in vivo, then it would be expected that protein clearance would occur through the liver. The kidney signal being greater than the liver signal suggested instability and half molecule formation in vivo.

Figure 12A:
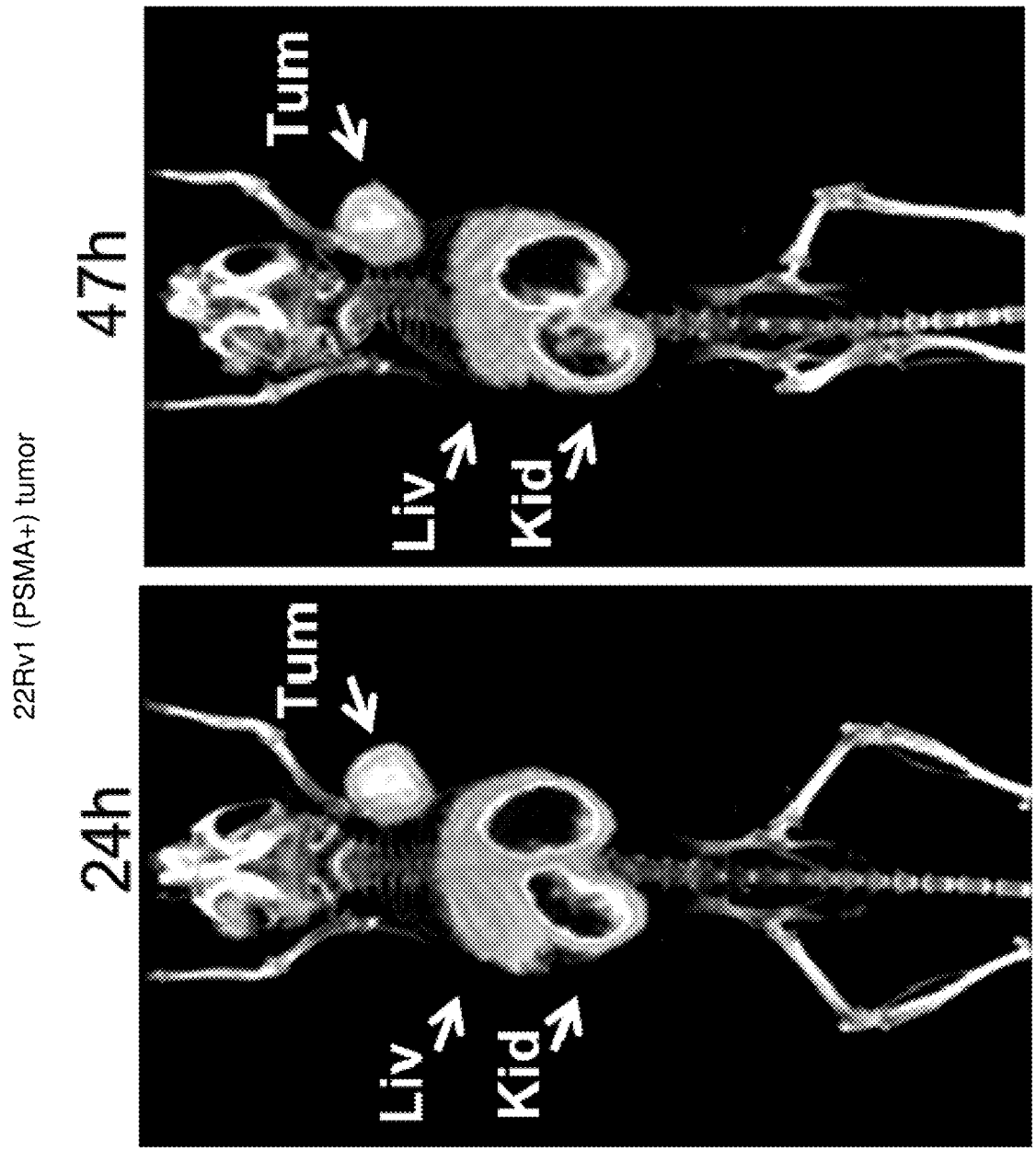
FIG. 12A shows images of PET/CT scans of $^{89}$Zr-Df-IAB2M γ1 EH2 in a nude mouse harboring 22Rv1 (PSMA+) tumor xenograft.
Figure 12B:
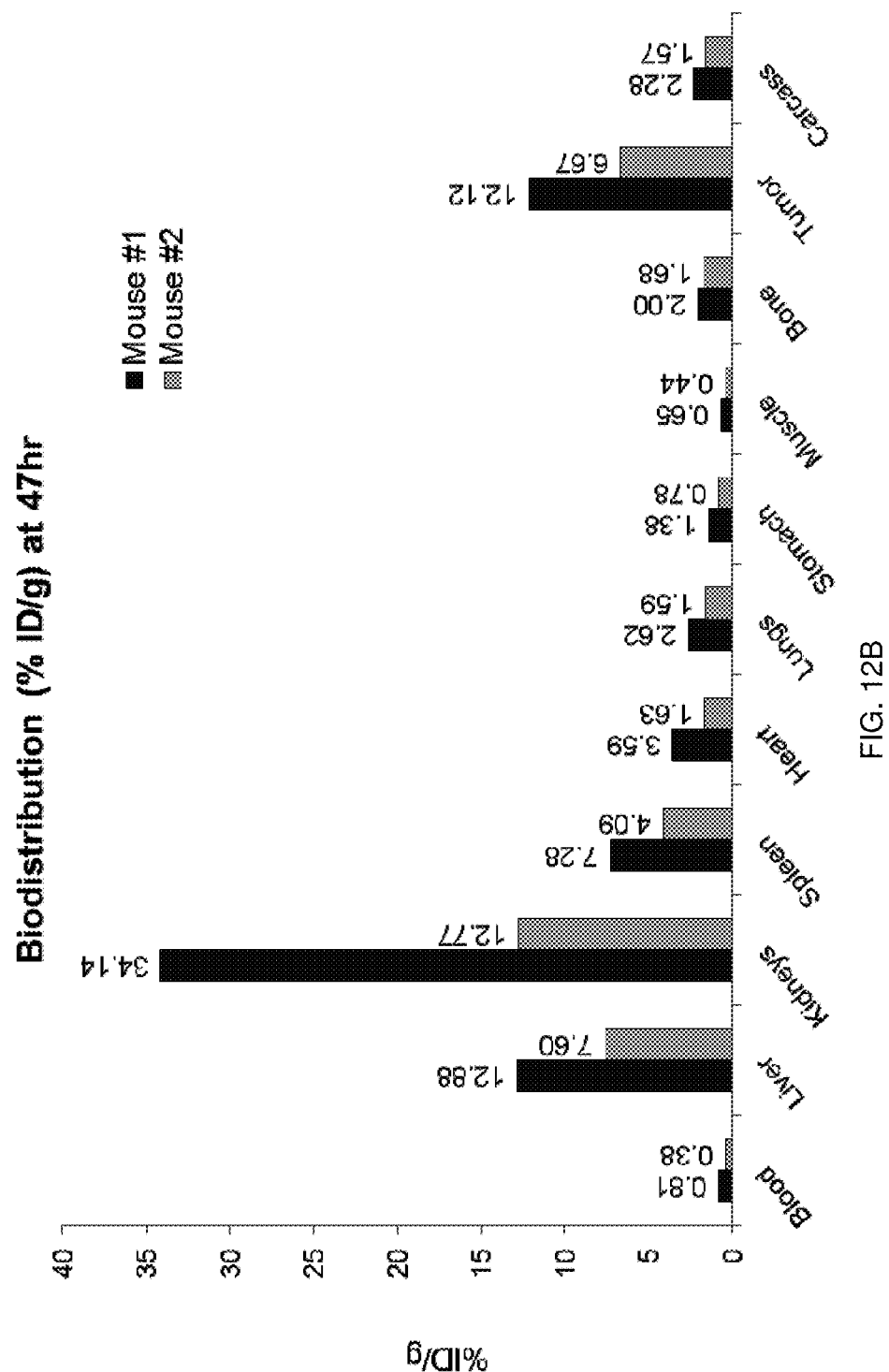
FIG. 12B shows a graph of biodistribution of $^{89}$Zr-Df-IAB2M γ1 EH2 in nude mice.

PET/CT and biodistribution of $^{89}$Zr-Df-IAB2M-γ1 EH2 (FIG. 5C) was performed in nude mice. MIP PET/CT images of nude mouse bearing a PSMA positive 22Rv1 xenograft on the right shoulder after administration of $^{89}$Zr-Df-IAB2M-γ1 EH2 at 24 h and 47 h are shown in FIG. 12A. The radioactive uptakes in the tissues from 2 mice at 47 h are shown as percentage of injected dose per gram (ID/g) (FIG. 12B). Again a 2- to 3-fold higher radioactive uptake was seen in the kidneys. As above, the kidney signal being greater than the liver signal indicated instability and half molecule formation in vivo.

Figure 13A:
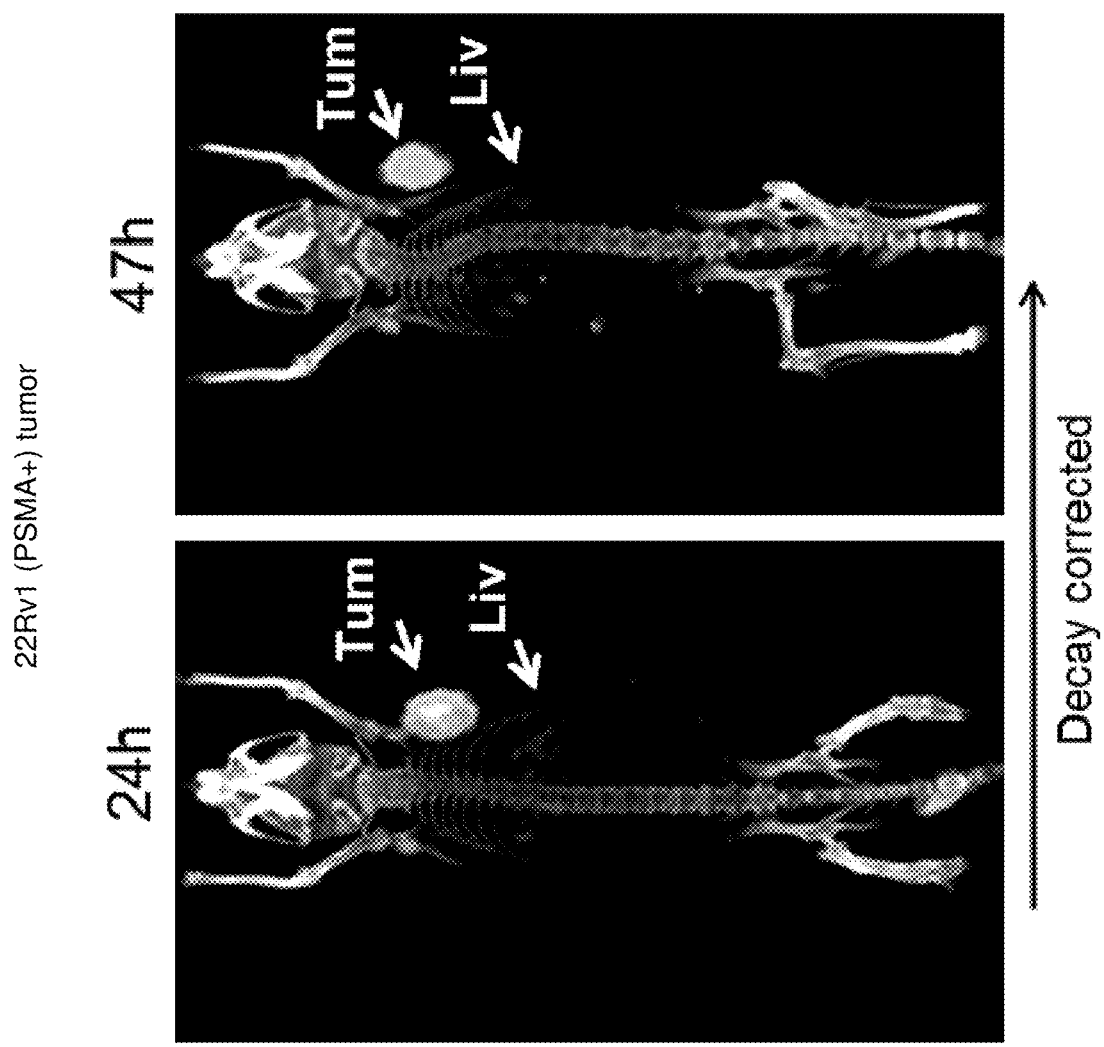
FIG. 13A shows images of PET/CT scans of $^{89}$Zr-Df-IAB2M γ2 EH2 in a nude mouse harboring 22Rv1 (PSMA+) tumor xenograft.
Figure 13B:
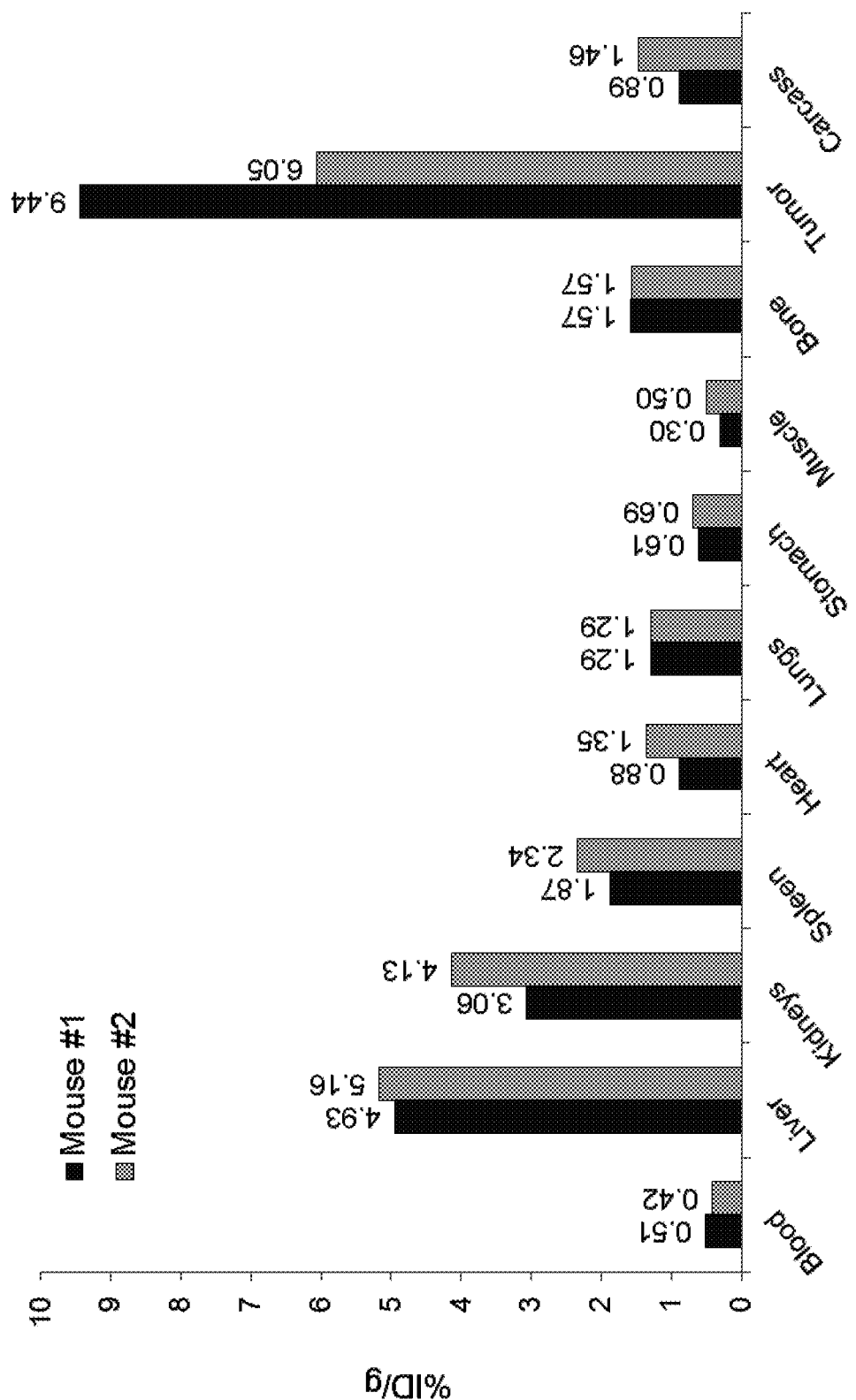
FIG. 13B shows a graph of biodistribution of $^{89}$Zr-Df-IAB2M γ2 EH2 in nude mice.

PET/CT and biodistribution of $^{89}$Zr-Df-IAB2M-γ2 EH2 (FIG. 5D) was performed in nude mice. MIP PET/CT images of a nude mouse bearing a PSMA positive 22Rv1 xenograft on the right shoulder after administration of $^{89}$Zr-Df-IAB2M-γ2 EH2 at 24 h and 47 h are shown in FIG. 13A. The radioactive uptakes in the tissues from the 2 mice at 47 h are shown as percentage of injected dose per gram (ID/g) (FIG. 13B). Low kidney uptake along with kidney to liver ratios <1 were obtained which indicated that the γ1 EH2 was a stable protein.

Example 4—Summary of IAB2M In Vivo Studies (Table 2)

Minibodies made with hinge sequences derived from hinge region of IgG1 showed high clearance through the kidneys suggesting protein instability and dissociation into half molecules in vivo (FIG. 11).

Mutation of the first hinge cysteine to serine in the IgG1 hinge region (γ1 EH2) (FIG. 5C) to prevent undesired interaction with other unpaired cysteine generated a protein with a better profile in vitro (for example, SDS-PAGE data of FIG. 5). However, the high clearance through the kidneys suggested protein instability and dissociation into half molecules in vivo (FIG. 12).

Minibodies made with an IgG2 hinge wherein the first hinge cysteine is mutated to a serine (γ2 EH2 (FIG. 5D) and others (Table 3, presenting summary of hinge regions)) were cleared through the liver as predicted for proteins of ~80 kDa and indicated that the molecule remained intact in vivo (FIGS. 13A and 13B). Results are also presented in Table 2.

TABLE 2

| | Conjugation Strategy | Tumor Model | Mouse strain | Time | Tumor % ID/g | Kidney % ID/g | Liver % ID/g | N- to C-terminal (SEQ ID NOS) |
|---|---|---|---|---|---|---|---|---|
| IAB2M-γ1 EH1 | $^{89}$Zr-Df-Lys | 22Rv1 | Nude | 48 h | 6.1% | 23.3% | 14% | VL (SEQ ID NO: 13); linker (SEQ ID NO: 62); VH (SEQ ID NO: 14); full hinge (SEQ ID NO: 22) [upper hinge (SEQ ID NO: 45), core hinge (SEQ ID NO: 50), lower hinge (SEQ ID NO: 59)]; IgG1 CH3 (SEQ ID NO: 40 or SEQ ID NO: 41) |
| IAB2M-γ1 EH1 | $^{89}$Zr-Df-Lys | 22Rv1 | Nude | 48 h | 9.3% | 26% | 16.3% | VL (SEQ ID NO: 13); linker (SEQ ID NO: 62); VH (SEQ ID NO: 14); full hinge (SEQ ID NO: 22) [upper hinge (SEQ ID NO: 45), core hinge (SEQ ID NO: 50), lower hinge (SEQ ID NO: 59)]; IgG1 CH3 (SEQ ID NO: 40 or SEQ ID NO: 41) |
| IAB2M-γ1 EH2 | $^{89}$Zr-Df-Lys | 22Rv1 | Nude | 48 h | 9.4% | 23.5% | 9.9% | VL (SEQ ID NO: 13); linker (SEQ ID NO: 62); VH (SEQ ID NO: 14); full hinge (SEQ ID NO: 24) [upper hinge (SEQ ID NO: 46), core hinge (SEQ ID |

TABLE 2-continued

| Conjugation Strategy | Tumor Model | Mouse strain | Time | Tumor % ID/g | Kidney % ID/g | Liver % ID/g | N- to C-terminal (SEQ ID NOS) |
|---|---|---|---|---|---|---|---|
| IAB2M-γ2 EH2 | ⁸⁹Zr-Df-Lys | 22Rv1 | Nude | 48 h | 7.8% | 3.6% | 5.1% | NO: 50), lower hinge (SEQ ID NO: 59)]; IgG1 CH3 (SEQ ID NO: 40 or SEQ ID NO: 41) VL (SEQ ID NO: 13); linker (SEQ ID NO: 62); VH (SEQ ID NO: 14); full hinge (SEQ ID NO: 34) [upper hinge (SEQ ID NO: 47), core hinge (SEQ ID NO: 56), lower hinge (SEQ ID NO: 59)]; IgG2 CH3 (SEQ ID NO: 42) |

TABLE 3

| Hinge Name | N- to C-terminal | | | CH3 domain | |
|---|---|---|---|---|---|
| | Full hinge | | | | |
| | Upper hinge | Core hinge | Lower Hinge | | |
| γ1 EH1 | Full hinge (SEQ ID NO: 22) | | | γ1 | Native upper and core IgG1 hinge |
| | EPKSCDKTHT (SEQ ID NO: 45) | CPPC (SEQ ID NO: 50) | GGGSSGGGSG (SEQ ID NO: 59) | (SEQ ID NO: 40 or SEQ ID NO: 41) | |
| γ1 EH2 | Full hinge (SEQ ID NO: 24) | | | γ1 | C→S |
| | EPKSCDKTHT (SEQ ID NO: 46) | CPPC (SEQ ID NO: 50) | GGGSSGGGSG (SEQ ID NO: 59) | (SEQ ID NO: 40 or SEQ ID NO: 41) | |
| γ1 EH3 | Full hinge (SEQ ID NO: 26) | | | γ1 | C→S |
| | EPKSCDKTHT (SEQ ID NO: 46) | CPPCPPC (SEQ ID NO: 52) | GGGSSGGGSG (SEQ ID NO: 59) | (SEQ ID NO: 40 or SEQ ID NO: 41) | |
| γ1 EH4 | Full hinge (SEQ ID NO: 28) | | | γ1 | C→S |
| | EPKSCDKTHT (SEQ ID NO: 46) | CPPCVECPPC (SEQ ID NO: 53) | GGGSSGGGSG (SEQ ID NO: 59) | (SEQ ID NO: 40 or SEQ ID NO: 41) | |
| γ1 EH5 | Full hinge (SEQ ID NO: 30) | | | γ1 | C→S |
| | EPKSCDKTHT (SEQ ID NO: 46) | CPPCPPCPPC (SEQ ID NO: 54) | GGGSSGGGSG (SEQ ID NO: 59) | (SEQ ID NO: 40 or SEQ ID NO: 41) | |
| γ2 EH1 | Full hinge (SEQ ID NO: 32) | | | γ2 | Native upper and core IgG2 hinge |
| | ERK (SEQ ID NO: 47) | CCVECPPCP (SEQ ID NO: 55) | GGGSSGGGSG (SEQ ID NO: 59) | (SEQ ID NO: 42) | |
| γ2 EH2 | Full hinge (SEQ ID NO: 34) | | | γ2 | C→S |
| | ERK (SEQ ID NO: 47) | SCVECPPCP (SEQ ID NO: 56) | GGGSSGGGSG (SEQ ID NO: 59) | (SEQ ID NO: 42) | |
| γ2 EH2 | Full hinge (SEQ ID NO: 34) | | | γ2 | T26S, L28A, M57V |
| | ERK (SEQ ID NO: 47) | SCVECPPCP (SEQ ID NO: 56) | GGGSSGGGSG (SEQ ID NO: 59) | (SEQ ID NO: 181) | |
| γ2 EH2 | Full hinge (SEQ ID NO: 34) | | | γ2 | T26W |
| | ERK (SEQ ID NO: 47) | SCVECPPCP (SEQ ID NO: 56) | GGGSSGGGSG (SEQ ID NO: 59) | (SEQ ID NO: 182) | |

TABLE 3-continued

| Hinge Name | N- to C-terminal | | | CH3 domain | Full hinge |
|---|---|---|---|---|---|
| | Upper hinge | Core hinge | Lower Hinge | | |
| γ2 NH1 | Full hinge (SEQ ID NO: 31) | | | γ2 (SEQ ID NO: 42) | Native IgG2 hinge |
| | ERK (SEQ ID NO: 47) | CCVECPPCP (SEQ ID NO: 55) | APPVAGP (SEQ ID NO: 60) | | |
| γ2 NH2 | Full hinge (SEQ ID NO: 33) | | | γ2 (SEQ ID NO: 42) | C→S |
| | ERK (SEQ ID NO: 47) | SCVECPPCP (SEQ ID NO: 56) | APPVAGP (SEQ ID NO: 60) | | |
| γ3/γ1 EH6 | Full hinge (SEQ ID NO: 35) | | | γ1 (SEQ ID NO: 40 or SEQ ID NO: 41) | Native γ3 upper hinge |
| | ELKTPLGDTTHT (SEQ ID NO: 48) | CVECPPCP (SEQ ID NO: 57) | GGGSSGGGSG (SEQ ID NO: 59) | | |
| γ3/γ1 EH7 | Full hinge (SEQ ID NO: 36) | | | γ1 (SEQ ID NO: 40 or SEQ ID NO: 41) | Native γ3 upper hinge |
| | ELKTPLGDTTHT (SEQ ID NO: 48) | CPPCPPC (SEQ ID NO: 52) | GGGSSGGGSG (SEQ ID NO: 59) | | |
| γ3/γ1 EH8 | Full hinge (SEQ ID NO: 37) | | | γ1 (SEQ ID NO: 40 or SEQ ID NO: 41) | Native γ3 upper hinge |
| | ELKTPLGDTTHT (SEQ ID NO: 48) | CPPCPPCPPC (SEQ ID NO: 54) | GGGSSGGGSG (SEQ ID NO: 59) | | |
| γ1 NH11 NH1 | EPKSCDKTHT (SEQ ID NO: 45) | CPPC (SEQ ID NO: 50) | APELLGGP (SEQ ID NO: 58) | γ1 (SEQ ID NO: 40 or SEQ ID NO: 41) | Native γ1 hinge |
| γ3 NH13 NH1 | ELKTPLGDTTHT (SEQ ID NO: 48) | (ERKSCDTPPPCPRCP)₃ CPRCP (SEQ ID NO: 256) | APELLGGP (SEQ ID NO: 58) | γ3 (SEQ ID NO: 43) | Native γ3 hinge |

Example 5—In Vitro Data for IAB22M IGG2 Minibodies

Figure 14A:
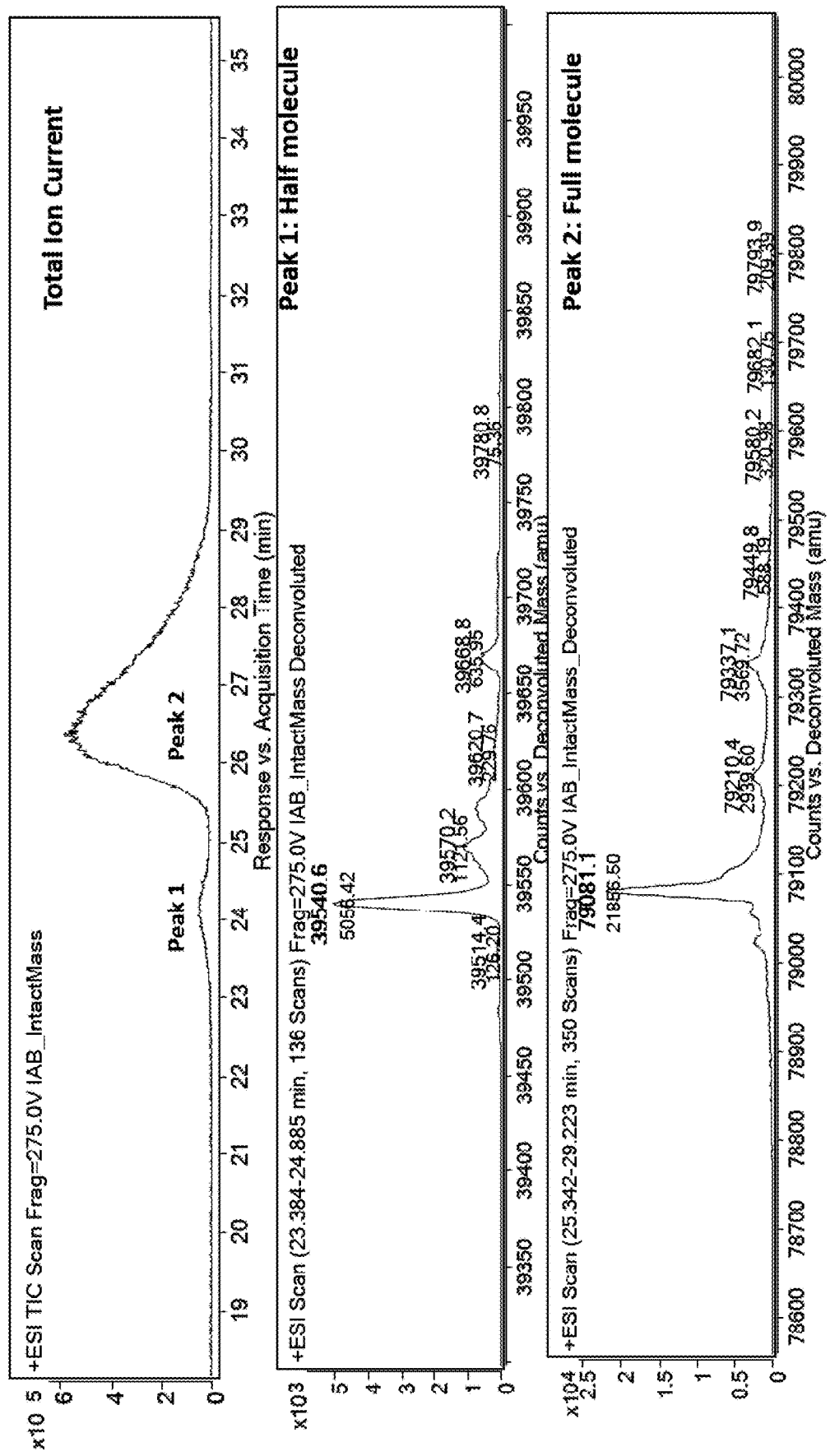
FIG. 14A shows the intact mass analysis of IAB22M γ2 EH1 variant. Upper panel shows the total ion chromatogram. Middle panel shows the deconvoluted intact masses confirming the presence of half molecules and the lower panel shows the full-size masses that were identified.
Figure 20A:
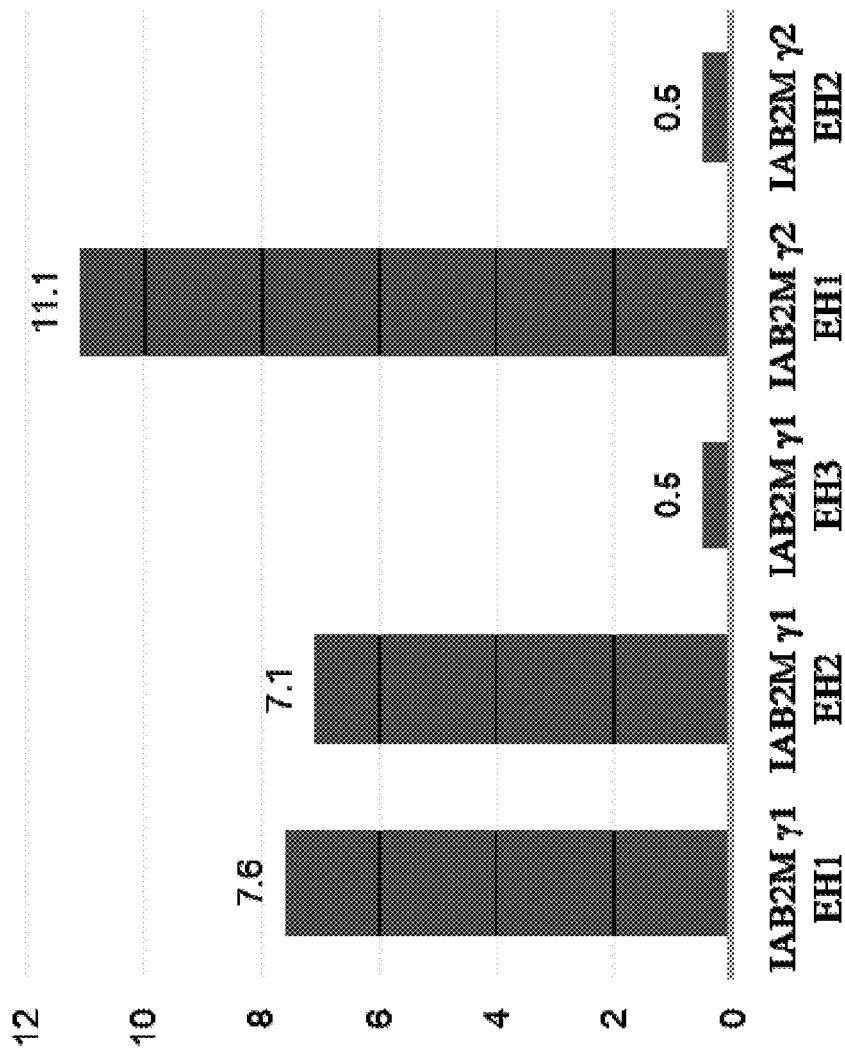
FIG. 20A shows a graph summarizing the percentage of half molecules present in different hinge variants for IAB2M as determined by mass spectrometry.
Figure 20B:
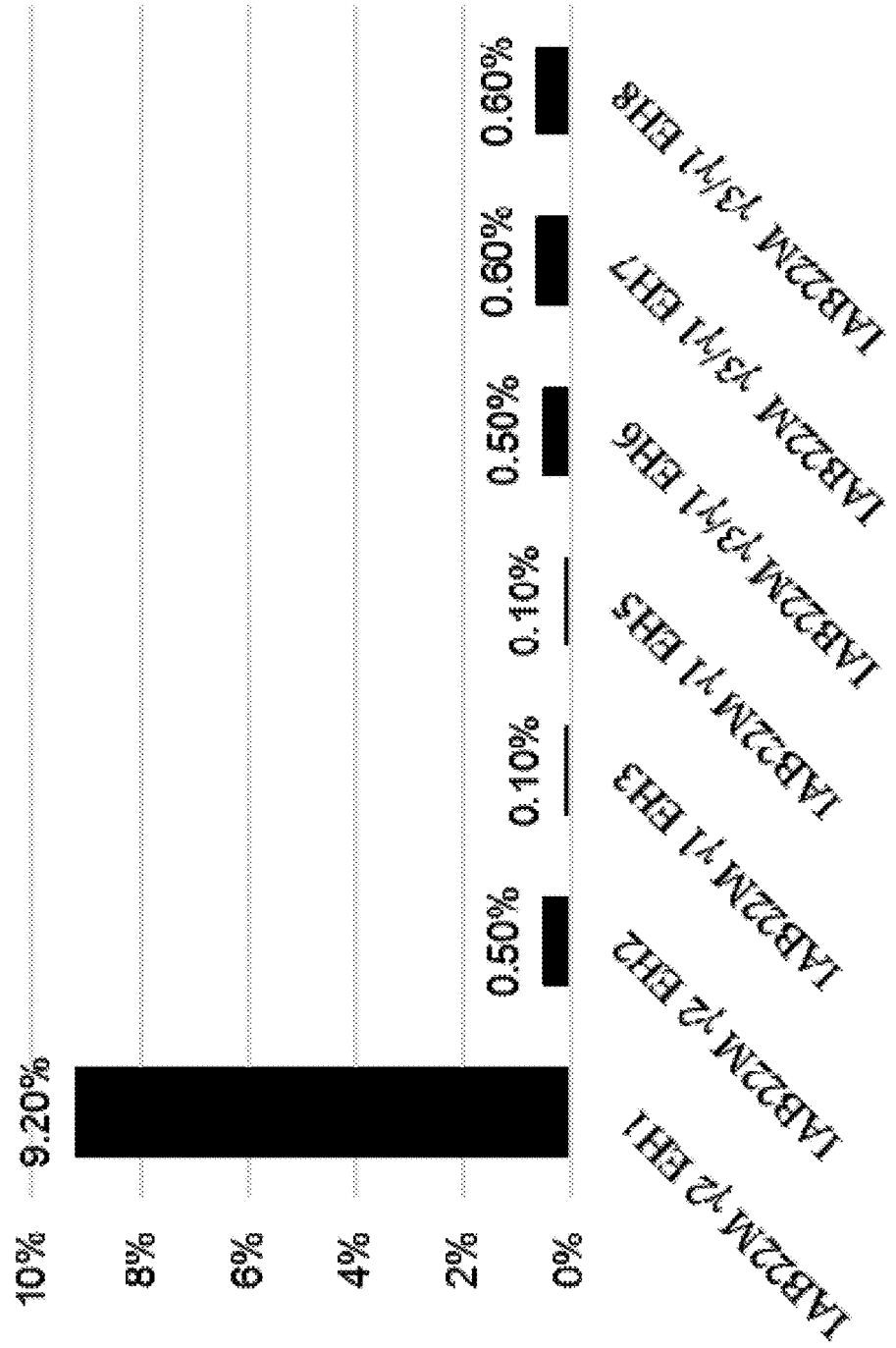
FIG. 20B shows a graph summarizing the percentage of half molecules present in different hinge variants for IAB22M as determined by mass spectrometry.

Intact mass analysis (FIG. 14A) of the IAB22M-γ2 EH1 variant (FIG. 14B) was performed by mass spectrometry. IAB22M with γ2 EH1 hinge had a potential unpaired first hinge cysteine which resulted in ~9.2% of half molecules (FIG. 20B). For intact mass analysis of IAB22M γ2 EH1, the samples were separated by a reverse phase chromatography column (TSKgel Phenyl-5PW (Tosoh, 2×75 mm) at 60° C. and analyzed by Agilent ESI-QTOF mass spectrometer. FIG. 14A shows the total ion chromatograms of the separated half-molecule and full-size molecule in the upper panel. The UV280 trace (not shown) was used for quantitation of the percent of half-molecules present in the minibody variant by peak integration. The deconvoluted masses were used for assignment and confirmed the identity of half molecules (middle panel) and of the full size masses (lower panel).

Figure 15A:
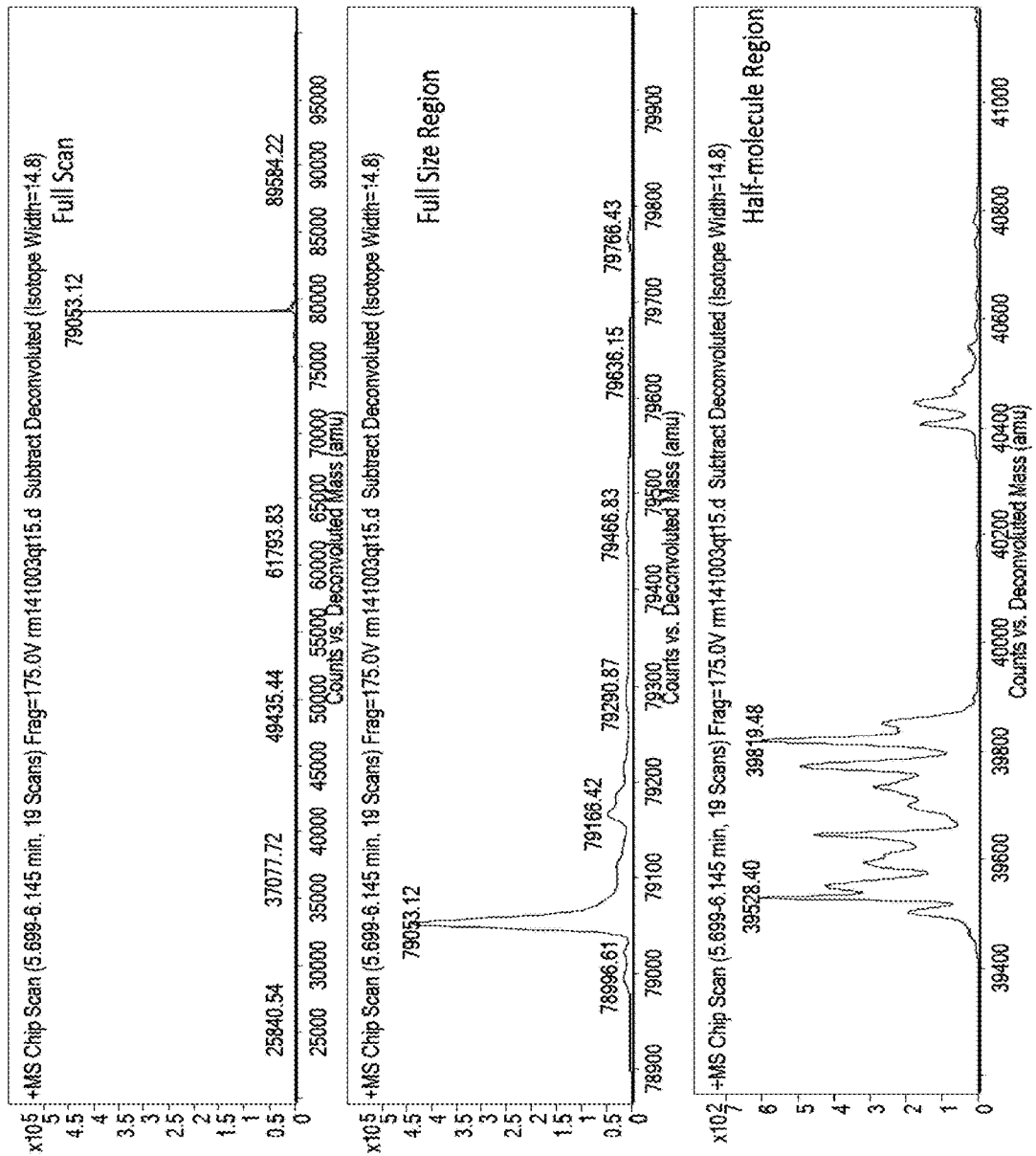
FIG. 15A shows intact mass analysis of IAB22 γ2 EH2 variant. The protein was separated under reverse phase conditions. Upper panel shows the full mass range scan. The zoomed-in full-size mass region emphasizes the presence of the intact, i.e. disulfide-bridge bonded protein (middle panel) while the zoomed-in half-molecule region showed that essentially no half-molecule is present (lower panel).

However, the intact mass analysis (FIG. 15A) of the IAB22M1-γ2 EH2 variant (FIG. 15B) with the first cysteine in IgG2 hinge mutated to serine showed greater than 99% intact dimeric protein with γ2 EH2 (theoretical MW=79051.2; obtained MW 79052). For intact mass analysis of IAB22M1 γ2 EH2, a protein sample was analyzed by LC/MS consisting of the following: Waters Synapt G2 HDMS fitted with a Trizaic nanoESI source coupled to a Waters nanoAcquity UPLC. The protein was separated using the reverse phase C4 nanotile column (150 μm ID×50 mm, Waters) operated at 30/min with 0.1% formic acid in water and 0.1% formic acid in acetonitrile as the mobile phases. FIG. 15A upper panel shows full range scan showing the single dominant molecular mass of the full-size minibody. FIG. 15A middle panel shows zoomed-in region of the dimers e.g. full size protein. FIG. 15A lower panel shows zoomed in region of the half-molecules. A half molecule is detected but its relative abundance is nearly 3 orders of magnitude lower than the full size protein.

Example 6—In Vivo Data for IAB22M IGG2 Mbs

Figure 16A:
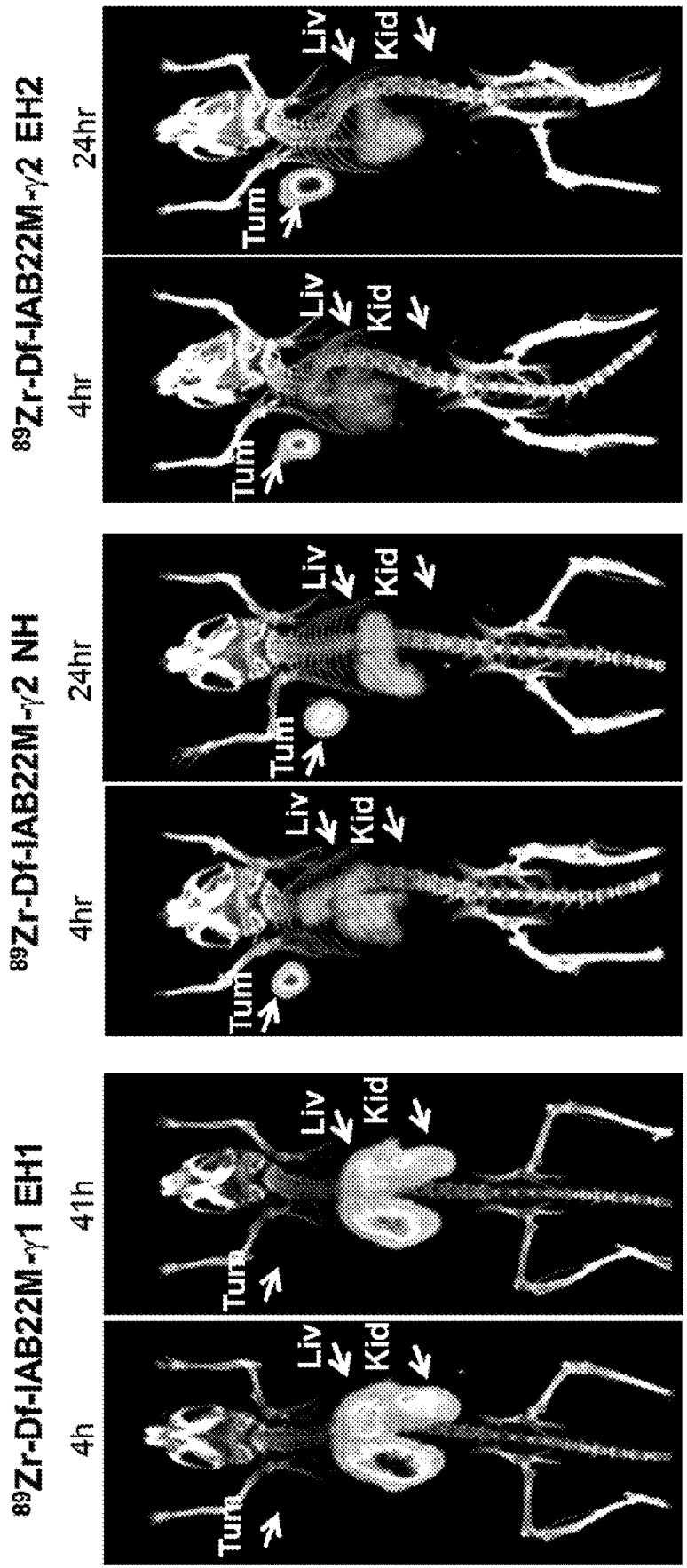
FIG. 16A shows PET/CT scan images of mice harboring HPB-ALL (CD8+) tumor xenograft comparing $^{89}$Zr-Df-IAB22M minibodies with human IgG1 and human IgG2 derived hinge sequences.

Comparison of the IAB22M Mbs with huIgG1 and huIgG2 derived hinge sequences was performed by PET/CT of $^{89}$Zr-Df-IAB22M variants. MIP PET/CT images of NOD-SCID mice bearing CD8 positive HPB-ALL xenografts on the left shoulder after administration of $^{89}$Zr-Df-IAB22M-γ1-EH1 (FIG. 16B), -γ2 NH1 (FIG. 16C) and -γ2 EH2 (FIG. 15B) variants are shown in FIG. 16A. The γ2 hinge variants resulted in lower kidney uptake.

IAB22M Mb made with a huIgG1 hinge (γ1 EH1) (FIG. 16B) was rapidly cleared through the kidney resulting in low tumor targeting. IAB22M Mbs made with huIgG2 hinge variants, either extended hinge (γ2 EH2) (FIG. 15B) or natural hinge (γ2 NH1) (FIG. 16C) showed greater stability in vivo with high tumor targeting and lower kidney clearance (FIG. 16A).

Figure 17:
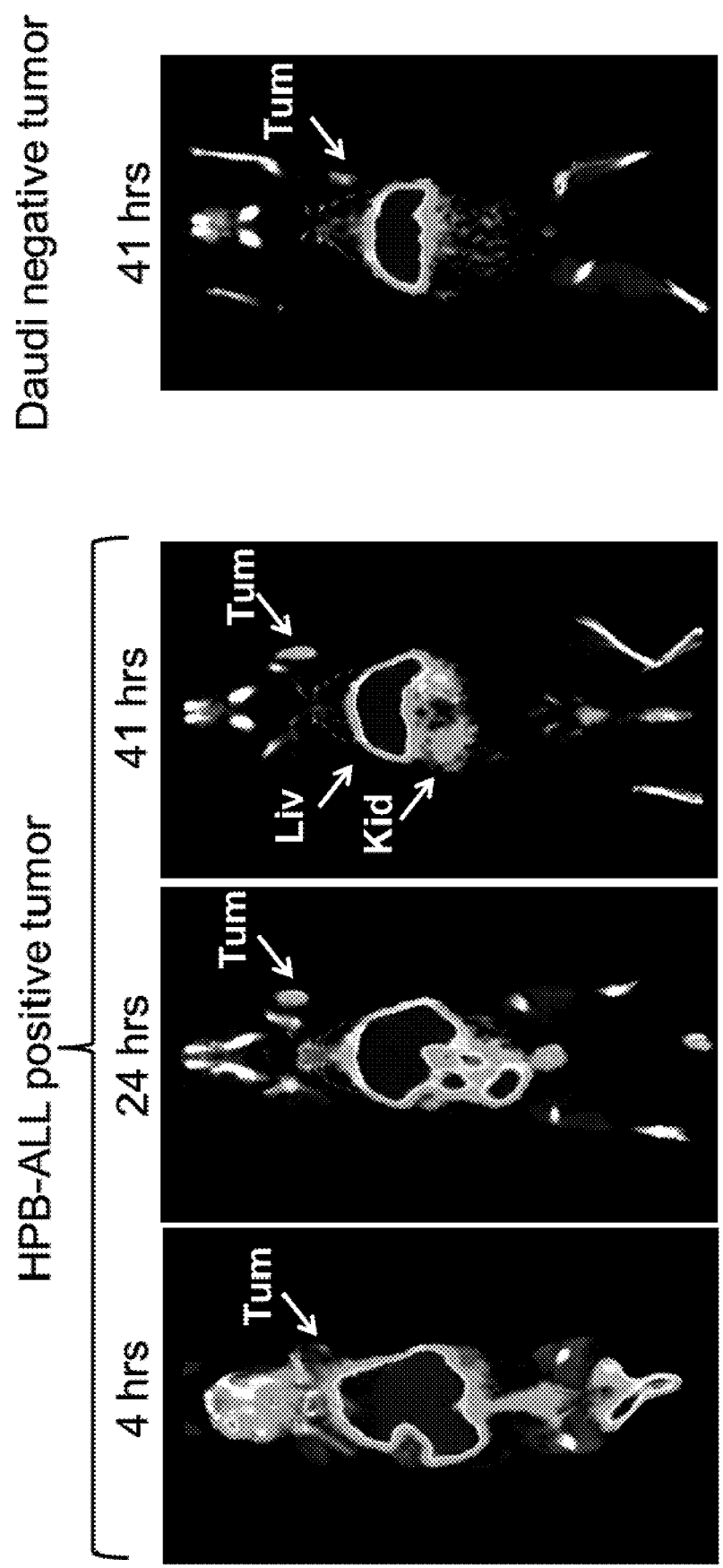
FIG. 17 shows PET/CT scan images comparing uptake of $^{89}$Zr-Df-IAB22M γ1 EH1 in a NOD-SCID mouse with antigen-positive HPB-ALL tumor and antigen-negative Daudi tumor (right panel only).

PET/CT of HPB-ALL tumors was performed for $^{89}$Zr-Df-IAB22M-γ1 EH1 (FIG. 16B). Serial coronal images of one mouse with antigen-positive HPB-ALL tumor at 4, 24 and 41 hrs are shown in FIG. 17. Radioactive uptake was clearly seen in the tumor at 24 and 41 hrs. Some background activity was also observed in the antigen negative Daudi tumor. High background activity was present in the abdominal region suggesting undesired clearance through the kidney.

Figure 18:
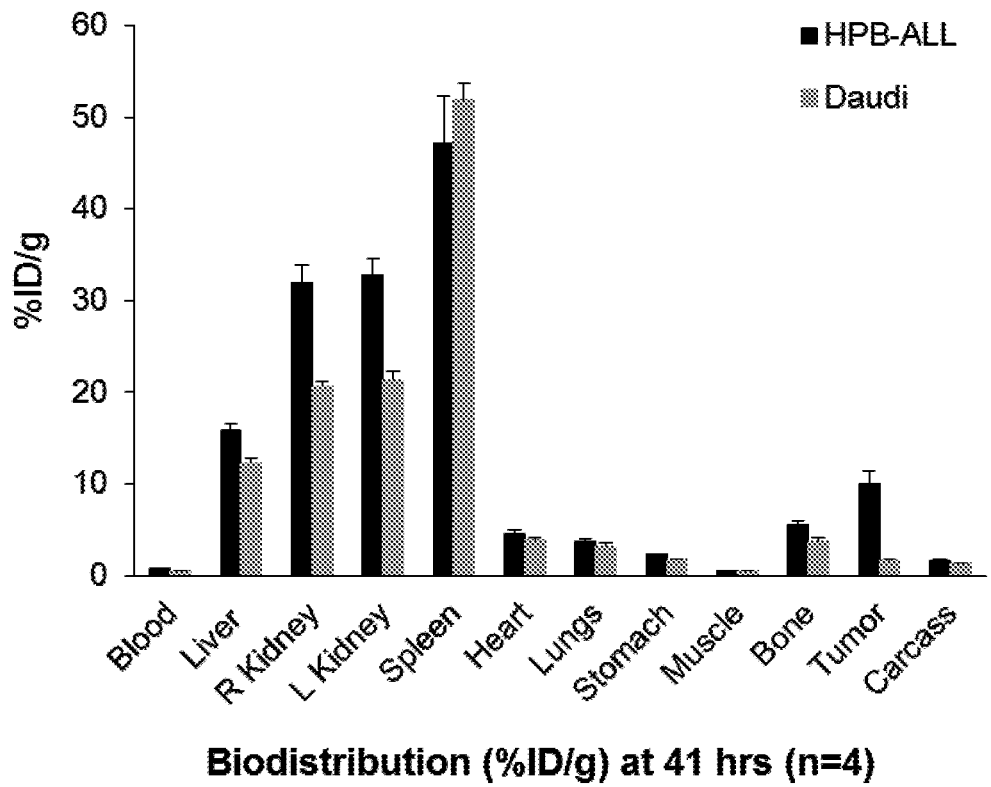
FIG. 18 shows a graph of biodistribution of $^{89}$Zr-Df-IAB22M γ1 EH1 in mice with antigen-positive HPB-ALL tumor and antigen-negative Daudi tumor. Numbers are shown on the right.

Biodistribution analysis was performed for $^{89}$Zr-Df-IAb22M-γ1 EH1 (FIG. 16B) in HPB-ALL tumor (FIG. 18). The tumor uptake in HPB-ALL was ~6-fold higher compared to Daudi (Daudi tumor does not express target antigen). The ratio of biodistribution between HPB-ALL tumor and blood was 13.5 and ratio of biodistribution between Daudi tumor and blood was 3.5. Kidney signal was higher than liver signal suggesting higher clearance through kidneys (FIG. 18) and a less stable in vivo construct.

Lessons Learned from Initial Constructs Used for Engineering Optimized Minibodies The above results showed that it was important to mutate the first hinge cysteine to prevent cysteine mis-pairing. However, more than 2 cysteine residues are beneficial in the hinge region to maintain the structural integrity of protein. Employing the IgG2 hinge provides a solution to increase stability in vivo. Mutation of the terminal lysine (K) in the Mb constructs did not impact protein expression but did generate protein with a more uniform charge.

Additional Mb variants were evaluated based on IgG3 and modification of IgG1 hinge sequences where the first hinge cysteine was mutated and at least 3 cysteine residues were present in the hinge region. Table 3 shows a list of hinge variants. The first native cysteine in the hinge sequence can be mutated to serine or alanine or any other amino acid. The lower hinge sequence can be an extension sequence (8-25 amino acids) or native lower hinge from γ1, γ2, γ3 or γ4. $C_H3$ domain for any construct can be from γ1, γ2 or γ3 or γ4 and any naturally occurring allele thereof. An illustration of some hinge variants is shown in FIG. 19. IAB2M, IAB22M, IAB20M and IAB1M constructs were evaluated to demonstrate universality of findings.

Example 7—In Vitro Data for Hinge Variants of IAB2M, IAB22M, IAB20M and IAB1M

Intact mass analysis was performed on IAB2M (FIG. 20A) hinge variants (FIGS. 5B, 5C, 7C, 5E, 5D). Intact mass analysis was also performed on IAB22M (FIG. 20B) hinge variants (FIGS. 14B, 15B, 20C, 20D, 20E, 20F, 20G). Expressed minibodies with engineered hinges (EH) were analyzed for intact mass and the amount of the half molecule (FIGS. 20A and 20B) by LC/MS using a Waters Synapt G2 HDMS fitted with a Trizaic nanoESI source coupled to a Waters nanoAcquity UPLC Waters C4 nanotile column (150 μm ID×50 mm length) operated at 30/min with 0.1% formic acid in water and 0.1% formic acid in acetonitrile as the buffers. For some molecules the samples were separated by reverse phase chromatography column (TSKgel Phenyl-5PW (Tosoh, 2×75 mm) and analyzed by Agilent ESI-QTOF mass spectrometer.

SDS-PAGE analyses of IAB2M hinge Mb variants (FIGS. 5C, 7C, 21B, 21C, 21D, 21E) and IAB22M hinge Mb variants (FIGS. 16B, 15B, 20C, 20D, 20E, 20F, 20G) were performed. The resulting data are shown in FIGS. 21A and 22A.

Figure 21A:
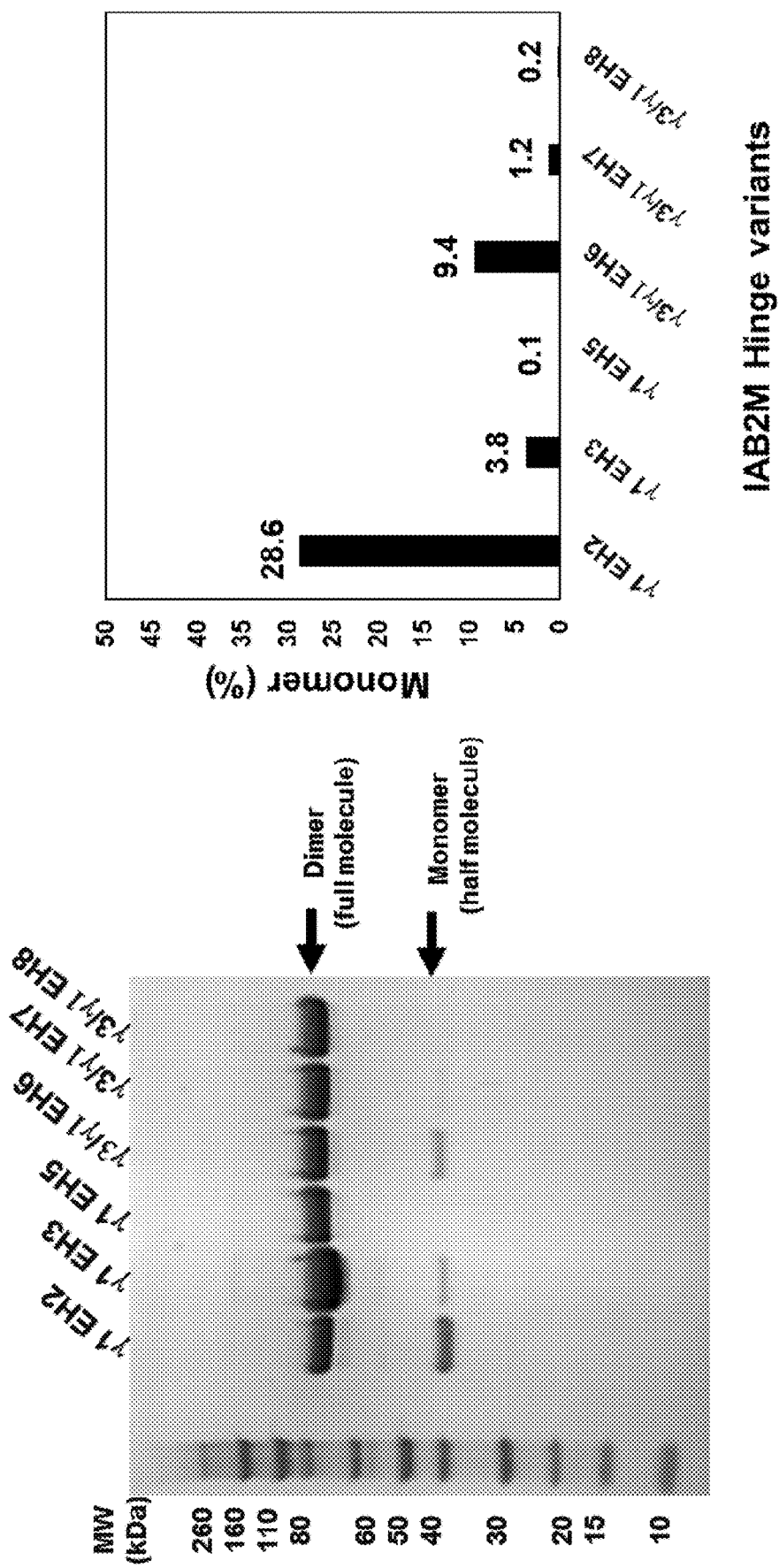
FIG. 21A shows an image of non-reduced SDS-PAGE analysis (left panel) of IAB2M hinge Mb variants and percentage of half molecules quantified by densitometry (right panel).
Figure 22A:
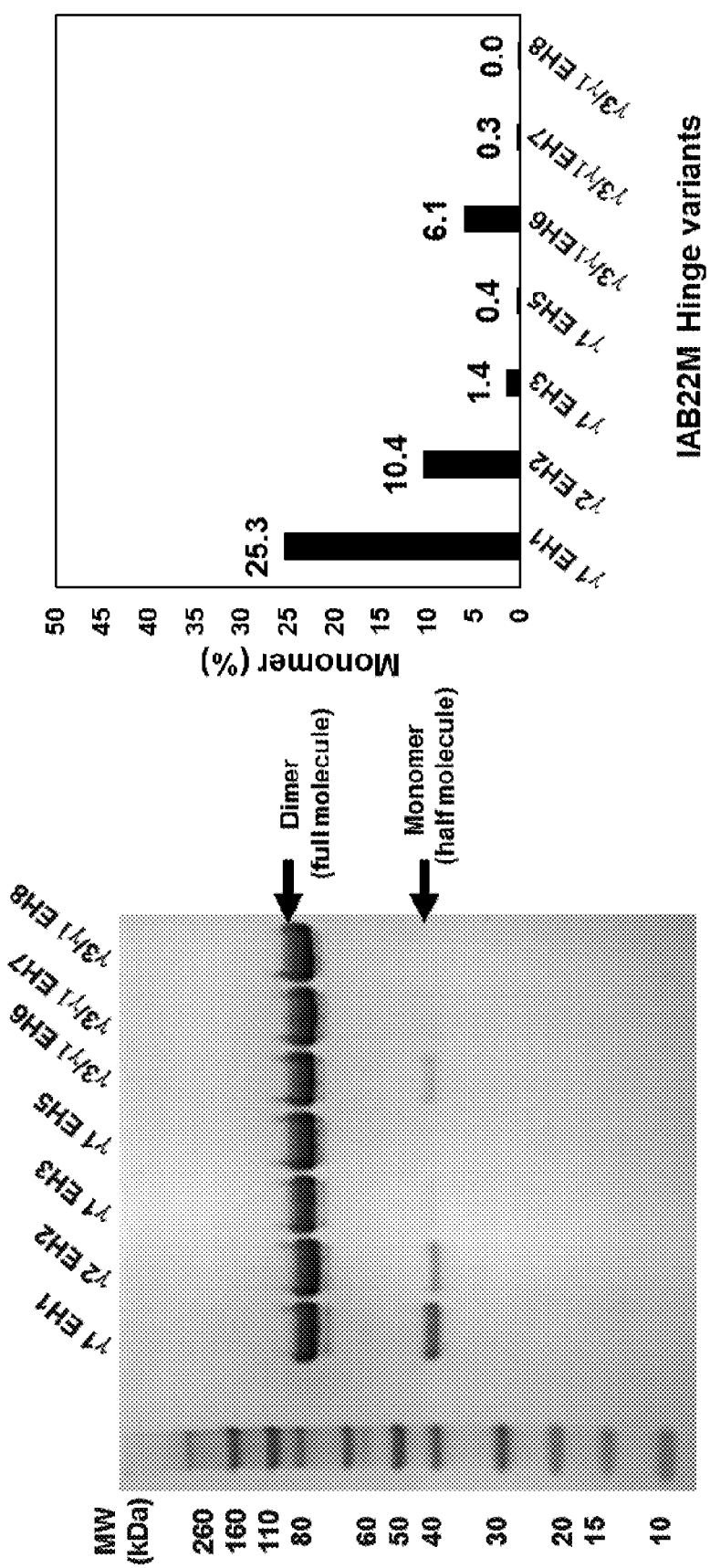
FIG. 22A shows an image of non-reduced SDS-PAGE analysis (left panel) of IAB22M hinge Mb variants and percentage of half molecules quantified by densitometry (right panel).

Mass spectrometry analysis was performed to obtained data to support the SDS-PAGE analyses data of FIGS. 21A and 22A. Two IAB22M constructs were evaluated using mass spectrometry to confirm the exact molecular weight, amount of half-molecule and post-translational modification, e.g. C-terminal lysine clipping. The protein constructs included minibodies with engineered hinges EH2, EH3 derived from IgG1 sequence (γ1 EH2 (FIG. 22B) and γ1 EH3 (FIG. 20C)). γ1 minibodies with EH2 hinge assembled properly into intact dimeric molecules but inclusion of only two cysteine yielded protein with high amount of half molecule. γ1 minibodies with EH3 hinge assembled properly into intact dimeric molecules and addition of third cysteine yielded protein with very low levels of half molecule.

Figure 23:
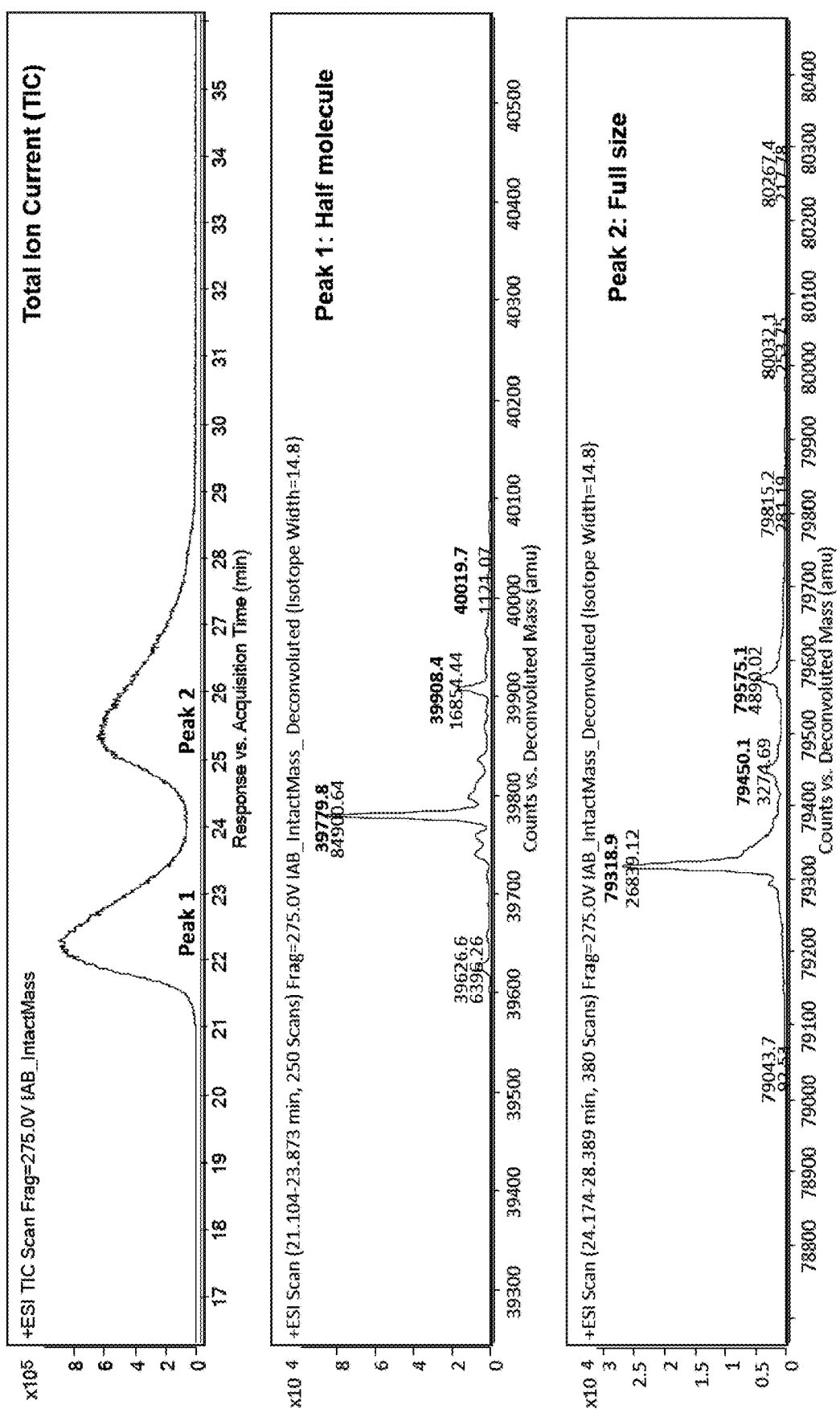
FIG. 23 shows the intact mass analysis of IAB22M γ1 EH1 variant. Upper panel shows the total ion chromatogram. Middle panel shows the deconvoluted intact masses confirming the presence of half molecules and the lower panel shows the full-size masses that were identified.

Intact mass analysis by mass spectrometry of IAB22M-γ1 EH1 (FIG. 16B) is shown in FIG. 23. The obtained molecular masses indicated C-terminal clipping. Of 3 species present (MW 79318.9, 79450.1 and 79575.1) only one matched the predicted MW of 79576. The obtained molecular masses indicated C-terminal clipping. Of 3 species present (MW 79318.9, 79450.1 and 79575.1) only one matched the predicted MW of 79576. The remainder were minibody with either 1 or both C-terminal lysines being clipped. Mbs constructed with only 2 disulfides in the hinge produced high levels of half molecule (~15%). For intact mass analysis of IAB22M γ1 EH1, the samples were separated by reverse phase chromatography column (TSKgel Phenyl-5PW (Tosoh, 2×75 mm) and analyzed using an Agilent ESI-QTOF mass spectrometer. FIG. 23 shows the total ion chromatograms of the separated half-molecule and full-size molecule (upper panel). The UV280 trace (not shown) was used for quantitation of the percent of half-molecules present in the minibody variant by peak integration. The deconvoluted masses were used for assignment and confirmed the identity of half molecules (middle panel) and of the full size masses (lower panel).

Figure 24:
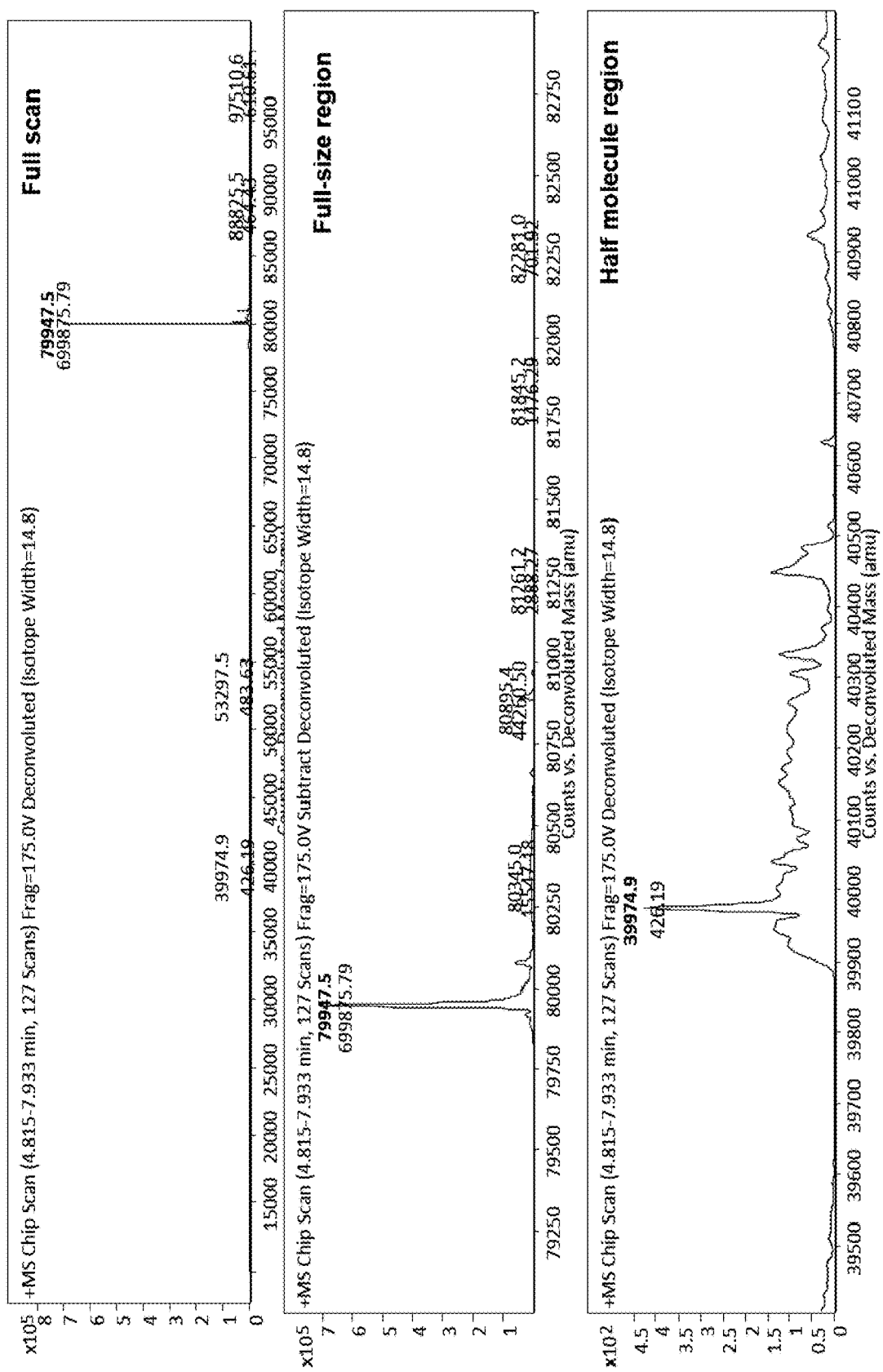
FIG. 24 shows intact mass analysis of IAB22M γ1 EH3 variant. The protein was separated under reverse phase conditions. Upper panel shows the full mass range scan. Zoomed-in full-size mass region emphasizes the presence of the intact protein (Middle panel). Zoomed-in half-molecule region showed that essentially no half-molecule is present (lower panel).
Figure 25A:
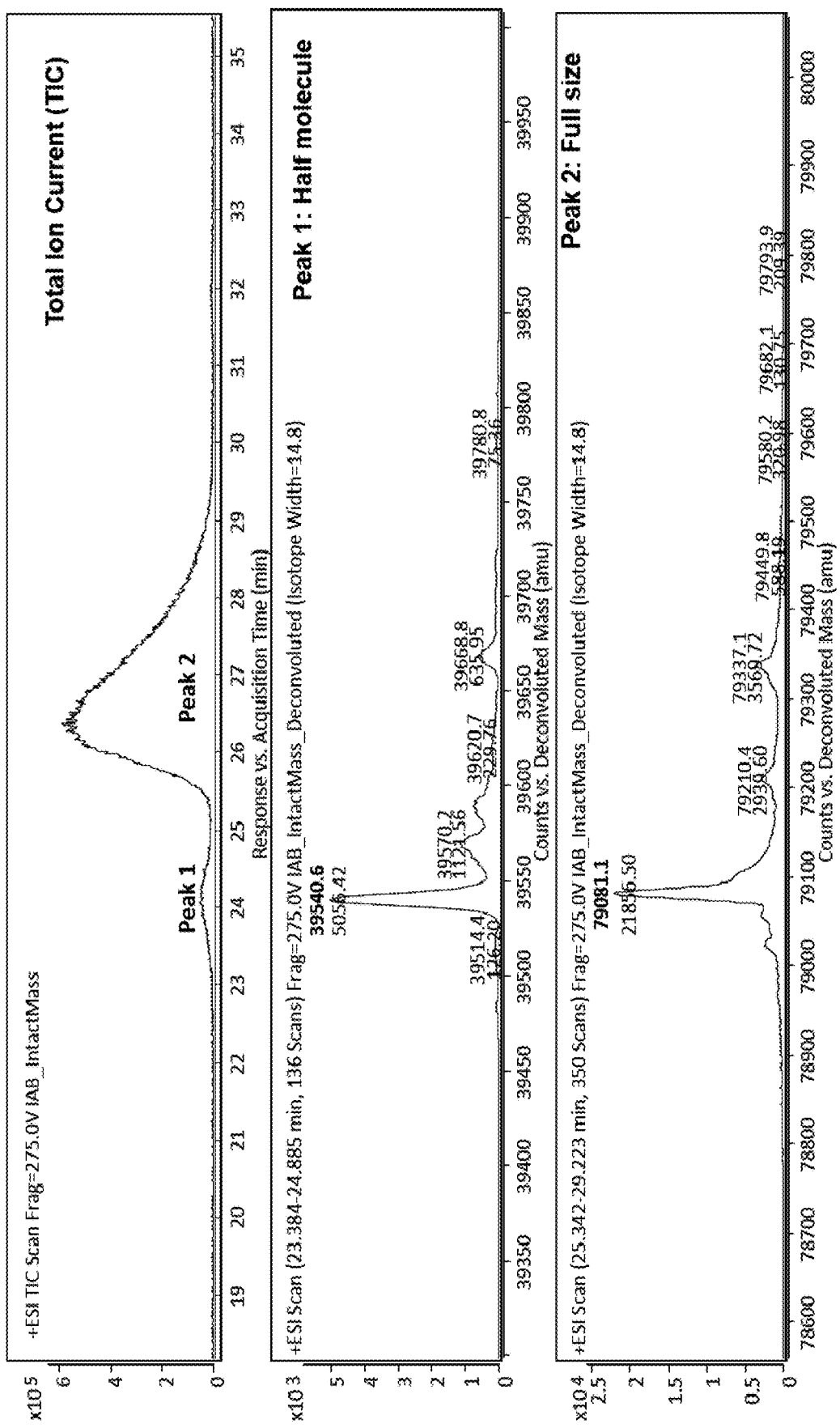
FIGS. 25A and 25B shows intact mass analyses of IAB22M γ2 hinge variants.
Figure 25B:
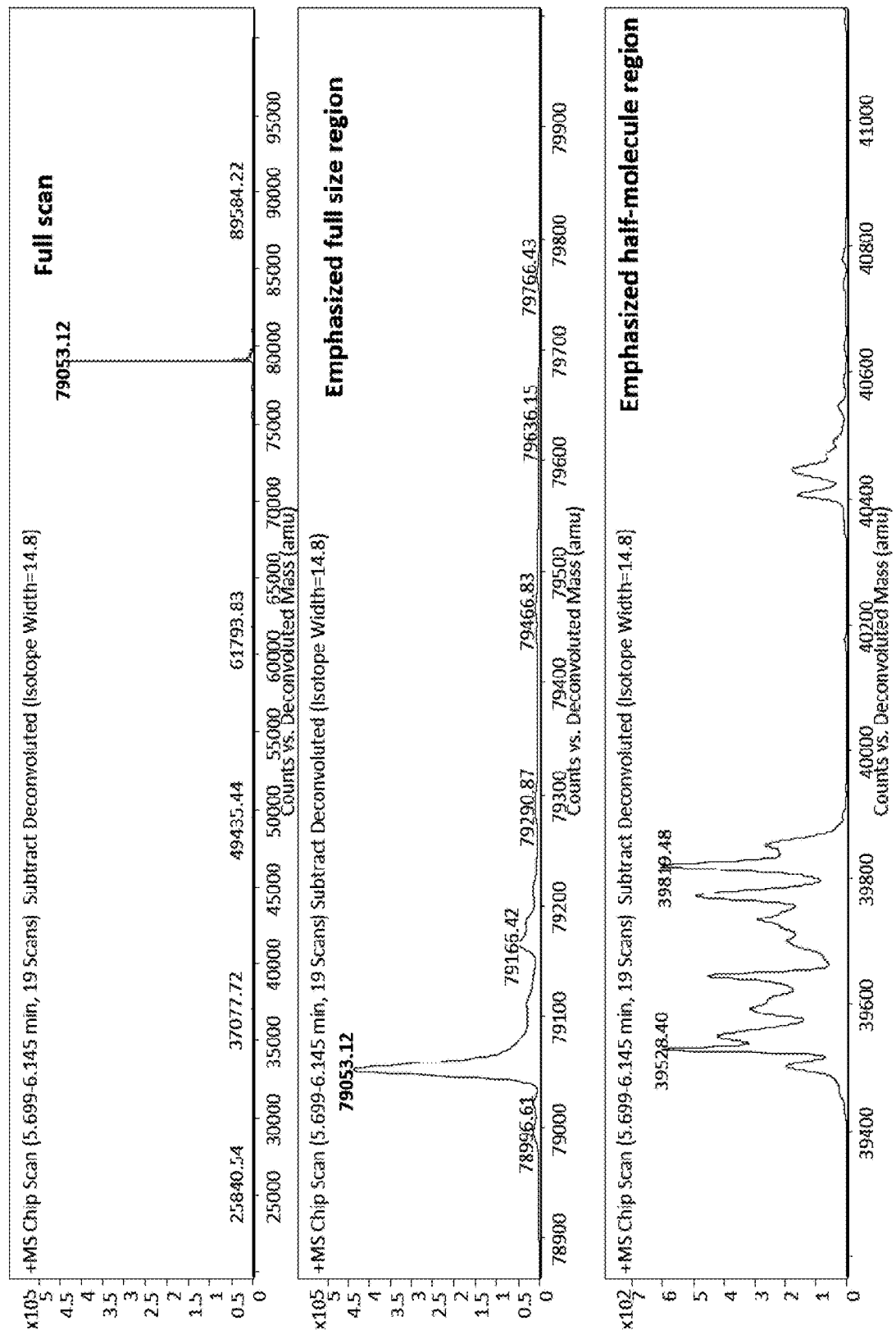

Intact mass analysis by mass spectrometry of IAB22M-γ1 EH3 variant (FIG. 20C) is shown in FIG. 24. Theoretical MW was 79946 matched the obtained MW of 79946. Modified IgG1 hinge constructed with three disulfide bonds in hinge yielded a minibody with greater than 99% full size protein. For intact mass analysis, a protein sample in acetate buffer was analyzed by LC/MS consisting of the following: Waters Synapt G2 HDMS fitted with a Trizaic nanoESI source coupled to a Waters nanoAcquity UPLC. The protein was separated using the reverse phase C4 nanotile column (150 μm ID×50 mm, Waters) operated at 30/min with 0.1% formic acid in water and 0.1% formic acid in acetonitrile as the mobile phases. FIG. 24 (upper panel) shows full mass range scan. Middle panel shows zoomed in region showing intact molecular mass. Lower panel shows zoomed in region showing half-molecule.

Table 9 shows a listing summarizing the theoretical predicted molecular weight (MW) mass and obtained MW mass by intact mass analysis for five IAB2M hinge variants (top; FIGS. 5B-5E, 7C) and seven IAB22M hinge variants (bottom; FIGS. 14B, 15B, 20C, 20D; 20E, 43, 44) and the respective content of half molecule. Actual masses of proteins matched their theoretically calculated molecular masses except where C terminal lysine residues were clipped leading to MW heterogeneity (FIGS. 6, 14A, 15A, 23 and 24).

TABLE 9

Half-molecule content obtained by intact mass analysis of IAB2M and IAB22M
(*C-terminal lysine clipping gives rise to heterogeneity)

| Minibody | Construct | Predicted Mass | Obtained mass | Percent Half Molecule |
|---|---|---|---|---|
| IAB2M | IAB2M-γ1 EH1 | 79433.6 | 79176.6, *79304, 79433.1 | 7.6 |
|  | IAB2M-γ2 EH1 | 79197.6 | 78938.7, 79069.7, 79195.9 | 11.1 |
|  | IAB2M-γ1 EH2 | 79145 | 79148 | 7.1 |
|  | IAB2M-γ2 EH2 | 78909 | 78909.2 | <0.5 |
|  | IAB2M-γ1 EH3 | 79739.8 | 79741.8 | <0.5 |
| IAB22M | IAB22M-γ2 EH1 | 79576 | 79318.9, 79450.1, 79575.1 | 9.2 |
|  | IAB22M-γ2 EH2 | 79051.5 | 79053 | <0.5 |
|  | IAB22M-γ1 EH3 | 79946.4 | 79947.5 | <0.1 |
|  | IAB22M-γ1 EH5 | 80541.2 | 80540 | <0.1 |
|  | IAB22M-γ3/γ1 EH6 | 80575.2 | 80576 | <0.5 |
|  | IAB22M-γ1 EH7 | 80312.8 | 80313.3 | <0.5 |
|  | IAB22M-γ1 EH8 | 80907.6 | 80907 | <0.5 |

Figure 26:
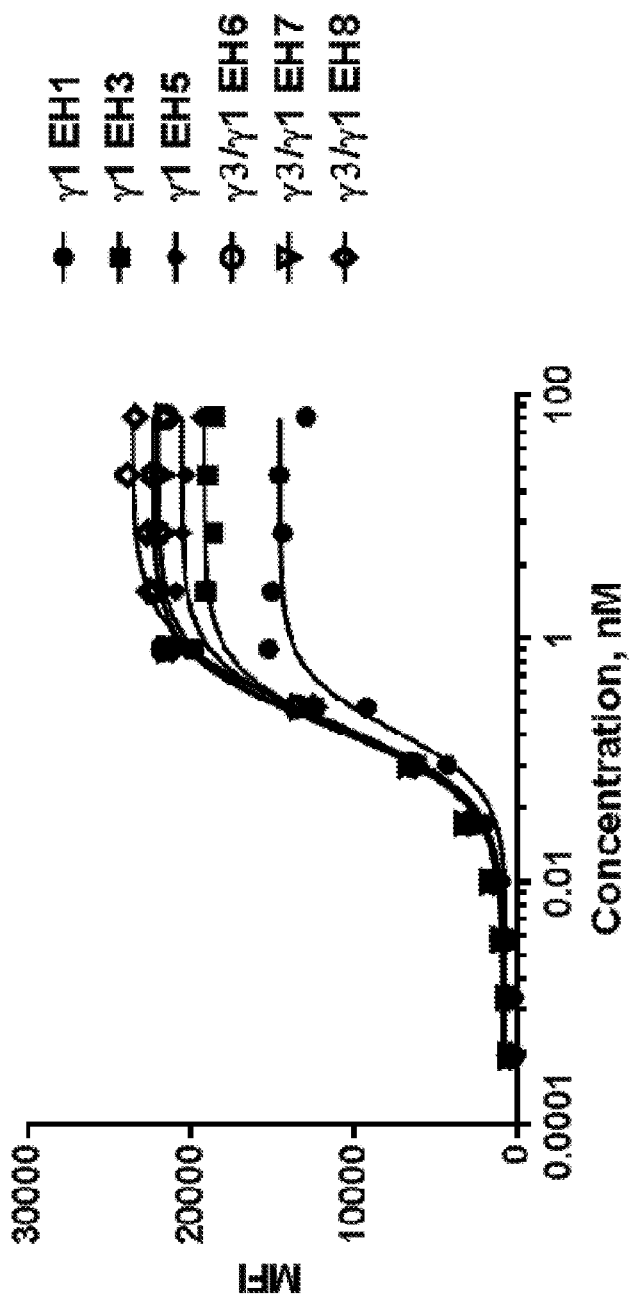
FIG. 26 shows binding curves and EC50 binding values of IAB2M engineered hinge variants determined by FACS using C4-2 XCL cells.

FAC analysis of was performed for IAB2M hinge variants (FIGS. 5E, 7C, 7D, 21B, 21C, 21D, 21E). All minibody hinge variants bound with similar affinity to the target antigen expressed on C4-2 XCL cells (FIG. 26).

Figure 27:
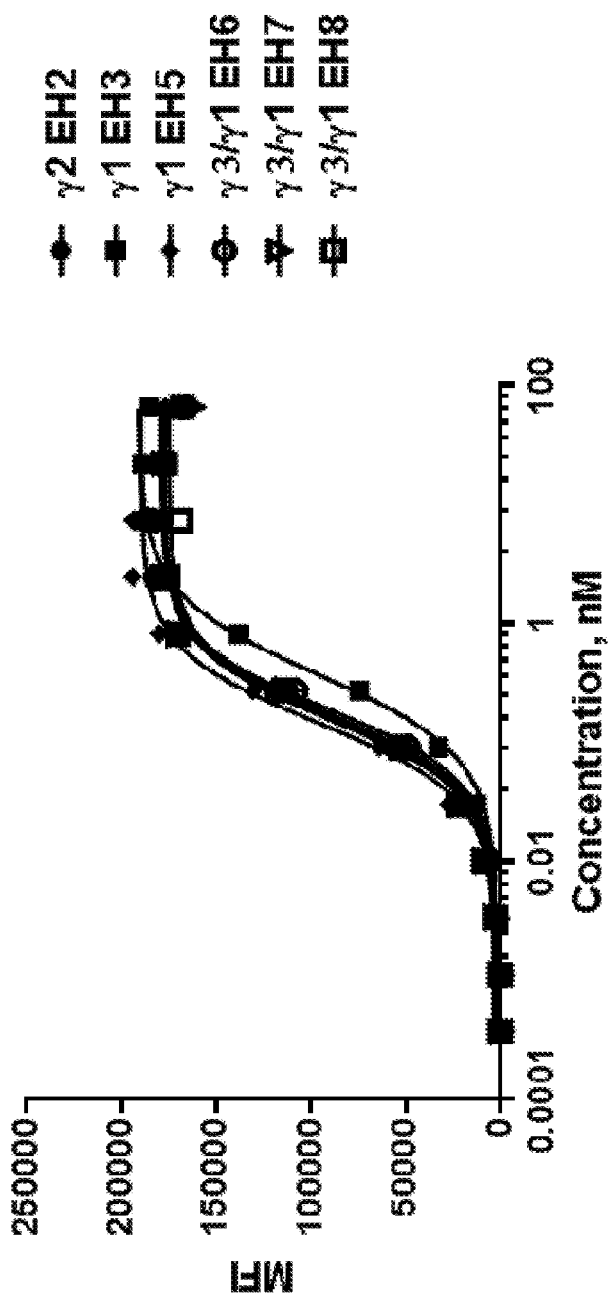
FIG. 27 shows binding curves and EC50 binding values of IAB22M engineered hinge variants determined by FACS using HPB-ALL cells.
Figure 28A:
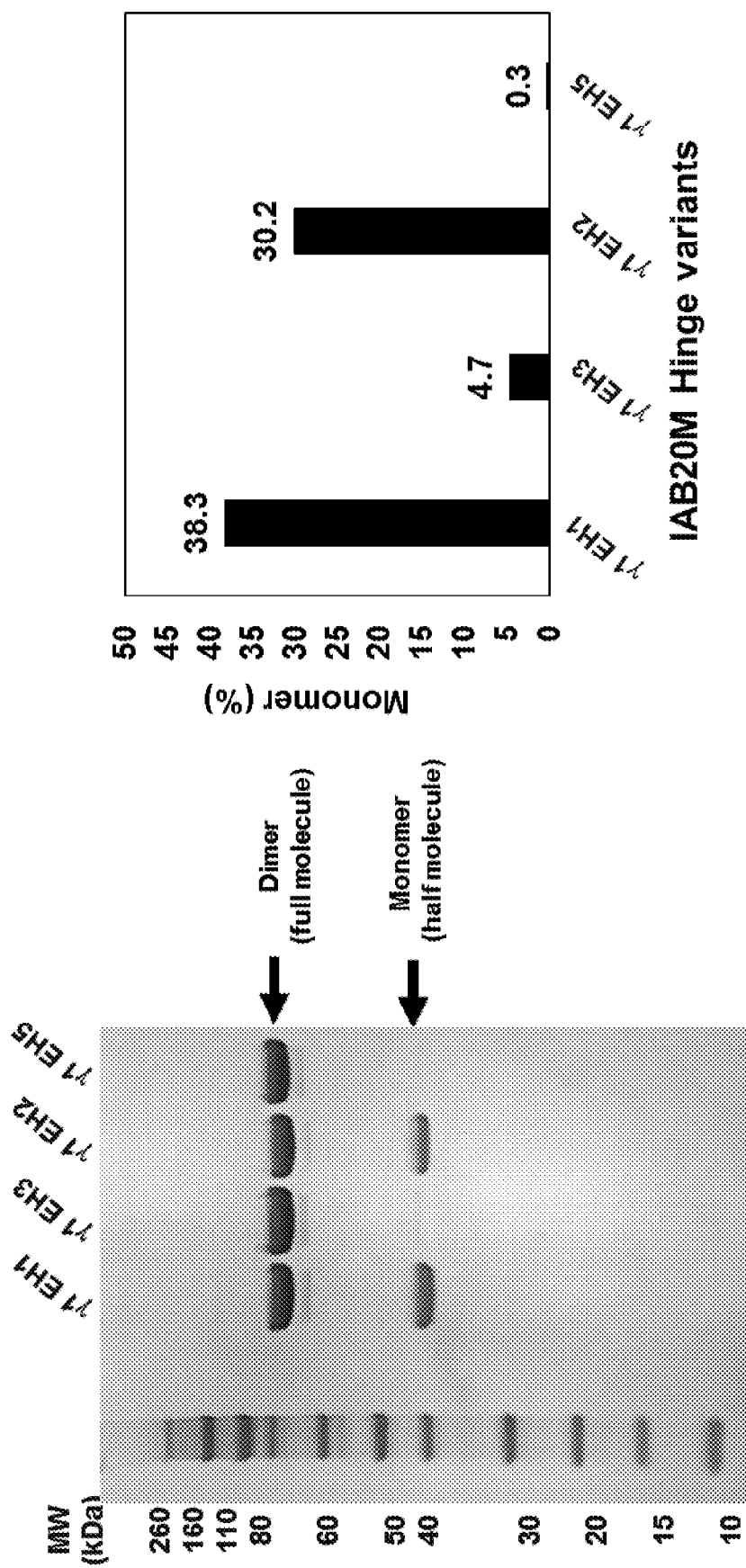
FIG. 28A shows an image of non-reduced SDS-PAGE analysis of IAB20M hinge Mb variants (left panel) and a percentage of half molecules quantified by densitometry (right panel).
Figure 29A:
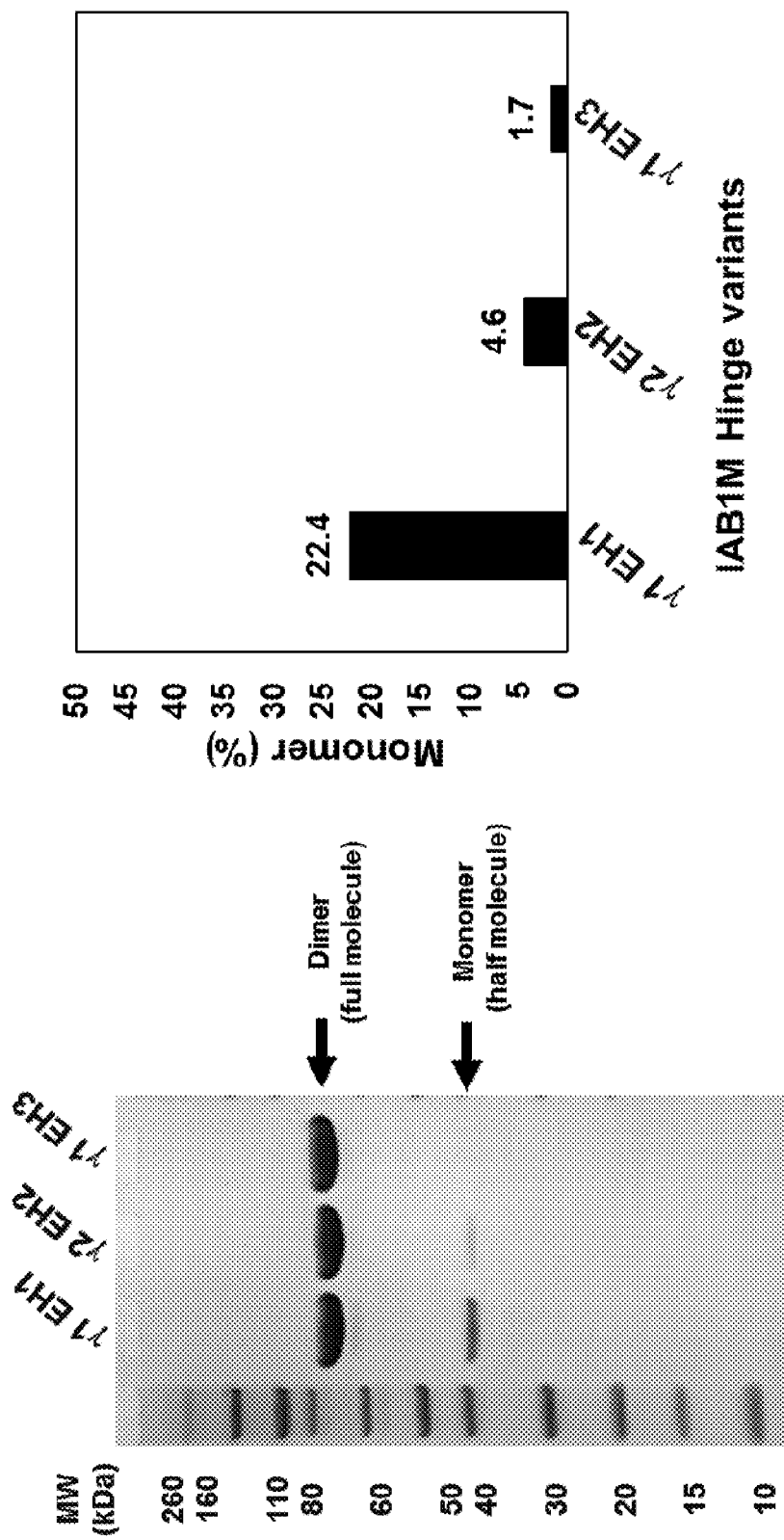
FIG. 29A shows an image of non-reduced SDS-PAGE analysis of IAB1M hinge Mb variants (left panel) and percentage of half molecules quantified by densitometry (right panel).

FAC analysis was performed for IAB22M hinge variants (FIGS. 15B, 20C, 20D, 20E, 20F, and 20G). Minibodies made with same scFv and $C_H3$ domains but different hinges all bound to cell surface CD8 on HPB-ALL cell with similar affinity (FIG. 27).

SDS-PAGE analysis (FIG. 28A) was performed for IAB20M hinge Mb variants (FIGS. 28B-28E) further confirming that the aspects of the hinge region noted herein can be applied across a wide range of target molecules (for example, that it works for a variety of minibodies directed to different target molecules). Additional embodiments of IAB20M variants are shown in FIGS. 54-59.

SDS-PAGE analysis (FIG. 29A) was performed for IAB1M hinge Mb variants (FIGS. 29B-29D) further confirming that the aspects of the hinge region noted herein can be applied across a wide range of target molecules (for example, that it works for a variety of minibodies directed to different target molecules). Additional embodiments of IAB1M variants are shown in FIGS. 60-65A, 65B, and 65C.

Example 8—In Vivo Data for Hinge Variants of IAB22M

Figure 30:
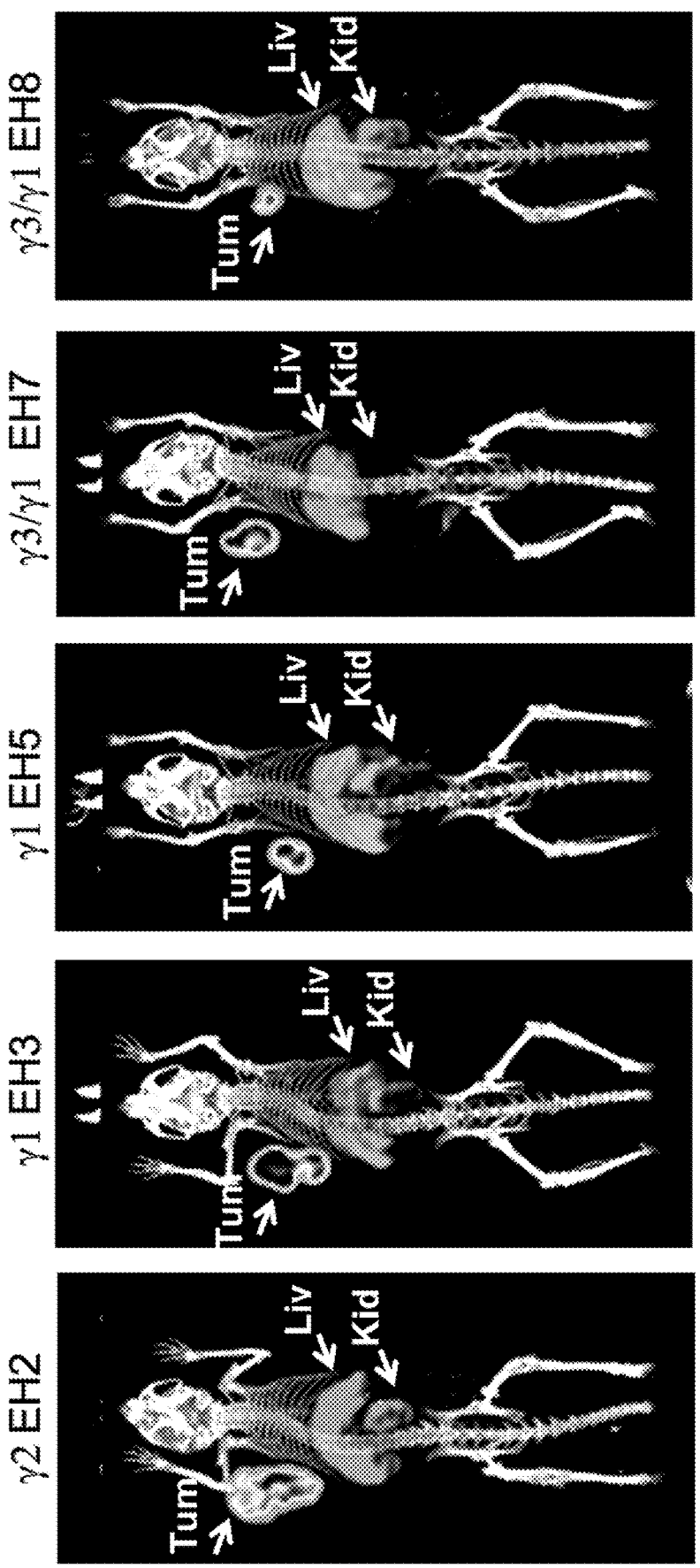
FIG. 30 shows PET/CT scan images comparing uptake of $^{89}$Zr radiolabeled IAB22 Mbs with different hinge sequences in NOD-SCID mice bearing antigen positive HPB-ALL xenografts on the left shoulder.

PET/CT analysis of $^{89}$Zr radiolabeled IAB22 Mbs with different hinge sequences (FIGS. 15B, 20C, 20D, 20F, 20G) was performed in NOD-SOD mice. MIP PET/CT images of NOD-SCID mice bearing CD8 positive HPB-ALL xenografts on the left shoulder after administration $^{89}$Zr-labeled Df-IAB22M hinge variants at 24 h are shown in FIG. 30. All new hinge variants resulted in lower kidney uptake. Good tumor targeting that ranged from 17-28% ID/g was obtained with all hinge variants. Overall, the liver signal was similar to the kidney signal.

Figure 31:
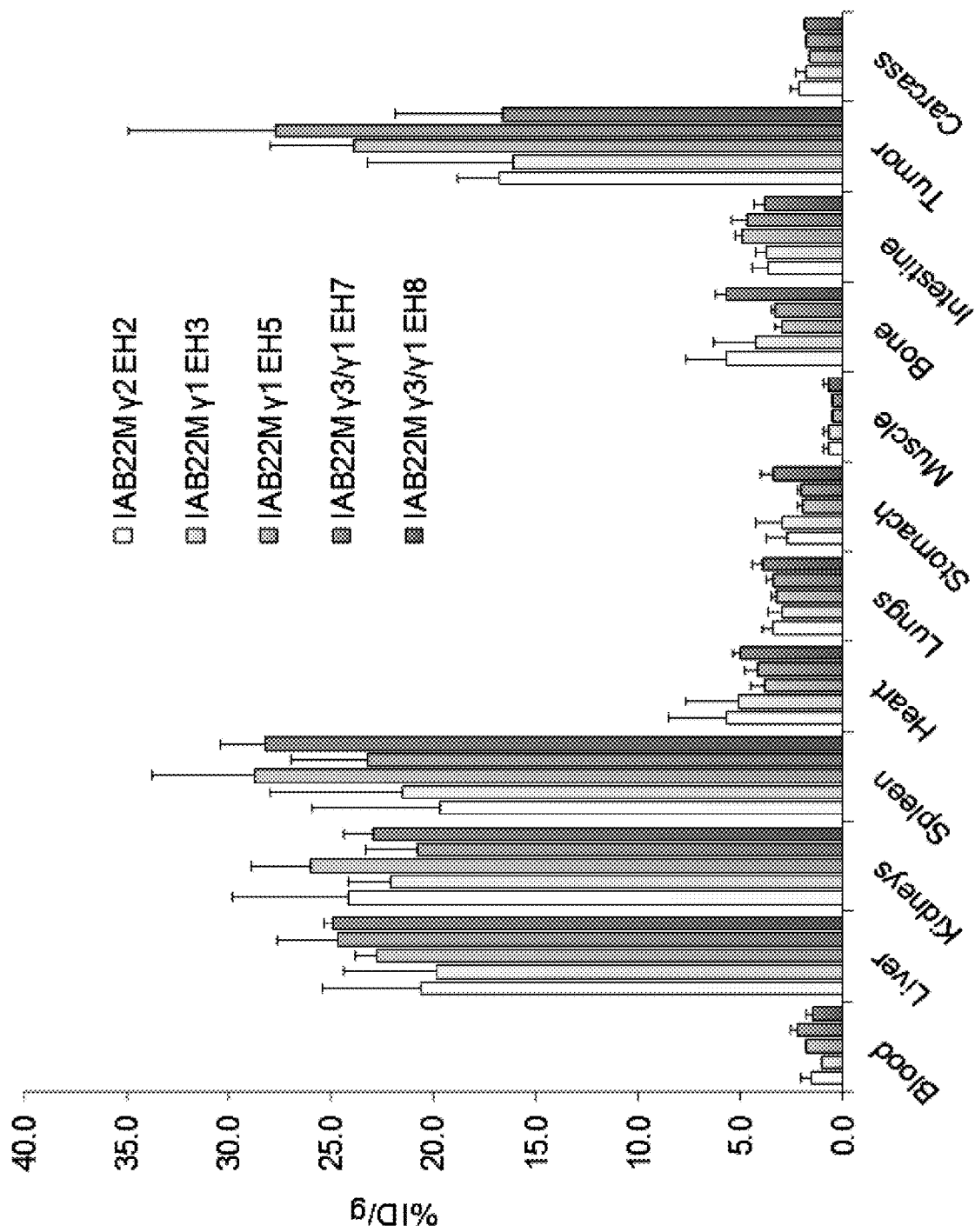
FIG. 31 shows a graph of biodistribution data of $^{89}$Zr radiolabeled IAB22 Mbs with different hinge sequences in NOD-SCID mice bearing antigen positive HPB-ALL xenografts on the left shoulder.

Biodistribution analysis (FIG. 31) was performed for $^{89}$Zr Radiolabeled IAB22 Mbs with the different hinge variants of FIG. 30. Similar biodistribution was observed for the IAB22M hinge variants. Excellent tumor targeting and uptake was detected compared to γ1 EH1. High clearance though liver was observed as predicted based on the data provided herein for a Mb that remained a dimer.

Example 9

A PSCA minibody from Table 0.2 is conjugated with a relevant chelating agent via cysteine residues on the minibody and subsequently radiolabeled with an isotope of In-111 (or in the alternative, Zirconium-89 or Copper-64). Alternatively, the minibody can be radiolabeled by directly radiolabeling with iodine via tyrosine residues.

The minibody is infused intravenously into a healthy human subject. The minibody is incubated in the human subject for 10 minutes post-infusion. On the same day as the incubation, the localization of the minibody is detected via a PET scan or external scintillation system.

Localization of minibody is used to determine localization of elevated levels of PSCA in the subject.

Example 10

A PSMA minibody from Table 0.2 is conjugated with a relevant chelating agent via cysteine residues on the minibody and subsequently radiolabeled with an isotope of In-111 (or in the alternative, Zirconium-89 or Copper-64). Alternatively, the minibody can be radiolabeled by directly radiolabeling with iodine via tyrosine residues.

The minibody is infused intravenously into a healthy human subject. The minibody is incubated in the human subject for 10 minutes post-infusion. On the same day as the incubation, the localization of the minibody is detected via a PET scan or external scintillation system.

Localization of minibody is used to determine localization of elevated levels of PSMA in the subject.

Example 11

Upon successful imaging of PSMA positive tumors by a PSMA minibody from Table 0.2, the biodistribution of the minibody may be investigated according to embodiments of the disclosure. These biodistribution studies can investigate the localization of the minibody at the tumor site versus other selected tissues over time following injection. These studies may be used to demonstrate high tumor to background ratios. Use of a minibody would likely produce a high tumor to background ratio when imaging a tumor that overexpresses PSMA, such as in prostate cancer. Positive results from these imaging and biodistribution experiments may lead to toxicology experiments in preparation for clinical studies.

Further, the ability of a minibody to target human PSMA in vivo by PET imaging studies may be demonstrated through clinical trials in cancer patients. Briefly, radiolabeled minibody can be injected intravenously into cancer patients having a form of cancer that is known to overexpress PSMA. At specific time points post-injection, each patient may be serially scanned by PET. After the final scan, patients may be scanned by CT for anatomical reference. The PET and CT images for each patient may then be analyzed to evaluate tumor targeting and specificity.

Example 12

A 5T4 minibody from Table 0.2 is conjugated with a relevant chelating agent via cysteine residues on the minibody and subsequently radiolabeled with an isotope of In-111 (or in the alternative, Zirconium-89 or Copper-64). Alternatively, the minibody can be radiolabeled by directly radiolabeling with iodine via tyrosine residues.

The minibody is infused intravenously into a healthy human subject. The minibody is incubated in the human subject for 10 minutes post-infusion. On the same day as the incubation, the localization of the minibody is detected via a PET scan or external scintillation system.

Localization of minibody is used to determine localization of elevated levels of 5T4 in the subject.

Example 13

A 5T4 minibody of Table 0.2 is provided. The minibody is infused intravenously into a subject having colorectal, renal, breast, ovarian, gastric, lung, and/or prostate cancer in an amount adequate to bind to sufficient levels of 5T4 in the subject to provide a lessening of the symptoms of colorectal, renal, breast, ovarian, gastric, lung, and/or prostate cancer in the subject.

Examples 14

A CD8 minibody from Table 0.2 is conjugated with a relevant chelator via cysteine residues on the minibody and subsequently radiolabeled with an isotope of In-111 (or in the alternative, Zirconium-89 or Copper-64). Alternatively, the minibody can be radiolabeled by directly radiolabeling with Iodine via tyrosine residues.

The minibody is infused intravenously into a healthy human subject. The minibody is incubated in the human subject for 10 minutes post-infusion. On the same day as the incubation, the localization of the minibody is detected via a PET scan or external scintillation system.

Localization of minibody is used to determine localization of CD8 in the subject.

Example 15

A CD8 minibody of Table 0.2 is provided. The minibody is infused intravenously into a healthy human subject.

The minibody is incubated in the human subject for 1 hour post-infusion. A secondary antibody, a humanized minibody that binds specifically to the CD8 minibody and is conjugated to $^{33}P$ is provided. Within the same day as the incubation, the secondary antibody is infused into to subject. The secondary antibody is incubated for one hour. The localization of the minibody is detected via PET imaging, via a marker on the secondary antibody.

Localization of minibody is used to determine localization of CD8 in the subject.

Example 16

A CD8 minibody of Table 0.2 is provided. The minibody is infused intravenously into a subject having a CD8 related disorder in an amount adequate to bind to sufficient levels of CD8 in the subject to provide a lessening of the symptoms of the CD8 related disorder. The minibody is conjugated to Yttrium-90.

Example 17

A CD8 minibody of Table 0.2 is provided. The minibody is injected into a patient who has been vaccinated with an antigen to an infectious disease or with a tumor associated antigen. The CD8 directed fragments augment the immune response and enhance the cytolytic activity of CD8 expressing T cells.

Example 18

A CD8 minibody of Table 0.2 is provided. The minibody is infused intravenously into a subject having a CD8 related disorder in an amount adequate to bind to sufficient levels of CD8 in the subject to provide a lessening of the symptoms of the CD8 related disorder. The minibody is conjugated to Lu-177. The CD8 minibody binds to a cell expressing CD8 and the Lu-177 results in the killing of the cell.

The results indicated that the constructs still bind to cellular human CD8.

Example 19

A CD3 minibody from Table 0.2 is conjugated with a relevant chelating agent via cysteine residues on the minibody and subsequently radiolabeled with an isotope of In-111 (or in the alternative, Zirconium-89 or Copper-64). Alternatively, the minibody can be radiolabeled by directly radiolabeling with iodine via tyrosine residues.

The minibody is infused intravenously into a healthy human subject. The minibody is incubated in the human subject for 10 minutes post-infusion. On the same day as the incubation, the localization of the minibody is detected via a PET scan or external scintillation system.

Localization of minibody is used to determine localization of elevated levels of CD3 in the subject.

Example 20

A CD3 minibody from Table 0.2 is provided. The minibody is infused intravenously into a subject having rheumatoid arthritis in an amount adequate to bind to sufficient levels of CD3 in the subject to provide a lessening of the symptoms of rheumatoid arthritis in the subject.

Example 21

A subject at risk of developing an unacceptably intense cytokine storm from the administration of OKT3 is identified. The subject has a need for reducing the level of CD3 proteins in his system as the subject has a CD3 dependent disorder. One of the minibodies to CD3 provided herein is selected and administered to the subject at a level that is effective for adequate binding to CD3 to occur, without a cytokine storm occurring.

Example 22

A humanized CD3 minibody of Table 0.2 is provided. The minibody is infused intravenously into a healthy human subject. The minibody is incubated in the human subject for 1 hour post-infusion. A secondary antibody, a humanized minibody that binds specifically to the CD3 minibody and is conjugated to $^{33}$P is provided. Immediately after the one-hour incubation, the secondary antibody is infused into to subject. The secondary antibody is incubated for one hour. Immediately after the one-hour incubation of the secondary antibody, the localization of the minibody is detected via PET imaging.

Localization of minibody is used to determine localization of CD3 in the subject.

Example 23

A subject at risk of developing an unacceptably intense cytokine storm from the administration of OKT3 is identified. The subject has a need for reducing the level of CD3 proteins in his system as the subject has a CD3 dependent disorder. One of the minibody or minibodies from the herein examples is selected and administered to the subject at a level that is effective for adequate binding to CD3 to occur, without a cytokine storm occurring.

If needed, the minibody or minibodies can be conjugated to a therapeutic agent for the treatment of the CD3 dependent disorder.

The subject can have any of a number of particular CD3 dependent disorders, which, each in the alternative can be rheumatoid arthritis, multiple sclerosis, type 1 diabetes, or lupus erythematosus.

Example 24

A PSCA minibody of Table 0.2 is provided. The minibody is infused intravenously into a subject having a PSCA related disorder in an amount adequate to bind to sufficient levels of PSCA in the subject to provide a lessening of the symptoms of the PSCA related disorder. The minibody is conjugated to Yttrium-90.

Example 25

A PSMA minibody of Table 0.2 is provided. The minibody is infused intravenously into a subject having a PSMA related disorder in an amount adequate to bind to sufficient levels of PSMA in the subject to provide a lessening of the symptoms of the PSMA related disorder. The minibody is conjugated to Yttrium-90.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

The foregoing description and examples detail certain embodiments. It will be appreciated, however, that no matter how detailed the foregoing may appear in text, the invention may be practiced in many ways and the invention should be construed in accordance with the appended claims and any equivalents thereof.

SEQUENCE LISTING

```
<160> NUMBER OF SEQ ID NOS: 256

<210> SEQ ID NO 1
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of: A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 1

Xaa Cys Xaa Xaa Cys Xaa Xaa Cys
1               5

<210> SEQ ID NO 2
<211> LENGTH: 13
<212> TYPE: PRT
<213> ORGANISM: Artificial Sequence
<220> FEATURE:
<223> OTHER INFORMATION: Hinge region
<220> FEATURE:
```

```
<221> NAME/KEY: VARIANT
<222> LOCATION: 1
<223> OTHER INFORMATION: Xaa = any amino acid that does not form a
      covalent crosslinking bond with another amino acid
<220> FEATURE:
<221> NAME/KEY: VARIANT
<222> LOCATION: 2-6, 8, 9, 11, 12
<223> OTHER INFORMATION: Xaa = any amino acid

<400> SEQUENCE: 2

Xaa Xaa Xaa Xaa Xaa Xaa Cys Xaa Xaa Cys Xaa Xaa Cys
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Minibody
<220> FEATURE:
<221> NAME/KEY: VARIANT
<222> LOCATION: 1
<223> OTHER INFORMATION: Xaa = any amino acid or no amino acid
<220> FEATURE:
<221> NAME/KEY: VARIANT
<222> LOCATION: 3, 4, 6, 7
<223> OTHER INFORMATION: Xaa = any amino acid

<400> SEQUENCE: 3

Xaa Cys Xaa Xaa Cys Xaa Xaa Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Minibody
<220> FEATURE:
<221> NAME/KEY: VARIANT
<222> LOCATION: 1
<223> OTHER INFORMATION: Xaa = any amino acid or no amino acid
<220> FEATURE:
<221> NAME/KEY: VARIANT
<222> LOCATION: 3, 4, 6, 7
<223> OTHER INFORMATION: Xaa = any amino acid
<220> FEATURE:
<221> NAME/KEY: VARIANT
<222> LOCATION: 9
<223> OTHER INFORMATION: Xaa = any amino acid, no amino acid, or P

<400> SEQUENCE: 4

Xaa Cys Xaa Xaa Cys Xaa Xaa Cys Xaa
1               5

<210> SEQ ID NO 5
<211> LENGTH: 1128
<212> TYPE: DNA
<213> ORGANISM: Artificial Sequence
<220> FEATURE:
<223> OTHER INFORMATION: IAB2M gamma 1 EH5 (Minibody 2)

<400> SEQUENCE: 5
gaagtgcagc tggtgcagag cggcgcggaa gtgaaaaaac cgggcgcgag cgtgaaaatt      60
agctgcaaaa ccagcggcta cctttacc gaatatacca ttcattgggt gaaacaggcg      120
agcggcaaag cctggaatg gattggcaac attaacccga caacggcgg caccacctat      180 aaccagaaat ttgaagatcg cgcgaccctg accgtggata aaagcaccag caccgcgtat      240
atggaactga gcagcctgcg cagcgaagat accgcggtgt attattgcgc ggcgggctgg      300
```

```
aactttgatt attggggcca gggcaccacc gtgaccgtga gcagcggcag caccagcggc      360
ggcggcagcg gcggcggcag cggcggcggc ggcagcagcg atattgtgat gacccagagc      420
ccgagcagcc tgagcgcgag cgtgggcgat cgcgtgacca ttacctgcaa agcgagccag      480
gatgtgggca ccgcgtgga ttggtatcag cagaaaccgg gcaaagcgcc gaaactgctg      540
atttattggg cgagcacccg ccataccggc gtgccggatc gctttaccgg cagcggcagc      600
ggcaccgatt ttaccctgac cattagcagc ctgcagccgg aagattttgc ggattatttt      660
tgccagcagt ataacagcta tccgctgacc tttggcggcg gcaccaaact ggaaattaaa      720
gaaccgaaaa gcagcgataa aacccatacc tgcccgccgt gcccgccgtg cccgccgtgc      780
ggcggcggca gcagcggcgg cggcagcggc ggccagccgc gcgaaccgca ggtgtatacc      840
ctgccgccga ccgcgaaga atgaccaaa aaccaggtga gcctgacctg cctggtgaaa      900
ggcttttatc cgagcgatat tgcggtggaa tgggaaagca cggccagcc ggaaaacaac      960 tataaaaacca ccccgccggt gctgatagc gatggcagct tttttctgta tagcaaactg     1020
accgtggata aagccgctg gcagcagggc aacgtgttta gctgcagcgt gatgcatgaa     1080
gcgctgcata accattatac ccagaaaagc ctgagcctga gcccgggc                    1128

<210> SEQ ID NO 6
<211> LENGTH: 1134
<212> TYPE: DNA
<213> ORGANISM: Artificial Sequence
<220> FEATURE:
<223> OTHER INFORMATION: IAB2M gamma 1 EH8 (Minibody 2)

<400> SEQUENCE: 6
gaagtgcagc tggtgcagag cggcgcgaa gtgaaaaaac cgggcgcgag cgtgaaaatt        60
agctgcaaaa ccagcggcta taccttacc gaatatacca ttcattgggt gaaacaggcg       120
agcggcaaag ccctggaatg gattggcaac attaaccccga caacggcgg caccacctat      180 aaccagaaat ttgaagatcg cgcgaccctg accgtggata aagcaccag caccgcgtat      240 atggaactga gcagcctgcg cagcgaagat accgcggtgt attattgcgc ggcgggctgg      300
aactttgatt attggggcca gggcaccacc gtgaccgtga gcagcggcag caccagcggc      360
ggcggcagcg gcggcggcag cggcggcggc ggcagcagcg atattgtgat gacccagagc      420
ccgagcagcc tgagcgcgag cgtgggcgat cgcgtgacca ttacctgcaa agcgagccag      480
gatgtgggca ccgcgtgga ttggtatcag cagaaaccgg gcaaagcgcc gaaactgctg      540
atttattggg cgagcacccg ccataccggc gtgccggatc gctttaccgg cagcggcagc      600
ggcaccgatt ttaccctgac cattagcagc ctgcagccgg aagattttgc ggattatttt      660
tgccagcagt ataacagcta tccgctgacc tttggcggcg gcaccaaact ggaaattaaa      720
gaactgaaaa ccccgctggg cgataccacc catacctgcc cgccgtgccc gccgtgcccg      780
ccgtgcggcg gcggcagcag cggcggcggc agcggcggcc agccgcgcga accgcaggtg      840
tataccctgc cgccgagccg cgaagaaatg accaaaaacc aggtgagcct gacctgcctg      900
gtgaaaggct tttatccgag cgatattgcg gtggaatggg aaagcaacgg ccagccggaa      960
aacaactata aaaccacccc gccggtgctg gatagcgatg gcagctttt tctgtatagc     1020 aaactgaccg tggataaaag ccgctggcag cagggcaacg tgtttagctg cagcgtgatg     1080
catgaagcgc tgcataacca ttatacccag aaaagcctga gcctgagccc gggc          1134

<210> SEQ ID NO 7
```

```
<211> LENGTH: 373
<212> TYPE: PRT
<213> ORGANISM: Artificial Sequence
<220> FEATURE:
<223> OTHER INFORMATION: IAB2M gamma 1 EH3 (Minibody 1)

<400> SEQUENCE: 7

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
            85                  90                  95

Thr Phe Gly Gly Gly Thr Lys Leu Glu Ile Lys Gly Ser Thr Ser Gly
        100                 105                 110

Gly Gly Ser Gly Gly Gly Ser Gly Gly Gly Ser Ser Glu Val Gln
            115                 120                 125

Leu Val Gln Ser Gly Ala Glu Val Lys Lys Pro Gly Ala Ser Val Lys
        130                 135                 140

Ile Ser Cys Lys Thr Ser Gly Tyr Thr Phe Thr Glu Tyr Thr Ile His
145                 150                 155                 160

Trp Val Lys Gln Ala Ser Gly Lys Gly Leu Glu Trp Ile Gly Asn Ile
            165                 170                 175

Asn Pro Asn Asn Gly Gly Thr Thr Tyr Asn Gln Lys Phe Glu Asp Arg
        180                 185                 190

Ala Thr Leu Thr Val Asp Lys Ser Thr Ser Thr Ala Tyr Met Glu Leu
    195                 200                 205

Ser Ser Leu Arg Ser Glu Asp Thr Ala Val Tyr Tyr Cys Ala Ala Gly
210                 215                 220

Trp Asn Phe Asp Tyr Trp Gly Gln Gly Thr Thr Val Thr Val Ser Ser
225                 230                 235                 240

Glu Pro Lys Ser Ser Asp Lys Thr His Thr Cys Pro Pro Cys Pro Pro
            245                 250                 255

Cys Gly Gly Gly Ser Gly Gly Gly Ser Gly Gly Gln Pro Arg Glu
        260                 265                 270

Pro Gln Val Tyr Thr Leu Pro Pro Ser Arg Glu Glu Met Thr Lys Asn
    275                 280                 285

Gln Val Ser Leu Thr Cys Leu Val Lys Gly Phe Tyr Pro Ser Asp Ile
290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
            325                 330                 335

Leu Thr Val Asp Lys Ser Arg Trp Gln Gln Gly Asn Val Phe Ser Cys
        340                 345                 350

Ser Val Met His Glu Ala Leu His Asn His Tyr Thr Gln Lys Ser Leu
    355                 360                 365

Ser Leu Ser Pro Gly
    370
```

<210> SEQ ID NO 8
<211> LENGTH: 376
<212> TYPE: PRT
<213> ORGANISM: Artificial Sequence
<220> FEATURE:
<223> OTHER INFORMATION: IAB2M gamma 1 EH5 (Minibody 1)

<400> SEQUENCE: 8

```
Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys Gly Ser Thr Ser Gly
            100                 105                 110

Gly Gly Ser Gly Gly Gly Ser Gly Gly Gly Ser Ser Glu Val Gln
            115                 120                 125

Leu Val Gln Ser Gly Ala Glu Val Lys Lys Pro Gly Ala Ser Val Lys
130                 135                 140

Ile Ser Cys Lys Thr Ser Gly Tyr Thr Phe Thr Glu Tyr Thr Ile His
145                 150                 155                 160

Trp Val Lys Gln Ala Ser Gly Lys Gly Leu Glu Trp Ile Gly Asn Ile
                165                 170                 175

Asn Pro Asn Asn Gly Gly Thr Thr Tyr Asn Gln Lys Phe Glu Asp Arg
            180                 185                 190

Ala Thr Leu Thr Val Asp Lys Ser Thr Ser Thr Ala Tyr Met Glu Leu
        195                 200                 205

Ser Ser Leu Arg Ser Glu Asp Thr Ala Val Tyr Tyr Cys Ala Ala Gly
    210                 215                 220

Trp Asn Phe Asp Tyr Trp Gly Gln Gly Thr Thr Val Thr Val Ser Ser
225                 230                 235                 240

Glu Pro Lys Ser Ser Asp Lys Thr His Thr Cys Pro Pro Cys Pro Pro
                245                 250                 255

Cys Pro Pro Cys Gly Gly Gly Ser Ser Gly Gly Ser Gly Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365
```

```
Lys Ser Leu Ser Leu Ser Pro Gly
    370             375
```

<210> SEQ ID NO 9
<211> LENGTH: 378
<212> TYPE: PRT
<213> ORGANISM: Artificial Sequence
<220> FEATURE:
<223> OTHER INFORMATION: IAB2M gamma 1 EH8 (Minibody 1)

<400> SEQUENCE: 9

```
Asp Ile Val Met Thr Gln Ser Pro Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys Gly Ser Thr Ser Gly
            100                 105                 110

Gly Gly Ser Gly Gly Gly Ser Gly Gly Gly Ser Ser Glu Val Gln
        115                 120                 125

Leu Val Gln Ser Gly Ala Glu Val Lys Lys Pro Gly Ala Ser Val Lys
130                 135                 140

Ile Ser Cys Lys Thr Ser Gly Tyr Thr Phe Thr Glu Tyr Thr Ile His
145                 150                 155                 160

Trp Val Lys Gln Ala Ser Gly Lys Gly Leu Glu Trp Ile Gly Asn Ile
                165                 170                 175

Asn Pro Asn Asn Gly Gly Thr Thr Tyr Asn Gln Lys Phe Glu Asp Arg
            180                 185                 190

Ala Thr Leu Thr Val Asp Lys Ser Thr Ser Thr Ala Tyr Met Glu Leu
        195                 200                 205

Ser Ser Leu Arg Ser Glu Asp Thr Ala Val Tyr Tyr Cys Ala Ala Gly
    210                 215                 220

Trp Asn Phe Asp Tyr Trp Gly Gln Gly Thr Thr Val Thr Val Ser Ser
225                 230                 235                 240

Glu Leu Lys Thr Pro Leu Gly Asp Thr Thr His Thr Cys Pro Pro Cys
                245                 250                 255

Pro Pro Cys Pro Pro Cys Gly Gly Ser Ser Gly Gly Gly Ser Gly
            260                 265                 270

Gly Gln Pro Arg Glu Pro Gln Val Tyr Thr Leu Pro Pro Ser Arg Glu
        275                 280                 285

Glu Met Thr Lys Asn Gln Val Ser Leu Thr Cys Leu Val Lys Gly Phe
    290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350
```

Asn Val Phe Ser Cys Ser Val Met His Glu Ala Leu His Asn His Tyr
            355                 360                 365

Thr Gln Lys Ser Leu Ser Leu Ser Pro Gly
            370                 375

<210> SEQ ID NO 10
<211> LENGTH: 373
<212> TYPE: PRT
<213> ORGANISM: Artificial Sequence
<220> FEATURE:
<223> OTHER INFORMATION: IAB2M gamma 1 EH3 (Minibody 2)

<400> SEQUENCE: 10

Glu Val Gln Leu Val Gln Ser Gly Ala Glu Val Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ala Ser Gly Lys Gly Leu Glu Trp Ile
            35                  40                  45

Gly Asn Ile Asn Pro Asn Asn Gly Gly Thr Thr Tyr Asn Gln Lys Phe
        50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser Gly Ser Thr Ser Gly Gly Gly Ser Gly Gly Gly Ser Gly
            115                 120                 125

Gly Gly Gly Ser Ser Asp Ile Val Met Thr Gln Ser Pro Ser Ser Leu
        130                 135                 140

Ser Ala Ser Val Gly Asp Arg Val Thr Ile Thr Cys Lys Ala Ser Gln
145                 150                 155                 160

Asp Val Gly Thr Ala Val Asp Trp Tyr Gln Gln Lys Pro Gly Lys Ala
                165                 170                 175

Pro Lys Leu Leu Ile Tyr Trp Ala Ser Thr Arg His Thr Gly Val Pro
            180                 185                 190

Asp Arg Phe Thr Gly Ser Gly Ser Gly Thr Asp Phe Thr Leu Thr Ile
            195                 200                 205

Ser Ser Leu Gln Pro Glu Asp Phe Ala Asp Tyr Phe Cys Gln Gln Tyr
        210                 215                 220

Asn Ser Tyr Pro Leu Thr Phe Gly Gly Gly Thr Lys Leu Glu Ile Lys
225                 230                 235                 240

Glu Pro Lys Ser Ser Asp Lys Thr His Thr Cys Pro Pro Cys Pro Pro
                245                 250                 255

Cys Gly Gly Gly Ser Ser Gly Gly Ser Gly Gly Gln Pro Arg Glu
            260                 265                 270

Pro Gln Val Tyr Thr Leu Pro Pro Ser Arg Glu Glu Met Thr Lys Asn
            275                 280                 285

Gln Val Ser Leu Thr Cys Leu Val Lys Gly Phe Tyr Pro Ser Asp Ile
        290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

```
Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
            355                 360                 365

Ser Leu Ser Pro Gly
            370

<210> SEQ ID NO 11
<211> LENGTH: 376
<212> TYPE: PRT
<213> ORGANISM: Artificial Sequence
<220> FEATURE:
<223> OTHER INFORMATION: IAB2M gamma 1 EH5 (Minibody 2)

<400> SEQUENCE: 11

Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ala Ser Gly Lys Gly Leu Glu Trp Ile
            35                  40                  45

Gly Asn Ile Asn Pro Asn Asn Gly Gly Thr Thr Tyr Asn Gln Lys Phe
    50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Ala Gly Trp Asn Phe Asp Tyr Trp Gly Gln Gly Thr Thr Val Thr
            100                 105                 110

Val Ser Ser Gly Ser Thr Ser Gly Gly Gly Ser Gly Gly Gly Ser Gly
            115                 120                 125

Gly Gly Ser Ser Asp Ile Val Met Thr Gln Ser Pro Ser Ser Leu
    130                 135                 140

Ser Ala Ser Val Gly Asp Arg Val Thr Ile Thr Cys Lys Ala Ser Gln
145                 150                 155                 160

Asp Val Gly Thr Ala Val Asp Trp Tyr Gln Gln Lys Pro Gly Lys Ala
            165                 170                 175

Pro Lys Leu Leu Ile Tyr Trp Ala Ser Thr Arg His Thr Gly Val Pro
            180                 185                 190

Asp Arg Phe Thr Gly Ser Gly Ser Gly Thr Asp Phe Thr Leu Thr Ile
            195                 200                 205

Ser Ser Leu Gln Pro Glu Asp Phe Ala Asp Tyr Phe Cys Gln Gln Tyr
            210                 215                 220

Asn Ser Tyr Pro Leu Thr Phe Gly Gly Gly Thr Lys Leu Glu Ile Lys
225                 230                 235                 240

Glu Pro Lys Ser Ser Asp Lys Thr His Thr Cys Pro Pro Cys Pro Pro
            245                 250                 255

Cys Pro Pro Cys Gly Gly Gly Ser Gly Gly Gly Ser Gly Gly Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Asn Gly Gln Pro Glu Asn Asn
305                 310                 315                 320
```

```
Tyr Lys Thr Thr Pro Pro Val Leu Asp Ser Asp Gly Ser Phe Phe Leu
                325             330             335

Tyr Ser Lys Leu Thr Val Asp Lys Ser Arg Trp Gln Gln Gly Asn Val
                340             345             350

Phe Ser Cys Ser Val Met His Glu Ala Leu His Asn His Tyr Thr Gln
                355             360             365

Lys Ser Leu Ser Leu Ser Pro Gly
    370             375

<210> SEQ ID NO 12
<211> LENGTH: 378
<212> TYPE: PRT
<213> ORGANISM: Artificial Sequence
<220> FEATURE:
<223> OTHER INFORMATION: IAB2M gamma 1 EH8 (Minibody 2)

<400> SEQUENCE: 12

Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
                20                  25                  30

Thr Ile His Trp Val Lys Gln Ala Ser Gly Lys Gly Leu Glu Trp Ile
            35                  40                  45

Gly Asn Ile Asn Pro Asn Asn Gly Gly Thr Thr Tyr Asn Gln Lys Phe
    50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser Gly Ser Thr Ser Gly Gly Gly Ser Gly Gly Gly Ser Gly
            115                 120                 125

Gly Gly Gly Ser Ser Asp Ile Val Met Thr Gln Ser Pro Ser Ser Leu
    130                 135                 140

Ser Ala Ser Val Gly Asp Arg Val Thr Ile Thr Cys Lys Ala Ser Gln
145                 150                 155                 160

Asp Val Gly Thr Ala Val Asp Trp Tyr Gln Gln Lys Pro Gly Lys Ala
                165                 170                 175

Pro Lys Leu Leu Ile Tyr Trp Ala Ser Thr Arg His Thr Gly Val Pro
            180                 185                 190

Asp Arg Phe Thr Gly Ser Gly Ser Gly Thr Asp Phe Thr Leu Thr Ile
            195                 200                 205

Ser Ser Leu Gln Pro Glu Asp Phe Ala Asp Tyr Phe Cys Gln Gln Tyr
    210                 215                 220

Asn Ser Tyr Pro Leu Thr Phe Gly Gly Gly Thr Lys Leu Glu Ile Lys
225                 230                 235                 240

Glu Leu Lys Thr Pro Leu Gly Asp Thr Thr His Thr Cys Pro Pro Cys
                245                 250                 255

Pro Pro Cys Pro Pro Cys Gly Gly Gly Ser Ser Gly Gly Gly Ser Gly
            260                 265                 270

Gly Gln Pro Arg Glu Pro Gln Val Tyr Thr Leu Pro Pro Ser Arg Glu
            275                 280                 285

Glu Met Thr Lys Asn Gln Val Ser Leu Thr Cys Leu Val Lys Gly Phe
    290                 295                 300
```

```
Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
            325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
            355                 360                 365

Thr Gln Lys Ser Leu Ser Leu Ser Pro Gly
            370                 375
```

<210> SEQ ID NO 13
<211> LENGTH: 107
<212> TYPE: PRT
<213> ORGANISM: Artificial Sequence
<220> FEATURE:
<223> OTHER INFORMATION: IAB2M variable light sequence

<400> SEQUENCE: 13

```
Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys
            100                 105
```

<210> SEQ ID NO 14
<211> LENGTH: 115
<212> TYPE: PRT
<213> ORGANISM: Artificial Sequence
<220> FEATURE:
<223> OTHER INFORMATION: IAB2M variable heavy sequence

<400> SEQUENCE: 14

```
Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ala Ser Gly Lys Gly Leu Glu Trp Ile
        35                  40                  45

Gly Asn Ile Asn Pro Asn Asn Gly Gly Thr Thr Tyr Asn Gln Lys Phe
50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
```

<210> SEQ ID NO 15
<211> LENGTH: 107
<212> TYPE: PRT
<213> ORGANISM: Artificial Sequence
<220> FEATURE:
<223> OTHER INFORMATION: IAB22M variable light sequence

<400> SEQUENCE: 15

Asp Val Gln Ile Thr Gln Ser Pro Ser Ser Leu Ser Ala Ser Val Gly
1               5                   10                  15

Asp Arg Val Thr Ile Thr Cys Arg Thr Ser Arg Ser Ile Ser Gln Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asn Glu Asn Pro Leu
                85                  90                  95

Thr Phe Gly Gly Gly Thr Lys Val Glu Ile Lys
            100                 105

<210> SEQ ID NO 16
<211> LENGTH: 118
<212> TYPE: PRT
<213> ORGANISM: Artificial Sequence
<220> FEATURE:
<223> OTHER INFORMATION: IAB22M variable heavy sequence

<400> SEQUENCE: 16

Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Phe Val Arg Gln Ala Pro Gly Lys Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Leu Val Thr Val Ser Ser
        115

<210> SEQ ID NO 17
<211> LENGTH: 107
<212> TYPE: PRT
<213> ORGANISM: Artificial Sequence
<220> FEATURE:
<223> OTHER INFORMATION: IAB20M variable light sequence

<400> SEQUENCE: 17

Asp Ile Val Met Thr Gln Ser Pro Ala Thr Leu Ser Val Ser Pro Gly
1               5                   10                  15

```
Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Ser Tyr Thr Ser Ser Arg Tyr Ala Gly Val Pro Asp Arg Phe Ser Gly
 50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Pro
                85                  90                  95

Thr Phe Gly Gln Gly Thr Lys Val Glu Ile Lys
            100                 105

<210> SEQ ID NO 18
<211> LENGTH: 120
<212> TYPE: PRT
<213> ORGANISM: Artificial Sequence
<220> FEATURE:
<223> OTHER INFORMATION: IAB20M variable heavy sequence

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly Arg Ile Asn Pro Asn Asn Gly Val Thr Leu Tyr Asn Gln Lys Phe
 50                  55                  60

Lys Asp Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120

<210> SEQ ID NO 19
<211> LENGTH: 106
<212> TYPE: PRT
<213> ORGANISM: Artificial Sequence
<220> FEATURE:
<223> OTHER INFORMATION: Anti-CD3 variable light sequence

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Gln Ala Pro Arg Leu Leu Ile Tyr
        35                  40                  45

Asp Thr Ser Lys Leu Ala Ser Gly Val Pro Ala His Phe Arg Gly Ser
 50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Phe Thr
```

85                  90                  95

Phe Gly Gln Gly Thr Lys Val Glu Ile Lys
                100                 105

<210> SEQ ID NO 20
<211> LENGTH: 119
<212> TYPE: PRT
<213> ORGANISM: Artificial Sequence
<220> FEATURE:
<223> OTHER INFORMATION: Anti-CD3 variable heavy sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Met
            35                  40                  45

Gly Tyr Ile Asn Pro Ser Arg Gly Tyr Thr Asn Tyr Asn Gln Lys Phe
    50                  55                  60

Lys Asp Arg Val Thr Met Thr Thr Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Leu Val Thr Val Ser Ser
        115

<210> SEQ ID NO 21
<211> LENGTH: 23
<212> TYPE: PRT
<213> ORGANISM: Artificial Sequence
<220> FEATURE:
<223> OTHER INFORMATION: Human IgG1 NH1

<400> SEQUENCE: 21

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 22
<211> LENGTH: 24
<212> TYPE: PRT
<213> ORGANISM: Artificial Sequence
<220> FEATURE:
<223> OTHER INFORMATION: Human IgG1 EH1

<400> SEQUENCE: 22

Glu Pro Lys Ser Cys Asp Lys Thr His Thr Cys Pro Pro Cys Gly Gly
1               5                   10                  15

Gly Ser Ser Gly Gly Gly Ser Gly
            20

<210> SEQ ID NO 23
<211> LENGTH: 23
<212> TYPE: PRT
<213> ORGANISM: Homo sapiens
<220> FEATURE:
<223> OTHER INFORMATION: Human IgG1 NH2

-continued

```
<400> SEQUENCE: 23

Glu Pro Lys Ser Ser Asp Lys Thr His Thr Cys Pro Pro Cys Pro Ala
1               5                   10                  15

Pro Glu Leu Leu Gly Gly Pro
            20

<210> SEQ ID NO 24
<211> LENGTH: 24
<212> TYPE: PRT
<213> ORGANISM: Artificial Sequence
<220> FEATURE:
<223> OTHER INFORMATION: Human IgG1 EH2

<400> SEQUENCE: 24

Glu Pro Lys Ser Ser Asp Lys Thr His Thr Cys Pro Pro Cys Gly Gly
1               5                   10                  15

Gly Ser Ser Gly Gly Gly Ser Gly
            20

<210> SEQ ID NO 25
<211> LENGTH: 25
<212> TYPE: PRT
<213> ORGANISM: Artificial Sequence
<220> FEATURE:
<223> OTHER INFORMATION: Human IgG1 NH3

<400> SEQUENCE: 25

Glu Pro Lys Ser Ser Asp Lys Thr His Thr Cys Pro Pro Cys Pro Pro
1               5                   10                  15

Cys Ala Pro Glu Leu Leu Gly Gly Pro
            20                  25

<210> SEQ ID NO 26
<211> LENGTH: 27
<212> TYPE: PRT
<213> ORGANISM: Artificial Sequence
<220> FEATURE:
<223> OTHER INFORMATION: Human IgG1 EH3

<400> SEQUENCE: 26

Glu Pro Lys Ser Ser Asp Lys Thr His Thr Cys Pro Pro Cys Pro Pro
1               5                   10                  15

Cys Gly Gly Gly Ser Ser Gly Gly Gly Ser Gly
            20                  25

<210> SEQ ID NO 27
<211> LENGTH: 28
<212> TYPE: PRT
<213> ORGANISM: Artificial Sequence
<220> FEATURE:
<223> OTHER INFORMATION: Human IgG1 NH4

<400> SEQUENCE: 27

Glu Pro Lys Ser Ser Asp Lys Thr His Thr Cys Pro Pro Cys Val Glu
1               5                   10                  15

Cys Pro Pro Cys Ala Pro Glu Leu Leu Gly Gly Pro
            20                  25

<210> SEQ ID NO 28
<211> LENGTH: 30
<212> TYPE: PRT
<213> ORGANISM: Artificial Sequence
<220> FEATURE:
<223> OTHER INFORMATION: Human IgG1 EH4
```

```
<400> SEQUENCE: 28

Glu Pro Lys Ser Ser Asp Lys Thr His Thr Cys Pro Pro Cys Val Glu
1               5                   10                  15

Cys Pro Pro Cys Gly Gly Gly Ser Ser Gly Gly Gly Ser Gly
            20                  25                  30

<210> SEQ ID NO 29
<211> LENGTH: 28
<212> TYPE: PRT
<213> ORGANISM: Artificial Sequence
<220> FEATURE:
<223> OTHER INFORMATION: Human IgG1 NH5

<400> SEQUENCE: 29

Glu Pro Lys Ser Ser Asp Lys Thr His Thr Cys Pro Pro Cys Pro Pro
1               5                   10                  15

Cys Pro Pro Cys Ala Pro Glu Leu Leu Gly Gly Pro
            20                  25

<210> SEQ ID NO 30
<211> LENGTH: 30
<212> TYPE: PRT
<213> ORGANISM: Artificial Sequence
<220> FEATURE:
<223> OTHER INFORMATION: Human IgG1 EH5

<400> SEQUENCE: 30

Glu Pro Lys Ser Ser Asp Lys Thr His Thr Cys Pro Pro Cys Pro Pro
1               5                   10                  15

Cys Pro Pro Cys Gly Gly Gly Ser Ser Gly Gly Gly Ser Gly
            20                  25                  30

<210> SEQ ID NO 31
<211> LENGTH: 19
<212> TYPE: PRT
<213> ORGANISM: Artificial Sequence
<220> FEATURE:
<223> OTHER INFORMATION: Human IgG2 NH1

<400> SEQUENCE: 31

Glu Arg Lys Cys Cys Val Glu Cys Pro Pro Cys Pro Ala Pro Pro Val
1               5                   10                  15

Ala Gly Pro

<210> SEQ ID NO 32
<211> LENGTH: 22
<212> TYPE: PRT
<213> ORGANISM: Artificial Sequence
<220> FEATURE:
<223> OTHER INFORMATION: Human IgG2 EH1

<400> SEQUENCE: 32

Glu Arg Lys Cys Cys Val Glu Cys Pro Pro Cys Pro Gly Gly Gly Ser
1               5                   10                  15

Ser Gly Gly Gly Ser Gly
            20

<210> SEQ ID NO 33
<211> LENGTH: 19
<212> TYPE: PRT
<213> ORGANISM: Artificial Sequence
<220> FEATURE:
<223> OTHER INFORMATION: Human IgG2 NH2
```

-continued

```
<400> SEQUENCE: 33

Glu Arg Lys Ser Cys Val Glu Cys Pro Pro Cys Pro Ala Pro Pro Val
1               5                   10                  15

Ala Gly Pro

<210> SEQ ID NO 34
<211> LENGTH: 22
<212> TYPE: PRT
<213> ORGANISM: Artificial Sequence
<220> FEATURE:
<223> OTHER INFORMATION: Human IgG2 EH2

<400> SEQUENCE: 34

Glu Arg Lys Ser Cys Val Glu Cys Pro Pro Cys Pro Gly Gly Gly Ser
1               5                   10                  15

Ser Gly Gly Gly Ser Gly
            20

<210> SEQ ID NO 35
<211> LENGTH: 29
<212> TYPE: PRT
<213> ORGANISM: Artificial Sequence
<220> FEATURE:
<223> OTHER INFORMATION: IgG3/IgG1 EH6

<400> SEQUENCE: 35

Glu Leu Lys Thr Pro Leu Gly Asp Thr Thr His Thr Cys Val Glu Cys
1               5                   10                  15

Pro Pro Cys Gly Gly Gly Ser Ser Gly Gly Gly Ser Gly
            20                  25

<210> SEQ ID NO 36
<211> LENGTH: 29
<212> TYPE: PRT
<213> ORGANISM: Artificial Sequence
<220> FEATURE:
<223> OTHER INFORMATION: IgG3/IgG1 EH7

<400> SEQUENCE: 36

Glu Leu Lys Thr Pro Leu Gly Asp Thr Thr His Thr Cys Pro Pro Cys
1               5                   10                  15

Pro Pro Cys Gly Gly Gly Ser Ser Gly Gly Gly Ser Gly
            20                  25

<210> SEQ ID NO 37
<211> LENGTH: 32
<212> TYPE: PRT
<213> ORGANISM: Artificial Sequence
<220> FEATURE:
<223> OTHER INFORMATION: IgG3/IgG1 EH8

<400> SEQUENCE: 37

Glu Leu Lys Thr Pro Leu Gly Asp Thr Thr His Thr Cys Pro Pro Cys
1               5                   10                  15

Pro Pro Cys Pro Pro Cys Gly Gly Gly Ser Ser Gly Gly Gly Ser Gly
            20                  25                  30

<210> SEQ ID NO 38
<211> LENGTH: 20
<212> TYPE: PRT
<213> ORGANISM: Artificial Sequence
<220> FEATURE:
<223> OTHER INFORMATION: IgG4 NH
```

-continued

<400> SEQUENCE: 38

Glu Ser Lys Tyr Gly Pro Pro Cys Pro Cys Pro Ala Pro Glu Phe
1               5                   10                  15

Leu Gly Gly Pro
            20

<210> SEQ ID NO 39
<211> LENGTH: 22
<212> TYPE: PRT
<213> ORGANISM: Artificial Sequence
<220> FEATURE:
<223> OTHER INFORMATION: IgG4 EH

<400> SEQUENCE: 39

Glu Ser Lys Tyr Gly Pro Pro Cys Pro Cys Pro Gly Gly Gly Ser
1               5                   10                  15

Ser Gly Gly Gly Ser Gly
            20

<210> SEQ ID NO 40
<211> LENGTH: 107
<212> TYPE: PRT
<213> ORGANISM: Artificial Sequence
<220> FEATURE:
<223> OTHER INFORMATION: Human IgG1 CH3 (G1m1 allotype)

<400> SEQUENCE: 40

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Human IgG1 CH3 (nG1m1 allotype)

<400> SEQUENCE: 41

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly

```
                65                  70                  75                  80
Asn Val Phe Ser Cys Ser Val Met His Glu Ala Leu His Asn His Tyr
                    85                  90                  95
Thr Gln Lys Ser Leu Ser Leu Ser Pro Gly Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: Human IgG2 CH3

<400> SEQUENCE: 42

Gly Gln Pro Arg Glu Pro Gln Val Tyr Thr Leu Pro Pro Ser Arg Glu
1               5                   10                  15
Glu Met Thr Lys Asn Gln Val Ser Leu Thr Cys Leu Val Lys Gly Phe
                20                  25                  30
Tyr Pro Ser Asp Ile Ala Val Glu Trp Glu Ser Asn Gly Gln Pro Glu
            35                  40                  45
Asn Asn Tyr Lys Thr Thr Pro Pro Met Leu Asp Ser Asp Gly Ser Phe
        50                  55                  60
Phe Leu Tyr Ser Lys Leu Thr Val Asp Lys Ser Arg Trp Gln Gln Gly
65                  70                  75                  80
Asn Val Phe Ser Cys Ser Val Met His Glu Ala Leu His Asn His Tyr
                    85                  90                  95
Thr Gln Lys Ser Leu Ser Leu Ser Pro Gly Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: Human IgG3 CH3

<400> SEQUENCE: 43

Gly Gln Pro Arg Glu Pro Gln Val Tyr Thr Leu Pro Pro Ser Arg Glu
1               5                   10                  15
Glu Met Thr Lys Asn Gln Val Ser Leu Thr Cys Leu Val Lys Gly Phe
                20                  25                  30
Tyr Pro Ser Asp Ile Ala Val Glu Trp Glu Ser Ser Gly Gln Pro Glu
            35                  40                  45
Asn Asn Tyr Asn Thr Thr Pro Pro Met Leu Asp Ser Asp Gly Ser Phe
        50                  55                  60
Phe Leu Tyr Ser Lys Leu Thr Val Asp Lys Ser Arg Trp Gln Gln Gly
65                  70                  75                  80
Asn Ile Phe Ser Cys Ser Val Met His Glu Ala Leu His Asn Arg Phe
                    85                  90                  95
Thr Gln Lys Ser Leu Ser Leu Ser Pro Gly Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: Human IgG4 CH3

<400> SEQUENCE: 44
```

-continued

```
Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

<210> SEQ ID NO 45
<211> LENGTH: 10
<212> TYPE: PRT
<213> ORGANISM: Artificial Sequence
<220> FEATURE:
<223> OTHER INFORMATION: Upper hinge

<400> SEQUENCE: 45

```
Glu Pro Lys Ser Cys Asp Lys Thr His Thr
1               5                   10
```

<210> SEQ ID NO 46
<211> LENGTH: 10
<212> TYPE: PRT
<213> ORGANISM: Artificial Sequence
<220> FEATURE:
<223> OTHER INFORMATION: Upper hinge

<400> SEQUENCE: 46

```
Glu Pro Lys Ser Ser Asp Lys Thr His Thr
1               5                   10
```

<210> SEQ ID NO 47
<211> LENGTH: 3
<212> TYPE: PRT
<213> ORGANISM: Artificial Sequence
<220> FEATURE:
<223> OTHER INFORMATION: Upper hinge

<400> SEQUENCE: 47

```
Glu Arg Lys
1
```

<210> SEQ ID NO 48
<211> LENGTH: 12
<212> TYPE: PRT
<213> ORGANISM: Artificial Sequence
<220> FEATURE:
<223> OTHER INFORMATION: Upper hinge

<400> SEQUENCE: 48

```
Glu Leu Lys Thr Pro Leu Gly Asp Thr Thr His Thr
1               5                   10
```

<210> SEQ ID NO 49
<211> LENGTH: 7
<212> TYPE: PRT
<213> ORGANISM: Artificial Sequence

```
<220> FEATURE:
<223> OTHER INFORMATION: Upper hinge

<400> SEQUENCE: 49

Glu Ser Lys Tyr Gly Pro Pro
1               5

<210> SEQ ID NO 50
<211> LENGTH: 4
<212> TYPE: PRT
<213> ORGANISM: Homo sapiens

<400> SEQUENCE: 50

Cys Pro Pro Cys
1

<210> SEQ ID NO 51
<211> LENGTH: 5
<212> TYPE: PRT
<213> ORGANISM: Homo sapiens

<400> SEQUENCE: 51

Cys Pro Pro Cys Pro
1               5

<210> SEQ ID NO 52
<211> LENGTH: 7
<212> TYPE: PRT
<213> ORGANISM: Homo sapiens

<400> SEQUENCE: 52

Cys Pro Pro Cys Pro Pro Cys
1               5

<210> SEQ ID NO 53
<211> LENGTH: 10
<212> TYPE: PRT
<213> ORGANISM: Homo sapiens

<400> SEQUENCE: 53

Cys Pro Pro Cys Val Glu Cys Pro Pro Cys
1               5                   10

<210> SEQ ID NO 54
<211> LENGTH: 10
<212> TYPE: PRT
<213> ORGANISM: Homo sapiens

<400> SEQUENCE: 54

Cys Pro Pro Cys Pro Pro Cys Pro Pro Cys
1               5                   10

<210> SEQ ID NO 55
<211> LENGTH: 9
<212> TYPE: PRT
<213> ORGANISM: Homo sapiens

<400> SEQUENCE: 55

Cys Cys Val Glu Cys Pro Pro Cys Pro
1               5

<210> SEQ ID NO 56
<211> LENGTH: 9
<212> TYPE: PRT
<213> ORGANISM: Homo sapiens
```

<400> SEQUENCE: 56

Ser Cys Val Glu Cys Pro Pro Cys Pro
1               5

<210> SEQ ID NO 57
<211> LENGTH: 7
<212> TYPE: PRT
<213> ORGANISM: Homo sapiens

<400> SEQUENCE: 57

Cys Val Glu Cys Pro Pro Cys
1               5

<210> SEQ ID NO 58
<211> LENGTH: 8
<212> TYPE: PRT
<213> ORGANISM: Homo sapiens

<400> SEQUENCE: 58

Ala Pro Glu Leu Leu Gly Gly Pro
1               5

<210> SEQ ID NO 59
<211> LENGTH: 10
<212> TYPE: PRT
<213> ORGANISM: Homo sapiens

<400> SEQUENCE: 59

Gly Gly Gly Ser Ser Gly Gly Gly Ser Gly
1               5                   10

<210> SEQ ID NO 60
<211> LENGTH: 7
<212> TYPE: PRT
<213> ORGANISM: Homo sapiens

<400> SEQUENCE: 60

Ala Pro Pro Val Ala Gly Pro
1               5

<210> SEQ ID NO 61
<211> LENGTH: 8
<212> TYPE: PRT
<213> ORGANISM: Homo sapiens

<400> SEQUENCE: 61

Ala Pro Glu Phe Leu Gly Gly Pro
1               5

<210> SEQ ID NO 62
<211> LENGTH: 18
<212> TYPE: PRT
<213> ORGANISM: Artificial Sequence
<220> FEATURE:
<223> OTHER INFORMATION: Linker sequence

<400> SEQUENCE: 62

Gly Ser Thr Ser Gly Gly Gly Ser Gly Gly Ser Gly Gly Gly
1               5                   10                  15

Ser Ser

<210> SEQ ID NO 63
<211> LENGTH: 12

```
<212> TYPE: PRT
<213> ORGANISM: Artificial Sequence
<220> FEATURE:
<223> OTHER INFORMATION: Linker sequence

<400> SEQUENCE: 63

Gly Ser Thr Ser Gly Gly Gly Ser Gly Gly Ser
1               5                   10

<210> SEQ ID NO 64
<211> LENGTH: 15
<212> TYPE: PRT
<213> ORGANISM: Artificial Sequence
<220> FEATURE:
<223> OTHER INFORMATION: Linker sequence

<400> SEQUENCE: 64

Gly Gly Gly Gly Ser Gly Gly Gly Gly Ser Gly Gly Gly Gly Ser
1               5                   10                  15

<210> SEQ ID NO 65
<211> LENGTH: 10
<212> TYPE: PRT
<213> ORGANISM: Artificial Sequence
<220> FEATURE:
<223> OTHER INFORMATION: Linker sequence

<400> SEQUENCE: 65

Gly Gly Gly Gly Ser Gly Gly Gly Gly Ser
1               5                   10

<210> SEQ ID NO 66
<211> LENGTH: 5
<212> TYPE: PRT
<213> ORGANISM: Artificial Sequence
<220> FEATURE:
<223> OTHER INFORMATION: Linker sequence

<400> SEQUENCE: 66

Gly Gly Gly Gly Ser
1               5

<210> SEQ ID NO 67
<211> LENGTH: 106
<212> TYPE: PRT
<213> ORGANISM: Artificial Sequence
<220> FEATURE:
<223> OTHER INFORMATION: IAB1M (A11) variable light sequence

<400> SEQUENCE: 67

Asp Ile Gln Leu Thr Gln Ser Pro Ser Thr Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
                35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Gly Ser Ser Pro Phe Thr
                85                  90                  95

Phe Gly Gln Gly Thr Lys Val Glu Ile Lys
                100                 105
```

```
<210> SEQ ID NO 68
<211> LENGTH: 112
<212> TYPE: PRT
<213> ORGANISM: Artificial Sequence
<220> FEATURE:
<223> OTHER INFORMATION: IAB1M (A11) variable heavy sequence

<400> SEQUENCE: 68

Glu Val Gln Leu Val Glu Tyr Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Ile His Trp Val Arg Gln Ala Pro Gly Lys Gly Leu Glu Trp Val
        35                  40                  45

Ala Trp Ile Asp Pro Glu Asn Gly Asp Thr Glu Phe Val Pro Lys Phe
    50                  55                  60

Gln Gly Arg Ala Thr Met Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Lys Thr Gly Gly Phe Trp Gly Gln Gly Thr Leu Val Thr Val Ser Ser
            100                 105                 110

<210> SEQ ID NO 69
<211> LENGTH: 20
<212> TYPE: PRT
<213> ORGANISM: Artificial Sequence
<220> FEATURE:
<223> OTHER INFORMATION: Mouse Ig kappa light chain

<400> SEQUENCE: 69

Met Glu Thr Asp Thr Leu Leu Leu Trp Val Leu Leu Leu Trp Val Pro
1               5                   10                  15

Gly Ser Thr Gly
            20

<210> SEQ ID NO 70
<211> LENGTH: 18
<212> TYPE: PRT
<213> ORGANISM: Artificial Sequence
<220> FEATURE:
<223> OTHER INFORMATION: Human Serum Albumin (HSA)

<400> SEQUENCE: 70

Met Lys Trp Val Thr Phe Ile Ser Leu Leu Phe Leu Phe Ser Ser Ala
1               5                   10                  15

Tyr Ser

<210> SEQ ID NO 71
<211> LENGTH: 19
<212> TYPE: PRT
<213> ORGANISM: Artificial Sequence
<220> FEATURE:
<223> OTHER INFORMATION: Human Azurocidin (HAZ)

<400> SEQUENCE: 71

Met Thr Arg Leu Thr Val Leu Ala Leu Leu Ala Gly Leu Leu Ala Ser
1               5                   10                  15

Ser Arg Ala
```

```
<210> SEQ ID NO 72
<211> LENGTH: 28
<212> TYPE: PRT
<213> ORGANISM: Artificial Sequence
<220> FEATURE:
<223> OTHER INFORMATION: Prolactin

<400> SEQUENCE: 72

Met Asp Ser Lys Gly Ser Ser Gln Lys Gly Ser Arg Leu Leu Leu Leu
1               5                   10                  15

Leu Trp Ser Asn Leu Leu Leu Cys Gln Gly Trp Ser
            20                  25

<210> SEQ ID NO 73
<211> LENGTH: 58
<212> TYPE: PRT
<213> ORGANISM: Artificial Sequence
<220> FEATURE:
<223> OTHER INFORMATION: LCMV-GPC

<400> SEQUENCE: 73

Met Gly Gln Ile Val Thr Met Phe Glu Ala Leu Pro His Ile Ile Asp
1               5                   10                  15

Glu Val Ile Asn Ile Asn Val Ile Ile Val Leu Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly
    50                  55

<210> SEQ ID NO 74
<211> LENGTH: 98
<212> TYPE: PRT
<213> ORGANISM: Artificial Sequence
<220> FEATURE:
<223> OTHER INFORMATION: MMTV-Rem

<400> SEQUENCE: 74

Met Pro Asn His Gln Ser Gly Ser Pro Thr Gly Ser Ser Asp Leu Leu
1               5                   10                  15

Leu Ser Gly Lys Lys Gln Arg Pro His Leu Ala Leu Arg Arg Lys Arg
            20                  25                  30

Arg Arg Glu Met Arg Lys Ile Asn Arg Lys Val Arg Arg Met Asn Leu
        35                  40                  45

Ala Pro Ile Lys Glu Lys Thr Ala Trp Gln His Leu Gln Ala Leu Ile
    50                  55                  60

Ser Glu Ala Glu Glu Val Leu Lys Thr Ser Gln Thr Pro Gln Asn Ser
65                  70                  75                  80

Leu Thr Leu Phe Leu Ala Leu Leu Ser Val Leu Gly Pro Pro Pro Val
                85                  90                  95

Thr Gly

<210> SEQ ID NO 75
<211> LENGTH: 7
<212> TYPE: PRT
<213> ORGANISM: Artificial Sequence
<220> FEATURE:
<223> OTHER INFORMATION: HCDR1 IAB22M (CD8)

<400> SEQUENCE: 75

Gly Phe Asn Ile Lys Asp Thr
1               5
```

```
<210> SEQ ID NO 76
<211> LENGTH: 6
<212> TYPE: PRT
<213> ORGANISM: Artificial Sequence
<220> FEATURE:
<223> OTHER INFORMATION: HCDR2 IAB22M (CD8)

<400> SEQUENCE: 76

Asp Pro Ala Asn Asp Asn
1               5

<210> SEQ ID NO 77
<211> LENGTH: 9
<212> TYPE: PRT
<213> ORGANISM: Artificial Sequence
<220> FEATURE:
<223> OTHER INFORMATION: HCDR3 IAB22M (CD8)

<400> SEQUENCE: 77

Gly Tyr Gly Tyr Tyr Val Phe Asp His
1               5

<210> SEQ ID NO 78
<211> LENGTH: 11
<212> TYPE: PRT
<213> ORGANISM: Artificial Sequence
<220> FEATURE:
<223> OTHER INFORMATION: LCDR1 IAB22M (CD8)

<400> SEQUENCE: 78

Arg Thr Ser Arg Ser Ile Ser Gln Tyr Leu Ala
1               5                   10

<210> SEQ ID NO 79
<211> LENGTH: 7
<212> TYPE: PRT
<213> ORGANISM: Artificial Sequence
<220> FEATURE:
<223> OTHER INFORMATION: LCDR2 IAB22M (CD8)

<400> SEQUENCE: 79

Ser Gly Ser Thr Leu Gln Ser
1               5

<210> SEQ ID NO 80
<211> LENGTH: 9
<212> TYPE: PRT
<213> ORGANISM: Artificial Sequence
<220> FEATURE:
<223> OTHER INFORMATION: LCDR3 IAB22M (CD8)

<400> SEQUENCE: 80

Gln Gln His Asn Glu Asn Pro Leu Thr
1               5

<210> SEQ ID NO 81
<211> LENGTH: 7
<212> TYPE: PRT
<213> ORGANISM: Artificial Sequence
<220> FEATURE:
<223> OTHER INFORMATION: HCDR1 IAB2M (PSMA)

<400> SEQUENCE: 81

Gly Tyr Thr Phe Thr Glu Tyr
1               5
```

<210> SEQ ID NO 82
<211> LENGTH: 8
<212> TYPE: PRT
<213> ORGANISM: Artificial Sequence
<220> FEATURE:
<223> OTHER INFORMATION: HCDR2 IAB2M (PSMA)

<400> SEQUENCE: 82

Asn Ile Asn Pro Asn Asn Gly Gly
1               5

<210> SEQ ID NO 83
<211> LENGTH: 6
<212> TYPE: PRT
<213> ORGANISM: Artificial Sequence
<220> FEATURE:
<223> OTHER INFORMATION: HCDR3 IAB2M (PSMA)

<400> SEQUENCE: 83

Gly Trp Asn Phe Asp Tyr
1               5

<210> SEQ ID NO 84
<211> LENGTH: 11
<212> TYPE: PRT
<213> ORGANISM: Artificial Sequence
<220> FEATURE:
<223> OTHER INFORMATION: LCDR1 IAB2M (PSMA)

<400> SEQUENCE: 84

Lys Ala Ser Gln Asp Val Gly Thr Ala Val Asp
1               5                   10

<210> SEQ ID NO 85
<211> LENGTH: 7
<212> TYPE: PRT
<213> ORGANISM: Artificial Sequence
<220> FEATURE:
<223> OTHER INFORMATION: LCDR2 IAB2M (PSMA)

<400> SEQUENCE: 85

Trp Ala Ser Thr Arg His Thr
1               5

<210> SEQ ID NO 86
<211> LENGTH: 9
<212> TYPE: PRT
<213> ORGANISM: Artificial Sequence
<220> FEATURE:
<223> OTHER INFORMATION: LCDR3 IAB2M (PSMA)

<400> SEQUENCE: 86

Gln Gln Tyr Asn Ser Tyr Pro Leu Thr
1               5

<210> SEQ ID NO 87
<211> LENGTH: 7
<212> TYPE: PRT
<213> ORGANISM: Artificial Sequence
<220> FEATURE:
<223> OTHER INFORMATION: HCDR1 IAB20M (5T4)

<400> SEQUENCE: 87

Gly Tyr Ser Phe Thr Gly Tyr
1               5

```
<210> SEQ ID NO 88
<211> LENGTH: 6
<212> TYPE: PRT
<213> ORGANISM: Artificial Sequence
<220> FEATURE:
<223> OTHER INFORMATION: HCDR2 IAB20M (5T4)

<400> SEQUENCE: 88

Asn Pro Asn Asn Gly Val
1               5

<210> SEQ ID NO 89
<211> LENGTH: 11
<212> TYPE: PRT
<213> ORGANISM: Artificial Sequence
<220> FEATURE:
<223> OTHER INFORMATION: HCDR3 IAB20M (5T4)

<400> SEQUENCE: 89

Ser Thr Met Ile Thr Asn Tyr Val Met Asp Tyr
1               5                   10

<210> SEQ ID NO 90
<211> LENGTH: 11
<212> TYPE: PRT
<213> ORGANISM: Artificial Sequence
<220> FEATURE:
<223> OTHER INFORMATION: LCDR1 IAB20M (5T4)

<400> SEQUENCE: 90

Lys Ala Ser Gln Ser Val Ser Asn Asp Val Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: LCDR2 IAB20M (5T4)

<400> SEQUENCE: 91

Tyr Thr Ser Ser Arg Tyr Ala
1               5

<210> SEQ ID NO 92
<211> LENGTH: 9
<212> TYPE: PRT
<213> ORGANISM: Artificial Sequence
<220> FEATURE:
<223> OTHER INFORMATION: LCDR3 IAB20M (5T4)

<400> SEQUENCE: 92

Gln Gln Asp Tyr Asn Ser Pro Pro Thr
1               5

<210> SEQ ID NO 93
<211> LENGTH: 7
<212> TYPE: PRT
<213> ORGANISM: Artificial Sequence
<220> FEATURE:
<223> OTHER INFORMATION: HCDR1 IAB1M (PSCA)

<400> SEQUENCE: 93

Gly Phe Asn Ile Lys Asp Tyr
1               5

<210> SEQ ID NO 94
```

```
<211> LENGTH: 6
<212> TYPE: PRT
<213> ORGANISM: Artificial Sequence
<220> FEATURE:
<223> OTHER INFORMATION: HCDR2 IAB1M (PSCA)

<400> SEQUENCE: 94

Asp Pro Glu Asn Gly Asp
1               5

<210> SEQ ID NO 95
<211> LENGTH: 3
<212> TYPE: PRT
<213> ORGANISM: Artificial Sequence
<220> FEATURE:
<223> OTHER INFORMATION: HCDR3 IAB1M (PSCA)

<400> SEQUENCE: 95

Gly Gly Phe
1

<210> SEQ ID NO 96
<211> LENGTH: 10
<212> TYPE: PRT
<213> ORGANISM: Artificial Sequence
<220> FEATURE:
<223> OTHER INFORMATION: LCDR1 IAB1M (PSCA)

<400> SEQUENCE: 96

Ser Ala Ser Ser Ser Val Arg Phe Ile His
1               5                   10

<210> SEQ ID NO 97
<211> LENGTH: 7
<212> TYPE: PRT
<213> ORGANISM: Artificial Sequence
<220> FEATURE:
<223> OTHER INFORMATION: LCDR2 IAB1M (PSCA)

<400> SEQUENCE: 97

Asp Thr Ser Lys Leu Ala Ser
1               5

<210> SEQ ID NO 98
<211> LENGTH: 9
<212> TYPE: PRT
<213> ORGANISM: Artificial Sequence
<220> FEATURE:
<223> OTHER INFORMATION: LCDR3 IAB1M (PSCA)

<400> SEQUENCE: 98

Gln Gln Trp Gly Ser Ser Pro Phe Thr
1               5

<210> SEQ ID NO 99
<211> LENGTH: 118
<212> TYPE: PRT
<213> ORGANISM: Artificial Sequence
<220> FEATURE:
<223> OTHER INFORMATION: IAB22M variable heavy (VH-K67R) sequence

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Phe Val Arg Gln Ala Pro Gly Lys Gly Leu Glu Trp Ile
        35                  40                  45

Gly Arg Ile Asp Pro Ala Asn Asp Asn Thr Leu Tyr Ala Ser Lys Phe
 50                  55                  60

Gln Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Leu Val Thr Val Ser Ser
            115
```

<210> SEQ ID NO 100
<211> LENGTH: 107
<212> TYPE: PRT
<213> ORGANISM: Artificial Sequence
<220> FEATURE:
<223> OTHER INFORMATION: IAB20M variable light (VL-Q79E, V83E)

<400> SEQUENCE: 100

```
Asp Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Ser Tyr Thr Ser Ser Arg Tyr Ala Gly Val Pro Asp Arg Phe Ser Gly
 50                  55                  60

Ser Gly Ser Gly Thr Asp Phe Thr Leu Thr Ile Ser Ser Leu Glu Ala
65                  70                  75                  80

Glu Asp Glu Ala Val Tyr Tyr Cys Gln Gln Asp Tyr Asn Ser Pro Pro
                85                  90                  95

Thr Phe Gly Gln Gly Thr Lys Val Glu Ile Lys
            100                 105
```

<210> SEQ ID NO 101
<211> LENGTH: 107
<212> TYPE: PRT
<213> ORGANISM: Artificial Sequence
<220> FEATURE:
<223> OTHER INFORMATION: IAB20M variable light (VL-A9D, T10S, S12A,
      P15L, L21I, S22N)

<400> SEQUENCE: 101

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Ser Tyr Thr Ser Ser Arg Tyr Ala Gly Val Pro Asp Arg Phe Ser Gly
 50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Pro
                85                  90                  95

Thr Phe Gly Gln Gly Thr Lys Val Glu Ile Lys
```

<210> SEQ ID NO 102
<211> LENGTH: 120
<212> TYPE: PRT
<213> ORGANISM: Artificial Sequence
<220> FEATURE:
<223> OTHER INFORMATION: IAB20M variable heavy (VH-Q1E, Q6E)

<400> SEQUENCE: 102

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120
```

<210> SEQ ID NO 103
<211> LENGTH: 106
<212> TYPE: PRT
<213> ORGANISM: Artificial Sequence
<220> FEATURE:
<223> OTHER INFORMATION: Anti-CD3 variable light (VL, R62S) sequence

<400> SEQUENCE: 103

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Gln Ala Pro Arg Leu Leu Ile Tyr
        35                  40                  45

Asp Thr Ser Lys Leu Ala Ser Gly Val Pro Ala His Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Phe Thr
                85                  90                  95

Phe Gly Gln Gly Thr Lys Val Glu Ile Lys
            100                 105
```

<210> SEQ ID NO 104
<211> LENGTH: 119
<212> TYPE: PRT
<213> ORGANISM: Artificial Sequence
<220> FEATURE:
<223> OTHER INFORMATION: Anti-CD3 variable heavy (VH, Q1E, Q6E) sequence

<400> SEQUENCE: 104

```
Glu Val Gln Leu Val Glu Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Arg Tyr
         20                  25                  30

Thr Met His Trp Val Arg Gln Ala Pro Gly Gln Gly Leu Glu Trp Met
         35                  40                  45

Gly Tyr Ile Asn Pro Ser Arg Gly Tyr Thr Asn Tyr Asn Gln Lys Phe
 50                  55                  60

Lys Asp Arg Val Thr Met Thr Thr Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Tyr Tyr Asp Asp His Tyr Ser Leu Asp Tyr Trp Gly Gln Gly
                 100                 105                 110

Thr Leu Val Thr Val Ser Ser
             115

<210> SEQ ID NO 105
<211> LENGTH: 394
<212> TYPE: PRT
<213> ORGANISM: Artificial Sequence
<220> FEATURE:
<223> OTHER INFORMATION: IAB22M gamma 1 EH1(Minibody 1)

<400> SEQUENCE: 105

Met Glu Thr Asp Thr Leu Leu Leu Trp Val Leu Leu Leu Trp Val Pro
 1               5                  10                  15

Gly Ser Thr Gly Asp Val Gln Ile Thr Gln Ser Pro Ser Ser Leu Ser
                 20                  25                  30

Ala Ser Val Gly Asp Arg Val Thr Ile Thr Cys Arg Thr Ser Arg Ser
                 35                  40                  45

Ile Ser Gln Tyr Leu Ala Trp Tyr Gln Gln Lys Pro Gly Lys Val Pro
 50                  55                  60

Lys Leu Leu Ile Tyr Ser Gly Ser Thr Leu Gln Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Val Ala Thr Tyr Tyr Cys Gln Gln His Asn
                 100                 105                 110

Glu Asn Pro Leu Thr Phe Gly Gly Gly Thr Lys Val Glu Ile Lys Gly
                 115                 120                 125

Ser Thr Ser Gly Gly Gly Ser Gly Gly Gly Ser Gly Gly Gly Gly Ser
         130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                 165                 170                 175

Thr Tyr Ile His Phe Val Arg Gln Ala Pro Gly Lys Gly Leu Glu Trp
             180                 185                 190

Ile Gly Arg Ile Asp Pro Ala Asn Asp Asn Thr Leu Tyr Ala Ser Lys
         195                 200                 205

Phe Gln Gly Lys Ala Thr Ile Ser Ala Asp Thr Ser Lys Asn Thr Ala
     210                 215                 220

Tyr Leu Gln Met Asn Ser Leu Arg Ala Glu Asp Thr Ala Val Tyr Tyr
225                 230                 235                 240

Cys Gly Arg Gly Tyr Gly Tyr Tyr Val Phe Asp His Trp Gly Gln Gly
                 245                 250                 255
```

```
Thr Leu Val Thr Val Ser Ser Glu Pro Lys Ser Cys Asp Lys Thr His
            260                 265                 270

Thr Cys Pro Pro Cys Gly Gly Gly Ser Gly Gly Gly Ser Gly Gly
        275                 280                 285

Gln Pro Arg Glu Pro Gln Val Tyr Thr Leu Pro Pro Ser Arg Asp Glu
    290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
    370                 375                 380

Gln Lys Ser Leu Ser Leu Ser Pro Gly Lys
385                 390
```

<210> SEQ ID NO 106
<211> LENGTH: 396
<212> TYPE: PRT
<213> ORGANISM: Artificial Sequence
<220> FEATURE:
<223> OTHER INFORMATION: IAB22M gamma 1 EH3(Minibody 1)

<400> SEQUENCE: 106

```
Met Glu Thr Asp Thr Leu Leu Leu Trp Val Leu Leu Leu Trp Val Pro
1               5                   10                  15

Gly Ser Thr Gly Asp Val Gln Ile Thr Gln Ser Pro Ser Ser Leu Ser
            20                  25                  30

Ala Ser Val Gly Asp Arg Val Thr Ile Thr Cys Arg Thr Ser Arg Ser
        35                  40                  45

Ile Ser Gln Tyr Leu Ala Trp Tyr Gln Gln Lys Pro Gly Lys Val Pro
50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Gln His Asn
            100                 105                 110

Glu Asn Pro Leu Thr Phe Gly Gly Gly Thr Lys Val Glu Ile Lys Gly
        115                 120                 125

Ser Thr Ser Gly Gly Gly Ser Gly Gly Gly Ser Gly Gly Gly Gly Ser
130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Thr Tyr Ile His Phe Val Arg Gln Ala Pro Gly Lys Gly Leu Glu Trp
            180                 185                 190

Ile Gly Arg Ile Asp Pro Ala Asn Asp Asn Thr Leu Tyr Ala Ser Lys
        195                 200                 205

Phe Gln Gly Lys Ala Thr Ile Ser Ala Asp Thr Ser Lys Asn Thr Ala
210                 215                 220
```

Tyr Leu Gln Met Asn Ser Leu Arg Ala Glu Asp Thr Ala Val Tyr Tyr
225                 230                 235                 240

Cys Gly Arg Gly Tyr Gly Tyr Tyr Val Phe Asp His Trp Gly Gln Gly
            245                 250                 255

Thr Leu Val Thr Val Ser Ser Glu Pro Lys Ser Ser Asp Lys Thr His
            260                 265                 270

Thr Cys Pro Pro Cys Pro Pro Cys Gly Gly Ser Gly Gly Gly
        275                 280                 285

Ser Gly Gly Gln Pro Arg Glu Pro Gln Val Tyr Thr Leu Pro Pro Ser
290                 295                 300

Arg Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
            325                 330                 335

Pro Glu Asn Asn Tyr Lys Thr Thr Pro Pro Val Leu Asp Ser Asp Gly
            340                 345                 350

Ser Phe Phe Leu Tyr Ser Lys Leu Thr Val Asp Lys Ser Arg Trp Gln
            355                 360                 365

Gln Gly Asn Val Phe Ser Cys Ser Val Met His Glu Ala Leu His Asn
    370                 375                 380

His Tyr Thr Gln Lys Ser Leu Ser Leu Ser Pro Gly
385                 390                 395

<210> SEQ ID NO 107
<211> LENGTH: 399
<212> TYPE: PRT
<213> ORGANISM: Artificial Sequence
<220> FEATURE:
<223> OTHER INFORMATION: IAB22M gamma 1 EH5(M1)

<400> SEQUENCE: 107

Met Glu Thr Asp Thr Leu Leu Leu Trp Val Leu Leu Leu Trp Val Pro
1               5                   10                  15

Gly Ser Thr Gly Asp Val Gln Ile Thr Gln Ser Pro Ser Ser Leu Ser
            20                  25                  30

Ala Ser Val Gly Asp Arg Val Thr Ile Thr Cys Arg Thr Ser Arg Ser
        35                  40                  45

Ile Ser Gln Tyr Leu Ala Trp Tyr Gln Gln Lys Pro Gly Lys Val Pro
    50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Gln His Asn
            100                 105                 110

Glu Asn Pro Leu Thr Phe Gly Gly Gly Thr Lys Val Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Thr Tyr Ile His Phe Val Arg Gln Ala Pro Gly Lys Gly Leu Glu Trp
            180                 185                 190

```
Ile Gly Arg Ile Asp Pro Ala Asn Asp Asn Thr Leu Tyr Ala Ser Lys
        195                 200                 205

Phe Gln Gly Lys Ala Thr Ile Ser Ala Asp Thr Ser Lys Asn Thr Ala
210                 215                 220

Tyr Leu Gln Met Asn Ser Leu Arg Ala Glu Asp Thr Ala Val Tyr Tyr
225                 230                 235                 240

Cys Gly Arg Gly Tyr Gly Tyr Tyr Val Phe Asp His Trp Gly Gln Gly
                245                 250                 255

Thr Leu Val Thr Val Ser Ser Glu Pro Lys Ser Ser Asp Lys Thr His
                260                 265                 270

Thr Cys Pro Pro Cys Pro Pro Cys Pro Pro Cys Gly Gly Gly Ser Ser
                275                 280                 285

Gly Gly Gly Ser Gly Gly Gln Pro Arg Glu Pro Gln Val Tyr Thr Leu
                290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
                340                 345                 350

Ser Asp Gly Ser Phe Phe Leu Tyr Ser Lys Leu Thr Val Asp Lys Ser
                355                 360                 365

Arg Trp Gln Gln Gly Asn Val Phe Ser Cys Ser Val Met His Glu Ala
                370                 375                 380

Leu His Asn His Tyr Thr Gln Lys Ser Leu Ser Leu Ser Pro Gly
385                 390                 395
```

<210> SEQ ID NO 108
<211> LENGTH: 398
<212> TYPE: PRT
<213> ORGANISM: Artificial Sequence
<220> FEATURE:
<223> OTHER INFORMATION: IAB22M gamma 1 EH7(Minibody 1)

<400> SEQUENCE: 108

```
Met Glu Thr Asp Thr Leu Leu Leu Trp Val Leu Leu Leu Trp Val Pro
1               5                   10                  15

Gly Ser Thr Gly Asp Val Gln Ile Thr Gln Ser Pro Ser Ser Leu Ser
                20                  25                  30

Ala Ser Val Gly Asp Arg Val Thr Ile Thr Cys Arg Thr Ser Arg Ser
                35                  40                  45

Ile Ser Gln Tyr Leu Ala Trp Tyr Gln Gln Lys Pro Gly Lys Val Pro
50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Gln His Asn
                100                 105                 110

Glu Asn Pro Leu Thr Phe Gly Gly Gly Thr Lys Val Glu Ile Lys Gly
                115                 120                 125

Ser Thr Ser Gly Gly Gly Ser Gly Gly Gly Ser Gly Gly Gly Gly Ser
                130                 135                 140

Ser Glu Val Gln Leu Val Glu Ser Gly Gly Gly Leu Val Gln Pro Gly
145                 150                 155                 160
```

Gly Ser Leu Arg Leu Ser Cys Ala Ala Ser Gly Phe Asn Ile Lys Asp
            165                 170                 175

Thr Tyr Ile His Phe Val Arg Gln Ala Pro Gly Lys Gly Leu Glu Trp
            180                 185                 190

Ile Gly Arg Ile Asp Pro Ala Asn Asp Asn Thr Leu Tyr Ala Ser Lys
            195                 200                 205

Phe Gln Gly Lys Ala Thr Ile Ser Ala Asp Thr Ser Lys Asn Thr Ala
210                 215                 220

Tyr Leu Gln Met Asn Ser Leu Arg Ala Glu Asp Thr Ala Val Tyr Tyr
225                 230                 235                 240

Cys Gly Arg Gly Tyr Gly Tyr Tyr Val Phe Asp His Trp Gly Gln Gly
            245                 250                 255

Thr Leu Val Thr Val Ser Ser Glu Leu Lys Thr Pro Leu Gly Asp Thr
            260                 265                 270

Thr His Thr Cys Pro Pro Cys Pro Pro Cys Gly Gly Gly Ser Ser Gly
            275                 280                 285

Gly Gly Ser Gly Gly Gln Pro Arg Glu Pro Gln Val Tyr Thr Leu Pro
290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
            325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
            355                 360                 365

Trp Gln Gln Gly Asn Val Phe Ser Cys Ser Val Met His Glu Ala Leu
370                 375                 380

His Asn His Tyr Thr Gln Lys Ser Leu Ser Leu Ser Pro Gly
385                 390                 395

<210> SEQ ID NO 109
<211> LENGTH: 401
<212> TYPE: PRT
<213> ORGANISM: Artificial Sequence
<220> FEATURE:
<223> OTHER INFORMATION: IAB22M gamma 1 EH8(Minibody 1)

<400> SEQUENCE: 109

Met Glu Thr Asp Thr Leu Leu Leu Trp Val Leu Leu Leu Trp Val Pro
1               5                   10                  15

Gly Ser Thr Gly Asp Val Gln Ile Thr Gln Ser Pro Ser Ser Leu Ser
            20                  25                  30

Ala Ser Val Gly Asp Arg Val Thr Ile Thr Cys Arg Thr Ser Arg Ser
            35                  40                  45

Ile Ser Gln Tyr Leu Ala Trp Tyr Gln Gln Lys Pro Gly Lys Val Pro
        50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Asp Phe Thr Leu Thr Ile Ser
            85                  90                  95

Ser Leu Gln Pro Glu Asp Val Ala Thr Tyr Tyr Cys Gln Gln His Asn
            100                 105                 110

Glu Asn Pro Leu Thr Phe Gly Gly Gly Thr Lys Val Glu Ile Lys Gly
            115                 120                 125

-continued

```
Ser Thr Ser Gly Gly Ser Gly Gly Gly Ser Gly Gly Gly Ser
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Thr Tyr Ile His Phe Val Arg Gln Ala Pro Gly Lys Gly Leu Glu Trp
            180                 185                 190

Ile Gly Arg Ile Asp Pro Ala Asn Asp Asn Thr Leu Tyr Ala Ser Lys
        195                 200                 205

Phe Gln Gly Lys Ala Thr Ile Ser Ala Asp Thr Ser Lys Asn Thr Ala
210                 215                 220

Tyr Leu Gln Met Asn Ser Leu Arg Ala Glu Asp Thr Ala Val Tyr Tyr
225                 230                 235                 240

Cys Gly Arg Gly Tyr Gly Tyr Tyr Val Phe Asp His Trp Gly Gln Gly
                245                 250                 255

Thr Leu Val Thr Val Ser Ser Glu Leu Lys Thr Pro Leu Gly Asp Thr
            260                 265                 270

Thr His Thr Cys Pro Pro Cys Pro Pro Cys Pro Pro Cys Pro Gly Gly
        275                 280                 285

Ser Ser Gly Gly Ser Gly Gly Gln Pro Arg Glu Pro Gln Val Tyr
290                 295                 300

Thr Leu Pro Pro Ser Arg Glu Glu Met Thr Lys Asn Gln Val Ser Leu
305                 310                 315                 320

Thr Cys Leu Val Lys Gly Phe Tyr Pro Ser Asp Ile Ala Val Glu Trp
                325                 330                 335

Glu Ser Asn Gly Gln Pro Glu Asn Asn Tyr Lys Thr Thr Pro Pro Val
            340                 345                 350

Leu Asp Ser Asp Gly Ser Phe Phe Leu Tyr Ser Lys Leu Thr Val Asp
        355                 360                 365

Lys Ser Arg Trp Gln Gln Gly Asn Val Phe Ser Cys Ser Val Met His
370                 375                 380

Glu Ala Leu His Asn His Tyr Thr Gln Lys Ser Leu Ser Leu Ser Pro
385                 390                 395                 400

Gly

<210> SEQ ID NO 110
<211> LENGTH: 391
<212> TYPE: PRT
<213> ORGANISM: Artificial Sequence
<220> FEATURE:
<223> OTHER INFORMATION: IAB22M gamma 2 EH2(Minibody 1)

<400> SEQUENCE: 110

Met Glu Thr Asp Thr Leu Leu Leu Trp Val Leu Leu Leu Trp Val Pro
1               5                   10                  15

Gly Ser Thr Gly Asp Val Gln Ile Thr Gln Ser Pro Ser Ser Leu Ser
            20                  25                  30

Ala Ser Val Gly Asp Arg Val Thr Ile Thr Cys Arg Thr Ser Arg Ser
        35                  40                  45

Ile Ser Gln Tyr Leu Ala Trp Tyr Gln Gln Lys Pro Gly Lys Val Pro
    50                  55                  60

Lys Leu Leu Ile Tyr Ser Gly Ser Thr Leu Gln Ser Gly Val Pro Ser
65                  70                  75                  80
```

```
Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Gln His Asn
            100                 105                 110

Glu Asn Pro Leu Thr Phe Gly Gly Gly Thr Lys Val Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Thr Tyr Ile His Phe Val Arg Gln Ala Pro Gly Lys Gly Leu Glu Trp
            180                 185                 190

Ile Gly Arg Ile Asp Pro Ala Asn Asp Asn Thr Leu Tyr Ala Ser Lys
        195                 200                 205

Phe Gln Gly Lys Ala Thr Ile Ser Ala Asp Thr Ser Lys Asn Thr Ala
    210                 215                 220

Tyr Leu Gln Met Asn Ser Leu Arg Ala Glu Asp Thr Ala Val Tyr Tyr
225                 230                 235                 240

Cys Gly Arg Gly Tyr Gly Tyr Tyr Val Phe Asp His Trp Gly Gln Gly
                245                 250                 255

Thr Leu Val Thr Val Ser Ser Glu Arg Lys Ser Cys Val Glu Cys Pro
            260                 265                 270

Pro Cys Pro Gly Gly Ser Gly Gly Gly Ser Gly Gly Gln Pro
        275                 280                 285

Arg Glu Pro Gln Val Tyr Thr Leu Pro Pro Ser Arg Glu Glu Met Thr
290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Met Leu Asp Ser Asp Gly Ser Phe Phe Leu Tyr
            340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
    370                 375                 380

Ser Leu Ser Leu Ser Pro Gly
385                 390

<210> SEQ ID NO 111
<211> LENGTH: 391
<212> TYPE: PRT
<213> ORGANISM: Artificial Sequence
<220> FEATURE:
<223> OTHER INFORMATION: IAB22M gamma 2 EH2(Minibody 1)(VH-K67R)

<400> SEQUENCE: 111

Met Glu Thr Asp Thr Leu Leu Leu Trp Val Leu Leu Leu Trp Val Pro
1               5                   10                  15

Gly Ser Thr Gly Asp Val Gln Ile Thr Gln Ser Pro Ser Ser Leu Ser
            20                  25                  30

Ala Ser Val Gly Asp Arg Val Thr Ile Thr Cys Arg Thr Ser Arg Ser
        35                  40                  45
```

```
Ile Ser Gln Tyr Leu Ala Trp Tyr Gln Gln Lys Pro Gly Lys Val Pro
 50                  55                  60
Lys Leu Leu Ile Tyr Ser Gly Ser Thr Leu Gln Ser Gly Val Pro Ser
 65                  70                  75                  80
Arg Phe Ser Gly Ser Gly Ser Gly Thr Asp Phe Thr Leu Thr Ile Ser
                 85                  90                  95
Ser Leu Gln Pro Glu Asp Val Ala Thr Tyr Tyr Cys Gln Gln His Asn
                100                 105                 110
Glu Asn Pro Leu Thr Phe Gly Gly Gly Thr Lys Val Glu Ile Lys Gly
                115                 120                 125
Ser Thr Ser Gly Gly Gly Ser Gly Gly Gly Ser Gly Gly Gly Gly Ser
130                 135                 140
Ser Glu Val Gln Leu Val Glu Ser Gly Gly Gly Leu Val Gln Pro Gly
145                 150                 155                 160
Gly Ser Leu Arg Leu Ser Cys Ala Ala Ser Gly Phe Asn Ile Lys Asp
                165                 170                 175
Thr Tyr Ile His Phe Val Arg Gln Ala Pro Gly Lys Gly Leu Glu Trp
                180                 185                 190
Ile Gly Arg Ile Asp Pro Ala Asn Asp Asn Thr Leu Tyr Ala Ser Lys
                195                 200                 205
Phe Gln Gly Arg Ala Thr Ile Ser Ala Asp Thr Ser Lys Asn Thr Ala
210                 215                 220
Tyr Leu Gln Met Asn Ser Leu Arg Ala Glu Asp Thr Ala Val Tyr Tyr
225                 230                 235                 240
Cys Gly Arg Gly Tyr Gly Tyr Tyr Val Phe Asp His Trp Gly Gln Gly
                245                 250                 255
Thr Leu Val Thr Val Ser Ser Glu Arg Lys Ser Cys Val Glu Cys Pro
                260                 265                 270
Pro Cys Pro Gly Gly Ser Gly Gly Gly Ser Gly Gly Gln Pro
                275                 280                 285
Arg Glu Pro Gln Val Tyr Thr Leu Pro Pro Ser Arg Glu Glu Met Thr
                290                 295                 300
Lys Asn Gln Val Ser Leu Thr Cys Leu Val Lys Gly Phe Tyr Pro Ser
305                 310                 315                 320
Asp Ile Ala Val Glu Trp Glu Ser Asn Gly Gln Pro Glu Asn Asn Tyr
                325                 330                 335
Lys Thr Thr Pro Pro Met Leu Asp Ser Asp Gly Ser Phe Phe Leu Tyr
                340                 345                 350
Ser Lys Leu Thr Val Asp Lys Ser Arg Trp Gln Gln Gly Asn Val Phe
                355                 360                 365
Ser Cys Ser Val Met His Glu Ala Leu His Asn His Tyr Thr Gln Lys
                370                 375                 380
Ser Leu Ser Leu Ser Pro Gly
385                 390

<210> SEQ ID NO 112
<211> LENGTH: 391
<212> TYPE: PRT
<213> ORGANISM: Artificial Sequence
<220> FEATURE:
<223> OTHER INFORMATION: IAB2M gamma 1 EH1(Minibody 2)

<400> SEQUENCE: 112

Met Glu Thr Asp Thr Leu Leu Leu Trp Val Leu Leu Leu Trp Val Pro
 1                   5                  10                  15
```

```
Gly Ser Thr Gly Glu Val Gln Leu Val Gln Ser Gly Ala Glu Val Lys
            20                  25                  30

Lys Pro Gly Ala Ser Val Lys Ile Ser Cys Lys Thr Ser Gly Tyr Thr
        35                  40                  45

Phe Thr Glu Tyr Thr Ile His Trp Val Lys Gln Ala Ser Gly Lys Gly
 50                  55                  60

Leu Glu Trp Ile Gly Asn Ile Asn Pro Asn Asn Gly Gly Thr Thr Tyr
 65                  70                  75                  80

Asn Gln Lys Phe Glu Asp Arg Ala Thr Leu Thr Val Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Ser Thr Ser Gly Gly Gly Ser Gly
130                 135                 140

Gly Gly Ser Gly Gly Gly Ser Ser Asp Ile Val Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asp Val Gly Thr Ala Val Asp Trp Tyr Gln Gln Lys
            180                 185                 190

Pro Gly Lys Ala Pro Lys Leu Leu Ile Tyr Trp Ala Ser Thr Arg His
        195                 200                 205

Thr Gly Val Pro Asp Arg Phe Thr Gly Ser Gly Ser Gly Thr Asp Phe
210                 215                 220

Thr Leu Thr Ile Ser Ser Leu Gln Pro Glu Asp Phe Ala Asp Tyr Phe
225                 230                 235                 240

Cys Gln Gln Tyr Asn Ser Tyr Pro Leu Thr Phe Gly Gly Gly Thr Lys
                245                 250                 255

Leu Glu Ile Lys Glu Pro Lys Ser Cys Asp Lys Thr His Thr Cys Pro
            260                 265                 270

Pro Cys Gly Gly Gly Ser Ser Gly Gly Ser Gly Gly Gln Pro Arg
        275                 280                 285

Glu Pro Gln Val Tyr Thr Leu Pro Pro Ser Arg Asp Glu Leu Thr Lys
290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 113
<211> LENGTH: 393
<212> TYPE: PRT
<213> ORGANISM: Artificial Sequence
<220> FEATURE:
<223> OTHER INFORMATION: IAB2M gamma 1 EH3(Minibody 2)
```

<400> SEQUENCE: 113

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Ala Ser Val Lys Ile Ser Cys Lys Thr Ser Gly Tyr Thr
        35                  40                  45

Phe Thr Glu Tyr Thr Ile His Trp Val Lys Gln Ala Ser Gly Lys Gly
50                  55                  60

Leu Glu Trp Ile Gly Asn Ile Asn Pro Asn Asn Gly Gly Thr Thr Tyr
65                  70                  75                  80

Asn Gln Lys Phe Glu Asp Arg Ala Thr Leu Thr Val Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Ser Thr Ser Gly Gly Ser Gly
130                 135                 140

Gly Gly Ser Gly Gly Gly Ser Ser Asp Ile Val Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asp Val Gly Thr Ala Val Asp Trp Tyr Gln Gln Lys
            180                 185                 190

Pro Gly Lys Ala Pro Lys Leu Leu Ile Tyr Trp Ala Ser Thr Arg His
        195                 200                 205

Thr Gly Val Pro Asp Arg Phe Thr Gly Ser Gly Ser Gly Thr Asp Phe
210                 215                 220

Thr Leu Thr Ile Ser Ser Leu Gln Pro Glu Asp Phe Ala Asp Tyr Phe
225                 230                 235                 240

Cys Gln Gln Tyr Asn Ser Tyr Pro Leu Thr Phe Gly Gly Gly Thr Lys
                245                 250                 255

Leu Glu Ile Lys Glu Pro Lys Ser Ser Asp Lys Thr His Thr Cys Pro
            260                 265                 270

Pro Cys Pro Cys Gly Gly Gly Ser Gly Gly Gly Ser Gly Gly
        275                 280                 285

Gln Pro Arg Glu Pro Gln Val Tyr Thr Leu Pro Pro Ser Arg Glu Glu
290                 295                 300

Met Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
370                 375                 380

Gln Lys Ser Leu Ser Leu Ser Pro Gly
385                 390

```
<210> SEQ ID NO 114
<211> LENGTH: 393
<212> TYPE: PRT
<213> ORGANISM: Artificial Sequence
<220> FEATURE:
<223> OTHER INFORMATION: IAB2M gamma 1 EH3 (Minibody 2)

<400> SEQUENCE: 114

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Ala Ser Val Lys Ile Ser Cys Lys Thr Ser Gly Tyr Thr
        35                  40                  45

Phe Thr Glu Tyr Thr Ile His Trp Val Lys Gln Ala Ser Gly Lys Gly
    50                  55                  60

Leu Glu Trp Ile Gly Asn Ile Asn Pro Asn Asn Gly Thr Thr Tyr
65                  70                  75                  80

Asn Gln Lys Phe Glu Asp Arg Ala Thr Leu Thr Val Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Ser Thr Ser Gly Gly Gly Ser Gly
    130                 135                 140

Gly Gly Ser Gly Gly Gly Ser Ser Asp Ile Val Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asp Val Gly Thr Ala Val Asp Trp Tyr Gln Gln Lys
            180                 185                 190

Pro Gly Lys Ala Pro Lys Leu Leu Ile Tyr Trp Ala Ser Thr Arg His
        195                 200                 205

Thr Gly Val Pro Asp Arg Phe Thr Gly Ser Gly Ser Gly Thr Asp Phe
    210                 215                 220

Thr Leu Thr Ile Ser Ser Leu Gln Pro Glu Asp Phe Ala Asp Tyr Phe
225                 230                 235                 240

Cys Gln Gln Tyr Asn Ser Tyr Pro Leu Thr Phe Gly Gly Gly Thr Lys
                245                 250                 255

Leu Glu Ile Lys Glu Pro Lys Ser Ser Asp Lys Thr His Thr Cys Pro
            260                 265                 270

Pro Cys Pro Cys Gly Gly Gly Ser Gly Gly Gly Ser Gly Gly
        275                 280                 285

Gln Pro Arg Glu Pro Gln Val Tyr Thr Leu Pro Pro Ser Arg Asp Glu
    290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
```

```
                  370                 375                 380
Gln Lys Ser Leu Ser Leu Ser Pro Gly
385                 390

<210> SEQ ID NO 115
<211> LENGTH: 396
<212> TYPE: PRT
<213> ORGANISM: Artificial Sequence
<220> FEATURE:
<223> OTHER INFORMATION: IAB2M gamma 1 EH5(Minibody 2)

<400> SEQUENCE: 115

Met Glu Thr Asp Thr Leu Leu Leu Trp Val Leu Leu Trp Val Pro
1               5                   10                  15

Gly Ser Thr Gly Glu Val Gln Leu Val Gln Ser Gly Ala Glu Val Lys
                20                  25                  30

Lys Pro Gly Ala Ser Val Lys Ile Ser Cys Lys Thr Ser Gly Tyr Thr
            35                  40                  45

Phe Thr Glu Tyr Thr Ile His Trp Val Lys Gln Ala Ser Gly Lys Gly
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Arg Ala Thr Leu Thr Val Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Ser Thr Ser Gly Gly Gly Ser Gly
    130                 135                 140

Gly Gly Ser Gly Gly Gly Ser Ser Asp Ile Val Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asp Val Gly Thr Ala Val Asp Trp Tyr Gln Gln Lys
            180                 185                 190

Pro Gly Lys Ala Pro Lys Leu Leu Ile Tyr Trp Ala Ser Thr Arg His
        195                 200                 205

Thr Gly Val Pro Asp Arg Phe Thr Gly Ser Gly Ser Gly Thr Asp Phe
    210                 215                 220

Thr Leu Thr Ile Ser Ser Leu Gln Pro Glu Asp Phe Ala Asp Tyr Phe
225                 230                 235                 240

Cys Gln Gln Tyr Asn Ser Tyr Pro Leu Thr Phe Gly Gly Gly Thr Lys
                245                 250                 255

Leu Glu Ile Lys Glu Pro Lys Ser Ser Asp Lys Thr His Thr Cys Pro
            260                 265                 270

Pro Cys Pro Pro Cys Pro Cys Gly Gly Ser Gly Gly Gly
        275                 280                 285

Ser Gly Gly Gln Pro Arg Glu Pro Gln Val Tyr Thr Leu Pro Pro Ser
    290                 295                 300

Arg Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
```

```
                    340                 345                 350
Ser Phe Phe Leu Tyr Ser Lys Leu Thr Val Asp Lys Ser Arg Trp Gln
                355                 360                 365

Gln Gly Asn Val Phe Ser Cys Ser Val Met His Glu Ala Leu His Asn
            370                 375                 380

His Tyr Thr Gln Lys Ser Leu Ser Leu Ser Pro Gly
385                 390                 395

<210> SEQ ID NO 116
<211> LENGTH: 395
<212> TYPE: PRT
<213> ORGANISM: Artificial Sequence
<220> FEATURE:
<223> OTHER INFORMATION: IAB2M gamma 1 EH7(Minibody 2)

<400> SEQUENCE: 116

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
                20                  25                  30

Lys Pro Gly Ala Ser Val Lys Ile Ser Cys Lys Thr Ser Gly Tyr Thr
            35                  40                  45

Phe Thr Glu Tyr Thr Ile His Trp Val Lys Gln Ala Ser Gly Lys Gly
        50                  55                  60

Leu Glu Trp Ile Gly Asn Ile Asn Pro Asn Asn Gly Thr Thr Thr Tyr
65                  70                  75                  80

Asn Gln Lys Phe Glu Asp Arg Ala Thr Leu Thr Val Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Ser Thr Ser Gly Gly Gly Ser Gly
    130                 135                 140

Gly Gly Ser Gly Gly Gly Ser Ser Asp Ile Val Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asp Val Gly Thr Ala Val Asp Trp Tyr Gln Gln Lys
            180                 185                 190

Pro Gly Lys Ala Pro Lys Leu Leu Ile Tyr Trp Ala Ser Thr Arg His
        195                 200                 205

Thr Gly Val Pro Asp Arg Phe Thr Gly Ser Gly Ser Gly Thr Asp Phe
    210                 215                 220

Thr Leu Thr Ile Ser Ser Leu Gln Pro Glu Asp Phe Ala Asp Tyr Phe
225                 230                 235                 240

Cys Gln Gln Tyr Asn Ser Tyr Pro Leu Thr Phe Gly Gly Gly Thr Lys
                245                 250                 255

Leu Glu Ile Lys Glu Leu Lys Thr Pro Leu Gly Asp Thr Thr His Thr
            260                 265                 270

Cys Pro Pro Cys Pro Pro Cys Gly Gly Ser Gly Gly Gly Ser
        275                 280                 285

Gly Gly Gln Pro Arg Glu Pro Gln Val Tyr Thr Leu Pro Pro Ser Arg
    290                 295                 300

Glu Glu Met Thr Lys Asn Gln Val Ser Leu Thr Cys Leu Val Lys Gly
```

```
                305                 310                 315                 320
        Phe Tyr Pro Ser Asp Ile Ala Val Glu Trp Glu Ser Asn Gly Gln Pro
                        325                 330                 335

Glu Asn Asn Tyr Lys Thr Thr Pro Pro Val Leu Asp Ser Asp Gly Ser
                        340                 345                 350

Phe Phe Leu Tyr Ser Lys Leu Thr Val Asp Lys Ser Arg Trp Gln Gln
                        355                 360                 365

Gly Asn Val Phe Ser Cys Ser Val Met His Glu Ala Leu His Asn His
                        370                 375                 380

Tyr Thr Gln Lys Ser Leu Ser Leu Ser Pro Gly
        385                 390                 395

<210> SEQ ID NO 117
<211> LENGTH: 398
<212> TYPE: PRT
<213> ORGANISM: Artificial Sequence
<220> FEATURE:
<223> OTHER INFORMATION: IAB2M gamma 1 EH8(Minibody 2)

<400> SEQUENCE: 117

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
                20                  25                  30

Lys Pro Gly Ala Ser Val Lys Ile Ser Cys Lys Thr Ser Gly Tyr Thr
            35                  40                  45

Phe Thr Glu Tyr Thr Ile His Trp Val Lys Gln Ala Ser Gly Lys Gly
50                  55                  60

Leu Glu Trp Ile Gly Asn Ile Asn Pro Asn Asn Gly Gly Thr Thr Tyr
65                  70                  75                  80

Asn Gln Lys Phe Glu Asp Arg Ala Thr Leu Thr Val Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Ser Thr Ser Gly Gly Gly Ser Gly
    130                 135                 140

Gly Gly Ser Gly Gly Gly Ser Ser Asp Ile Val Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asp Val Gly Thr Ala Val Asp Trp Tyr Gln Gln Lys
            180                 185                 190

Pro Gly Lys Ala Pro Lys Leu Leu Ile Tyr Trp Ala Ser Thr Arg His
        195                 200                 205

Thr Gly Val Pro Asp Arg Phe Thr Gly Ser Gly Ser Gly Thr Asp Phe
    210                 215                 220

Thr Leu Thr Ile Ser Ser Leu Gln Pro Glu Asp Phe Ala Asp Tyr Phe
225                 230                 235                 240

Cys Gln Gln Tyr Asn Ser Tyr Pro Leu Thr Phe Gly Gly Gly Thr Lys
                245                 250                 255

Leu Glu Ile Lys Glu Leu Lys Thr Pro Leu Gly Asp Thr Thr His Thr
            260                 265                 270

Cys Pro Pro Cys Pro Pro Cys Pro Pro Cys Gly Gly Gly Ser Ser Gly
```

```
            275                 280                 285
Gly Gly Ser Gly Gly Gln Pro Arg Glu Pro Gln Val Tyr Thr Leu Pro
            290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
            355                 360                 365

Trp Gln Gln Gly Asn Val Phe Ser Cys Ser Val Met His Glu Ala Leu
            370                 375                 380

His Asn His Tyr Thr Gln Lys Ser Leu Ser Leu Ser Pro Gly
385                 390                 395

<210> SEQ ID NO 118
<211> LENGTH: 393
<212> TYPE: PRT
<213> ORGANISM: Artificial Sequence
<220> FEATURE:
<223> OTHER INFORMATION: IAB2M gamma 1 EH3(Minibody 1)

<400> SEQUENCE: 118

Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Gly Thr Ala Val Asp Trp Tyr Gln Gln Lys Pro Gly Lys Ala Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Ser Leu Gln Pro Glu Asp Phe Ala Asp Tyr Phe Cys Gln Gln Tyr Asn
            100                 105                 110

Ser Tyr Pro Leu Thr Phe Gly Gly Gly Thr Lys Leu Glu Ile Lys Gly
        115                 120                 125

Ser Thr Ser Gly Gly Gly Ser Gly Gly Ser Gly Gly Gly Gly Ser
    130                 135                 140

Ser Glu Val Gln Leu Val Gln Ser Gly Ala Glu Val Lys Lys Pro Gly
145                 150                 155                 160

Ala Ser Val Lys Ile Ser Cys Lys Thr Ser Gly Tyr Thr Phe Thr Glu
                165                 170                 175

Tyr Thr Ile His Trp Val Lys Gln Ala Ser Gly Lys Gly Leu Glu Trp
            180                 185                 190

Ile Gly Asn Ile Asn Pro Asn Asn Gly Gly Thr Thr Tyr Asn Gln Lys
        195                 200                 205

Phe Glu Asp Arg Ala Thr Leu Thr Val Asp Lys Ser Thr Ser Thr Ala
    210                 215                 220

Tyr Met Glu Leu Ser Ser Leu Arg Ser Glu Asp Thr Ala Val Tyr Tyr
225                 230                 235                 240

Cys Ala Ala Gly Trp Asn Phe Asp Tyr Trp Gly Gln Gly Thr Thr Val
```

```
                     245                 250                 255
Thr Val Ser Ser Glu Pro Lys Ser Ser Asp Lys Thr His Thr Cys Pro
            260                 265                 270

Pro Cys Pro Cys Gly Gly Gly Ser Ser Gly Gly Ser Gly Gly
            275                 280                 285

Gln Pro Arg Glu Pro Gln Val Tyr Thr Leu Pro Pro Ser Arg Glu Glu
        290                 295                 300

Met Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
    370                 375                 380

Gln Lys Ser Leu Ser Leu Ser Pro Gly
385                 390

<210> SEQ ID NO 119
<211> LENGTH: 396
<212> TYPE: PRT
<213> ORGANISM: Artificial Sequence
<220> FEATURE:
<223> OTHER INFORMATION: IAB20M gamma 1 EH1 (Minibody 2)

<400> SEQUENCE: 119

Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ala Ser Val Lys Val Ser Cys Lys Ala Ser Gly Tyr Ser
        35                  40                  45

Phe Thr Gly Tyr Tyr Met His Trp Val Arg Gln Ala Pro Gly Gln Gly
    50                  55                  60

Leu Glu Trp Ile Gly Arg Ile Asn Pro Asn Asn Gly Val Thr Leu Tyr
65                  70                  75                  80

Asn Gln Lys Phe Lys Asp Arg Val Thr Met Thr Val Asp Thr Ser Ile
                85                  90                  95

Ser Thr Ala Tyr Met Glu Leu Ser Arg Leu Arg Ser Asp Asp Thr Ala
            100                 105                 110

Val Tyr Tyr Cys Ala Arg Ser Thr Met Ile Thr Asn Tyr Val Met Asp
        115                 120                 125

Tyr Trp Gly Gln Gly Thr Leu Val Thr Val Ser Ser Gly Ser Thr Ser
    130                 135                 140

Gly Gly Gly Ser Gly Gly Gly Ser Gly Gly Gly Ser Ser Asp Ile
145                 150                 155                 160

Val Met Thr Gln Ser Pro Ala Thr Leu Ser Val Ser Pro Gly Glu Arg
                165                 170                 175

Ala Thr Leu Ser Cys Lys Ala Ser Gln Ser Val Ser Asn Asp Val Ala
            180                 185                 190

Trp Tyr Gln Gln Lys Pro Gly Gln Ala Pro Arg Leu Leu Ile Ser Tyr
        195                 200                 205

Thr Ser Ser Arg Tyr Ala Gly Val Pro Asp Arg Phe Ser Gly Ser Gly
```

```
                210                 215                 220

Ser Gly Thr Asp Phe Thr Leu Thr Ile Ser Ser Leu Gln Ala Glu Asp
225                 230                 235                 240

Val Ala Val Tyr Tyr Cys Gln Gln Asp Tyr Asn Ser Pro Pro Thr Phe
                245                 250                 255

Gly Gln Gly Thr Lys Val Glu Ile Lys Glu Pro Lys Ser Cys Asp Lys
                260                 265                 270

Thr His Thr Cys Pro Pro Cys Gly Gly Gly Ser Gly Gly Gly Ser
            275                 280                 285

Gly Gly Gln Pro Arg Glu Pro Gln Val Tyr Thr Leu Pro Pro Ser Arg
            290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
                340                 345                 350

Phe Phe Leu Tyr Ser Lys Leu Thr Val Asp Lys Ser Arg Trp Gln Gln
                355                 360                 365

Gly Asn Val Phe Ser Cys Ser Val Met His Glu Ala Leu His Asn His
            370                 375                 380

Tyr Thr Gln Lys Ser Leu Ser Leu Ser Pro Gly Lys
385                 390                 395

<210> SEQ ID NO 120
<211> LENGTH: 398
<212> TYPE: PRT
<213> ORGANISM: Artificial Sequence
<220> FEATURE:
<223> OTHER INFORMATION: IAB20M gamma 1 EH3 (Minibody 2)

<400> SEQUENCE: 120

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Ala Glu Val Lys
            20                  25                  30

Lys Pro Gly Ala Ser Val Lys Val Ser Cys Lys Ala Ser Gly Tyr Ser
        35                  40                  45

Phe Thr Gly Tyr Tyr Met His Trp Val Arg Gln Ala Pro Gly Gln Gly
    50                  55                  60

Leu Glu Trp Ile Gly Arg Ile Asn Pro Asn Asn Gly Val Thr Leu Tyr
65                  70                  75                  80

Asn Gln Lys Phe Lys Asp Arg Val Thr Met Thr Val Asp Thr Ser Ile
                85                  90                  95

Ser Thr Ala Tyr Met Glu Leu Ser Arg Leu Arg Ser Asp Asp Thr Ala
            100                 105                 110

Val Tyr Tyr Cys Ala Arg Ser Thr Met Ile Thr Asn Tyr Val Met Asp
        115                 120                 125

Tyr Trp Gly Gln Gly Thr Leu Val Thr Val Ser Ser Gly Ser Thr Ser
    130                 135                 140

Gly Gly Gly Ser Gly Gly Gly Ser Gly Gly Gly Ser Ser Asp Ile
145                 150                 155                 160

Val Met Thr Gln Ser Pro Ala Thr Leu Ser Val Ser Pro Gly Glu Arg
                165                 170                 175

Ala Thr Leu Ser Cys Lys Ala Ser Gln Ser Val Ser Asn Asp Val Ala
```

```
                    180                 185                 190
Trp Tyr Gln Gln Lys Pro Gly Gln Ala Pro Arg Leu Leu Ile Ser Tyr
            195                 200                 205

Thr Ser Ser Arg Tyr Ala Gly Val Pro Asp Arg Phe Ser Gly Ser Gly
            210                 215                 220

Ser Gly Thr Asp Phe Thr Leu Thr Ile Ser Ser Leu Glu Ala Glu Asp
225                 230                 235                 240

Glu Ala Val Tyr Tyr Cys Gln Gln Asp Tyr Asn Ser Pro Pro Thr Phe
                245                 250                 255

Gly Gln Gly Thr Lys Val Glu Ile Lys Glu Pro Lys Ser Ser Asp Lys
            260                 265                 270

Thr His Thr Cys Pro Pro Cys Pro Cys Gly Gly Ser Ser Gly
            275                 280                 285

Gly Gly Ser Gly Gly Gln Pro Arg Glu Pro Gln Val Tyr Thr Leu Pro
            290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
            355                 360                 365

Trp Gln Gln Gly Asn Val Phe Ser Cys Ser Val Met His Glu Ala Leu
            370                 375                 380

His Asn His Tyr Thr Gln Lys Ser Leu Ser Leu Ser Pro Gly
385                 390                 395

<210> SEQ ID NO 121
<211> LENGTH: 398
<212> TYPE: PRT
<213> ORGANISM: Artificial Sequence
<220> FEATURE:
<223> OTHER INFORMATION: IAB20M gamma 1 EH3(Minibody 2)

<400> SEQUENCE: 121

Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ala Ser Val Lys Val Ser Cys Lys Ala Ser Gly Tyr Ser
            35                  40                  45

Phe Thr Gly Tyr Tyr Met His Trp Val Arg Gln Ala Pro Gly Gln Gly
        50                  55                  60

Leu Glu Trp Ile Gly Arg Ile Asn Pro Asn Asn Gly Val Thr Leu Tyr
65                  70                  75                  80

Asn Gln Lys Phe Lys Asp Arg Val Thr Met Thr Val Asp Thr Ser Ile
                85                  90                  95

Ser Thr Ala Tyr Met Glu Leu Ser Arg Leu Arg Ser Asp Asp Thr Ala
            100                 105                 110

Val Tyr Tyr Cys Ala Arg Ser Thr Met Ile Thr Asn Tyr Val Met Asp
            115                 120                 125

Tyr Trp Gly Gln Gly Thr Leu Val Thr Val Ser Ser Gly Ser Thr Ser
            130                 135                 140

Gly Gly Gly Ser Gly Gly Gly Ser Gly Gly Gly Ser Ser Asp Ile
```

```
                145                 150                 155                 160
Val Met Thr Gln Ser Pro Ala Thr Leu Ser Val Ser Pro Gly Glu Arg
                    165                 170                 175

Ala Thr Leu Ser Cys Lys Ala Ser Gln Ser Val Ser Asn Asp Val Ala
                    180                 185                 190

Trp Tyr Gln Gln Lys Pro Gly Gln Ala Pro Arg Leu Leu Ile Ser Tyr
                    195                 200                 205

Thr Ser Ser Arg Tyr Ala Gly Val Pro Asp Arg Phe Ser Gly Ser Gly
            210                 215                 220

Ser Gly Thr Asp Phe Thr Leu Thr Ile Ser Ser Leu Gln Ala Glu Asp
225                 230                 235                 240

Val Ala Val Tyr Tyr Cys Gln Gln Asp Tyr Asn Ser Pro Pro Thr Phe
                245                 250                 255

Gly Gln Gly Thr Lys Val Glu Ile Lys Glu Pro Lys Ser Ser Asp Lys
                260                 265                 270

Thr His Thr Cys Pro Pro Cys Pro Pro Cys Gly Gly Gly Ser Ser Gly
            275                 280                 285

Gly Gly Ser Gly Gly Gln Pro Arg Glu Pro Gln Val Tyr Thr Leu Pro
290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
                340                 345                 350

Asp Gly Ser Phe Phe Leu Tyr Ser Lys Leu Thr Val Asp Lys Ser Arg
                355                 360                 365

Trp Gln Gln Gly Asn Val Phe Ser Cys Ser Val Met His Glu Ala Leu
                370                 375                 380

His Asn His Tyr Thr Gln Lys Ser Leu Ser Leu Ser Pro Gly
385                 390                 395

<210> SEQ ID NO 122
<211> LENGTH: 398
<212> TYPE: PRT
<213> ORGANISM: Artificial Sequence
<220> FEATURE:
<223> OTHER INFORMATION: IAB20M gamma 1 EH3(Minibody 2)

<400> SEQUENCE: 122

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Ala Glu Val Lys
                20                  25                  30

Lys Pro Gly Ala Ser Val Lys Val Ser Cys Lys Ala Ser Gly Tyr Ser
            35                  40                  45

Phe Thr Gly Tyr Tyr Met His Trp Val Arg Gln Ala Pro Gly Gln Gly
        50                  55                  60

Leu Glu Trp Ile Gly Arg Ile Asn Pro Asn Asn Gly Val Thr Leu Tyr
65                  70                  75                  80

Asn Gln Lys Phe Lys Asp Arg Val Thr Met Thr Val Asp Thr Ser Ile
                85                  90                  95

Ser Thr Ala Tyr Met Glu Leu Ser Arg Leu Arg Ser Asp Asp Thr Ala
                100                 105                 110

Val Tyr Tyr Cys Ala Arg Ser Thr Met Ile Thr Asn Tyr Val Met Asp
```

```
            115                 120                 125
Tyr Trp Gly Gln Gly Thr Leu Val Thr Val Ser Ser Gly Ser Thr Ser
    130                 135                 140

Gly Gly Gly Ser Gly Gly Gly Ser Gly Gly Gly Ser Ser Asp Ile
145                 150                 155                 160

Val Met Thr Gln Ser Pro Asp Ser Leu Ala Val Ser Leu Gly Glu Arg
                165                 170                 175

Ala Thr Ile Asn Cys Lys Ala Ser Gln Ser Val Ser Asn Asp Val Ala
            180                 185                 190

Trp Tyr Gln Gln Lys Pro Gly Gln Ala Pro Arg Leu Leu Ile Ser Tyr
        195                 200                 205

Thr Ser Ser Arg Tyr Ala Gly Val Pro Asp Arg Phe Ser Gly Ser Gly
    210                 215                 220

Ser Gly Thr Asp Phe Thr Leu Thr Ile Ser Ser Leu Gln Ala Glu Asp
225                 230                 235                 240

Val Ala Val Tyr Tyr Cys Gln Gln Asp Tyr Asn Ser Pro Pro Thr Phe
                245                 250                 255

Gly Gln Gly Thr Lys Val Glu Ile Lys Glu Pro Lys Ser Ser Asp Lys
            260                 265                 270

Thr His Thr Cys Pro Pro Cys Pro Cys Gly Gly Ser Ser Gly
        275                 280                 285

Gly Gly Ser Gly Gly Gln Pro Arg Glu Pro Gln Val Tyr Thr Leu Pro
    290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
        355                 360                 365

Trp Gln Gln Gly Asn Val Phe Ser Cys Ser Val Met His Glu Ala Leu
    370                 375                 380

His Asn His Tyr Thr Gln Lys Ser Leu Ser Leu Ser Pro Gly
385                 390                 395

<210> SEQ ID NO 123
<211> LENGTH: 401
<212> TYPE: PRT
<213> ORGANISM: Artificial Sequence
<220> FEATURE:
<223> OTHER INFORMATION: IAB20M gamma 1 EH5(Minibody 2)

<400> SEQUENCE: 123

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Ala Glu Val Lys
            20                  25                  30

Lys Pro Gly Ala Ser Val Lys Val Ser Cys Lys Ala Ser Gly Tyr Ser
        35                  40                  45

Phe Thr Gly Tyr Tyr Met His Trp Val Arg Gln Ala Pro Gly Gln Gly
    50                  55                  60

Leu Glu Trp Ile Gly Arg Ile Asn Pro Asn Asn Gly Val Thr Leu Tyr
65                  70                  75                  80

Asn Gln Lys Phe Lys Asp Arg Val Thr Met Thr Val Asp Thr Ser Ile
```

85                  90                  95

Ser Thr Ala Tyr Met Glu Leu Ser Arg Leu Arg Ser Asp Asp Thr Ala
                100                 105                 110

Val Tyr Tyr Cys Ala Arg Ser Thr Met Ile Thr Asn Tyr Val Met Asp
            115                 120                 125

Tyr Trp Gly Gln Gly Thr Leu Val Thr Val Ser Ser Gly Ser Thr Ser
        130                 135                 140

Gly Gly Gly Ser Gly Gly Gly Ser Gly Gly Gly Ser Ser Asp Ile
145                 150                 155                 160

Val Met Thr Gln Ser Pro Ala Thr Leu Ser Val Ser Pro Gly Glu Arg
                165                 170                 175

Ala Thr Leu Ser Cys Lys Ala Ser Gln Ser Val Ser Asn Asp Val Ala
            180                 185                 190

Trp Tyr Gln Gln Lys Pro Gly Gln Ala Pro Arg Leu Leu Ile Ser Tyr
        195                 200                 205

Thr Ser Ser Arg Tyr Ala Gly Val Pro Asp Arg Phe Ser Gly Ser Gly
    210                 215                 220

Ser Gly Thr Asp Phe Thr Leu Thr Ile Ser Ser Leu Glu Ala Glu Asp
225                 230                 235                 240

Glu Ala Val Tyr Tyr Cys Gln Gln Asp Tyr Asn Ser Pro Pro Thr Phe
                245                 250                 255

Gly Gln Gly Thr Lys Val Glu Ile Lys Glu Pro Lys Ser Ser Asp Lys
            260                 265                 270

Thr His Thr Cys Pro Pro Cys Pro Pro Cys Pro Pro Cys Gly Gly Gly
        275                 280                 285

Ser Ser Gly Gly Gly Ser Gly Gly Gln Pro Arg Glu Pro Gln Val Tyr
    290                 295                 300

Thr Leu Pro Pro Ser Arg Glu Glu Met Thr Lys Asn Gln Val Ser Leu
305                 310                 315                 320

Thr Cys Leu Val Lys Gly Phe Tyr Pro Ser Asp Ile Ala Val Glu Trp
                325                 330                 335

Glu Ser Asn Gly Gln Pro Glu Asn Asn Tyr Lys Thr Thr Pro Pro Val
            340                 345                 350

Leu Asp Ser Asp Gly Ser Phe Phe Leu Tyr Ser Lys Leu Thr Val Asp
        355                 360                 365

Lys Ser Arg Trp Gln Gln Gly Asn Val Phe Ser Cys Ser Val Met His
    370                 375                 380

Glu Ala Leu His Asn His Tyr Thr Gln Lys Ser Leu Ser Leu Ser Pro
385                 390                 395                 400

Gly

<210> SEQ ID NO 124
<211> LENGTH: 401
<212> TYPE: PRT
<213> ORGANISM: Artificial Sequence
<220> FEATURE:
<223> OTHER INFORMATION: IAB20M gamma 1 EH5(Minibody 2)

<400> SEQUENCE: 124

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Ala Glu Val Lys
            20                  25                  30

Lys Pro Gly Ala Ser Val Lys Val Ser Cys Lys Ala Ser Gly Tyr Ser
        35                  40                  45

```
Phe Thr Gly Tyr Tyr Met His Trp Val Arg Gln Ala Pro Gly Gln Gly
 50                  55                  60
Leu Glu Trp Ile Gly Arg Ile Asn Pro Asn Asn Gly Val Thr Leu Tyr
 65                  70                  75                  80
Asn Gln Lys Phe Lys Asp Arg Val Thr Met Thr Val Asp Thr Ser Ile
                 85                  90                  95
Ser Thr Ala Tyr Met Glu Leu Ser Arg Leu Arg Ser Asp Asp Thr Ala
                100                 105                 110
Val Tyr Tyr Cys Ala Arg Ser Thr Met Ile Thr Asn Tyr Val Met Asp
                115                 120                 125
Tyr Trp Gly Gln Gly Thr Leu Val Thr Val Ser Ser Gly Ser Thr Ser
130                 135                 140
Gly Gly Gly Ser Gly Gly Ser Gly Gly Gly Ser Ser Asp Ile
145                 150                 155                 160
Val Met Thr Gln Ser Pro Asp Ser Leu Ala Val Ser Leu Gly Glu Arg
                165                 170                 175
Ala Thr Ile Asn Cys Lys Ala Ser Gln Ser Val Ser Asn Asp Val Ala
                180                 185                 190
Trp Tyr Gln Gln Lys Pro Gly Gln Ala Pro Arg Leu Leu Ile Ser Tyr
                195                 200                 205
Thr Ser Ser Arg Tyr Ala Gly Val Pro Asp Arg Phe Ser Gly Ser Gly
                210                 215                 220
Ser Gly Thr Asp Phe Thr Leu Thr Ile Ser Ser Leu Gln Ala Glu Asp
225                 230                 235                 240
Val Ala Val Tyr Tyr Cys Gln Gln Asp Tyr Asn Ser Pro Pro Thr Phe
                245                 250                 255
Gly Gln Gly Thr Lys Val Glu Ile Lys Glu Pro Lys Ser Ser Asp Lys
                260                 265                 270
Thr His Thr Cys Pro Pro Cys Pro Pro Cys Pro Pro Cys Gly Gly Gly
                275                 280                 285
Ser Ser Gly Gly Gly Ser Gly Gly Gln Pro Arg Glu Pro Gln Val Tyr
290                 295                 300
Thr Leu Pro Pro Ser Arg Glu Glu Met Thr Lys Asn Gln Val Ser Leu
305                 310                 315                 320
Thr Cys Leu Val Lys Gly Phe Tyr Pro Ser Asp Ile Ala Val Glu Trp
                325                 330                 335
Glu Ser Asn Gly Gln Pro Glu Asn Asn Tyr Lys Thr Thr Pro Pro Val
                340                 345                 350
Leu Asp Ser Asp Gly Ser Phe Phe Leu Tyr Ser Lys Leu Thr Val Asp
                355                 360                 365
Lys Ser Arg Trp Gln Gln Gly Asn Val Phe Ser Cys Ser Val Met His
                370                 375                 380
Glu Ala Leu His Asn His Tyr Thr Gln Lys Ser Leu Ser Leu Ser Pro
385                 390                 395                 400
Gly
```

<210> SEQ ID NO 125
<211> LENGTH: 387
<212> TYPE: PRT
<213> ORGANISM: Artificial Sequence
<220> FEATURE:
<223> OTHER INFORMATION: IAB1M gamma 1 EH1(Minibody 1)

<400> SEQUENCE: 125

```
Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Thr Leu Ser
            20                  25                  30

Ala Ser Val Gly Asp Arg Val Thr Ile Thr Cys Ser Ala Ser Ser Ser
            35                  40                  45

Val Arg Phe Ile His Trp Tyr Gln Gln Lys Pro Gly Lys Ala Pro Lys
50                  55                  60

Arg Leu Ile Tyr Asp Thr Ser Lys Leu Ala Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Trp Gly Ser
            100                 105                 110

Ser Pro Phe Thr Phe Gly Gln Gly Thr Lys Val Glu Ile Lys Gly Ser
            115                 120                 125

Thr Ser Gly Gly Gly Ser Gly Gly Gly Ser Gly Gly Gly Gly Ser Ser
    130                 135                 140

Glu Val Gln Leu Val Glu Tyr Gly Gly Gly Leu Val Gln Pro Gly Gly
145                 150                 155                 160

Ser Leu Arg Leu Ser Cys Ala Ala Ser Gly Phe Asn Ile Lys Asp Tyr
                165                 170                 175

Tyr Ile His Trp Val Arg Gln Ala Pro Gly Lys Gly Leu Glu Trp Val
            180                 185                 190

Ala Trp Ile Asp Pro Glu Asn Gly Asp Thr Glu Phe Val Pro Lys Phe
            195                 200                 205

Gln Gly Arg Ala Thr Met Ser Ala Asp Thr Ser Lys Asn Thr Ala Tyr
210                 215                 220

Leu Gln Met Asn Ser Leu Arg Ala Glu Asp Thr Ala Val Tyr Tyr Cys
225                 230                 235                 240

Lys Thr Gly Gly Phe Trp Gly Gln Gly Thr Leu Val Thr Val Ser Ser
                245                 250                 255

Glu Pro Lys Ser Cys Asp Lys Thr His Thr Cys Pro Pro Cys Gly Gly
            260                 265                 270

Gly Ser Ser Gly Gly Gly Ser Gly Gln Pro Arg Glu Pro Gln Val
            275                 280                 285

Tyr Thr Leu Pro Pro Ser Arg Asp Glu Leu Thr Lys Asn Gln Val Ser
290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
            355                 360                 365

His Glu Ala Leu His Asn His Tyr Thr Gln Lys Ser Leu Ser Leu Ser
370                 375                 380

Pro Gly Lys
385

<210> SEQ ID NO 126
<211> LENGTH: 389
<212> TYPE: PRT
```

<213> ORGANISM: Artificial Sequence
<220> FEATURE:
<223> OTHER INFORMATION: IAB1M gamma 1 EH3(Minibody 1)

<400> SEQUENCE: 126

```
Met Glu Thr Asp Thr Leu Leu Leu Trp Val Leu Leu Leu Trp Val Pro
1               5                   10                  15
Gly Ser Thr Gly Asp Ile Gln Leu Thr Gln Ser Pro Ser Thr Leu Ser
            20                  25                  30
Ala Ser Val Gly Asp Arg Val Thr Ile Thr Cys Ser Ala Ser Ser Ser
        35                  40                  45
Val Arg Phe Ile His Trp Tyr Gln Gln Lys Pro Gly Lys Ala Pro Lys
    50                  55                  60
Arg Leu Ile Tyr Asp Thr Ser Lys Leu Ala Ser Gly Val Pro Ser Arg
65                  70                  75                  80
Phe Ser Gly Ser Gly Ser Gly Thr Asp Phe Thr Leu Thr Ile Ser Ser
                85                  90                  95
Leu Gln Pro Glu Asp Phe Ala Thr Tyr Tyr Cys Gln Gln Trp Gly Ser
            100                 105                 110
Ser Pro Phe Thr Phe Gly Gln Gly Thr Lys Val Glu Ile Lys Gly Ser
        115                 120                 125
Thr Ser Gly Gly Gly Ser Gly Gly Gly Ser Gly Gly Gly Gly Ser Ser
    130                 135                 140
Glu Val Gln Leu Val Glu Tyr Gly Gly Gly Leu Val Gln Pro Gly Gly
145                 150                 155                 160
Ser Leu Arg Leu Ser Cys Ala Ala Ser Gly Phe Asn Ile Lys Asp Tyr
                165                 170                 175
Tyr Ile His Trp Val Arg Gln Ala Pro Gly Lys Gly Leu Glu Trp Val
            180                 185                 190
Ala Trp Ile Asp Pro Glu Asn Gly Asp Thr Glu Phe Val Pro Lys Phe
        195                 200                 205
Gln Gly Arg Ala Thr Met Ser Ala Asp Thr Ser Lys Asn Thr Ala Tyr
    210                 215                 220
Leu Gln Met Asn Ser Leu Arg Ala Glu Asp Thr Ala Val Tyr Tyr Cys
225                 230                 235                 240
Lys Thr Gly Gly Phe Trp Gly Gln Gly Thr Leu Val Thr Val Ser Ser
                245                 250                 255
Glu Pro Lys Ser Ser Asp Lys Thr His Thr Cys Pro Pro Cys Pro Pro
            260                 265                 270
Cys Gly Gly Gly Ser Ser Gly Gly Gly Ser Gly Gly Gln Pro Arg Glu
        275                 280                 285
Pro Gln Val Tyr Thr Leu Pro Pro Ser Arg Glu Glu Met Thr Lys Asn
    290                 295                 300
Gln Val Ser Leu Thr Cys Leu Val Lys Gly Phe Tyr Pro Ser Asp Ile
305                 310                 315                 320
Ala Val Glu Trp Glu Ser Asn Gly Gln Pro Glu Asn Asn Tyr Lys Thr
                325                 330                 335
Thr Pro Pro Val Leu Asp Ser Asp Gly Ser Phe Phe Leu Tyr Ser Lys
            340                 345                 350
Leu Thr Val Asp Lys Ser Arg Trp Gln Gln Gly Asn Val Phe Ser Cys
        355                 360                 365
Ser Val Met His Glu Ala Leu His Asn His Tyr Thr Gln Lys Ser Leu
    370                 375                 380
Ser Leu Ser Pro Gly
```

<210> SEQ ID NO 127
<211> LENGTH: 384
<212> TYPE: PRT
<213> ORGANISM: Artificial Sequence
<220> FEATURE:
<223> OTHER INFORMATION: IAB1M gamma 1 EH2(Minibody 1)

<400> SEQUENCE: 127

```
Met Glu Thr Asp Thr Leu Leu Leu Trp Val Leu Leu Leu Trp Val Pro
 1               5                  10                  15

Gly Ser Thr Gly Asp Ile Gln Leu Thr Gln Ser Pro Ser Thr Leu Ser
             20                  25                  30

Ala Ser Val Gly Asp Arg Val Thr Ile Thr Cys Ser Ala Ser Ser Ser
         35                  40                  45

Val Arg Phe Ile His Trp Tyr Gln Gln Lys Pro Gly Lys Ala Pro Lys
     50                  55                  60

Arg Leu Ile Tyr Asp Thr Ser Lys Leu Ala Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Trp Gly Ser
            100                 105                 110

Ser Pro Phe Thr Phe Gly Gln Gly Thr Lys Val Glu Ile Lys Gly Ser
        115                 120                 125

Thr Ser Gly Gly Gly Ser Gly Gly Gly Ser Gly Gly Gly Ser Ser Ser
    130                 135                 140

Glu Val Gln Leu Val Glu Tyr Gly Gly Gly Leu Val Gln Pro Gly Gly
145                 150                 155                 160

Ser Leu Arg Leu Ser Cys Ala Ala Ser Gly Phe Asn Ile Lys Asp Tyr
                165                 170                 175

Tyr Ile His Trp Val Arg Gln Ala Pro Gly Lys Gly Leu Glu Trp Val
            180                 185                 190

Ala Trp Ile Asp Pro Glu Asn Gly Asp Thr Glu Phe Val Pro Lys Phe
        195                 200                 205

Gln Gly Arg Ala Thr Met Ser Ala Asp Thr Ser Lys Asn Thr Ala Tyr
    210                 215                 220

Leu Gln Met Asn Ser Leu Arg Ala Glu Asp Thr Ala Val Tyr Tyr Cys
225                 230                 235                 240

Lys Thr Gly Gly Phe Trp Gly Gln Gly Thr Leu Val Thr Val Ser Ser
                245                 250                 255

Glu Arg Lys Ser Cys Val Glu Cys Pro Pro Cys Pro Gly Gly Gly Ser
            260                 265                 270

Ser Gly Gly Gly Ser Gly Gln Pro Arg Glu Pro Gln Val Tyr Thr
        275                 280                 285

Leu Pro Pro Ser Arg Glu Glu Met Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Met Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
```

```
                    355                 360                 365
Ala Leu His Asn His Tyr Thr Gln Lys Ser Leu Ser Leu Ser Pro Gly
        370                 375                 380
```

<210> SEQ ID NO 128
<211> LENGTH: 392
<212> TYPE: PRT
<213> ORGANISM: Artificial Sequence
<220> FEATURE:
<223> OTHER INFORMATION: IAB1M gamma 1 EH5(Minibody 1)

<400> SEQUENCE: 128

```
Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Thr Leu Ser
            20                  25                  30

Ala Ser Val Gly Asp Arg Val Thr Ile Thr Cys Ser Ala Ser Ser Ser
        35                  40                  45

Val Arg Phe Ile His Trp Tyr Gln Gln Lys Pro Gly Lys Ala Pro Lys
50                  55                  60

Arg Leu Ile Tyr Asp Thr Ser Lys Leu Ala Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Trp Gly Ser
            100                 105                 110

Ser Pro Phe Thr Phe Gly Gln Gly Thr Lys Val Glu Ile Lys Gly Ser
        115                 120                 125

Thr Ser Gly Gly Gly Ser Gly Gly Ser Gly Gly Gly Ser Ser
130                 135                 140

Glu Val Gln Leu Val Glu Tyr Gly Gly Gly Leu Val Gln Pro Gly Gly
145                 150                 155                 160

Ser Leu Arg Leu Ser Cys Ala Ala Ser Gly Phe Asn Ile Lys Asp Tyr
                165                 170                 175

Tyr Ile His Trp Val Arg Gln Ala Pro Gly Lys Gly Leu Glu Trp Val
            180                 185                 190

Ala Trp Ile Asp Pro Glu Asn Gly Asp Thr Glu Phe Val Pro Lys Phe
        195                 200                 205

Gln Gly Arg Ala Thr Met Ser Ala Asp Thr Ser Lys Asn Thr Ala Tyr
210                 215                 220

Leu Gln Met Asn Ser Leu Arg Ala Glu Asp Thr Ala Val Tyr Tyr Cys
225                 230                 235                 240

Lys Thr Gly Gly Phe Trp Gly Gln Gly Thr Leu Val Thr Val Ser Ser
                245                 250                 255

Glu Pro Lys Ser Ser Asp Lys Thr His Thr Cys Pro Pro Cys Pro Pro
            260                 265                 270

Cys Pro Pro Cys Gly Gly Gly Ser Ser Gly Gly Gly Ser Gly Gly Gln
        275                 280                 285

Pro Arg Glu Pro Gln Val Tyr Thr Leu Pro Pro Ser Arg Glu Glu Met
290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
```

```
                340                 345                 350
Tyr Ser Lys Leu Thr Val Asp Lys Ser Arg Trp Gln Gln Gly Asn Val
            355                 360                 365

Phe Ser Cys Ser Val Met His Glu Ala Leu His Asn His Tyr Thr Gln
        370                 375                 380

Lys Ser Leu Ser Leu Ser Pro Gly
385                 390

<210> SEQ ID NO 129
<211> LENGTH: 391
<212> TYPE: PRT
<213> ORGANISM: Artificial Sequence
<220> FEATURE:
<223> OTHER INFORMATION: IAB1M gamma 1 EH7(Minibody 1)

<400> SEQUENCE: 129

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Thr Leu Ser
            20                  25                  30

Ala Ser Val Gly Asp Arg Val Thr Ile Thr Cys Ser Ala Ser Ser Ser
        35                  40                  45

Val Arg Phe Ile His Trp Tyr Gln Gln Lys Pro Gly Lys Ala Pro Lys
    50                  55                  60

Arg Leu Ile Tyr Asp Thr Ser Lys Leu Ala Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Trp Gly Ser
            100                 105                 110

Ser Pro Phe Thr Phe Gly Gln Gly Thr Lys Val Glu Ile Lys Gly Ser
        115                 120                 125

Thr Ser Gly Gly Gly Ser Gly Gly Ser Gly Gly Gly Gly Ser Ser
130                 135                 140

Glu Val Gln Leu Val Glu Tyr Gly Gly Gly Leu Val Gln Pro Gly Gly
145                 150                 155                 160

Ser Leu Arg Leu Ser Cys Ala Ala Ser Gly Phe Asn Ile Lys Asp Tyr
                165                 170                 175

Tyr Ile His Trp Val Arg Gln Ala Pro Gly Lys Gly Leu Glu Trp Val
            180                 185                 190

Ala Trp Ile Asp Pro Glu Asn Gly Asp Thr Glu Phe Val Pro Lys Phe
        195                 200                 205

Gln Gly Arg Ala Thr Met Ser Ala Asp Thr Ser Lys Asn Thr Ala Tyr
    210                 215                 220

Leu Gln Met Asn Ser Leu Arg Ala Glu Asp Thr Ala Val Tyr Tyr Cys
225                 230                 235                 240

Lys Thr Gly Gly Phe Trp Gly Gln Gly Thr Leu Val Thr Val Ser Ser
                245                 250                 255

Glu Leu Lys Thr Pro Leu Gly Asp Thr Thr His Thr Cys Pro Pro Cys
            260                 265                 270

Pro Pro Cys Gly Gly Gly Ser Gly Gly Gly Ser Gly Gly Gln Pro
        275                 280                 285

Arg Glu Pro Gln Val Tyr Thr Leu Pro Pro Ser Arg Glu Glu Met Thr
    290                 295                 300

Lys Asn Gln Val Ser Leu Thr Cys Leu Val Lys Gly Phe Tyr Pro Ser
```

```
305                 310                 315                 320
Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
                340                 345                 350

Ser Lys Leu Thr Val Asp Lys Ser Arg Trp Gln Gln Gly Asn Val Phe
                355                 360                 365

Ser Cys Ser Val Met His Glu Ala Leu His Asn His Tyr Thr Gln Lys
                370                 375                 380

Ser Leu Ser Leu Ser Pro Gly
385                 390

<210> SEQ ID NO 130
<211> LENGTH: 394
<212> TYPE: PRT
<213> ORGANISM: Artificial Sequence
<220> FEATURE:
<223> OTHER INFORMATION: IAB1M gamma 1 EH8(Minibody 1)

<400> SEQUENCE: 130

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Thr Leu Ser
                20                  25                  30

Ala Ser Val Gly Asp Arg Val Thr Ile Thr Cys Ser Ala Ser Ser Ser
                35                  40                  45

Val Arg Phe Ile His Trp Tyr Gln Gln Lys Pro Gly Lys Ala Pro Lys
50                  55                  60

Arg Leu Ile Tyr Asp Thr Ser Lys Leu Ala Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Trp Gly Ser
                100                 105                 110

Ser Pro Phe Thr Phe Gly Gln Gly Thr Lys Val Glu Ile Lys Gly Ser
                115                 120                 125

Thr Ser Gly Gly Gly Ser Gly Gly Gly Ser Gly Gly Gly Gly Ser Ser
130                 135                 140

Glu Val Gln Leu Val Glu Tyr Gly Gly Gly Leu Val Gln Pro Gly Gly
145                 150                 155                 160

Ser Leu Arg Leu Ser Cys Ala Ala Ser Gly Phe Asn Ile Lys Asp Tyr
                165                 170                 175

Tyr Ile His Trp Val Arg Gln Ala Pro Gly Lys Gly Leu Glu Trp Val
                180                 185                 190

Ala Trp Ile Asp Pro Glu Asn Gly Asp Thr Glu Phe Val Pro Lys Phe
                195                 200                 205

Gln Gly Arg Ala Thr Met Ser Ala Asp Thr Ser Lys Asn Thr Ala Tyr
                210                 215                 220

Leu Gln Met Asn Ser Leu Arg Ala Glu Asp Thr Ala Val Tyr Tyr Cys
225                 230                 235                 240

Lys Thr Gly Gly Phe Trp Gly Gln Gly Thr Leu Val Thr Val Ser Ser
                245                 250                 255

Glu Leu Lys Thr Pro Leu Gly Asp Thr Thr His Thr Cys Pro Pro Cys
                260                 265                 270

Pro Pro Cys Pro Pro Cys Gly Gly Gly Ser Ser Gly Gly Gly Ser Gly
```

275                 280                 285
Gly Gln Pro Arg Glu Pro Gln Val Tyr Thr Leu Pro Pro Ser Arg Glu
290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
                340                 345                 350

Phe Leu Tyr Ser Lys Leu Thr Val Asp Lys Ser Arg Trp Gln Gln Gly
                355                 360                 365

Asn Val Phe Ser Cys Ser Val Met His Glu Ala Leu His Asn His Tyr
370                 375                 380

Thr Gln Lys Ser Leu Ser Leu Ser Pro Gly
385                 390

<210> SEQ ID NO 131
<211> LENGTH: 750
<212> TYPE: PRT
<213> ORGANISM: Homo sapiens

<400> SEQUENCE: 131

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
                35                  40                  45

Ala Thr Asn Ile Thr Pro Lys His Asn Met Lys Ala Phe Leu Asp Glu
50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
                115                 120                 125

Ser Ile Ile Asn Glu Asp Gly Asn Glu Ile Phe Asn Thr Ser Leu Phe
                130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
                195                 200                 205

Phe Arg Gly Asn Lys Val Lys Asn Ala Gln Leu Ala Gly Ala Lys Gly
                210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

```
Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
        290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
        450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
        610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
```

```
            675                 680                 685
His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
            725                 730                 735

Phe Thr Val Gln Ala Ala Glu Thr Leu Ser Glu Val Ala
        740                 745                 750

<210> SEQ ID NO 132
<211> LENGTH: 123
<212> TYPE: PRT
<213> ORGANISM: Homo sapiens

<400> SEQUENCE: 132

Met Lys Ala Val Leu Ala Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ile Leu Ala Leu Leu Pro Ala
            100                 105                 110

Leu Gly Leu Leu Leu Trp Gly Pro Gly Gln Leu
        115                 120

<210> SEQ ID NO 133
<211> LENGTH: 420
<212> TYPE: PRT
<213> ORGANISM: Homo sapiens

<400> SEQUENCE: 133

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
```

```
            130                 135                 140
Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
        355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420

<210> SEQ ID NO 134
<211> LENGTH: 235
<212> TYPE: PRT
<213> ORGANISM: Homo sapiens

<400> SEQUENCE: 134

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80
```

```
Ala Glu Gly Leu Asp Thr Gln Arg Phe Ser Gly Lys Arg Leu Gly Asp
            85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
            130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
            210                 215                 220

Gly Asp Lys Pro Ser Leu Ser Ala Arg Tyr Val
225                 230                 235

<210> SEQ ID NO 135
<211> LENGTH: 210
<212> TYPE: PRT
<213> ORGANISM: Homo sapiens

<400> SEQUENCE: 135

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
        50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
            85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
            130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Val Thr Leu Gly Leu Leu
                165                 170                 175

Val Ala Gly Val Leu Val Leu Leu Val Ser Leu Gly Val Ala Met His
            180                 185                 190

Leu Cys Cys Arg Arg Arg Arg Ala Arg Leu Arg Phe Met Lys Gln Phe
            195                 200                 205

Tyr Lys
    210
```

<210> SEQ ID NO 136
<211> LENGTH: 171
<212> TYPE: PRT
<213> ORGANISM: Homo sapiens

<400> SEQUENCE: 136

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 137
<211> LENGTH: 182
<212> TYPE: PRT
<213> ORGANISM: Homo sapiens

<400> SEQUENCE: 137

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160
```

Gln Pro Leu Lys Asp Arg Glu Asp Gln Tyr Ser His Leu Gln Gly
                165                 170                 175

Asn Gln Leu Arg Arg Asn
            180

<210> SEQ ID NO 138
<211> LENGTH: 207
<212> TYPE: PRT
<213> ORGANISM: Homo sapiens

<400> SEQUENCE: 138

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 139
<211> LENGTH: 164
<212> TYPE: PRT
<213> ORGANISM: Homo sapiens

<400> SEQUENCE: 139

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 140
<211> LENGTH: 1191
<212> TYPE: DNA
<213> ORGANISM: Artificial Sequence
<220> FEATURE:
<223> OTHER INFORMATION: IAB22M gamma 1 EH3(M1)

<400> SEQUENCE: 140

| | |
|---|---|
| atggagaccg ataccctgct gctgtgggtg ctgctgctgt gggtgcccgg ctccacaggc | 60 |
| gatgtgcaga tcacacagag ccctagcagc ctgagcgcca gcgtgggaga tagagtcacc | 120 |
| atcacatgca ggaccagcag aagcattagc cagtacctgg cctggtacca gcaaaagccc | 180 |
| ggcaaggtgc ccaagctgct gatctacagc ggctccaccc tgcagagcgg cgtgcccagc | 240 |
| agattctccg gctccggaag cggcacagac tttaccctga ccatctcctc cctgcagccc | 300 |
| gaggatgtcg ccacctacta ctgccagcag cacaacgaaa cccccctgac atttggcggc | 360 |
| ggcaccaagg tggagatcaa gggcagcacc agcggtggag aagtggagg tggaagtgga | 420 |
| ggaggcggaa gcagcgaggt gcagctggtg gagagtggtg gaggactggt gcagcccgga | 480 |
| ggcagcctga ctgagctg tgctgcctcc ggattcaata tcaaggacac ctacatccac | 540 |
| ttcgtgagac aggccccgg caagggactg gagtggattg aaggatcga ccccgccaac | 600 |
| gacaacaccc tgtacgccag caaattccag ggcaaggcca atcagcgc cgacaccagc | 660 |
| aagaacaccg cctatctgca gatgaactcc ctgagagccg aggacacagc cgtgtactac | 720 |
| tgcggcaggg gctacggcta ttacgtgttc gaccactggg gccagggcac cctggtgaca | 780 |
| gtgagcagcg aacccaagag ctccgacaag acccacacct gtccccttg ccctccttgt | 840 |
| ggcggaggaa gctccggagg cggaagcgga ggacagccta gggagcccca ggtgtatacc | 900 |
| ctcccccct ccaggaaga gatgaccaag aaccaggtga gcctgacctg cctcgtgaag | 960 |
| ggcttttatc cctccgatat cgccgtggag tgggagagca cggccagcc tgagaacaat | 1020 |
| tacaagacca ccccccctgt gctggactcc gatggcagct tcttcctgta ttccaagctg | 1080 |
| accgtcgaca agtccaggtg gcaacagggc aacgtcttca gctgcagcgt gatgcacgag | 1140 |
| gccctgcaca tcactacac ccagaagtcc ctctccctga gccccggctg a | 1191 |

<210> SEQ ID NO 141
<211> LENGTH: 1200
<212> TYPE: DNA
<213> ORGANISM: Artificial Sequence
<220> FEATURE:
<223> OTHER INFORMATION: IAB22M gamma 1 EH5(M1)

<400> SEQUENCE: 141

| | |
|---|---|
| atggagacag acaccctcct cctgtgggtg ctgctgctgt gggtgcccgg atccaccgga | 60 |
| gacgtgcaga tcacacagag ccccagctcc ctgtccgcta gcgtgggcga cagagtgacc | 120 |

| | |
|---|---|
| atcacctgca ggaccagcag gagcatctcc cagtacctcg cttggtacca gcagaagcct | 180 |
| ggcaaggtgc ccaagctgct gatttacagc ggatccaccc tgcagagcgg cgtgcctagc | 240 |
| aggtttagcg gcagcggatc cggaacagac ttcaccctga ccatcagcag cctgcagcct | 300 |
| gaagatgtgg ccacctacta ctgtcagcag cacaacgaaa accccctcac cttcggcggc | 360 |
| ggcacaaagg tggaaatcaa gggcagcacc tccggaggag gcagcggcgg aggcagcgga | 420 |
| ggcggcggct ccagcgaagt gcagctggtc gagagcggag gcggactggt gcaacccgga | 480 |
| ggaagcctga ggctgagctg tgccgccagc ggcttcaaca tcaaggacac atacattcac | 540 |
| tttgtgaggc aggctcctgg aaagggcctg agtggatcg gcagaatcga ccccgctaac | 600 |
| gacaacaccc tgtacgccag caagttccag ggcaaggcca ccatctccgc cgacacaagc | 660 |
| aagaataccg cctacctgca gatgaactcc ctgagggccg aggataccgc cgtgtactac | 720 |
| tgcggcaggg gctatggcta ctacgtgttt gaccactggg gccagggcac actggtgaca | 780 |
| gtgagctccg agcccaagag ctccgacaag acacacacct gccctccttg cccccccttgt | 840 |
| cctcccctgtg gaggaggaag cagcggagga ggaagcggcg gacagcccag agagcctcaa | 900 |
| gtgtataccc tgccccccte cagggaagag atgaccaaga accaggtgag cctgacatgc | 960 |
| ctggtcaaag gcttctaccc cagcgatatt gctgtggagt gggagagcaa cggccagccc | 1020 |
| gagaacaact acaagaccac acccccgtc ctggatagcg atggcagctt cttcctgtac | 1080 |
| agcaagctga ccgtggacaa gtccaggtgg cagcagggca cgtcttctc ctgcagcgtg | 1140 |
| atgcacgagg ctctgcataa ccactacaca cagaagtccc tcagcctgag ccctggatga | 1200 |

<210> SEQ ID NO 142
<211> LENGTH: 1197
<212> TYPE: DNA
<213> ORGANISM: Artificial Sequence
<220> FEATURE:
<223> OTHER INFORMATION: IAB22M gamma 1 EH7(Minibody 1)

<400> SEQUENCE: 142

| | |
|---|---|
| atggagacag acaccctcct cctgtgggtg ctgctgctgt gggtgcccgg atccaccgga | 60 |
| gacgtgcaga tcacacagag ccccagctcc ctgtccgcta gcgtgggcga cagagtgacc | 120 |
| atcacctgca ggaccagcag gagcatctcc cagtacctcg cttggtacca gcagaagcct | 180 |
| ggcaaggtgc ccaagctgct gatttacagc ggatccaccc tgcagagcgg cgtgcctagc | 240 |
| aggtttagcg gcagcggatc cggaacagac ttcaccctga ccatcagcag cctgcagcct | 300 |
| gaagatgtgg ccacctacta ctgtcagcag cacaacgaaa accccctcac cttcggcggc | 360 |
| ggcacaaagg tggaaatcaa gggcagcacc tccggaggag gcagcggcgg aggcagcgga | 420 |
| ggcggcggct ccagcgaagt gcagctggtc gagagcggag gcggactggt gcaacccgga | 480 |
| ggaagcctga ggctgagctg tgccgccagc ggcttcaaca tcaaggacac atacattcac | 540 |
| tttgtgaggc aggctcctgg aaagggcctg agtggatcg gcagaatcga ccccgctaac | 600 |
| gacaacaccc tgtacgccag caagttccag ggcaaggcca ccatctccgc cgacacaagc | 660 |
| aagaataccg cctacctgca gatgaactcc ctgagggccg aggataccgc cgtgtactac | 720 |
| tgcggcaggg gctatggcta ctacgtgttt gaccactggg gccagggcac actggtgaca | 780 |
| gtgagctccg agctgaagac acctctgggc gacacaacac acacctgccc ccttgtcct | 840 |
| ccctgtggag gaggaagcag cggaggagga agcggcggac agcccagaga gcctcaagtg | 900 |
| tatacccctgc cccctccag ggaagagatg accaagaacc aggtgagcct gacatgcctg | 960 |
| gtcaaaggct tctaccccag cgatattgct gtggagtggg agagcaacgg ccagcccgag | 1020 |

-continued

| | |
|---|---|
| aacaactaca agaccacacc ccccgtcctg gatagcgatg gcagcttctt cctgtacagc | 1080 |
| aagctgaccg tggacaagtc caggtggcag cagggcaacg tcttctcctg cagcgtgatg | 1140 |
| cacgaggctc tgcataacca ctacacacag aagtccctca gcctgagccc tggatga | 1197 |

<210> SEQ ID NO 143
<211> LENGTH: 1206
<212> TYPE: DNA
<213> ORGANISM: Artificial Sequence
<220> FEATURE:
<223> OTHER INFORMATION: IAB22M gamma 1 EH8(Minibody 1)

<400> SEQUENCE: 143

| | |
|---|---|
| atggagacag acaccctcct cctgtgggtg ctgctgctgt gggtgcccgg atccaccgga | 60 |
| gacgtgcaga tcacacagag ccccagctcc ctgtccgcta gcgtgggcga cagagtgacc | 120 |
| atcacctgca ggaccagcag gagcatctcc cagtacctcg cttggtacca gcagaagcct | 180 |
| ggcaaggtgc ccaagctgct gatttacagc ggatccaccc tgcagagcgg cgtgcctagc | 240 |
| aggtttagcg gcagcggatc cggaacagac ttcaccctga ccatcagcag cctgcagcct | 300 |
| gaagatgtgg ccacctacta ctgtcagcag cacaacgaaa accccctcac cttcggcggc | 360 |
| ggcacaaagg tggaaatcaa gggcagcacc tccggaggag gcagcggcgg aggcagcgga | 420 |
| ggcggcggct ccagcgaagt gcagctggtc gagagcggag gcggactggt gcaacccgga | 480 |
| ggaagcctga gctgagctg tgccgccagc ggcttcaaca tcaaggacac atacattcac | 540 |
| tttgtgaggc aggctcctgg aaagggcctg gagtggatcg gcagaatcga ccccgctaac | 600 |
| gacaacaccc tgtacgccag caagttccag ggcaaggcca ccatctccgc cgacacaagc | 660 |
| aagaataccg cctacctgca gatgaactcc ctgagggccg aggataccgc cgtgtactac | 720 |
| tgcggcaggg gctatggcta ctacgtgttt gaccactggg gccagggcac actggtgaca | 780 |
| gtgagctccg agctgaagac cctctgggc gacacaacac acacctgccc tccttgcccc | 840 |
| ccttgtcctc cctgtggagg aggaagcagc ggaggaggaa gcggcggaca gcccagagag | 900 |
| cctcaagtgt ataccctgcc ccctccagg gaagagatga ccaagaacca ggtgagcctg | 960 |
| acatgcctgg tcaaaggctt ctaccccagc gatattgctg tggagtggga gagcaacggc | 1020 |
| cagcccgaga caactacaa gaccacaccc ccgtcctgg atagcgatgg cagcttcttc | 1080 |
| ctgtacagca agctgaccgt ggacaagtcc aggtggcagc agggcaacgt cttctcctgc | 1140 |
| agcgtgatgc acgaggctct gcataaccac tacacacaga gtccctcag cctgagccct | 1200 |
| ggatga | 1206 |

<210> SEQ ID NO 144
<211> LENGTH: 1236
<212> TYPE: DNA
<213> ORGANISM: Artificial Sequence
<220> FEATURE:
<223> OTHER INFORMATION: IAB22M gamma 2 EH2(Minibody 1)

<400> SEQUENCE: 144

| | |
|---|---|
| atggaaaccg acacactgct gctgtgggtg ctgctgctgt gggtccctgg ctccaccgga | 60 |
| gacgtccaga tcacacagag ccccagcagc ctgtccgcca gcgtgggaga cagggtgacc | 120 |
| gacgtccaga tcacacagag ccccagcagc ctgtccgcca gcgtgggaga cagggtgacc | 180 |
| gacgtccaga tcacacagag ccccagcagc ctgtccgcca gcgtgggaga cagggtgacc | 240 |
| ggcaaggtcc ccaaactgct gatctacagc ggctccaccc tgcagtccgg cgtgcctagc | 300 |

```
aggttctccg gcagcggatc cggcaccgac ttcaccctga ccatcagctc cctgcagcct    360
gaggacgtgg ctacctacta ctgccaacag cacaacgaga accccctgac ctttggaggc    420
ggcaccaagg tggaaatcaa gggcagcacc agcggcggag aagcggagg aggatccgga    480 ggaggcggaa gctccgaggt gcagctggtg gaaagcggcg gcggactggt gcagcctgga    540
ggaagcctca gactgagctg tgccgccagc ggattcaaca tcaaagacac ctacattcat    600
ttcgtgagac aggcccccgg caagggcctc gaatggatcg gaaggatcga ccccgctaac    660
gacaataccc tgtacgcctc caagttccag ggaaaggcca ccatctccgc cgatacctcc    720
aagaacaccg cctacctcca gatgaactcc ctgagggccg aagataccgc cgtctactac    780
tgtggcaggg gctacggcta ctatgtgttc gatcactggg gccaaggaac cctggtgacc    840
gtgagcagcg aaaggaagag ctgcgtggag tgtcctcctt gtcccggcgg cggctccagc    900
ggcggaggct ccggcggcca gcctagagaa cctcaggtgt acaccctccc ccctccaga    960 gaggagatga ccaagaacca ggtgtccctg acctgcctgg tgaaaggctt ctatcccagc   1020
gacatcgccg tggaatggga gtccaacggc cagcccgaga caactacaa gaccacccct   1080 cccatgctgg attccgacgg cagcttttc ctgtacagca agctcaccgt ggacaagagc   1140
agatggcagc agggcaacgt gttcagctgc agcgtgatgc acgaggctct gcataaccac   1200
tacacccaga gagcctgtc cctgtcccc ggatga                                1236
```

<210> SEQ ID NO 145
<211> LENGTH: 1176
<212> TYPE: DNA
<213> ORGANISM: Artificial Sequence
<220> FEATURE:
<223> OTHER INFORMATION: IAB22M gamma 2 EH2(Minibody 1)

<400> SEQUENCE: 145

```
atggagaccg acaccctcct cctgtggggtg ctgctgctgt gggtgcctgg aagcaccggc     60
gatgtgcaga tcacccagag ccctagcagc ctgtccgctt ccgtgggcga cagggtgacc    120
atcacctgta ggacctccag gagcatctcc cagtacctgg cctggtacca gcagaagccc    180
ggcaaggtgc ccaaactgct catctactcc ggcagcacac tccagagcgg cgtccctagc    240
agattcagcg gaagcggcag cggcaccgac ttcaccctga ccatcagctc cctgcagccc    300
gaggacgtgg ccacctatta ctgtcagcag cacaacgaaa accccctgac cttcggcggc    360
ggcacaaaag tggagatcaa gggcagcacc agcggaggcg gatccggcgg cggcagcggc    420
ggcggaggat ccagcgaagt gcagctggtc gaaagcggag gcggactggt gcagcctgga    480
ggaagcctga gactcagctg cgccgcctcc ggattcaaca tcaaggacac ctacatccac    540
ttcgtgaggc aggctcccgg caaaggcctc gagtggattg aaggattga ccccgccaac    600 gacaacaccc tgtacgccag caagttccaa ggaagggcca ccatctccgc cgacaccagc    660
aagaataccg cctacctgca gatgaactcc ctgagggctg aggacaccgc cgtgtactac    720
tgcggcagag gctacggcta ctacgtgttc gaccactggg gacagggcac actggtgaca    780
gtgagcagcg agaggaaaag ctgcgtggag tgcccccct gccctggcgg cggcagctcc    840
ggcggaggaa gcggaggaca acccagggag ccccaggtgt acacactccc cctagcagg    900 gaagagatga ccaagaacca ggtgtccctg acctgcctcg tgaagggatt ctaccccagc    960
gacattgccg tcgagtggga gagcaacggc cagcctgaga caactacaa gacaaccccc   1020 cctatgctcg atagcgatgg ctccttcttc ctgtactcca agctcaccgt cgacaagagc   1080
aggtggcagc agggcaacgt cttctcctgt agcgtgatgc acgaggctct gcacaaccac   1140
```

```
tacacccaga agagcctgag cctgagcccc ggctga                                1176
```

<210> SEQ ID NO 146
<211> LENGTH: 1182
<212> TYPE: DNA
<213> ORGANISM: Artificial Sequence
<220> FEATURE:
<223> OTHER INFORMATION: IAB2M gamma 1 EH3(Minibody 2)

<400> SEQUENCE: 146

```
atggaaaccg acaccctgct gctgtgggtg ctgctgctgt gggtgccagg atctacaggc     60
gaggtgcagc tggtgcagtc tggcgccgaa gtgaagaaac tggcgcctc cgtgaagatc    120
tcctgcaaga cctccggcta caccttcacc gagtacacca tccactgggt caagcaggcc    180
tccggcaagg gcctggaatg gatcggcaac atcaacccca caacggcgg caccacctac    240
aaccagaagt tcgaggaccg ggccaccctg accgtggaca gtctacctc caccgcctac    300
atggaactgt cctccctgcg gagcgaggac accgccgtgt actattgtgc cgctggctgg    360
aacttcgact actggggcca gggcaccacc gtgacagtgt cctctggctc tacctccggc    420
ggaggaagtg gcgaggatc aggcggaggc ggctcctctg atatcgtgat gacccagtcc    480
ccctccagcc tgtctgcttc cgtgggcgac agagtgacca tcacatgcaa ggcctcccag    540
gacgtgggca ccgctgtgga ctggtatcag cagaagcctg gcaaggcccc caagctgctg    600
atctactggg cctctaccag acacaccggc gtgcccgata gattcaccgg ctctggatcc    660
ggcaccgact ttaccctgac catcagctcc ctgcagcccg aggacttcgc cgactacttc    720
tgccagcagt acaactccta cccctgacc tttggcggag gcaccaagct ggaaatcaaa    780
gagcccaagt cctccgacaa gacccacacc tgtcccctt gcctccatg tggtggcgga    840
agttctgggg gaggttctgg tggccagcct cgggaacctc aggtgtacac actgcccct    900
agccgggaag agatgaccaa gaaccaggtg tccctgacct gcctcgtgaa gggcttctac    960
ccctccgata tcgccgtgga atgggagtcc aacggccagc cgagaacaa ctacaagacc   1020
accccccctg tgctggactc cgacggctca ttcttcctgt actccaagct gacagtggat   1080
aagtcccggt ggcagcaggg caacgtgttc tcctgctccg tgatgcacga ggccctgcac   1140
aaccactata cccagaagtc cctgtccctg agccccggct ga                    1182
```

<210> SEQ ID NO 147
<211> LENGTH: 1182
<212> TYPE: DNA
<213> ORGANISM: Artificial Sequence
<220> FEATURE:
<223> OTHER INFORMATION: IAB2M gamma 1 EH3 (Minibody 2)

<400> SEQUENCE: 147

```
atggaaaccg ataccctgct gctgtgggtg ctgctgctgt gggtgccggg cagcaccggc     60
gaagtgcagc tggtgcagag cggcgcggaa gtgaaaaaac cgggcgcgag cgtgaaaatt    120
agctgcaaaa ccagcggcta ccctttacc gaatatacca ttcattgggt gaaacaggcg    180
agcggcaaag gcctggaatg gattggcaac attaacccga caacggcgg caccacctat    240
aaccagaaat ttgaagatcg cgcgaccctg accgtggata aaagcaccag caccgcgtat    300
atggaactga gcagcctgcg cagcgaagat accgccggtgt attattgcgc ggcgggctgg    360
aactttgatt attgggggcca gggcaccacc gtgaccgtga gcagcggcag caccagcggc    420
ggcggcagcg gcggcggcag cggcggcggc ggcagcagcg atattgtgat gacccagagc    480
```

-continued

```
ccgagcagcc tgagcgcgag cgtgggcgat cgcgtgacca ttacctgcaa agcgagccag      540
gatgtgggca ccgcggtgga ttggtatcag cagaaaccgg gcaaagcgcc gaaactgctg      600
atttattggg cgagcacccg ccataccggc gtgccggatc gctttaccgg cagcggcagc      660
ggcaccgatt ttaccctgac cattagcagc ctgcagccgg aagattttgc ggattatttt      720
tgccagcagt ataacagcta ccgctgacc tttggcggcg gcaccaaact ggaaattaaa       780
gaaccgaaaa gcagcgataa aacccatacc tgcccgccgt gcccgccgtg cggcggcggc      840
agcagcggcg gcggcagcgg cggccagccg cgcgaaccgc aggtgtatac cctgccgccg      900
agccgcgatg aactgaccaa aaaccaggtg agcctgacct gcctggtgaa aggcttttat      960
ccgagcgata ttgcggtgga atgggaaagc aacggccagc cggaaaacaa ctataaaacc     1020
accccgccgg tgctggatag cgatggcagc ttttttctgt atagcaaact gaccgtggat     1080
aaaagccgct ggcagcaggg caacgtgttt agctgcagcg tgatgcatga agcgctgcat     1140
aaccattata cccagaaaag cctgagcctg agcccgggct ga                       1182
```

<210> SEQ ID NO 148
<211> LENGTH: 1191
<212> TYPE: DNA
<213> ORGANISM: Artificial Sequence
<220> FEATURE:
<223> OTHER INFORMATION: IAB2M gamma 1 EH5(Minibody 2)

<400> SEQUENCE: 148

```
atggaaaccg ataccctgct gctgtgggtg ctgctgctgt gggtgccggg cagcaccggc      60
gaagtgcagc tggtgcagag cggcgcggaa gtgaaaaaac cgggcgcgag cgtgaaaatt     120
agctgcaaaa ccagcggcta tacctttacc gaatatacca ttcattgggt gaaacaggcg     180
agcggcaaag gcctggaatg gattggcaac attaacccga caacggcgg caccacctat     240
aaccagaaat ttgaagatcg cgcgaccctg accgtggata aaagcaccag caccgcgtat     300
atggaactga gcagcctgcg cagcgaagat accgcggtgt attatgcgc ggcgggctgg     360
aactttgatt attggggcca gggcaccacc gtgaccgtga gcagcggcag caccagcggc     420
ggcggcagcg gcggcggcag cggcggcggc ggcagcagcg atattgtgat gacccagagc     480
ccgagcagcc tgagcgcgag cgtgggcgat cgcgtgacca ttacctgcaa agcgagccag     540
gatgtgggca ccgcggtgga ttggtatcag cagaaaccgg gcaaagcgcc gaaactgctg     600
atttattggg cgagcacccg ccataccggc gtgccggatc gctttaccgg cagcggcagc     660
ggcaccgatt ttaccctgac cattagcagc ctgcagccgg aagattttgc ggattatttt     720
tgccagcagt ataacagcta ccgctgacc tttggcggcg gcaccaaact ggaaattaaa      780
gaaccgaaaa gcagcgataa aacccatacc tgcccgccgt gcccgccgtg cccgccgtgc     840
ggcggcggca gcggcggcgg cggcagcggc ggccagccgc gcgaaccgca ggtgtatacc     900
ctgccgccga gccgcgaaga atgaccaaa aaccaggtga gcctgacctg cctggtgaaa      960
ggcttttatc cgagcgatat tgcggtggaa tgggaaagca acggccagcc ggaaaacaac    1020
tataaaacca ccccgccggt gctggatagc gatggcagct ttttctgta tagcaaactg     1080
accgtggata aaagccgctg gcagcagggc aacgtgttta gctgcagcgt gatgcatgaa     1140
gcgctgcata accattatac ccagaaaagc ctgagcctga gcccgggctg a             1191
```

<210> SEQ ID NO 149
<211> LENGTH: 1188
<212> TYPE: DNA
<213> ORGANISM: Artificial Sequence
<220> FEATURE:
<223> OTHER INFORMATION: IAB2M gamma 1 EH7(Minibody 2)

<400> SEQUENCE: 149

```
atggagacag acaccctcct cctgtgggtg ctgctgctgt gggtccccgg aagcaccgga      60
gaagtgcagc tggtgcaatc cggagccgag gtgaagaaac ccggcgccag cgtgaagatt     120
agctgcaaaa ccagcggcta caccttcacc gagtacacca tccactgggt caagcaggcc    180
agcggcaagg gcctggagtg gatcggcaac attaacccca ataacggcgg caccacctac    240
aatcagaaat tcgaggacag ggccaccctg accgtggata gtccacctc accgcctac      300
atggagctgt cctccctgag aagcgaggat acagccgtct actactgcgc tgccggatgg    360
aatttcgact actggggcca gggcacaacc gtgaccgtga gcagcggatc cacctccggc    420
ggcggcagcg gaggcggcag cggcggagga ggcagcagcg acatcgtgat gacacagtcc    480
cccagcagcc tgtccgctag cgtgggcgac agagtgacca tcacctgcaa ggcctcccag    540
gacgtgggaa ccgctgtgga ctggtaccag cagaagcccg gcaaggcccc caagctgctg    600
atctactggg ccagcaccag acacaccggc gtgcctgaca gattcaccgg ctccggaagc    660
ggcaccgact caccctgac catcagctcc ctccagcccg aggacttcgc cgactacttc    720
tgccagcagt ataatagcta ccccctgacc ttcggcggcg gcacaaagct cgaaatcaag    780
gagctgaaga cccctctggg agacaccacc cacacctgcc ccccttgccc tcctgtgga    840
ggcggaagca gcggaggagg aagcggagga cagcccaggg aaccccaggt gtacacactg    900
cccccctcca gagaggagat gacaaagaac caggtgtccc tcacctgcct ggtgaaaggc    960
ttctatccca gcgacatcgc cgtggagtgg gagtccaacg gccaacccga aacaactac    1020
aagaccaccc ctcccgtgct ggattccgac ggctccttt tcctgtacag caagctgacc    1080
gtggacaagt ccaggtggca gcagggcaat gtctttagct cagcgtcat gcacgaggcc    1140
ctgcataacc actataccca gaagtccctg tccctcagcc tggatga              1188
```

<210> SEQ ID NO 150
<211> LENGTH: 1197
<212> TYPE: DNA
<213> ORGANISM: Artificial Sequence
<220> FEATURE:
<223> OTHER INFORMATION: IAB2M gamma 1 EH8(Minibody 2)

<400> SEQUENCE: 150

```
atggaaaccg ataccctgct gctgtgggtg ctgctgctgt gggtgccggg cagcaccggc     60
gaagtgcagc tggtgcagag cggcgcggaa gtgaaaaaac cggcgcgag cgtgaaaatt     120
agctgcaaaa ccagcggcta cacctttacc gaatatacca tccattgggt gaaacaggcg    180
agcggcaaag gcctggaatg gattggcaac attaacccga caacggcgg caccacctat    240
aaccagaaat ttgaagatcg cgcgaccctg accgtggata aaagcaccag caccgcgtat    300
atggaactga gcagcctgcg cagcgaagat accgcggtgt attattgcgc ggcgggctgg    360
aactttgatt attggggcca gggcaccacc gtgaccgtga gcagcggcag caccagcggc    420
ggcggcagcg gcggcggcag cggcggcggc ggcagcagcg atattgtgat gacccagagc    480
ccgagcagcc tgagcgcgag cgtgggcgat cgcgtgacca ttacctgcaa agcgagccag    540
gatgtgggca ccgcgtgga ttggtatcag cagaaaccgg gcaaagcgcc gaaactgctg    600
atttattggg cgagcacccg ccataccggc gtgccggatc gctttaccgg cagcggcagc    660
ggcaccgatt tacccctgac cattagcagc ctgcagccgg aagatttgc ggattatttt    720
```

```
tgccagcagt ataacagcta tccgctgacc tttggcggcg gcaccaaact ggaaattaaa        780
gaactgaaaa ccccgctggg cgataccacc catacctgcc cgccgtgccc gccgtgcccg        840
ccgtgcggcg gcggcagcag cggcggcggc agcggcggcc agccgcgcga accgcaggtg        900 tatacccctgc cgccgagccg cgaagaaatg accaaaaacc aggtgagcct gacctgcctg       960
gtgaaaggct tttatccgag cgatattgcg gtggaatggg aaagcaacgg ccagccggaa       1020
aacaactata aaaccacccc gccggtgctg gatagcgatg gcagctttt tctgtatagc        1080 aaactgaccg tggataaaag ccgctggcag cagggcaacg tgtttagctg cagcgtgatg       1140
catgaagcgc tgcataacca ttatacccag aaaagcctga gcctgagccc gggctga         1197
```

<210> SEQ ID NO 151
<211> LENGTH: 1182
<212> TYPE: DNA
<213> ORGANISM: Artificial Sequence
<220> FEATURE:
<223> OTHER INFORMATION: IAB2M gamma 1 EH3(Minibody 1)

<400> SEQUENCE: 151

```
atggaaaccg ataccctgct gctgtgggtg ctgctgctgt gggtgccggg cagcaccggc        60
gatattgtga tgacccagag cccgagcagc ctgagcgcga gcgtgggcga tcgcgtgacc       120
attacctgca aagcgagcca ggatgtgggc accgcggtgg attggtatca gcagaaaccg       180
ggcaaagcgc cgaaactgct gatttattgg gcgagcaccc gccataccgg cgtgccggat       240
cgctttaccg gcagcggcag cggcaccgat tttaccctga ccattagcag cctgcagccg       300
gaagattttg cggattattt tgccagcag tataacagct atccgctgac ctttggcggc       360
ggcaccaaac tggaaattaa aggcagcacc agcggcggcg gcagcggcgg cggcagcggc       420
ggcggcggca gcgcgaagt gcagctggtg cagagcggcg gaagtgaa aaaccgggc          480 gcgagcgtga aaattagctg caaaaccagc ggctatacct ttaccgaata ccattcat        540 tgggtgaaac aggcgagcgg caaaggcctg aatggattg caacattaa cccgaacaac        600 ggcggcacca cctataacca gaaatttgaa gatcgcgcga ccctgaccgt ggataaaagc       660
accagcaccg cgtatatgga actgagcagc ctgcgcagca agataccgc ggtgtattat        720 tgcgcggcgg gctggaactt tgattattgg ggccagggca ccaccgtgac cgtgagcagc       780
gaaccgaaaa gcagcgataa acccataccc tgcccgccgt gccgccgtg cggcggcggc       840 agcagcggcg gcggcagcgg cggccagccg cgcgaaccgc aggtgtatac cctgccgccg       900
agccgcgaag aaatgaccaa aaaccaggtg agcctgacct gcctggtgaa aggctttttat       960 ccgagcgata ttgcggtgga atgggaaagc aacggccagc cggaaaacaa ctataaaacc      1020
accccgccgg tgctgatag gcatggcagc tttttttctgt atagcaaaact gaccgtggat      1080 aaaagccgct ggcagcaggg caacgtgttt agctgcagcg tgatgcatga agcgctgcat      1140
aaccattata cccagaaaag cctgagcctg agcccgggct ga                        1182
```

<210> SEQ ID NO 152
<211> LENGTH: 1197
<212> TYPE: DNA
<213> ORGANISM: Artificial Sequence
<220> FEATURE:
<223> OTHER INFORMATION: IAB20M gamma 1 EH3(Minibody 2)

<400> SEQUENCE: 152

```
atggaaaccg ataccctgct gctgtgggtg ctgctgctgt gggtgccggg cagcacagga        60
gaggtgcagc tggtggagag cggcgctgaa gtgaagaagc ccggcgccag cgtgaaggtg       120
```

```
agctgcaagg ccagcggcta cagcttcaca ggctactaca tgcactgggt gagacaagcc      180
cctggccagg gcctcgagtg gattggaagg atcaaccca acaacggagt gacactgtac      240
aaccagaaat tcaaggacag ggtcaccatg accgtggaca ccagcatcag caccgcctat      300
atggagctgt ccaggctgag gagcgacgac accgctgtgt actactgcgc caggagcacc      360
atgatcacca actacgtgat ggattattgg gccagggca cactggtgac agtgagcagc      420
ggcagcacca gcgaggagg cagcggagga ggaagcggcg gaggcggctc ctccgatatc      480
gtcatgaccc agagccccgc taccctcagc gtgtccctg gcgagagagc cacctgagc      540 tgcaaggcca gccagtccgt gtccaacgac gtggcctggt atcaacagaa gcccggccag      600
gctcctaggc tgctgatctc ctacaccagc agcaggtacg ccggcgtgcc tgataggttc      660
agcggctccg gcagcggcac agacttcacc ctgacaatca gcagcctgga ggccgaggat      720
gaggccgtgt actactgtca gcaggactac aactcccccc ccaccttcgg ccagggcaca      780
aaggtcgaga tcaaggagcc caagtcctcc gacaagaccc acacctgtcc cccctgccct      840
ccttgtggag gcggaagcag cggaggcggg agcggaggac agcccagaga accccaggtg      900 tatacccctgc ccccctccag ggaggagatg accaaaaacc aggtgagcct gacatgcctg      960
gtgaagggct tctacccctc cgacatcgcc gtggagtggg aaagcaacgg ccagcccgag     1020
aacaactaca agaccacacc ccccgtgctg gatagcgacg gctccttctt tctgtacagc     1080
aagctgaccg tggataaaag caggtggcag caaggcaacg tgttctcctg ctccgtcatg     1140
cacgaggctc tgcataacca ctacacccaa aaatccctga gcctgagccc cggctga       1197

<210> SEQ ID NO 153
<211> LENGTH: 1197
<212> TYPE: DNA
<213> ORGANISM: Artificial Sequence
<220> FEATURE:
<223> OTHER INFORMATION: IAB20M gamma 1 EH3(Minibody 2)

<400> SEQUENCE: 153
atggaaaccg ataccctgct gctgtggtg ctgctgctgt gggtgccggg cagcaccggc       60
caggtgcagc tggtgcagag cggcgcggaa gtgaaaaaac cgggcgcgag cgtgaaagtg      120
agctgcaaag cgagcggcta tagctttacc ggctattata tgcattgggt gcgccaggcg      180
ccgggccagg gcctggaatg gattggccgc attaacccga caacggcgt gacccctgtat      240 aaccagaaat ttaaagatcg cgtgaccatg accgtggata ccagcattag caccgcgtat      300
atggaactga gccgcctgcg cagcgatgat accgcggtgt attattgcgc gcgcagcacc      360
atgattacca actatgtgat ggattattgg gccagggca ccctggtgac cgtgagcagc      420
ggcagcacca gcgcgggcgg cagcggcggc ggcagcggcg gcggcggcag cagcgatatt      480
gtgatgaccc agagccccgc gaccctgagc gtgagcccgg gcgaacgcgc gaccctgagc      540
tgcaaagcga gccagagcgt gagcaacgat gtggcgtggt atcagcagaa accgggccag      600
gcgccgcgcc tgctgattag ctataccagc agccgctatg cgggcgtgcc ggatcgcttt      660
agcggcagcg gcagcggcac cgatttacc ctgaccatta gcagcctgca ggcggaagat      720
gtggcggtgt attattgcca gcaggattat aacagcccgc cgacctttgg ccagggcacc      780
aaagtggaaa ttaagaacc gaaagcagc gataaaaccc atacctgccc gccgtgcccg      840
ccgtgcggcg gcggcagcag cggcggcggc agcggcggcg agcgcgcgga accgcaggtg      900 tatacccctgc gccgagccg cgaagaaatg accaaaaaacc aggtgagcct gacctgcctg      960
```

```
gtgaaaggct tttatccgag cgatattgcg gtggaatggg aaagcaacgg ccagccggaa    1020
aacaactata aaaccacccc gccggtgctg gatagcgatg gcagctttt tctgtatagc     1080 aaactgaccg tggataaaag ccgctggcag cagggcaacg tgtttagctg cagcgtgatg    1140
catgaagcgc tgcataacca ttatacccag aaaagcctga gcctgagccc gggctga      1197
```

<210> SEQ ID NO 154
<211> LENGTH: 1197
<212> TYPE: DNA
<213> ORGANISM: Artificial Sequence
<220> FEATURE:
<223> OTHER INFORMATION: IAB20M gamma 1 EH3(Minibody 2)

<400> SEQUENCE: 154

```
atggaaaccg ataccctgct gctgtgggtg ctgctgctgt gggtgcctgg cagcacagga      60
gaggtgcagc tggtggagag cggcgctgaa gtgaagaagc ccggcgccag cgtgaaggtg     120
agctgcaagg ccagcggcta cagcttcaca ggctactaca tgcactgggt gagacaagcc     180
cctggccagg gcctcgagtg gattggaagg atcaaccccc acaacggagt gacactgtac     240
aaccagaaat tcaaggacag ggtcaccatg accgtggaca ccagcatcag caccgcctat     300
atggagctgt ccaggctgag gagcgacgac accgctgtgt actactgcgc caggagcacc     360
atgatcacca actacgtgat ggattattgg ggccagggca cactggtgac agtgagcagc     420
ggcagcacca gcgaggagg cagcggagga ggaagcggcg gaggcggctc ctccgatatc      480
gtcatgaccc agagccccga tagcctggcc gtgagcctgg gcgagagagc caccatcaat     540
tgcaaggcca gccagtccgt gtccaacgac gtggcctggt atcaacagaa gcccggccag     600
gctcctaggc tgctgatctc ctacaccagc agcaggtacg ccggcgtgcc tgataggttc     660
agcggctccg gcagcggcac agacttcacc ctgacaatca gcagcctgca agccgaagat     720
gtggccgtgt actactgtca gcaggactac aactcccccc caccttcgg ccagggcaca      780 aaggtcgaga tcaaggagcc caagtcctcc gacaagaccc acacctgtcc ccctgccct     840 ccttgtggag gcggaagcag cggaggcggg agcggaggac agcccagaga accccaggtg     900 tatacctgc ccccctccag ggaggagatg accaaaaaac cagg tgagcct gacatgcctg    960 gtgaagggct tctacccctc cgacatcgcc gtggagtggg aaagcaacgg ccagcccgag    1020
aacaactaca gaccacacc cccgtgctg gatagcgacg gctccttctt tctgtacagc      1080
aagctgaccg tggataaaag caggtggcag caaggcaacg tgttctcctg ctccgtcatg    1140
cacgaggctc tgcataacca ctacacccaa aaatccctga gcctgagccc cggctga      1197
```

<210> SEQ ID NO 155
<211> LENGTH: 1206
<212> TYPE: DNA
<213> ORGANISM: Artificial Sequence
<220> FEATURE:
<223> OTHER INFORMATION: IAB20M gamma 1 EH5(Minibody 2)

<400> SEQUENCE: 155

```
atggagacag acaccctcct cctgtgggtc ctgctcctgt gggtgcccgg atccacaggc      60
gaggtccagc tggtggaatc cggagccgag gtgaagaaac ccggcgcctc cgtgaaagtc    120
tcctgcaagg cctccggcta ctccttcacc ggctactaca tgcactgggt gaggcaggcc    180
cctggacagg gactgaatg gatcggcagg attaacccca caacggagt gaccctgtac      240 aaccagaagt tcaaggacag ggtcaccatg accgtggaca ccagcatttc caccgcctac    300
atggagctgt ccaggctgag aagcgacgac accgctgtgt actactgcgc caggagcacc    360
```

```
atgatcacca actacgtgat ggattattgg ggccagggca ccctcgtgac agtgagcagc    420
ggatccacaa gcggaggcgg aagcggaggc ggcagcggcg gcggcggcag cagcgatatc    480
gtgatgaccc agagccccgc caccctgagc gtgagccccg gcgaaagggc cacactgagc    540
tgcaaggcca gccagtccgt ctccaacgat gtggcctggt accagcagaa gcccggacag    600
gcccctaggc tcctgatctc ctacaccagc tccaggtacg ccggcgtccc tgacagattc    660
tccggcagcg gcagcggcac cgatttcacc ctcaccatca gcagcctgga agccgaagat    720
gaagctgtgt attactgcca gcaggactac aacagccccc ccacatttgg ccagggaacc    780
aaggtggaga tcaaggagcc caagagcagc gacaagaccc ataccctgcc ccttgccct    840 ccttgtcctc cctgtggagg cggaagctcc ggaggaggat ccggaggcca gcctagagag    900
ccccaggtgt acaccctgcc ccctagcagg gaggagatga ccaagaacca ggtgagcctg    960
acatgtctgg tcaagggctt ttaccccagc gacatcgccg tggagtggga gagcaacggc   1020
cagcctgaga caaactacaa gaccaccct cctgtgctgg actccgacgg cagcttttc   1080 ctgtacagca agctgaccgt ggataagagc aggtggcagc agggcaacgt cttcagctgc   1140
agcgtgatgc acgaggctct gcataaccac tacacccaga gagcctgag cctgagccct   1200 ggatga                                                             1206
```

<210> SEQ ID NO 156
<211> LENGTH: 1206
<212> TYPE: DNA
<213> ORGANISM: Artificial Sequence
<220> FEATURE:
<223> OTHER INFORMATION: IAB20M gamma 1 EH5(Minibody 2)

<400> SEQUENCE: 156

```
atggagacag acaccctcct cctgtgggtc ctgctcctgt gggtgcccgg atccacaggc     60
gaggtccagc tggtggaatc cggagccgag gtgaagaaac ccggcgcctc cgtgaaagtc    120
tcctgcaagg cctccggcta ctccttcacc ggctactaca tgcactgggt gaggcaggcc    180
cctggacagg gactggaatg gatcggcagg attaacccca caacggagt gaccctgtac    240 aaccagaagt tcaaggacag ggtcaccatg accgtggaca ccagcatttc caccgcctac    300
atggagctgt ccaggctgag aagcgacgac accgctgtgt actactgcgc caggagcacc    360
atgatcacca actacgtgat ggattattgg ggccagggca ccctcgtgac agtgagcagc    420
ggatccacaa gcggaggcgg aagcggaggc ggcagcggcg gcggcggcag cagcgatatc    480
gtgatgaccc agagccccga ttccctcgcc gtgagcctgg gcgaaagggc cacaatcaac    540
tgcaaggcca gccagtccgt ctccaacgat gtggcctggt accagcagaa gcccggacag    600
gcccctaggc tcctgatctc ctacaccagc tccaggtacg ccggcgtccc tgacagattc    660
tccggcagcg gcagcggcac cgatttcacc ctcaccatca gcagcctgca ggccgaggac    720
gtggctgtgt attactgcca gcaggactac aacagccccc ccacatttgg ccagggaacc    780
aaggtggaga tcaaggagcc caagagcagc gacaagaccc ataccctgcc ccttgccct    840 ccttgtcctc cctgtggagg cggaagctcc ggaggaggat ccggaggcca gcctagagag    900
ccccaggtgt acaccctgcc ccctagcagg gaggagatga ccaagaacca ggtgagcctg    960
acatgtctgg tcaagggctt ttaccccagc gacatcgccg tggagtggga gagcaacggc   1020
cagcctgaga caaactacaa gaccaccct cctgtgctgg actccgacgg cagcttttc   1080 ctgtacagca agctgaccgt ggataagagc aggtggcagc agggcaacgt cttcagctgc   1140
```

```
agcgtgatgc acgaggctct gcataaccac tacacccaga agagcctgag cctgagccct    1200
ggatga                                                               1206
```

<210> SEQ ID NO 157
<211> LENGTH: 1170
<212> TYPE: DNA
<213> ORGANISM: Artificial Sequence
<220> FEATURE:
<223> OTHER INFORMATION: IAB1M gamma 1 EH3(Minibody 1)

<400> SEQUENCE: 157

```
atggagaccg ataccctgct gctgtgggtg ctgctgctgt gggtgcctgg cagcaccggc     60
gacattcagc tgacccagtc ccttccaca ctgagcgcct ccgtgggcga cagggtcaca    120
attacatgtt ccgcctccag cagcgtcagg tttatccact ggtatcagca aagcccggc    180 aaggccccca agagactgat ctacgacaca agcaagctgg cctccggagt gcccagcaga    240
ttcagcggca gcggatccgg caccgatttc acactgacca tcagcagcct gcagcccgaa    300
gacttcgcca cctactactg ccagcagtgg ggctcctccc ccttcacctt cggacagggc    360
accaaggtgg agatcaaggg ctccacaagc ggcggcggaa gcggcggcgg cagcggcggc    420
ggcggctcca gcgaagtgca gctggtggag tacggcggcg actggtcca gcctggagga    480 agcctgaggc tgagctgcgc cgcctccggc tttaacatca agattacta cattcactgg    540 gtcagacagg cccctggcaa aggcctggag tgggtggcct ggatcgatcc cgagaacgga    600
gacaccgagt tcgtgcccaa gttccaggga agagccacca tgagcgccga caccagcaag    660
aacaccgcct acctgcagat gaattccctc agggccgagg ataccgctgt gtactactgc    720
aagaccggcg gattttgggg ccagggaacc ctggtgaccg tcagctccga gcctaagagc    780
agcgataaga cccacacctg ccctccttgc cccccttgtg gcggaggatc ctccggagga    840
ggatccggag acagcccag ggagcctcag gtgtacaccc tccctccag cagggaggag    900 atgaccaaga accaggtgtc cctgacctgc ctcgtcaagg gcttctaccc cagcgacatc    960
gctgtggagt gggagagcaa cggccagccc gaaaacaact acaagaccac ccctcccgtg   1020
ctggacagcg acggcagctt cttcctctac tccaagctga cagtggacaa gagcaggtgg   1080
cagcagggca acgtgttcag ctgctccgtg atgcacgagg ccctgcacaa tcactatacc   1140
cagaagtccc tgtccctctc ccccggctag                                    1170
```

<210> SEQ ID NO 158
<211> LENGTH: 1155
<212> TYPE: DNA
<213> ORGANISM: Artificial Sequence
<220> FEATURE:
<223> OTHER INFORMATION: IAB1M gamma 1 EH2(Minibody 1)

<400> SEQUENCE: 158

```
atggagaccg ataccctgct gctgtgggtg ctgctgctgt gggtgcctgg cagcaccggc     60
gacattcagc tgacccagtc ccttccaca ctgagcgcct ccgtgggcga cagggtcaca    120
attacatgtt ccgcctccag cagcgtcagg tttatccact ggtatcagca aagcccggc    180 aaggccccca agagactgat ctacgacaca agcaagctgg cctccggagt gcccagcaga    240
ttcagcggca gcggatccgg caccgatttc acactgacca tcagcagcct gcagcccgaa    300
gacttcgcca cctactactg ccagcagtgg ggctcctccc ccttcacctt cggacagggc    360
accaaggtgg agatcaaggg ctccacaagc ggcggcggaa gcggcggcgg cagcggcggc    420
ggcggctcca gcgaagtgca gctggtggag tacggcggcg actggtcca gcctggagga    480
```

```
agcctgaggc tgagctgcgc cgcctccggc tttaacatca aagattacta cattcactgg    540
gtcagacagg cccctggcaa aggcctggag tgggtggcct ggatcgatcc cgagaacgga    600
gacaccgagt tcgtgcccaa gttccaggga agagccacca tgagcgccga caccagcaag    660
aacaccgcct acctgcagat gaattccctc agggccgagg ataccgctgt gtactactgc    720
aagaccggcg gattttgggg ccagggaacc ctggtgaccg tcagctccga gagaaagagc    780
tgcgtggagt gtcctccttg tcccggcgga ggatcctccg gaggaggatc cggaggacag    840
cccagggagc ctcaggtgta cacccctccct cccagcaggg aggagatgac caagaaccag    900
gtgtccctga cctgcctcgt caagggcttc taccccagcg acatcgctgt ggagtgggag    960
agcaacggcc agcccgaaaa caactacaag accacccctc ccatgctgga cagcgacggc   1020
agcttcttcc tctactccaa gctgacagtg gacaagagca ggtggcagca gggcaacgtg   1080
ttcagctgct ccgtgatgca cgaggccctg cacaatcact atacccagaa gtccctgtcc   1140
ctctcccccg gctag                                                    1155

<210> SEQ ID NO 159
<211> LENGTH: 1179
<212> TYPE: DNA
<213> ORGANISM: Artificial Sequence
<220> FEATURE:
<223> OTHER INFORMATION: IAB1M gamma 1 EH5(Minibody 1)

<400> SEQUENCE: 159
atggaaaccg ataccctgct gctgtgggtg ctgctgctgt gggtgccggg cagcaccggc     60
gatattcagc tgacccagag cccgagcacc ctgagcgcga gcgtgggcga tcgcgtgacc    120
attacctgca gcgcgagcag cagcgtgcgc tttattcatt ggtatcagca gaaaccgggc    180
aaagcgccga acgcctgat ttatgatacc agcaaactgg cgagcggcgt gccgagccgc    240
tttagcggca gcggcagcgg caccgatttt accctgacca ttagcagcct gcagccggaa    300
gattttgcga cctattattg ccagcagtgg ggcagcagcc cgtttacctt tggccagggc    360
accaaagtgg aaattaaagg cagcaccagc ggcggcggca gcggcggcgg cagcggcggc    420
ggcggcagca gcgaagtgca gctggtggaa tatggcggcg gcctggtgca gccgggcggc    480
agcctgcgcc tgagctgcgc ggcgagcggc tttaacatta agattatta tattcattgg    540 gtgcgccagg cgccgggcaa aggcctggaa tgggtggcgt ggattgatcc ggaaaacggc    600
gataccgaat ttgtgccgaa atttcagggc cgcgcgacca tgagcgcgga taccagcaaa    660
aacaccgcgt atctgcagat gaacagcctg cgcgcggaag ataccgcggt gtattattgc    720
aaaaccggcg gcttttgggg ccagggcacc ctggtgaccg tgagcagcga accgaaaagc    780
agcgataaaa cccatacctg cccgccgtgc ccgccgtgcc cgccgtgcgg cggcggcagc    840
agcggcggcg gcagcggcgg ccagccgcgc gaaccgcagg tgtataccct gccgccgagc    900
cgcgaagaaa tgaccaaaaa ccaggtgagc ctgacctgcc tggtgaaagg ctttatccg    960 agcgatattg cggtggaatg ggaaagcaac ggccagccgg aaaacaacta taaaaccacc   1020
ccgccggtgc tggatagcga tggcagcttt tttctgtata gcaaactgac cgtggataaa   1080
agccgctggc agcagggcaa cgtgtttagc tgcagcgtga tgcatgaagc gctgcataac   1140
cattataccc agaaaagcct gagcctgagc ccgggctga                          1179

<210> SEQ ID NO 160
<211> LENGTH: 1176
<212> TYPE: DNA
```

<213> ORGANISM: Artificial Sequence
<220> FEATURE:
<223> OTHER INFORMATION: IAB1M gamma 1 EH7(Minibody 1)

<400> SEQUENCE: 160

| | |
|---|---|
| atggaaaccg ataccctgct gctgtgggtg ctgctgctgt gggtgccggg cagcaccggc | 60 |
| gatattcagc tgacccagag cccgagcacc ctgagcgcga gcgtgggcga tcgcgtgacc | 120 |
| attacctgca gcgcgagcag cagcgtgcgc tttattcatt ggtatcagca gaaaccgggc | 180 |
| aaagcgccga aacgcctgat ttatgatacc agcaaactgg cgagcggcgt gccgagccgc | 240 |
| tttagcggca gcggcagcgg caccgatttt accctgacca ttagcagcct gcagccggaa | 300 |
| gattttgcga cctattattg ccagcagtgg ggcagcagcc cgtttacctt tggccagggc | 360 |
| accaaagtgg aaattaaagg cagcaccagc ggcggcggca gcggcggcgg cagcggcggc | 420 |
| ggcggcagca gcgaagtgca gctggtggaa tatggcggcg cctggtgca gccgggcggc | 480 |
| agcctgcgcc tgagctgcgc ggcgagcggc tttaacatta agattatta tattcattgg | 540 |
| gtgcgccagg cgccgggcaa aggcctggaa tgggtggcgt ggattgatcc ggaaaacggc | 600 |
| gataccgaat ttgtgccgaa atttcagggc cgcgcgacca tgagcgcgga taccagcaaa | 660 |
| aacaccgcgt atctgcagat gaacagcctg cgcgcggaag ataccgcggt gtattattgc | 720 |
| aaaaccggcg cttttgggg ccagggcacc ctggtgaccg tgagcagcga actgaaaacc | 780 |
| ccgctgggcg ataccaccca tacctgcccg ccgtgcccgc cgtgcggcgg cggcagcagc | 840 |
| ggcggcggca gcggcggcca gccgcgcgaa ccgcaggtgt ataccctgcc gccgagccgc | 900 |
| gaagaaatga ccaaaaacca ggtgagcctg acctgcctgg tgaaaggctt ttatccgagc | 960 |
| gatattgcgg tggaatggga aagcaacggc cagccggaaa acaactataa aacccacccg | 1020 |
| ccggtgctgg atagcgatgg cagctttttt ctgtatagca aactgaccgt ggataaaagc | 1080 |
| cgctggcagc agggcaacgt gtttagctgc agcgtgatgc atgaagcgct gcataaccat | 1140 |
| tatacccaga aaagcctgag cctgagcccg ggctga | 1176 |

<210> SEQ ID NO 161
<211> LENGTH: 1185
<212> TYPE: DNA
<213> ORGANISM: Artificial Sequence
<220> FEATURE:
<223> OTHER INFORMATION: IAB1M gamma 1 EH8(Minibody 1)

<400> SEQUENCE: 161

| | |
|---|---|
| atggaaaccg ataccctgct gctgtgggtg ctgctgctgt gggtgccggg cagcaccggc | 60 |
| gatattcagc tgacccagag cccgagcacc ctgagcgcga gcgtgggcga tcgcgtgacc | 120 |
| attacctgca gcgcgagcag cagcgtgcgc tttattcatt ggtatcagca gaaaccgggc | 180 |
| aaagcgccga aacgcctgat ttatgatacc agcaaactgg cgagcggcgt gccgagccgc | 240 |
| tttagcggca gcggcagcgg caccgatttt accctgacca ttagcagcct gcagccggaa | 300 |
| gattttgcga cctattattg ccagcagtgg ggcagcagcc cgtttacctt tggccagggc | 360 |
| accaaagtgg aaattaaagg cagcaccagc ggcggcggca gcggcggcgg cagcggcggc | 420 |
| ggcggcagca gcgaagtgca gctggtggaa tatggcggcg cctggtgca gccgggcggc | 480 |
| agcctgcgcc tgagctgcgc ggcgagcggc tttaacatta agattatta tattcattgg | 540 |
| gtgcgccagg cgccgggcaa aggcctggaa tgggtggcgt ggattgatcc ggaaaacggc | 600 |
| gataccgaat ttgtgccgaa atttcagggc cgcgcgacca tgagcgcgga taccagcaaa | 660 |
| aacaccgcgt atctgcagat gaacagcctg cgcgcggaag ataccgcggt gtattattgc | 720 |

```
aaaaccggcg gcttttgggg ccagggcacc ctggtgaccg tgagcagcga actgaaaacc      780
ccgctgggcg ataccaccca tacctgcccg ccgtgcccgc cgtgcccgcc gtgcggcggc      840
ggcagcagcg gcggcggcag cggcggccag ccgcgcgaac cgcaggtgta taccctgccg      900
ccgagccgcg aagaaatgac caaaaaccag gtgagcctga cctgcctggt gaaaggcttt      960
tatccgagcg atattgcggt ggaatgggaa agcaacggcc agccggaaaa caactataaa     1020
accaccccgc cggtgctgga tagcgatggc agctttttc tgtatagcaa actgaccgtg     1080
gataaaagcc gctggcagca gggcaacgtg tttagctgca gcgtgatgca tgaagcgctg     1140
cataaccatt atacccagaa aagcctgagc ctgagcccgg gctga                     1185

<210> SEQ ID NO 162
<211> LENGTH: 1119
<212> TYPE: DNA
<213> ORGANISM: Artificial Sequence
<220> FEATURE:
<223> OTHER INFORMATION: IAB2M gamma 1 EH3 (Minibody 1)

<400> SEQUENCE: 162
gatattgtga tgacccagag cccgagcagc ctgagcgcga gcgtgggcga tcgcgtgacc       60
attacctgca aagcgagcca ggatgtgggc accgcggtgg attggtatca gcagaaaccg      120
ggcaaagcgc cgaaactgct gatttattgg gcgagcaccc gccataccgg cgtgccggat      180
cgctttaccg gcagcggcag cggcaccgat tttaccctga ccattagcag cctgcagccg      240
gaagattttg cggattattt ttgccagcag tataacagct atccgctgac ctttggcggc      300
ggcaccaaac tggaaattaa aggcagcacc agcggcggcg gcagcggcgg cggcagcggc      360
ggcggcggca gcgcgaagt gcagctggtg cagagcggcg cggaagtgaa aaaaccgggc      420
gcgagcgtga aaattagctg caaaaccagc ggctatacct ttaccgaata taccattcat      480
tgggtgaaac aggcgagcgg caaaggcctg aatggattg caacattaa cccgaacaac      540 ggcggcacca cctataacca gaaatttgaa gatcgcgcga ccctgaccgt ggataaaagc      600
accagcaccg tgtatatgga actgagcagc ctgcgcagcg aagataccgc ggtgtattat      660
tgcgcggcgg gctggaactt tgattattgg ggccagggca ccaccgtgac cgtgagcagc      720
gaaccgaaaa gcagcgataa aacccatacc tgcccgccgt gccgccgtg cggcggcggc      780 agcagcggcg gcggcagcgg cggccagccg cgcgaaccgc aggtgtatac cctgccgccg      840
agccgcgaag aaatgaccaa aaaccaggtg agcctgacct gcctggtgaa aggcttttat      900
ccgagcgata ttgcggtgga atgggaaagc aacggccagc cggaaaacaa ctataaaacc      960
accccgccgg tgctggatag cgatggcagc ttttttctgt atagcaaact gaccgtggat     1020
aaaagccgct ggcagcaggg caacgtgttt agctgcagcg tgatgcatga agcgctgcat     1080
aaccattata cccagaaaag cctgagcctg agcccgggc                            1119

<210> SEQ ID NO 163
<211> LENGTH: 1128
<212> TYPE: DNA
<213> ORGANISM: Artificial Sequence
<220> FEATURE:
<223> OTHER INFORMATION: IAB2M gamma 1 EH5 (Minibody 1)

<400> SEQUENCE: 163
gatattgtga tgacccagag cccgagcagc ctgagcgcga gcgtgggcga tcgcgtgacc       60
attacctgca aagcgagcca ggatgtgggc accgcggtgg attggtatca gcagaaaccg      120
```

| | |
|---|---|
| ggcaaagcgc cgaaactgct gatttattgg gcgagcaccc gccataccgg cgtgccggat | 180 |
| cgctttaccg gcagcggcag cggcaccgat tttacccctga ccattagcag cctgcagccg | 240 |
| gaagattttg cggattattt tgccagcag tataacagct atccgctgac ctttggcggc | 300 |
| ggcaccaaac tggaaattaa aggcagcacc agcggcggcg gcagcggcgg cggcagcggc | 360 |
| ggcggcggca gcagcgaagt gcagctggtg cagagcggcg cggaagtgaa aaaaccgggc | 420 |
| gcgagcgtga aaattagctg caaaaccagc ggctatacct ttaccgaata taccattcat | 480 |
| tgggtgaaac aggcgagcgg caaaggcctg aatggattg gcaacattaa cccgaacaac | 540 |
| ggcggcacca cctataacca gaaatttgaa gatcgcgcga ccctgaccgt ggataaaagc | 600 |
| accagcaccg cgtatatgga actgagcagc ctgcgcagcg aagataccgc ggtgtattat | 660 |
| tgcgcggcgg gctggaactt tgattattgg ggccagggca ccaccgtgac cgtgagcagc | 720 |
| gaaccgaaaa gcagcgataa aacccatacc tgcccgccgt gcccgccgtg cccgccgtgc | 780 |
| ggcggcggca gcagcggcgg cggcagcggc ggccagccgc gcgaaccgca ggtgtatacc | 840 |
| ctgccgccga gccgcgaaga aatgaccaaa aaccaggtga gcctgacctg cctggtgaaa | 900 |
| ggctttatc cgagcgatat tgcggtggaa tgggaaagca cggccagcc ggaaaacaac | 960 |
| tataaaacca cccccgccggt gctggatagc gatggcagct tttttctgta tagcaaactg | 1020 |
| accgtggata aagccgctg gcagcagggc aacgtgttta gctgcagcgt gatgcatgaa | 1080 |
| gcgctgcata accattatac ccagaaaagc ctgagcctga gcccgggc | 1128 |

<210> SEQ ID NO 164
<211> LENGTH: 1134
<212> TYPE: DNA
<213> ORGANISM: Artificial Sequence
<220> FEATURE:
<223> OTHER INFORMATION: IAB2M gamma 1 EH8 (Minibody 1)

<400> SEQUENCE: 164

| | |
|---|---|
| gatattgtga tgacccagag cccgagcagc ctgagcgcga gcgtgggcga tcgcgtgacc | 60 |
| attacctgca aagcgagcca ggatgtgggc accgcgtgg attggtatca gcagaaaccg | 120 |
| ggcaaagcgc cgaaactgct gatttattgg gcgagcaccc gccataccgg cgtgccggat | 180 |
| cgctttaccg gcagcggcag cggcaccgat tttacccctga ccattagcag cctgcagccg | 240 |
| gaagattttg cggattattt tgccagcag tataacagct atccgctgac ctttggcggc | 300 |
| ggcaccaaac tggaaattaa aggcagcacc agcggcggcg gcagcggcgg cggcagcggc | 360 |
| ggcggcggca gcagcgaagt gcagctggtg cagagcggcg cggaagtgaa aaaaccgggc | 420 |
| gcgagcgtga aaattagctg caaaaccagc ggctatacct ttaccgaata taccattcat | 480 |
| tgggtgaaac aggcgagcgg caaaggcctg aatggattg gcaacattaa cccgaacaac | 540 |
| ggcggcacca cctataacca gaaatttgaa gatcgcgcga ccctgaccgt ggataaaagc | 600 |
| accagcaccg cgtatatgga actgagcagc ctgcgcagcg aagataccgc ggtgtattat | 660 |
| tgcgcggcgg gctggaactt tgattattgg ggccagggca ccaccgtgac cgtgagcagc | 720 |
| gaactgaaaa ccccgctggg cgataccacc catacctgcc cgccgtgccc gccgtgcccg | 780 |
| ccgtgcggcg gcggcagcag cggcggcggc agcggcggcc agccgcgcga accgcaggtg | 840 |
| tatacccctgc cgccgagccg cgaagaaatg accaaaaacc aggtgagcct gacctgcctg | 900 |
| gtgaaaggct ttatccgag cgatattgcg gtggaatggg aaagcaacgg ccagccggaa | 960 |
| aacaactata aaccacccc gccggtgctg gatagcgatg gcagcttttt tctgtatagc | 1020 |
| aaactgaccg tggataaaag ccgctggcag cagggcaacg tgtttagctg cagcgtgatg | 1080 |

-continued

```
catgaagcgc tgcataacca ttatacccag aaaagcctga gcctgagccc gggc      1134
```

<210> SEQ ID NO 165
<211> LENGTH: 1119
<212> TYPE: DNA
<213> ORGANISM: Artificial Sequence
<220> FEATURE:
<223> OTHER INFORMATION: IAB2M gamma 1 EH3 (Minibody 2)

<400> SEQUENCE: 165

```
gaagtgcagc tggtgcagag cggcgcggaa gtgaaaaaac cgggcgcgag cgtgaaaatt    60
agctgcaaaa ccagcggcta cctttacc gaatatacca ttcattgggt gaaacaggcg     120
agcggcaaag cctggaatg gattggcaac attaacccga caacggcgg caccacctat     180
aaccagaaat tgaagatcg cgcgaccctg accgtggata aagcaccag caccgcgtat    240
atggaactga gcagcctgcg cagcgaagat accgcggtgt attattgcgc ggcgggctgg   300
aactttgatt attggggcca gggcaccacc gtgaccgtga gcagcggcag caccagcggc  360
ggcggcagcg gcggcggcag cggcggcggc ggcagcagcg atattgtgat gacccagagc   420
ccgagcagcc tgagcgcgag cgtgggcgat cgcgtgacca ttacctgcaa agcgagccag    480
gatgtgggca ccgcggtgga ttggtatcag cagaaaccgg gcaaagcgcc gaaactgctg    540
atttattggg cgagcacccg ccataccggc gtgccggatc gctttaccgg cagcggcagc    600
ggcaccgatt ttaccctgac cattagcagc ctgcagccgg aagattttgc ggattatttt   660
tgccagcagt ataacagcta tccgctgacc tttggcggcg gcaccaaact ggaaattaaa    720
gaaccgaaaa gcagcgataa acccatacc tgcccgccgt gccgccgtg cggcggcggc      780
agcagcggcg gcggcagcgg cggccagccg cgcgaaccgc aggtgtatac cctgccgccg    840
agccgcgaag aaatgaccaa aaaccaggtg agcctgacct gcctggtgaa aggctttat    900
ccgagcgata ttgcggtgga atgggaaagc aacggccagc cggaaaacaa ctataaaacc    960
acccccgccgg tgctggatag cgatggcagc ttttttctgt atagcaaaact gaccgtggat    1020
aaaagccgct ggcagcaggg caacgtgttt agctgcagcg tgatgcatga agcgctgcat    1080
aaccattata cccagaaaag cctgagcctg agcccgggc                           1119
```

<210> SEQ ID NO 166
<211> LENGTH: 8
<212> TYPE: PRT
<213> ORGANISM: Homo sapiens

<400> SEQUENCE: 166

Thr Cys Pro Pro Cys Pro Pro Cys
1               5

<210> SEQ ID NO 167
<211> LENGTH: 12
<212> TYPE: PRT
<213> ORGANISM: Homo sapiens

<400> SEQUENCE: 167

Glu Arg Lys Ser Cys Val Glu Cys Pro Pro Cys Pro
1               5                   10

<210> SEQ ID NO 168
<211> LENGTH: 17
<212> TYPE: PRT
<213> ORGANISM: Homo sapiens

```
<400> SEQUENCE: 168

Glu Pro Lys Ser Ser Asp Lys Thr His Thr Cys Pro Pro Cys Pro Pro
1               5                   10                  15

Cys

<210> SEQ ID NO 169
<211> LENGTH: 20
<212> TYPE: PRT
<213> ORGANISM: Homo sapiens

<400> SEQUENCE: 169

Glu Pro Lys Ser Ser Asp Lys Thr His Thr Cys Pro Pro Cys Val Glu
1               5                   10                  15

Cys Pro Pro Cys
            20

<210> SEQ ID NO 170
<211> LENGTH: 20
<212> TYPE: PRT
<213> ORGANISM: Homo sapiens

<400> SEQUENCE: 170

Glu Pro Lys Ser Ser Asp Lys Thr His Thr Cys Pro Pro Cys Pro Pro
1               5                   10                  15

Cys Pro Pro Cys
            20

<210> SEQ ID NO 171
<211> LENGTH: 9
<212> TYPE: PRT
<213> ORGANISM: Homo sapiens
<220> FEATURE:
<223> OTHER INFORMATION: Hinge region
<220> FEATURE:
<221> NAME/KEY: VARIANT
<222> LOCATION: 2, 3, 5, 6, 8, 9
<223> OTHER INFORMATION: Xaa = P, V, or E

<400> SEQUENCE: 171

Cys Xaa Xaa Cys Xaa Xaa Cys Xaa Xaa
1               5

<210> SEQ ID NO 172
<211> LENGTH: 6
<212> TYPE: PRT
<213> ORGANISM: Homo sapiens
<220> FEATURE:
<221> NAME/KEY: VARIANT
<222> LOCATION: 2, 3, 5, 6
<223> OTHER INFORMATION: Xaa = P, V, or E

<400> SEQUENCE: 172

Cys Xaa Xaa Cys Xaa Xaa
1               5

<210> SEQ ID NO 173
<211> LENGTH: 12
<212> TYPE: PRT
<213> ORGANISM: Homo sapiens
<220> FEATURE:
<221> NAME/KEY: VARIANT
<222> LOCATION: 2, 3, 5, 6, 8, 9, 11, 12
<223> OTHER INFORMATION: Xaa = P, V, or E

<400> SEQUENCE: 173
```

```
Cys Xaa Xaa Cys Xaa Xaa Cys Xaa Xaa Cys Xaa Xaa
1               5                   10
```

<210> SEQ ID NO 174
<211> LENGTH: 7
<212> TYPE: PRT
<213> ORGANISM: Homo sapiens

<400> SEQUENCE: 174

```
Gly Tyr Thr Phe Thr Arg Tyr
1               5
```

<210> SEQ ID NO 175
<211> LENGTH: 6
<212> TYPE: PRT
<213> ORGANISM: Homo sapiens

<400> SEQUENCE: 175

```
Asn Pro Ser Arg Gly Tyr
1               5
```

<210> SEQ ID NO 176
<211> LENGTH: 10
<212> TYPE: PRT
<213> ORGANISM: Homo sapiens

<400> SEQUENCE: 176

```
Tyr Tyr Asp Asp His Tyr Ser Leu Asp Tyr
1               5                   10
```

<210> SEQ ID NO 177
<211> LENGTH: 10
<212> TYPE: PRT
<213> ORGANISM: Homo sapiens

<400> SEQUENCE: 177

```
Ser Ala Ser Ser Ser Val Ser Tyr Met Asn
1               5                   10
```

<210> SEQ ID NO 178
<211> LENGTH: 9
<212> TYPE: PRT
<213> ORGANISM: Homo sapiens

<400> SEQUENCE: 178

```
Gln Gln Trp Ser Ser Asn Pro Phe Thr
1               5
```

<210> SEQ ID NO 179
<211> LENGTH: 742
<212> TYPE: PRT
<213> ORGANISM: Homo sapiens

<400> SEQUENCE: 179

```
Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ala Ser Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Ala Thr Leu Thr Val Asp Lys Ser Thr Ser Thr Ala Tyr
```

```
            65                  70                  75                  80
Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser Gly Ser Thr Ser Gly Gly Ser Gly Gly Gly Ser Gly
        115                 120                 125

Gly Gly Gly Ser Ser Asp Ile Val Met Thr Gln Ser Pro Ser Ser Leu
        130                 135                 140

Ser Ala Ser Val Gly Asp Arg Val Thr Ile Thr Cys Lys Ala Ser Gln
145                 150                 155                 160

Asp Val Gly Thr Ala Val Asp Trp Tyr Gln Gln Lys Pro Gly Lys Ala
                165                 170                 175

Pro Lys Leu Leu Ile Tyr Trp Ala Ser Thr Arg His Thr Gly Val Pro
                180                 185                 190

Asp Arg Phe Thr Gly Ser Gly Ser Gly Thr Asp Phe Thr Leu Thr Ile
            195                 200                 205

Ser Ser Leu Gln Pro Glu Asp Phe Ala Asp Tyr Phe Cys Gln Gln Tyr
    210                 215                 220

Asn Ser Tyr Pro Leu Thr Phe Gly Gly Gly Thr Lys Leu Glu Ile Lys
225                 230                 235                 240

Glu Pro Lys Ser Cys Asp Lys Thr His Thr Cys Pro Pro Cys Gly Gly
                245                 250                 255

Gly Ser Ser Gly Gly Gly Ser Gly Gly Gln Pro Arg Glu Pro Gln Val
            260                 265                 270

Tyr Thr Leu Pro Pro Ser Arg Asp Glu Leu Thr Lys Asn Gln Val Ser
        275                 280                 285

Leu Thr Cys Leu Val Lys Gly Phe Tyr Pro Ser Asp Ile Ala Val Glu
        290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
                340                 345                 350

His Glu Ala Leu His Asn His Tyr Thr Gln Lys Ser Leu Ser Leu Ser
            355                 360                 365

Pro Gly Lys Glu Val Gln Leu Val Gln Ser Gly Ala Glu Val Lys Lys
    370                 375                 380

Pro Gly Ala Ser Val Lys Ile Ser Cys Lys Thr Ser Gly Tyr Thr Phe
385                 390                 395                 400

Thr Glu Tyr Thr Ile His Trp Val Lys Gln Ala Ser Gly Lys Gly Leu
                405                 410                 415

Glu Trp Ile Gly Asn Ile Asn Pro Asn Asn Gly Gly Thr Thr Tyr Asn
            420                 425                 430

Gln Lys Phe Glu Asp Arg Ala Thr Leu Thr Val Asp Lys Ser Thr Ser
        435                 440                 445

Thr Ala Tyr Met Glu Leu Ser Ser Leu Arg Ser Glu Asp Thr Ala Val
        450                 455                 460

Tyr Tyr Cys Ala Ala Gly Trp Asn Phe Asp Tyr Trp Gly Gln Gly Thr
465                 470                 475                 480

Thr Val Thr Val Ser Ser Gly Ser Thr Ser Gly Gly Ser Gly Gly
        485                 490                 495
```

```
Gly Ser Gly Gly Gly Ser Asp Ile Val Met Thr Gln Ser Pro
            500                 505                 510

Ser Ser Leu Ser Ala Ser Val Gly Asp Arg Val Thr Ile Thr Cys Lys
        515                 520                 525

Ala Ser Gln Asp Val Gly Thr Ala Val Asp Trp Tyr Gln Gln Lys Pro
530                 535                 540

Gly Lys Ala Pro Lys Leu Leu Ile Tyr Trp Ala Ser Thr Arg His Thr
545                 550                 555                 560

Gly Val Pro Asp Arg Phe Thr Gly Ser Gly Ser Gly Thr Asp Phe Thr
                565                 570                 575

Leu Thr Ile Ser Ser Leu Gln Pro Glu Asp Phe Ala Asp Tyr Phe Cys
            580                 585                 590

Gln Gln Tyr Asn Ser Tyr Pro Leu Thr Phe Gly Gly Gly Thr Lys Leu
            595                 600                 605

Glu Ile Lys Glu Pro Lys Ser Cys Asp Lys Thr His Thr Cys Pro Pro
610                 615                 620

Cys Gly Gly Gly Ser Ser Gly Gly Gly Ser Gly Gly Gln Pro Arg Glu
625                 630                 635                 640

Pro Gln Val Tyr Thr Leu Pro Pro Ser Arg Asp Glu Leu Thr Lys Asn
                645                 650                 655

Gln Val Ser Leu Thr Cys Leu Val Lys Gly Phe Tyr Pro Ser Asp Ile
            660                 665                 670

Ala Val Glu Trp Glu Ser Asn Gly Gln Pro Glu Asn Asn Tyr Lys Thr
            675                 680                 685

Thr Pro Pro Val Leu Asp Ser Asp Gly Ser Phe Phe Leu Tyr Ser Lys
        690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
                725                 730                 735

Ser Leu Ser Pro Gly Lys
            740

<210> SEQ ID NO 180
<211> LENGTH: 738
<212> TYPE: PRT
<213> ORGANISM: Homo sapiens

<400> SEQUENCE: 180

Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ala Ser Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser Gly Ser Thr Ser Gly Gly Gly Ser Gly Gly Gly Ser Gly
```

-continued

```
            115                 120                 125
Gly Gly Gly Ser Ser Asp Ile Val Met Thr Gln Ser Pro Ser Ser Leu
            130                 135                 140

Ser Ala Ser Val Gly Asp Arg Val Thr Ile Thr Cys Lys Ala Ser Gln
145                 150                 155                 160

Asp Val Gly Thr Ala Val Asp Trp Tyr Gln Gln Lys Pro Gly Lys Ala
                165                 170                 175

Pro Lys Leu Leu Ile Tyr Trp Ala Ser Thr Arg His Thr Gly Val Pro
            180                 185                 190

Asp Arg Phe Thr Gly Ser Gly Ser Gly Thr Asp Phe Thr Leu Thr Ile
            195                 200                 205

Ser Ser Leu Gln Pro Glu Asp Phe Ala Asp Tyr Phe Cys Gln Gln Tyr
        210                 215                 220

Asn Ser Tyr Pro Leu Thr Phe Gly Gly Gly Thr Lys Leu Glu Ile Lys
225                 230                 235                 240

Glu Arg Lys Cys Cys Val Glu Cys Pro Pro Cys Pro Gly Gly Gly Ser
                245                 250                 255

Ser Gly Gly Gly Ser Gly Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Met Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys Glu Val Gln Leu Val Gln Ser Gly Ala Glu Val Lys Lys Pro Gly
        370                 375                 380

Ala Ser Val Lys Ile Ser Cys Lys Thr Ser Gly Tyr Thr Phe Thr Glu
385                 390                 395                 400

Tyr Thr Ile His Trp Val Lys Gln Ala Ser Gly Lys Gly Leu Glu Trp
                405                 410                 415

Ile Gly Asn Ile Asn Pro Asn Asn Gly Gly Thr Thr Tyr Asn Gln Lys
            420                 425                 430

Phe Glu Asp Arg Ala Thr Leu Thr Val Asp Lys Ser Thr Ser Thr Ala
        435                 440                 445

Tyr Met Glu Leu Ser Ser Leu Arg Ser Glu Asp Thr Ala Val Tyr Tyr
        450                 455                 460

Cys Ala Ala Gly Trp Asn Phe Asp Tyr Trp Gly Gln Gly Thr Thr Val
465                 470                 475                 480

Thr Val Ser Ser Gly Ser Thr Ser Gly Gly Gly Ser Gly Gly Gly Ser
                485                 490                 495

Gly Gly Gly Gly Ser Ser Asp Ile Val Met Thr Gln Ser Pro Ser Ser
            500                 505                 510

Leu Ser Ala Ser Val Gly Asp Arg Val Thr Ile Thr Cys Lys Ala Ser
        515                 520                 525

Gln Asp Val Gly Thr Ala Val Asp Trp Tyr Gln Gln Lys Pro Gly Lys
        530                 535                 540
```

```
Ala Pro Lys Leu Leu Ile Tyr Trp Ala Ser Thr Arg His Thr Gly Val
545                 550                 555                 560

Pro Asp Arg Phe Thr Gly Ser Gly Ser Gly Thr Asp Phe Thr Leu Thr
            565                 570                 575

Ile Ser Ser Leu Gln Pro Glu Asp Phe Ala Asp Tyr Phe Cys Gln Gln
                580                 585                 590

Tyr Asn Ser Tyr Pro Leu Thr Phe Gly Gly Gly Thr Lys Leu Glu Ile
            595                 600                 605

Lys Glu Arg Lys Cys Cys Val Glu Cys Pro Cys Pro Gly Gly Gly
        610                 615                 620

Ser Ser Gly Gly Gly Ser Gly Gly Gln Pro Arg Glu Pro Gln Val Tyr
625                 630                 635                 640

Thr Leu Pro Pro Ser Arg Glu Glu Met Thr Lys Asn Gln Val Ser Leu
            645                 650                 655

Thr Cys Leu Val Lys Gly Phe Tyr Pro Ser Asp Ile Ala Val Glu Trp
            660                 665                 670

Glu Ser Asn Gly Gln Pro Glu Asn Asn Tyr Lys Thr Thr Pro Pro Met
            675                 680                 685

Leu Asp Ser Asp Gly Ser Phe Phe Leu Tyr Ser Lys Leu Thr Val Asp
            690                 695                 700

Lys Ser Arg Trp Gln Gln Gly Asn Val Phe Ser Cys Ser Val Met His
705                 710                 715                 720

Glu Ala Leu His Asn His Tyr Thr Gln Lys Ser Leu Ser Leu Ser Pro
                725                 730                 735

Gly Lys

<210> SEQ ID NO 181
<211> LENGTH: 106
<212> TYPE: PRT
<213> ORGANISM: Homo sapiens

<400> SEQUENCE: 181

Gly Gln Pro Arg Glu Pro Gln Val Tyr Thr Leu Pro Pro Ser Arg Glu
1               5                   10                  15

Glu Met Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 182
<211> LENGTH: 106
<212> TYPE: PRT
<213> ORGANISM: Homo sapiens

<400> SEQUENCE: 182

Gly Gln Pro Arg Glu Pro Gln Val Tyr Thr Leu Pro Pro Ser Arg Glu
1               5                   10                  15
```

```
Glu Met Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 183
<211> LENGTH: 6
<212> TYPE: PRT
<213> ORGANISM: Artificial Sequence
<220> FEATURE:
<223> OTHER INFORMATION: C5 forms a disulfide bond with C27 of SEQ ID
      184; C5 forms a disulfide bond with C34 of SEQ ID 185

<400> SEQUENCE: 183

Val Thr Ile Thr Cys Lys
1               5

<210> SEQ ID NO 184
<211> LENGTH: 42
<212> TYPE: PRT
<213> ORGANISM: Artificial Sequence
<220> FEATURE:
<223> OTHER INFORMATION: C27 forms a disulfide bond with C5 of SEQ ID
      183

<400> SEQUENCE: 184

Phe Thr Gly Ser Gly Ser Gly Thr Asp Phe Thr Leu Thr Ile Ser Ser
1               5                   10                  15

Leu Gln Pro Glu Asp Phe Ala Asp Tyr Phe Cys Gln Gln Tyr Asn Ser
            20                  25                  30

Tyr Pro Leu Thr Phe Gly Gly Gly Thr Lys
            35                  40

<210> SEQ ID NO 185
<211> LENGTH: 49
<212> TYPE: PRT
<213> ORGANISM: Artificial Sequence
<220> FEATURE:
<223> OTHER INFORMATION: C34 forms a disulfide bond with C5 of SEQ ID
      183

<400> SEQUENCE: 185

His Thr Gly Val Pro Asp Arg Phe Thr Gly Ser Gly Ser Gly Thr Asp
1               5                   10                  15

Phe Thr Leu Thr Ile Ser Ser Leu Gln Pro Glu Asp Phe Ala Asp Tyr
            20                  25                  30

Phe Cys Gln Gln Tyr Asn Ser Tyr Pro Leu Thr Phe Gly Gly Gly Thr
                35                  40                  45

Lys

<210> SEQ ID NO 186
<211> LENGTH: 21
<212> TYPE: PRT
<213> ORGANISM: Artificial Sequence
```

```
<220> FEATURE:
<223> OTHER INFORMATION: C4 forms a disulfide bond with C4 of SEQ ID
      186; C7 forms a disulfide bond with C7 of SEQ ID 186

<400> SEQUENCE: 186

Thr His Thr Cys Pro Pro Cys Gly Gly Gly Ser Ser Gly Gly Gly Ser
1               5                   10                  15

Gly Gly Gln Pro Arg
            20

<210> SEQ ID NO 187
<211> LENGTH: 4
<212> TYPE: PRT
<213> ORGANISM: Artificial Sequence
<220> FEATURE:
<223> OTHER INFORMATION: C2 forms a disulfide bond with C7 of SEQ ID 188

<400> SEQUENCE: 187

Ser Cys Asp Lys
1

<210> SEQ ID NO 188
<211> LENGTH: 10
<212> TYPE: PRT
<213> ORGANISM: Artificial Sequence
<220> FEATURE:
<223> OTHER INFORMATION: C7 forms a disulfide bond with C2 of SEQ ID
      187; C7 forms a disulfide bond with C9 of SEQ ID 189;
      C7 forms a disulfide bond with C11 of SEQ ID 190;
      Alkylation of C7

<400> SEQUENCE: 188

Asn Gln Val Ser Leu Thr Cys Leu Val Lys
1               5                   10

<210> SEQ ID NO 189
<211> LENGTH: 23
<212> TYPE: PRT
<213> ORGANISM: Artificial Sequence
<220> FEATURE:
<223> OTHER INFORMATION: C9 forms a disulfide bond with C7 of SEQ ID
      188; Alkylation of C9

<400> SEQUENCE: 189

Trp Gln Gln Gly Asn Val Phe Ser Cys Ser Val Met His Glu Ala Leu
1               5                   10                  15

His Asn His Tyr Thr Gln Lys
            20

<210> SEQ ID NO 190
<211> LENGTH: 25
<212> TYPE: PRT
<213> ORGANISM: Artificial Sequence
<220> FEATURE:
<223> OTHER INFORMATION: C11 forms a disulfide bond with C7 of SEQ ID
      188

<400> SEQUENCE: 190

Ser Arg Trp Gln Gln Gly Asn Val Phe Ser Cys Ser Val Met His Glu
1               5                   10                  15

Ala Leu His Asn His Tyr Thr Gln Lys
            20                  25

<210> SEQ ID NO 191
<211> LENGTH: 8
<212> TYPE: PRT
```

```
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa does not form a covalent crosslinking bond
      with another amino acid
<220> FEATURE:
<221> NAME/KEY: VARIANT
<222> LOCATION: 3
<223> OTHER INFORMATION: Xaa = any one of: A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 191

Xaa Cys Xaa Xaa Cys Xaa Xaa Cys
1               5

<210> SEQ ID NO 192
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa is not a cysteine
<220> FEATURE:
<221> NAME/KEY: VARIANT
<222> LOCATION: 3
<223> OTHER INFORMATION: Xaa = any one of: A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 192

Xaa Cys Xaa Xaa Cys Xaa Xaa Cys
1               5

<210> SEQ ID NO 193
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = one of A, R, N, D, E, Q, G, H, I, L, K,
      M, F, P, S, T, W, Y, or V
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 193

Xaa Cys Xaa Xaa Cys Xaa Xaa Cys
1               5

<210> SEQ ID NO 194
<211> LENGTH: 8
```

```
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = P, V, or E
<220> FEATURE:
<221> NAME/KEY: VARIANT
<222> LOCATION: 4, 6, 7
<223> OTHER INFORMATION: Xaa = any amino acid

<400> SEQUENCE: 194

Xaa Cys Xaa Xaa Cys Xaa Xaa Cys
1               5

<210> SEQ ID NO 195
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = P or V
<220> FEATURE:
<221> NAME/KEY: VARIANT
<222> LOCATION: 4, 6, 7
<223> OTHER INFORMATION: Xaa = any amino acid

<400> SEQUENCE: 195

Xaa Cys Xaa Xaa Cys Xaa Xaa Cys
1               5

<210> SEQ ID NO 196
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 7
<223> OTHER INFORMATION: Xaa = any amino acid
<220> FEATURE:
<221> NAME/KEY: VARIANT
<222> LOCATION: 6
<223> OTHER INFORMATION: Xaa = P, V, or E

<400> SEQUENCE: 196

Xaa Cys Xaa Xaa Cys Xaa Xaa Cys
1               5
```

<210> SEQ ID NO 197
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 7
<223> OTHER INFORMATION: Xaa = any amino acid
<220> FEATURE:
<221> NAME/KEY: VARIANT
<222> LOCATION: 6
<223> OTHER INFORMATION: Xaa = P or V

<400> SEQUENCE: 197

Xaa Cys Xaa Xaa Cys Xaa Xaa Cys
1               5

<210> SEQ ID NO 198
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4
<223> OTHER INFORMATION: P or E
<220> FEATURE:
<221> NAME/KEY: VARIANT
<222> LOCATION: 6, 7
<223> OTHER INFORMATION: Xaa = any amino acid

<400> SEQUENCE: 198

Xaa Cys Xaa Xaa Cys Xaa Xaa Cys
1               5

<210> SEQ ID NO 199
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of A, R, N, D, E, Q, G, H, I, L,

```
        K, M, F, P, S, T, W, Y, or V
<220> FEATURE:
<221> NAME/KEY: VARIANT
<222> LOCATION: 4, 6
<223> OTHER INFORMATION: Xaa = any amino acid
<220> FEATURE:
<221> NAME/KEY: VARIANT
<222> LOCATION: 7
<223> OTHER INFORMATION: Xaa = P or E

<400> SEQUENCE: 199

Xaa Cys Xaa Xaa Cys Xaa Xaa Cys
1               5

<210> SEQ ID NO 200
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4
<223> OTHER INFORMATION: Xaa = P or E
<220> FEATURE:
<221> NAME/KEY: VARIANT
<222> LOCATION: 6, 7
<223> OTHER INFORMATION: Xaa = any amino acid

<400> SEQUENCE: 200

Xaa Cys Xaa Xaa Cys Xaa Xaa Cys
1               5

<210> SEQ ID NO 201
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3, 4
<223> OTHER INFORMATION: Xaa = VE
<220> FEATURE:
<221> NAME/KEY: VARIANT
<222> LOCATION: 6, 7
<223> OTHER INFORMATION: Xaa = any amino acid

<400> SEQUENCE: 201

Xaa Cys Xaa Xaa Cys Xaa Xaa Cys
1               5

<210> SEQ ID NO 202
<211> LENGTH: 8
<212> TYPE: PRT
<213> ORGANISM: Artificial Sequence
<220> FEATURE:
<223> OTHER INFORMATION: Hinge region
```

-continued

```
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3, 4
<223> OTHER INFORMATION: Xaa = PP
<220> FEATURE:
<221> NAME/KEY: VARIANT
<222> LOCATION: 6, 7
<223> OTHER INFORMATION: Xaa = any amino acid

<400> SEQUENCE: 202

Xaa Cys Xaa Xaa Cys Xaa Xaa Cys
1               5

<210> SEQ ID NO 203
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4
<223> OTHER INFORMATION: Xaa = any amino acid
<220> FEATURE:
<221> NAME/KEY: VARIANT
<222> LOCATION: 6, 7
<223> OTHER INFORMATION: Xaa = VE

<400> SEQUENCE: 203

Xaa Cys Xaa Xaa Cys Xaa Xaa Cys
1               5

<210> SEQ ID NO 204
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4
<223> OTHER INFORMATION: Xaa = any amino acid
<220> FEATURE:
<221> NAME/KEY: VARIANT
<222> LOCATION: 6, 7
<223> OTHER INFORMATION: Xaa = PP

<400> SEQUENCE: 204

Xaa Cys Xaa Xaa Cys Xaa Xaa Cys
```

```
1               5

<210> SEQ ID NO 205
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3, 4
<223> OTHER INFORMATION: Xaa = VE
<220> FEATURE:
<221> NAME/KEY: VARIANT
<222> LOCATION: 6, 7
<223> OTHER INFORMATION: Xaa = PP

<400> SEQUENCE: 205

Xaa Cys Xaa Xaa Cys Xaa Xaa Cys
1               5

<210> SEQ ID NO 206
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3, 4
<223> OTHER INFORMATION: Xaa = PP
<220> FEATURE:
<221> NAME/KEY: VARIANT
<222> LOCATION: 6, 7
<223> OTHER INFORMATION: Xaa = PP or VE

<400> SEQUENCE: 206

Xaa Cys Xaa Xaa Cys Xaa Xaa Cys
1               5

<210> SEQ ID NO 207
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3, 4
<223> OTHER INFORMATION: Xaa = VE
<220> FEATURE:
<221> NAME/KEY: VARIANT
<222> LOCATION: 6, 7
<223> OTHER INFORMATION: Xaa = VE or PP

<400> SEQUENCE: 207

Xaa Cys Xaa Xaa Cys Xaa Xaa Cys
1               5
```

```
<210> SEQ ID NO 208
<211> LENGTH: 13
<212> TYPE: PRT
<213> ORGANISM: Artificial Sequence
<220> FEATURE:
<223> OTHER INFORMATION: Minibody
<220> FEATURE:
<221> NAME/KEY: VARIANT
<222> LOCATION: 1
<223> OTHER INFORMATION: Xaa = any amino acid that does not form a
      covalent crosslinking bond with another identical amino
      acid
<220> FEATURE:
<221> NAME/KEY: VARIANT
<222> LOCATION: 2-6, 8-9, 11-12
<223> OTHER INFORMATION: Xaa = any amino acid

<400> SEQUENCE: 208

Xaa Xaa Xaa Xaa Xaa Xaa Cys Xaa Xaa Cys Xaa Xaa Cys
1               5                   10

<210> SEQ ID NO 209
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = serine, threonine, or alanine
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 209

Xaa Cys Xaa Xaa Cys Xaa Xaa Cys
1               5

<210> SEQ ID NO 210
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = serine
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 210

Xaa Cys Xaa Xaa Cys Xaa Xaa Cys
1               5

<210> SEQ ID NO 211
<211> LENGTH: 8
```

```
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = alanine
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 211

Xaa Cys Xaa Xaa Cys Xaa Xaa Cys
1               5

<210> SEQ ID NO 212
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 5, 8, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine

<400> SEQUENCE: 212

Xaa Xaa Xaa Xaa Xaa Xaa Cys Xaa Xaa Cys Xaa Xaa Cys
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids and is not a cysteine
<220> FEATURE:
<221> NAME/KEY: VARIANT
<222> LOCATION: 2, 3, 4, 5, 8, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine

<400> SEQUENCE: 213

Xaa Xaa Xaa Xaa Xaa Xaa Cys Xaa Xaa Cys Xaa Xaa Cys
1               5                   10

<210> SEQ ID NO 214
<211> LENGTH: 13
<212> TYPE: PRT
<213> ORGANISM: Artificial Sequence
```

```
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2
<223> OTHER INFORMATION: Xaa = not a cysteine
<220> FEATURE:
<221> NAME/KEY: VARIANT
<222> LOCATION: 3, 4, 5, 8, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine

<400> SEQUENCE: 214

Xaa Xaa Xaa Xaa Xaa Xaa Cys Xaa Xaa Cys Xaa Xaa Cys
1               5                   10

<210> SEQ ID NO 215
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2
<223> OTHER INFORMATION: Xaa = D
<220> FEATURE:
<221> NAME/KEY: VARIANT
<222> LOCATION: 3, 4, 5, 8, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine

<400> SEQUENCE: 215

Xaa Xaa Xaa Xaa Xaa Xaa Cys Xaa Xaa Cys Xaa Xaa Cys
1               5                   10

<210> SEQ ID NO 216
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 4, 5, 8, 9, 11, 12
<223> OTHER INFORMATION: Xaa = any amino acid
<220> FEATURE:
<221> NAME/KEY: VARIANT
<222> LOCATION: 3
<223> OTHER INFORMATION: Xaa = K
<220> FEATURE:
<221> NAME/KEY: VARIANT
<222> LOCATION: 6
<223> OTHER INFORMATION: Xaa = any amino acid other than a cysteine
```

```
<400> SEQUENCE: 216

Xaa Xaa Xaa Xaa Xaa Xaa Cys Xaa Xaa Cys Xaa Xaa Cys
1               5                   10

<210> SEQ ID NO 217
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 5, 8, 9, 11, 12
<223> OTHER INFORMATION: Xaa = any amino acid
<220> FEATURE:
<221> NAME/KEY: VARIANT
<222> LOCATION: 4
<223> OTHER INFORMATION: Xaa = T
<220> FEATURE:
<221> NAME/KEY: VARIANT
<222> LOCATION: 6
<223> OTHER INFORMATION: Xaa = any amino acid other than a cysteine

<400> SEQUENCE: 217

Xaa Xaa Xaa Xaa Xaa Xaa Cys Xaa Xaa Cys Xaa Xaa Cys
1               5                   10

<210> SEQ ID NO 218
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 8, 9, 11, 12
<223> OTHER INFORMATION: Xaa = any amino acid
<220> FEATURE:
<221> NAME/KEY: VARIANT
<222> LOCATION: 5
<223> OTHER INFORMATION: Xaa = H
<220> FEATURE:
<221> NAME/KEY: VARIANT
<222> LOCATION: 6
<223> OTHER INFORMATION: Xaa = any amino acid other than a cysteine

<400> SEQUENCE: 218

Xaa Xaa Xaa Xaa Xaa Xaa Cys Xaa Xaa Cys Xaa Xaa Cys
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
```

```
<221> NAME/KEY: VARIANT
<222> LOCATION: 2, 3, 4, 5, 8, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = T

<400> SEQUENCE: 219

Xaa Xaa Xaa Xaa Xaa Xaa Cys Xaa Xaa Cys Xaa Xaa Cys
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 5, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine
<220> FEATURE:
<221> NAME/KEY: VARIANT
<222> LOCATION: 8
<223> OTHER INFORMATION: Xaa = a P or a V

<400> SEQUENCE: 220

Xaa Xaa Xaa Xaa Xaa Xaa Cys Xaa Xaa Cys Xaa Xaa Cys
1               5                   10

<210> SEQ ID NO 221
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 5, 8, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine
<220> FEATURE:
<221> NAME/KEY: VARIANT
<222> LOCATION: 9
<223> OTHER INFORMATION: Xaa = a P or a E

<400> SEQUENCE: 221

Xaa Xaa Xaa Xaa Xaa Xaa Cys Xaa Xaa Cys Xaa Xaa Cys
1               5                   10

<210> SEQ ID NO 222
<211> LENGTH: 13
<212> TYPE: PRT
<213> ORGANISM: Artificial Sequence
<220> FEATURE:
```

```
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 5, 8, 9, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine
<220> FEATURE:
<221> NAME/KEY: VARIANT
<222> LOCATION: 11
<223> OTHER INFORMATION: Xaa = a P or a V

<400> SEQUENCE: 222

Xaa Xaa Xaa Xaa Xaa Xaa Cys Xaa Xaa Cys Xaa Xaa Cys
 1               5                  10

<210> SEQ ID NO 223
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 5, 8, 9, 11
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine
<220> FEATURE:
<221> NAME/KEY: VARIANT
<222> LOCATION: 12
<223> OTHER INFORMATION: Xaa = a P or a E

<400> SEQUENCE: 223

Xaa Xaa Xaa Xaa Xaa Xaa Cys Xaa Xaa Cys Xaa Xaa Cys
 1               5                  10

<210> SEQ ID NO 224
<211> LENGTH: 17
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 2, 3, 7, 8, 9, 12, 13, 15, 16
<223> OTHER INFORMATION: Xaa = any amino acid
<220> FEATURE:
<221> NAME/KEY: VARIANT
<222> LOCATION: 5
<223> OTHER INFORMATION: Xaa = any m amino acids where m is any number
      of amino acids of any type
<220> FEATURE:
<221> NAME/KEY: VARIANT
<222> LOCATION: 6
<223> OTHER INFORMATION: Xaa = any amino acid residue other than a
      cysteine
<220> FEATURE:
<221> NAME/KEY: VARIANT
<222> LOCATION: 10
<223> OTHER INFORMATION: Xaa = any amino acid other than a cysteine
```

<400> SEQUENCE: 224

Cys Xaa Xaa Cys Xaa Xaa Xaa Xaa Xaa Xaa Cys Xaa Xaa Cys Xaa Xaa
1               5                   10                  15

Cys

<210> SEQ ID NO 225
<211> LENGTH: 17
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 2, 6, 7, 8, 9, 12, 13, 15, 16
<223> OTHER INFORMATION: Xaa = any amino acid
<220> FEATURE:
<221> NAME/KEY: VARIANT
<222> LOCATION: 3
<223> OTHER INFORMATION: Xaa = any amino acids other than the amino acid
      at position 2
<220> FEATURE:
<221> NAME/KEY: VARIANT
<222> LOCATION: 5
<223> OTHER INFORMATION: Xaa = any m amino acids where m is any number
      of amino acids of any type
<220> FEATURE:
<221> NAME/KEY: VARIANT
<222> LOCATION: 10
<223> OTHER INFORMATION: Xaa = any amino acid other than a cysteine

<400> SEQUENCE: 225

Cys Xaa Xaa Cys Xaa Xaa Xaa Xaa Xaa Xaa Cys Xaa Xaa Cys Xaa Xaa
1               5                   10                  15

Cys

<210> SEQ ID NO 226
<211> LENGTH: 16
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 5, 8, 9, 11, 12, 14, 15
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine

<400> SEQUENCE: 226

Xaa Xaa Xaa Xaa Xaa Xaa Cys Xaa Xaa Cys Xaa Xaa Cys Xaa Xaa Cys
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type

```
<220> FEATURE:
<221> NAME/KEY: VARIANT
<222> LOCATION: 2, 3, 4, 5, 8, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine
<220> FEATURE:
<221> NAME/KEY: VARIANT
<222> LOCATION: 14
<223> OTHER INFORMATION: Xaa = a P or a V
<220> FEATURE:
<221> NAME/KEY: VARIANT
<222> LOCATION: 15
<223> OTHER INFORMATION: Xaa = a P or an E

<400> SEQUENCE: 227

Xaa Xaa Xaa Xaa Xaa Xaa Cys Xaa Xaa Cys Xaa Xaa Cys Xaa Xaa Cys
1               5                   10                  15

<210> SEQ ID NO 228
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = serine
<220> FEATURE:
<221> NAME/KEY: VARIANT
<222> LOCATION: 2
<223> OTHER INFORMATION: Xaa = D
<220> FEATURE:
<221> NAME/KEY: VARIANT
<222> LOCATION: 3
<223> OTHER INFORMATION: Xaa = K
<220> FEATURE:
<221> NAME/KEY: VARIANT
<222> LOCATION: 4, 6
<223> OTHER INFORMATION: Xaa = T
<220> FEATURE:
<221> NAME/KEY: VARIANT
<222> LOCATION: 5
<223> OTHER INFORMATION: Xaa = H
<220> FEATURE:
<221> NAME/KEY: VARIANT
<222> LOCATION: (7)...(10)
<223> OTHER INFORMATION: Xaa = P

<400> SEQUENCE: 228

Xaa Xaa Xaa Xaa Xaa Xaa Cys Xaa Xaa Cys Xaa Xaa Cys
1               5                   10

<210> SEQ ID NO 229
<211> LENGTH: 8
<212> TYPE: PRT
<213> ORGANISM: Artificial Sequence
<220> FEATURE:
<223> OTHER INFORMATION: Core hinge region of the minibody
<220> FEATURE:
<221> NAME/KEY: VARIANT
<222> LOCATION: 1
<223> OTHER INFORMATION: Xaa = any amino acid other than a cysteine
<220> FEATURE:
<221> NAME/KEY: VARIANT
<222> LOCATION: 3, 4, 6, 7
<223> OTHER INFORMATION: Xaa = any amino acid

<400> SEQUENCE: 229

Xaa Cys Xaa Xaa Cys Xaa Xaa Cys
1               5
```

<210> SEQ ID NO 230
<211> LENGTH: 8
<212> TYPE: PRT
<213> ORGANISM: Artificial Sequence
<220> FEATURE:
<223> OTHER INFORMATION: Core hinge region of the minibody
<220> FEATURE:
<221> NAME/KEY: VARIANT
<222> LOCATION: 1
<223> OTHER INFORMATION: Xaa - = serine
<220> FEATURE:
<221> NAME/KEY: VARIANT
<222> LOCATION: 3, 4, 6, 7
<223> OTHER INFORMATION: Xaa = any amino acid

<400> SEQUENCE: 230

Xaa Cys Xaa Xaa Cys Xaa Xaa Cys
1               5

<210> SEQ ID NO 231
<211> LENGTH: 1167
<212> TYPE: DNA
<213> ORGANISM: Artificial Sequence
<220> FEATURE:
<223> OTHER INFORMATION: IAB25M gamma 2 NH (M1)

<400> SEQUENCE: 231

```
atggaaaccg acaccctgct gctgtgggtg ctgctgctct gggtcccagg ctccaccggt      60
gaaattgtgt tgacacagtc tccagccacc ctgtctttgt ctccagggga agagccacc     120 ctctcctgca gtgccagctc aagtgtaagt tacatgaact ggtaccaaca gaaacctggc    180
caggctccca ggctcctcat ctatgacaca tccaaactgg cttctggagt ccctgctcac    240
ttcaggggca gtgggtctgg gacagacttc actctcacca tcagcagcct agagcctgaa    300
gattttgcag tttattactg tcagcagtgg agtagtaacc cattcacgtt cggccaaggg    360
accaaggtgg aaatcaaagg ctccacatcc ggcggaggc ctggcggtgg atctggcgga    420
ggcggctcat cccaggtgca gctggtgcag tctggggctg aggtgaagaa gcctggggcc    480
tcagtgaagg tctcctgcaa ggcttctgga tacaccttca ccaggtacac gatgcactgg    540
gtgcgacagg cccctggaca agggcttgag tggatgggat acattaatcc tagccgtggt    600
tatactaatt acaatcagaa gttcaaggac agggtcacca tgaccacaga cacgtccatc    660
agcacagcct acatggagct gagcaggctg agatctgacg acacggccgt gtattactgt    720
gcgagatatt atgatgatca ttactcactt gactactggg gccagggcac cctggtcacc    780
gtctcctcag agcgcaaatg ttgtgtcgag tgcccaccgt gcccagcacc acctgtggca    840
ggaccggggc agccccgaga accacaggtg tacaccctgc ccccatcccg ggaggagatg    900
accaagaacc aggtcagcct gacctgcctg gtcaaaggct tctacccag cgacatcgcc    960 gtggagtggg agagcaatgg gcagccggag aacaactaca agaccacgcc tcccatgctg   1020
gactccgacg gctccttctt cctctacagc aagctcaccg tggacaagag caggtggcag   1080
caggggaacg tcttctcatg ctccgtgatg catgaggctc tgcacaacca ctacacgcag   1140
aagagcctct ccctgtctcc gggtaaa                                       1167
```

<210> SEQ ID NO 232
<211> LENGTH: 389
<212> TYPE: PRT
<213> ORGANISM: Artificial Sequence
<220> FEATURE:
<223> OTHER INFORMATION: IAB25M gamma 2 NH (M1)

<400> SEQUENCE: 232

```
Met Glu Thr Asp Thr Leu Leu Leu Trp Val Leu Leu Leu Trp Val Pro
1               5                   10                  15

Gly Ser Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Val Ser Tyr Met Asn Trp Tyr Gln Gln Lys Pro Gly Gln Ala Pro Arg
    50                  55                  60

Leu Leu Ile Tyr Asp Thr Ser Lys Leu Ala Ser Gly Val Pro Ala His
65                  70                  75                  80

Phe Arg Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Ser Ser
            100                 105                 110

Asn Pro Phe Thr Phe Gly Gln Gly Thr Lys Val Glu Ile Lys Gly Ser
        115                 120                 125

Thr Ser Gly Gly Gly Ser Gly Gly Gly Ser Gly Gly Gly Gly Ser Ser
    130                 135                 140

Gln Val Gln Leu Val Gln Ser Gly Ala Glu Val Lys Lys Pro Gly Ala
145                 150                 155                 160

Ser Val Lys Val Ser Cys Lys Ala Ser Gly Tyr Thr Phe Thr Arg Tyr
                165                 170                 175

Thr Met His Trp Val Arg Gln Ala Pro Gly Gln Gly Leu Glu Trp Met
            180                 185                 190

Gly Tyr Ile Asn Pro Ser Arg Gly Tyr Thr Asn Tyr Asn Gln Lys Phe
        195                 200                 205

Lys Asp Arg Val Thr Met Thr Thr Asp Thr Ser Ile Ser Thr Ala Tyr
    210                 215                 220

Met Glu Leu Ser Arg Leu Arg Ser Asp Asp Thr Ala Val Tyr Tyr Cys
225                 230                 235                 240

Ala Arg Tyr Tyr Asp Asp His Tyr Ser Leu Asp Tyr Trp Gly Gln Gly
                245                 250                 255

Thr Leu Val Thr Val Ser Ser Glu Arg Lys Cys Cys Val Glu Cys Pro
            260                 265                 270

Pro Cys Pro Ala Pro Pro Val Ala Gly Pro Gly Gln Pro Arg Glu Pro
        275                 280                 285

Gln Val Tyr Thr Leu Pro Pro Ser Arg Glu Glu Met Thr Lys Asn Gln
    290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Met Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
        355                 360                 365

Val Met His Glu Ala Leu His Asn His Tyr Thr Gln Lys Ser Leu Ser
    370                 375                 380

Leu Ser Pro Gly Lys
385
```

<210> SEQ ID NO 233
<211> LENGTH: 1176
<212> TYPE: DNA
<213> ORGANISM: Artificial Sequence
<220> FEATURE:
<223> OTHER INFORMATION: IAB25M gamma 2 EH (M1)

<400> SEQUENCE: 233

```
atggagaccg acaccctcct cctgtgggtc ctgctgctgt gggtgcctgg aagcaccggc      60
gagattgtgc tgacccagtc ccctgccacc ctgagcctgt cccctggaga aagagccaca     120
ctgagctgtt ccgcctcctc cagcgtgagc tacatgaact ggtaccagca gaagcccgga     180
caggctccca ggctgctcat ctacgacaca agcaagctgg ctagcggcgt gcccgctcat     240
ttcagaggca gcggaagcgg cacagatttt accctgacca tttcctccct ggagcctgag     300
gacttcgccg tgtattactg ccagcagtgg agctccaacc ccttcacatt cggccagggc     360
accaaggtgg aaatcaaggg atccacaagc ggaggcggca gcggcggcgg cagcggaggc     420
ggaggcagca gccaggtgca actggtgcag agcggagccg aggtgaagaa gcccggagcc     480
agcgtgaagg tgtcctgcaa agcctccgga tacaccttca ccaggtacac aatgcactgg     540
gtgaggcagg ctcccggcca gggcctggag tggatgggat acatcaaccc cagcaggggc     600
tacaccaact ataaccagaa gttcaaggac agggtgacca tgaccaccga caccagcatt     660
tccaccgctt atatggagct cagcagactg aggtccgacg acaccgccgt gtactactgc     720
gccaggtatt acgacgacca ctacagcctg gactactggg gccagggaac actcgtgacc     780
gtgtccagcg agaggaagtg ctgcgtggaa tgtccccctt gtcctggagg cggaagctcc     840
ggaggaggat ccggcggaca gcccagggaa cctcaggtgt acaccctgcc ccccagcagg     900
gaggagatga caaagaacca ggtgagcctg acctgtctgg tgaagggctt ctacccccagc     960
gacatcgccg tggagtggga gagcaacggc cagcctgaga caactacaa gacaaccccc    1020
cctatgctgg atagcgacgg cagcttcttc ctgtactcca agctcaccgt ggataagagc    1080
aggtggcagc agggaaacgt ctttagctgt tccgtgatgc acgaggccct gcacaaccac    1140
tacacccaga gagcctctct cctgtccccc ggcaag                              1176
```

<210> SEQ ID NO 234
<211> LENGTH: 392
<212> TYPE: PRT
<213> ORGANISM: Artificial Sequence
<220> FEATURE:
<223> OTHER INFORMATION: IAB25M gamma 2 EH (M1)

<400> SEQUENCE: 234

```
Met Glu Thr Asp Thr Leu Leu Leu Trp Val Leu Leu Leu Trp Val Pro
1               5                   10                  15

Gly Ser Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Val Ser Tyr Met Asn Trp Tyr Gln Gln Lys Pro Gly Gln Ala Pro Arg
    50                  55                  60

Leu Leu Ile Tyr Asp Thr Ser Lys Leu Ala Ser Gly Val Pro Ala His
65                  70                  75                  80

Phe Arg Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Ser Ser
            100                 105                 110
```

```
Asn Pro Phe Thr Phe Gly Gln Gly Thr Lys Val Glu Ile Lys Gly Ser
        115                 120                 125

Thr Ser Gly Gly Gly Ser Gly Gly Gly Ser Gly Gly Gly Ser Ser
    130                 135                 140

Gln Val Gln Leu Val Gln Ser Gly Ala Glu Val Lys Lys Pro Gly Ala
145                 150                 155                 160

Ser Val Lys Val Ser Cys Lys Ala Ser Gly Tyr Thr Phe Thr Arg Tyr
                165                 170                 175

Thr Met His Trp Val Arg Gln Ala Pro Gly Gln Gly Leu Glu Trp Met
            180                 185                 190

Gly Tyr Ile Asn Pro Ser Arg Gly Tyr Thr Asn Tyr Asn Gln Lys Phe
        195                 200                 205

Lys Asp Arg Val Thr Met Thr Thr Asp Thr Ser Ile Ser Thr Ala Tyr
    210                 215                 220

Met Glu Leu Ser Arg Leu Arg Ser Asp Asp Thr Ala Val Tyr Tyr Cys
225                 230                 235                 240

Ala Arg Tyr Tyr Asp Asp His Tyr Ser Leu Asp Tyr Trp Gly Gln Gly
                245                 250                 255

Thr Leu Val Thr Val Ser Ser Glu Arg Lys Cys Cys Val Glu Cys Pro
            260                 265                 270

Pro Cys Pro Gly Gly Gly Ser Gly Gly Gly Ser Gly Gly Gln Pro
        275                 280                 285

Arg Glu Pro Gln Val Tyr Thr Leu Pro Pro Ser Arg Glu Glu Met Thr
    290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Met Leu Asp Ser Asp Gly Ser Phe Phe Leu Tyr
            340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
    370                 375                 380

Ser Leu Ser Leu Ser Pro Gly Lys
385                 390

<210> SEQ ID NO 235
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = a serine or an alanine
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 235

Xaa Cys Xaa Xaa Cys Xaa Xaa Cys
```

```
1               5

<210> SEQ ID NO 236
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = T
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 6, 7
<223> OTHER INFORMATION: Xaa = any amino acid

<400> SEQUENCE: 236

Xaa Cys Xaa Xaa Cys Xaa Xaa Cys
1               5

<210> SEQ ID NO 237
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 7
<223> OTHER INFORMATION: Xaa = P or E
<220> FEATURE:
<221> NAME/KEY: VARIANT
<222> LOCATION: 6
<223> OTHER INFORMATION: Xaa = any amino acid

<400> SEQUENCE: 237

Xaa Cys Xaa Xaa Cys Xaa Xaa Cys
1               5

<210> SEQ ID NO 238
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3, 4
<223> OTHER INFORMATION: Xaa = VE or PP
<220> FEATURE:
<221> NAME/KEY: VARIANT
<222> LOCATION: 6, 7
<223> OTHER INFORMATION: Xaa = any amino acid
```

<400> SEQUENCE: 238

Xaa Cys Xaa Xaa Cys Xaa Xaa Cys
1               5

<210> SEQ ID NO 239
<211> LENGTH: 8
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond
<220> FEATURE:
<221> NAME/KEY: VARIANT
<222> LOCATION: 3, 4
<223> OTHER INFORMATION: Xaa = VE
<220> FEATURE:
<221> NAME/KEY: VARIANT
<222> LOCATION: 6, 7
<223> OTHER INFORMATION: Xaa = any amino acid

<400> SEQUENCE: 239

Xaa Cys Xaa Xaa Cys Xaa Xaa Cys
1               5

<210> SEQ ID NO 240
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond with another amino acid
<220> FEATURE:
<221> NAME/KEY: VARIANT
<222> LOCATION: 2-6, 8-9, 11-12
<223> OTHER INFORMATION: Xaa = any amino acid

<400> SEQUENCE: 240

Xaa Xaa Xaa Xaa Xaa Xaa Cys Xaa Xaa Cys Xaa Xaa Cys
1               5                   10

<210> SEQ ID NO 241
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1-5, 8-9, 11-12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine

<400> SEQUENCE: 241

Xaa Xaa Xaa Xaa Xaa Xaa Cys Xaa Xaa Cys Xaa Xaa Cys
1               5                   10

<210> SEQ ID NO 242
<211> LENGTH: 13
<212> TYPE: PRT

<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = serine or alanine
<220> FEATURE:
<221> NAME/KEY: VARIANT
<222> LOCATION: 2, 3, 4, 5, 8, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine

<400> SEQUENCE: 242

Xaa Xaa Xaa Xaa Xaa Xaa Cys Xaa Xaa Cys Xaa Xaa Cys
1               5                   10

<210> SEQ ID NO 243
<211> LENGTH: 13
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2
<223> OTHER INFORMATION: Xaa = D
<220> FEATURE:
<221> NAME/KEY: VARIANT
<222> LOCATION: 3
<223> OTHER INFORMATION: Xaa = K
<220> FEATURE:
<221> NAME/KEY: VARIANT
<222> LOCATION: 4, 6
<223> OTHER INFORMATION: Xaa = T
<220> FEATURE:
<221> NAME/KEY: VARIANT
<222> LOCATION: 8, 11
<223> OTHER INFORMATION: Xaa = P or V
<220> FEATURE:
<221> NAME/KEY: VARIANT
<222> LOCATION: (5)...(5)
<223> OTHER INFORMATION: Xaa = H
<220> FEATURE:
<221> NAME/KEY: VARIANT
<222> LOCATION: (9)...(9)
<223> OTHER INFORMATION: Xaa = P or E
<220> FEATURE:
<221> NAME/KEY: VARIANT
<222> LOCATION: (12)...(12)
<223> OTHER INFORMATION: Xaa = any amino acid

<400> SEQUENCE: 243

Xaa Xaa Xaa Xaa Xaa Xaa Cys Xaa Xaa Cys Xaa Xaa Cys
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any amino acid that does not form a
      covalent crosslinking bond

```
<220> FEATURE:
<221> NAME/KEY: VARIANT
<222> LOCATION: 3
<223> OTHER INFORMATION: Xaa = any one of A, R, N, D, E, Q, G, H, I, L,
      K, M, F, P, S, T, W, Y, or V
<220> FEATURE:
<221> NAME/KEY: VARIANT
<222> LOCATION: 4, 6, 7, 9, 10
<223> OTHER INFORMATION: Xaa = any amino acid

<400> SEQUENCE: 244

Xaa Cys Xaa Xaa Cys Xaa Xaa Cys Xaa Xaa Cys
1               5                   10

<210> SEQ ID NO 245
<211> LENGTH: 16
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 5, 8, 9, 11, 12, 14, 15
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine

<400> SEQUENCE: 245

Xaa Xaa Xaa Xaa Xaa Xaa Cys Xaa Xaa Cys Xaa Xaa Cys Xaa Xaa Cys
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = any m amino acids where m is any number
      of amino acids of any type
<220> FEATURE:
<221> NAME/KEY: VARIANT
<222> LOCATION: 2, 3, 4, 5, 8, 9, 11, 12
<223> OTHER INFORMATION: Xaa = any amino acid
<220> FEATURE:
<221> NAME/KEY: VARIANT
<222> LOCATION: 6
<223> OTHER INFORMATION: Xaa = any amino acid other than a cysteine
<220> FEATURE:
<221> NAME/KEY: VARIANT
<222> LOCATION: 14
<223> OTHER INFORMATION: Xaa = P or V
<220> FEATURE:
<221> NAME/KEY: VARIANT
<222> LOCATION: 15
<223> OTHER INFORMATION: Xaa = P or E

<400> SEQUENCE: 246

Xaa Xaa Xaa Xaa Xaa Xaa Cys Xaa Xaa Cys Xaa Xaa Cys Xaa Xaa Cys
1               5                   10                  15

<210> SEQ ID NO 247
<211> LENGTH: 13
<212> TYPE: PRT
```

```
<213> ORGANISM: Artificial Sequence
<220> FEATURE:
<223> OTHER INFORMATION: Hinge region
<220> FEATURE:
<221> NAME/KEY: VARIANT
<222> LOCATION: 1
<223> OTHER INFORMATION: Xaa = serine
<220> FEATURE:
<221> NAME/KEY: VARIANT
<222> LOCATION: 2
<223> OTHER INFORMATION: Xaa = D
<220> FEATURE:
<221> NAME/KEY: VARIANT
<222> LOCATION: 3
<223> OTHER INFORMATION: Xaa = K
<220> FEATURE:
<221> NAME/KEY: VARIANT
<222> LOCATION: 4, 6
<223> OTHER INFORMATION: Xaa = T
<220> FEATURE:
<221> NAME/KEY: VARIANT
<222> LOCATION: 8, 9, 11, 12
<223> OTHER INFORMATION: Xaa = P
<220> FEATURE:
<221> NAME/KEY: VARIANT
<222> LOCATION: (5)...(5)
<223> OTHER INFORMATION: Xaa = H

<400> SEQUENCE: 247

Xaa Xaa Xaa Xaa Xaa Xaa Cys Xaa Xaa Cys Xaa Xaa Cys
1               5                   10

<210> SEQ ID NO 248
<211> LENGTH: 9
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 2, 3, 5, 6, 8, 9
<223> OTHER INFORMATION: Xaa = not a cysteine

<400> SEQUENCE: 248

Cys Xaa Xaa Cys Xaa Xaa Cys Xaa Xaa
1               5

<210> SEQ ID NO 249
<211> LENGTH: 6
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 2, 3, 5, 6
<223> OTHER INFORMATION: Xaa = not a cysteine

<400> SEQUENCE: 249

Cys Xaa Xaa Cys Xaa Xaa
1               5

<210> SEQ ID NO 250
<211> LENGTH: 12
<212> TYPE: PRT
<213> ORGANISM: Artificial Sequence
<220> FEATURE:
<223> OTHER INFORMATION: Hinge region
<220> FEATURE:
<221> NAME/KEY: VARIANT
<222> LOCATION: 2, 3, 5, 6, 8, 9, 11, 12
<223> OTHER INFORMATION: Xaa = not a cysteine
```

```
<400> SEQUENCE: 250

Cys Xaa Xaa Cys Xaa Xaa Cys Xaa Xaa Cys Xaa Xaa
1               5                   10

<210> SEQ ID NO 251
<211> LENGTH: 8
<212> TYPE: PRT
<213> ORGANISM: Artificial Sequence
<220> FEATURE:
<223> OTHER INFORMATION: Minibody
<220> FEATURE:
<221> NAME/KEY: VARIANT
<222> LOCATION: 1, 3, 4, 6, 7
<223> OTHER INFORMATION: Xaa = cannot be a cysteine

<400> SEQUENCE: 251

Xaa Cys Xaa Xaa Cys Xaa Xaa Cys
1               5

<210> SEQ ID NO 252
<211> LENGTH: 9
<212> TYPE: PRT
<213> ORGANISM: Artificial Sequence
<220> FEATURE:
<223> OTHER INFORMATION: Minibody
<220> FEATURE:
<221> NAME/KEY: VARIANT
<222> LOCATION: 1
<223> OTHER INFORMATION: Xaa = any amino acid or no amino acid
<220> FEATURE:
<221> NAME/KEY: VARIANT
<222> LOCATION: 3, 4, 6, 7
<223> OTHER INFORMATION: Xaa = any amino acid
<220> FEATURE:
<221> NAME/KEY: VARIANT
<222> LOCATION: 9
<223> OTHER INFORMATION: Xaa = any amino acid, no amino acid, or P

<400> SEQUENCE: 252

Xaa Cys Xaa Xaa Cys Xaa Xaa Cys Xaa
1               5

<210> SEQ ID NO 253
<211> LENGTH: 9
<212> TYPE: PRT
<213> ORGANISM: Artificial Sequence
<220> FEATURE:
<223> OTHER INFORMATION: Minibody
<220> FEATURE:
<221> NAME/KEY: VARIANT
<222> LOCATION: 1, 3, 4, 6, 7
<223> OTHER INFORMATION: Xaa = cannot be a cysteine
<220> FEATURE:
<221> NAME/KEY: VARIANT
<222> LOCATION: 9
<223> OTHER INFORMATION: Xaa = any amino acid, no amino acid, or P

<400> SEQUENCE: 253

Xaa Cys Xaa Xaa Cys Xaa Xaa Cys Xaa
1               5

<210> SEQ ID NO 254
<211> LENGTH: 9
<212> TYPE: PRT
<213> ORGANISM: Artificial Sequence
<220> FEATURE:
<223> OTHER INFORMATION: Minibody
<220> FEATURE:
<221> NAME/KEY: VARIANT
<222> LOCATION: 1
<223> OTHER INFORMATION: Xaa = any amino acid other than a cysteine
```

```
<220> FEATURE:
<221> NAME/KEY: VARIANT
<222> LOCATION: 3, 4, 6, 7
<223> OTHER INFORMATION: Xaa = any amino acid
<220> FEATURE:
<221> NAME/KEY: VARIANT
<222> LOCATION: 9
<223> OTHER INFORMATION: Xaa = any amino acid, no amino acid, or P

<400> SEQUENCE: 254

Xaa Cys Xaa Xaa Cys Xaa Xaa Cys Xaa
1               5

<210> SEQ ID NO 255
<211> LENGTH: 9
<212> TYPE: PRT
<213> ORGANISM: Artificial Sequence
<220> FEATURE:
<223> OTHER INFORMATION: Minibody
<220> FEATURE:
<221> NAME/KEY: VARIANT
<222> LOCATION: 1
<223> OTHER INFORMATION: Xaa = Serine
<220> FEATURE:
<221> NAME/KEY: VARIANT
<222> LOCATION: 3, 4, 6, 7
<223> OTHER INFORMATION: Xaa = any amino acid
<220> FEATURE:
<221> NAME/KEY: VARIANT
<222> LOCATION: 9
<223> OTHER INFORMATION: Xaa = any amino acid, no amino acid, or P

<400> SEQUENCE: 255

Xaa Cys Xaa Xaa Cys Xaa Xaa Cys Xaa
1               5

<210> SEQ ID NO 256
<211> LENGTH: 50
<212> TYPE: PRT
<213> ORGANISM: Homo sapiens

<400> SEQUENCE: 256

Cys Pro Arg Cys Pro Glu Pro Lys Ser Cys Asp Thr Pro Pro Cys
1               5                   10                  15

Pro Arg Cys Pro Glu Pro Lys Ser Cys Asp Thr Pro Pro Cys Pro
            20                  25                  30

Arg Cys Pro Glu Pro Lys Ser Cys Asp Thr Pro Pro Cys Pro Arg
        35                  40                  45

Cys Pro
    50
```

What is claimed is:

1. An amino acid sequence comprising EPKSSDKTH-TCPPCPPC (SEQ ID NO: 168),
   wherein the amino acid sequence is in a polypeptide of a minibody comprising an artificial hinge linking a scFv and a $C_H3$, wherein the artificial hinge comprises the amino acid sequence, wherein an upper hinge of the artificial hinge does not comprise a cysteine, and wherein the minibody does not comprise a native hinge.

2. The amino acid sequence of claim 1, wherein the amino acid sequence comprises EPKSSDKTHTCPPCPP-CAPELLGGP (SEQ ID NO: 25).

3. The amino acid sequence of claim 1, wherein the minibody is a bispecific minibody, wherein the bispecific minibody is assembled in a 1:1 ratio.

4. The amino acid sequence of claim 1, wherein the amino acid sequence comprises EPKSSDKTHTCPPCPPCPPC (SEQ ID NO: 170).

5. The amino acid sequence of claim 1, wherein the amino acid sequence comprises EPKSSDKTH-TCPPCPPCGGGSSGGGSG (SEQ ID NO: 26).

6. A pharmaceutical composition comprising the amino acid sequence of claim 1, wherein the pharmaceutical composition has less than 5% aggregation of the minibody present in the composition.

7. An amino acid sequence comprising EPKSSDKTH-TCPPCPPC (SEQ ID NO: 168),
   wherein the amino acid sequence is in a polypeptide of a minibody comprising an artificial hinge linking a variable region and a $C_H3$, the variable region comprising a $V_H$ and a $V_L$, wherein the artificial hinge comprises the amino acid sequence, wherein an upper hinge of the artificial hinge does not comprise a cysteine, and wherein the minibody does not comprise a native hinge.

8. The amino acid sequence of claim 7, wherein the amino acid sequence comprises EPKSSDKTHTCPPCPPCGGGSSGGGSG (SEQ ID NO: 26).

9. A protein comprising an amino acid sequence comprising EPKSSDKTHTCPPCPPCGGGSSGGGSG (SEQ ID NO: 26), wherein the protein is a minibody comprising the amino acid sequence as an artificial hinge that links either:
 i) a $V_H$ and $C_H3$ of the protein, or
 ii) a $V_L$ and $C_H3$ of the protein.

10. An amino acid sequence within a minibody, the amino acid sequence comprising EPKSSDKTHTCPPCPPC (SEQ ID NO: 168),
 wherein the amino acid sequence is part of an artificial hinge of a minibody, and wherein an upper hinge of the artificial hinge does not comprise a cysteine.

11. The amino acid sequence of claim 10, wherein the amino acid sequence comprises EPKSSDKTHTCPPCPPCGGGSSGGGSG (SEQ ID NO: 26).

12. An amino acid sequence within a minibody, the amino acid sequence comprising:
 a first amino acid sequence comprising EPKSSDKTHTCPPCPPC (SEQ ID NO: 168); and
 a second amino acid sequence adjacent and C-terminal to the first amino acid sequence, wherein the second amino acid sequence is GGGSSGGGSG (SEQ ID NO: 59),
 wherein the first and second amino acid sequences are at least part of an artificial hinge of a minibody, and wherein an upper hinge of the artificial hinge does not comprise a cysteine.

13. An amino acid sequence within a minibody, the amino acid sequence comprising:
 a first amino acid sequence of CPPCPPC (SEQ ID NO: 52) as a core hinge of an artificial hinge of a minibody; and a second amino acid sequence of EPKSSDKTHT (SEQ ID NO: 46) as an upper hinge of the artificial hinge of the minibody, and wherein the upper hinge does not comprise a cysteine.

14. The amino acid sequence of claim 13, wherein the amino acid sequence comprises EPKSSDKTHTCPPCPPCGGGSSGGGSG (SEQ ID NO: 26) comprising the first amino acid sequence and the second amino acid sequence.

15. An amino acid sequence within a minibody, the amino acid sequence comprising EPKSSDKTHTCPPCPPCGGGSSGGGSG (SEQ ID NO: 26) or EPKSSDKTHTCPPCPPCAPELLGGP (SEQ ID NO: 25),
 wherein the amino acid sequence is at least part of an artificial hinge of a minibody, and wherein an upper hinge of the artificial hinge does not comprise a cysteine.

16. The amino acid sequence of claim 15, wherein the amino acid sequence comprises EPKSSDKTHTCPPCPPCGGGSSGGGSG (SEQ ID NO: 26).

17. A minibody comprising EPKSSDKTHTCPPCPPC (SEQ ID NO: 168) as part of an artificial hinge of the minibody, wherein an upper hinge of the artificial hinge does not comprise a cysteine, and
 wherein the minibody does not comprise a native hinge.

18. The minibody of claim 17, wherein the minibody comprises EPKSSDKTHTCPPCPPCGGGSSGGGSG (SEQ ID NO: 26) as at least part of the artificial hinge of the minibody.

19. A minibody comprising:
 a first amino acid sequence comprising: EPKSSDKTHTCPPCPPC (SEQ ID NO: 168); and
 a second amino acid sequence adjacent and C-terminal to the first amino acid sequence, wherein the second amino acid sequence is GGGSSGGGSG (SEQ ID NO: 59),
 and wherein the first and second amino acid sequences are at least part of an artificial hinge of the minibody, wherein an upper hinge of the artificial hinge does not comprise a cysteine,
 wherein the minibody does not comprise a native hinge.

20. A minibody comprising:
 a first amino acid sequence of CPPCPPC (SEQ ID NO: 52) as a core hinge of an artificial hinge of the minibody; and
 a second amino acid sequence of EPKSSDKTHT (SEQ ID NO: 46) as an upper hinge of the artificial hinge of the minibody.

21. The minibody of claim 20, wherein the minibody comprises EPKSSDKTHTCPPCPPCGGGSSGGGSG (SEQ ID NO: 26) comprising the first amino acid sequence and the second amino acid sequence.

22. A minibody comprising:
 a scFv;
 a $C_H3$; and
 an amino acid sequence comprising EPKSSDKTHTCPPCPPCGGGSSGGGSG (SEQ ID NO: 26), wherein the amino acid sequence links the scFv to the CH3.

23. A minibody comprising:
 a first polypeptide comprising:
  a first scFv;
  a first amino acid sequence comprising:
   (a) EPKSSDKTHTCPPCPPC (SEQ ID NO: 168);
  a first $C_H3$; and
  a first artificial hinge linking the first scFv and the first CH3,
   wherein the first artificial hinge comprises the first amino acid sequence, and wherein a first upper hinge of the first artificial hinge does not comprise a cysteine; and
 a second polypeptide comprising:
  a second scFv;
  a second amino acid sequence comprising:
   (b) EPKSSDKTHTCPPCPPC (SEQ ID NO: 168);
  a second $C_H3$; and
  a second artificial hinge linking the second scFv and the second CH3,
   wherein the second artificial hinge comprises the second amino acid sequence, and wherein a second upper hinge of the second artificial hinge does not comprise a cysteine,
 wherein the first polypeptide is cross-linked to the second polypeptide by at least two disulfide bridges, wherein each disulfide bridge is between a cysteine of (a) and a cysteine of (b), and wherein the minibody does not comprise a native hinge.

24. The minibody of claim 23, wherein the first polypeptide comprises EPKSSDKTHTCPPCPPCGGGSSGGGSG (SEQ ID NO: 26) comprising (a), and wherein the second polypeptide comprises EPKSSDKTHTCPPCPPCGGGSSGGGSG (SEQ ID NO: 26) comprising (b).

25. A minibody comprising:
a first polypeptide comprising:
   a first amino acid sequence comprising:
      (a) EPKSSDKTHT (SEQ ID NO: 46) as a first upper hinge, wherein the first upper hinge does not comprise a cysteine; and
      (b) a first core hinge comprising CPPCPPC (SEQ ID NO: 52);
   a first variable region;
   a first $C_H3$; and
   a first hinge linking the first variable region and the first $C_H3$,
      wherein the first hinge comprises (a) and (b); and
a second polypeptide comprising:
   a second amino acid sequence comprising:
      (c) EPKSSDKTHT (SEQ ID NO: 46) as a second upper hinge, wherein the second upper hinge does not comprise a cysteine; and
      (d) a second core hinge comprising CPPCPPC (SEQ ID NO: 52);
   a second variable region; and
   a second $C_H3$; and
   a second hinge linking the second variable region and the second $C_H3$,
      wherein the second hinge comprises (c) and (d).

26. The minibody of claim 25, wherein the first polypeptide comprises EPKSSDKTHTCPPCPPCGGGSSGGGSG (SEQ ID NO: 26) comprising (a) and (b), and wherein the second polypeptide comprises EPKSSDKTH-TCPPCPPCGGGSSGGGSG (SEQ ID NO: 26) comprising (c) and (d).

27. An amino acid sequence of a hinge of a minibody, comprising:
   EPKSSDKTHTCPPCPPC (SEQ ID NO: 168), comprising an upper hinge sequence and a core hinge sequence of the hinge, wherein the upper hinge sequence does not comprise a cysteine.

28. The amino acid sequence of claim 27, wherein the amino acid sequence is EPKSSDKTH-TCPPCPPCGGGSSGGGSG (SEQ ID NO: 26).

29. A minibody comprising an amino acid sequence comprising:
   (a) EPKSSDKTHT (SEQ ID NO: 46) as an upper hinge of the minibody, wherein the upper hinge does not comprise a cysteine; and
   (b) a core hinge comprising a sequence of CPPCPPC (SEQ ID NO: 52).

30. The minibody of claim 29, wherein the amino acid sequence is EPKSSDKTHTCPPCPPCGGGSSGGGSG (SEQ ID NO: 26), which comprises (a) and (b).

31. A minibody comprising:
a first amino acid sequence comprising:
   (a) EPKSSDKTHT (SEQ ID NO: 46) as an upper hinge of the minibody, wherein the upper hinge does not comprise a cysteine; and
   (b) a core hinge comprising a sequence of CPPCPPC (SEQ ID NO: 52); and
a second amino acid sequence C-terminal to the first amino acid sequence, wherein the second amino acid sequence is GGGSSGGGSG (SEQ ID NO: 59).

32. A minibody comprising:
a scFv;
a $C_H3$; and
an artificial hinge linking the scFV to the CH3, wherein the artificial hinge comprises an amino acid sequence comprising:
   (a) EPKSSDKTHT (SEQ ID NO: 46) as an upper hinge of the minibody, wherein the upper hinge does not comprise a cysteine; and
   (b) a core hinge comprising a sequence of CPPCPPC (SEQ ID NO: 52), wherein the minibody does not comprise a native hinge.

* * * * *

UNITED STATES PATENT AND TRADEMARK OFFICE
CERTIFICATE OF CORRECTION

PATENT NO. : 11,254,744 B2  
APPLICATION NO. : 15/228616  
DATED : February 22, 2022  
INVENTOR(S) : Chan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 110 days.

Signed and Sealed this  
Eleventh Day of February, 2025

Coke Morgan Stewart  
*Acting Director of the United States Patent and Trademark Office*